(12) United States Patent
Touti et al.

(10) Patent No.: US 12,305,217 B2
(45) Date of Patent: May 20, 2025

(54) EX VIVO PROTEASE ACTIVITY DETECTION FOR DISEASE DETECTION/DIAGNOSTIC, STAGING, MONITORING AND TREATMENT

(71) Applicant: Sunbird Bio, Inc., Cambridge, MA (US)

(72) Inventors: Faycal Touti, Belmont, MA (US); Wendy Winckler Adamovich, Melrose, MA (US); Sophie Cazanave, Cambridge, MA (US); Mehar Cheema, Medford, MA (US); Robert S. Langer, Newton, MA (US)

(73) Assignee: Sunbird Bio, Inc., Cambridge, MA (US)

( * ) Notice: Subject to any disclaimer, the term of this patent is extended or adjusted under 35 U.S.C. 154(b) by 0 days.

(21) Appl. No.: 18/063,812

(22) Filed: Dec. 9, 2022

(65) Prior Publication Data

US 2023/0175037 A1   Jun. 8, 2023

Related U.S. Application Data

(63) Continuation of application No. 17/573,129, filed on Jan. 11, 2022, now Pat. No. 11,604,193, which is a
(Continued)

(51) Int. Cl.
*C12Q 1/37* (2006.01)
*G01N 21/64* (2006.01)
(Continued)

(52) U.S. Cl.
CPC ........... *C12Q 1/37* (2013.01); *G01N 21/6428* (2013.01); *G01N 33/542* (2013.01);
(Continued)

(58) Field of Classification Search
CPC .... C12Q 1/37; G01N 21/6428; G01N 33/573; G01N 33/582; G01N 2021/6432;
(Continued)

(56) References Cited

U.S. PATENT DOCUMENTS

| 5,387,503 A | 2/1995 | Selmer et al. |
| 6,083,486 A | 7/2000 | Weissleder et al. |

(Continued)

FOREIGN PATENT DOCUMENTS

| CA | 3103079 A1 | 12/2019 |
| CN | 105452481 A | 3/2016 |

(Continued)

OTHER PUBLICATIONS

Dudani et al. (Sustained-release synthetic biomarkers for monitoring thrombosis and inflammation using point-of-care compatible readouts), Adv Funct Mater. May 3, 2016; 26(17): 2919-2928. doi: 10.1002/adfm.201505142. (Year: 2016).*

(Continued)

*Primary Examiner* — Mohamed K Amara
(74) *Attorney, Agent, or Firm* — Clark & Elbing LLP

(57) ABSTRACT

The present application provides compositions and methods for determining a disease or condition in a subject. The method comprises contacting a body fluid with a molecule comprising a reporter thereof and the reported is cleaved by an agent in the body fluid. Diseases and conditions that can be determined by the method are also described.

26 Claims, 58 Drawing Sheets
Specification includes a Sequence Listing.

Related U.S. Application Data continuation-in-part of application No. PCT/US2021/049948, filed on Sep. 10, 2021.

(60) Provisional application No. 63/077,525, filed on Sep. 11, 2020.

(51) Int. Cl.
  *G01N 33/542* (2006.01)
  *G01N 33/573* (2006.01)
  *G01N 33/58* (2006.01)

(52) U.S. Cl.
  CPC ......... *G01N 33/573* (2013.01); *G01N 33/582* (2013.01); *G01N 2021/6432* (2013.01); *G01N 2021/6439* (2013.01); *G01N 2021/6441* (2013.01); *G01N 2333/95* (2013.01); *G01N 2800/085* (2013.01); *G01N 2800/26* (2013.01); *G01N 2800/7028* (2013.01)

(58) Field of Classification Search
  CPC ....... G01N 2021/6441; G01N 2333/95; G01N 2800/085; G01N 2800/26; G01N 2800/7028
  See application file for complete search history.

(56) References Cited

U.S. PATENT DOCUMENTS

| Patent/Pub No. | Date | Inventor | Classification |
|---|---|---|---|
| 6,210,912 B1 | 4/2001 | Koyama et al. | |
| 6,495,357 B1 | 12/2002 | Fuglsang et al. | |
| 6,592,847 B1 | 7/2003 | Weissleder et al. | |
| 7,179,655 B2 | 2/2007 | Patricelli | |
| 7,329,506 B2 | 2/2008 | Ward et al. | |
| 7,531,317 B2 | 5/2009 | Fox et al. | |
| 7,833,728 B2 | 11/2010 | Pastorek et al. | |
| 8,209,130 B1 | 6/2012 | Kennedy et al. | |
| 8,519,115 B2 | 8/2013 | Webster et al. | |
| 8,551,727 B2 | 10/2013 | Kwon et al. | |
| 8,673,267 B2 | 3/2014 | Bhatia et al. | |
| 8,958,999 B1 | 2/2015 | Ptasinski et al. | |
| 9,006,415 B2 | 4/2015 | Ren et al. | |
| 10,006,916 B2 | 6/2018 | Kwong et al. | |
| 10,029,017 B2* | 7/2018 | Savariar | A61K 47/645 |
| 10,100,198 B2* | 10/2018 | Kundu | C09B 23/0008 |
| 10,385,380 B2* | 8/2019 | Whitney | C12Q 1/37 |
| 10,619,219 B2* | 4/2020 | McNamara | C12Q 1/689 |
| 10,689,429 B2* | 6/2020 | Linderoth | A61P 43/00 |
| 10,802,027 B2 | 10/2020 | Kearney et al. | |
| 11,028,425 B2 | 6/2021 | Bhatia et al. | |
| 11,604,193 B2 | 3/2023 | Touti et al. | |
| 11,732,009 B2* | 8/2023 | Bhatia | G01N 33/54393 435/23 |
| 11,851,697 B2 | 12/2023 | Touti et al. | |
| 2002/0004202 A1* | 1/2002 | Cornish | C07J 41/0066 435/6.1 |
| 2002/0013003 A1* | 1/2002 | Wagner | G01N 33/54353 436/518 |
| 2002/0164390 A1 | 11/2002 | Wong | |
| 2003/0077608 A1* | 4/2003 | Coull | C40B 20/04 435/6.14 |
| 2003/0100707 A1 | 5/2003 | Hwang et al. | |
| 2003/0119059 A1* | 6/2003 | Still | G01N 33/543 435/7.1 |
| 2003/0129589 A1* | 7/2003 | Koster | C07F 9/2408 422/68.1 |
| 2003/0143626 A1* | 7/2003 | Colas | A61P 35/00 514/3.3 |
| 2003/0152932 A1* | 8/2003 | Kumar | C12Q 1/6804 435/6.12 |
| 2004/0091943 A1 | 5/2004 | Schneider | |
| 2004/0236091 A1* | 11/2004 | Chicz | C07K 14/47 435/6.16 |
| 2005/0191680 A1* | 9/2005 | Bruno | C12N 15/115 435/6.12 |
| 2005/0214890 A1 | 9/2005 | Tan et al. | |
| 2005/0266425 A1 | 12/2005 | Zauderer et al. | |
| 2006/0041105 A1* | 2/2006 | Jiang | A61K 51/088 530/324 |
| 2006/0115485 A1 | 6/2006 | Losonsky et al. | |
| 2006/0121552 A1 | 6/2006 | Ward | |
| 2007/0093443 A1 | 4/2007 | Madison et al. | |
| 2008/0269063 A1 | 10/2008 | Sproles | |
| 2010/0015607 A1 | 1/2010 | Geiss et al. | |
| 2010/0047924 A1 | 2/2010 | Webster et al. | |
| 2010/0113743 A1 | 5/2010 | DeFrees et al. | |
| 2010/0124757 A1* | 5/2010 | Kwon | A61K 49/0032 435/23 |
| 2010/0131432 A1 | 5/2010 | Kennedy et al. | |
| 2010/0240050 A1 | 9/2010 | Bhatia et al. | |
| 2011/0136727 A1 | 6/2011 | Svarovsky | |
| 2011/0189680 A1* | 8/2011 | Keown | G01N 33/6842 435/7.4 |
| 2011/0229888 A1 | 9/2011 | Hengen et al. | |
| 2011/0244483 A1 | 10/2011 | Leeming et al. | |
| 2011/0256567 A1 | 10/2011 | Berthelot et al. | |
| 2012/0105853 A1 | 5/2012 | Pang et al. | |
| 2013/0017223 A1 | 1/2013 | Hope et al. | |
| 2013/0017971 A1 | 1/2013 | Geiss et al. | |
| 2013/0078188 A1* | 3/2013 | Tsien | C07K 14/4728 530/323 |
| 2013/0116405 A1 | 5/2013 | Yu et al. | |
| 2013/0273027 A1 | 10/2013 | Leach et al. | |
| 2014/0010861 A1* | 1/2014 | Bancel | C07K 14/485 536/23.4 |
| 2014/0242612 A1 | 8/2014 | Wang et al. | |
| 2014/0303014 A1 | 10/2014 | Kwong et al. | |
| 2014/0342384 A1* | 11/2014 | Nagano | C07F 7/0812 556/406 |
| 2015/0018517 A1 | 1/2015 | Rajopadhye et al. | |
| 2015/0038435 A1 | 2/2015 | Hubalek | |
| 2015/0065420 A1 | 3/2015 | Soliman et al. | |
| 2015/0132230 A1 | 5/2015 | Bossmann et al. | |
| 2015/0132785 A1 | 5/2015 | Bossmann et al. | |
| 2015/0133752 A1* | 5/2015 | Iverson | A61B 5/1459 600/316 |
| 2015/0301058 A1 | 10/2015 | Schettini et al. | |
| 2015/0352234 A1* | 12/2015 | Achilefu | A61K 51/1251 530/331 |
| 2016/0011209 A1* | 1/2016 | Jin | A61P 1/02 435/7.92 |
| 2016/0109401 A1 | 4/2016 | Wardell et al. | |
| 2016/0139143 A1 | 5/2016 | Hong et al. | |
| 2016/0153053 A1 | 6/2016 | Skog et al. | |
| 2016/0160263 A1* | 6/2016 | Whitney | C12Q 1/37 435/23 |
| 2016/0206726 A1 | 7/2016 | Cobbold et al. | |
| 2016/0222463 A1 | 8/2016 | Baker et al. | |
| 2016/0223532 A1 | 8/2016 | Rakestraw | |
| 2016/0289324 A1 | 10/2016 | Moore et al. | |
| 2016/0305930 A1 | 10/2016 | Everson | |
| 2017/0023476 A1 | 1/2017 | Altug et al. | |
| 2017/0049904 A1 | 2/2017 | Lin et al. | |
| 2017/0080088 A1* | 3/2017 | Savariar | A61K 47/65 |
| 2017/0108502 A1 | 4/2017 | Mulvihill et al. | |
| 2017/0114116 A1* | 4/2017 | Linderoth | A61P 3/04 |
| 2017/0176458 A1 | 6/2017 | Veidal et al. | |
| 2017/0218455 A1 | 8/2017 | Steelman | |
| 2017/0219548 A1 | 8/2017 | Troyer et al. | |
| 2017/0262604 A1 | 9/2017 | Francois | |
| 2017/0369843 A1 | 12/2017 | Kahvejian et al. | |
| 2018/0003712 A1* | 1/2018 | Haam | C12Q 1/37 |
| 2018/0023114 A1 | 1/2018 | Morin et al. | |
| 2018/0085466 A1* | 3/2018 | Bradley | C12Q 1/37 |
| 2018/0106818 A1* | 4/2018 | Datwyler | C12N 9/16 |
| 2018/0140703 A1* | 5/2018 | Advani | C07K 16/32 |
| 2018/0335429 A1 | 11/2018 | Bhatia et al. | |
| 2019/0064167 A1* | 2/2019 | Ahrens | G01N 33/535 |
| 2019/0128873 A1* | 5/2019 | Bhatia | C07K 14/001 |
| 2019/0212291 A1 | 7/2019 | Dudani et al. | |
| 2019/0271704 A1* | 9/2019 | Bhatia | G01N 33/497 |

(56) References Cited

U.S. PATENT DOCUMENTS

| | | | |
|---|---|---|---|
| 2019/0345534 A1* | 11/2019 | Kwong | C12Q 1/25 |
| 2019/0375793 A1 | 12/2019 | Touti et al. | |
| 2019/0375796 A1 | 12/2019 | Touti et al. | |
| 2019/0376113 A1 | 12/2019 | Bhatia et al. | |
| 2019/0376114 A1 | 12/2019 | Bhatia et al. | |
| 2019/0376115 A1 | 12/2019 | Bhatia et al. | |
| 2020/0096514 A1* | 3/2020 | Bhatia | C12Q 1/37 |
| 2020/0116727 A1 | 4/2020 | Geiger et al. | |
| 2020/0150041 A1* | 5/2020 | Harootunian | G01N 21/6456 |
| 2020/0232986 A1 | 7/2020 | Bhatia et al. | |
| 2020/0245926 A1 | 8/2020 | Bhatia et al. | |
| 2020/0246489 A1 | 8/2020 | Bhatia et al. | |
| 2020/0249229 A1 | 8/2020 | Bhatia et al. | |
| 2020/0264171 A1 | 8/2020 | Jain et al. | |
| 2021/0253734 A1* | 8/2021 | Lu | G01N 33/6893 |
| 2021/0330218 A1 | 10/2021 | Bowen et al. | |
| 2021/0333283 A1 | 10/2021 | Bowen et al. | |
| 2021/0333286 A1 | 10/2021 | Bowen et al. | |
| 2021/0396762 A1* | 12/2021 | Chee | G01N 33/581 |
| 2022/0090162 A1 | 3/2022 | Bhatia et al. | |
| 2022/0128567 A1* | 4/2022 | Touti | G01N 33/573 |
| 2022/0178935 A1* | 6/2022 | Touti | G01N 33/542 |
| 2022/0290262 A1 | 9/2022 | Apte et al. | |
| 2023/0175037 A1* | 6/2023 | Touti | G01N 33/582 436/172 |
| 2024/0094222 A1* | 3/2024 | Field | G01N 33/6893 |

FOREIGN PATENT DOCUMENTS

| | | | | |
|---|---|---|---|---|
| CN | 106461641 A | * | 2/2017 | A61K 33/24 |
| CN | 111308074 A | | 6/2020 | |
| EP | 1361438 A1 | * | 11/2003 | G01N 33/6848 |
| EP | 3060915 A2 | | 8/2016 | |
| EP | 3121587 A1 | | 1/2017 | |
| EP | 1725572 B1 | * | 5/2017 | C07H 19/06 |
| ES | 2325584 T3 | | 9/2009 | |
| WO | WO-0214867 A2 | | 2/2002 | |
| WO | WO-2004005348 A1 | | 1/2004 | |
| WO | WO-2004113377 A1 | | 12/2004 | |
| WO | WO-2007076129 A2 | | 7/2007 | |
| WO | WO-2008018933 A2 | | 2/2008 | |
| WO | WO-2008127019 A1 | | 10/2008 | |
| WO | WO-2009111470 A2 | | 9/2009 | |
| WO | WO-2010002976 A2 | | 1/2010 | |
| WO | WO-2010019826 A1 | | 2/2010 | |
| WO | WO-2010101628 A2 | | 9/2010 | |
| WO | WO-2011008996 A2 | * | 1/2011 | A61K 47/595 |
| WO | WO-2011040868 A1 | | 4/2011 | |
| WO | WO-2011116088 A2 | | 9/2011 | |
| WO | WO-2012125808 A2 | | 9/2012 | |
| WO | WO-2012178046 A2 | | 12/2012 | |
| WO | WO-2013178581 A1 | | 12/2013 | |
| WO | WO-2014079802 A2 | | 5/2014 | |
| WO | WO-2014197816 A1 | | 12/2014 | |
| WO | WO-2014197840 A1 | | 12/2014 | |
| WO | WO-2015026963 A2 | | 2/2015 | |
| WO | WO-2015148622 A1 | | 10/2015 | |
| WO | WO-2015188182 A1 | | 12/2015 | |
| WO | WO-2016141151 A1 | | 9/2016 | |
| WO | WO-2016151297 A1 | | 9/2016 | |
| WO | WO-2016160131 A1 | | 10/2016 | |
| WO | WO-2017011820 A2 | | 1/2017 | |
| WO | WO-2017139254 A1 | | 8/2017 | |
| WO | WO-2017151912 A1 | | 9/2017 | |
| WO | WO-2017177115 A1 | | 10/2017 | |
| WO | WO-2017180587 A2 | | 10/2017 | |
| WO | WO-2017193070 A1 | | 11/2017 | |
| WO | WO-2017193115 A1 | | 11/2017 | |
| WO | WO-2018064383 A1 | | 4/2018 | |
| WO | WO-2018068135 A1 | | 4/2018 | |
| WO | WO-2019018572 A1 | | 1/2019 | |
| WO | WO-2019075292 A1 | | 4/2019 | |
| WO | WO-2019/237040 A1 | | 12/2019 | |
| WO | WO-2019/237066 A1 | | 12/2019 | |
| WO | WO-2019232037 A1 | | 12/2019 | |
| WO | WO-2019236989 A1 | | 12/2019 | |
| WO | WO-2019236991 A1 | | 12/2019 | |
| WO | WO-2019236992 A1 | | 12/2019 | |
| WO | WO-2019236992 A9 | | 1/2020 | |
| WO | WO-2020157706 A1 | | 8/2020 | |
| WO | WO-2020160227 A1 | | 8/2020 | |
| WO | WO-2020160232 A1 | | 8/2020 | |
| WO | WO-2020160234 A1 | | 8/2020 | |
| WO | WO-2021216968 A1 | | 10/2021 | |
| WO | WO-2021216969 A1 | | 10/2021 | |
| WO | WO-2021216971 A1 | | 10/2021 | |
| WO | WO-2022056313 A2 | | 3/2022 | |
| WO | WO-2022/147138 A1 | | 7/2022 | |
| WO | WO-2023076638 A2 | | 5/2023 | |
| WO | WO-2023076640 A2 | | 5/2023 | |
| WO | WO-2023081235 A2 | | 5/2023 | |
| WO | WO-2023/172648 A2 | | 9/2023 | |
| WO | WO-2023/172654 A2 | | 9/2023 | |
| WO | WO-2023/192417 A2 | | 10/2023 | |

OTHER PUBLICATIONS

Dudani et al. (Sustained-release synthetic biomarkers for monitoring thrombosis and inflammation using point-of-care compatible readouts), Adv Funct Mater. May 3, 2016; 26(17): 2919-2928. (Supplemental Information) (Year: 2016).*

Ortiz-Otin et al. (Emerging roles of proteases in tumour suppression) Nature, vol. 7 pp. 800-808 (Year: 2007).*

Kaminskas et al. (Targeting the lymphatics using dendritic polymers (dendrimers)), Advanced Drug Delivery Reviews 63 (2011) 890-900 (Year: 2011).*

Nov. 7, 2022 Final Office Action U.S. Appl. No. 17/573,110.

May 13, 2022 Non-Final Office Action U.S. Appl. No. 17/573,129.

Jun. 27, 2022 Non-Final Office Action U.S. Appl. No. 17/573,110.

Barchetta, et al. "Circulating dipeptidyl peptidase-4 is independently associated with the presence and severtiy of NAFLD/NASH in individuals with and without obesity and metabolic disease" Journal of Endocrinological Inverstigation (2021) 44: 979-988.

Canal et al., Drug delivery properties of macroporous polystyrene solid foams. J Pharm Pharm Sci. 2012;15(1):197-207. doi: 10.18433/j3x884. PMID: 22365097.

Chi, Qingjia et al. "DNA Nanostructure as an Efficient Drug Delivery Platform for Immunotherapy." Frontiers in pharmacology vol. 10 1585. Jan. 28, 2020, doi:10.3389/fphar.2019.01585.

Dovgan et al. On the use of DNA as a linker in antibody-drug conjugates: synthesis, stability and in vitro potency. Sci Rep 10, 7691 (2020).

Gonzaga et al., Perspectives About Self-Immolative Drug Delivery Systems. J Pharm Sci. Nov. 2020;109(11):3262-3281. doi: 10.1016/j.xphs.2020.08.014. Epub Aug. 27, 2020. PMID: 32860799.

Ho et al., A self-immolative reporter for beta-galactosidase sensing. Chembiochem. Mar. 26, 2007;8(5):560-6. doi: 10.1002/cbic.200600386. PMID: 17300128.

International Search Report and Written Opinion for PCT Application No. PCT/US2017/054105, dated Jan. 18, 2018.

International Search Report and Written Opinion issued in PCT/US2021/049948 on Feb. 28, 2022.

Kalubowilage, et al., "Early detection of pancreatic cancewrs in liquid biopsies by ultrasensitive fluorescence nanobiosensors" Nanomedicine: Nanotechnology, Biology, and Medicine 14 (2018) 1823-1832.

Karan et al., Near-Infrared Fluorescent Probe Activated by Nitroreductase for In Vitro and In Vivo Hypoxic Tumor Detection. J Med Chem. Mar. 25, 2021;64(6):2971-2981. doi: 10.1021/acs.jmedchem.0c02162. Epub Mar. 12, 2021. PMID: 33711229.

Knapp et al., Fluorescent labeling of (oligo)nucleotides by a new fluoride cleavable linker capable of versatile attachment modes. Bioconjug Chem. Jun. 16, 2010;21(6):1043-55. doi: 10.1021/bc900542f. PMID: 20509599.

Knapp et al.: Fluorescent labeling of (oligo)nucleotides by a new fluoride cleavable linker capable of versatile attachment modes. Bioconjug Chem. 21(6):1043-55 (2010).

(56) References Cited

OTHER PUBLICATIONS

Leriche et al., Cleavable linkers in chemical biology. Bioorg Med Chem. Jan. 15, 2012;20(2):571-82. doi: 10.1016/j.bmc.2011.07.048. Epub Jul. 30, 2011. PMID: 21880494.
Li et al., In Situ Imaging of Furin Activity with a Highly Stable Probe by Releasing of Precipitating Fluorochrome. Anal Chem. Oct. 2, 2018;90(19):11680-11687. doi: 10.1021/acs.analchem.8b03335. Epub Sep. 19, 2018. PMID: 30191711.
Liu et al., In Situ Localization of Enzyme Activity in Live Cells by a Molecular Probe Releasing a Precipitating Fluorochrome. Angew Chem Int Ed Engl. Sep. 18, 2017;56(39):11788-11792. doi: 10.1002/anie.201705747. Epub Aug. 15, 2017. PMID: 28755456.
Matheeussen, et al., "Method comparison of dipeptidyl peptidase IV activity assays and their applications in biological samples containing reversible inhibitors" Clinica Chimica Acta 413 (212) 456-462. Olinga (J. Hapatol. 2013 58:1252). (year 2013).
Panchal, Rekha G et al. "Peptide conjugated phosphorodiamidate morpholino oligomers increase survival of mice challenged with Ames Bacillus anthracis." Nucleic acid therapeutics vol. 22,5 (2012): 316-22. doi:10.1089/nat.2012.0362.
S. Hong et al., Protein-Based Nanoparticles as Drug Delivery Systems. Pharmaceutics. Jun. 29, 2020;12(7):604. doi: 10.3390/pharmaceutics12070604. PMID: 32610448; PMCID: PMC7407889.
Shekhawat, S.S. et al., "An autoinhibited coiled-coil design strategy for split-protein protease sensors," J. Am. Chem. Soc., 2009, vol. 131, pp. 15824-15290.
Tung et al., In vivo imaging of beta-galactosidase activity using far red fluorescent switch. Cancer Res. Mar. 1, 2004;64(5):1579-83. doi: 10.1158/0008-5472.can-03-3226. PMID: 14996712.
Udukala, et al. "Early detection of non-small cell lung cancer in liquid biopsies by ultrasensitive protease activity analysis" J Cancer Metastasis Treat (2020); 6;25.
Y. Malam et al., Liposomes and nanoparticles: nanosized vehicles for drug delivery in cancer. Trends Pharmacol Sci. Nov. 2009;30(11):592-9. doi: 10.1016/j.tips.2009.08.004. PMID: 19837467.
Yongchao Liu et al., Precipitated Fluorophore-Based Molecular Probe for In Situ Imaging of Aminopeptidase N in Living Cells and Tumors. Anal Chem. Apr. 27, 2021;93(16):6463-6471. doi: 10.1021/acs.analchem.1c00280. Epub Apr. 14, 2021. PMID: 33852265.
Zhe Li et al., Precipitated Fluorophore-Based Probe for Accurate Detection of Mitochondrial Analytes. Anal Chem. Feb. 2, 2021;93(4):2235-2243. doi: 10.1021/acs.analchem.0c04094. Epub Jan. 5, 2021. PMID: 33400485.
Mar. 10, 2023 Non-Final Office Action US Appl. No. 17/573,123.
Abudayyeh, 2012, Nanoparticle-chaperoned urinary "synthetic biomarkers" for profiling proteases in cancer, MIT Thesis.
Agrawal, R. et al., "Fast algorithms for mining association rules in large databases", Proceedings of the 20th International Conference on Very Large Data Bases (VLDB), 1994, pp. 487-499.
Agrawal, R. et al., "Mining association rules between sets of items in large databases", Proceedings of the 1993 Acm Sigmod International Conference on Management of Data.1993, pp. 207-2016.
Aungier, 2016, The extracellular matrix: a new dimension in disease diagnosis and treatment, Biochemist 38(4): 10-15.
Ben-Hur, A. et al., "Support Vector Clustering, Journal of Machine Learning Research," Journal of Machine Learning Research, 2001, vol. 2, No. 12, pp. 125-137.
Bhalodiya, D. et al., "An Efficient way to Find Frequent Pattern with Dynamic Programming Approach" Nirma University International Conference on Engineering (NUiCONE), 2013, pp. 1-5.
Bonnans, 2014, Remodelling the extracellular matrix in development and disease, Nat Rev Mol cell Biol 15(12):786-801.
Breiman, L. "Random Forests", Machine Learning, 2001, vol. 45, pp. 5-32.
Buss et al., EBio Medicine, 2018, 38:248-256.
Cazanave, S. et al., "Peptide-based urinary monitoring of fibrotic nonalcoholic steatohepatitis by mass-barcoded activity-based sensors," Sci. Transl. Med, Oct. 2021, vol. 13, No. 20, pp. 1-15.

Cazanave, S. et al., "The Transcriptomic Signature Of Disease Development And Progression Of Nonalcoholic Fatty Liver Disease," Sci. Rep., 2017, vol. 7, No. 17193, pp. 1-13.
Charniak, E. "Bayesian Networks without Tears", Al Magazine, 1991, vol. 12, No. 4, pp. 50-63.
Cohen, J.D. et al., "Detection and localization of surgically resectable cancers with a multianalyte blood test," Science, 2018, vol. 359, No. 6378, pp. 926-930.
Deng, Z. et al., "A New Algorithm for Fast Mining Frequent Itemsets Using N-Lists", Science China Information Sciences, 2012, vol. 55, No. 9, pp. 2008-2030.
Deng, Z. et al., "A New Fast Vertical Method for Mining Frequent Patterns", International Journal of Computational Intelligence Systems, 2010, vol. 3, No. 6, pp. 733-737 44.
Deng, Z. et al., "Fast mining frequent itemsets using Nodesets", Expert Systems with Applications, 2014, vol. 41, No. 10, pp. 4505-4512.
Deshpande, 2013, Current trends in the use of liposomes for tumor targeting, Nano med 8(9): 1509-28.
Dudani, 2015, Photoactivated spatiotemporally responsive nanosensors of in vivo protease activity, ACS Nano 9(12):11708-11717.
Dudani, 2018, Classification of prostate cancer using a protease activity nanosensor library, PNAS 115(36):8954-8959.
Dudani, 2018, Harnessing protease activity to improve cancer care, Ann Rev Cell Biol 2:353-76.
Extended European Search Report issued in European Application No. 19814644.1, date of mailing: Feb. 21, 2022, 7 pages.
Extended European Search Report issued in European Application No. 19815722.4, date of mailing: Jun. 15, 2022, 9 pages.
Extended European Search Report issued in European Application No. 19815896.6, date of mailing: Feb. 23, 2022, 8 pages.
Extended European Search Report issued in European Application No. 20748141.7, date of mailing: Jul. 21, 2023, 8 pages.
Extended European Search Report issued in European Application No. 20748142.5, date of mailing: Jul. 4, 2023, 9 pages.
Extended European Search Report issued in European Application No. 20748755.4, date of mailing: Jun. 13, 2024, 7 pages.
Extended European Search Report issued in European Application No. 20749205.9, date of mailing: Jan. 23, 2023, 15 pages.
Extended European Search Report issued in European Application No. 20749564.9, date of mailing: Oct. 25, 2022, 9 pages.
Extended European Search Report issued in European Application No. 21791724.4, date of mailing: Apr. 19, 2024, 7 pages.
Extended European Search Report issued in European Application No. 21792071.9, date of mailing: Apr. 23, 2024, 9 pages.
Extended European Search Report issued in European Application No. 21867712.8, date of mailing: Sep. 10, 2024, 14 pages.
Friedman, 2013, The smart targeting of nanoparticles, Curr Pharm Des 19(35):6315-6329.
Gang, "Cyclic Peptides: Promising Scaffolds for Biopharmaceuticals", Genes, 9:557 (2018).
Gentleman, R.C. et al., "Bioconductor: open software development for computational biology and bioinformatics," Genome Biology, 2004, vol. 5, r80.
Gootenberg et al., "Multiplexed and portable nucleic acid detection platform with Cas13, Cas12a and Csm6," Science. 360(6387):439-444 (2018) (10 pages).
Gootenberg, 2017, Nucleic acid detection with CRISPR-Cas13a/C2c2, Science 356(6336):438-442.
Gural, 2018, Engineered livers for infection diseases, Cell Mol Gastroent Hepat 5(2):131-144.
Haines, B.B. et al., "A quantitative volumetric micro-computed tomography method to analyze lung tumors in genetically engineered mouse models," Neoplasia, 2009, vol. 11, No. 1, pp. 39-47.
Han, J. et al., "Mining Frequent Patterns Without Candidate Generation", Proceedings of the 2000 ACM SIGMOD International Conference on Management of Data, 2000, vol. 29, No. 2, pp. 1-12.
Hann, H.W. et al., "Usefulness of Highly Sensitive AFP-L3 and DCP in Surveillance for Hepatocellular Carcinoma in Patients with a Normal Alpha-Fetoprotein," J Med Microb Diagn, 2014, vol. 3, No. 1, pp. 1-6.
Hardwick, R. N. et al., "Altered UDP-Glucuronosyltransferase and Sulfotransferase Expression and Function during Progressive Stages

(56) References Cited

OTHER PUBLICATIONS of Human Nonalcoholic Fatty Liver Disease," Drug Metabolism and Disposition, 2013, vol. 41, No. 3, pp. 554-561.
Harris, 2008, Protease-triggered unveiling of bioactive nanoparticles, Small 4(9):1307-1312.
Holt, 2018, Nanosensors to detect protease activity in vivo for noninvasive diagnostics, J Vis Exp 137:e57937.
Hovind P et al. (2000). Elevated vascular endothelial growth factor in type 1 diabetic patients with diabetic nephropathy. Kidney Int Suppl; 75: S56-S61. (Year: 2000).
Huber, W. et al., "Orchestrating high-throughput genomic analysis with Bioconductor," Nat Methods, 2015, vol. 12, pp. 115-121.
Hughes, 2017, Dissecting the role of the extracellular matrix in heart disease, Vet Sci 4(24):1-28.
International Search Report and Written Opinion for PCT Application No. PCT/US2019/036039, dated Oct. 24, 2019.
International Search Report and Written Opinion issued in International Application No. PCT/US2020/015828, date of mailing: Jun. 18, 2020, 7 pages.
International Search Report and Written Opinion mailed Sep. 12, 2019, for PCT/US2019/036036, filed Jun. 7, 2019 (9 pages).
International Search Report and Written Opinion mailed Sep. 19, 2019, for PCT/US2019/036041, filed Jun. 7, 2019 (8 pages).
International Preliminary Report on Patentability issued in PCT/US2020/015831, dated Jul. 27, 2021.
International Preliminary Report on Patentability issued in PCT/US2021/028794, dated Oct. 25, 2022.
International Preliminary Report on Patentability issued in PCT/US2021/028795, dated Oct. 25, 2022.
International Search Report and Written Opinion for PCT Application No. PCT/IB2020/050764, dated Aug. 6, 2020.
International Search Report and Written Opinion for PCT Application No. PCT/IB2020/050765, dated Aug. 6, 2020.
International Search Report and Written Opinion for PCT Application No. PCT/US2019/036155, mailed Sep. 4, 2019.
International Search Report and Written Opinion for PCT Application No. PCT/US2020/015823, dated Apr. 28, 2020.
International Search Report and Written Opinion for PCT Application No. PCT/US2020/015831, dated Apr. 30, 2020.
International Search Report and Written Opinion for PCT Application No. PCT/US2021/028794, dated Oct. 6, 2021.
International Search Report and Written Opinion for PCT Application No. PCT/US2021/028795, dated Aug. 10, 2021.
International Search Report and Written Opinion for PCT Application No. PCT/US2021/028797, dated Oct. 28, 2021.
International Search Report and Written Opinion for PCT Application No. PCT/US2022/048299, dated Apr. 25, 2023.
International Search Report and Written Opinion for PCT Application No. PCT/US2022/048302, dated May 5, 2023.
International Search Report and Written Opinion for PCT Application No. PCT/US2022/048743, dated May 11, 2023.
Kappelhoff, 2017, Overview of transcriptomic analysis of all human proteases, non-proteolytic homologs and inhibitors, BBA Mol Cell Res 1864:2210-2219.
Kircher, 2004, A dual fluorochrome probe for imaging proteases, Bioconjugate Chem 15:242-248.
Klingler, 2012, Profiling protease activities with dynamic proteomics workflows, Proteomics 12(4-5):587-596.
Kristensen, 2016, Cell-penetrating peptides as tools to enhance non-injectable delivery of biopharmaceuticals, Tissue Barriers 4(2):e1178369.
Kulkarni et al., PNAS Early Edition, 2016, pp. 1-10 as printed.
Kutlu, 2018, Molecular pathogenesis of nonalcoholic steatohepatitis (NASH) related hepatocellular carcinoma, Can J Gast Hepat 2018:8543763.
Kwon, 2017, Ultrasensitive tumor-penetrating nanosensors of protease activity, Nat Biomed Eng 1: art0054 (10 pages.
Kwong et al., "Mass-encoded synthetic biomarkers for multiplexed urinary monitoring of disease," Nat Biotechnol. 31(1):63-70 (Jan. 2013).
Kwong et al., "Mathematical framework for activity-based cancer biomarkers," Proc Natl Acad Sci USA. 112(41):12627-32 (Oct. 2013).
Larimer, B. et al., "Granzyme B PET imaging as a predictive biomarker of immunotherapy response," Cancer Research, 2017, vol. 77, No. 9, pp. 2318-2327.
Lau, 2018, Therapeutic peptides: Historical perspectives, current developmental trends, and future directions, Bioorganic & Med Chem 26:2700-2707.
Lee, 2018, Implementation of a multiplex and quantitative proteomics platform for assessin protein lysates using DNA-barcoded antibodies, Mol Cell Proteomics 17(6):1245-1258.
Lin, 2009, PEG Hydrogels for the controlled release of biomolecules in regenerative medicine, Pharma Res 26(3):631-643.
Lin, 2013, Nanoparticles that sense thrombin activity as synthetic urinary biomarkers of thrombosis, ACS nano 7(10):9001-9009.
Lin, 2013, The biodegradation of biodegradable polymeric biomaterials, Chapter 11.4.3 in Biomaterials Science 3d Ed., Ratner et al., Eds Academic Press 716-728.
Lo, 2018, IRGD-guided tumor-penetrating nanocomplexes for therapeutic siRNA delivery to pancreatic cancer, Mol Cancer Ther 17(11):2377-2388.
Luther, 2018, Hepatic connexin 32 associates with nonalcoholic fatty liver disease severity, Hepatol Comm 2(7):786-797.
Mallinckrodt, 2003, Assessing and interpreting treatment effects in longitudinal clinical trials with missing data, Biol Psychiatry 53:754-760.
Mason RM et al. (2003) Extracellular matrix metabolism in diabetic nephropathy. J Am Soc Nephrol 14: 1358-1373. (Year: 2003).
Metz, C.E., "Basic principles of ROC analysis," Sem Nuc Med., 1978, vol. 8, No. 4, pp. 283-298.
Milletti, F. "Cell-penetrating peptides: classes, origin, and current landscape," Drug Discovery Today, 2012, vol. 17, No. 15/16, pp. 850-860.
Muggleton, S. et al., "Inductive Logic Programming: Theory and methods", The Journal of Logic Programming, 1994, vol. 19, No. 20, pp. 629-679.
Nguyen, 2011, The prototype HIV-1 maturation inhibitor, bevirimat, binds to the CA-SP1 cleavage site in immature Gag particles, Retrovirology 8:101 (13 pages).
Okazaki et al., "Fibrogenesis and Carcinogenesis in Nonalcoholic Steatohepatitis (NASH): Involvement of Matrix Metalloproteinases (MMPs) and Tissue Inhibitors of Metalloproteinase (TIMPs)," Cancers (Basel). 6(3):1220-55 (Jun. 2014).
Partial European Search Report issued in European Application No. 20749205.9, date of mailing: Sep. 26, 2022, 13 pages.
Patterson et a., "SPARC-derived protease substrates to enhance the plasmin sensitivity of molecularly engineered PEG hydrogels," Biomaterials. 32(5):1301-10 (Feb. 2011).
Perco et al. (2006) Protein biomarkers associated with acute renal failure and chronic kidney disease. European journal of clinical investigation 36.11: 753-763. (Year: 2006).
Qiu et al., PLOS One, vol. 8, e73591; pp. 1-8, published Sep. 16, 2013.
Raagel, 2010, Peptide-mediate protein delivery-which pathways are penetrable?, Biochim et Biophys Acta 1798:2240-2248.
Schuerle et al., "Magnetically Actuated Protease Sensors for in Vivo Tumor Profiling," Nano Lett. 16(10):6303-6310 (Oct. 2016).
Singal, A. et al., "Meta-analysis: surveillance with ultrasound for early-stage hepatocellular carcinoma in patients with cirrhosis," Aliment Pharmacol Ther., 2009, vol. 30, pp. 37-47.
Sjoblom et al. The consensus coding sequences of human breast and colorectal cancers. Science. 2006;314 (5797):268-274.
Song, J. et al., "Prosper: An integrated feature-based tool for predicting protease substrate cleavage sites," PLoSOne, 2012, vol. 7, No. 11, pp. 1-23.
Tarhini et al., Cancer Treatment Reviews, 2018, 71:8-18.
Tascilar, 1999, Role of tumor markers and mutations in cells and pancreatic juice in the diagnosis of pancreatic cancer A\nn One 10(Suppl 4):s107-s110.
Tockman, 1992, Consideratoins in bringing a cancer biomarker to clinical application, Cane Res 52:2711s-2718s.

(56) References Cited

OTHER PUBLICATIONS

Van Lehn, 2011, Penetration of lipid bilayers by nanoparticles with environmentally-responsive surfaces, Soft Matter 7:11392-11404.
Vasiljeva, O. et al., "The multifaceted roles of tumor-associated proteases and harnessing their activity for prodrug activation," Biol Chem., 2019, vol. 400, No. 8, pp. 965-977.
Veronese and Pasut, DDT vol. 10, No. 21, 2005, 1451-1458 (Year: 2005).
Vignozzi et al., Mol. and Cell. Endocrin., vol. 384, pp. 143-154, published Jan. 31, 2014.
Wang, M. et al., "Changes in the Glycosylation of Kininogen and the Development of a Kininogen-Based Algorithm for the Early Detection of HCC," Cancer Epidemiol Biomarkers Prev, 2017, vol. 26, No. 5, pp. 795-803.
Wang, Z. et al., "RNA-Seq: a revolutionary tool for transcriptomics," Nat Rev Genetics, 2009, vol. 10, No. 1, pp. 57-63.
Warren et al., "Disease detection by ultrasensitive quantification of microdosed synthetic urinary biomarkers," J Am Chem Soc. 136(39):13709-14 (Oct. 2014).
Warren et al., "Point-of-care diagnostics for noncommunicable diseases using synthetic urinary biomarkers and paper microfluidics," Proc Natl Acad Sci USA. 111(10):3671-76 (Mar. 2014).
Yu, N. et al., "CT and MRI Improve Detection of Hepatocellular Carcinoma, Compared With Ultrasound Alone, in Patients With Cirrhosis," Clinical Gastroenterology and Hepatology, 2011, vol. 9, pp. 161-167.
Cho et al., "Polycation gene delivery systems: escape from endosomes to cytosol," J Pharm Pharmacol. 55(6):721-34 (Jun. 2003) (14 pages).
Extended European Search Report issued in European Application No. 19815800.8 date of mailing: Apr. 4, 2022, 8 pages.
Glycotest 2017 Investor Presentation.
Glycotest 2018 Press Release.
Harris and Chess, Nature Reviews Drug Discovery, Mar. 2003, vol. 2, 214-221 (Year: 2003) (8 pages).
Hmmier et al., "Proteomic analysis of bronchoalveolar lavage fluid (BALF) from lung cancer patients using label-free mass spectrometry," BBA Clin. 7:97-104 (Mar. 2017) (8 pages).
International Search Report and Written Opinion for PCT/US2019/036119, dated Dec. 12, 2019 (8 pages).
International Search Report and Written Opinion for PCT/US2021/065529, dated Apr. 8, 2022 (9 pages).
International Search Report and Written Opinion for PCT/US2023/014844, dated Oct. 25, 2023 (12 pages).
International Search Report and Written Opinion for PCT/US2023/014851, dated Aug. 10, 2023 (29 pages).
International Search Report and Written Opinion for PCT/US2023/016794, dated Feb. 15, 2024 (13 pages).
Jarosz et al., "Antioxidant and anti-inflammatory effects of zinc. Zinc-dependent NF-? B signaling," Inflammopharmacology. 25(1): 11-24 (Feb. 2017) (14 pages).
Liu et al., "Strategy for successful expression of the Pseudomonas putida nitrile hydratase activator P14K in Escherichia coli," BMC Biotechnol. 13(48) (7 pages) (Jun. 2013).
Mac et al., "Non-invasive early detection of acute transplant rejection via nanosensors of granzyme B activity," Nat Biomed Eng. 3(4):281-291 (Apr. 2019) (25 pages).
Muller PY et al. (2009) Tissue-specific, non-invasive toxicity biomarkers: translation from preclinical safety assessment to clinical safety monitoring. Expert Opinion on Drug Metabolism & Toxicology vol. 5(9): 1023-1038. (Year: 2009) (17 pages).
Reed et al., "Thiol proteinase expression and pathogenicity of Entamoeba histolytica." J Clin Microbiol. 27(12):2772-2777 (Dec. 1989) (6 pages).
Shi, T. et al., "Unsupervised Learning with Random Forest Predictors", Journal of Computational and Graphical Statistics, 2006, vol. 15, No. 1, pp. 118-138 (21 pages).
Svensson et al., "Structural studies on microvillus aminopeptidase from pig small intestine," Eur J Biochem. 126(3):481-8 (Sep. 1982) (8 pages).
Takeguchi-Yorimoto et al., Tox. Lett., vol. 258, pp. 159-169, published 2016.
Zaki, M. J. et al., "Scalable algorithms for association mining", IEEE Transactions on Knowledge and Data Engineering, 2000, vol. 12, No. 3, pp. 372-390 (19 pages).
Visnes et al., "Small-molecule inhibitor of OGG1 suppresses proinflammatory gene expression and inflammation", Science 362(6416): 834-847, (Nov. 2018) (14 pages).
Wallner et al., "Optimization of N-Piperidinyl-Benzimidazolone Derivatives as Potent and Selective Inhibitors of 8-Oxo-Guanine DNA Glycosylase 1" ChemMedChem 18, 2023 (18 pages).
Vrtaric et al., "K2-EDTA and K3-EDTA Greiner Tubes for HbA1c Measurement", Laboratory Medicine 47(1): 39-42, 2015.
Zlobovskaya et al., "Sensors for Caspase Activities", Russian Journal of Bioorganic Chemistry 44(6): 645-652 (2018) (8 pages).
Deng et al., "Gold nanoparticles based molecular beacons for in vitro and in vivo detection of the matriptase expression on tumor", Biosensors and Bioelectronics, 49: 216-221, (Nov. 2013).

* cited by examiner

| Substrate | Proteases |
|---|---|
| Probe#677 | None |
| Probe#102 | Major: CTSD, CTSK, CTSL, CTSS, ELA2, KLK2, KLK14, Trypsin3<br>Minor: ADAM10, ADAM17, CTSB, MMP1 |
| Probe#428 | CTSB, CTSH, CTSK, CTSL, CTSS, KLK1, MMP3, Trypsin3 |
| Probe#460 | Major: ELA2, KLK2, KLK14, CTSD, CTSK, CTSL, CTSS, Trypsin3<br>Minor: ADAM10, CAPN1, MMP13, MMP19, NAPSINA |
| Probe#48 | Major: ADAM10, CTSB, CTSD, CTSK, CTSS, KLK14, MMP13, MMP20, Trypsin3<br>Minor: ADAM17, CTSL, ELA2, MMP1, MMP3, PLAU |
| Probe#480 | CTSB, CTSL, GZMB, KLK14, Trypsin3 |
| Probe#492 | Major: CTSB, CTSS, ELA2, KLK14, Trypsin3<br>Minor: CTSK, CTSL, GzmA, MMP1, MMP3, MMP13, MMP20, PLAU |
| Probe#647 | Major: Caspase 1, Caspase 3, Caspase 5, Caspase 6, Caspase 8, GzmB<br>Minor: Caspase 10 |
| Probe#648 | Major: Caspase 6, KLK14<br>Minor: Caspase 3, Caspase 8, Caspase 10 |
| Probe#1 | Major: KLK14, PLAU, Trypsin3<br>Minor: CTSB |
| Probe#8 | Major: Caspase 3, Caspase 2, CTSB, CTSS<br>Minor: Caspase 7 |
| Probe#9 | Major: Caspase 1, Caspase 3, Caspase 8, CTSB<br>Minor: Caspase 6, Caspase 7, Caspase 10, CTSD, CTSK |
| Probe#12 | Major: Caspase 2, Caspase 3, Caspase 6, Caspase 7, Caspase 8, Caspase 10<br>Minor: CTSB |
| Probe#3 | Major: Caspase 1, Caspase 8, Caspase 10, GzmB<br>Minor: Caspase 5, Caspase 6, Caspase 7, CTSB |
| Probe#30 | Major: CTSB, CTSK, CTSS, MMP1, MMP13<br>Minor: CTSL, MMP14 |
| Probe#92 | Major: KLK6, KLK14, Trypsin3<br>Minor: CTSK |

Fig. 10

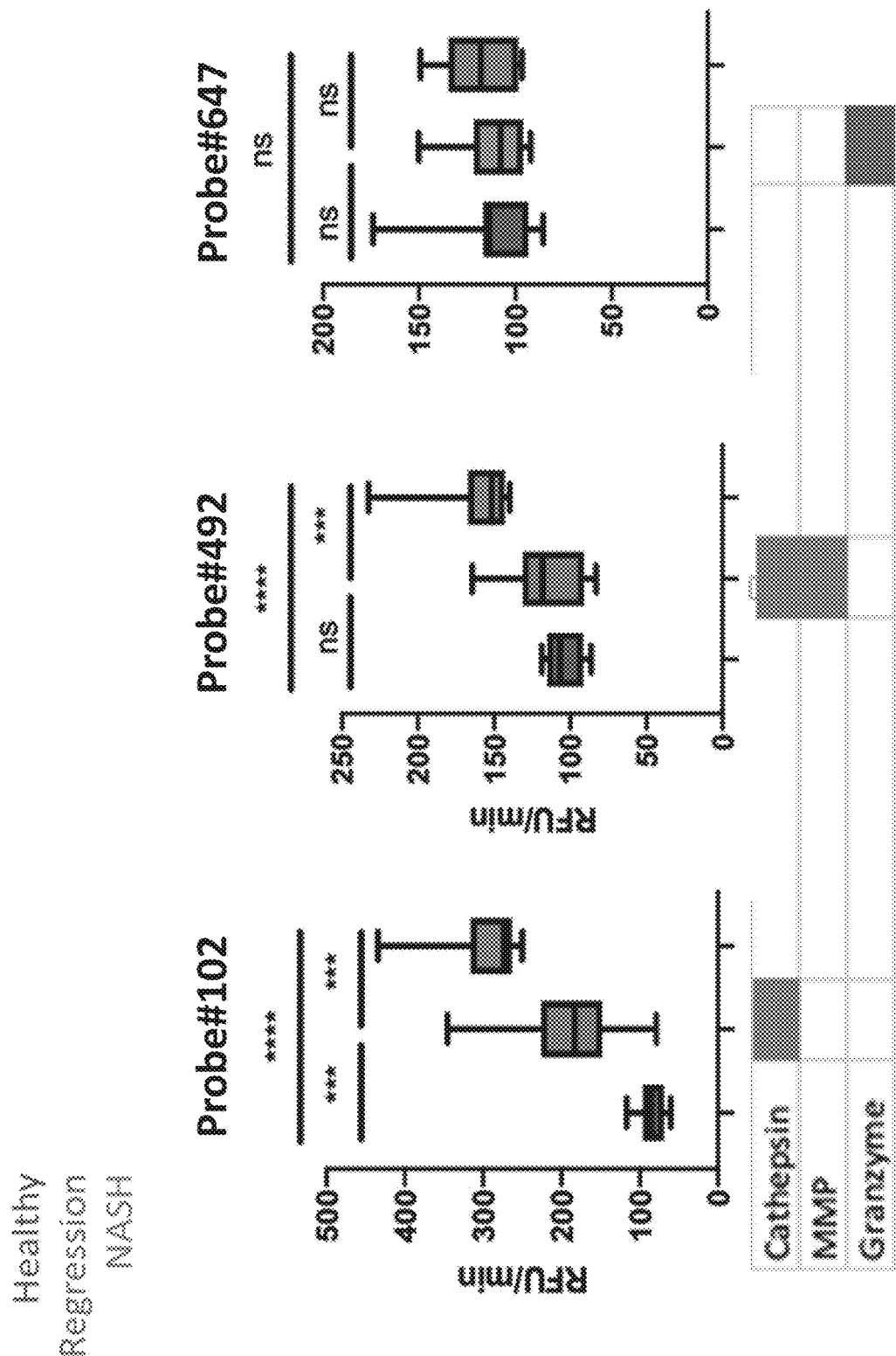

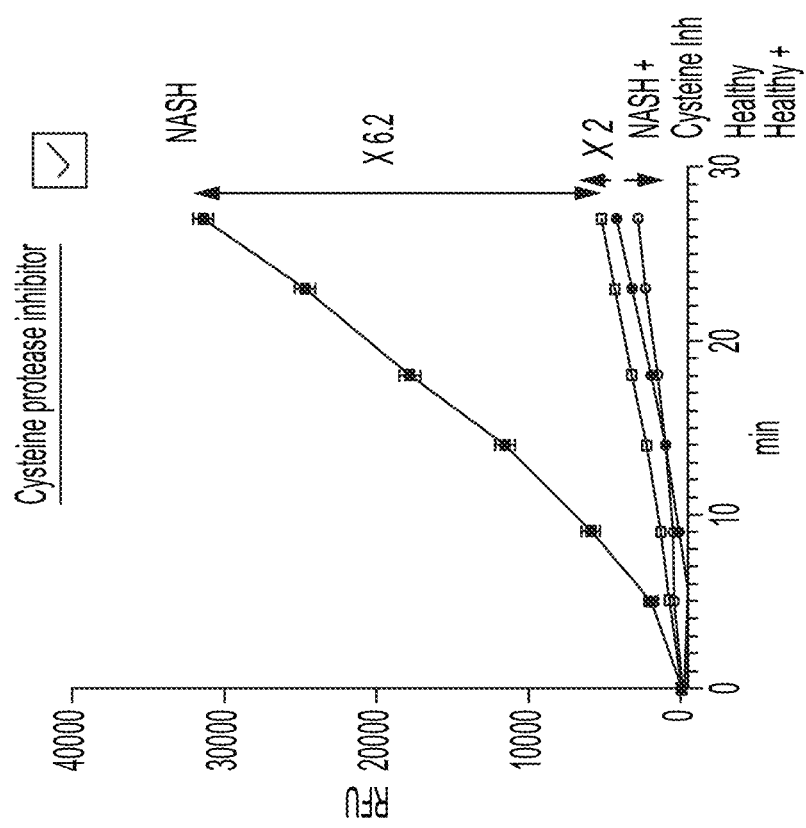
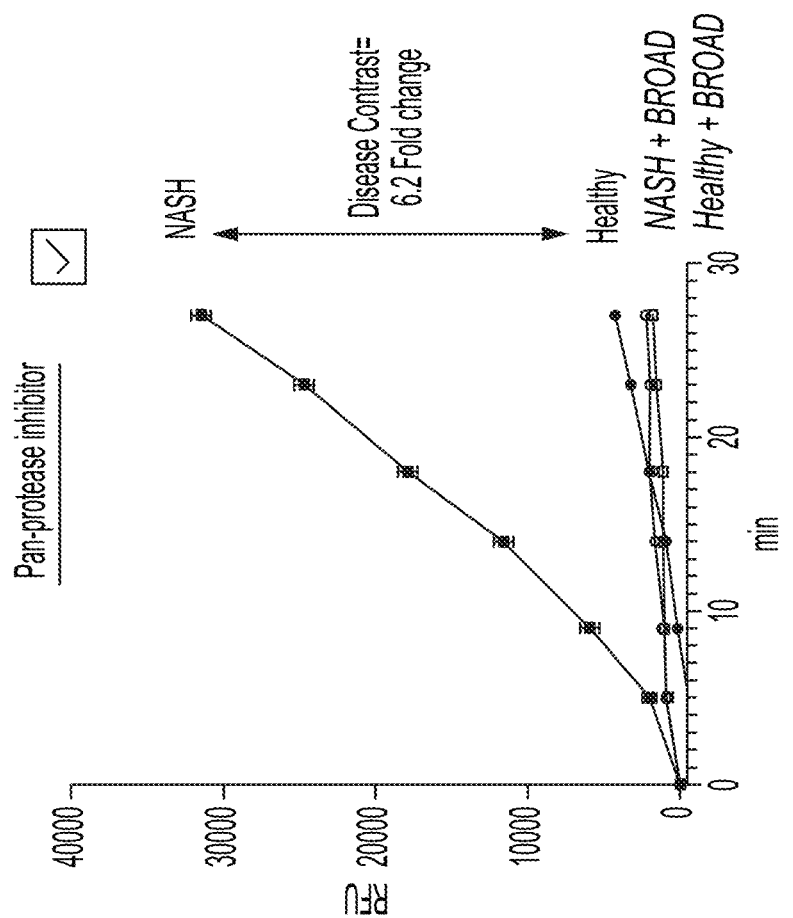
Fig. 30B
Fig. 30A

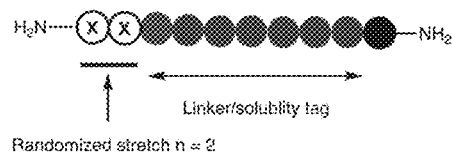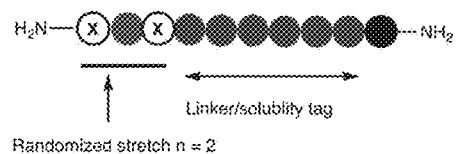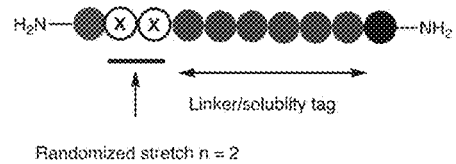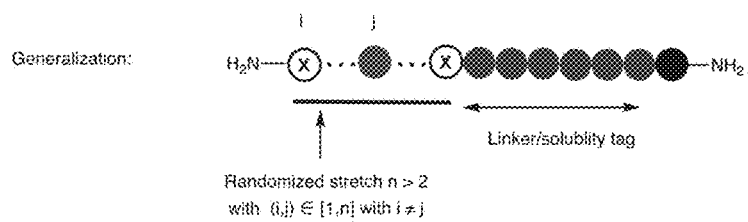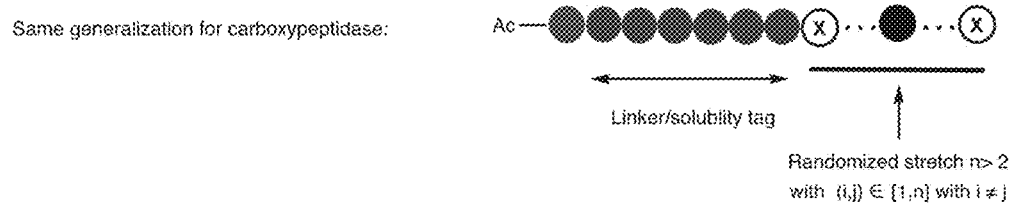
Fig. 46C

EX VIVO PROTEASE ACTIVITY DETECTION FOR DISEASE DETECTION/DIAGNOSTIC, STAGING, MONITORING AND TREATMENT

CROSS REFERENCE

This application is a continuation of U.S. application Ser. No. 17/573,129, filed Jan. 11, 2022 which is a continuation-in-part of International Application No. PCT/US2021/049948, filed on Sep. 10, 2021 which claims the benefit of U.S. Provisional Application No. 63/077,525, filed on Sep. 11, 2020, each of which is entirely incorporated herein by reference for all purposes.

SEQUENCE LISTING

The instant application contains a Sequence Listing which has been submitted electronically in XML format and is hereby incorporated by reference in its entirety. Said XML copy, created on Feb. 24, 2023, is named 61226-702_301_SL.xml and is 1,837,237 bytes in size.

BRIEF SUMMARY

Provided herein is a method comprising contacting a plasma sample from a subject with a molecule ex vivo and detecting a rate of formation or an amount of said released reporter. Further provided herein is a method. Further provided herein is a method wherein said molecule comprises a cleavable linker and a reporter and wherein said cleavable linker is cleaved by an agent from said plasma, releasing said reporter from said molecule.

Further provided herein is a method further comprising introducing an anticoagulant to said plasma sample. Further provided herein is a method wherein said anticoagulant is an EDTA, a citrate, a heparin, an oxalate, any salt, solvate, enantiomer, tautomer and geometric isomer thereof, or any mixtures thereof.

Provided herein is a method comprising contacting a body fluid sample from a subject having a disease or condition with a molecule ex vivo. Further provided herein is a method wherein said molecule comprises a cleavable linker and a reporter and wherein said cleavable linker is cleaved by an agent from said body fluid, releasing said reporter from said molecule. Further provided herein is a method wherein said rate of formation or said amount of said released reporter is significantly different from a healthy subject.

Provided herein is a method comprising contacting a body fluid sample from a subject with a first molecule ex vivo wherein said first molecule comprises a first cleavable linker and a first reporter and wherein said first cleavable linker is cleaved by a first agent from said body fluid, releasing said first reporter from said first molecule. Further provided herein is a method detecting a rate of formation or an amount of said first released reporter. Further provided herein is a method contacting said body fluid sample from said subject with a second molecule ex vivo wherein said second molecule comprises a second cleavable linker and a second reporter, and wherein said second cleavable linker is cleaved by a second agent from said body fluid, releasing said second reporter from said second molecule. Further provided herein is a method detecting a rate of formation or an amount of said second released reporter and determining a disease or condition of subject based on said detection of said first released reporter and said detection of said second released reporter.

Further provided herein is a method wherein said determination comprises a supervised Machine Learning classification algorithm, Logistic Regression, Naive Bayes, Support Vector Machine, Random Forest, Gradient Boosting, Neural Networks, a continuous regression approach, Ridge Regression, Kernel Ridge Regression, Support Vector Regression or any combination thereof.

Provided herein is a method comprising contacting a body fluid sample from a subject with a molecule ex vivo, wherein said molecule comprises a cleavable linker and a reporter and wherein said cleavable linker is cleaved by an agent from said body fluid, releasing said reporter from said molecule. Further provided herein is a method comprising detecting a rate of formation or an amount of said released reporter and determining a disease or condition of said subject based on said detection, wherein said disease or condition is a certain fibrosis stage or a certain nonalcoholic fatty liver disease activity score (NAS) of Non-alcoholic steatohepatitis (NASH).

Provided herein is a method comprising contacting a body fluid sample from a subject with a molecule ex vivo wherein said molecule comprises a cleavable linker and a reporter and wherein said cleavable linker is cleaved by an agent from said body fluid, releasing said reporter from said molecule. Further provided herein is a method detecting a rate of formation or an amount of said released reporter and determining a disease or condition of said subject based on said detection, wherein said disease or condition is selected from the group consisting of a liver disease a cancer, an organ transplant rejection, an infectious disease, an allergic disease, an autoimmunity, an Alzheimer's and a chronic inflammation; wherein said cancer is not pancreatic ductal adenocarcinoma or non-small cell lung cancer.

Further provided herein is a method wherein said liver disease comprises a Non-alcoholic steatohepatitis (NASH), a non-alcoholic fatty liver disease (NAFLD), a toxin mediated liver injury, a viral hepatitis, a fulminant hepatitis, an alcoholic hepatitis, an autoimmune hepatitis, a cirrhosis of the liver, a hepatocellular carcinoma (HCC), a primary biliary cholangitis (PBC), a cholangiocarcinoma, a primary sclerosing cholangitis, an acute or chronic rejection of a transplanted liver, an inherited liver disease or a combination thereof.

Further provided herein is a method wherein said body fluid sample is selected from the group consisting of blood, plasma, bone marrow fluid, lymphatic fluid, bile, amniotic fluid, mucosal fluid, saliva, urine, cerebrospinal fluid, spinal fluid, synovial fluid, semen, ductal aspirate, feces, stool, vaginal effluent, lachrymal fluid, tissue lysate and patient-derived cell line supernatant.

Further provided herein is a method wherein said body fluid sample comprises a rinse fluid, a conditioning media or buffer, a swab viral transport media, a saline, a culture media, or a cell culture supernatant.

Further provided herein is a method wherein said rinse fluid is selected from the group consisting of a mouthwash rinse, a bronchioalveolar rinse, a lavage fluid, a hair wash rinse, a nasal spray effluent, a swab of any bodily surface, orifice, organ structure or solid tumor biopsies applied to saline or any media or any derivatives thereof.

Further provided herein is a method wherein said agent is selected from the group consisting of a oxidoreductase, a transferase, a hydrolase, a lyase, a isomerase, a ligase, a protease (peptidase), a hydrolase, an esterase, a β-glycosidase, a phospholipase and a phosphodiesterase, peroxidase, lipase, amylase a nucleophilic reagent, a reducing reagent, a electrophilic/acidic reagent, an organometallic/metal catalyst, an oxidizing reagent, a hydroxyl ion, a thiols nucleophile, a nitrogen nucleophile, a sodium dithionite and a sodium periodate.

Further provided herein is a method wherein said agent is a protease. Further provided herein is a method wherein said protease is an endopeptidase or an exopeptidase. Further provided herein is a method wherein said protease is selected from the group consisting of an A20 (TNFa-induced protein 3), an abhydrolase domain containing 4, an abhydrolase domain containing 12, an abhydrolase domain containing 12B, an abhydrolase domain containing 13, an acrosin, an acylaminoacyl-peptidase, a disintegrin and metalloproteinase (ADAM), an ADAM1a, an ADAM2 (Fertilin-b), an ADAM3B, an ADAM4, an ADAM4B, an ADAM5, an ADAM6, an ADAM7, an ADAM8, an ADAM9, an ADAM10, an ADAM11, an ADAM12 metalloprotease, an ADAM15, an ADAM17, an ADAM18, an ADAM19, an ADAM20, an ADAM21, an ADAM22, an ADAM23, an ADAM28, an ADAM29, an ADAM30, an ADAM32, an ADAM33, a disintegrin and metalloproteinase with thrombospondin motifs (ADAMTS), an ADAMTS1, an ADAMTS2, an ADAMTS3, an ADAMTS4, an ADAMTS5/11, an ADAMTS6, an ADAMTS7, an ADAMTS8, an ADAMTS9, an ADAMTS10, an ADAMTS12, an ADAMTS13, an ADAMTS14, an ADAMTS15, an ADAMTS16, an ADAMTS17, an ADAMTS18, an ADAMTS19, an ADAMTS20, an adipocyte-enh. binding protein 1, an Afg3-like protein 1, an Afg3-like protein 2, an airway-trypsin-like protease, an aminoacylase, an aminopeptidase A, an aminopeptidase B, an aminopeptidase B-like 1, an aminopeptidase MAMS/L-RAP, an aminopeptidase N, an aminopeptidase O, an aminopeptidase P homologue, an aminopeptidase P1, an aminopeptidase PILS, an aminopeptidase Q, an aminopeptidase-like 1, an AMSH/STAMBP, an AMSH-LP/STAMBPL1, an angiotensin-converting enzyme 1 (ACE1), an angiotensin-converting enzyme 2 (ACE2), an angiotensin-converting enzyme 3 (ACE3), an anionic trypsin (II), an apolipoprotein (a), an archaemetzincin-1, an archaemetzincin-2, an aspartoacylase, an aspartoacylase-3, an aspartyl aminopeptidase, an ataxin-3, an ataxin-3 like, an ATP/GTP binding protein 1, an ATP/GTP binding protein-like 2, an ATP/GTP binding protein-like 3, an ATP/GTP binding protein-like 4, an ATP/GTP binding protein-like 5, an ATP23 peptidase, an autophagin-1, an autophagin-2, an autophagin-3, an autophagin-4, an azurocidin, a beta lactamase, a beta-secretase 1, a beta-secretase 2, a bleomycin hydrolase, a brain serine proteinase 2, a BRCC36 (BRCA2-containing complex, sub 3), a calpain, a calpain 1, a calpain 2, a calpain 3, a calpain 4, a calpain 5, a calpain 6, a calpain 7, a calpain 7-like, a calpain 8, a calpain 9, a calpain 10, a calpain 11, a calpain 12, a calpain 13, a calpain 14, a calpain 15 (Solh protein), a cysteine protease, a carboxypeptidase A1, a carboxypeptidase A2, a carboxypeptidase A3, a carboxypeptidase A4, a carboxypeptidase A5, a carboxypeptidase A6, a carboxypeptidase B, a carboxypeptidase D, a carboxypeptidase E, a carboxypeptidase M, a carboxypeptidase N, a carboxypeptidase O, a carboxypeptidase U, a carboxypeptidase X1, a carboxypeptidase X2, a carboxypeptidase Z, a carnosine dipeptidase 1, a carnosine dipeptidase 2, a caspase recruitment domain family, member 8, a caspase, a caspase-1, a caspase-2, a caspase-3, a caspase-4/11, a caspase-5, a caspase-6, a caspase-7, a caspase-8, a caspase-9, a caspase-10, a caspase-12, a caspase-14, a caspase-14-like, a casper/FLIP, a cathepsin, a cathepsin A (CTSA), a cathepsin B (CTSB), a cathepsin C (CTSC), a cathepsin D (CTSD), a cathepsin E (CTSE), a cathepsin F, a cathepsin G, a cathepsin H (CTSH), a cathepsin K (CTSK), a cathepsin L (CTSL), a cathepsin L2, a cathepsin O, a cathepsin S (CTSS), a cathepsin V (CTSV), a cathepsin W, a cathepsin Z (CTSZ), a cationic trypsin, a cezanne/OTU domain containing 7B, a cezanne-2, a CGI-58, a chymase, a chymopasin, a chymosin, a chymotrypsin B, a chymotrypsin C, a coagulation factor IXa, a coagulation factor VIIa, a coagulation factor Xa, a coagulation factor XIa, a coagulation factor XIIa, a collagenase 1, a collagenase 2, a collagenase 3, a complement protease C1r serine protease, a complement protease C1s serine protease, a complement C1r-homolog, a complement component 2, a complement component C1ra, a complement component C1sa, a complement factor B, a complement factor D, a complement factor D-like, a complement factor I, a COPS6, a corin, a CSN5 (JAB1), a cylindromatosis protein, a cytosol alanyl aminopep.-like 1, a cytosol alanyl aminopeptidase, a DDI-related protease, a DECYSIN, a Der1-like domain family, member 1, a Der1-like domain family, member 2, a Der1-like domain family, member 3, a DESC1 protease, a desert hedgehog protein, a desumoylating isopeptidase 1, a desumoylating isopeptidase 2, a dihydroorotase, a dihydropyrimidinase, a dihydropyrimidinase-related protein 1, a dihydropyrimidinase-related protein 2, a dihydropyrimidinase-related protein 3, a dihydropyrimidinase-related protein 4, a dihydropyrimidinase-related protein 5, a DINE peptidase, a dipeptidyl peptidase (DPP), a dipeptidyl peptidase (DPP1), a dipeptidyl-peptidase 4 (DPP4), a dipeptidyl-peptidase 6 (DPP6), a dipeptidyl-peptidase 8 (DPP8), a dipeptidyl-peptidase 9 (DPP9), a dipeptidyl-peptidase II, a dipeptidyl-peptidase III, a dipeptidyl-peptidase 10 (DPP10), a DJ-1, a DNA-damage inducible protein, a DNA-damage inducible protein 2, a DUB-1, a DUB-2, a DUB2a, a DUB2a-like, a DUB2a-like2, a DUB6, or a combination thereof. Further provided herein is a method wherein said protease is selected from the group consisting of a T cell protease, a complement protease, a fibrosis protease, and an inflammation-related protease.

Further provided herein is a method wherein said cleavable linker is a peptide, a carbohydrate, a nucleic acid, a lipid, an ester, a glycoside, a phospholipid, a phosphodiester, a nucleophile/base sensitive linker, a reduction sensitive linker, an electrophile/acid sensitive linker, a metal cleavable linker, an oxidation sensitive linker or a combination thereof. Further provided herein is a method wherein said cleavable linker is a peptide. Further provided herein is a method wherein said peptide comprises an amino acid sequence selected from the group consisting of SEQ ID Nos: 1-677.

Further provided herein is a method wherein said cleavable linker is directly connected to said reporter through a covalent bond. Further provided herein is a method wherein said reporter comprises a fluorescent label, a mass tag, a chromophore, an electrochemically active molecule, a bio-Layer interferometry or surface plasmon resonance detectable molecule, a precipitating substance, a mass spectrometry and liquid chromatography substrate, a magnetically active molecule, a gel forming and/or viscosity changing molecule, an immunoassay detectable molecule, a cell-based amplification detectable or a nucleic acid barcode, or any combinations thereof. Further provided herein is a method wherein said reporter comprises a fluorescent label. Further provided herein is a method wherein said fluorescent label is selected from a group consisting of a 5-carboxyfluorescein (5-FAM), a 7-amino-4-carbamoylmethylcoumarin (ACC), a 7-Amino-4-methylcoumarin (AMC), a 2-Aminobenzoyl (Abz), a Cy7, a Cy5, a Cy3 and a (5-((2-Aminoethyl)amino)naphthalene-1-sulfonic acid) (EDANS).

Further provided herein is a method wherein said molecule further comprises a fluorescent quencher. Further provided herein is a method wherein said fluorescent quencher is selected from the group consisting of BHQ0, BHQ1, BHQ2, BHQ3, BBQ650, ATTO 540Q, ATTO 580Q, ATTO 612Q, CPQ2, QSY-21, QSY-35, QSY-7, QSY-9, DABCYL (4-([4'-dimethylamino)phenyl]azo)benzoyl), Dnp (2,4-dinitrophenyl) and Eclipse. Further provided herein is a method wherein said fluorescent quencher is directly connected to said cleavable linker through a covalent bond.

Further provided herein is a method wherein said molecule further comprises a carrier. Further provided herein is a method wherein said carrier comprises a native, labeled or synthetic protein, a synthetic chemical polymer of precisely known chemical composition or with a distribution around a mean molecular weight, an oligonucleotide, a phosphorodiamidate morpholino oligomer (PMO), a foldamer, a lipid, a lipid micelle, a nanoparticle, a solid support made of polystyrene, polypropylene or any other type of plastic, or any combination thereof.

Further provided herein is a method wherein said subject is a mammal. Further provided herein is a method wherein said mammal is a human.

Further provided herein is a method wherein said reporter is linked to said cleavable linker through a self-immolative spacer. Further provided herein is a method wherein said self-immolative spacer is selected from the group consisting of a disulfide, a hetheroaminebifuncional disulfide, a thiol-based pirydazinediones, a p-aminebenzyloxycarbonyl, a dipeptide, a Gly-Pro (SEQ ID NO: 530), a L-Phe-Sar, a trans-cyclooctene tetrazine, a ortho Hydroxy-protected Aryl sulfate, a phosphoramidate-based spacer, a hydroxybenzyl, a trimethyl carbamate and a quinone methide-based spacer.

Further provided herein is a method wherein said detection comprises fluorescent detection, spectroscopic detection, mass spectrometry, immunological detection or imaging detection. Further provided herein is a method wherein said detection comprises fluorescent detection. Further provided herein is a method wherein said fluorescent detection is fluorescence resonance energy transfer (FRET).

Further provided herein is a method wherein said cleaved reporter comprises a precipitating fluorophore. Further provided herein is a method wherein said precipitating fluorophore comprises HPQ, Cl-HPQ, HTPQ, HBPQ, or HQPQ.

Provided herein is a method comprising measuring activity of two or more agents in a body fluid sample from a subject and determining a disease or condition of said subject based on said activity wherein said disease or condition is selected from the group consisting of a liver disease, an organ transplant rejection, an infectious disease, an allergic disease, an autoimmunity, an Alzheimer's and a chronic inflammation.

Further provided herein is a method wherein said liver disease comprises a Non-alcoholic steatohepatitis (NASH), a non-alcoholic fatty liver disease (NAFLD), a toxin mediated liver injury, a viral hepatitis, a fulminant hepatitis, an alcoholic hepatitis, an autoimmune hepatitis, a cirrhosis of the liver, a hepatocellular carcinoma (HCC), a primary biliary cholangitis (PBC), a cholangiocarcinoma, a primary sclerosing cholangitis, an acute or chronic rejection of a transplanted liver, an inherited liver disease or a combination thereof.

Provided herein is a method comprising measuring activity of two or more agents in a body fluid sample from a subject and determining a disease or condition of said subject based on said activity wherein said disease or condition is a certain fibrosis stage or a certain nonalcoholic fatty liver disease activity score (NAS) of Non-alcoholic steatohepatitis (NASH).

Further provided herein is a method which further comprises contacting said body fluid sample from said subject with a molecule ex vivo, wherein said molecule comprises a cleavable linker and a reporter and wherein said cleavable linker is cleaved by said protease from said plasma, releasing said reporter from said molecule, and detecting a rate of formation or an amount of said released reporter.

Further provided herein is a method wherein said agent is selected from the group consisting of a oxidoreductase, a transferase, a hydrolase, a lyase, a isomerase, a ligase, a protease (peptidase), a hydrolase, an esterase, a β-glycosidase, a phospholipase and a phosphodiesterase, peroxidase, lipase, amylase a nucleophilic reagent, a reducing reagent, a electrophilic/acidic reagent, an organometallic/metal catalyst, an oxidizing reagent, a hydroxyl ion, a thiols nucleophile, a nitrogen nucleophile, a sodium dithionite and a sodium periodate. Further provided herein is a method wherein said agent is a protease. Further provided herein is a method wherein said protease is an endopeptidase or an exopeptidase. Further provided herein is a method wherein said protease is selected from the group consisting of an A20 (TNFa-induced protein 3), an abhydrolase domain containing 4, an abhydrolase domain containing 12, an abhydrolase domain containing 12B, an abhydrolase domain containing 13, an acrosin, an acylaminoacyl-peptidase, a disintegrin and metalloproteinase (ADAM), an ADAM1a, an ADAM2 (Fertilin-b), an ADAM3B, an ADAM4, an ADAM4B, an ADAM5, an ADAM6, an ADAM7, an ADAM8, an ADAM9, an ADAM10, an ADAM11, an ADAM12 metalloprotease, an ADAM15, an ADAM17, an ADAM18, an ADAM19, an ADAM20, an ADAM21, an ADAM22, an ADAM23, an ADAM28, an ADAM29, an ADAM30, an ADAM32, an ADAM33, a disintegrin and metalloproteinase with thrombospondin motifs (ADAMTS), an ADAMTS1, an ADAMTS2, an ADAMTS3, an ADAMTS4, an ADAMTS5/11, an ADAMTS6, an ADAMTS7, an ADAMTS8, an ADAMTS9, an ADAMTS10, an ADAMTS12, an ADAMTS13, an ADAMTS14, an ADAMTS15, an ADAMTS16, an ADAMTS17, an ADAMTS18, an ADAMTS19, an ADAMTS20, an adipocyte-enh. binding protein 1, an Afg3-like protein 1, an Afg3-like protein 2, an airway-trypsin-like protease, an aminoacylase, an aminopeptidase A, an aminopeptidase B, an aminopeptidase B-like 1, an aminopeptidase MAMS/L-RAP, an aminopeptidase N, an aminopeptidase O, an aminopeptidase P homologue, an aminopeptidase P1, an aminopeptidase PILS, an aminopeptidase Q, an aminopeptidase-like 1, an AMSH/STAMBP, an AMSH-LP/STAMBPL1, an angiotensin-converting enzyme 1 (ACE1), an angiotensin-converting enzyme 2 (ACE2), an angiotensin-converting enzyme 3 (ACE3), an anionic trypsin (II), an apolipoprotein (a), an archaemetzincin-1, an archaemetzincin-2, an aspartoacylase, an aspartoacylase-3, an aspartyl aminopeptidase, an ataxin-3, an ataxin-3 like, an ATP/GTP binding protein 1, an ATP/GTP binding protein-like 2, an ATP/GTP binding protein-like 3, an ATP/GTP binding protein-like 4, an ATP/GTP binding protein-like 5, an ATP23 peptidase, an autophagin-1, an autophagin-2, an autophagin-3, an autophagin-4, an azurocidin, a beta lactamase, a beta-secretase 1, a beta-secretase 2, a bleomycin hydrolase, a brain serine proteinase 2, a BRCC36 (BRCA2-containing complex, sub 3), a calpain, a calpain 1, a calpain 2, a calpain 3, a calpain 4, a calpain 5, a calpain 6, a calpain 7, a calpain 7-like, a calpain 8, a calpain 9, a calpain 10, a calpain 11, a calpain 12, a calpain 13, a calpain 14, a calpain 15 (Solh protein), a cysteine protease, a carboxypeptidase A1, a carboxypeptidase A2, a carboxypeptidase A3, a carboxypeptidase A4, a carboxypeptidase A5, a carboxypeptidase A6, a carboxypeptidase B, a carboxypeptidase D, a carboxypeptidase E, a carboxypeptidase M, a carboxypeptidase N, a carboxypeptidase O, a carboxypeptidase U, a carboxypeptidase X1, a carboxypeptidase X2, a carboxypeptidase Z, a carnosine dipeptidase 1, a carnosine dipeptidase 2, a caspase recruitment domain family, member 8, a caspase, a caspase-1, a caspase-2, a caspase-3, a caspase-4/11, a caspase-5, a caspase-6, a caspase-7, a caspase-8, a caspase-9, a caspase-10, a caspase-12, a caspase-14, a caspase-14-like, a casper/FLIP, a cathepsin, a cathepsin A (CTSA), a cathepsin B (CTSB), a cathepsin C (CTSC), a cathepsin D (CTSD), a cathepsin E (CTSE), a cathepsin F, a cathepsin G, a cathepsin H (CTSH), a cathepsin K (CTSK), a cathepsin L (CTSL), a cathepsin L2, a cathepsin O, a cathepsin S (CTSS), a cathepsin V (CTSV), a cathepsin W, a cathepsin Z (CTSZ), a cationic trypsin, a cezanne/OTU domain containing 7B, a cezanne-2, a CGI-58, a chymase, a chymopasin, a chymosin, a chymotrypsin B, a chymotrypsin C, a coagulation factor IXa, a coagulation factor VIIa, a coagulation factor Xa, a coagulation factor XIa, a coagulation factor XIIa, a collagenase 1, a collagenase 2, a collagenase 3, a complement protease C1r serine protease, a complement protease C1s serine protease, a complement C1r-homolog, a complement component 2, a complement component C1ra, a complement component C1sa, a complement factor B, a complement factor D, a complement factor D-like, a complement factor I, a COPS6, a corin, a CSN5 (JAB1), a cylindromatosis protein, a cytosol alanyl aminopep.-like 1, a cytosol alanyl aminopeptidase, a DDI-related protease, a DECYSIN, a Der1-like domain family, member 1, a Der1-like domain family, member 2, a Der1-like domain family, member 3, a DESC1 protease, a desert hedgehog protein, a desumoylating isopeptidase 1, a desumoylating isopeptidase 2, a dihydroorotase, a dihydropyrimidinase, a dihydropyrimidinase-related protein 1, a dihydropyrimidinase-related protein 2, a dihydropyrimidinase-related protein 3, a dihydropyrimidinase-related protein 4, a dihydropyrimidinase-related protein 5, a DINE peptidase, a dipeptidyl peptidase (DPP), a dipeptidyl peptidase (DPP1), a dipeptidyl-peptidase 4 (DPP4), a dipeptidyl-peptidase 6 (DPP6), a dipeptidyl-peptidase 8 (DPP8), a dipeptidyl-peptidase 9 (DPP9), a dipeptidyl-peptidase II, a dipeptidyl-peptidase III, a dipeptidyl-peptidase 10 (DPP10), a DJ-1, a DNA-damage inducible protein, a DNA-damage inducible protein 2, a DUB-1, a DUB-2, a DUB2a, a DUB2a-like, a DUB2a-like2, a DUB6, or a combination thereof.

Further provided herein is a method wherein said protease is selected from the group consisting of a T cell protease, a complement protease, a fibrosis protease, and an inflammation-related protease. Further provided herein is a method wherein said cleavable linker is a peptide, a carbohydrate, a nucleic acid, a lipid, an ester, a glycoside, a phospholipid, a phosphodiester, a nucleophile/base sensitive linker, a reduction sensitive linker, an electrophile/acid sensitive linker, a metal cleavable linker, an oxidation sensitive linker or a combination thereof. Further provided herein is a method wherein said cleavable linker is a peptide. Further provided herein is a method wherein said peptide comprises an amino acid sequence selected from the group consisting of SEQ ID Nos: 1-677. Further provided herein is a method wherein said cleavable linker is directly connected to said reporter through a covalent bond.

Further provided herein is a method wherein said reporter comprises a fluorescent label, a mass tag, a chromophore, an electrochemically active molecule, a bio-Layer interferometry or surface plasmon resonance detectable molecule, a precipitating substance, a mass spectrometry and liquid chromatography substrate, a magnetically active molecule, a gel forming and/or viscosity changing molecule, an immunoassay detectable molecule, a cell-based amplification detectable or a nucleic acid barcode, or any combinations thereof. Further provided herein is a method wherein said reporter comprises a fluorescent label. Further provided herein is a method wherein said fluorescent label is selected from a group consisting of a 5-carboxyfluorescein (5-FAM), a 7-amino-4-carbamoylmethylcoumarin (ACC), a 7-Amino-4-methylcoumarin (AMC), a 2-Aminobenzoyl (Abz), a Cy7, a Cy5, a Cy3 and a (5-((2-Aminoethyl)amino)naphthalene-1-sulfonic acid) (EDANS).

Further provided herein is a method wherein said molecule further comprises a fluorescent quencher. Further provided herein is a method wherein said fluorescent quencher is selected from the group consisting of BHQ0, BHQ1, BHQ2, BHQ3, BBQ650, ATTO 540Q, ATTO 580Q, ATTO 612Q, CPQ2, QSY-21, QSY-35, QSY-7, QSY-9, DABCYL (4-([4'-dimethylamino)phenyl]azo)benzoyl), Dnp (2,4-dinitrophenyl) and Eclipse. Further provided herein is a method wherein said fluorescent quencher is directly connected to said cleavable linker through a covalent bond.

Further provided herein is a method wherein said molecule further comprises a carrier. Further provided herein is a method wherein said carrier comprises a native, labeled or synthetic protein, a synthetic chemical polymer of precisely known chemical composition or with a distribution around a mean molecular weight, an oligonucleotide, a phosphorodiamidate morpholino oligomer (PMO), a foldamer, a lipid, a lipid micelle, a nanoparticle, a solid support made of polystyrene, polypropylene or any other type of plastic, or any combination thereof.

Further provided herein is a method wherein said subject is a mammal. Further provided herein is a method wherein said mammal is a human.

Further provided herein is a method wherein said reporter is linked to said cleavable linker through a self-immolative spacer. Further provided herein is a method wherein said self-immolative spacer is selected from the group consisting of a disulfide, a hetheroaminebifuncional disulfide, a thiol-based pirydazinediones, a p-aminebenzyloxycarbonyl, a dipeptide, a Gly-Pro (SEQ ID NO: 530), a L-Phe-Sar, a trans-cyclooctene tetrazine, a ortho Hydroxy-protected Aryl sulfate, a phosphoramidate-based spacer, a hydroxybenzyl, a trimethyl carbamate and a quinone methide-based spacer.

Further provided herein is a method wherein said detection comprises fluorescent detection, spectroscopic detection, mass spectrometry, immunological detection or imaging detection. Further provided herein is a method wherein said detection comprises fluorescent detection. Further provided herein is a method wherein said fluorescent detection is fluorescence resonance energy transfer (FRET).

Further provided herein is a method wherein said cleaved reporter comprises a precipitating fluorophore. Further provided herein is a method wherein said precipitating fluorophore comprises HPQ, Cl-HPQ, HTPQ, HBPQ, or HQPQ.

Further provided herein is a method wherein said body fluid sample is selected from the group consisting of blood, plasma, bone marrow fluid, lymphatic fluid, bile, amniotic fluid, mucosal fluid, saliva, urine, cerebrospinal fluid, spinal fluid, synovial fluid, semen, ductal aspirate, feces, stool, vaginal effluent, lachrymal fluid, tissue lysate and patient-derived cell line supernatant. Further provided herein is a method wherein said body fluid sample comprises a rinse fluid, a conditioning media or buffer, a swab viral transport media, a saline, a culture media, or a cell culture supernatant. Further provided herein is a method wherein said rinse fluid is selected from the group consisting of a mouthwash rinse, a bronchioalveolar rinse, a lavage fluid, a hair wash rinse, a nasal spray effluent, a swab of any bodily surface, orifice, organ structure or solid tumor biopsies applied to saline or any media or any derivatives thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings ("FIGURE." or "FIGURES." herein), of which:

FIG. 6A shows that the probe 601 includes a fluorescent reporter 603 and a quencher 605. The probe 601 may also include a spacer 507, a solubility tag 509, and/or a covalent or non-covalent attachment site 511. FIG. 6B shows the cleavage process of two components probe. FIG. 6C shows the cleavage process of three components probe.

FIG. 7A shows a probe 701 with an auto-immolative spacer 705 and precipitating fluorescent reporter 703. The spacer 705 connects the precipitating fluorophore reporter to an exopeptidase substrate 707, which is surrounded by the rectangle for clarity. A specific, predetermined exopeptidase cleaves the exopeptidase substrate 707. As a result, the auto-immolative spacer 705 dissociates from the precipitating fluorophore reporter 703. This allows establishment of a particular hydrogen bond 709 in the reporter 703, such that it enters a solid state, precipitates from the fluid sample, and provides an intense fluorescent signal. FIG. 7B shows de detailed process. FIG. 7C shows the reaction process with both endopeptidase and exopeptidase.

FIG. 10 shows in vivo probes used to detect protease activity.

FIG. 15A shows the results from healthy samples. FIG. 15B shows results from NASH+ samples.

FIG. 19A shows the results of testing for protease abundance levels and FIG. 19B shows the results of testing for protease activity levels.

FIG. 21A-F provide experimental results showing that several probes can differentiate among healthy K2EDTA plasma samples (left), regression samples (center), and NASH samples (right). FIG. 21A shows the results of Probe #428, FIG. 21B shows the results of Probe #520, FIG. 21C shows the results of Probe #96, FIG. 21D shows the results of Probe #102, FIG. 21E shows the results of Probe #492, and FIG. 21F shows the results of Probe #647.

FIG. 30A-F provide experimental results demonstrating the association of specific proteases in the detection of disease-specific activity differences in NASH samples in mice K2EDTA plasma. FIG. 30A shows the results when testing with a pan-protease inhibitor. FIG. 30B shows the results when testing with a cysteine protease family inhibitor. FIG. 30C shows the results when testing with a cathepsin family inhibitor. FIG. 30D shows the results when testing with a CTSB specific inhibitor. FIG. 30E shows the results when testing with a CTSK specific inhibitor. FIG. 30F shows the results when testing with a CTSL specific inhibitor. These results show that this substrate is cleaved by CTSL.

FIG. 31A shows the results of testing with a trypsin specific inhibitor and FIG. 31B shows the results when testing with a thrombin specific inhibitor.

FIG. 32A shows the results of testing pooled samples of healthy and NASH plasma when comparing protease activity.

FIG. 32B shows the quantitation ratio for protease activity between healthy and NASH samples.

FIG. 33A shows the results of testing for CTSL abundance levels and FIG. 33B shows that testing for CTSL activity levels is superior to testing for CTSL abundance.

FIG. 34A shows the results from the K2EDTA plasma cohort while FIG. 34B shows the results from the LiHeparin plasma cohort. Probe #18 is a Neutrophil elastase substrate. Probe #409 is a SARS-COV2 3C protease. Probe #462 is a MMP8 substrate. Probe #84 is a Furin substrate. Probe #26 is a Cathepsin K/B, Trypsin, Thrombin, Tryptase substrate.

FIG. 36A shows the results from saliva samples while FIG. 36B shows the results from swab samples conditioned in VTM (Viral Transport Media containing up to 10% FBS).

FIG. 39A shows the results of inhibition experiments involving Granzyme B while FIG.

39B shows the results of inhibition experiments involving caspases. Differential protease activity is more sensitive to the GzmB specific inhibitor than the caspase inhibitor, implicating GzmB, a hallmark of T-cell activity, in the disease signal detected in swabs.

Figure 40:
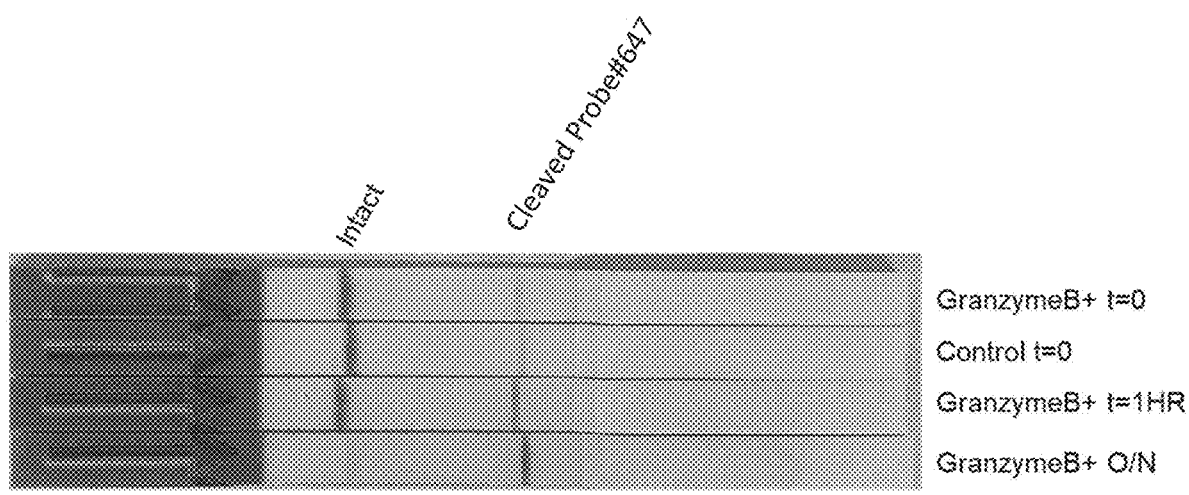

FIG. 40 shows a paper strip test capable of monitoring Granzyme B activity.

Figure 41A:
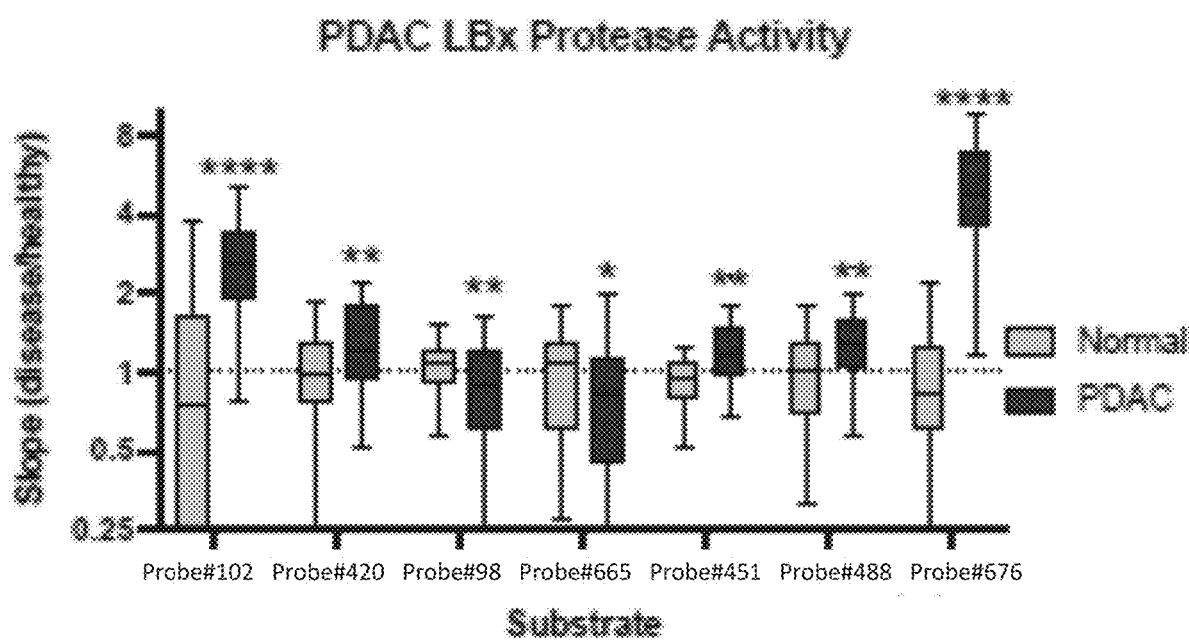
Figure 41B:
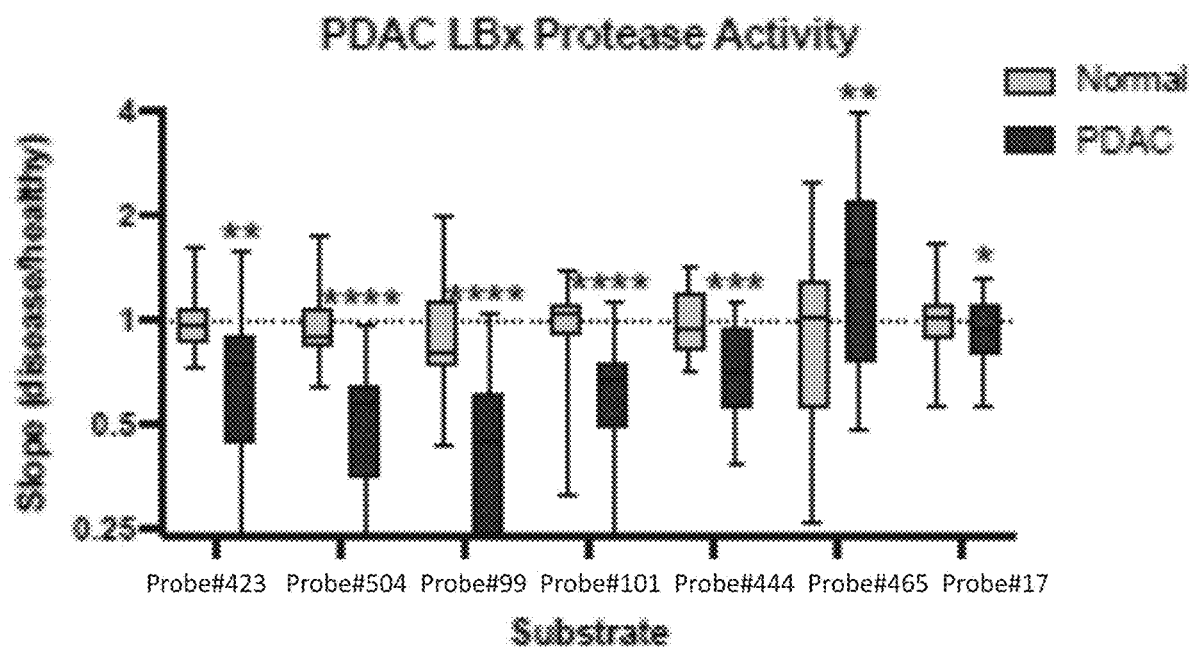

FIG. 41A-B provides experimental evidence showing that the peptide fragments can distinguish between healthy and pancreatic ductal adenocarcinoma (PDAC) samples. FIG. 41A shows the results of first set of experiments, while FIG. 41B shows the results of second set of experiments.

Figure 42:
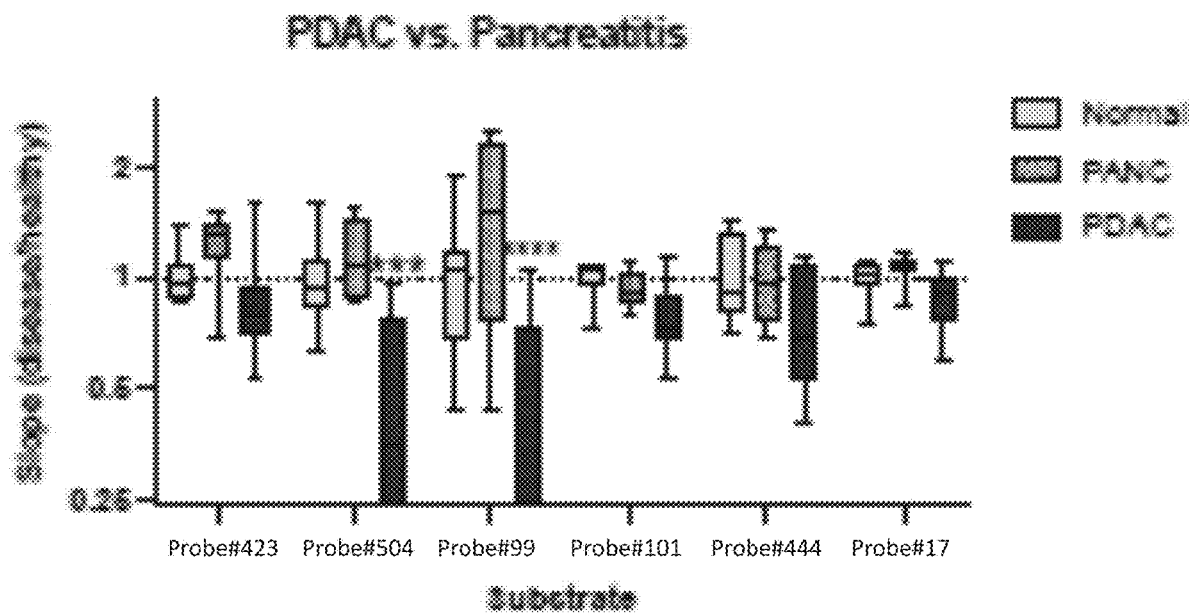

FIG. 42 provides experimental evidence showing that the peptide fragments can distinguish between healthy samples, PDAC samples, and pancreatitis samples.

Figure 43:
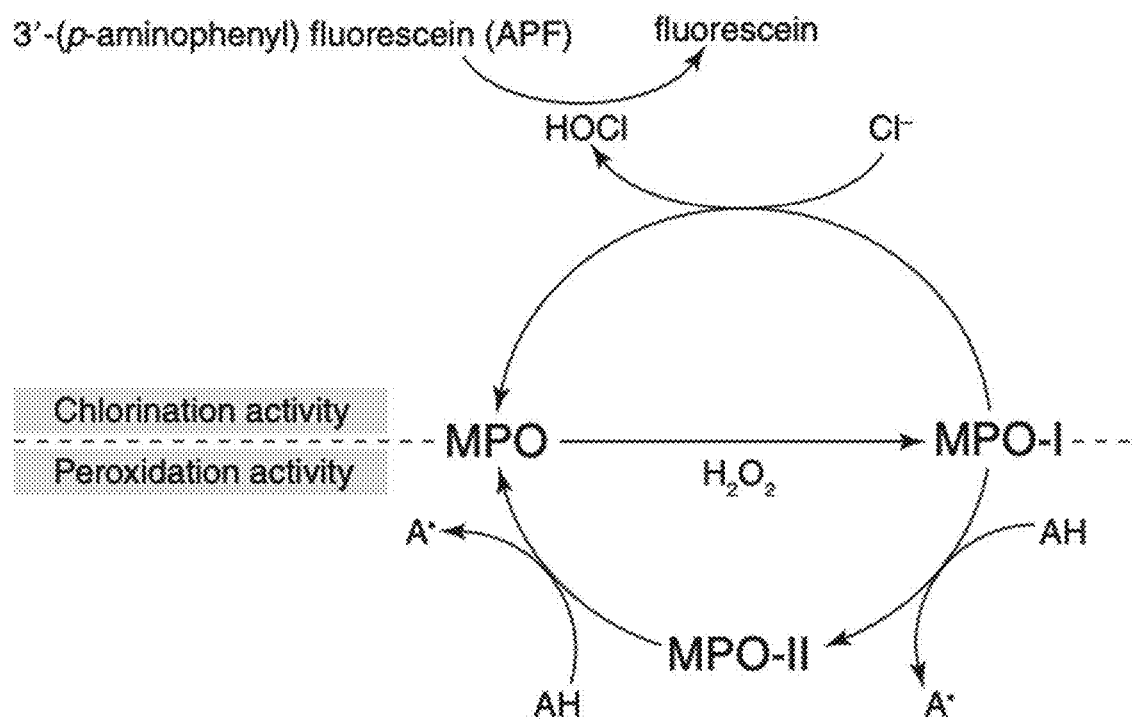

FIG. 43 shows a schematic diagram for detection of Chlorination and peroxidation activity of MPO using the EnzChek® Myeloperoxidase Activity Assay Kit. AH represents the nonfluorescent Amplex® UltraRed substrate, and A represents its fluorescent oxidation product. Hydrogen peroxide converts MPO to MPO-I and MPO is inactive without the presence of hydrogen peroxide. Amplex® UltraRed is then oxidized by MPO-I and creates the fluorescent oxidation product A which can be read at Ex/Em=530/590.

Figure 44A:
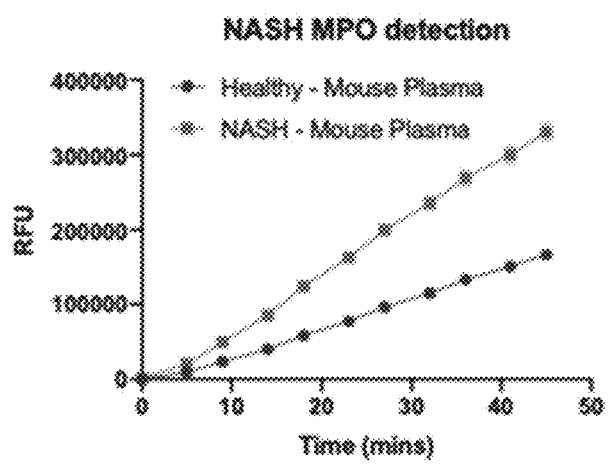
Figure 44B:
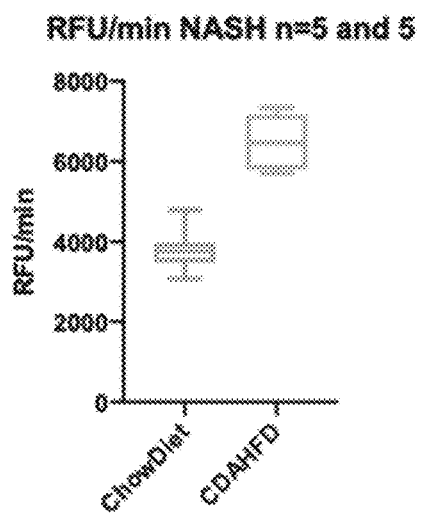
Figure 44C:
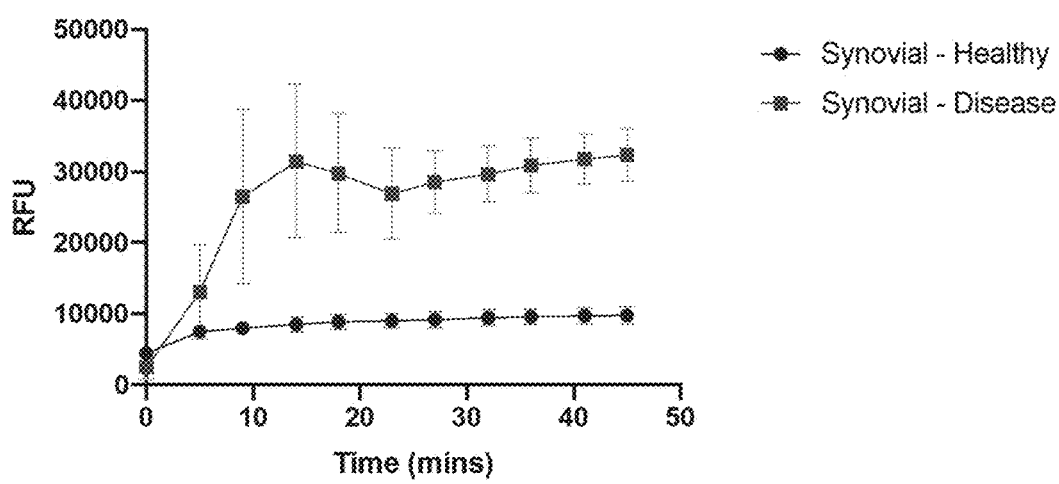

FIG. 44A-C shows the results for detecting peroxidases. FIG. 44A shows that MPO activities are different between healthy mice and mice with NASH. FIG. 44B shows that MPO activities are different between mice fed on a standard ChowDiet (CD), mice feed on a choline-deficient, L-amino acid-defined, high-fat diet (CDAHFD). FIG. 44C shows that MPO activities are different between healthy human subject and subjects with rheumatoid arthritis.

Figure 45A:
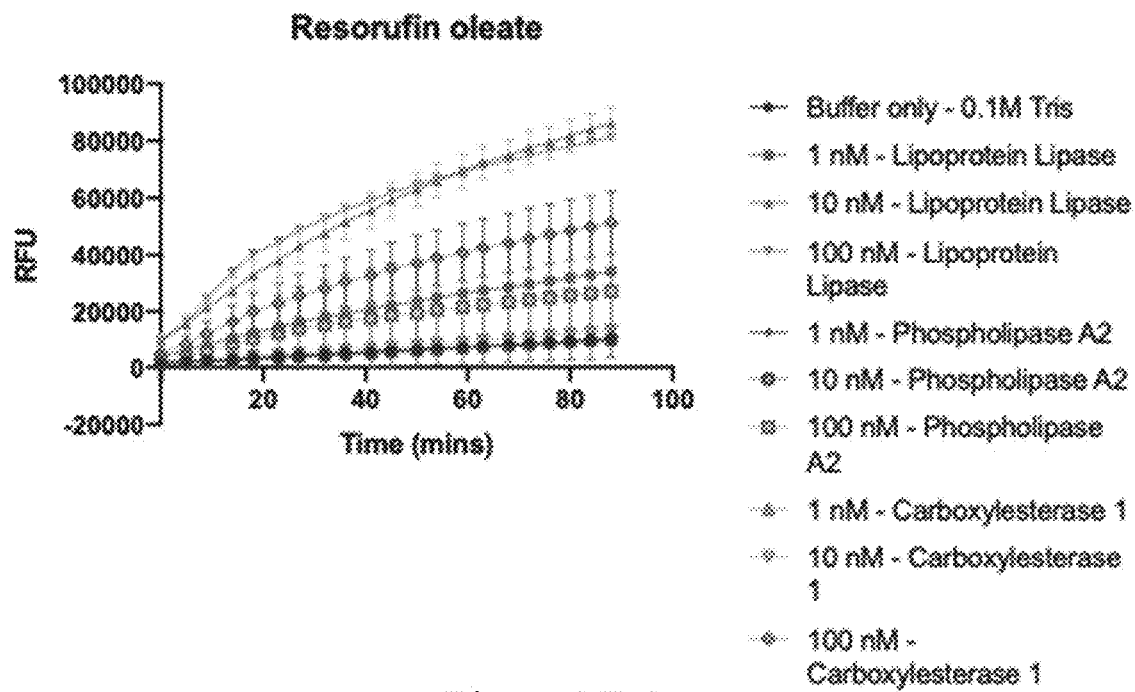
Figure 45B:
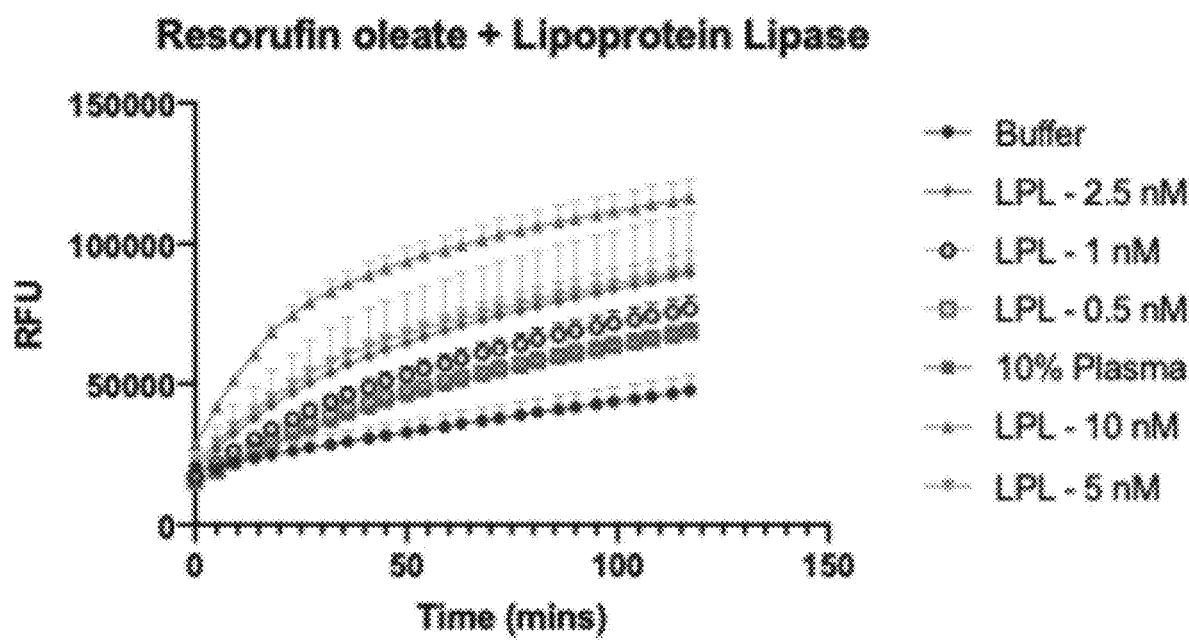
Figure 46A:
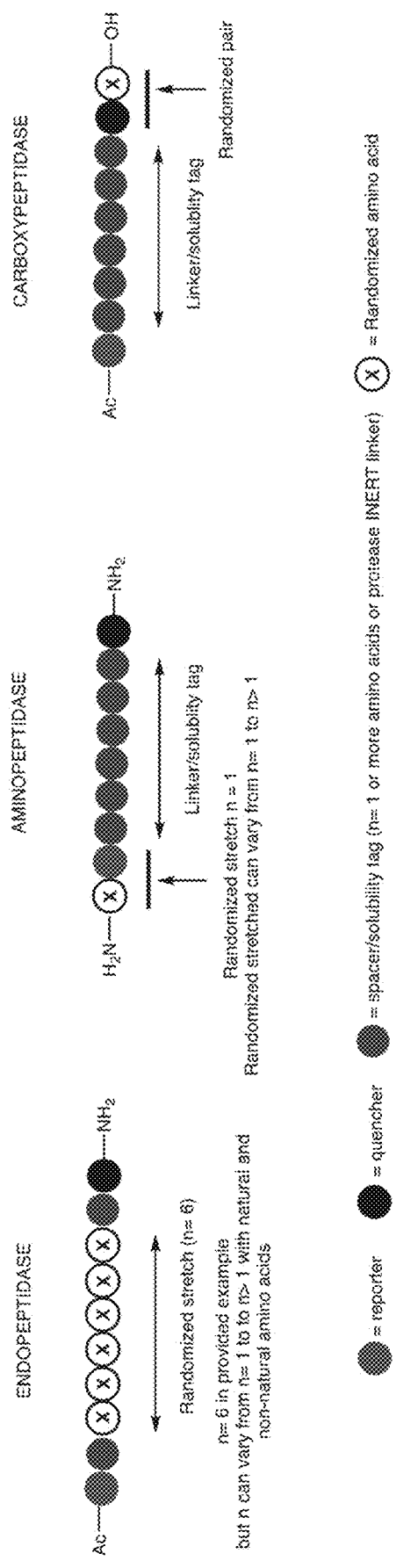
Figure 46B:
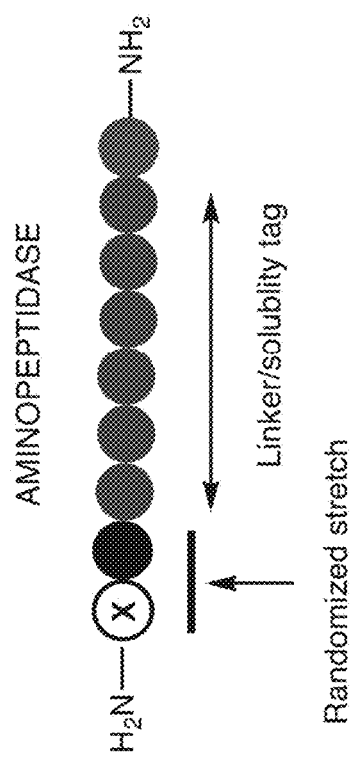

FIG. 45A-B shows the pooled results of spiked recombinant protease in human plasma using resorufin oleate as substrate. FIG. 46A shows result of 3 recombinant enzymes—carboxylesterase 1, phospholipase A2 and lipoprotein lipase. FIG. 46B shows the result of various concentrations of lipoprotein lipase.

FIG. 46A-C shows general designs of the exemplary cleavable linkers for FRET substrates. FIG. 46A shows general designs for endopeptidase, aminopeptidase and carboxypeptidase substrates. FIG. 46B shows an example that reporter and quencher can be inverted. FIG. 46C shows the generalized substrate designs for aminopeptidase and carboxypeptidase.

DETAILED DESCRIPTION

Provided herein are methods comprising contacting a body fluid sample from a subject with a molecule ex vivo. In some embodiments, the molecule comprises a cleavable linker and a reporter, and the cleavable linker is cleaved by an agent from the body fluid, releasing the reporter from the molecule. In some embodiments, the method further comprises detecting a rate of formation or an amount of the released reporter. In some embodiments, the rate of formation or amount of the released report is significantly different from a healthy subject. In some embodiments, the body fluid may be plasma. In some embodiments, the method further comprises determining a disease or condition of the subject based on the detection.

In one aspect, the body fluid sample is contacted by a second molecule with a second cleavable linker and a second reporter. In some embodiments, the second cleavable linker is cleaved by a second agent from the body fluid, releasing the second reporter from the second molecule. In some embodiments, the method further comprises detecting a rate of formation or an amount of the second released reporter. In some embodiments, the method further comprises determining a disease or condition of the subject based on the detection of the first released reporter and the detection of the second released reporter. In some embodiments, the method described herein can be used in a multiplexed format, such that a single body fluid sample can be used to ascertain the activity of multiple, select agents. This allows diagnostic panels to be created for specific pathologies and conditions, which leverage the activity of multiple agents to provide a more complete and accurate assessment of a certain condition. These panels can be used to correlate the activity of multiple agents with a particular condition or disease-state. These signatures can be saved, for example, in a database and used to assess the conditions or disease-state for subsequent individuals assessed by a particular protease activity panel. In some embodiments, a classification tool is used in the analysis to differentiate between healthy and diseased patients, or between discrete stages of disease. The classification tool may be supervised Machine Learning classification algorithms including but not limited to Logistic Regression, Naive Bayes, Support Vector Machine, Random Forest, Gradient Boosting or Neural Networks. Furthermore, if the modeled variable is continuous in nature (e.g. tumor volume), one could use continuous regression approaches such as Ridge Regression, Kernel Ridge Regression, or Support Vector Regression. These algorithms would operate on the multi-dimensional feature space defined by the measurements of multiple probes (or a mathematical function of those measurements such as probe ratios) in order to learn the relationship between probe measurements and disease status. Finally, one could combine probe measurements with clinical variables such as age, gender, or patients' comorbid status. In that case, one could either incorporate clinical features in the classifier directly or, alternatively, learn a second-order classifier which combines a probe-only prediction with clinical features to produce a result that is calibrated for those variables.

In some embodiments, the disease or condition may be a certain fibrosis stage or a certain nonalcoholic fatty liver disease activity score (NAS) of Non-alcoholic steatohepatitis (NASH). In some embodiments, the disease or condition may be a liver disease, a cancer, an organ transplant rejection, an infectious disease, an allergic disease, an autoimmunity and a chronic inflammation.

In another aspect, the methods described herein comprises ex vivo, multiplex detection of enzyme activity to diagnose and monitor pathologies and treatments in a subject. This enzyme activity can be used to diagnose and monitor a disease and condition in an internal organ of the subject.

Detection Probe/Molecule

Determination of the disease or condition is based on the rate of formation or amount of the released reporter detected in the sample. A probe/molecule is introduced to the body fluid samples. The probe/molecule comprises a cleavable linker and a reporter, and an agent of from the body fluid cleave the cleavable linker, releasing a cleaved reporter. The probe/molecule may have any structure that can fulfill this function. In some embodiments, the reporter may be covalently linked to a cleavable linker. In some embodiments, the reporter may be a fluorescent label, a mass tag, a chromophore, an electrochemically active molecule, a bio-Layer interferometry or surface plasmon resonance detectable molecule, a precipitating substance, a mass spectrometry and liquid chromatography substrate (including size exclusion, reverse phase, isoelectric point, etc.), a magnetically active molecule, a gel forming and/or viscosity changing molecule, an immunoassay detectable molecule, a cell-based amplification detectable molecule, a nucleic acid barcode, or any combinations thereof.

In some embodiments, the reporter may be a fluorescent label and the molecule also comprises a quencher. In some embodiments, the quencher is covalently linked to the cleavable linker. In some embodiments an internally quenched fluorophore is linked to the cleavable linker. In some embodiments, the molecule further comprises a self-immolative spacer. In some other embodiments, the molecule further comprises a carrier.

Cleavable Linker

In some aspects, the probe/molecule described herein comprises a cleavable linker. The cleavable linker as described herein may be in any structure that is capable of being cleaved by an agent. In some embodiments, the cleavable linker may be a peptide, a carbohydrate, a nucleic acid, a lipid, an ester, a glycoside, a phospholipid, a phosphodiester, a nucleophile/base sensitive linker, a reduction sensitive linker, an electrophile/acid sensitive linker, a metal cleavable linker, an oxidation sensitive linker, an auto-immolable linker (three component probe=enzyme substrate+linker+reporter) or a combination thereof. In some embodiments, the reporter can be in an inactive form and under disease activity becomes detectable. Geoffray Leriche, Louise Chisholm, Alain Wagner, Cleavable linkers in chemical biology, Bioorganic & Medicinal Chemistry, Volume 20, Issue 2, 2012, Pages 571-582, ISSN 0968-0896, https://doi.org/10.1016/j.bmc.2011.07.048.

Cross-linking agents aim to form a covalent bond between two spatially adjacent residues within one or two polymer chains. To identify protein binding partners, the cross-linking agents need to be able to detect and stabilize transient interactions. The crosslinking agents frequently form covalent links between lysine or cysteine residues in the proteins. Alternatively, the cross-linking agent can be photoreactive. Cross-linking cleavable linkers can be used to distinguish between inter- and intra-protein interactions of receptors, signaling cascades, and the structure of multi-protein complexes.

In some embodiments, the cleavable linker may be a peptide. The core structure of a peptide linker sometimes comprises of either a di-peptide or a tetra-peptide that is recognized and cleaved by lysosomal enzymes. Proteases (also called peptidases) catalyze the breakdown of peptide bonds by hydrolysis, and is restricted to a specific sequence of amino acids recognizable by the proteases. Commonly used proteases comprise pepsin, trypsin or chymotrypsin. Since proteases have key roles in many diseases, peptide linkers are widely used in drug release systems or in diagnostic tools. In some embodiments, the peptide linkers comprise a short peptide sequence. In some embodiments, the peptide linkers may include at least one non-naturally occurring amino acid.

In some embodiments, the peptide linkers may be less than about 20 amino acids in length. In some embodiments, the peptide linkers may be between 10 and 100 amino acids in length. In some embodiments, the peptide linkers may be 1 to 5, 1 to 10, 1 to 20, 1 to 30, 1 to 50, 1 to 70, 1 to 90, 1 to 100, 5 to 10, 5 to 20, 5 to 30, 5 to 50, 5 to 70, 5 to 90, 5 to 100, 10 to 20, 10 to 30, 10 to 50, 10 to 70, 10 to 90, 10 to 100, 20 to 30, 20 to 50, 20 to 70, 20 to 90, 20 to 100, 30 to 50, 30 to 70, 30 to 90, 30 to 100, 50 to 70, 50 to 90, 50 to 100, 70 to 90, 70 to 100, or 90 to 100 amino acids in length.

TABLE 1

Exemplary sequences for peptide linkers and corresponding probe construct designs

| SEQ ID NO | Sequence | Exemplary probe name | Exemplary probe construct | SEQ ID NOS |
|---|---|---|---|---|
| 1 | SGRSG | Probe #1 | 5-FAM-GSGRSGGK(CPQ2)-PEG2-kk-GC | 678 & 1363 |
| 2 | PGPREG | Probe #2 | 5-FAM-GPGPREGGK(CPQ2)-PEG2-kk-GC | 679 & 1363 |
| 3 | IEPDSGSQ | Probe #3 | 5-FAM-GIEPDSGSQGK(CPQ2)-PEG2-kk-GC | 680 & 1363 |
| 4 | VVADSSMES | Probe #4 | 5-FAM-GVVADSSMESGK(CPQ2)-PEG2-kk-GC | 681 & 1363 |
| 5 | PTSY | Probe #5 | 5-FAM-GPTSYGK(CPQ2)-PEG2-kk-GC | 682 & 1363 |
| 6 | YRFK | Probe #6 | 5-FAM-GYRFKGK(CPQ2)-PEG2-kk-GC | 683 & 1363 |
| 7 | KVPL | Probe #7 | 5-FAM-GKVPLGK(CPQ2)-PEG2-kk-GC | 684 & 1363 |
| 8 | VDVAD | Probe #8 | 5-FAM-GVDVADGK(CPQ2)-PEG2-kk-GC | 685 & 1363 |
| 9 | LETD | Probe #9 | 5-FAM-GLETDGK(CPQ2)-PEG2-kk-GC | 686 & 1363 |
| 10 | LEHD | Probe #10 | 5-FAM-GLEHDGK(CPQ2)-PEG2-kk-GC | 687 & 1363 |
| 11 | REQD | Probe #11 | 5-FAM-GREQDGK(CPQ2)-PEG2-kk-GC | 688 & 1363 |

TABLE 1-continued

Exemplary sequences for peptide linkers and corresponding probe construct designs

| SEQ ID NO | Sequence | Exemplary probe name | Exemplary probe construct | SEQ ID NOS |
|---|---|---|---|---|
| 12 | DEVD | Probe #12 | 5-FAM-GDEVDGK(CPQ2)-PEG2-kk-GC | 689 & 1363 |
| 13 | VEID | Probe #13 | 5-FAM-GVEIDGK(CPQ2)-PEG2-kk-GC | 690 & 1363 |
| 14 | VQVDGW | Probe #14 | 5-FAM-GVQVDGWGK(CPQ2)-PEG2-kk-GC | 691 & 1363 |
| 15 | YEVDGW | Probe #15 | 5-FAM-GYEVDGWGK(CPQ2)-PEG2-kk-GC | 692 & 1363 |
| 16 | LEVD | Probe #16 | 5-FAM-GLEVDGK(CPQ2)-PEG2-kk-GC | 693 & 1363 |
| 17 | IEVE | Probe #17 | 5-FAM-GIEVEGK(CPQ2)-PEG2-kk-GC | 694 & 1363 |
| 18 | AAPV | Probe #18 | 5-FAM-GAAPVGK(CPQ2)-PEG2-kk-GC | 695 & 1363 |
| 19 | FFKF | Probe #19 | 5-FAM-GFFKFGK(CPQ2)-PEG2-kk-GC | 696 & 1363 |
| 20 | GRRGKGG | Probe #20 | 5-FAM-GGRRGKGGGK(CPQ2)-PEG2-kk-GC | 697 & 1363 |
| 21 | VKKR | Probe #21 | 5-FAM-GVKKRGK(CPQ2)-PEG2-kk-GC | 698 & 1363 |
| 22 | FAAF(NO2)FVL | Probe #22 | 5-FAM-GFAAF(NO2)FVLGK(CPQ2)-PEG2-kk-GC | 699 & 1363 |
|  | VVR | Probe #23 | 5-FAM-GVVRGK(CPQ2)-PEG2-kk-GC | 700 & 1363 |
| 24 | KQKLR | Probe #24 | 5-FAM-GKQKLRGK(CPQ2)-PEG2-kk-GC | 701 & 1363 |
| 25 | RPPGFSAF | Probe #25 | 5-FAM-GRPPGFSAFGK(CPQ2)-PEG2-kk-GC | 702 & 1363 |
|  | GPR | Probe #26 | 5-FAM-GGPRGK(CPQ2)-PEG2-kk-GC | 703 & 1363 |
|  | FR | Probe #27 | 5-FAM-GFRGK(CPQ2)-PEG2-kk-GC | 704 & 1363 |
| 28 | LPLGL | Probe #28 | 5-FAM-GLPLGLGK(CPQ2)-PEG2-kk-GC | 705 & 1363 |
| 29 | KPLGL | Probe #29 | 5-FAM-GKPLGLGK(CPQ2)-PEG2-kk-GC | 706 & 1363 |
| 30 | (Gaba)PQGLE | Probe #30 | 5-FAM-G(Gaba)PQGLEGK(CPQ2)-PEG2-kk-GC | 707 & 1363 |
| 31 | PKPLAL | Probe #31 | 5-FAM-GPKPLALGK(CPQ2)-PEG2-kk-GC | 708 & 1363 |
| 32 | GPSGIHV | Probe #32 | 5-FAM-GGPSGIHVGK(CPQ2)-PEG2-kk-GC | 709 & 1363 |
| 33 | WAHRTTFYRRGA | Probe #33 | 5-FAM-GWAHRTTFYRRGAGK(CPQ2)-PEG2-kk-GC | 710 & 1363 |
| 34 | WKLRSSKQ | Probe #34 | 5-FAM-GWKLRSSKQGK(CPQ2)-PEG2-kk-GC | 711 & 1363 |
|  | PFR | Probe #35 | 5-FAM-GPFRGK(CPQ2)-PEG2-kk-GC | 712 & 1363 |

TABLE 1-continued

Exemplary sequences for peptide linkers and corresponding probe construct designs

| SEQ ID NO | Sequence | Exemplary probe name | Exemplary probe construct | SEQ ID NOS |
|---|---|---|---|---|
| 36 | SYRIF | Probe #36 | 5-FAM-GSYRIFGK(CPQ2)-PEG2-kk-GC | 713 & 1363 |
|  | RPY | Probe #37 | 5-FAM-GRPYGK(CPQ2)-PEG2-kk-GC | 714 & 1363 |
| 38 | TAFRSAYG | Probe #38 | 5-FAM-GTAFRSAYGGK(CPQ2)-PEG2-kk-GC | 715 & 1363 |
| 39 | WAAFRFSQA | Probe #39 | 5-FAM-GWAAFRFSQAGK(CPQ2)-PEG2-kk-GC | 716 & 1363 |
|  | VPR | Probe #40 | 5-FAM-GVPRGK(CPQ2)-PEG2-kk-GC | 717 & 1363 |
|  | G | Probe #41 | 5-FAM-GGK(CPQ2)-PEG2-kk-GC | 1363 |
| 42 | KLRSSKQ | Probe #42 | 5-FAM-GKLRSSKQGK(CPQ2)-PEG2-kk-GC | 719 & 1363 |
| 43 | YASR | Probe #43 | 5-FAM-GYASRGK(CPQ2)-PEG2-kk-GC | 720 & 1363 |
| 44 | RFAQAQQQLP | Probe #44 | 5-FAM-GRFAQAQQQLPGK(CPQ2)-PEG2-kk-GC | 721 & 1363 |
| 45 | KPAKFFRL | Probe #45 | 5-FAM-GKPAKFFRLGK(CPQ2)-PEG2-kk-GC | 722 & 1363 |
| 46 | PRAAA(hF)TSP | Probe #46 | 5-FAM-GPRAAA(hF)TSPGK(CPQ2)-PEG2-kk-GC | 723 & 1363 |
| 47 | VGPQRFSGAP | Probe #47 | 5-FAM-GVGPQRFSGAPGK(CPQ2)-PEG2-kk-GC | 724 & 1363 |
| 48 | FFLAQA(hF)RS | Probe #48 | 5-FAM-GFFLAQA(hF)RSGK(CPQ2)-PEG2-kk-GC | 725 & 1363 |
| 49 | PLAQAV | Probe #49 | 5-FAM-GPLAQAVGK(CPQ2)-PEG2-kk-GC | 726 & 1363 |
| 50 | RTAAVFRP | Probe #50 | 5-FAM-GRTAAVFRPGK(CPQ2)-PEG2-kk-GC | 727 & 1363 |
| 51 | DVQEFRGVTAVIR | Probe #51 | 5-FAM-GDVQEFRGVTAVIRGK(CPQ2)-PEG2-kk-GC | 728 & 1363 |
| 52 | TEGEARGSVI | Probe #52 | 5-FAM-GTEGEARGSVIGK(CPQ2)-PEG2-kk-GC | 729 & 1363 |
|  | l-TR | Probe #53 | 5-FAM-G-l-TRGK(CPQ2)-PEG2-kk-GC | 730 & 1363 |
| 54 | PLFAERK | Probe #54 | 5-FAM-GPLFAERKGK(CPQ2)-PEG2-kk-GC | 731 & 1363 |
| 55 | LLVY | Probe #55 | 5-FAM-GLLVYGK(CPQ2)-PEG2-kk-GC | 732 & 1363 |
| 56 | QQKRKIVL | Probe #56 | 5-FAM-GQQKRKIVLGK(CPQ2)-PEG2-kk-GC | 733 & 1363 |
| 57 | ASHLGLAR | Probe #57 | 5-FAM-GASHLGLARGK(CPQ2)-PEG2-kk-GC | 734 & 1363 |
| 58 | LPSRSSKI | Probe #58 | 5-FAM-GLPSRSSKIGK(CPQ2)-PEG2-kk-GC | 735 & 1363 |
| 59 | STGRNGFK | Probe #59 | 5-FAM-GSTGRNGFKGK(CPQ2)-PEG2-kk-GC | 736 & 1363 |
| 60 | SLLRSEET | Probe #60 | 5-FAM-GSLLRSEETGK(CPQ2)-PEG2-kk-GC | 737 & 1363 |

TABLE 1-continued

Exemplary sequences for peptide linkers and corresponding probe construct designs

| SEQ ID NO | Sequence | Exemplary probe name | Exemplary probe construct | SEQ ID NOS |
|---|---|---|---|---|
| 61 | HRGRTLEI | Probe #61 | 5-FAM-GHRGRTLEIGK(CPQ2)-PEG2-kk-GC | 738 & 1363 |
| 62 | YLGRSYKV | Probe #62 | 5-FAM-GYLGRSYKVGK(CPQ2)-PEG2-kk-GC | 739 & 1363 |
| 63 | EKQRIIGG | Probe #63 | 5-FAM-GEKQRIIGGGK(CPQ2)-PEG2-kk-GC | 740 & 1363 |
| 64 | QRQRIIGG | Probe #64 | 5-FAM-GQRQRIIGGGK(CPQ2)-PEG2-kk-GC | 741 & 1363 |
| 65 | LQRIYK | Probe #65 | 5-FAM-GLQRIYKGK(CPQ2)-PEG2-kk-GC | 742 & 1363 |
| 66 | SLGRKIQI | Probe #66 | 5-FAM-GSLGRKIQIGK(CPQ2)-PEG2-kk-GC | 743 & 1363 |
| 67 | HAAPRSADIQIDI | Probe #67 | 5-FAM-GHAAPRSADIQIDIGK(CPQ2)-PEG2-kk-GC | 744 & 1363 |
|  | FGR | Probe #68 | 5-FAM-GFGRGK(CPQ2)-PEG2-kk-GC | 745 & 1363 |
| 69 | SLGR | Probe #69 | 5-FAM-GSLGRGK(CPQ2)-PEG2-kk-GC | 746 & 1363 |
| 70 | GLQR | Probe #70 | 5-FAM-GGLQRGK(CPQ2)-PEG2-kk-GC | 747 & 1363 |
| 71 | SVARTLLV | Probe #71 | 5-FAM-GSVARTLLVGK(CPQ2)-PEG2-kk-GC | 748 & 1363 |
| 72 | GRIFG | Probe #72 | 5-FAM-GGRIFGGK(CPQ2)-PEG2-kk-GC | 749 & 1363 |
|  | APK | Probe #73 | 5-FAM-GAPKGK(CPQ2)-PEG2-kk-GC | 750 & 1363 |
| 74 | GFSPY | Probe #74 | 5-FAM-GGFSPYGK(CPQ2)-PEG2-kk-GC | 751 & 1363 |
| 75 | WELRHAGH | Probe #75 | 5-FAM-GWELRHAGHGK(CPQ2)-PEG2-kk-GC | 752 & 1363 |
| 76 | RQSRIVGGE | Probe #76 | 5-FAM-GRQSRIVGGEGK(CPQ2)-PEG2-kk-GC | 753 & 1363 |
| 77 | EQAVYQTI | Probe #77 | 5-FAM-GEQAVYQTIGK(CPQ2)-PEG2-kk-GC | 754 & 1363 |
| 78 | VAYSGENTFGF | Probe #78 | 5-FAM-GVAYSGENTFGFGK(CPQ2)-PEG2-kk-GC | 755 & 1363 |
|  | GGR | Probe #79 | 5-FAM-GGGRGK(CPQ2)-PEG2-kk-GC | 756 & 1363 |
| 80 | ATAD | Probe #80 | 5-FAM-GATADGK(CPQ2)-PEG2-kk-GC | 757 & 1363 |
| 81 | RPLESNAV | Probe #81 | 5-FAM-GRPLESNAVGK(CPQ2)-PEG2-kk-GC | 758 & 1363 |
| 82 | RPLGLAR | Probe #82 | 5-FAM-GRPLGLARGK(CPQ2)-PEG2-kk-GC | 759 & 1363 |
| 83 | AAFF | Probe #83 | 5-FAM-GAAFFGK(CPQ2)-PEG2-kk-GC | 760 & 1363 |
| 84 | RVKRGLA | Probe #84 | 5-FAM-GRVKRGLAGK(CPQ2)-PEG2-kk-GC | 761 & 1363 |

TABLE 1-continued

Exemplary sequences for peptide linkers and corresponding probe construct designs

| SEQ ID NO | Sequence | Exemplary probe name | Exemplary probe construct | SEQ ID NOS |
|---|---|---|---|---|
|  | AAL | Probe #85 | 5-FAM-GAALGK(CPQ2)-PEG2-kk-GC | 762 & 1363 |
| 86 | CGGmeGVndne eGFFsAr | Probe #86 | 5-FAM-CGGmeGVndneeGFFsArGK(CPQ2) | 763 |
| 87 | GPQGIWGQ | Probe #87 | 5FAM-GGPQGIWGQK(CPQ2)-PEG2-C | 764 |
| 88 | GLVPRGS | Probe #88 | 5FAM-GGLVPRGSK(CPQ2)-PEG2-C | 765 |
| 89 | GPVGLI | Probe #89 | 5FAM-GGPVGLIGK(CPQ2)-PEG2-C | 766 |
| 90 | GPWGIWGQ | Probe #90 | 5FAM-GGPWGIWGQK(CPQ2)-PEG2-C | 767 |
| 91 | GPVPLSLVM | Probe #91 | 5FAM-GGPVPLSLVMK(CPQ2)-PEG2-C | 768 |
| 92 | Gf-Pip-RSGG | Probe #92 | 5FAM-GGf-Pip-RSGGGK(CPQ2)-PEG2-C | 769 |
| 93 | PLGMRG | Probe #93 | 5FAM-GGf-Pip-KSGGGK(CPQ2)-PEG2-C | 770 |
| 94 | PLGMRG | Probe #94 | (FAM)-GPLGMRGG-K(CPQ2)-PEG2-k-GC | 771 |
| 95 | P-(Cha)-G-Cys(Me)-HA | Probe #95 | (FAM)-GP-(Cha)-G-Cys(Me)-HAG-K(CPQ2)-PEG2-kk-GC | 772 & 1363 |
| 96 | RPLALWESQ | Probe #96 | (FAM)-GRPLALWESQG-K(CPQ2)-PEG2-k-GC | 773 |
| 97 | SGKGPRQITA | Probe #97 | (FAM)-SGKGPRQITA-K(CPQ2)-PEG2-k-GC | 774 |
| 98 | SGPLFYSVTA | Probe #98 | (FAM)-SGPLFYSVTA-K(CPQ2)-PEG2-kk-GC | 775 & 1363 |
| 99 | SGRIFLRTA | Probe #99 | (FAM)-SGRIFLRTA-K(CPQ2)-PEG2-GC | 776 |
| 100 | SGRSENIRTA | Probe #100 | (FAM)-SGRSENIRTA-K(CPQ2)-PEG2-GC | 777 |
| 101 | GSGGS | Probe #101 | (FAM)-GGSGGS-K(CPQ2)-PEG2-kk-GC | 778 & 1363 |
| 102 | KPILFFRLKG | Probe #102 | (FAM)-GKPILFFRLKG-K(CPQ2)-PEG2-kk-GC | 779 & 1363 |
| 103 | AWESR(Nle) | Probe #103 | (FAM)-GAWESR(Nle)GK(CPQ2)-NH2 | 780 |
| 104 | NEKSG(Nle) | Probe #104 | (FAM)-GNEKSG(Nle)GK(CPQ2)-NH2 | 781 |
| 105 | NATIVY | Probe #105 | (FAM)-GNATIVYGK(CPQ2)-PEG2-k-NH2 | 782 |
| 106 | DPFVVS | Probe #106 | (FAM)-GDPFVVSGK(CPQ2)-PEG2-k-NH2 | 783 |
| 107 | FH(Nle)FTK | Probe #107 | (FAM)-GFH(Nle)FTKGK(CPQ2)-PEG2-k-NH2 | 784 |
| 108 | (Nle)NWHKH | Probe #108 | (FAM)-G(Nle)NWHKHGK(CPQ2)-NH2 | 785 |
| 109 | FARRWG | Probe #109 | (FAM)-GFARRWGGK(CPQ2)-PEG2-k-NH2 | 786 |
| 110 | PGKWSK | Probe #110 | (FAM)-GPGKWSKGK(CPQ2)-PEG2-k-NH2 | 787 |
| 111 | YEEAQP | Probe #111 | (FAM)-GYEEAQPGK(CPQ2)-PEG2-k-NH2 | 788 |
| 112 | YGAIKK | Probe #112 | (FAM)-GYGAIKKGK(CPQ2)-PEG2-k-NH2 | 789 |
| 113 | TS(Nle)EGY | Probe #113 | (FAM)-GTS(Nle)EGYGK(CPQ2)-PEG2-k | 790 |
| 114 | PNNFGS | Probe #114 | (FAM)-GPNNFGSGK(CPQ2)-PEG2-k-NH2 | 791 |
| 115 | EDTRNT | Probe #115 | (FAM)-GEDTRNTGK(CPQ2)-NH2 | 792 |
| 116 | KDLEQS | Probe #116 | (FAM)-GKDLEQSGK(CPQ2)-NH2 | 793 |
| 117 | AALHND | Probe #117 | (FAM)-GAALHNDGK(CPQ2)-PEG2-k-NH2 | 794 |
| 118 | ADSFFK | Probe #118 | (FAM)-GADSFFKGK(CPQ2)-NH2 | 795 |

TABLE 1-continued

Exemplary sequences for peptide linkers and corresponding probe construct designs

| SEQ ID NO | Sequence | Exemplary probe name | Exemplary probe construct | SEQ ID NOS |
|---|---|---|---|---|
| 119 | ITFWRA | Probe #119 | (FAM)-GITFWRAGK(CPQ2)-NH2 | 796 |
| 120 | LSD(Nle)RL | Probe #120 | (FAM)-GLSD(Nle)RLGK(CPQ2)-NH2 | 797 |
| 121 | EVGWTY | Probe #121 | (FAM)-GEVGWTYGK(CPQ2)-PEG2-k-NH2 | 798 |
| 122 | IAFRQ(Nle) | Probe #122 | (FAM)-GIAFRQ(Nle)GK(CPQ2)-NH2 | 799 |
| 123 | YNIHT(Nle) | Probe #123 | (FAM)-GYNIHT(Nle)GK(CPQ2)-PEG2-kk-NH2 | 800 |
| 124 | (Nle)LWANH | Probe #124 | (FAM)-G(Nle)LWANHGK(CPQ2)-PEG2-kk-NH2 | 801 |
| 125 | LYSVQV | Probe #125 | (FAM)-GLYSVQVGK(CPQ2)-PEG2-k-NH2 | 802 |
| 126 | SHI(Nle)SN | Probe #126 | (FAM)-GSHI(Nle)SNGK(CPQ2)-PEG2-kk-NH2 | 803 |
| 127 | KLLIDV | Probe #127 | (FAM)-GKLLIDVGK(CPQ2)-NH2 | 804 |
| 128 | E(Nle)GVFD | Probe #128 | (FAM)-GE(Nle)GVFDGK(CPQ2)-PEG2-k-NH2 | 805 |
| 129 | HQAYTL | Probe #129 | (FAM)-GHQAYTLGK(CPQ2)-PEG2-kk-NH2 | 806 |
| 130 | YVRKIQ | Probe #130 | (FAM)-GYVRKIQGK(CPQ2)-PEG2-k-NH2 | 807 |
| 131 | DRENSP | Probe #131 | (FAM)-GDRENSPGK(CPQ2)-NH2 | 808 |
| 132 | KYDKPR | Probe #132 | (FAM)-GKYDKPRGK(CPQ2)-NH2 | 809 |
| 133 | RPWKQL | Probe #133 | (FAM)-GRPWKQLGK(CPQ2)-PEG2-k-NH2 | 810 |
| 134 | APLQRY | Probe #134 | (FAM)-GAPLQRYGK(CPQ2)-NH2 | 811 |
| 135 | YQGQK(Nle) | Probe #135 | (FAM)-GYQGQK(Nle)GK(CPQ2)-NH2 | 812 |
| 136 | GRISSI | Probe #136 | (FAM)-GGRISSIGK(CPQ2)-NH2 | 813 |
| 137 | HSLTNV | Probe #137 | (FAM)-GHSLTNVGK(CPQ2)-PEG2-kk-NH2 | 814 |
| 138 | EWDFPE | Probe #138 | (FAM)-GEWDFPEGK(CPQ2)-PEG2-k-NH2 | 815 |
| 139 | YLA(Nle)DG | Probe #139 | (FAM)-GYLA(Nle)DGGK(CPQ2)-PEG2-k-NH2 | 816 |
| 140 | FIY(Nle)PT | Probe #140 | (FAM)-GFIY(Nle)PTGK(CPQ2)-PEG2-k-NH2 | 817 |
| 141 | GHETWV | Probe #141 | (FAM)-GGHETWVGK(CPQ2)-PEG2-kk-NH2 | 818 |
| 142 | DYIGDE | Probe #142 | (FAM)-GDYIGDEGK(CPQ2)-PEG2-k-NH2 | 819 |
| 143 | AGTAHP | Probe #143 | (FAM)-GAGTAHPGK(CPQ2)-PEG2-kk-NH2 | 820 |
| 144 | V(Nle)TEIW | Probe #144 | (FAM)-GV(Nle)TEIWGK(CPQ2)-PEG2-k-NH2 | 821 |
| 145 | PDDWQN | Probe #145 | (FAM)-GPDDWQNGK(CPQ2)-PEG2-k-NH2 | 822 |
| 146 | GLNQEY | Probe #146 | (FAM)-GGLNQEYGK(CPQ2)-PEG2-k-NH2 | 823 |
| 147 | YRDAVA | Probe #147 | (FAM)-GYRDAVAGK(CPQ2)-NH2 | 824 |
| 148 | TGPKGN | Probe #148 | (FAM)-GTGPKGNGK(CPQ2)-NH2 | 825 |
| 149 | DHVPQI | Probe #149 | (FAM)-GDHVPQIGK(CPQ2)-PEG2-kk-NH2 | 826 |
| 150 | NKEPIL | Probe #150 | (FAM)-GNKEPILGK(CPQ2)-NH2 | 827 |
| 151 | VWN(Nle)VH | Probe #151 | (FAM)-GVWN(Nle)VHGK(CPQ2)-PEG2-kk-NH2 | 828 |
| 152 | PVIIEH | Probe #152 | (FAM)-GPVIIEHGK(CPQ2)-PEG2-kk-NH2 | 829 |
| 153 | FQTDNL | Probe #153 | (FAM)-GFQTDNLGK(CPQ2)-PEG2-k-NH2 | 830 |
| 154 | RF(Nle)HGI | Probe #154 | (FAM)-GRF(Nle)HGIGK(CPQ2)-PEG2-k-NH2 | 831 |
| 155 | YAERTT | Probe #155 | (FAM)-GYAERTTGK(CPQ2)-NH2 | 832 |

TABLE 1-continued

Exemplary sequences for peptide
linkers and corresponding probe construct designs

| SEQ ID NO | Sequence | Exemplary probe name | Exemplary probe construct | SEQ ID NOS |
|---|---|---|---|---|
| 156 | NRGELP | Probe #156 | (FAM)-GNRGELPGK(CPQ2)-NH2 | 833 |
| 157 | HHYFNY | Probe #157 | (FAM)-GHHYFNYGK(CPQ2)-PEG2-k-NH2 | 834 |
| 158 | STPYYH | Probe #158 | (FAM)-GSTPYYHGK(CPQ2)-PEG2-kk-NH2 | 835 |
| 159 | WFYPSA | Probe #159 | (FAM)-GWFYPSAGK(CPQ2)-PEG2-k-NH2 | 836 |
| 160 | SEFLFS | Probe #160 | (FAM)-GSEFLFSGK(CPQ2)-PEG2-k-NH2 | 837 |
| 161 | WYKTQY | Probe #161 | (FAM)-GWYKTQYGK(CPQ2)-NH2 | 838 |
| 162 | VTHLKV | Probe #162 | (FAM)-GVTHLKVGK(CPQ2)-PEG2-k-NH2 | 839 |
| 163 | INGGFS | Probe #163 | (FAM)-GINGGFSGK(CPQ2)-PEG2-k-NH2 | 840 |
| 164 | TVLGLD | Probe #164 | (FAM)-GTVLGLDGK(CPQ2)-PEG2-k-NH2 | 841 |
| 165 | SYWP(Nle)Q | Probe #165 | (FAM)-GSYWP(Nle)QGK(CPQ2)-PEG2-k-NH2 | 842 |
| 166 | ASQQHR | Probe #166 | (FAM)-GASQQHRGK(CPQ2)-PEG2-k-NH2 | 843 |
| 167 | KNPAKA | Probe #167 | (FAM)-GKNPAKAGK(CPQ2)-PEG2-k-NH2 | 844 |
| 168 | (Nle)YWLVE | Probe #168 | (FAM)-G(Nle)YWLVEGK(CPQ2)-PEG2-k-NH2 | 845 |
| 169 | SWWIFE | Probe #169 | (FAM)-GSWWIFEGK(CPQ2)-PEG2-k-NH2 | 846 |
| 170 | VNYEQD | Probe #170 | (FAM)-GVNYEQDGK(CPQ2)-PEG2-k-NH2 | 847 |
| 171 | HFF(Nle)AE | Probe #171 | (FAM)-GHFF(Nle)AEGK(CPQ2)-PEG2-kk-NH2 | 848 |
| 172 | DIPPHW | Probe #172 | (FAM)-GDIPPHWGK(CPQ2)-PEG2-kk-NH2 | 849 |
| 173 | VDQW(Nle)W | Probe #173 | (FAM)-GVDQW(Nle)WGK(CPQ2)-PEG2-k-NH2 | 850 |
| 174 | LRSL(Nle)K | Probe #174 | (FAM)-GLRSL(Nle)KGK(CPQ2)-PEG2-k-NH2 | 851 |
| 175 | (Nle)(Nle)IRHA | Probe #175 | (FAM)-G(Nle)(Nle)IRHAGK(CPQ2)-PEG2-k-NH2 | 852 |
| 176 | HDVKFI | Probe #176 | (FAM)-GHDVKFIGK(CPQ2)-PEG2-kk-NH2 | 853 |
| 177 | KRVQFL | Probe #177 | (FAM)-GKRVQFLGK(CPQ2)-PEG2-k-NH2 | 854 |
| 178 | RD(Nle)YAE | Probe #178 | (FAM)-GRD(Nle)YAEGK(CPQ2)-NH2 | 855 |
| 179 | L(Nle)IYFE | Probe #179 | (FAM)-GL(Nle)IYFEGK(CPQ2)-PEG2-k-NH2 | 856 |
| 180 | LRTKQS | Probe #180 | (FAM)-GLRTKQSGK(CPQ2)-PEG2-k-NH2 | 857 |
| 181 | WHGQQY | Probe #181 | (FAM)-GWHGQQYGK(CPQ2)-PEG2-kk-NH2 | 858 |
| 182 | GPEGTI | Probe #182 | (FAM)-GGPEGTIGK(CPQ2)-PEG2-k-NH2 | 859 |
| 183 | ELDPIP | Probe #183 | (FAM)-GELDPIPGK(CPQ2)-PEG2-k-NH2 | 860 |
| 184 | GRAADF | Probe #184 | (FAM)-GGRAADFGK(CPQ2)-NH2 | 861 |
| 185 | HFIDYI | Probe #185 | (FAM)-GHFIDYIGK(CPQ2)-PEG2-kk-NH2 | 862 |
| 186 | S(Nle)(Nle)RVH | Probe #186 | (FAM)-GS(Nle)(Nle)RVHGK(CPQ2)-PEG2-k-NH2 | 863 |
| 187 | SFRKII | Probe #187 | (FAM)-GSFRKIIGK(CPQ2)-PEG2-k-NH2 | 864 |
| 188 | TYE(Nle)FS | Probe #188 | (FAM)-GTYE(Nle)FSGK(CPQ2)-PEG2-k-NH2 | 865 |
| 189 | HLLGFY | Probe #189 | (FAM)-GHLLGFYGK(CPQ2)-PEG2-kk-NH2 | 866 |
| 190 | (Nle)WTALT | Probe #190 | (FAM)-G(Nle)WTALTGK(CPQ2)-PEG2-k-NH2 | 867 |
| 191 | IWN(Nle)VY | Probe #191 | (FAM)-GIWN(Nle)VYGK(CPQ2)-PEG2-k-NH2 | 868 |
| 192 | RRNPLW | Probe #192 | (FAM)-GRRNPLWGK(CPQ2)-PEG2-k-NH2 | 869 |

TABLE 1-continued

Exemplary sequences for peptide linkers and corresponding probe construct designs

| SEQ ID NO | Sequence | Exemplary probe name | Exemplary probe construct | SEQ ID NOS |
|---|---|---|---|---|
| 193 | RWYGGI | Probe #193 | (FAM)-GRWYGGIGK(CPQ2)-NH2 | 870 |
| 194 | KTGDAR | Probe #194 | (FAM)-GKTGDARGK(CPQ2)-PEG2-k-NH2 | 871 |
| 195 | NYWEAN | Probe #195 | (FAM)-GNYWEANGK(CPQ2)-PEG2-k-NH2 | 872 |
| 196 | (Nle)QFDTS | Probe #196 | (FAM)-G(Nle)QFDTSGK(CPQ2)-PEG2-k-NH2 | 873 |
| 197 | KRGAVE | Probe #197 | (FAM)-GKRGAVEGK(CPQ2)-PEG2-k-NH2 | 874 |
| 198 | SLKPTE | Probe #198 | (FAM)-GSLKPTEGK(CPQ2)-NH2 | 875 |
| 199 | ENDRLP | Probe #199 | (FAM)-GENDRLPGK(CPQ2)-NH2 | 876 |
| 200 | NSYQVQ | Probe #200 | (FAM)-GNSYQVQGK(CPQ2)-PEG2-k-NH2 | 877 |
| 201 | YPKEYL | Probe #201 | (FAM)-GYPKEYLGK(CPQ2)-NH2 | 878 |
| 202 | INNKWQ | Probe #202 | (FAM)-GINNKWQGK(CPQ2)-NH2 | 879 |
| 203 | (Nle)EFQGW | Probe #203 | (FAM)-G(Nle)EFQGWGK(CPQ2)-PEG2-k-NH2 | 880 |
| 204 | PVRSTN | Probe #204 | (FAM)-GPVRSTNGK(CPQ2)-NH2 | 881 |
| 205 | SQAIKV | Probe #205 | (FAM)-GSQAIKVGK(CPQ2)-NH2 | 882 |
| 206 | WA(Nle)LYH | Probe #206 | (FAM)-GWA(Nle)LYHGK(CPQ2)-PEG2-kk-NH2 | 883 |
| 207 | ISWIHA | Probe #207 | (FAM)-GISWIHAGK(CPQ2)-PEG2-kk-NH2 | 884 |
| 208 | AHDIV | Probe #208 | (FAM)-GAHDIVNGK(CPQ2)-PEG2-kk-NH2 | 885 |
| 209 | RHNVAS | Probe #209 | (FAM)-GRHNVASGK(CPQ2)-PEG2-k-NH2 | 886 |
| 210 | SVFVIE | Probe #210 | (FAM)-GSVFVIEGK(CPQ2)-PEG2-k-NH2 | 887 |
| 211 | FAKYYK | Probe #211 | (FAM)-GFAKYYKGK(CPQ2)-PEG2-k-NH2 | 888 |
| 212 | PYNTLQ | Probe #212 | (FAM)-GPYNTLQGK(CPQ2)-PEG2-k-NH2 | 889 |
| 213 | (Nle)DWGH(Nle) | Probe #213 | (FAM)-G(Nle)DWGH(Nle)GK(CPQ2)-PEG2-kk-NH2 | 890 |
| 214 | SNREWF | Probe #214 | (FAM)-GSNREWFGK(CPQ2)-NH2 | 891 |
| 215 | GKSEHT | Probe #215 | (FAM)-GGKSEHTGK(CPQ2)-PEG2-kk-NH2 | 892 |
| 216 | FP(Nle)TDQ | Probe #216 | (FAM)-GFP(Nle)TDQGK(CPQ2)-PEG2-k-NH2 | 893 |
| 217 | WSKFW(Nle) | Probe #217 | (FAM)-GWSKFW(Nle)GK(CPQ2) | 894 |
| 218 | RFTRPH | Probe #218 | (FAM)-GRFTRPHGK(CPQ2)-NH2 | 895 |
| 219 | QET(Nle)KD | Probe #219 | (FAM)-GQET(Nle)KDGK(CPQ2)-NH2 | 896 |
| 220 | HWWDVL | Probe #220 | (FAM)-GHWWDVLGK(CPQ2)-PEG2-kk-NH2 | 897 |
| 221 | FNLV(Nle)S | Probe #221 | (FAM)-GFNLV(Nle)SGK(CPQ2)-PEG2-k-NH2 | 898 |
| 222 | SAWRQR | Probe #222 | (FAM)-GSAWRQRGK(CPQ2)-PEG2-k-NH2 | 899 |
| 223 | TFHIFL | Probe #223 | (FAM)-GTFHIFLGK(CPQ2)-PEG2-kk-NH2 | 900 |
| 224 | WPQHVK | Probe #224 | (FAM)-GWPQHVKGK(CPQ2)-PEG2-k-NH2 | 901 |
| 225 | LI(Nle)HKN | Probe #225 | (FAM)-GLI(Nle)HKNGK(CPQ2)-PEG2-k-NH2 | 902 |
| 226 | QDLEQP | Probe #226 | (FAM)-GQDLEQPGK(CPQ2)-PEG2-k-NH2 | 903 |
| 227 | HQKK(Nle)P | Probe #227 | (FAM)-GHQKK(Nle)PGK(CPQ2)-NH2 | 904 |
| 228 | GVTWLN | Probe #228 | (FAM)-GGVTWLNGK(CPQ2)-PEG2-k-NH2 | 905 |
| 229 | AGEPFK | Probe #229 | (FAM)-GAGEPFKGK(CPQ2)-NH2 | 906 |

TABLE 1-continued

Exemplary sequences for peptide linkers and corresponding probe construct designs

| SEQ ID NO | Sequence | Exemplary probe name | Exemplary probe construct | SEQ ID NOS |
|---|---|---|---|---|
| 230 | SR(Nle)ATT | Probe #230 | (FAM)-GSR(Nle)ATTGK(CPQ2)-NH2 | 907 |
| 231 | LAF(Nle)NH | Probe #231 | (FAM)-GLAF(Nle)NHGK(CPQ2)-PEG2-kk-NH2 | 908 |
| 232 | PPSGLS | Probe #232 | (FAM)-GPPSGLSGK(CPQ2)-PEG2-k-NH2 | 909 |
| 233 | YTHSSP | Probe #233 | (FAM)-GYTHSSPGK(CPQ2)-PEG2-kk-NH2 | 910 |
| 234 | DGSHYR | Probe #234 | (FAM)-GDGSHYRGK(CPQ2)-PEG2-kk-NH2 | 911 |
| 235 | Y(Nle)GNGY | Probe #235 | (FAM)-GY(Nle)GNGYGK(CPQ2)-PEG2-k-NH2 | 912 |
| 236 | DSITVS | Probe #236 | (FAM)-GDSITVSGK(CPQ2)-PEG2-k-NH2 | 913 |
| 237 | QTPNIQ | Probe #237 | (FAM)-GQTPNIQGK(CPQ2)-PEG2-k-NH2 | 914 |
| 238 | KLFFGY | Probe #238 | (FAM)-GKLFFGYGK(CPQ2)-NH2 | 915 |
| 239 | TQNFNW | Probe #239 | (FAM)-GTQNFNWGK(CPQ2)-PEG2-k-NH2 | 916 |
| 240 | YSDHEV | Probe #240 | (FAM)-GYSDHEVGK(CPQ2)-PEG2-kk-NH2 | 917 |
| 241 | RYVVPA | Probe #241 | (FAM)-GRYVVPAGK(CPQ2)-NH2 | 918 |
| 242 | ILHRIR | Probe #242 | (FAM)-GILHRIRGK(CPQ2)-NH2 | 919 |
| 243 | ESDNQ(Nle) | Probe #243 | (FAM)-GESDNQ(Nle)GK(CPQ2)-PEG2-k-NH2 | 920 |
| 244 | YDDKG(Nle) | Probe #244 | (FAM)-GYDDKG(Nle)GK(CPQ2)-NH2 | 921 |
| 245 | QLS(Nle)VW | Probe #245 | (FAM)-GQLS(Nle)VWGK(CPQ2)-PEG2-k-NH2 | 922 |
| 246 | PGGER(Nle) | Probe #246 | (FAM)-GPGGER(Nle)GK(CPQ2)-NH2 | 923 |
| 247 | WKHHPD | Probe #247 | (FAM)-GWKHHPDGK(CPQ2)-NH2 | 924 |
| 248 | QWVDED | Probe #248 | (FAM)-GQWVDEDGK(CPQ2)-PEG2-k-NH2 | 925 |
| 249 | NAYNEI | Probe #249 | (FAM)-GNAYNEIGK(CPQ2)-PEG2-k-NH2 | 926 |
| 250 | EEKAPR | Probe #250 | (FAM)-GEEKAPRGK(CPQ2)-PEG2-kk-NH2 | 927 |
| 251 | PWQIGK | Probe #251 | (FAM)-GPWQIGKGK(CPQ2)-NH2 | 928 |
| 252 | IAQVGN | Probe #252 | (FAM)-GIAQVGNGK(CPQ2)-PEG2-k-NH2 | 929 |
| 253 | V(Nle)RQSE | Probe #253 | (FAM)-GV(Nle)RQSEGK(CPQ2)-NH2 | 930 |
| 254 | TERVDA | Probe #254 | (FAM)-GTERVDAGK(CPQ2)-NH2 | 931 |
| 255 | WLRWRL | Probe #255 | (FAM)-GWLRWRLGK(CPQ2)-PEG2-k-NH2 | 932 |
| 256 | WKTKGQ | Probe #256 | (FAM)-GWKTKGQGK(CPQ2)-PEG2-k-NH2 | 933 |
| 257 | QSNGDV | Probe #257 | (FAM)-GQSNGDVGK(CPQ2)-PEG2-k-NH2 | 934 |
| 258 | TLFYAL | Probe #258 | (FAM)-GTLFYALGK(CPQ2)-PEG2-k-NH2 | 935 |
| 259 | TVTLNP | Probe #259 | (FAM)-GTVTLNPGK(CPQ2)-PEG2-k-NH2 | 936 |
| 260 | YAFGRK | Probe #260 | (FAM)-GYAFGRKGK(CPQ2)-PEG2-k-NH2 | 937 |
| 261 | DYNYWD | Probe #261 | (FAM)-GDYNYWDGK(CPQ2)-PEG2-k-NH2 | 938 |
| 262 | EWHEII | Probe #262 | (FAM)-GEWHEIIGK(CPQ2)-PEG2-kk-NH2 | 939 |
| 263 | QKAAWD | Probe #263 | (FAM)-GQKAAWDGK(CPQ2)-NH2 | 940 |
| 264 | DNTSAD | Probe #264 | (FAM)-GDNTSADGK(CPQ2)-PEG2-k-NH2 | 941 |
| 265 | HEGEYV | Probe #265 | (FAM)-GHEGEYVGK(CPQ2)-PEG2-kk-NH2 | 942 |
| 266 | WSPSFK | Probe #266 | (FAM)-GWSPSFKGK(CPQ2)-NH2 | 943 |

TABLE 1-continued

Exemplary sequences for peptide
linkers and corresponding probe construct designs

| SEQ ID NO | Sequence | Exemplary probe name | Exemplary probe construct | SEQ ID NOS |
|---|---|---|---|---|
| 267 | HDEHWT | Probe #267 | (FAM)-GHDEHWTGK(CPQ2)-PEG2-kk-NH2 | 944 |
| 268 | YVW(Nle)RD | Probe #268 | (FAM)-GYVW(Nle)RDGK(CPQ2)-NH2 | 945 |
| 269 | (Nle)DP(Nle)KF | Probe #269 | (FAM)-G(Nle)DP(Nle)KFGK(CPQ2)-NH2 | 946 |
| 270 | (Nle)R(Nle)FWD | Probe #270 | (FAM)-G(Nle)R(Nle)FWDGK(CPQ2)-NH2 | 947 |
| 271 | DIAIT(Nle) | Probe #271 | (FAM)-GDIAIT(Nle)GK(CPQ2)-PEG2-k-NH2 | 948 |
| 272 | PI(Nle)RFH | Probe #272 | (FAM)-GPI(Nle)RFHGK(CPQ2)-PEG2-k-NH2 | 949 |
| 273 | VWQGYI | Probe #273 | (FAM)-GVWQGYIGK(CPQ2)-PEG2-k-NH2 | 950 |
| 274 | KK(Nle)SNP | Probe #274 | (FAM)-GKK(Nle)SNPGK(CPQ2)-PEG2-k-NH2 | 951 |
| 275 | GHPLSP | Probe #275 | (FAM)-GGHPLSPGK(CPQ2)-PEG2-kk-NH2 | 952 |
| 276 | VRQHKP | Probe #276 | (FAM)-GVRQHKPGK(CPQ2)-NH2 | 953 |
| 277 | AQNFYR | Probe #277 | (FAM)-GAQNFYRGK(CPQ2)-NH2 | 954 |
| 278 | VAGKSI | Probe #278 | (FAM)-GVAGKSIGK(CPQ2)-NH2 | 955 |
| 279 | LVGQVN | Probe #279 | (FAM)-GLVGQVNGK(CPQ2)-PEG2-k-NH2 | 956 |
| 280 | QVKHFT | Probe #280 | (FAM)-GQVKHFTGK(CPQ2)-PEG2-k-NH2 | 957 |
| 281 | QKSVVS | Probe #281 | (FAM)-GQKSVVSGK(CPQ2)-NH2 | 958 |
| 282 | Y(Nle)QEWL | Probe #282 | (FAM)-GY(Nle)QEWLGK(CPQ2)-PEG2-k-NH2 | 959 |
| 283 | G(Nle)YIDE | Probe #283 | (FAM)-GG(Nle)YIDEGK(CPQ2)-PEG2-k-NH2 | 960 |
| 284 | NAGSKF | Probe #284 | (FAM)-GNAGSKFGK(CPQ2)-NH2 | 961 |
| 285 | EFVHNP | Probe #285 | (FAM)-GEFVHNPGK(CPQ2)-PEG2-kk-NH2 | 962 |
| 286 | WE(Nle)VKI | Probe #286 | (FAM)-GWE(Nle)VKIGK(CPQ2)-NH2 | 963 |
| 287 | WVGASH | Probe #287 | (FAM)-GWVGASHGK(CPQ2)-PEG2-kk-NH2 | 964 |
| 288 | ITTLY(Nle) | Probe #288 | (FAM)-GITTLY(Nle)GK(CPQ2)-PEG2-k-NH2 | 965 |
| 289 | GHIDEY | Probe #289 | (FAM)-GGHIDEYGK(CPQ2)-PEG2-kk-NH2 | 966 |
| 290 | KV(Nle)DYG | Probe #290 | (FAM)-GKV(Nle)DYGGK(CPQ2)-NH2 | 967 |
| 291 | QEKQT(Nle) | Probe #291 | (FAM)-GQEKQT(Nle)GK(CPQ2)-NH2 | 968 |
| 292 | EVGHEA | Probe #292 | (FAM)-GEVGHEAGK(CPQ2)-PEG2-kk-NH2 | 969 |
| 293 | AWEGQY | Probe #293 | (FAM)-GAWEGQYGK(CPQ2)-PEG2-k-NH2 | 970 |
| 294 | FLVQWT | Probe #294 | (FAM)-GFLVQWTGK(CPQ2)-PEG2-k-NH2 | 971 |
| 295 | SKWGYW | Probe #295 | (FAM)-GSKWGYWGK(CPQ2)-NH2 | 972 |
| 296 | TWIS(Nle)Q | Probe #296 | (FAM)-GTWIS(Nle)QGK(CPQ2)-PEG2-k-NH2 | 973 |
| 297 | VIDKDF | Probe #297 | (FAM)-GVIDKDFGK(CPQ2)-NH2 | 974 |
| 298 | VKFAIY | Probe #298 | (FAM)-GVKFAIYGK(CPQ2)-NH2 | 975 |
| 299 | HNQ(Nle)KS | Probe #299 | (FAM)-GHNQ(Nle)KSGK(CPQ2)-PEG2-k-NH2 | 976 |
| 300 | QYVFF(Nle) | Probe #300 | (FAM)-GQYVFF(Nle)GK(CPQ2)-PEG2-k-NH2 | 977 |
| 301 | YNPRE(Nle) | Probe #301 | (FAM)-GYNPRE(Nle)GK(CPQ2)-NH2 | 978 |
| 302 | KHG(Nle)PE | Probe #302 | (FAM)-GKHG(Nle)PEGK(CPQ2)-PEG2-kk-NH2 | 979 |
| 303 | WSREYW | Probe #303 | (FAM)-GWSREYWGK(CPQ2)-NH2 | 980 |

TABLE 1-continued

Exemplary sequences for peptide linkers and corresponding probe construct designs

| SEQ ID NO | Sequence | Exemplary probe name | Exemplary probe construct | SEQ ID NOS |
|---|---|---|---|---|
| 304 | IDRVDK | Probe #304 | (FAM)-GIDRVDKGK(CPQ2)-PEG2-kk-NH2 | 981 |
| 305 | GDRENSPK(CPQ2)L-OH | Probe #305 | (FAM)-kkGDRENSPK(CPQ2)L-OH | 982 |
| 306 | GDRENSPLK(CPQ2)-OH | Probe #306 | (FAM)-kkGDRENSPLK(CPQ2)-OH | 983 |
| 307 | NAGSKFK(CPQ2)Q-OH | Probe #307 | (FAM)-GNAGSKFK(CPQ2)Q-OH | 984 |
| 308 | NAGSKFQK(CPQ2)-OH | Probe #308 | (FAM)-GNAGSKFQK(CPQ2)-OH | 985 |
| 309 | GHLLGFYK(CPQ2)V-OH | Probe #309 | (FAM)-kkGHLLGFYK(CPQ2)V-OH | 986 |
| 310 | GHLLGFYVK(CPQ2)-OH | Probe #310 | (FAM)-kkGHLLGFYVK(CPQ2)-OH | 987 |
| 311 | GQEKQT(Nle)K(CPQ2)(Nle)-OH | Probe #311 | (FAM)-kkGQEKQT(Nle)K(CPQ2)(Nle)-OH | 988 |
| 312 | GQEKQT(Nle)(Nle)K(CPQ2)-OH | Probe #312 | (FAM)-kkGQEKQT(Nle)(Nle)K(CPQ2)-OH | 989 |
| 313 | kGDPFVVSK(CPQ2)W-OH | Probe #313 | (FAM)-kGDPFVVSK(CPQ2)W-OH | 990 |
| 314 | kGDPFVVSWK(CPQ2)-OH | Probe #314 | (FAM)-kGDPFVVSWK(CPQ2)-OH | 991 |
| 315 | NAYNEIK(CPQ2)R-OH | Probe #315 | (FAM)-GNAYNEIK(CPQ2)R-OH | 992 |
| 316 | NAYNEIRK(CPQ2)-OH | Probe #316 | (FAM)-GNAYNEIRK(CPQ2)-OH | 993 |
| 317 | V(Nle)RQSEK(CPQ2)N-OH | Probe #317 | (FAM)-GV(Nle)RQSEK(CPQ2)N-OH | 994 |
| 318 | V(Nle)RQSENK(CPQ2)-OH | Probe #318 | (FAM)-GV(Nle)RQSENK(CPQ2) | 995 |
| 319 | YNPRE(Nle)K(CPQ2)I-OH | Probe #319 | (FAM)-GYNPRE(Nle)K(CPQ2)I-OH | 996 |
| 320 | YNPRE(Nle)IK(CPQ2)-OH | Probe #320 | (FAM)-GYNPRE(Nle)IK(CPQ2)-OH | 997 |
| 321 | EFVHNPK(CPQ2)K-OH | Probe #321 | (FAM)-kGEFVHNPK(CPQ2)K-OH | 998 |
| 322 | EFVHNPKK(CPQ2)-OH | Probe #322 | (FAM)-kGEFVHNPKK(CPQ2)-OH | 999 |
| 323 | KRVQFLK(CPQ2)H-OH | Probe #323 | (FAM)-GKRVQFLK(CPQ2)H-OH | 1000 |
| 324 | KRVQFLHK(CPQ2)-OH | Probe #324 | (FAM)-GKRVQFLHK(CPQ2)-OH | 1001 |
| 325 | LI(Nle)HKNK(CPQ2)G-OH | Probe #325 | (FAM)-kGLI(Nle)HKNK(CPQ2)G-OH | 1002 |
| 326 | LI(Nle)HKNGK(CPQ2)-OH | Probe #326 | (FAM)-kGLI(Nle)HKNGK(CPQ2)-OH | 1003 |
| 327 | WA(Nle)LYHK(CPQ2)S-OH | Probe #327 | (FAM)-kkGWA(Nle)LYHK(CPQ2)S-OH | 1004 |
| 328 | WA(Nle)LYHSK(CPQ2)-OH | Probe #328 | (FAM)-kkGWA(Nle)LYHSK(CPQ2)-OH | 1005 |

TABLE 1-continued

Exemplary sequences for peptide
linkers and corresponding probe construct designs

| SEQ ID NO | Sequence | Exemplary probe name | Exemplary probe construct | SEQ ID NOS |
|---|---|---|---|---|
| 329 | AHDIVNK(CPQ2)Y-OH | Probe #329 | (FAM)-kkGAHDIVNK(CPQ2)Y-OH | 1006 |
| 330 | AHDIVNYK(CPQ2)-OH | Probe #330 | (FAM)-kkGAHDIVNYK(CPQ2)-OH | 1007 |
| 331 | SVFVIEK(CPQ2)P-OH | Probe #331 | (FAM)-kGSVFVIEK(CPQ2)P-OH | 1008 |
| 332 | SVFVIEPK(CPQ2)-OH | Probe #332 | (FAM)-kGSVFVIEPK(CPQ2)-OH | 1009 |
| 333 | PPSGLSK(CPQ2)E-OH | Probe #333 | (FAM)-kGPPSGLSK(CPQ2)E-OH | 1010 |
| 334 | PPSGLSEK(CPQ2)-OH | Probe #334 | (FAM)-kGPPSGLSEK(CPQ2)-OH | 1011 |
| 335 | RWYGGIK(CPQ2)F-OH | Probe #335 | (FAM)-kkGRWYGGIK(CPQ2)F-OH | 1012 |
| 336 | RWYGGIFK(CPQ2)-OH | Probe #336 | (FAM)-kkGRWYGGIFK(CPQ2)-OH | 1013 |
| 337 | QYVFF(Nle)K(CPQ2)D-OH | Probe #337 | (FAM)-kGQYVFF(Nle)K(CPQ2)D-OH | 1014 |
| 338 | QYVFF(Nle)DK(CPQ2)-OH | Probe #338 | (FAM)-kGQYVFF(Nle)DK(CPQ2)-OH | 1015 |
| 339 | FAKYYKK(CPQ2)T-OH | Probe #339 | (FAM)-kGFAKYYKK(CPQ2)T-OH | 1016 |
| 340 | FAKYYKTK(CPQ2)-OH | Probe #340 | (FAM)-kGFAKYYKTK(CPQ2)-OH | 1017 |
| 341 | QVKHFTK(CPQ2)A-OH | Probe #341 | (FAM)-kGQVKHFTK(CPQ2)A-OH | 1018 |
| 342 | QVKHFTAK(CPQ2)-OH | Probe #342 | (FAM)-kGQVKHFTAK(CPQ2)-OH | 1019 |
|  | APK(CPQ2)-OH | Probe #343 | FAM-APK(CPQ2)-OH |  |
| 344 | NH2-HK(FAM)DRENSP | Probe #344 | NH2-HK(FAM)DRENSPGK(CPQ2)-NH2 | 1021 |
| 345 | NH2-K(FAM)HDRENSP | Probe #345 | NH2-K(FAM)HDRENSPGK(CPQ2)-NH2 | 1022 |
| 346 | NH2-WK(FAM)NAGSKF | Probe #346 | NH2-WK(FAM)NAGSKFGkK(CPQ2)-NH2 | 1023 |
| 347 | NH2-K(FAM)WNAGSKF | Probe #347 | NH2-K(FAM)WNAGSKFGkK(CPQ2)-NH2 | 1024 |
| 348 | NH2-SK(FAM)HLLGFY | Probe #348 | NH2-SK(FAM)HLLGFYGkK(CPQ2)-NH2 | 1025 |
| 349 | NH2-K(FAM)SHLLGFY | Probe #349 | NH2-K(FAM)SHLLGFYGkK(CPQ2)-NH2 | 1026 |
| 350 | NH2-KK(FAM)QEKQT(Nle) | Probe #350 | NH2-KK(FAM)QEKQT(Nle)GK(CPQ2)-NH2 | 1027 |
| 351 | NH2-K(FAM)KQEKQT(Nle) | Probe #351 | NH2-K(FAM)KQEKQT(Nle)GK(CPQ2)-NH2 | 1028 |
| 352 | NH2-GK(FAM)DPFVVS | Probe #352 | NH2-GK(FAM)DPFVVSGK(CPQ2)-NH2 | 1029 |
| 353 | NH2-K(FAM)GDPFVVS | Probe #353 | NH2-K(FAM)GDPFVVSGK(CPQ2)-NH2 | 1030 |

TABLE 1-continued

Exemplary sequences for peptide linkers and corresponding probe construct designs

| SEQ ID NO | Sequence | Exemplary probe name | Exemplary probe construct | SEQ ID NOS |
|---|---|---|---|---|
| 354 | NH2-PK(FAM)NAYNEI | Probe #354 | NH2-PK(FAM)NAYNEIGK(CPQ2)-NH2 | 1031 |
| 355 | NH2-K(FAM)PNAYNEI | Probe #355 | NH2-K(FAM)PNAYNEIGK(CPQ2)-NH2 | 1032 |
| 356 | NH2-DK(FAM)V(Nle)RQSE | Probe #356 | NH2-DK(FAM)V(Nle)RQSEGkK(CPQ2)-NH2 | 1033 |
| 357 | NH2-K(FAM)DV(Nle)RQSE | Probe #357 | NH2-K(FAM)DV(Nle)RQSEGkK(CPQ2)-NH2 | 1034 |
| 358 | NH2-EK(FAM)YNPRE(Nle) | Probe #358 | NH2-EK(FAM)YNPRE(Nle)GkK(CPQ2)-NH2 | 1035 |
| 359 | NH2-K(FAM)EYNPRE(Nle) | Probe #359 | NH2-K(FAM)EYNPRE(Nle)GkK(CPQ2)-NH2 | 1036 |
| 360 | NH2-TK(FAM)EFVHNP | Probe #360 | NH2-TK(FAM)EFVHNPGkK(CPQ2)-NH2 | 1037 |
| 361 | NH2-K(FAM)TEFVHNP | Probe #361 | NH2-K(FAM)TEFVHNPGkK(CPQ2)-NH2 | 1038 |
| 362 | NH2-QK(FAM)KRVQFL | Probe #362 | NH2-QK(FAM)KRVQFLGK(CPQ2)-NH2 | 1039 |
| 363 | NH2-K(FAM)QKRVQFL | Probe #363 | NH2-K(FAM)QKRVQFLGK(CPQ2)-NH2 | 1040 |
| 364 | NH2-YK(FAM)LI(Nle)HKN | Probe #364 | NH2-YK(FAM)LI(Nle)HKNGK(CPQ2)-NH2 | 1041 |
| 365 | NH2-K(FAM)YLI(Nle)HKN | Probe #365 | NH2-K(FAM)YLI(Nle)HKNGK(CPQ2)-NH2 | 1042 |
| 366 | NH2-FK(FAM)WA(Nle)LYH | Probe #366 | NH2-FK(FAM)WA(Nle)LYHGkK(CPQ2)-NH2 | 1043 |
| 367 | NH2-K(FAM)FWA(Nle)LYH | Probe #367 | NH2-K(FAM)FWA(Nle)LYHGkK(CPQ2)-NH2 | 1044 |
| 368 | NH2-IK(FAM)AHDIVN | Probe #368 | NH2-IK(FAM)AHDIVNGkK(CPQ2)-NH2 | 1045 |
| 369 | NH2-K(FAM)IAHDIVN | Probe #369 | NH2-K(FAM)IAHDIVNGkK(CPQ2)-NH2 | 1046 |
| 370 | NH2-VK(FAM)SVFVIE | Probe #370 | NH2-VK(FAM)SVFVIEGK(CPQ2)-NH2 | 1047 |
| 371 | NH2-K(FAM)VSVFVIE | Probe #371 | NH2-K(FAM)VSVFVIEGK(CPQ2)-NH2 | 1048 |
| 372 | NH2-(Nle)K(FAM)PPSGLS | Probe #372 | NH2-(Nle)K(FAM)PPSGLSGK(CPQ2)-NH2 | 1049 |
| 373 | NH2-K(FAM)(Nle)PPSGLS | Probe #373 | NH2-K(FAM)(Nle)PPSGLSGK(CPQ2)-NH2 | 1050 |
| 374 | NH2-LK(FAM)RWYGGI | Probe #374 | NH2-LK(FAM)RWYGGIGkK(CPQ2)-NH2 | 1051 |
| 375 | NH2-K(FAM)LRWYGGI | Probe #375 | NH2-K(FAM)LRWYGGIGkK(CPQ2)-NH2 | 1052 |
| 376 | NH2-NK(FAM)QYVFF(Nle) | Probe #376 | NH2-NK(FAM)QYVFF(Nle)GK(CPQ2)-NH2 | 1053 |
| 377 | NH2-K(FAM)NQYVFF(Nle) | Probe #377 | NH2-K(FAM)NQYVFF(Nle)GK(CPQ2)-NH2 | 1054 |
| 378 | NH2-AK(FAM)FAKYYK | Probe #378 | NH2-AK(FAM)FAKYYKGK(CPQ2)-NH2 | 1055 |

TABLE 1-continued

Exemplary sequences for peptide linkers and corresponding probe construct designs

| SEQ ID NO | Sequence | Exemplary probe name | Exemplary probe construct | SEQ ID NOS |
|---|---|---|---|---|
| 379 | NH2-K(FAM)AFAKYYK | Probe #379 | NH2-K(FAM)AFAKYYKGK(CPQ2)-NH2 | 1056 |
| 380 | NH2-RK(FAM)QVKHFT | Probe #380 | NH2-RK(FAM)QVKHFTGK(CPQ2)-NH2 | 1057 |
| 381 | NH2-K(FAM)RQVKHFT | Probe #381 | NH2-K(FAM)RQVKHFTGK(CPQ2)-NH2 | 1058 |
|  | NH2-K(FAM)PP | Probe #382 | NH2-K(FAM)PPK(CPQ2)-NH2 | 1059 |
| 383 | kpilffrlk | Probe #383 | 5FAM-GkpilffrlkGK(CPQ2)-PEG2-kk-NH2 | 1060 |
|  | LRR | Probe #384 | Boc-Leu-Arg-Arg-AMC |  |
|  | R | Probe #385 | Arg-AMC |  |
|  | VR | Probe #386 | Boc-Val-Arg-AMC |  |
|  | RR | Probe #387 | Z-Arg-Arg-AMC |  |
|  | GR | Probe #388 | Gly-Arg-AMC |  |
|  | FR | Probe #389 | Z-Phe-Arg-AMC |  |
|  | RGK | Probe #390 | Ac-Arg-Gly-Lys-AMC |  |
|  | GGR | Probe #391 | Z-Gly-Gly-Arg-AMC | 1068 |
|  | F | Probe #392 | Glutaryl-Phe-AMC |  |
|  | D | Probe #393 | H-Asp-AMC |  |
|  | RR | Probe #394 | H-Arg-Arg-AMC |  |
|  | R | Probe #395 | Z-Arg-AMC |  |
|  | Bz-R | Probe #396 | Bz-Arg-AMC |  |
|  | Bz-R | Probe #397 | Bz-Arg-AMC |  |
|  | PR | Probe #398 | Z-Pro-Arg-AMC |  |
|  | GPR | Probe #399 | Z-Gly-Pro-Arg-AMC | 1075 |
|  | LR | Probe #400 | Z-Leu-Arg-AMC |  |
|  | PFR | Probe #401 | H-Pro-Phe-Arg-AMC |  |
|  | LLR | Probe #402 | Z-Leu-Leu-Arg-AMC | 1078 |
|  | QRR | Probe #403 | Boc-Gln-Arg-Arg-AMC |  |
|  | GR | Probe #404 | Glutaryl-Gly-Arg-AMC |  |
|  | GRR | Probe #405 | Boc-Gly-Arg-Arg-AMC |  |
| 406 | LRGG | Probe #406 | Z-Leu-Arg-Gly-Gly-AMC | 1082 |
| 407 | RLRGG | Probe #407 | 5-FAM-GRLRGGGK(CPQ2)-PEG2-kk-GC | 1083 & 1363 |
| 408 | RELNGGAPI | Probe #408 | 5-FAM-GRELNGGAPIGK(CPQ2)-PEG2-kk-GC | 1084 & 1363 |
| 409 | TSAVLQSGFRK | Probe #409 | 5-FAM-GTSAVLQSGFRKGK(CPQ2)-PEG2-kk-GC | 1085 & 1363 |
| 410 | SGVTFQGKFKK | Probe #410 | 5-FAM-GSGVTFQGKFKKGK(CPQ2)-PEG2-kk-GC | 1086 & 1363 |
| 411 | AAFA | Probe #411 | 5-FAM-GAAFAGK(CPQ2)-PEG2-kk-GC | 1087 & 1363 |

TABLE 1-continued

Exemplary sequences for peptide linkers and corresponding probe construct designs

| SEQ ID NO | Sequence | Exemplary probe name | Exemplary probe construct | SEQ ID NOS |
|---|---|---|---|---|
| 412 | HGDQMAQKS | Probe #412 | 5FAM-GHGDQMAQKS-K(CPQ2)-PEG2-DLys-DLys-GC-NH2 | 1088 & 1364 |
| 413 | GPLGMR | Probe #413 | 5FAM-GGPLGMRG-K(CPQ2)-PEG2-DLys-DLys-GC-NH2 | 1089 & 1364 |
| 414 | FFLAQA-HomoPhe-RSK | Probe #414 | 5FAM-GFFLAQA-HomoPhe-RSK-K(CPQ2)-PEG2-DLys-DLys-GC-NH2 | 1090 & 1364 |
| 415 | AHAVSRIRIYLLPAK | Probe #415 | 5FAM-GAHAVSRIRIYLLPAK-K(CPQ2)-PEG2-DLys-DLys-GC-NH2 | 1091 & 1364 |
| 416 | PLALWAR | Probe #416 | 5FAM-GPLALWAR-K(CPQ2)-PEG2-DLys-DLys-GC-NH2 | 1092 & 1364 |
| 417 | PLA-C(OMeBzl)-WAR | Probe #417 | 5FAM-GPLA-C(OMeBzl)-WAR-K(CPQ2)-PEG2-DLys-DLys-GC-NH2 | 1093 & 1364 |
| 418 | APRWIQD | Probe #418 | 5FAM-GAPRWIQD-K(CPQ2)-PEG2-DLys-DLys-GC-NH2 | 1094 & 1364 |
| 419 | LREQQRLKS | Probe #419 | 5FAM-GLREQQRLKS-K(CPQ2)-PEG2-DLys-DLys-GC-NH2 | 1095 & 1364 |
| 420 | EFPIYVFLPAKK | Probe #420 | 5FAM-GEFPIYVFLPAKK-K(CPQ2)-PEG2-DLys-DLys-GC-NH2 | 1096 & 1364 |
| 421 | GAANLVRGG | Probe #421 | 5FAM-GGAANLVRGG-K(CPQ2)-PEG2-DLys-DLys-GC-NH2 | 1097 & 1364 |
| 422 | GYAELRMG | Probe #422 | 5FAM-GGYAELRMGG-K(CPQ2)-PEG2-DLys-DLys-GC-NH2 | 1098 & 1364 |
| 423 | AAGAMFLEA | Probe #423 | 5FAM-GAAGAMFLEA-K(CPQ2)-PEG2-DLys-DLys-GC-NH2 | 1099 & 1364 |
| 424 | LGGSGQRGRKALE | Probe #424 | (FAM)-GLGGSGQRGRKALEG-K(CPQ2)-(PEG2)-DLys-DLys-GC | 1100 & 1363 |
| 425 | LGGSGHYGRSGLE | Probe #425 | (FAM)-GLGGSGHYGRSGLEG-K(CPQ2)-(PEG2)-DLys-DLys-GC | 1101 & 1363 |
| 426 | YGRS | Probe #426 | (FAM)-GYGRSG-K(CPQ2)-(PEG2)-DLys-DLys-GC | 1102 & 1363 |
| 427 | FRGRK | Probe #427 | (FAM)-GFRGRKG-K(CPQ2)-(PEG2)-DLys-DLys-GC | 1103 & 1363 |
| 428 | DRRKKLTQ | Probe #428 | (FAM)-GDRRKKLTQG-K(CPQ2)-(PEG2)-DLys-DLys-GC | 1104 & 1363 |
| 429 | HPGGPQ | Probe #429 | (FAM)-GHPGGPQG-K(CPQ2)-(PEG2)-DLys-DLys-GC | 1105 & 1363 |
| 430 | KLRFSKQ | Probe #430 | (FAM)-GKLRFSKQG-K(CPQ2)-(PEG2)-DLys-DLys-GC | 1106 & 1363 |
| 431 | AIKFFSAQ | Probe #431 | (FAM)-GAIKFFSAQG-K(CPQ2)-(PEG2)-DLys-DLys-GC | 1107 & 1363 |
| 432 | AIKFFVRQ | Probe #432 | (FAM)-GAIKFFVRQG-K(CPQ2)-(PEG2)-DLys-DLys-GC | 1108 & 1363 |
| 433 | RPPGFSAFK | Probe #433 | (FAM)-GRPPGFSAFKG-K(CPQ2)-(PEG2)-DLys-DLys-GC | 1109 & 1363 |
| 434 | FAP-QLS | Probe #434 | (FAM)-GFAP-QLSG-K(CPQ2)-(PEG2)-DLys-DLys-GC | 1110 & 1363 |
| 435 | FAA-QMA | Probe #435 | (FAM)-GFAA-QMAG-K(CPQ2)-(PEG2)-DLys-DLys-GC | 1111 & 1363 |

TABLE 1-continued

Exemplary sequences for peptide linkers and corresponding probe construct designs

| SEQ ID NO | Sequence | Exemplary probe name | Exemplary probe construct | SEQ ID NOS |
|---|---|---|---|---|
| 436 | GMP-ANQ | Probe #436 | (FAM)-GGMP-ANQG-K(CPQ2)-(PEG2)-DLys-DLys-GC | 1112 & 1363 |
| 437 | LSGRSDNH | Probe #437 | (FAM)-GLSGRSDNHG-K(CPQ2)-(PEG2)-DLys-DLys-GC | 1113 & 1363 |
| 438 | MAALITRPDF | Probe #438 | (FAM)-GMAALITRPDFG-K(CPQ2)-(PEG2)-DLys-DLys-GC | 1114 & 1363 |
| 439 | MAAAITRPRF | Probe #439 | (FAM)-GMAAAITRPRFG-K(CPQ2)-(PEG2)-DLys-DLys-GC | 1115 & 1363 |
| 440 | MAALIVRPDL | Probe #440 | (FAM)-GMAALIVRPDLG-K(CPQ2)-(PEG2)-DLys-DLys-GC | 1116 & 1363 |
| 441 | TSGPNQEQE | Probe #441 | (FAM)-GTSGPNQEQEG-K(CPQ2)-(PEG2)-DLys-DLys-GC | 1117 & 1363 |
| 442 | TAGPNQEQE | Probe #442 | (FAM)-GTAGPNQEQEG-K(CPQ2)-(PEG2)-DLys-DLys-GC | 1118 & 1363 |
| 443 | GPGPNQA | Probe #443 | (FAM)-GGPGPNQAG-K(CPQ2)-(PEG2)-DLys-DLys-GC | 1119 & 1363 |
| 444 | ASGPAGPA | Probe #444 | (FAM)-GASGPAGPAG-K(CPQ2)-(PEG2)-DLys-DLys-GC | 1120 & 1363 |
| 445 | ERGETGPSG | Probe #445 | (FAM)-GERGETGPSGG-K(CPQ2)-(PEG2)-DLys-DLys-GC | 1121 & 1363 |
| 446 | VSQELGQR | Probe #446 | (FAM)-GVSQELGQRG-K(CPQ2)-(PEG2)-DLys-DLys-GC | 1122 & 1363 |
| 447 | TGPPGYPTG | Probe #447 | (FAM)-GTGPPGYPTGG-K(CPQ2)-(PEG2)-DLys-DLys-GC | 1123 & 1363 |
| 448 | TRLPVYQ | Probe #448 | (FAM)-GTRLPVYQG-K(CPQ2)-(PEG2)-DLys-DLys-GC | 1124 & 1363 |
| 449 | RQARVVGG | Probe #449 | (FAM)-GRQARVVGGG-K(CPQ2)-(PEG2)-DLys-DLys-GC | 1125 & 1363 |
| 450 | RQRRVVGG | Probe #450 | (FAM)-GRQRRVVGGG-K(CPQ2)-(PEG2)-DLys-DLys-GC | 1126 & 1363 |
| 451 | RQARAVGG | Probe #451 | (FAM)-GRQARAVGGG-K(CPQ2)-(PEG2)-DLys-DLys-GC | 1127 & 1363 |
| 452 | RKRRGSRG | Probe #452 | (FAM)-GRKRRGSRGG-K(CPQ2)-(PEG2)-DLys-DLys-GC | 1128 & 1363 |
| 453 | KQSRKFVP | Probe #453 | (FAM)-GKQSRKFVPG-K(CPQ2)-(PEG2)-DLys-DLys-GC | 1129 & 1363 |
| 454 | VTGRS | Probe #454 | (FAM)-GVTGRSG-K(CPQ2)-(PEG2)-DLys-DLys-GC | 1130 & 1363 |
| 455 | LKSRVK | Probe #455 | (FAM)-GLKSRVKG-K(CPQ2)-(PEG2)-DLys-DLys-GC | 1131 & 1363 |
| 456 | GIGAVLKVLT | Probe #456 | (FAM)-GGIGAVLKVLTG-K(CPQ2)-(PEG2)-DLys-DLys-GC | 1132 & 1363 |
| 457 | GLPALISWIK | Probe #457 | (FAM)-GGLPALISWIKG-K(CPQ2)-(PEG2)-DLys-DLys-GC | 1133 & 1363 |
| 458 | SEVNLDAEF | Probe #458 | (FAM)-GSEVNLDAEFG-K(CPQ2)-(PEG2)-DLys-DLys-GC | 1134 & 1363 |
| 459 | EEKPICFFRLGKE | Probe #459 | (FAM)-GEEKPICFFRLGKEG-K(CPQ2)-(PEG2)-DLys-DLys-GC | 1135 & 1363 |

TABLE 1-continued

Exemplary sequences for peptide linkers and corresponding probe construct designs

| SEQ ID NO | Sequence | Exemplary probe name | Exemplary probe construct | SEQ ID NOS |
|---|---|---|---|---|
| 460 | EEKPILFFRLGKE | Probe #460 | (FAM)-GEEKPILFFRLGKEG-K(CPQ2)-(PEG2)-DLys-DLys-GC | 1136 & 1363 |
| 461 | APSSVIAA | Probe #461 | (FAM)-GAPSSVIAAG-K(CPQ2)-(PEG2)-DLys-DLys-GC | 1137 & 1363 |
| 462 | KKAKRNAL | Probe #462 | (FAM)-GKKAKRNALG-K(CPQ2)-(PEG2)-DLys-DLys-GC | 1138 & 1363 |
| 463 | WTNTSANYNL | Probe #463 | (FAM)-GWTNTSANYNLG-K(CPQ2)-(PEG2)-DLys-DLys-GC | 1139 & 1363 |
| 464 | RVRR | Probe #464 | (FAM)-GRVRRG-K(CPQ2)-(PEG2)-DLys-DLys-GC | 1140 & 1363 |
| 465 | ERTKR | Probe #465 | (FAM)-GERTKRG-K(CPQ2)-(PEG2)-DLys-DLys-GC | 1141 & 1363 |
| 466 | RYQIKPLKSTDE | Probe #466 | (FAM)-GRYQIKPLKSTDEG-K(CPQ2)-(PEG2)-DLys-DLys-GC | 1142 & 1363 |
| 467 | WELRHQA-(Hfe)-RSK | Probe #467 | (FAM)-GWELRHQA-(Hfe)-RSKG-K(CPQ2)-(PEG2)-DLys-DLys-GC | 1143 & 1363 |
| 468 | SGAFK-C(Me)-LKDGAG | Probe #468 | (FAM)-GSGAFK-C(Me)-LKDGAGG-K(CPQ2)-(PEG2)-DLys-DLys-GC | 1144 & 1363 |
| 469 | YVADGW | Probe #469 | (FAM)-GYVADGWG-K(CPQ2)-(PEG2)-DLys-DLys-GC | 1145 & 1363 |
| 470 | WEHDGW | Probe #470 | (FAM)-GWEHDGWG-K(CPQ2)-(PEG2)-DLys-DLys-GC | 1146 & 1363 |
| 471 | YVADAPV | Probe #471 | (FAM)-GYVADAPVG-K(CPQ2)-(PEG2)-DLys-DLys-GC | 1147 & 1363 |
| 472 | RPPGFSA | Probe #472 | (FAM)-GRPPGFSAG-K(CPQ2)-(PEG2)-DLys-DLys-GC | 1148 & 1363 |
| 473 | GSPAFLA | Probe #473 | (FAM)-GGSPAFLAG-K(CPQ2)-(PEG2)-DLys-DLys-GC | 1149 & 1363 |
| 474 | AGFSLPA | Probe #474 | (FAM)-GAGFSLPAG-K(CPQ2)-(PEG2)-DLys-DLys-GC | 1150 & 1363 |
| 475 | RWHTVGLRWE | Probe #475 | (FAM)-GRWHTVGLRWEG-K(CPQ2)-(PEG2)-DLys-DLys-GC | 1151 & 1363 |
|  | LEQ | Probe #476 | (FAM)-GLEQG-K(CPQ2)-(PEG2)-DLys-DLys-GC | 1152 & 1363 |
| 477 | RWPPMGLPWE | Probe #477 | (FAM)-GRWPPMGLPWEG-K(CPQ2)-(PEG2)-DLys-DLys-GC | 1153 & 1363 |
| 478 | RPKPVE | Probe #478 | (FAM)-GRPKPVEG-K(CPQ2)-(PEG2)-DLys-DLys-GC | 1154 & 1363 |
| 479 | IETD | Probe #479 | (FAM)-GIETDG-K(CPQ2)-(PEG2)-DLys-DLys-GC | 1155 & 1363 |
| 480 | VGPDFGR | Probe #480 | (FAM)-GVGPDFGRG-K(CPQ2)-(PEG2)-DLys-DLys-GC | 1156 & 1363 |
| 481 | GIEFDSGGC | Probe #481 | (FAM)-GGIEFDSGGCG-K(CPQ2)-(PEG2)-DLys-DLys-GC | 1157 & 1363 |
| 482 | GDFLRRV | Probe #482 | (FAM)-GGDFLRRVG-K(CPQ2)-(PEG2)-DLys-DLys-GC | 1158 & 1363 |
|  | AAL | Probe #483 | (FAM)-GAALG-K(CPQ2)-(PEG2)-DLys-DLys-GC | 1159 & 1363 |

TABLE 1-continued

Exemplary sequences for peptide linkers and corresponding probe construct designs

| SEQ ID NO | Sequence | Exemplary probe name | Exemplary probe construct | SEQ ID NOS |
|---|---|---|---|---|
| 484 | YATWSMIAAH | Probe #484 | (FAM)-GYATWSMIAAHG-K(CPQ2)-(PEG2)-DLys-DLys-GC | 1160 & 1363 |
| 485 | VIMWRLTVGT | Probe #485 | (FAM)-GVIMWRLTVGTG-K(CPQ2)-(PEG2)-DLys-DLys-GC | 1161 & 1363 |
| 486 | RRVLALQQEL | Probe #486 | (FAM)-GRRVLALQQELG-K(CPQ2)-(PEG2)-DLys-DLys-GC | 1162 & 1363 |
| 487 | LATWPLSGLW | Probe #487 | (FAM)-GLATWPLSGLWG-K(CPQ2)-(PEG2)-DLys-DLys-GC | 1163 & 1363 |
| 488 | NTPNWLVNAV | Probe #488 | (FAM)-GNTPNWLVNAVG-K(CPQ2)-(PEG2)-DLys-DLys-GC | 1164 & 1363 |
| 489 | SPLAQAVRSSSRK | Probe #489 | (FAM)-GSPLAQAVRSSSRKG-K(CPQ2)-(PEG2)-DLys-DLys-GC | 1165 & 1363 |
| 490 | QMPGRLSMAF | Probe #490 | (FAM)-GQMPGRLSMAFG-K(CPQ2)-(PEG2)-DLys-DLys-GC | 1166 & 1363 |
| 491 | PLGLR | Probe #491 | (FAM)-GPLGLRG-K(CPQ2)-(PEG2)-DLys-DLys-GC | 1167 & 1363 |
| 492 | QRANSIRVTW | Probe #492 | (FAM)-GQRANSIRVTWG-K(CPQ2)-(PEG2)-DLys-DLys-GC | 1168 & 1363 |
| 493 | PLAVR | Probe #493 | (FAM)-GPLAVRG-K(CPQ2)-(PEG2)-DLys-DLys-GC | 1169 & 1363 |
| 494 | LLAVPAANTV | Probe #494 | (FAM)-GLLAVPAANTVG-K(CPQ2)-(PEG2)-DLys-DLys-GC | 1170 & 1363 |
| 495 | GPQGLRGQ | Probe #495 | (FAM)-GGPQGLRGQG-K(CPQ2)-(PEG2)-DLys-DLys-GC | 1171 & 1363 |
| 496 | RTGLYLYNST | Probe #496 | (FAM)-GRTGLYLYNSTG-K(CPQ2)-(PEG2)-DLys-DLys-GC | 1172 & 1363 |
| 497 | RKKLTQSKFVGGAE | Probe #497 | (FAM)-GRKKLTQSKFVGGAEG-K(CPQ2)-(PEG2)-DLys-DLys-GC | 1173 & 1363 |
| 498 | KHYR | Probe #498 | (FAM)-GKHYRG-K(CPQ2)-(PEG2)-DLys-DLys-GC | 1174 & 1363 |
|  | QAR | Probe #499 | (FAM)-GQARG-K(CPQ2)-(PEG2)-DLys-DLys-GC | 1175 & 1363 |
| 500 | PRPFNYL | Probe #500 | (FAM)-GPRPFNYLG-K(CPQ2)-(PEG2)-DLys-GC | 1176 |
| 501 | APFEMSA | Probe #501 | (FAM)-GAPFEMSAG-K(CPQ2)-(PEG2)-DLys-DLys-GC | 1177 & 1363 |
| 502 | APFEFSA | Probe #502 | (FAM)-GAPFEFSAG-K(CPQ2)-(PEG2)-DLys-DLys-GC | 1178 & 1363 |
| 503 | PLGFRV | Probe #503 | (FAM)-GPLGFRVG-K(CPQ2)-(PEG2)-DLys-GC | 1179 |
| 504 | RPLALWRS | Probe #504 | (FAM)-GRPLALWRSG-K(CPQ2)-(PEG2)-GC | 1180 |
| 505 | RPLALEESQ | Probe #505 | (FAM)-GRPLALEESQG-K(CPQ2)-(PEG2)-DLys-GC | 1181 |
| 506 | RPLALWRSQ | Probe #506 | (FAM)-GRPLALWRSQG-K(CPQ2)-(PEG2)-GC | 1182 |
| 507 | RNALAVERTAS | Probe #507 | (FAM)-GRNALAVERTASG-K(CPQ2)-(PEG2)-GC | 1183 |
| 508 | RPKPQQFW | Probe #508 | (FAM)-GRPKPQQFWG-K(CPQ2)-(PEG2)-DLys-GC | 1184 |
| 509 | SGSNPYKYTA | Probe #509 | (FAM)-SGSNPYKYTA-K(CPQ2)-(PEG2)-DLys-DLys-GC | 1185 & 1363 |
| 510 | SGSNPYGYTA | Probe #510 | (FAM)-SGSNPYGYTA-K(CPQ2)-(PEG2)-DLys-DLys-GC | 1186 & 1363 |

TABLE 1-continued

Exemplary sequences for peptide linkers and corresponding probe construct designs

| SEQ ID NO | Sequence | Exemplary probe name | Exemplary probe construct | SEQ ID NOS |
|---|---|---|---|---|
| 511 | SGTLSELHTA | Probe #511 | (FAM)-SGTLSELHTA-K(CPQ2)-(PEG2)-DLys-DLys-GC | 1187 & 1363 |
| 512 | SGTISHLHTA | Probe #512 | (FAM)-SGTISHLHTA-K(CPQ2)-(PEG2)-DLys-DLys-GC | 1188 & 1363 |
| 513 | SG-(Orn)-RSHP-(Hfe)-TLYTA | Probe #513 | (FAM)-SG-(Orn)-RSHP-(Hfe)-TLYTA-K(CPQ2)-(PEG2)-DLys-GC | 1189 |
| 514 | SG-(Orn)-RSHG-(Hfe)-FLYTA | Probe #514 | (FAM)-SG-(Orn)-RSHG-(Hfe)-FLYTA-K(CPQ2)-(PEG2)-DLys-GC | 1190 |
| 515 | SGESLAYYTA | Probe #515 | (FAM)-SGESLAYYTA-K(CPQ2)-(PEG2)-DLys-DLys-GC | 1191 & 1363 |
| 516 | SGHMHAALTA | Probe #516 | (FAM)-SGHMHAALTA-K(CPQ2)-(PEG2)-DLys-DLys-GC | 1192 & 1363 |
| 517 | ILSR-(DIle)-VGG | Probe #517 | (FAM)-GILSR-(DIle)-VGG-K(CPQ2)-(PEG2)-DLys-GC | 1193 |
| 518 | ILS-(DArg)-(DIle)-(DVal)-GG | Probe #518 | (FAM)-GILS-(DArg)-(DIle)-(DVal)-GGG-K(CPQ2)-(PEG2)-DLys-GC | 1194 |
| 519 | RQRRALEK | Probe #519 | 5FAM-GRQRRALEKG-K(CPQ2)-PEG2-GC | 1195 |
| 520 | KPISLISS | Probe #520 | 5FAM-GKPISLISSG-K(CPQ2)-PEG2-GC | 1196 |
| 521 | QKGRYKQE | Probe #521 | 5FAM-GQKGRYKQEG-K(CPQ2)-PEG2-GC | 1197 |
| 522 | GPLGLRSW | Probe #522 | 5FAM-GGPLGLRSWK(CPQ2)-PEG2-C | 1198 |
| 523 | GPLGVRGK | Probe #523 | 5FAM-GGPLGVRGKK(CPQ2)-PEG2-C | 1199 |
| 524 | GfPRSGG | Probe #524 | 5FAM-GGfPRSGGGK(CPQ2)-PEG2-C | 1200 |
|  | Pyr | Probe #525 | Pyr-AMC |  |
|  | SY | Probe #526 | H-Ser-Tyr-AMC |  |
|  | GF | Probe #527 | H-Gly-Phe-AMC |  |
|  | Y | Probe #528 | H-Tyr-AMC |  |
|  | Cit | Probe #529 | H-Cit-AMC Hydrobromide salt |  |
|  | GP | Probe #530 | Suc-Gly-Pro-AMC |  |
|  | T | Probe #531 | H-Thr-AMC |  |
|  | I | Probe #532 | H-Ile-AMC |  |
|  | GA | Probe #533 | H-Gly-Ala-AMC hydrochloride salt |  |
|  | Cys(Bzl) | Probe #534 | H-Cys(Bzl)-AMC |  |
|  | A | Probe #535 | H-Ala-AMC |  |
|  | K | Probe #536 | Ac-Lys-AMC acetate salt |  |
|  | GLF | Probe #537 | MeOSuc-Gly-Leu-Phe-AMC |  |
|  | L | Probe #538 | H-Leu-AMC |  |
|  | VAN | Probe #539 | Z-Val-Ala-Asn-AMC | 1215 |
|  | AAA | Probe #540 | Suc-Ala-Ala-Ala-AMC |  |
|  | K | Probe #541 | H-Lys-AMC acetate salt |  |
|  | F | Probe #542 | H-Phe-AMC trifluoroacetate salt |  |
|  | FSR | Probe #543 | Boc-Phe-Ser-Arg-AMC |  |

TABLE 1-continued

Exemplary sequences for peptide
linkers and corresponding probe construct designs

| SEQ ID NO | Sequence | Exemplary probe name | Exemplary probe construct | SEQ ID NOS |
|---|---|---|---|---|
|  | VVR | Probe #544 | Z-Val-Val-Arg-AMC hydrochloride salt | 1220 |
|  | KA | Probe #545 | H-Lys-Ala-AMC hydrochloride salt |  |
|  | PR | Probe #546 | H-Pro-Arg-AMC hydrochloride salt |  |
|  | MGP | Probe #547 | H-Met-Gly-Pro-AMC hydrochloride salt |  |
|  | KP | Probe #548 | H-Lys-Pro-AMC hydrochloride salt |  |
|  | QGR | Probe #549 | Boc-Gln-Gly-Arg-AMC hydrochloride salt |  |
|  | Glu(OBzl)-AR | Probe #550 | Boc-Glu(OBzl)-Ala-Arg-AMC hydrochloride salt |  |
| 551 | WEHD | Probe #551 | Ac-Trp-Glu-His-Asp-AMC | 1227 |
|  | QAR | Probe #552 | Boc-Gln-Ala-Arg-AMC hydrochloride salt |  |
|  | AAF | Probe #553 | H-Ala-Ala-Phe-AMC (free base) |  |
|  | GPK | Probe #554 | Tos-Gly-Pro-Lys-AMC trifluoroacetate salt |  |
| 555 | AAPM | Probe #555 | MeOSuc-Ala-Ala-Pro-Met-AMC | 1231 |
| 556 | AEPF | Probe #556 | Suc-Ala-Glu-Pro-Phe-AMC | 1232 |
|  | GG | Probe #557 | H-Gly-Gly-AMC hydrochloride salt |  |
|  | VLK | Probe #558 | Boc-Val-Leu-Lys-AMC acetate salt |  |
|  | EKK | Probe #559 | Boc-Glu-Lys-Lys-AMC acetate salt |  |
|  | VPR | Probe #560 | Boc-Val-Pro-Arg-AMC hydrochloride salt |  |
|  | GKR | Probe #561 | Boc-Gly-Lys-Arg-AMC hydrochloride salt |  |
|  | Glu(OBzl)-GR | Probe #562 | Boc-Glu(OBzl)-Gly-Arg-AMC hydrochloride salt |  |
|  | LR | Probe #563 | Z-Leu-Arg-AMC hydrochloride salt |  |
|  | AFK | Probe #564 | MeOSuc-Ala-Phe-Lys-AMC trifluoroacetate salt |  |
|  | LGR | Probe #565 | Boc-Leu-Gly-Arg-AMC acetate salt |  |
|  | PFR | Probe #566 | H-Pro-Phe-Arg-AMC acetate salt |  |
| 567 | AAPV | Probe #567 | Suc-Ala-Ala-Pro-Val-AMC | 1243 |
|  | AFK | Probe #568 | H-Ala-Phe-Lys-AMC trifluoroacetate salt |  |
|  | VKM | Probe #569 | Z-Val-Lys-Met-AMC acetate salt | 1245 |
| 570 | GPLGP | Probe #570 | Suc-Gly-Pro-Leu-Gly-Pro-AMC | 1246 |
| 571 | KQKER | Probe #571 | Ac-Lys-Gln-Lys-Leu-Arg-AMC trifluoroacetate salt | 1247 |
| 572 | RVRR | Probe #572 | Boc-Arg-Val-Arg-Arg-AMC acetate salt | 1248 |
| 573 | IEGR | Probe #573 | Boc-Ile-Glu-Gly-Arg-AMC acetate salt | 1249 |
|  | GP | Probe #574 | H-Gly-Pro-AMC HBr |  |
| 575 | AAPV | Probe #575 | MeOSuc-Ala-Ala-Pro-Val-AMC | 1251 |
| 576 | RPFHLLVY | Probe #576 | Suc-Arg-Pro-Phe-His-Leu-Leu-Val-Tyr-AMC trifluoroacetate salt | 1252 |
| 577 | Anb-WS-Gnf-TVF | Probe #577 | H-Anb-Trp-Ser-Gnf-Thr-Val-Phe-AMC | 1253 |

TABLE 1-continued

Exemplary sequences for peptide linkers and corresponding probe construct designs

| SEQ ID NO | Sequence | Exemplary probe name | Exemplary probe construct | SEQ ID NOS |
|---|---|---|---|---|
| 578 | HSSKLQ | Probe #578 | Mu-His-Ser-Ser-Lys-Leu-Gln-AMC | 1254 |
|  | RPY | Probe #579 | MeO-Succ-Arg-Pro-Tyr-AMC |  |
| 580 | DRENSPK(Dnp)L-OH | Probe #580 | (ACC)-kkDRENSPK(Dnp)L | 1256 |
| 581 | kkDRENSPLK(Dnp)-OH | Probe #581 | (ACC)-kkDRENSPLK(Dnp) | 1257 |
| 582 | NAGSKFK(Dnp)Q-OH | Probe #582 | (ACC)-NAGSKFK(Dnp)Q | 1258 |
| 583 | NAGSKFQK(Dnp)-OH | Probe #583 | (ACC)-NAGSKFQK(Dnp) | 1259 |
| 584 | HLLGFYK(Dnp)V-OH | Probe #584 | (ACC)-kkHLLGFYK(Dnp)V | 1260 |
| 585 | HLLGFYVK(Dnp)-OH | Probe #585 | (ACC)-kkHLLGFYVK(Dnp) | 1261 |
| 586 | QEKQT(Nle)K(Dnp)(Nle)-OH | Probe #586 | (ACC)-kkQEKQT(Nle)K(Dnp)(Nle) | 1262 |
| 587 | QEKQT(Nle)(Nle)K(Dnp)-OH | Probe #587 | (ACC)-kkQEKQT(Nle)(Nle)K(Dnp) | 1263 |
| 588 | DPFVVSK(Dnp)W-OH | Probe #588 | (ACC)-kDPFVVSK(Dnp)W | 1264 |
| 589 | DPFVVSWK(Dnp)-OH | Probe #589 | (ACC)-kDPFVVSWK(Dnp) | 1265 |
| 590 | NAYNEIK(Dnp)R-OH | Probe #590 | (ACC)-NAYNEIK(Dnp)R | 1266 |
| 591 | NAYNEIRK(Dnp)-OH | Probe #591 | (ACC)-NAYNEIRK(Dnp) | 1267 |
| 592 | V(Nle)RQSEK(Dnp)N-OH | Probe #592 | (ACC)-V(Nle)RQSEK(Dnp)N | 1268 |
| 593 | V(Nle)RQSENK(Dnp)-OH | Probe #593 | (ACC)-V(Nle)RQSENK(Dnp) | 1269 |
| 594 | YNPRE(Nle)K(Dnp)I-OH | Probe #594 | (ACC)-YNPRE(Nle)K(Dnp)I | 1270 |
| 595 | YNPRE(Nle)IK(Dnp)-OH | Probe #595 | (ACC)-YNPRE(Nle)IK(Dnp) | 1271 |
| 596 | EFVHNPK(Dnp)K-OH | Probe #596 | (ACC)-kEFVHNPK(Dnp)K | 1272 |
| 597 | EFVHNPKK(Dnp)-OH | Probe #597 | (ACC)-kEFVHNPKK(Dnp) | 1273 |
| 598 | KRVQFLK(Dnp)H-OH | Probe #598 | (ACC)-KRVQFLK(Dnp)H | 1274 |
| 599 | KRVQFLHK(Dnp)-OH | Probe #599 | (ACC)-KRVQFLHK(Dnp) | 1275 |
| 600 | LI(Nle)HKNK(Dnp)G-OH | Probe #600 | (ACC)-kLI(Nle)HKNK(Dnp)G | 1276 |
| 601 | LI(Nle)HKNGK(Dnp)-OH | Probe #601 | (ACC)-kLI(Nle)HKNGK(Dnp) | 1277 |
| 602 | WA(Nle)LYHK(Dnp)S-OH | Probe #602 | (ACC)-kkWA(Nle)LYHK(Dnp)S | 1278 |

TABLE 1-continued

Exemplary sequences for peptide linkers and corresponding probe construct designs

| SEQ ID NO | Sequence | Exemplary probe name | Exemplary probe construct | SEQ ID NOS |
|---|---|---|---|---|
| 603 | WA(Nle)LYHSK(Dnp)-OH | Probe #603 | (ACC)-kkWA(Nle)LYHSK(Dnp) | 1279 |
| 604 | AHDIVNK(Dnp)Y-OH | Probe #604 | (ACC)-kkAHDIVNK(Dnp)Y | 1280 |
| 605 | AHDIVNYK(Dnp)-OH | Probe #605 | (ACC)-kkAHDIVNYK(Dnp) | 1281 |
| 606 | SVFVIEK(Dnp)P-OH | Probe #606 | (ACC)-kSVFVIEK(Dnp)P | 1282 |
| 607 | SVFVIEPK(Dnp)-OH | Probe #607 | (ACC)-kSVFVIEPK(Dnp) | 1283 |
| 608 | PPSGLSK(Dnp)E-OH | Probe #608 | (ACC)-kPPSGLSK(Dnp)E | 1284 |
| 609 | PPSGLSEK(Dnp)-OH | Probe #609 | (ACC)-kPPSGLSEK(Dnp) | 1285 |
| 610 | RWYGGIK(Dnp)F-OH | Probe #610 | (ACC)-kkRWYGGIK(Dnp)F | 1286 |
| 611 | RWYGGIFK(Dnp)-OH | Probe #611 | (ACC)-kkRWYGGIFK(Dnp) | 1287 |
| 612 | QYVFF(Nle)K(Dnp)D-OH | Probe #612 | (ACC)-kQYVFF(Nle)K(Dnp)D | 1288 |
| 613 | QYVFF(Nle)DK(Dnp)-OH | Probe #613 | (ACC)-kQYVFF(Nle)DK(Dnp) | 1289 |
| 614 | FAKYYKK(Dnp)T-OH | Probe #614 | (ACC)-kFAKYYKK(Dnp)T | 1290 |
| 615 | FAKYYKTK(Dnp)-OH | Probe #615 | (ACC)-kFAKYYKTK(Dnp) | 1291 |
| 616 | QVKHFTK(Dnp)A-OH | Probe #616 | (ACC)-kQVKHFTK(Dnp)A | 1292 |
| 617 | QVKHFTAK(Dnp)-OH | Probe #617 | (ACC)-kQVKHFTAK(Dnp) | 1293 |
| 618 | YVADAPK(Dnp)-OH | Probe #618 | (ACC)-kYVADAPK(Dnp) | 1294 |
| 619 | KGISSQY | Probe #619 | ACC-GKGISSQYK(Dnp)-NH2 | 1295 |
| 620 | ALPALQN | Probe #620 | ACC-GALPALQNK(Dnp)-PEG2-Dlys-Dlys-NH2 | 1296 |
| 621 | HRFRG | Probe #621 | ACC-GHRFRGK(Dnp)-NH2 | 1297 |
| 622 | APEEIMDQQ | Probe #622 | ACC-GAPEEIMDQQK(Dnp)-PEG2-Dlys-Dlys-NH2 | 1298 |
| 623 | SRKSQQY | Probe #623 | ACC-GSRKSQQYK(Dnp)-NH2 | 1299 |
| 624 | SKGRSLI | Probe #624 | ACC-GSKGRSLIGK(Dnp)-NH2 | 1300 |
| 625 | FAQSIPK | Probe #625 | ACC-GFAQSIPKK(Dnp)-PEG2-Dlys-Dlys-NH2 | 1301 |
| 626 | RQRRVVG | Probe #626 | ACC-GRQRRVVGGK(Dnp)-NH2 | 1302 |
| 627 | ERGETGPS | Probe #627 | ACC-GERGETGPSGK(Dnp)-NH2 | 1303 |
| 628 | ASGPSS | Probe #628 | ACC-GASGPSSGK(Dnp)-PEG2-Dlys-Dlys-NH2 | 1304 |
| 629 | YRFR | Probe #629 | ACC-GYRFRGK(Dnp)-NH2 | 1305 |
| 630 | KLFSSKQ | Probe #630 | ACC-GKLFSSKQK(Dnp)-NH2 | 1306 |
| 631 | IVPRG | Probe #631 | ACC-GIVPRGK(Dnp)-NH2 | 1307 |

TABLE 1-continued

Exemplary sequences for peptide linkers and corresponding probe construct designs

| SEQ ID NO | Sequence | Exemplary probe name | Exemplary probe construct | SEQ ID NOS |
|---|---|---|---|---|
| 632 | IRRSSYFK | Probe #632 | ACC-GIRRSSYFKK(Dnp)-NH2 | 1308 |
| 633 | His(Bzl)-Tle-PSD-Met(O) | Probe #633 | ACC-Gly-His(Bzl)-Tle-Pro-Ser-Asp-Met(O)-Gly-K(Dnp)-Gly-PEG2-Dlys-Dlys-NH2 | 1309 |
| 634 | Nva-IE-Oic-DFGR | Probe #634 | ACC-Nva-Ile-Glu-Oic-Asp-Phe-Gly-Arg-Lys(Dnp)-NH2 | 1310 |
|  | H-DThr-Phe(F5)-R | Probe #635 | Ac-His-DThr-Phe(F5)-Arg-ACC | 1311 |
|  | Dap-Orn-Phe(3Cl)-Cys(MeOBzl) | Probe #636 | Ac-Dap-Orn-Phe(3Cl)-Cys(MeOBzl)-ACC |  |
|  | Cha-L-hSer(Bzl)-R | Probe #637 | Ac-Cha-Leu-hSer(Bzl)-Arg-ACC |  |
| 638 | His(Bzl)-Tle-PSD-Met(O) | Probe #638 | ACC-Gly-His(Bzl)-Tle-Pro-Ser-Asp-Met(O)-Gly-K(Dnp)-Gly-PEG2-Dlys-Dlys-NH2 | 1309 |
|  | hCha-Phe(guan)-Oic-R | Probe #639 | Ac-hCha-Phe(guan)-Oic-Arg-ACC |  |
|  | Abu-Nle(O-Bzl) | Probe #640 | NH2-Abu-Nle(O-Bzl)-ACC |  |
|  | Nle(O-Bzl)-Met(O)2-Oic-Abu | Probe #641 | Ac-Nle(O-Bzl)-Met(O)2-Oic-Abu-ACC |  |
|  | Dap-Orn-Phe(3Cl)-Cys(MeOBz) | Probe #642 | ACC-G-Dap-Orn-Phe(3Cl)-Cys(MeOBz)-G-K(Dnp)-NH2 | 1317 |
|  | Cha-L-hSer-R | Probe #643 | ACC-Gly-Cha-Leu-hSer-Arg-Gly-K(Dnp)-NH2 | 1318 |
| 644 | FVT-Gnf-SW | Probe #644 | ACC-Phe-Val-Thr-Gnf-Ser-Trp-K(Dnp)-NH2 | 1319 |
|  | hCha-Phe(guan)-Oic-R | Probe #645 | ACC-Gly-hCha-Phe(guan)-Oic-Arg-Gly-K(Dnp)-NH2 | 1320 |
|  | Nle(OBz)-Met(O2)-Oic-Abu | Probe #646 | ACC-Gly-Nle(OBz)-Met(O2)-Oic-Abu-Gly-K(Dnp)-NH2 | 1321 |
| 647 | AIEPDSG | Probe #647 | 5FAM-GAIEPDSGG-Lys(CPQ2)-PEG2-Dlys-Dlys-GC-NH2 | 1322 & 1364 |
| 648 | AIEFDSG | Probe #648 | 5FAM-GAIEFDSGG-Lys(CPQ2)-Dlys-Dlys-GC-NH2 | 1323 |
| 649 | AAEAISD | Probe #649 | 5FAM-GGAAEAISDAK(CPQ2)-kk-PEG2-C | 1324 |
| 650 | AGGAQMGA | Probe #650 | 5FAM-GGAGGAQMGAK(CPQ2)-kk-PEG2-C | 1325 |
| 651 | AQPDALNV | Probe #651 | 5FAM-GGAQPDALNVK(CPQ2)-kk-PEG2-C | 1326 |
| 652 | ATDVTTTP | Probe #652 | 5FAM-GGATDVTTTPK(CPQ2)-kk-PEG2-C | 1327 |
| 653 | DIVTVANA | Probe #653 | 5FAM-GGDIVTVANAK(CPQ2)-kk-PEG2-C | 1328 |
| 654 | DLGLKSVP | Probe #654 | 5FAM-GGDLGLKSVPK(CPQ2)-kk-PEG2-C | 1329 |
| 655 | DVMASNKR | Probe #655 | 5FAM-GGDVMASNKRK(CPQ2)-kk-PEG2-C | 1330 |
| 656 | ESDELNTI | Probe #656 | 5FAM-GGESDELNTIK(CPQ2)-kk-PEG2-C | 1331 |
| 657 | FHPLHSKI | Probe #657 | 5FAM-GGFHPLHSKIK(CPQ2)-kk-PEG2-C | 1332 |
| 658 | HARLVHV | Probe #658 | 5FAM-GGGHARLVHVK(CPQ2)-kk-PEG2-C | 1333 |
| 659 | HIANVERV | Probe #659 | 5FAM-GGHIANVERVK(CPQ2)-kk-PEG2-C | 1334 |
| 660 | KAAATQKK | Probe #660 | 5FAM-GGKAAATQKKK(CPQ2)-kk-PEG2-C | 1335 |

TABLE 1-continued

Exemplary sequences for peptide linkers and corresponding probe construct designs

| SEQ ID NO | Sequence | Exemplary probe name | Exemplary probe construct | SEQ ID NOS |
|---|---|---|---|---|
| 661 | LATASTMD | Probe #661 | 5FAM-GGLATASTMDK(CPQ2)-kk-PEG2-C | 1336 |
| 662 | LGPKGQT | Probe #662 | 5FAM-GGLGPKGQTGK(CPQ2)-kk-PEG2-C | 1337 |
| 663 | LSLPETGE | Probe #663 | 5FAM-GGLSLPETGEK(CPQ2)-kk-PEG2-C | 1338 |
| 664 | NLAGILKE | Probe #664 | 5FAM-GGNLAGILKEK(CPQ2)-kk-PEG2-C | 1339 |
| 665 | NPGMSEPV | Probe #665 | 5FAM-GGNPGMSEPVK(CPQ2)-kk-PEG2-C | 1340 |
| 666 | PFGCHAK | Probe #666 | 5FAM-GGPFGCHAKK(CPQ2)-kk-PEG2-C | 1341 |
| 667 | PLGLRWW | Probe #667 | 5FAM-GGPLGLRWWK(CPQ2)-kk-PEG2-C | 1342 |
| 668 | QMGVMQGV | Probe #668 | 5FAM-GGQMGVMQGVK(CPQ2)-kk-PEG2-C | 1343 |
| 669 | QTCKCSCK | Probe #669 | 5FAM-GGQTCKCSCKK(CPQ2)-kk-PEG2-C | 1344 |
| 670 | QWAGLVEK | Probe #670 | 5FAM-GGQWAGLVEKK(CPQ2)-kk-PEG2-C | 1345 |
| 671 | RPAVMTSP | Probe #671 | 5FAM-GGRPAVMTSPK(CPQ2)-kk-PEG2-C | 1346 |
| 672 | TLRELHLD | Probe #672 | 5FAM-GGTLRELHLDK(CPQ2)-kk-PEG2-C | 1347 |
| 673 | TPPPSQGK | Probe #673 | 5FAM-GGTPPPSQGKK(CPQ2)-kk-PEG2-C | 1348 |
| 674 | TSEDLVVQ | Probe #674 | 5FAM-GGTSEDLVVQK(CPQ2)-kk-PEG2-C | 1349 |
| 675 | VWAAEAIS | Probe #675 | 5FAM-GGVWAAEAISK(CPQ2)-kk-PEG2-C | 1350 |
|  | R | Probe #676 | H-R-AMC |  |
|  | GC | Probe #677 | FAM-GGC-PEG8 |  |

Nle = norleucine
K(FAM) = carboxy-fluorescein-L-lysine
HomoPhe = Hfe = L-homophenylalanine
Cys(OMeBzl) = C(OMeBzl) = S-para-methoxybenzyl cysteine
DIle = d-isoleucine
DArg = D-arginine
DVal = D-valine
Pyr = pyroglutamic acid
Cit = citrulline
C(Bzl) = S-benzyl-L-cysteine
Glu(OBzl) = benzyl-L-glutamate
Anb = amino-n-butyric acid
Gnf = guamidine-L-phenylalanine
K(Dnp) = dinitrobenzylation of lysine
His(Bzl) = benzyl-L-histidine
Tle = L-tert-leucine
Met(O) = L-methionine-sulfoxide
Bz = Benzoyl
Oic = L-octahydroindole-2-carboxylic acid
Nva = norvaline (click to see farther down list)
DThr = d-threonine
Phe(F5) = 2,3,4,5,6-pentafluoro-L-penylalanine
Phe(3Cl) = 3-chloro-L-phenylalanine
hSer(Bzl) = benzyl homoserine
hCha = homocyclohexylalnine
Phe(guan) = phenylalanine derivative with a guanidine group in the para position
Nle(O-Bz) = Nle(OBz) = benzyloxy-L-norleucine
Met(O)2 = L-methionine sulfone
Dap = 2,3-diaminopropionic acid
hSer = homoserine
Met(O2) = methylsulfonylbutanoic acid
Abu = L-alpha-aminobutyric acid
Cha = L-cyclohexylalanine
Cys(Me) = L-Methyl cysteine
Orn = L-Ornithine
hF = L-Homophenylalanine
GABA = gamma aminobutyric acid
Pip = piperidine carboxylic acid
lower case = D-amino acids The peptide linkers described herein for endoproteases may follow a design: $X_mAY_n$ or $AX_nB$, wherein respectively, A is a single amino acid and A and B are amino acid pairs recognized by a particular endoprotease, X and Y are any amino acid labeled or not with a reporter, and m, n are zero or any integer. This design is for exemplification only and should not be construed as the only possible design for the peptide linker.

The peptide linkers described herein for exoproteases may follow a design: $X_mAY_n$, wherein A is amino acid pairs recognized by a particular exoprotease, X and Y are any amino acid labeled or not with a reporter, and n is zero or any integer. This design is for exemplification only and should not be construed as the only possible design for the peptide linker.

TABLE 2

Exemplary peptide linker designs.

| amino acid in P1' | amino acid in P1 | amino acid in P2 | amino acid in P3 | amino acid in P4 | Example probe name | Example prob design | SEQ ID NO | Protease family | Critical amino acid (single or pair) |
|---|---|---|---|---|---|---|---|---|---|
|  | R/K |  |  |  | Probe #161 | (FAM)-GWYKTQYGK(CPQ2)-NH2 | 1353 | Endo | Single |
|  | R/K |  |  |  | Probe #109 | (FAM)-GFARRWGGK(CPQ2)-PEG2-k-NH2 | 1354 | Endo | Single |
|  | F/Y/L/W |  |  |  | Probe #165 | (FAM)-GSYWP(Nle)QGK(CPQ2)-PEG2-k-NH2 | 1355 | Endo | Single |
|  | F/Y |  |  |  | Probe #140 | (FAM)-GFIY(Nle)PTGK(CPQ2)-PEG2-k-NH2 | 1356 | Endo | Single |
|  | P |  |  |  | Probe #148 | (FAM)-GTGPKGNGK(CPQ2)-NH2 | 825 | Endo | Single |
| F | K |  |  |  | Probe #217 | (FAM)-GWSKFW(Nle)GK(CPQ2) | 894 | Endo | Pair (AB) |
| D | G |  |  |  | Probe #194 | (FAM)-GKTGDARGK(CPQ2)-PEG2-k-NH2 | 871 | Endo | Pair (AB) |
| L | P |  |  |  | Probe #275 | (FAM)-GGHPLSPGK(CPQ2)-PEG2-kk-NH2 | 952 | Endo | Pair (AB) |
|  |  | D | T/I/V |  | Probe #297 | (FAM)-GVIDKDFGK(CPQ2)-NH2 | 1357 | Endo | Pair (AB) |
|  |  | R | K/R |  | Probe #109 | (FAM)-GFARRWGGK(CPQ2)-PEG2-k-NH2 | 1358 | Endo | Pair (AB) |
| S |  | R |  |  | Probe #204 | (FAM)-GPVRSTNGK(CPQ2)-NH2 | 881 | Endo | Pair (AB) |
|  |  | D |  | E | Probe #199 | (FAM)-GENDRLPGK(CPQ2)-NH2 | 876 | Endo | Pair (near neighbor AXB) |
|  |  | D |  | V | Probe #248 | (FAM)-GQWVDEDGK(CPQ2)-PEG2-k-NH2 | 925 | Endo | Pair (near neighbor AXXB) |
|  | K/R at C-terminus |  |  |  | Probe #321 | (FAM)-kGEFVHNPK(CPQ2)K-OH | 1359 | Exo | Single |
|  | K/R/H at C-terminus |  |  |  | Probe #315 | (FAM)-GNAYNEIK(CPQ2)R-OH | 1360 | Exo | Single |
|  | W/G/F at N-terminus |  |  |  | Probe #346 | NH2-WK(FAM)NAGSKFGkK(CPQ2)-NH2 | 1361 | Exo | Single |
|  | Q/K at N-terminus |  |  |  | Probe #362 | NH2-QK(FAM)KRVQFLGK(CPQ2)-NH2 | 1362 | Exo | Single |

In some embodiments, the cleavable linker may be a carbohydrate. Tung et al. reported a conjugate of β-galactoside and 7-hydroxy-9H-(1,3-dichloro-9,9-dimethylacridin-2-one), which has far-red fluorescence properties after a cleavage by β-galactosidase. Tung C H, Zeng Q, Shah K, Kim D E, Schellingerhout D, Weissleder R. In vivo imaging of beta-galactosidase activity using far red fluorescent switch. Cancer Res. 2004 Mar. 1; 64(5):1579-83. Ho et al. reported combining P3-galactosidase substrate with p-benzyloxycarbonyl as a self-immolative linker. β-D-Galactopyranoside, the substrate of β-galactosidase, was conjugated to an optical probe through a para-substituted benzyloxycarbonyl group (serves as a first self-immolative linker) and a glycine residue (serves as a quencher and a second self-immolative linker). Enzymatic cleavage of the β-D-Galactopyranoside triggered a series of spontaneous reactions that resulted in a release of optically active probe. Ho, N.-H., Weissleder, R. and Tung, C.-H. (2007), A Self-Immolative Reporter For β-Galactosidase Sensing. ChemBioChem, 8: 560-566. Some carbohydrate linkers are commercially available.

In some embodiments, the cleavable linker may be a nucleic acid. The effect of a DNA linker on the behavior of its conjugate both reduces the toxicity of the free drug by reducing its cell penetration, which is positive in case of premature deconjugation in the bloodstream and increases the off-target toxicity on low antigen-expressing cells, presumably due to nonspecific interaction of the nucleic acid-based linker with the cell surface. For example, in an antibody-drug conjugates, the antibody and drug can be non-covalently connected using complementary DNA linkers. Dovgan, I., Ehkirch, A., Lehot, V. et al. On the use of DNA as a linker in antibody-drug conjugates: synthesis, stability and in vitro potency. Sci Rep 10, 7691 (2020). Dovgan et al. disclosed a trastuzumab to be connected to monomethyl auristatin E (MMAE) through a 37-mer oligonucleotide.

In some embodiments, the cleavable linker may be a lipid. In some embodiments, the cleavable linker may be a phospholipid. The insertion of phospholipid groups between two fluorescent dyes or a dye/quencher pair allows the detection of phospholipase cleavage activity. In some embodiments, the cleavable linker may be a phosphodiester. The insertion of phosphodiester groups between two fluorescent dyes or a dye/quencher pair allows the detection of phosphodiesterase cleavage activity. In some embodiments, the lipid is directly attached to the fluorophore: once the covalent bond between the lipid and fluorophore is cleaved, the increase of fluorescent activity allows for the detection of the enzyme presence In some embodiments, the cleavable linker may be an ester. Ester groups are often cleaved by saponification. The reactivity of the ester to cleavage can be enhanced by the use of electron-withdrawing groups or stabilized by the use of auto-immolative spacers to precluded spontaneous hydrolysis. In chemical biology, ester-based cleavable compounds were initially used for protein purification and in structural biology. FRET-based probes were designed to image esterase activities.

In some embodiments, the cleavable linker may be a glycoside. For example, cellulase enzymes deconstruct cellulose to glucose, and are often comprised of glycosylated linkers connecting glycoside hydrolases (GHs) to carbohydrate-binding modules (CBMs).

In some embodiments, the cleavable linker may be a nucleophile/base sensitive linker. These can include, but are not limited to, halogen nucleophiles, oxygen nucleophiles, safety-catch linkers, thiol nucleophiles, nitrogen nucleophiles, and phenacyl ester derivatives.

In some embodiments, the cleavable linker may be sensitive to activity from all enzyme families, including but is not limited to oxidoreductases, transferases, hydrolases, lyases, isomerases, and ligases.

Fluoridolyzable linkers are widely used in organic chemistry as silicon-based protecting groups for alcohols. The high thermodynamic affinity of fluorine for silicon allows their removal in orthogonal and mild conditions using a fluorine source. In this reaction a fluoride ion reacts with silicon as nucleophilic species and the cleavage conditions depend on the steric hindrance of the silicon's alkyl group. Fluoride ions can also trigger bond cleavage due to their basic properties.

Oxygen nucleophiles include sulfone and ester linkers while safety-catch linkers allow greater control over the timing of the bond breakage, because the linker will remain stable until it is activated for cleavage by a chemical modification.

In secondary amine synthesis or solid phase synthesis, nitrobenzenesulfonamides are known to be cleaved with a thiol nucleophile, like b-mercaptoethanol. Cysteines can be modified by electron-deficient alkynes to form a vinyl sulfide linkage.

Displacement reactions involving a specific nitrogen species as a nucleophile can occur in mild cleavable conditions. These reactions can be classified into two groups; cleavage by aminolysis or exchange reaction. For aminolysis cleavage, examples include the cleavage of a malondialdehyde (MDA) indole derivative by either pyrrolidine or hydrazine, and the cleavage of an ester linker by hydroxylamine or hydrazine. Acylhydrazones44 and hydrazones45,156 can be used as cleavable linkers through transimination in a mildly acidic medium. An amine catalyst (e.g., aniline, p-anisidine or hydroxylamine) accelerates hydrolysis and enables the effective transition between stable and dynamic states, which is required for cleavage and exchange.

In some embodiments, the cleavable linker may be a reduction sensitive linker. Reduction sensitive linkages have been used in chemical biology for a long time and it is a commonly used class of cleavable linker. Examples of cleavable linkers sensitive to reductive conditions include: nitroreductases, disulfide bridges and azo compounds. Karan et al. reported a fluorescent probe to detect nitroreductase. Sanu Karan, Mi Young Cho, Hyunseung Lee, Hwunjae Lee, Hye Sun Park, Mahesh Sundararajan, Jonathan L. Sessler, and Kwan Soo Hong. Near-Infrared Fluorescent Probe Activated by Nitroreductase for In Vitro and In Vivo Hypoxic Tumor Detection. Journal of Medicinal Chemistry 2021 64 (6), 2971-2981. In naturally occurring proteins, disulfide bridges generally play a role in maintaining the protein structure. They are known to be efficiently and rapidly cleaved by mild reducing agents like dithiothreitol (DTT), b-mercaptoethanol or tris(2-carboxyethyl)phosphine (TCEP). In chemical biology, disulfide bridges have been used in a wide range of applications including functional and structural proteomics, drug delivery, tumor imaging, DNA and protein-DNA complex purifications. The disulfide-based cleavable linker is commonly used due to its straightforward synthesis and rapid cleavage. Azo linkers are very appealing to chemical biologists since they are able to undergo cleavage following treatment with sodium dithionite, a mild and potentially bio-orthogonal reducing agent. The azo compound is reduced into two aniline moieties via an electrochemical reduction mechanism and this allows the use of reducing agents that are commonly used in many biological protocols, such as TCEP, DTT. In chemical biology, azo compounds have been used to cross-link proteins for over a decade and more recently for protein affinity purification.

In some embodiments, the cleavable linker may be an electrophile/acid sensitive linker. Acid sensitive linkers can be combined with other type of linkers. For example, a first β-galactosidase cleavage of the β-D-Galactopyranoside triggers the self-immolation of a benzyloxycarbonyl group, resulting in a release of optically active probe. Ho, N.-H., Weissleder, R. and Tung, C.-H. (2007), A Self-Immolative Reporter For β-Galactosidase Sensing. ChemBioChem, 8: 560-566. Two different modes of electrophilic cleavage are used in chemical biology: acidic sensitive linkers that are sensitive to proton sources, and alkyl 2-(diphenylphosphino) benzoate derivatives sensitive to azide compounds. Proton sensitive bonds are among the most frequently used cleavable functions in organic chemistry; illustrated by the development of the BOC group which protects amines, or the Merrifield resin used in solid phase synthesis. In organic chemistry, the cleavage conditions that can be tolerated are very flexible regarding the acids' reagents, solvents, temperatures and pH. In contrast, biocompatible acid cleavable linkers must be responsive to minor changes in pH. Strong acidic conditions can lead to the denaturation of proteins and DNA. Biocompatible acid cleavable linkers are chosen for their instability near physiological pH and are often different from the classical protecting groups, which are cleaved with strong acids. Chemical reactions that can break or form bonds in water can be used as the basis of a cleavable linker, for example the Staudinger ligation. This reaction is proceeded by the nucleophilic attack of an alkyl 2-(diphenylphosphino)benzoate derivative on an azide, to form an aza-ylide intermediate. Then the ester traps the aza-ylide, which leads to the formation of an amide. In this process, the ester acts as a cleavable linker, and the azide as a bioorthogonal chemical agent, which guarantees a chemoselective and bioorthogonal cleavage.

In some embodiments, the cleavable linker may be a metal cleavable linker. Organometallic compounds are used to catalyze the modification of proteins containing non-natural amino acids, but their use as cleavage reagent in chemical biology has only been reported a few times. The allyl function is a commonly used protecting group for alcohols in organic synthesis and it is also used as a cleavable linker in DNA sequencing by synthesis Metal cleavable linkers were also used in the design of peptide nucleic acids (PNAs), which were developed for enzyme-independent DNA/RNA hybridization methods.

In some embodiments, the cleavable linker may be an oxidation sensitive linker. Sodium periodate is undoubtedly the most frequently used biocompatible oxidizing agent due to its ability to cleave vicinal diols to form two aldehydes compounds. One example of this type of cleavable linker consists of a vicinal diol with a tartaric acid spacer and two functional groups at both ends. Selenium based linkers also contain cleavable bonds sensitive to oxidizing agents, such as sodium periodate or N-chlorobenzenesulfonamide immobilized on polystyrene beads (iodo-beads). The trigger agent oxidizes the labile bond to selenium oxide, which is then cleaved directly via intramolecular b-elimination or rearrangement.

Reporter and Detection Methods

In some aspects, the probe/molecule described herein comprises a reporter. The reporter as described herein may be in any structure that may be capable of being detected by any method, including but not limited to fluorescent detection, spectroscopic detection, immunological detection or imaging detection. In some embodiments, the reporter may be a fluorescent label, a mass tag or a nucleic acid barcode.

In some embodiments, the reporter may be a fluorescent label. Labels, tags and probes containing small compounds such as florescence can be used to label proteins and nucleic acids. Bio-affinity towards other molecules (biotin, digoxygenin), enzymatic (AP, HRP) or chemiluminescent (esters or acridine) can be used as well. Genetically encoded markers like the fluorescent proteins of the GFP family have become a reporter of choice for gene expression studies and protein localization. In combination with subcellular tags, GFP can be used to label subcellular structures like synapses allowing novel approaches to study developmental processes like synapse formation. Other fluorescent labels include but are not limited to small organic dyes and lipophilic dyes. The fluorescence label may serve itself as the activity substrate without addition of linkers.

Some reporters are "internally quenched", thus does not require a quencher, wherein the cleavage of a bond linking the internally quenched fluorophore to the substrate linker directly yields a fluorescent molecule. Many described probes for proteases, esterases, peroxidases and others function this way.

In some embodiments, the reporter may be a mass tag. Mass tag reagents are designed to enable identification and quantitation of proteins in different samples using mass spectrometry (MS). Mass tagging reagents within a set typically have the same nominal mass (i.e., are isobaric) and chemical structure composed of an amine-reactive NHS ester group, a spacer arm (mass normalizer), and a mass reporter.

In some embodiments, the reporter may be a nucleic acid barcode. For example, DNA barcoding is a system for species identification focused on the use of a short, standardized genetic region acting as a "barcode" in a similar way that Universal Product Codes are used by supermarket scanners to distinguish commercial products.

In some embodiments, the reporter may be detected using a ligand binding assay. A ligand binding assay often involves a detection step, such as an ELISA, including fluorescent, colorimetric, bioluminescent and chemiluminescent ELISAs, a paper test strip or lateral flow assay, or a bead-based fluorescent assay. In some embodiments, a paper-based ELISA test may be used to detect the cleaved reporter in the fluid sample. The paper-based ELISA may be created inexpensively, such as by reflowing wax deposited from a commercial solid ink printer to create an array of test spots on a single piece of paper. When the solid ink is heated to a liquid or semi-liquid state, the printed wax permeates the paper, creating hydrophobic barriers. The space between the hydrophobic barriers may then be used as individual reaction wells. The ELISA assay may be performed by drying the detection antibody on the individual reaction wells, constituting test spots on the paper, followed by blocking and washing steps. Fluid from a sample taken from the subject may then be added to the test spots. Then, for example, a streptavidin alkaline phosphate (ALP) conjugate may be added to the test spots, as the detection antibody. Bound ALP may then be exposed to a color reacting agent, such as BCIP/NBT (5-bromo-4-chloro-3"-indolyphosphate p-toluidine salt/nitro-blue tetrazolium chloride), which causes a purple colored precipitate, indicating presence of the reporter.

In some embodiments, the reporter can be detected using volatile organic compounds. Volatile organic compounds may be detected by analysis platforms such as gas chromatography instrument, a breathalyzer, a mass spectrometer, or use of optical or acoustic sensors. Gas chromatography may be used to detect compounds that can be vaporized without decomposition (e.g., volatile organic compounds). A gas chromatography instrument includes a mobile phase (or moving phase) that is a carrier gas, for example, an inert gas such as helium or an unreactive gas such as nitrogen, and a stationary phase that is a microscopic layer of liquid or polymer on an inert solid support, inside a piece of glass or metal tubing called a column. The column is coated with the stationary phase and the gaseous compounds analyzed interact with the walls of the column, causing them to elute at different times (i.e., have varying retention times in the column). Compounds may be distinguished by their retention times.

Mass spectrometry and enrichment/chromatography methods may be used to separate and distinguish/detect cleaved from intact reporters used in the present invention based on differences in mass and or presence of a label. For example, enzymatic reactions can result in the fragmentation of a parent molecule resulting in a mass shift of the starting substrate, this can be exploited in different chromatography/enrichment methods such as size exclusion chromatography and affinity enrichments. In mass spectrometry, a sample is ionized, for example by bombarding it with electrons. The sample may be solid, liquid, or gas. By ionizing the sample, some of the sample's molecules are broken into charged fragments. These ions may then be separated according to their mass-to-charge ratio. This is often performed by accelerating the ions and subjecting them to an electric or magnetic field, where ions having the same mass-to-charge ratio will undergo the same amount of deflection. When deflected, the ions may be detected by a mechanism capable of detecting charged particles, for example, an electron multiplier. The detected results may be displayed as a spectrum of the relative abundance of detected ions as a function of the mass-to-charge ratio. The molecules in the sample can then be identified by correlating known masses, such as the mass of an entire molecule to the identified masses or through a characteristic fragmentation pattern.

When the reporter includes a nucleic acid, the reporter may be detected by various sequencing methods known in the art, for example, traditional Sanger sequencing methods or by next-generation sequencing (NGS). NGS generally refers to non-Sanger-based high throughput nucleic acid sequencing technologies, in which many (i.e., thousands, millions, or billions) of nucleic acid strands can be sequenced in parallel. Examples of such NGS sequencing includes platforms produced by Illumina (e.g., HiSeq, MiSeq, NextSeq, MiniSeq, and iSeq 100), Pacific Biosciences (e.g., Sequel and RSII), and Ion Torrent by ThermoFisher (e.g., Ion S5, Ion Proton, Ion PGM, and Ion Chef systems). It is understood that any suitable NGS sequencing platform may be used for NGS to detect nucleic acid of the detectable analyte as described herein.

Analysis may be performed directly on the biological sample or the detectable cleaved reporters may be purified to some degree first. For example, a purification step may involve isolating the detectable analyte from other components in the biological sample. Purification may include methods such as affinity chromatography. The isolated or purified detectable analyte does not need to be 100% pure or even substantially pure prior to analysis. Detecting the cleaved reporters may provide a qualitative assessment (e.g., whether the detectable cleaved reporters, and thus the predetermined protease is present or absent) or a quantitative assessment (e.g., the amount of the detectable cleaved reporters present) to indicate a comparative activity level of the predetermined proteases in the fluid sample. The quantitative value may be calculated by any means, such as, by determining the percent relative amount of each fraction present in the sample. Methods for making these types of calculations are known in the art.

The cleaved reporters may be detected by any detection method that may be suitable for the particular reporter. In some aspects, the detection method comprises fluorescent detection, spectroscopic detection, mass spectrometry, immunological detection or imaging detection. In some aspects, the detection method may be fluorescence resonance energy transfer (FRET).

In some embodiments, the detection method may be spectroscopic detection. Spectroscopic methods of detection are very commonly employed in ion chromatography (IC) and are second only to conductivity detection in their frequency of usage. These methods can be divided broadly into the categories of molecular spectroscopic techniques and atomic spectroscopic techniques. Molecular spectroscopy includes UV-visible spectrophotometry, refractive index measurements, and photoluminescence techniques (fluorescence and phosphorescence). Atomic spectroscopy includes atomic emission spectroscopy (using various excitation sources) and atomic absorption spectroscopy. Many of the spectroscopic detection methods can operate in a direct or indirect mode. The definitions of these terms are the same as those used to describe the electrochemical detection modes. That is, direct spectroscopic detection results when the solute ion has a greater value of the measured detection parameter than does the eluent ion. Indirect detection results when the reverse is true.

In some embodiments, the detection method may be mass spectrometry. Mass spectrometry (MS) is an analytical technique that is used to measure the mass-to-charge ratio of ions. The results are typically presented as a mass spectrum, a plot of intensity as a function of the mass-to-charge ratio.

In some embodiments, the detection method may be fluorescence resonance energy transfer (FRET). FRET (Fluorescence Resonance Energy Transfer) is a distance dependent dipole-dipole interaction without the emission of a photon, which results in the transfer of energy from an initially excited donor molecule to an acceptor molecule. It allows the detection of molecular interactions in the nanometer range. FRET peptides are labeled with a donor molecule and an acceptor (quencher) molecule. In most cases, the donor and acceptor pairs are two different dyes. The transferred energy from a fluorescent donor is converted into molecular vibrations if the acceptor is a non-fluorescent dye (quencher). When the FRET is terminated (by separating donor and acceptor), an increase of donor fluorescence can be detected. When both the donor and acceptor dyes are fluorescent, the transferred energy is emitted as light of longer wavelength so that the intensity ratio change of donor and acceptor fluorescence can be measured. In order for efficient FRET quenching to take place, the fluorophore and quencher molecules must be close to each other (approximately 10-100 Å) and the absorption spectrum of the quencher must overlap with the emission spectrum of the fluorophore.

Precipitating Fluorophore

In some aspects, the cleaved reporter may be a precipitating fluorophore. In some embodiments, the precipitating fluorophore may be HPQ, Cl-HPQ, HTPQ, HTPQA, HBPQ, or HQPQ.

In some embodiments, the precipitating fluorophore may be HPQ, also known as 2-(2″-hydroxyphenyl)-4(3H)-quinazolinone. HPQ is a small organic dye known for its classic luminescence mechanism through excited-state intramolecular proton transfer (ESIPT), shows strong light emission in the solid state, but no emission in solution. HPQ is found to be strictly insoluble in water and exhibits intense solid-state fluorescence similar to that of tetraphenyl ethylene. Moreover, its essential properties of insolubility and intense solid-state fluorescence can be countered and reversed, by prohibiting the establishment of an internal hydrogen bond between the imine nitrogen and phenolic hydroxyl group.

In some embodiments, the precipitating fluorophore may be Cl-HPQ. Cl-HPQ is released when HPQF, a water soluble and non-fluorescent molecule, reacts with furin. Cl-HPQ starts to precipitate near the enzyme activity site, and the precipitates emit bright solid-state fluorescence with more than 60-fold fluorescence enhancement. Li et al. In Situ Imaging of Furin Activity with a Highly Stable Probe by Releasing of Precipitating Fluorochrome. Anal. Chem. 2018, 90, 19, 11680-11687.

In some embodiments, the precipitating fluorophore may be HTPQ. HTPQ is found to be strictly insoluble in water and shows intense fluorescence in the solid state with maximum excitation and emission wavelengths at 410 nm and 550 nm respectively. This makes it far better suited to the use with a confocal microscope. The large Stokes shift of HTPQ contributes additional and highly desirable advantages: increased sensitivity, minimized background fluorescence and enhanced bioimaging contrast. Liu et al. In Situ Localization of Enzyme activity in Live Cells by a Molecular Probe Releasing a Precipitating Fluorochrome. Angew Chem Int Ed Engl. 2017 Sep. 18; 56(39):11788-11792.

In some embodiments, the precipitating fluorophore may be HTPQA. HTPQA is another enzyme-responsive fluorogenic probe derived from HTPQ. When converted by ALP, the probe releases free HTPQ which starts to precipitate after a very short delay; the precipitate emits bright solid-state fluorescence with more than 100-fold fluorescence enhancement.

In some embodiments, the precipitating fluorophore may be HBPQ. HBPQ is completely insoluble in water and shows strong yellow solid emission when excited with a 405 nm laser. Liu et al. Precipitated Fluorophore-Based Molecular Probe for In Situ Imaging of Aminopeptidase N in Living Cells and Tumors. Anal. Chem. 2021, 93, 16, 6463-6471, Publication Date: Apr. 14, 2021.

In some embodiments, the precipitating fluorophore may be HQPQ. HQPQ is, a novel solid-state fluorophore that is insoluble in water. Li et al. Precipitated Fluorophore-Based Probe for Accurate Detection of Mitochondrial Analytes. Anal. Chem. 2021, 93, 4, 2235-2243. Publication Date: Jan. 5, 2021.

The precipitating and non-precipitating fluorophores can be separated from the enzyme substrate by a self-immolative substrate to stabilize the initial probe and ensure that the enzymatic cleavage is transduced via the immolative spacer into the formation of the precipitating fluorophore or the non-internally quenched soluble fluorophore.

Fluorescent Quencher

In some aspects, the probe/molecule described herein comprises a fluorescent quencher. The fluorescent quencher as described herein may be in any structure that is capable of decreasing the fluorescence intensity of a given substance. In some embodiments, the fluorescent quencher may be BHQ0, BHQ1, BHQ2, BHQ3, BBQ650, ATTO 540Q, ATTO 580Q, ATTO 612Q, CPQ2, QSY-21, QSY-35, QSY-7, QSY-9, DABCYL (4-([4'-dimethylamino)phenyl]azo)benzoyl), Dnp (2,4-dinitrophenyl) or Eclipse®.

In some embodiments, the fluorescent quencher may be a BHQ quencher including, but not limited to, BHQ0, BHQ1, BHQ2, BHQ3, or BBQ650. BHQ, or black hole quencher, dyes work through a combination of FRET and static quenching to enable avoidance of the residual background signal common to fluorescing quenchers such as TAMRA, or low signal-to-noise ratio. The different types of BHQ dyes are used to quench different colored dyes with BHQ1 used to quench green and yellow dyes such as FAM, TET, or HEX and BHQ2 used for quenching orange and red dyes. BHQ dyes are true dark quenchers with no native emission due to their polyacromatic-azo backbone. Substituting electron-donating and withdrawing groups on the aromatic rings produces a complete series of quenchers with broad absorption curves that span the visible spectrum.

In some embodiments, the fluorescent quencher may be an ATTO quencher including, but not limited to ATTO 540Q, ATTO 580Q, or ATTO 612Q. ATTO quenchers have characteristic properties of strong absorption (high extinction coefficient) and high photo-stability. ATTO quenchers are often utilized as fluorescent quenchers on amine-labeled nucleotides for FRET experiments.

In some embodiments, the fluorescent quencher may be CPQ2. The quencher CPQ2 is often used as a pair with the fluorescent donor 5-carboxylfluorescein.

In some embodiments, the fluorescent quencher may be a QSY quencher including but not limited to QSY-21, QSY-35, QSY-7, or QSY-9. QSY probes are dark quenchers, substances that absorb excitation energy from a fluorophore and dissipate the energy as heat.

In some embodiments, the fluorescent quencher may be DABCYL (4-([4'-dimethylamino)phenyl]azo)benzoyl). DABCYL is one of the most popular acceptors for developing FRET-based nucleic acid probes and protease substrates. DABCYL dyes are often paired with EDANS in FRET-based fluorescent probes. DABCYL has a broad and intense visible absorption but no fluorescence.

In some embodiments, the fluorescent quencher may be Dnp (2,4-dinitrophenyl). Dnp is a stable quencher and its absorption spectrum does not change with pH, which makes this group a convenient marker for substrate quantitation in solutions.

In some embodiments, the fluorescent quencher may be Eclipse®. Eclipse® is a non-fluorescent chromophore and a dark quencher often used in dual-labelled probes. As dark quenchers, Eclipse® absorbs energy without emitting fluorescence. Eclipse® has an absorption range from 390 nm to 625 nm and is capable of effective performance in a wide range of colored FRET probes.

Carrier

In some aspects, the probe/molecule described herein comprises a carrier. The fluorescent quencher as described herein may be in any structure. In some embodiments, the carrier may be a native, labeled or synthetic protein, a synthetic chemical polymer of precisely known chemical composition or with a distribution around a mean molecular weight (e.g. a linear or branched PEG polymers), an oligonucleotide, a phosphorodiamidate morpholino oligomer (PMO), or a foldamer, a lipid, a lipid micelle, a nanoparticle (e.g., iron oxide, gold, and non-metallic nanoparticles), a solid support made of polystyrene, polypropylene or any other type of plastic or polymer. In some embodiments, the carrier may be a peptide longer than the peptide linker. A carrier can be covalently or non-covalently attached to the cleavable linker.

In some embodiments, the carrier may be a nanoparticle. The transport of insoluble drugs via nanoparticles is improving because of their small particle size. Nanoparticle carrier is a kind of sub-micro particle delivery system, which belongs to a nanoscale microscope. Drugs encapsulated in sub-particles can adjust the speed of drug release, increase the permeability of biofilm, change the distribution in vivo, and improve the bioavailability. Nanoparticles are solid colloidal particles ranging in size from 10 to 100 nm used as a core in functionalization systems. They are generally composed of natural or synthetic macromolecule substances and can be used as carriers for conducting or transporting drugs. Nanospheres and nanocapsules can be formed. The chemical materials of nanomaterials are chitosan, gelatin, branched polymers, carbon-based carriers, etc. Gold nanoparticles consist of a core of gold atoms that can be functionalized by addition of a monolayer of moieties containing a thiol (SH) group.

In some embodiments, the carrier may be a native, labeled or synthetic protein. Proteins can be used as carriers for the delivery of chemicals and biomolecular drugs, such as anticancer drugs and therapeutic proteins. Protein nanoparticles have several advantages as a drug delivery system, such as biodegradability, stability, surface modification of particles, ease of particle size control, and they have less problems associated with toxicity issues, such as immunogenicity. Protein nanoparticles can be generated using proteins, such as fibroins, albumin, gelatin, gliadine, legumin, 30Kc19, lipoprotein, and ferritin proteins, and are prepared through emulsion, electrospray, and desolvation methods. Hong S, Choi D W, Kim H N, Park C G, Lee W, Park H H. Protein-Based Nanoparticles as Drug Delivery Systems. Pharmaceutics. 2020; 12(7):604. Published 2020 Jun. 29. For example, albumin, a plasma protein with a molecular weight of 66 kDa, has been extensively investigated as a drug carrier In some embodiments, the carrier may be a synthetic chemical polymer. Polymeric nanoparticles have been extensively investigated as drug nanocarriers. Drug loading is achieved either by (i) entrapment of an aqueous drug phase using the polymer to form nanoscale structures such as cages and capsules or (ii) chemical linking of the drug molecules to the polymer backbone by means of a simple ester or amide bond that can be hydrolyzed in vivo. The most widely researched synthetic polymers include polylactide (PLA), poly(D,L-lactide-co-glycolide) (PLGA) and PEG. All three polymers are hydrolyzed in vivo and are biodegradable. Malam Y, Loizidou M, Seifalian A M. Liposomes and nanoparticles: nanosized vehicles for drug delivery in cancer. Trends Pharmacol Sci. 2009 Nov.; 30(11):592-9.

In some embodiments, the carrier may be a polyethylene glycol (PEG). PEG has been studied comprehensively as a carrier because it is soluble in both organic and hydrophilic solvents. Unlike many other synthetic polymers, PEG is relatively hydrophilic. Conjugation with PEG increases the solubility of hydrophobic molecules and prolongs the circulation time in the organism. PEG also minimizes the nonspecific absorption of a molecule, such as a drug, provides specific affinity toward the targeted tissue, and increases the drug accumulation in malignant tissue. PEG can be conjugated to other polymers to make them less hydrophobic (i.e., PEGylation). The changes in surface hydrophilicity prevent protein adsorption, thereby enabling cell adhesion and proliferation on biomaterial scaffolds. The PMO backbone is made of morpholino rings with phosphorodiamidate linkage, which protects them from nuclease degradation while still maintaining the complementary base pairing. The potential application of PMO-based antisense technology targeting bacterial pathogens is being explored for the development of a new class of antibacterial drugs. Panchal R G, Geller B L, Mellbye B, Lane D, Iversen P L, Bavari S. Peptide conjugated phosphorodiamidate morpholino oligomers increase survival of mice challenged with Ames Bacillus anthracis. Nucleic Acid Ther. 2012; 22(5): 316-322. Fluorescein-tagged Morpholinos combined with fluorescein-specific antibodies can be used as probes for in-situ hybridization to miRNAs.

In some embodiments, the carrier may be an oligonucleotide. Biostable, high-payload DNA nanoassemblies of various structures, including cage-like DNA nanostructure, DNA particles, DNA polypods, and DNA hydrogel, have been reported. Cage-like DNA structures hold drug molecules firmly inside the structure and leave a large space within the cavity. These DNA nanostructures use their unique structure to carry abundant CpG, and their biocompatibility and size advantages to enter immune cells to achieve immunotherapy for various diseases. Part of the DNA nanostructures can also achieve more effective treatment in conjunction with other functional components such as aPD1, RNA, TLR ligands. DNA-based nanoparticles, such as spherical nucleic acids, hybrid DNA-based nanoparticles, polypod-like DNA nanostructure, DNA hydrogels have been reported. Chi Q, Yang Z, Xu K, Wang C and Liang H (2020) DNA Nanostructure as an Efficient Drug Delivery Platform for Immunotherapy. Front. Pharmacol. 10:1585.

In some embodiments, the carrier may be a phosphorodiamidate Morpholino oligomer (PMO). Antisense phosphorodiamidate morpholino oligomers (PMOs) and their derivatives downregulate target gene expression in a sequence-dependent manner by interfering with the binding of ribosome to mRNA and thereby inhibiting protein translation.

In some embodiments, the carrier may be a lipid or a lipid micelle. The liposome bilayer can be composed of either synthetic or natural phospholipids. The predominant physical and chemical properties of a liposome are based on the net properties of the constituent phospholipids, including permeability, charge density and steric hindrance. The lipid bilayer closes in on itself due to interactions between water molecules and the hydrophobic phosphate groups of the phospholipids. This process of liposome formation is spontaneous because the amphiphilic phospholipids self-associate into bilayers. Drug loading into liposomes can be achieved through (i) liposome formation in an aqueous solution saturated with soluble drug; (ii) the use of organic solvents and solvent exchange mechanisms; (iii) the use of lipophilic drugs; and (iv) pH gradient methods. Malam Y, Loizidou M, Seifalian A M. Liposomes and nanoparticles: nanosized vehicles for drug delivery in cancer. Trends Pharmacol Sci. 2009 Nov. 30(11):592-9.

In some embodiments, the carrier may be a solid support made of polystyrene, polypropylene or any other type of plastic. For example, drug delivery properties of microporous polystyrene solid foams have been reported by Canal et al. These materials were obtained by polymerization in the continuous phase of highly concentrated emulsions prepared by the phase inversion temperature method. Their porosity, specific surface and surface topography are associated with drug incorporation and release characteristics. Canal, Cristina & Aparicio, Rosa & Vilchez, Alejandro & Esquena, Jordi & Garcia-Celma, Maria. (2012). Drug Delivery Properties of Macroporous Polystyrene Solid Foams. Journal of pharmacy & pharmaceutical sciences: a publication of the Canadian Society for Pharmaceutical Sciences, Société canadienne des sciences pharmaceutiques. 15. 197-207.

In some embodiments, the carrier may be a foldamer. Foldamer, is a folded oligomer or polymer with a well-defined conformation. The conformation of foldamers is highly predictable from their primary sequences, therefore, it is possible to arrange functional groups at target positions and it may be possible to design functional foldamers, such as for efficient cellular uptake. For example, Cell-penetrating peptide (CPP) foldamers are peptide-based foldamers equipped with cell membrane permeabilities. Peptide foldamers contain unnatural amino acids, non-proteinogenic amino acids, which make the peptide adopt a stable secondary structure, especially helical structures, even in short sequences. This property is helpful for the design of amphipathic CPPs with a stable helical structure. Furthermore, peptides containing unnatural amino acids generally exhibit resistance to hydrolysis by proteases, which are abundant throughout the body and in the cells. High stability of the peptide foldamers against enzymatic degradation can lead to their prolonged function in vivo. Makoto Oba, Cell-Penetrating Peptide Foldamers: Drug Delivery Tools. ChemBioChem 10.1002/cbic.201900204.

Self-Immolative Spacer

In some aspects, the probe/molecule described herein comprises a self-immolative spacer. In some embodiments, the self-immolative spacer comprise a disulfide, a p-amino benzyl alcohol, an a-quinone methide spacer, a hetheroaminebifuncional disulfide, a thiol-based pirydazinediones, a p-aminebenzyloxycarbonyl, a dipeptide, a Gly-Pro, a L-Phe-Sar, a trans-cyclooctene tetrazine, a ortho Hydroxy-protected Aryl sulfate, a phosphoramidate-based spacer, a hydroxybenzyl, a trimethyl carbamate, a quinone methide-based spacer, a cyclizing spacer, a Trimethyl lock, a 2-amino methyl piperidine or an ethylene diamine derived cyclizing spacer. Gonzaga et al. Perspective about self-immolative drug delivery systems. Journal of Pharmaceutical Sciences 109 (2020) 3262-3281.

Cleavage of the cleavable linker by a predetermined protease or enzyme makes the self-immolative spacer dissociate from the precipitating fluorescent or non-fluorescent reporter, thereby resulting in a detectable signal. The cleavable linker of the plurality of probes/molecules may be cleavable by a predetermined endoprotease in the body fluid sample resulting in auto immolation and reporter release or results in a protease substrate that can be cleaved by a predetermined exopeptidase. In some embodiments, the predetermined exopeptidase is added to the body fluid sample. In some embodiments, the predetermined exopeptidase cleaves the protease substrate, thereby causing the self-immolative spacer to dissociate from the precipitating fluorescent reporter, thereby resulting in a detectable signal.

Body Fluid Samples

Determination of the disease or condition is based on the rate of formation or amount of the released reporter detected in the body fluid sample. In some embodiments, the body fluid sample may be blood, serum, plasma, bone marrow fluid, lymphatic fluid, bile, amniotic fluid, mucosal fluid, saliva, urine, cerebrospinal fluid, synovial fluid, semen, ductal aspirate, feces, vaginal effluent, cyst fluid, tissue homogenate, tissue-derived fluid, lachrymal fluid and patient-derived cell line supernatant. In some embodiments, the body fluid sample comprises a rinse fluid. In some embodiments, the rinse fluid may be a mouthwash rinse, a bronchioalveolar rinse, a lavage fluid, a hair wash rinse, a nasal spray effluent, a swab of any bodily surface, orifice or organ structure applied to saline or any media or any derivatives thereof.

In some embodiments, the body fluid sample may be blood. Blood is a constantly circulating fluid providing the body with nutrition, oxygen, and waste removal. Blood is mostly liquid, with numerous cells and proteins suspended in it. Blood is made of several main factors including plasma, red blood cells, white blood cells, and platelets.

In some embodiments, the body fluid sample may be a plasma. Plasma is the liquid that remains when clotting is prevented with the addition of an anticoagulant. Serum is the conventional term in the art for the fluid that remains when clotting factors are removed from plasma. Anticoagulants are medicines that help prevent blood clots. Examples of anticoagulants include, but are not limited to, an ethylenediamine tetraacetic acid (EDTA), a citrate, a heparin, an oxalate, any salt, solvate, enantiomer, tautomer and geometric isomer thereof, or any mixtures thereof.

In some embodiments, the anticoagulant may be EDTA. The main property of EDTA, a polyprotic acid containing four carboxylic acid groups and two amine groups with lone pair electrons, is the ability to chelate or complex metal ions in 1:1 metal-EDTA complexes. Owing to its strong complexation with metal ions that are cofactors for enzymes, EDTA is widely used as a sequestering agent to prevent some enzyme reactions from occurring. When blood is collected with no additives within an appropriate container (blood tube), it clots fairly quickly. As calcium ions are necessary for this process, the specific association between the carboxylic groups of EDTA and calcium is a reliable solution to prevent clotting, stabilizing whole blood in a fluid form, as required for some laboratory analyses. Moreover, EDTA showed optimal extended stabilization of blood cells and particles. Three EDTA formulations can be employed as anticoagulants: $Na_2EDTA$, $K_2EDTA$ and $K_3EDTA$, choice of which mostly depends on the type of analyses to be performed.

In some embodiments, the anticoagulant may be a citrate. Citrate (C6H7O7) is a small negatively charged molecule with a molecular weight of 191 Daltons. Citrate can be used as the anticoagulant of choice for stored blood products, typically as acid citrate dextrose (ACD), (3.22% citrate, 112.9 mmol/l citrate, 123.6 mmol/l glucose, 224.4 mmol/l sodium and 114.2 mmol/l hydrogen ions), or trisodium citrate (TCA) $Na_3C_3H_5O(COO)_3$, (4% TCA, 136 mmol/l citrate, 420 mmol/l sodium). Citrate chelates calcium, and at a concentration of 4-6 mmol/l with an ionized calcium of <0.2 mmol/l prevents activation of both coagulation cascades and platelets. As such, citrate has been the standard anticoagulant used by hematologists and blood transfusion services for stored blood products and also as an extracorporeal anticoagulant for centrifugal platelet and leucopheresis techniques and plasma exchange.

In some embodiments, the anticoagulant may be a heparin. The molecular basis for the anticoagulant action of heparin lies in its ability to bind to and enhance the inhibitory activity of the plasma protein antithrombin against several serine proteases of the coagulation system, most importantly factors IIa (thrombin), Xa and IXa. Two major mechanisms underlie heparin's potentiation of antithrombin. The conformational changes induced by heparin binding cause both expulsion of the reactive loop and exposure of exosites of the surface of antithrombin, which bind directly to the enzyme target; and a template mechanism exists in which both inhibitor and enzyme bind to the same heparin molecule. The relative importance of these two modes of action varies between enzymes. In addition, heparin can act through other serine protease inhibitors such as heparin co-factor II, protein C inhibitor and tissue factor plasminogen inhibitor. The antithrombotic action of heparin in vivo, though dominated by anticoagulant mechanisms, is more complex, and interactions with other plasma proteins and cells play significant roles in the living vasculature.

In some embodiments, the anticoagulant may be an oxalate. Sodium, potassium, ammonium, and lithium oxalates inhibit blood coagulation by forming insoluble complex with calcium. Potassium oxalate at concentration of 1-2 mg/ml of blood is widely used. Combined ammonium and/or potassium oxalate does not cause shrinkage of erythrocytes. It consists of three parts by weight of ammonium oxalate, which causes swelling of the erythrocytes, balanced by two parts of potassium oxalate which causes shrinkage. NH4+& K+ oxalate mixture in the ratio of 3:2, and 2 mg/ml of blood is the required amount.

In some embodiments, the body fluid sample may be bone marrow fluid. Bone marrow is found in the center of most bones and has many blood vessels. There are two types of bone marrow: red and yellow. Red marrow contains blood stem cells that can become red blood cells, white blood cells, or platelets. Yellow marrow is made mostly of fat.

In some embodiments, the body fluid sample may be lymphatic fluid. Lymphatic fluid, also called lymph, is a collection of the extra fluid that drains from cells and tissues, that is not reabsorbed into the capillaries.

In some embodiments, the body fluid sample may be bile. Bile is a digestive fluid produced by the liver and stored in the gallbladder. During bile reflux, digestive fluid backs up into the stomach and, in some cases, the esophagus.

In some embodiments, the body fluid sample may be amniotic fluid. Amniotic fluid is a clear, slightly yellowish liquid that surrounds the unborn baby (fetus) during pregnancy. It is contained in the amniotic sac.

In some embodiments, the body fluid sample may be mucosal fluid. Mucosal fluid, also called mucus, is a thick protective fluid that is secreted by mucous membranes and used to stop pathogens and dirt from entering the body. Mucus is also used to prevent bodily tissues from being dehydrated.

In some embodiments, the body fluid sample may be saliva. Saliva is an extracellular fluid produced and secreted by salivary glands in the mouth.

In some embodiments, the body fluid sample may be urine. Urine is a liquid by-product of metabolism in humans and in many other animals. Urine flows from the kidneys through the ureters to the urinary bladder.

In some embodiments, the body fluid sample may be cerebrospinal fluid. Cerebrospinal fluid is a clear fluid that surrounds the brain and spinal cord. It cushions the brain and spinal cord from injury and also serves as a nutrient delivery and waste removal system for the brain In some embodiments, the body fluid sample may be synovial fluid. Synovial fluid, also known as joint fluid, is a thick liquid located between your joints. The fluid cushions the ends of bones and reduces friction when joints are moved.

In some embodiments, the body fluid sample may be semen. Semen is the male reproductive fluid which contains spermatozoa in suspension.

In some embodiments, the body fluid sample may be ductal aspirate. Ductal aspirate, also known as ductal lavage, ductal fluid, or lavage fluid, is fluid collected from a duct, such as the milk duct of the breast.

In some embodiments, the body fluid sample may be feces. Feces, also known as excrement or stool is waste matter discharged from the bowels after food has been digested.

In some embodiments, the body fluid sample may be vaginal effluent. Vaginal effluent, also known as vaginal discharge, is a clear or whitish fluid that comes out of the vagina.

In some embodiments, the body fluid sample may be lachrymal fluid. Lachrymal fluid, also known as lacrimal fluid, is secreted by the lacrimal glands to lubricate the eye and fight bacteria.

In some embodiments, the body fluid sample may be tissue homogenate. A tissue homogenate is obtained through mechanical micro-disruption of fresh tissue and the cell membranes are mechanically permeabilized.

Proteases and Other Agents

The probe/molecule described herein may be cleaved by a protease from the body fluid. In some embodiments, the protease comprises an endopeptidase or an exopeptidase.

In some embodiments, the protease comprises an endopeptidase. An endopeptidase is an enzyme which breaks peptide bonds other than terminal ones in a peptide chain.

In some embodiments, the protease comprises an exopeptidase. An exopeptidase is an enzyme that catalyzes the cleavage of the terminal or penultimate peptide bond; the process releases a single amino acid or dipeptide from the peptide chain.

In some embodiments, the protease comprises an A20 (TNFa-induced protein 3), an abhydrolase domain containing 4, an abhydrolase domain containing 12, an abhydrolase domain containing 12B, an abhydrolase domain containing 13, an acrosin, an acylaminoacyl-peptidase, a disintegrin and metalloproteinase (ADAM), an ADAM1a, an ADAM2 (Fertilin-b), an ADAM3B, an ADAM4, an ADAM4B, an ADAM5, an ADAM6, an ADAM7, an ADAM8, an ADAM9, an ADAM10, an ADAM11, an ADAM12 metalloprotease, an ADAM15, an ADAM17, an ADAM18, an ADAM19, an ADAM20, an ADAM21, an ADAM22, an ADAM23, an ADAM28, an ADAM29, an ADAM30, an ADAM32, an ADAM33, a disintegrin and metalloproteinase with thrombospondin motifs (ADAMTS), an ADAMTS1, an ADAMTS2, an ADAMTS3, an ADAMTS4, an ADAMTS5/11, an ADAMTS6, an ADAMTS7, an ADAMTS8, an ADAMTS9, an ADAMTS10, an ADAMTS12, an ADAMTS13, an ADAMTS14, an ADAMTS15, an ADAMTS16, an ADAMTS17, an ADAMTS18, an ADAMTS19, an ADAMTS20, an adipocyte-enh. binding protein 1, an Afg3-like protein 1, an Afg3-like protein 2, an airway-trypsin-like protease, an aminoacylase, an aminopeptidase A, an aminopeptidase B, an aminopeptidase B-like 1, an aminopeptidase MAMS/L-RAP, an aminopeptidase N, an aminopeptidase O, an aminopeptidase P homologue, an aminopeptidase P1, an aminopeptidase PILS, an aminopeptidase Q, an aminopeptidase-like 1, an AMSH/STAMBP, an AMSH-LP/STAMBPL1, an angiotensin-converting enzyme 1 (ACE1), an angiotensin-converting enzyme 2 (ACE2), an angiotensin-converting enzyme 3 (ACE3), an anionic trypsin (II), an apolipoprotein (a), an archaemetzincin-1, an archaemetzincin-2, an aspartoacylase, an aspartoacylase-3, an aspartyl aminopeptidase, an ataxin-3, an ataxin-3 like, an ATP/GTP binding protein 1, an ATP/GTP binding protein-like 2, an ATP/GTP binding protein-like 3, an ATP/GTP binding protein-like 4, an ATP/GTP binding protein-like 5, an ATP23 peptidase, an autophagin-1, an autophagin-2, an autophagin-3, an autophagin-4, an azurocidin, or a combination hereof.

In some embodiments, the protease comprises a beta lactamase, a beta-secretase 1, a beta-secretase 2, a bleomycin hydrolase, a brain serine proteinase 2, a BRCC36 (BRCA2-containing complex, sub 3), a calpain, a calpain 1, a calpain 2, a calpain 3, a calpain 4, a calpain 5, a calpain 6, a calpain 7, a calpain 7-like, a calpain 8, a calpain 9, a calpain 10, a calpain 11, a calpain 12, a calpain 13, a calpain 14, a calpain 15 (Solh protein), or a combination hereof.

In some embodiments, the protease comprises a cysteine protease, a carboxypeptidase A1, a carboxypeptidase A2, a carboxypeptidase A3, a carboxypeptidase A4, a carboxypeptidase A5, a carboxypeptidase A6, a carboxypeptidase B, a carboxypeptidase D, a carboxypeptidase E, a carboxypeptidase M, a carboxypeptidase N, a carboxypeptidase O, a carboxypeptidase U, a carboxypeptidase X1, a carboxypeptidase X2, a carboxypeptidase Z, a carnosine dipeptidase 1, a carnosine dipeptidase 2, a caspase recruitment domain family, member 8, a caspase, a caspase-1, a caspase-2, a caspase-3, a caspase-4/11, a caspase-5, a caspase-6, a caspase-7, a caspase-8, a caspase-9, a caspase-10, a caspase-12, a caspase-14, a caspase-14-like, a casper/FLIP, a cathepsin, a cathepsin A (CTSA), a cathepsin B (CTSB), a cathepsin C (CTSC), a cathepsin D (CTSD), a cathepsin E (CTSE), a cathepsin F, a cathepsin G, a cathepsin H (CTSH), a cathepsin K (CTSK), a cathepsin L (CTSL), a cathepsin L2, a cathepsin O, a cathepsin S (CTSS), a cathepsin V (CTSV), a cathepsin W, a cathepsin Z (CTSZ), a cationic trypsin, a cezanne/OTU domain containing 7B, a cezanne-2, a CGI-58, a chymase, a chymopasin, a chymosin, a chymotrypsin B, a chymotrypsin C, a coagulation factor IXa, a coagulation factor VIIa, a coagulation factor Xa, a coagulation factor XIa, a coagulation factor XIIa, a collagenase 1, a collagenase 2, a collagenase 3, a complement protease C1r serine protease, a complement protease C1s serine protease, a complement C1r-homolog, a complement component 2, a complement component C1ra, a complement component C1sa, a complement factor B, a complement factor D, a complement factor D-like, a complement factor I, a COPS6, a corin, a CSN5 (JAB1), a cylindromatosis protein, a cytosol alanyl aminopep.-like 1, a cytosol alanyl aminopeptidase, or a combination hereof.

In some embodiments, the protease comprises a DDI-related protease, a DECYSIN, a Der1-like domain family, member 1, a Der1-like domain family, member 2, a Der1-like domain family, member 3, a DESC1 protease, a desert hedgehog protein, a desumoylating isopeptidase 1, a desumoylating isopeptidase 2, a dihydroorotase, a dihydropyrimidinase, a dihydropyrimidinase-related protein 1, a dihydropyrimidinase-related protein 2, a dihydropyrimidinase-related protein 3, a dihydropyrimidinase-related protein 4, a dihydropyrimidinase-related protein 5, a DINE peptidase, a dipeptidyl peptidase (DPP), a dipeptidyl peptidase (DPP1), a dipeptidyl-peptidase 4 (DPP4), a dipeptidyl-peptidase 6 (DPP6), a dipeptidyl-peptidase 8 (DPP8), a dipeptidyl-peptidase 9 (DPP9), a dipeptidyl-peptidase II, a dipeptidyl-peptidase III, a dipeptidyl-peptidase 10 (DPP10), a DJ-1, a DNA-damage inducible protein, a DNA-damage inducible protein 2, a DUB-1, a DUB-2, a DUB2a, a DUB2a-like, a DUB2a-like2, a DUB6, or a combination hereof.

In some embodiments, the protease comprises an enamelysin, an endopeptidase C1p, an endoplasmic reticulum metallopeptidase 1, an endothelin-converting enzyme 1, an endothelin-converting enzyme 2, an enteropeptidase, an epidermis-specific SP-like, an epilysin, an epithelial cell transforming sequence 2 oncogene-like, an epitheliasin, an epoxide hydrolase, an epoxyde hydrolase related protein, an eukar. translation initiation F3SF, an eukar. translation initiation F3SH, or a combination hereof.

In some embodiments, the protease comprises a Factor VII activating protease, a FACE-1/ZMPSTE24, a FACE-2/RCE1, a family with sequence similarity 108, member A1, a family with sequence similarity 108, member B1, a family with sequence similarity 108, member C1, a family with sequence similarity 111, A, a family with sequence similarity 111, B, a furin, or a combination hereof.

In some embodiments, the protease comprises a gamma-glutamyl hydrolase, a gamma-glutamyltransferase 1, a gamma-glutamyltransferase 2, a gamma-glutamyltransferase 5, a gamma-glutamyltransferase 6, a gamma-glutamyltransferase m-3, a gamma-glutamyltransferase-like 3, a GCDFP15, a gelatinase A, a gelatinase B, a Gln-fructose-6-P transamidase 1, a Gln-fructose-6-P transamidase 2, a Gln-fructose-6-P transamidase 3, a Gln-PRPP amidotransferase, a glutamate carboxypeptidase II, a glutaminyl cyclase, a glutaminyl cyclase 2, a glycosylasparaginase, a glycosylasparaginase-2, a granzyme, a granzyme A, a granzyme B, a granzyme H, a granzyme K, a granzyme M, a haptoglobin-1, or a combination hereof.

In some embodiments, the protease comprises a histone deacetylase (HDAC), a haptoglobin-related protein, a HAT-like 2, a HAT-like 3, a HAT-like 4, a HAT-like 5, a HAT-related protease, HSP90AA1? (a heat shock 90 kDa protein 1, alpha), HSP90AB1? (a heat shock 90 kDa protein 1, beta), a heat shock protein 75, a heat shock protein 90 kDa beta (Grp94), member 1/tumor rejection antigen (gp96), a hepatocyte growth factor, a hepsin, a HetF-like, a HGF activator, a hGPI8, a Hin-1/OTU domain containing 4, a homologue ICEY, a HP43.8KD, a HTRA1 serine protease, a HTRA2, a HTRA3, a HTRA4, a hyaluronan-binding ser-protease, a implantation serine protease 2, a indian hedgehog protein, a insulysin, a intestinal serine protease 1, a josephin-1, a josephin-2, or a combination hereof.

In some embodiments, the protease comprises a Kallikrein (KLK), a kallikrein hK1, a kallikrein hK2, a kallikrein hK3, a kallikrein hK4, a kallikrein hK5, a kallikrein hK6, a kallikrein hK7, a kallikrein hK8, a kallikrein hK9, a kallikrein hK10, a kallikrein hK11, a kallikrein hK12, a kallikrein hK13, a kallikrein hK14, a kallikrein hK15, a Kell blood-group protein, a KHNYN KH and NYN domain containing, a lactotransferrin, a legumain, a leishmanolysin-2, a leucyl aminopeptidase, a leucyl-cystinyl aminopeptidase, a leukotriene A4 hydrolase, a lysosomal carboxypeptidase A, a lysosomal Pro-X C-peptidase, or a combination hereof.

In some embodiments, the protease comprises a membrane metallo-endopeptidase (MME), a macrophage elastase, a macrophage-stimulating protein, a mammalian tolloid-like 1 protein, a mammalian tolloid-like 2 protein, a MAP1D methione aminopeptidase 1D, a marapsin, a marapsin 2, a MASP1/3 (a MBL associated serine protease 3), a MBL associated serine protease 2 (MASP2), a mastin, a matrilysin, a matrilysin-2, a matriptase, a matriptase-2, a matriptase-3, a membrane dipeptidase, a membrane dipeptidase 2, a membrane dipeptidase 3, a membrane-type mosaic Ser-protein, a meprin alpha subunit, a meprin beta subunit, a mesoderm-specific transcript, a mesotrypsin, a methionyl aminopeptidase I, a methionyl aminopeptidase II, a methionyl aminopeptidase II-like, a mitochondrial inner membrane protease 2, a mitochondrial Intermediate peptidase, a mitochondrial Proc. peptidase b-subunit, a mitochondrial proc. protease, a mitochondrial signal peptidase, a matrix metalloproteinase (MMP), a MMP19, a MMP21, a MMP23A, a MMP23B, a MMP27, a MPND, a MT1-MMP, a MT2-MMP, a MT3-MMP, a MT4-MMP, a MT5-MMP, a MT6-MMP, a MYSM1, or a combination hereof.

In some embodiments, the protease comprises a NAALADASE II, a NAALADASE like 2, a NAALADASE like1, a napsin A, a napsin B, a nardilysin, a nasal embryonic LHRH factor, a NEDD4 binding protein 1, a neprilysin, a neprilysin-2, a neurolysin, a neurotrypsin, a neutrophil elastase (ELANE, ELA2), a NLRP1 self-cleaving protein, a nuclear recept. interacting protein 2, a nuclear recept. interacting protein 3, a nucleoporin 98, a NYN domain and retroviral integrase containing, a NY-REN-60, an OMA1, an O-sialoglycoprotein endopeptidase, an O-sialoglycoprotein endopeptidase like 1, an osteoblast serine protease, an OTU domain containing 6B, an OTU domain containing-1, an OTU domain containing-3, an OTU domain containing-5, an OTU domain containing-6A, an otubain-1, an otubain-2, an OTUD2/YOD1, an ovastacin, an oviductin-like/ovochymase-2, an ovochymase-like, or a combination hereof.

In some embodiments, the protease comprises a proteinase 3 (PRTN3), a papain, a PACE4 proprotein convertase, a pancreatic elastase, a pancreatic elastase II (IIA), a pancreatic elastase II form B, a pancreatic endopeptidase E (A), a pancreatic endopeptidase E (B), a pappalysin-1, a pappalysin-2, a paracaspase, a paraplegin, a pepsin A, a pepsin C, a PHEX endopeptidase, a PIDD auto-processing protein unit 1, a PIM1 endopeptidase, a PIM2 endopeptidase, a pitrilysin metalloproteinase 1, a plasma Glu-carboxypeptidase, a plasma kallikrein, a plasma-kallikrein-like 2, a plasma-kallikrein-like 3, a plasma-kallikrein-like 4, a plasmin (plasminogen), a PM20D2 peptidase, a POH1/PSMD14, a polyserase-2, a polyserase-3, a polyserase-I, a Ppnx, a presenilin 1, a presenilin 2, a presenilin homolog 1/SPPL3, a presenilin homolog 2, a presenilin homolog 3/SPP, a presenilin homolog 4/SPPL2B, a presenilin homolog 5, a presenilins-assoc. rhomboid like, a procollagen C-proteinase, a proliferation-association protein 1, a prolyl oligopeptidase, a prolyl oligopeptidase-like, a proprotein convertase 1, a proprotein convertase 2, a proprotein convertase 4, a proprotein convertase 5, a proprotein convertase 7, a proprotein convertase 9 (a proprotein convertase subtilisin/kexin type 9, PCSK9), a prostasin, (a protease, serine, 56), a proteasome alpha 1 subunit, a proteasome alpha 2 subunit, a proteasome alpha 3 subunit, a proteasome alpha 3-like subunit, a proteasome alpha 4 subunit, a proteasome alpha 5 subunit, a proteasome alpha 6 subunit, a proteasome alpha 7 subunit, a proteasome alpha 8 subunit, a proteasome b subunit LMP7-like, a proteasome beta 1 subunit, a proteasome beta 2 subunit, a proteasome beta 3 subunit, a proteasome beta 3-like subunit, a proteasome beta 4 subunit, a proteasome catalytic sub. 1-like, a proteasome catalytic subunit 1, a proteasome catalytic subunit 1i, a proteasome catalytic subunit 2, a proteasome catalytic subunit 2i, a proteasome catalytic subunit 3, a proteasome catalytic subunit 3i, a protein C, a protein C-like, a protein Z, a proteinase 3, a PRPF8, a PSMD7, a pyroglutamyl-peptidase I, a pyroglutamyl-peptidase II, or a combination hereof.

In some embodiments, the protease comprises a reelin, a renin, a retinol binding protein 3, a rhomboid 5 homolog 1, a rhomboid 5 homolog 2, a rhomboid domain containing 1, a rhomboid domain containing 2, a rhomboid, veinlet-like 2, a rhomboid, einlet-like 3, a rhomboid-like protein 1, or a combination hereof.

In some embodiments, the protease comprises a serine protease, a serine protease 3 (PRSS3), a S2P protease, a SAD1, a secernin-1, a secernin-2, a secernin-3, a sentrin (SUMO protease 1), a sentrin (SUMO protease 2), a sentrin (SUMO protease 3), a sentrin (SUMO protease 5), a sentrin (SUMO protease 5-like 1), a sentrin (SUMO protease 6), a sentrin (SUMO protease 7), a sentrin (SUMO protease 8), a sentrin (SUMO protease 9), a sentrin (SUMO protease 11), a sentrin (SUMO protease 12), a sentrin (SUMO protease 13), a sentrin (SUMO protease 14), a sentrin (SUMO protease 15), a sentrin (SUMO protease 16), a sentrin (SUMO protease 17), a sentrin (SUMO protease 18), a sentrin (SUMO protease 19), a separase, a seprase, a serine carboxypeptidase 1, a signalase 18 kDa component, a signalase 21 kDa component, a signalase-like 1, a similar to *Arabidopsis* Ser-prot., a similar to SPUVE, a site-1 protease, a sonic hedgehog protein, a spinesin, a SprT-like N-terminal domain, a stromelysin 1, a stromelysin 2, a stromelysin 3, a suppressor of Ty 16 homolog, or a combination hereof.

In some embodiments, the protease comprises a taspase, a TBP-associated factor 2, a TESP2, a TESP3, a testase 2, a testis serine protease 2, a testis serine protease 3, a testis serine protease 4, a testis serine protease 5, a testis serine protease 6, a testisin, a testis-specific protein tsp50, a thimet oligopeptidase, a thrombin, a thymus-specific serine peptidase, a TINAG related protein, a TMPRSS11A, a t-plasminogen activator, a TRAF-binding protein domain, a transferrin receptor 2 protein, a transferrin receptor protein, a transmembrane Ser-protease 3, a transmembrane Ser-protease 4, a transthyretin, a TRH-degrading ectoenzyme, a tripeptidyl-peptidase I, a tripeptidyl-peptidase II, a trypsin, a trypsin 10, a trypsin 15, a trypsin C, a trypsin X2, a tryptase, a tryptase alpha/beta 1, a tryptase beta 2, a tryptase delta 1, a tryptase gamma 1, a tryptase homolog 2/EOS, a tryptase homolog 3, a tubulointerstitial nephritis antigen, or a combination hereof.

In some embodiments, the protease comprises a ubiquitin C-term. hydrolase BAP1, a ubiquitin C-terminal hydrolase 1, a ubiquitin C-terminal hydrolase 3, a ubiquitin C-terminal hydrolase 4, a ubiquitin C-terminal hydrolase 5, a ubiquitin specific peptidase like 1, a UCR1, a UCR2, a UDP-N-acetylglucosaminyltransferase subunit, a Ufm-1 specific protease 1, a Ufm-1 specific protease 2, a urokinase (PLAU, uPA) a umbelical vein proteinase, a u-plasminogen activator, a USP1, a USP2, a USP3, a USP4, a USP5, a USP6, a USP7, a USP8, a USP9X, a USP9Y, a USP10, a USP11, a USP12, a USP13, a USP14, a USP15, a USP16, a USP17, a USP17-like, a USP18, a USP19, a USP20, a USP21, a USP22, a USP24, a USP25, a USP26, a USP27, a USP28, a USP29, a USP30, a USP31, a USP34, a USP35, a USP36, a USP37, a USP40, a USP41, a USP42, a USP43, a USP44, a USP45, a USP46, a USP47, a USP48, a USP49, a USP50, a USP51, a USP52, a USP53, a USP54, or a combination hereof.

In some embodiments, the protease comprises a VCP (p97)/p47-interacting protein, a VDU1, a vitellogenic carboxypeptidase-L, a X-Pro dipeptidase, a X-prolyl aminopeptidase 2, a YME1-like 1, a zinc finger CCCH-type containing 12A, a zinc finger CCCH-type containing 12B, a zinc finger CCCH-type containing 12C, a zinc finger CCCH-type containing 12D, a Zinc finger containing ubiquitin peptidase 1, or a combination hereof.

In some embodiments, the protease comprises an A20 (Tumor necrosis factor, alpha-induced protein 3, TNF a-induced protein 3). A20 is a zinc finger protein and a deubiquitinating enzyme. A20 has been shown to inhibit NF-kappa B activation as well as TNF-mediated apoptosis, limit inflammation.

In some embodiments, the protease comprises an Angiotensin-converting enzyme 2 (ACE2). ACE2 is an enzyme attached to the membrane cells located to the membrane of cells located in the intestines, kidney, testis, gallbladder, and heart. ACE2 counters the activity of the related angiotensin-converting enzyme, ACE, by reducing the amount of angiostatin II.

In some embodiments, the protease comprises a cathepsin. The cathepsin may be, but is not limited to, a cathepsin A (CTSA), a cathepsin B (CTSB), a cathepsin C (CTSC), a cathepsin D (CTSD), a cathepsin E (CTSE), a cathepsin H (CTSH), a cathepsin K (CTSK), a cathepsin L (CTSL), a cathepsin S (CTSS), a cathepsin V (CTSV), and a cathepsin Z (CTSZ). Cathepsins are a subset of proteases, many of which become activated in low pH. Cathepsisns comprise serine proteases, cysteine proteases, and aspartyl proteases, among others. Cathepsins have been implicated in cancer, Alzheimer's disease, arthritis, Ebola, pancreatitis, glaucoma, COPD, and other diseases.

In some embodiments, the protease comprises a caspase. The caspase may be, but is not limited to, a caspase 1, a caspase 2, a caspase 3, a caspase 4, a caspase 5, a caspase 6, a caspase 7, a caspase 8, a caspase 9, a caspase 10, a caspase 11, a caspase 12, a caspase 13, and a caspase 14.

In some embodiments, the protease comprises a calpain. The calpain may be, but is not limited to a calpain 1, a calpain 2, a calpain 3, a calpain 4, a calpain 5, a calpain 6, a calpain 7, a calpain 8, a calpain 9, a calpain 10, a calpain 11, a calpain 12, a calpain 13, a calpain 14, and a calpain 15. Caspases are a family of protease enzymes that play essential roles in programmed cell death and cell homeostasis.

In some embodiments, the protease comprises a cysteine protease. Cysteine proteases, also known as thiol proteases, are hydrolase enzymes that degrade proteins. These proteases share a common catalytic mechanism that involves a nucleophilic cysteine thiol in a catalytic triad or dyad. The cysteine protease family comprises Papain (*Carica papaya*), bromelain (*Ananas comosus*), cathepsin K (liverwort), calpain (*Homo sapiens*), aspase-1 (*Rattus norvegicus*), separase (*Saccharomyces cerevisiae*), Adenain (human adenovirus type 2), Pyroglutamyl-peptidase I (*Bacillus amyloliquefaciens*), Sortase A (*Staphylococcus aureus*), Hepatitis C virus peptidase 2 (hepatitis C virus), Sindbis virus-type nsP2 peptidase (sindbis virus), Dipeptidyl-peptidase VI (*Lysinibacillus sphaericus*), DeSI-1 peptidase (*Mus musculus*), TEV protease (tobacco etch virus), Amidophosphoribosyltransferase precursor (*Homo sapiens*), Gamma-glutamyl hydrolase (*Rattus norvegicus*), Hedgehog protein (*Drosophila melanogaster*) and DmpA aminopeptidase (*Ochrobactrum anthropi*), etc.

In some embodiments, the protease comprises a complement C1r serine protease (Complement component 1r). In some embodiments, the protease comprises a complement C1s serine protease (Complement component is). C1r along with C1q and C1s form the C1 complex. C1r has very narrow trypsin-like specificity that is responsible for activation of the C1 complex. C1 activation is a two-step process involving (1) C1r intramolecular autoactivation and (2) C1s cleavage by activated C1r. C1r contains a chymotrypsin-like serine protease domain at its C-terminal, and cleaves a single Arg-Ile bond in C1r and in C1s. Zvi Fishelson, in xPharm: The Comprehensive Pharmacology Reference, 2007.

In some embodiments, the protease comprises a chymotrypsin (chymotrypsins A and B, alpha-chymar ophth, avazyme, chymar, chymotest, enzeon, quimar, quimotrase, alpha-chymar, alpha-chymotrypsin A, alpha-chymotrypsin)). Chymotrypsin is a digestive enzyme component of pancreatic juice acting in the duodenum, where it performs proteolysis, the breakdown of proteins and polypeptides. Chymotrypsin preferentially cleaves peptide amide bonds where the side chain of the amino acid N-terminal to the scissile amide bond is a large hydrophobic amino acid (tyrosine, tryptophan, and phenylalanine).

In some embodiments, the protease comprises a chymase (mast cell protease 1, skeletal muscle protease, skin chymotryptic proteinase, mast cell serine proteinase, skeletal muscle protease). Chymases are a family of serine proteases found in mast cells, basophil granulocytes. Chymases show broad peptidolytic activity and are involved in inflammatory response, hypertension and atherosclerosis.

In some embodiments, the protease comprises a dipeptidyl peptidase (DPP). DPP comprises cathepsin C (DPP1), DPP2, DPP3, DPP4, DPP 6, DPP7, DPP8, DPP9, DPP10.

In some embodiments, the protease comprises a DPP4 (adenosine deaminase complexing protein 2, CD26). DPP4 is expressed on cell surface and is associated with immune regulation, signal transduction, and apoptosis. DPP4 is a serine exopeptidase that cleaves X-proline or X-alanine dipeptides from the N-terminus of polypeptides. DPP-4 is known to cleave a broad range of substrates including growth factors, chemokines, neuropeptides, and vasoactive peptides. DPP4 plays a major role in glucose metabolism, is responsible for the degradation of incretins such as GLP-1, and appears to work as a suppressor in the development of some tumors In some embodiments, the protease comprises a DPP1 (Cathepsin C, CTSC). DPP1 is a lysosomal exo-cysteine protease belonging to the peptidase C1 family. Cathepsin C appears to be a central coordinator for activation of many serine proteases in immune/inflammatory cells. Cathepsin C catalyzes excision of dipeptides from the N-terminus of protein and peptide substrates, In some embodiments, the protease comprises a disintegrin and metalloproteinase (ADAM). ADAMs are a family of single-pass transmembrane and secreted metalloendopeptidases. Not all human ADAMs have a functional protease domain. Those ADAMs which are active proteases are classified as sheddases because they cut off or shed extracellular portions of transmembrane proteins.

In some embodiments, the protease comprises an ADAM12 metalloprotease. ADAM12 binds insulin growth factor binding protein-3 (IGFBP-3), appears to be an early Down syndrome marker, and has been implicated in a variety of biological processes involving cell-cell and cell-matrix interactions, including fertilization, muscle development, and neurogenesis.

In some embodiments, the protease comprises a disintegrin and metalloproteinase with thrombospondin motifs (ADAMTS). ADAMTS is a family of multidomain extracellular protease enzymes, comprising ADAMTS1, ADAMTS2, ADAMTS3, ADAMTS4, ADAMTS5 (=ADAMTS11), ADAMTS6, ADAMTS7, ADAMTS8 (or METH-2), ADAMTS9, ADAMTS10, ADAMTS12, ADAMTS13, ADAMTS14, ADAMTS15, ADAMTS16, ADAMTS17, ADAMTS18, ADAMTS19, and ADAMTS20. Known functions of the ADAMTS proteases include processing of procollagens and von Willebrand factor as well as cleavage of aggrecan, versican, brevican and neurocan, making them key remodeling enzymes of the extracellular matrix. They have been demonstrated to have important roles in connective tissue organization, coagulation, inflammation, arthritis, angiogenesis and cell migration.

In some embodiments, the protease comprises an ADAMTS1. ADAMTS1 is a member of the ADAMTS protein family. The expression of ADAMTS1 may be associated with various inflammatory processes, development of cancer cachexia, normal growth, fertility, and organ morphology and function.

In some embodiments, the protease comprises a Factor VII activating protease (FSAP). FSAP is a circulating serine protease with high homology to fibrinolytic enzymes, and may be associated with the regulation of coagulation and fibrinolysis.

In some embodiments, the protease comprises a furin. Furin belongs to the subtilisin-like proprotein convertase family, and is a calcium-dependent serine endoprotease. Furin's substrates includes: proparathyroid hormone, transforming growth factor beta 1 precursor, proalbumin, pro-beta-secretase, membrane type-1 matrix metalloproteinase, beta subunit of pro-nerve growth factor and von Willebrand factor.

In some embodiments, the protease comprises a histone deacetylase (HDAC). HDACs are a class of enzymes that remove acetyl groups (O=C—CH3) from an ε-N-acetyl lysine amino acid on a histone, allowing the histones to wrap the DNA more tightly.

In some embodiments, the protease comprises a HTRA1 serine protease. HTRA1 is a secreted enzyme that is proposed to regulate the availability of insulin-like growth factors (IGFs) by cleaving IGF-binding proteins. It has also been suggested to be a regulator of cell growth.

In some embodiments, the protease comprises a granzyme. Granzymes are serine proteases released by cytoplasmic granules within cytotoxic T cells and natural killer (NK) cells. Granzymes induce programmed cell death in the target cell. Granzymes also kill bacteria and inhibit viral replication.

In some embodiments, the protease comprises, a Kallikrein (KLK). Kallikreins are a subgroup of serine proteases. Kallikreins are responsible for the coordination of various physiological functions including blood pressure, semen liquefaction and skin desquamation.

In some embodiments, the protease comprises a matrix metalloproteinase (MMP, matrix metallopeptidases, matrixins). MPPs are calcium-dependent zinc-containing endopeptidases. MMPs have been implicated in cleavage of cell surface receptors, the release of apoptotic ligands, chemokine/cytokine inactivation, cell proliferation and cell migration.

In some embodiments, the protease comprises a membrane metallo-endopeptidase (MME). MME is a zinc-dependent metalloprotease that cleaves peptides at the amino side of hydrophobic residues and inactivates several peptide hormones including glucagon, enkephalins, substance P, neurotensin, oxytocin, and bradykinin. MME is expressed in a wide variety of tissues and is particularly abundant in kidney. MME is also a common acute lymphocytic leukemia antigen.

In some embodiments, the protease comprises a mannose-binding protein-associated serine protease 2 (MASP2, Mannan-binding lectin serine protease 2, MBL associated serine protease 2). MASP2 is involved in the complement system, cleaves complement components C4 and C2 into C4a, C4b, C2a, and C2b.

In some embodiments, the protease comprises a mannose-binding protein-associated serine protease 3 (MBL associated serine protease 3, MASP3). MASP3 originates from the MASP1 gene through differential splicing, it circulates in high serum concentrations predominantly in complex with Ficolin-3 and regulates Ficolin-3 mediated complement activation.

In some embodiments, the protease comprises a neutrophil elastase (ELANE, ELA2). ELANE is a serine proteinase secreted by neutrophils and microphages during inflammation and destroys bacteria and host tissue.

In some embodiments, the protease comprises a proteinase 3 (PRTN3). PRTN3 is a serine protease enzyme expressed mainly in neutrophil granulocytes and contributes to the proteolytic generation of antimicrobial peptides.

In some embodiments, the protease comprises a plasmin (a.k.a. plasminogen). Plasmin is a proteolytic enzyme derived from an inert plasma precursor known as plasminogen. It is present in blood that degrades many blood plasma proteins, including fibrin clots. In human, plasmin is encoded by PLG gene.

In some embodiments, the protease comprises a pepsin. Pepsin is an endopeptidase that cleaves proteins into smaller peptides. It is an aspartic protease, using a catalytic aspartate in its active site.

In some embodiments, the protease comprises a presenilin-1 (PS-1). PS-1 is a presenilin protein that is one of the four core proteins in the gamma secretase complex, which is considered to play an important role in generation of amyloid beta from amyloid precursor protein.

In some embodiments, the protease comprises a proprotein convertase subtilisin/kexin type 9 (PCSK9). PCSK9 is a member of the peptidase S8 family.

In some embodiments, the protease comprises a serine protease. Serine protease cleaves peptide bonds in proteins, in which serine serves as the nucleophilic amino acid at the enzyme's active site. Serine protease includes many subfamilies.

In some embodiments, the protease comprises a tryptase. Tryptase is a the most abundant secretory granule-derived serine proteinase contained in mast cells and has been used as aa marker for mast cell activation. It is released from mask cells when they are activated as part of a normal immune response as well as in allergic responses.

In some embodiments, the protease comprises, a trypsin. Trypsin is a serine protease from the PA clan superfamily, found in the digestive system. Trypsin cuts peptide chains mainly at the carboxyl side of the amino acids lysine or arginine.

In some embodiments, the protease comprises a urokinase (PLAU, uPA). Urokinase is a serine protease present in humans and other animals. It is present in human urine, blood and in the extracellular matrix of many tissues. It is involved in degradation of the extracellular matrix and possibly tumor cell migration and proliferation. Urokinase is a 411-residue protein, consisting of three domains: the serine protease domain, the kringle domain, and the EGF-like domain. Urokinase is synthesized as a zymogen form (prourokinase or single-chain urokinase), and is activated by proteolytic cleavage between Lys158 and Ile159. The two resulting chains are kept together by a disulfide bond.

Described herein are agents to be detected including but are not limited to a oxidoreductase, a transferase, a hydrolase, a lyase, a isomerase, a ligase, a protease, a hydrolase, an esterase, a p-glycosidase, a phospholipase and a phosphodiesterase, peroxidase, lipase, amylase a nucleophilic reagent, a reducing reagent, a electrophilic/acidic reagent, an organometallic/metal catalyst, an oxidizing reagent, a hydroxyl ion, a thiols nucleophile, a nitrogen nucleophile, a sodium dithionite and a sodium periodate.

As described herein, the activity detection of some agents does not rely on cleavage. For example, some oxidoreductases, transferases, hydrolases, lyases, isomerases, and ligases lead to the substrate linker modification and release or formation of a reporter molecule that can be detected. As a way of illustration, a certain oxidation processes can modify an inactive fluorophore and render it fluorescent/detectable without the need of a substrate linker or binding events (for non-covalent processes) can change magnetic/fluorescent physical-chemical properties of certain reporters and render them detectable.

Disease and Condition

The method described herein comprise determining a disease or condition of the subject. In some aspects, the disease or condition comprises a liver disease, a cancer, a metabolic disease, a fibrotic disease, an organ transplant rejection, an infectious disease, an allergic disease, an auto-immunity, Alzheimer's or a chronic inflammation. In some embodiments, the liver disease may be a non-alcoholic steatohepatitis (NASH), a non-alcoholic fatty liver disease (NAFLD), a toxin mediated liver injury (drug/medication, alcohol, environmental), a viral hepatitis (HAV, HBV, HCV, HDV, HEV, other virus infecting the liver), an autoimmune hepatitis, a primary biliary cholangitis, a primary sclerosing cholangitis, a fulminant hepatitis, a cirrhosis of the liver, a hepatocellular carcinoma (HCC), a cholangiocarcinoma, an acute or chronic rejection of a transplanted liver, an inherited liver disease (e.g. Wilson disease, hemochromatosis, or alpha-1 antitrypsin) or a combination thereof.

In some embodiments, the cancer comprises adenoid cystic carcinoma, adrenal gland tumors, amyloidosis, anal cancer, appendix cancer, astrocytoma, ataxia-telangiectasia, Beckwith-Wiedemann syndrome, bile duct cancer (cholangiocarcinoma), Birt-Hogg-Dubé Syndrome, bladder cancer, bone cancer (sarcoma of the bone), brain stem glioma, brain tumors, breast cancer, Carney complex, central nervous system tumors, cervical cancer, colorectal cancer, Cowden Syndrome, craniopharyngioma, Desmoid tumors, desmoplastic infantile ganglioglioma, ependymoma, esophageal cancer, Ewing sarcoma, eye cancer, eyelid cancer, familial adenomatous polyposis, familial GIST, familial malignant melanoma, familial pancreatic cancer, gallbladder cancer, gastrointestinal stromal tumors (GIST), germ cell tumors, gestational trophoblastic disease, head and neck cancer, breast and ovarian cancer, diffuse gastric cancer, leiomyosarcoma and renal cell cancer, mixed polyposis syndrome, papillary renal carcinoma, juvenile polyposis syndrome, kidney cancer, lacrimal gland tumors, laryngeal and hypopharyngeal cancer, leukemia, myeloid leukemia, lymphoblastic leukemia, eosinophilic leukemia, Li-Fraumeni syndrome, liver cancer, lung cancer, Hodgkin lung cancer, non-Hodgkin lung cancer, Lynch syndrome, mastocytosis, medulloblastoma, melanoma, meningioma, mesothelioma, multiple endocrine neoplasia, multiple myeloma, myelodysplastic syndrome, nasal cavity and paranasal sinus cancer, nasopharyngeal cancer, neuroblastoma, neuroendocrine tumors, neurofibromatosis, nevoid basal cell carcinoma syndrome, oral and oropharyngeal cancer, osteosarcoma, ovarian cancer, fallopian tube cancer, peritoneal cancer, pancreatic cancer, parathyroid cancer, penile cancer, Peutz-Jeghers syndrome, phenochromocytoma, paraganglioma, pituitary gland tumors, pleuropulmonary blastoma, prostate cancer, retinoblastoma, rhabdomyosarcoma, salivary gland cancer, Kaposi sarcoma, soft tissue sarcoma, sarcoma, non-melanoma skin cancer, small bowel cancer, stomach cancer, testicular cancer, thymoma and thymic carcinoma, thyroid cancer, tuberous sclerosis complex, uterine cancer, vaginal cancer, von Hippel-Lindau syndrome, vulvar cancer, Waldenstrom macroglobulinemia, Werner syndrome, Wilms tumors, or xeroderma pigmentosum.

In some embodiments, the disease may be NASH. Non-alcoholic steatohepatitis, also called NASH, is a more active inflammatory form of non-alcoholic fatty liver disease (NAFLD). NAFLD is caused by buildup of fat in the liver. When this buildup causes inflammation and damage, it is known as NASH, which can lead to scarring of the liver. There are often no outward signs or symptoms associated with NASH, although the most common symptoms are fatigue or mild pain in the upper right abdomen. NASH may lead to cirrhosis of the liver, causing one or more of the following symptoms as the condition progresses: bleeding easily, bruising easily, itchy skin, jaundice, abdominal fluid accumulation, loss of appetite, nausea, leg swelling, confusion, drowsiness, slurred speech, or spider-like blood vessels.

NASH is most common in patients who are overweight or obese; other risk factors include diabetes, high cholesterol, high triglycerides, poor diet, metabolic syndrome, polycystic ovary syndrome, sleep apnea, and hyperthyroidism.

NAFLD encompasses the entire spectrum of fatty liver disease in individuals without significant alcohol consumption, ranging from fatty liver to steatohepatitis to cirrhosis. Non-alcoholic fatty liver is the presence of >5% hepatic steatosis without evidence of hepatocellular injury in the form of ballooning of the hepatocytes or evidence of fibrosis. The risk of progression to cirrhosis and liver failure is considered minimal. NASH is the presence of >5% hepatic steatosis with inflammation and hepatocyte injury (ballooning) with or without fibrosis. This can progress to cirrhosis, liver failure, and rarely liver cancer. NASH cirrhosis is presence of cirrhosis with current or previous histological evidence of steatosis or steatohepatitis.

NAS is an unweighted composite of steatosis, lobular inflammation, and ballooning scores. NAS is a useful tool to measure changes in liver histology in patients with NAFLD in clinical trials. Fibrosis is scored separately and can be classified as F1 through F4; specifically, stage 1 is zone 3 (perivenular), perisinusoidal, or periportal fibrosis; stage 2 is both zone 3 and periportal fibrosis; stage 3 is bridging fibrosis with nodularity; and stage 4 is cirrhosis.

TABLE 3

The histological scoring system for nonalcoholic fatty liver disease: components of NAFLD activity score (NAS) and fibrosis staging.

| Item | Score | Extent | Definition and Comment |
|---|---|---|---|
| NAS Components (see scoring interpretation) | | | |
| Steatosis | 0 | <5% | Refers to amount of surface |
|  | 1 | 5-33% | area involved by steatosis |
|  | 2 | >33-66% | as evaluated on low to |
|  | 3 | >66% | medium power examination. |
| Lobular Inflammation | 0 | No foci | Acidophil bodies are not |
|  | 1 | <2 foci/200x | included in this assessment, |
|  | 2 | 2-4 foci/200x | nor is portal inflammation |
|  | 3 | >4 foci/200x |  |
| Hepatocyte Ballooning | 0 | None |  |
|  | 1 | Few ballooned cells | "Few" means rare but definite ballooned hepatocytes |
|  | 2 | Many cells/prominent ballooning | as well as cases that are diagnostically borderline Most cases with prominent ballooning also had Mallory"s hyalin, but Mallory"s hyaline is not scored separately for the NAS |
| Fibrosis Stage (Evaluated separately from NAS) | | | |
| Fibrosis | 0 | None |  |
|  | 1 | Perisinusoidal or periportal |  |
|  | 1A | Mild, zone 3, perisinusoidal | "delicate" fibrosis |
|  | 1B | Moderate, zone 3, perisinusoidal | "dense" fibrosis |

TABLE 3-continued

The histological scoring system for nonalcoholic fatty liver disease: components of NAFLD activity score (NAS) and fibrosis staging.

| Item | Score | Extent | Definition and Comment |
|---|---|---|---|
| | 1C | Portal/periportal | This category is included to accommodate cases with portal and/or peri portal fibrosis without accompanying pericellular/ perisinusoidal fibrosis |
| | 2 | Perisinusoidal and portal/periportal | |
| | 3 | Bridging fibrosis | |
| | 4 | Cirrhosis | |

Scoring interpretation: Total NAS score represents the sum of scores for steatosis, lobular inflammation, and ballooning, and ranges from 0-8. Diagnosis of NASH (or, alternatively, fatty liver not diagnostic of NASH) should be made first, then NAS is used to grade activity. In the reference study, NAS scores of 0-2 occurred in cases largely considered not diagnostic of NASH, scores of 3-4 were evenly divided among those considered not diagnostic, borderline, or positive for NASH. Scores of 5-8 occurred in cases that were largely considered diagnostic of NASH In some embodiments, the disease may be NAFLD. Nonalcoholic fatty liver disease (NAFLD) is an umbrella term for a range of liver conditions affecting people who drink little to no alcohol. As the name implies, the main characteristic of NAFLD is too much fat stored in liver cells. There are often no outward signs or symptoms associated with NAFLD, although the most common symptoms are fatigue or mild pain in the upper right abdomen.

In some embodiments, the disease may be fulminant hepatitis. Fulminant hepatitis, or fulminant hepatic failure, is defined as a clinical syndrome of severe liver function impairment, which causes hepatic coma and the decrease in synthesizing capacity of liver. Then they rapidly develop severe, often life-threatening liver failure. This can happen within hours, days, or sometimes weeks. Symptoms of severe liver failure include confusion, extreme irritability, altered consciousness, blood clotting defects, and buildup of fluid in the abdominal cavity and multiorgan system failure.

In some embodiments, the disease may be a hepatocellular carcinoma (HCC). HCC is the most common type of primary liver cancer. HCC occurs most often in people with chronic liver diseases leading to advanced fibrosis or cirrhosis. The most common liver diseases associated with HCC are viral hepatitis B or C, alcohol related liver disease and NASH.

In some embodiments, the disease may be a primary biliary cholangitis (PBC). Primary biliary cholangitis, previously called primary biliary cirrhosis, is a chronic disease in which the bile ducts in the liver are slowly destroyed. Bile is a fluid made in the liver. Chronic inflammation in the liver can lead to bile duct damage, irreversible scarring of liver tissue (cirrhosis) and eventually, liver failure. PBC is considered an autoimmune disease, which means the body's immune system is mistakenly attacking healthy cells and tissue. Researchers think a combination of genetic and environmental factors triggers the disease. It usually develops slowly. At this time, there's no cure for primary biliary cholangitis, but medication can slow liver damage, especially if treatment begins early.

In some embodiments, the liver disease may be a toxin mediated liver injury (e.g., from drug/medication, alcohol, environmental). Toxin mediated liver injury is an inflammation of liver in reaction to certain substances, such as alcohol, chemicals, drugs/medication, environmental factors or nutritional supplements. The liver normally removes and breaks down most drugs and chemicals from the bloodstream, which creates byproducts that can damage the liver. Although the liver has a great capacity for regeneration, constant exposure to toxic substances can cause serious, sometimes irreversible harm.

In some embodiments, the liver disease may be a viral hepatitis (HAV, HBV, HCV, HDV, HEV, other virus infecting the liver). Viral hepatitis is a liver inflammation due to a viral infection. It may present in acute form as a recent infection with relatively rapid onset, or in chronic form. The most common causes of viral hepatitis are the five unrelated hepatotropic viruses hepatitis A, B, C, D, and E. Other viruses can also cause liver inflammation, including cytomegalovirus, Epstein-Barr virus, and yellow fever. There also have been scores of recorded cases of viral hepatitis caused by herpes simplex virus. Viral hepatitis is either transmitted through contaminated food or water (A, E) or via blood and body fluids (B, C). Hepatitis A and hepatitis B can be prevented by vaccination. Effective treatments for hepatitis C are available but costly.

In some embodiments, the liver disease may be an autoimmune hepatitis. Autoimmune hepatitis is liver inflammation that occurs when the immune system attacks liver cells. The exact cause of autoimmune hepatitis is unclear, but genetic and environmental factors appear to interact over time in triggering the disease. Untreated autoimmune hepatitis can lead to scarring of the liver (cirrhosis) and eventually to liver failure. When diagnosed and treated early, autoimmune hepatitis often can be controlled with drugs that suppress the immune system. A liver transplant may be an option when autoimmune hepatitis doesn't respond to drug treatments or in cases of advanced liver disease. There are two main forms of autoimmune hepatitis: (1) Type 1 autoimmune hepatitis. Type I autoimmune hepatitis is the most common type and can occur at any age. About half the people with type 1 autoimmune hepatitis have other autoimmune disorders, such as celiac disease, rheumatoid arthritis or ulcerative colitis; (2) Type 2 autoimmune hepatitis. Although adults can develop type 2 autoimmune hepatitis, it's most common in children and young people. Other autoimmune diseases may accompany type 2 autoimmune hepatitis.

In some embodiments, the liver disease may be a primary sclerosing cholangitis. Primary sclerosing cholangitis is a disease of the bile ducts. In primary sclerosing cholangitis, inflammation causes scars within the bile ducts. These scars make the ducts hard and narrow and gradually cause serious liver damage. A majority of people with primary sclerosing cholangitis also have inflammatory bowel disease, such as ulcerative colitis or Crohn's disease. In most cases of primary sclerosing cholangitis, the disease progresses slowly. It can eventually lead to liver failure, repeated infections, and tumors of the bile duct or liver.

In some embodiments, the liver disease may be a cirrhosis of the liver. Cirrhosis is a late stage of scarring (fibrosis) of the liver caused by many forms of liver diseases and conditions, such as hepatitis and chronic alcoholism. In the process of liver self-repair, scar tissue forms. As cirrhosis progresses, more and more scar tissue forms, making it difficult for the liver to function (decompensated cirrhosis).

In some embodiments, the liver disease may be a cholangiocarcinoma. Cholangiocarcinoma (bile duct cancer) is a type of cancer that forms in the bile ducts. Risk factors for cholangiocarcinoma include primary sclerosing cholangitis (an inflammatory disease of the bile ducts), ulcerative colitis, cirrhosis, hepatitis C, hepatitis B, infection with certain liver flukes, and some congenital liver malformations. Cholangiocarcinoma can be categorized based on the location of the cancer occurs in the bile ducts: intrahepatic cholangiocarcinoma, hilar cholangiocarcinoma, distal cholangiocarcinoma. Cholangiocarcinoma is often diagnosed when it is advanced, making successful treatment difficult to achieve.

In some embodiments, the liver disease may be an inherited liver disease (e.g., Wilson disease, hemochromatosis, or alpha-1 antitrypsin, etc.) Inherited liver diseases are genetic disorders that can cause severe liver disease and other health problems. Wilson's disease is a rare inherited disorder that causes copper to accumulate in your liver, brain and other vital organs. Hemochromatosis is a disease in which deposits of iron collect in the liver and other organs. The primary form of hemochromatosis is one of the most common inherited diseases in the U.S. The alpha-1 antitrypsin protein is synthesized mainly in the liver by hepatocytes, secreted into the blood stream, and acts as an inhibitor of neutrophil elastase released primarily in the lung during inflammation. Alpha-1 antitrypsin deficiency is caused when alpha-1 antitrypsin protein is either lacking or exists in lower than normal levels in the blood.

In some embodiments, the disease may be an organ transplant rejection. Transplant rejection occurs when transplanted tissue is rejected by the recipient's immune system, which destroys the transplanted tissue. Transplant rejection can be lessened by determining the molecular similitude between donor and recipient and by use of immunosuppressant drugs after transplant.

In some embodiments, the disease may be an infectious disease, Infectious diseases are disorders caused by organisms such as bacteria, viruses, fungi or parasites. Bacteria are one-cell organisms responsible for illnesses such as streptococcal upper respiratory infection, urinary tract infections and tuberculosis. Viruses cause a multitude of diseases ranging from the common cold to AIDS. Many skin diseases, such as ringworm and athlete's foot, are caused by fungi. Other types of fungi can infect the lungs or nervous system. Malaria is caused by a tiny parasite that is transmitted by a mosquito bite. Other parasites may be transmitted to humans from animal feces. In some embodiments, the infectious disease is COVID-19.

In some embodiments, the disease may be an allergic disease. Allergic diseases are caused by allergen-induced unfavorable immune responses initiating various symptoms in different organs, which often cannot be completely controlled by modern medicine. The immunologic basis of allergic diseases is observed in two phases: sensitization and development of memory T and B cell responses, and IgE production and effector functions, which are related to eosinophils, innate lymphoid cells, dendritic cell subsets, epithelial cells and tissue inflammation/injury, epithelial barrier, tissue remodeling and chronicity in asthma, atopic dermatitis (AD) and allergic rhinitis (AR). Different disease phenotypes and endotypes may become apparent with different dominant molecular mechanisms, related biomarkers and responses to biologic therapy. Multiple mechanistic factors are complexly involved in the pathogenesis of allergic inflammations In some embodiments, the disease may be an autoimmune disease/autoimmunity. An autoimmune disease is a condition in which the immune system mistakenly attacks one's own body. Normally, the immune system can tell the difference between foreign cells and one's own cells. In an autoimmune disease, the immune system mistakes part of the body, like the joints or skin, as foreign. It releases proteins called autoantibodies that attack healthy cells. Some autoimmune diseases target only one organ. Type 1 diabetes damages the pancreas. Other diseases, like systemic lupus erythematosus (SLE), affect many different organ systems. In some embodiments, the autoimmune disease may be Rheumatoid arthritis, Crohns disease, Multiple sclerosis (MS) or psoriatic arthritis (PsA).

In some embodiments, the disease may be a chronic inflammation. Chronic inflammation is also referred to as slow, long-term inflammation lasting for prolonged periods of several months to years. Generally, the extent and effects of chronic inflammation vary with the cause of the injury and the ability of the body to repair and overcome the damage. Most of the features of acute inflammation continue as the inflammation becomes chronic, including the expansion of blood vessels (vasodilation), increase in blood flow, capillary permeability and migration of neutrophils into the infected tissue through the capillary wall (diapedesis). However, the composition of the white blood cells changes soon and the macrophages and lymphocytes begin to replace short-lived neutrophils. Thus the hallmarks of chronic inflammation are the infiltration of the primary inflammatory cells such as macrophages, lymphocytes, and plasma cells in the tissue site, producing inflammatory cytokines, growth factors, enzymes and hence contributing to the progression of tissue damage and secondary repair including fibrosis and granuloma formation, etc.

In some embodiments, the disease may be a fibrotic disease. Fibrotic disease is defined by the overgrowth, hardening, and/or scarring of various tissues and is attributed to excess deposition of extracellular matrix components including collagen. Fibrosis is the end result of chronic inflammatory reactions induced by a variety of stimuli including persistent infections, autoimmune reactions, allergic responses, chemical insults, radiation, and tissue injury. The fibrotic disorders include but are not limited to systemic fibrotic diseases such as systemic sclerosis (SSc), sclerodermatous graft vs. host disease, idiopathic pulmonary fibrosis (IPF), nephrogenic systemic fibrosis, and organ-specific disorders including radiation-induced fibrosis and cardiac, pulmonary, liver, and kidney fibrosis.

In some embodiments, the disease may be a metabolic disease. A metabolic disorder/disease occurs when abnormal chemical reactions in the body disrupt metabolism. When this happens, one might have too much of some substances or too little of other ones that an individual needs to stay healthy. There are different groups of disorders. Some affect the breakdown of amino acids, carbohydrates, or lipids. Another group, mitochondrial diseases, affects the parts of the cells that produce the energy. one can develop a metabolic disorder when some organs, such as the liver or pancreas, become diseased or do not function normally. Diabetes is an example.

In some embodiments, the disease may be Alzheimer's. Alzheimer's is a type of dementia that affects memory, thinking and behavior. Symptoms eventually grow severe enough to interfere with daily tasks. Alzheimer's changes typically begin in the part of the brain that affects learning. As Alzheimer's advances through the brain, it leads to increasingly severe symptoms, including disorientation, mood and behavior changes; deepening confusion about events, time and place; unfounded suspicions about family, friends and professional caregivers; more serious memory loss and behavior changes; and difficulty speaking, swallowing and walking.

Examples

These examples are provided for illustrative purposes only and not to limit the scope of the claims provided herein. It will be appreciated that variations in proportions and alternatives in elements of the components shown will be apparent to those skilled in the art and are within the scope of the embodiments presented herein.

Example 1. Diagnosing NASH Using Probes in Mice

In this experiment, the probes of the present application were shown to accurately detect the activity levels of proteases associated with non-alcoholic steatohepatitis (NASH) in a fluid sample to diagnose NASH in a subject.

Protease activity levels associated with NASH were assessed in vivo in two mice populations, one healthy and one with NASH. The probes used in vivo are shown in FIG. 10.

Figure 11:
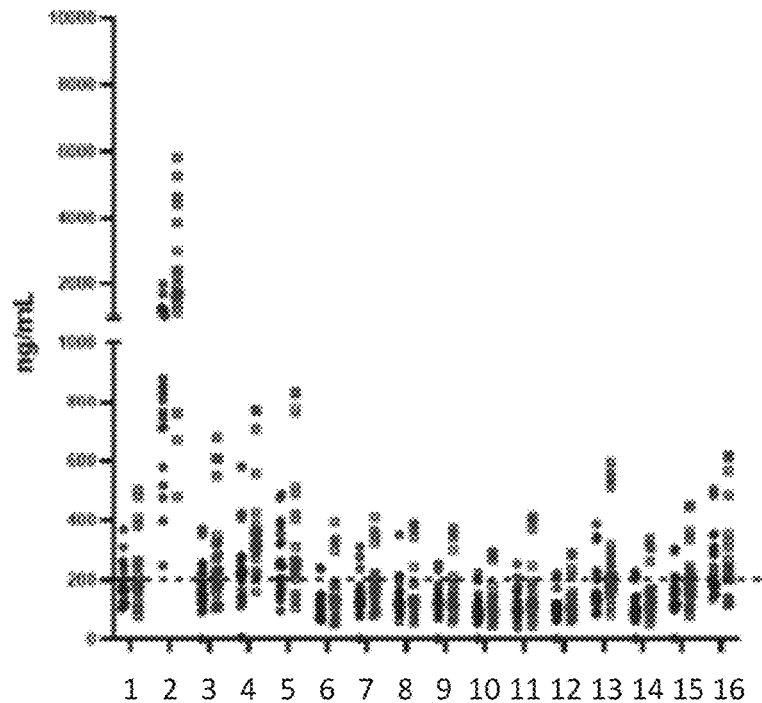
FIG. 11 shows the protease activities measured using the in vivo probes.

Mass-barcoded reporters urinary concentration levels obtained from proteolytic cleavage of these probes by proteases in healthy mice, which were fed on a standard Chow Diet (CD), and NASH mice, which were fed a choline-deficient, L-amino acid-defined, high-fat diet (CDAHFD) are shown in FIG. 11. NASH-related probes, cleaved by increased NASH-related protease activity, associated with higher mass-barcoded reporters accumulation in urine from NASH mice compared to healthy mice.

Figure 12:
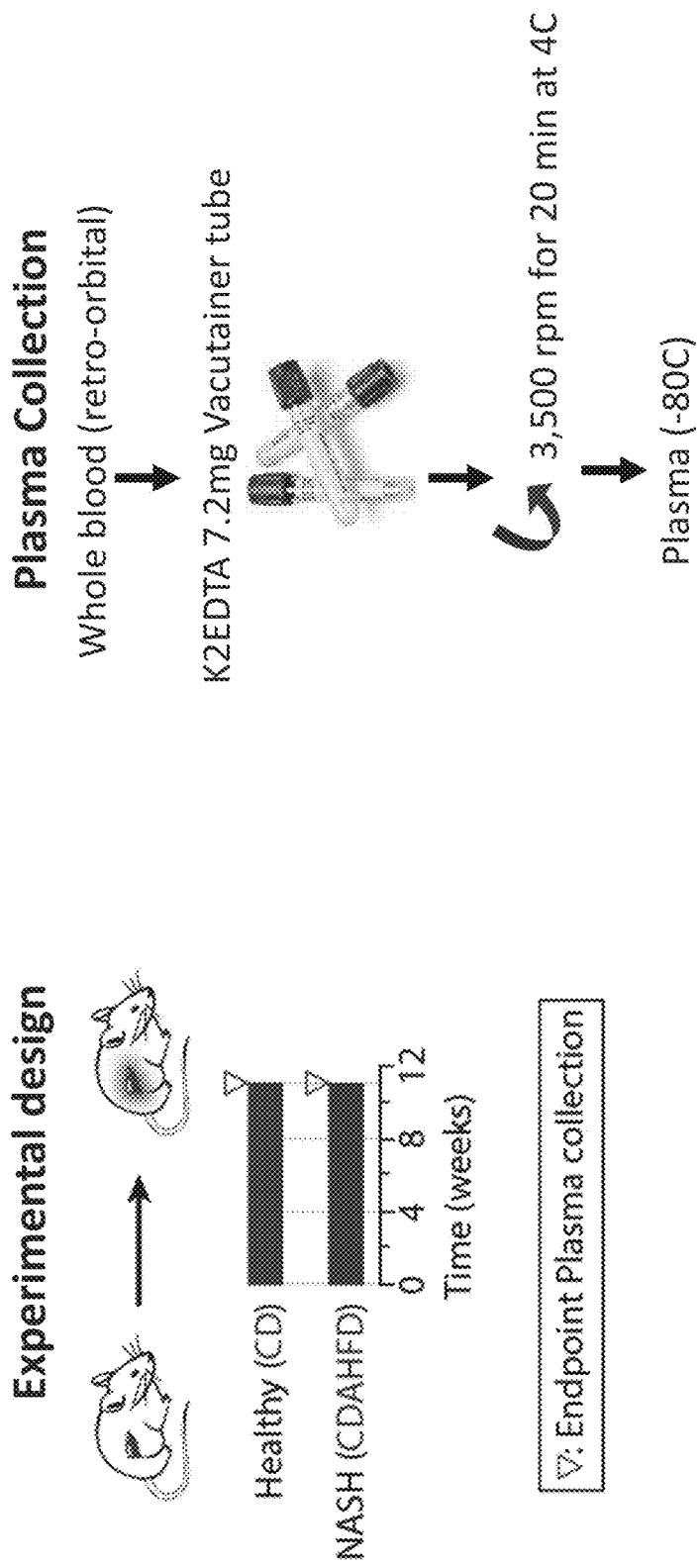
FIG. 12 outlines an experiment of present application.

As shown in FIG. 12, blood samples were collected in K2EDTA tubes from mice that were either healthy (CD) or had NASH (CDAHFD) after 12 weeks on their respective diet. All animals were used in accordance with animal care guidelines. Plasma was obtained from these blood samples by centrifugation at 3,500 RPM for 20 min at 4° C. The plasma was stored at −80° C. until it was needed for experimental purposes.

Figure 13:
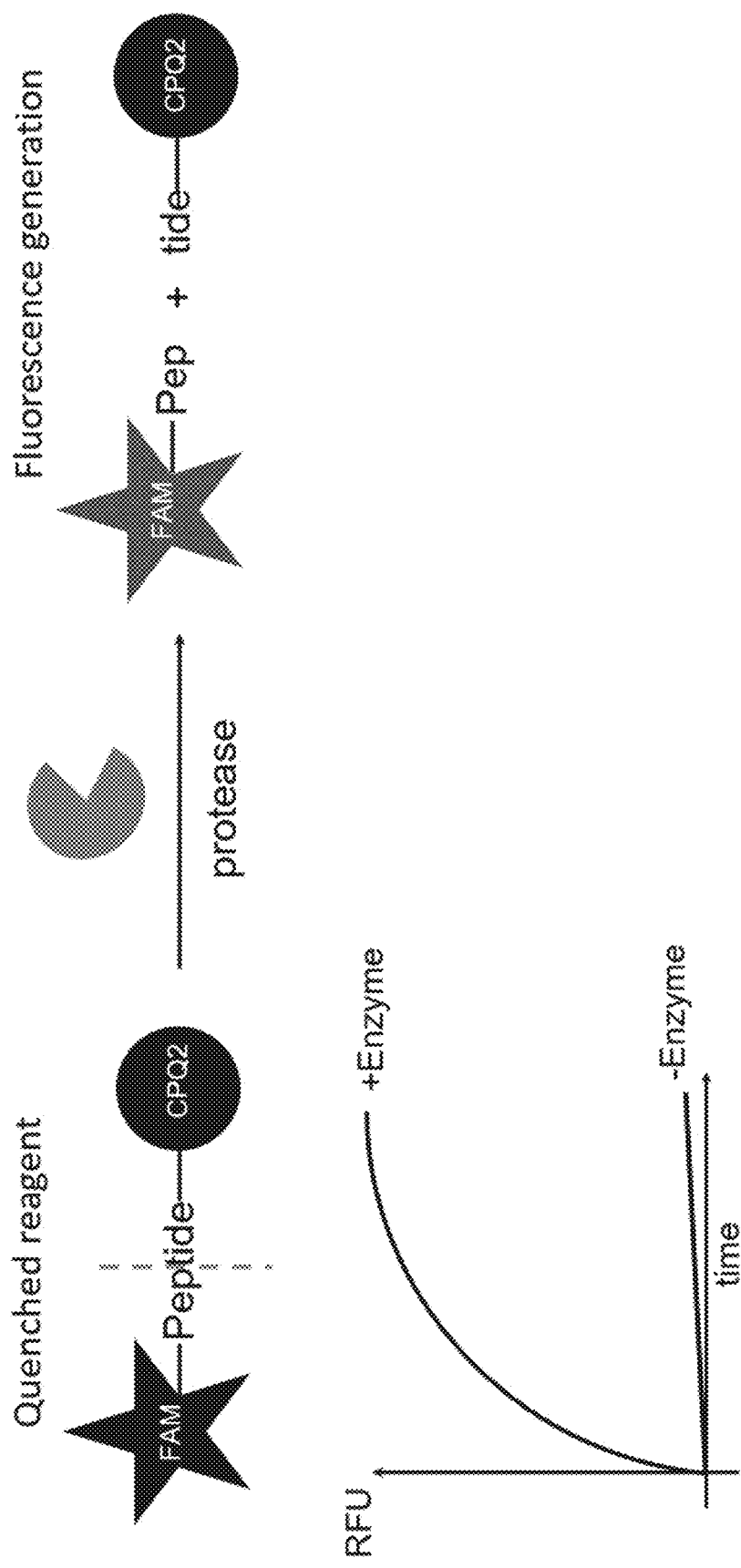
FIG. 13 outlines an experiment of present application.

As shown in FIG. 13, thawed plasma samples were pooled and contacted with probes with fluorescent quenchers and protease-cleavable fluorescent reporters at various peptide and serum concentrations. Samples were mixed with protease substrates and quenchers/reporters in 96-well plates. The 96-well plates were read on a Biotech Synergy H1, using 465,535 excitation/emission settings.

Figure 1:
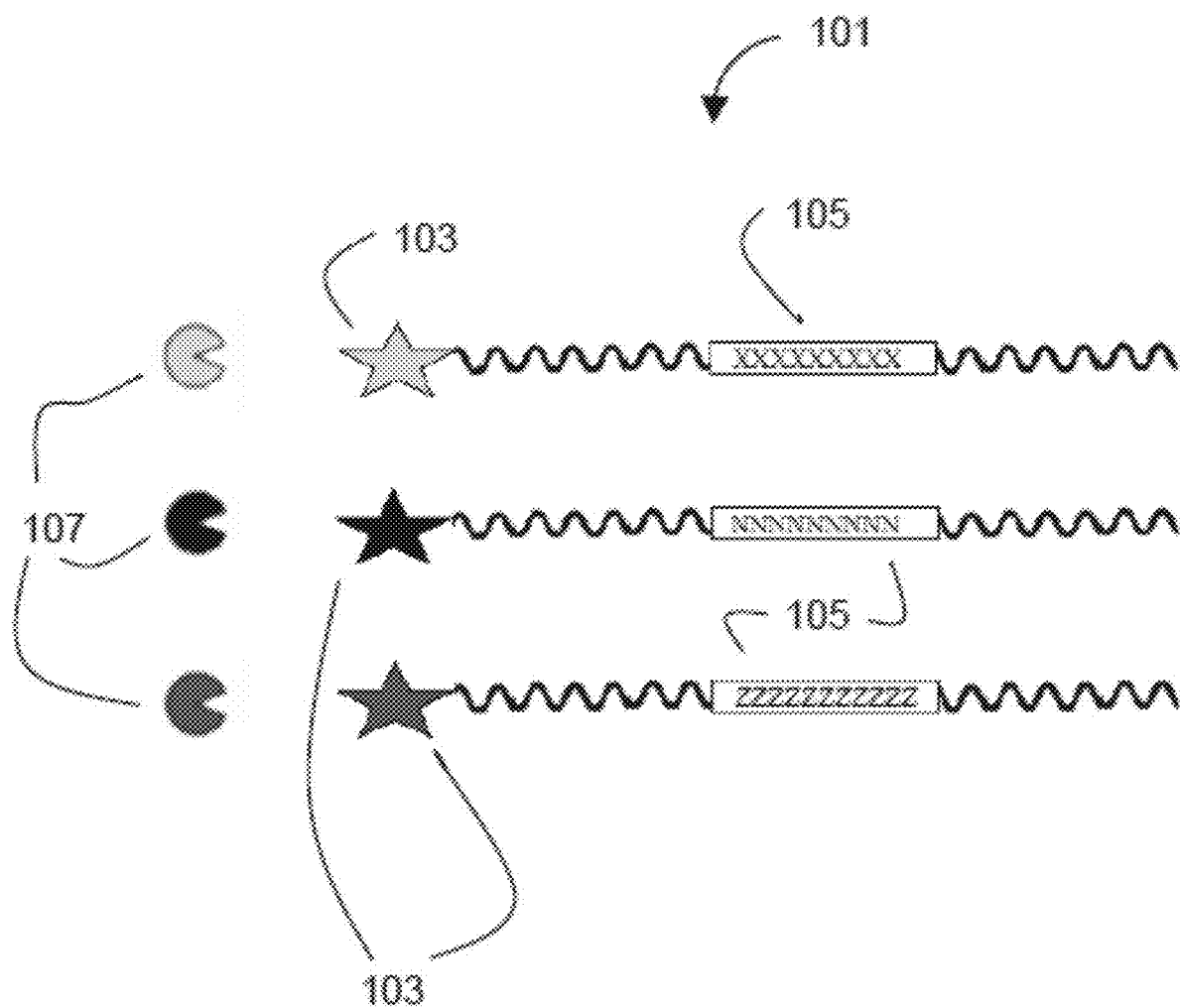
FIG. 1 shows a plurality of probes according to the current application. Each probe 101 includes a reporter 103, shown as a star in FIG. 1. The reporters 103, are linked to a cleavable linker 105, which is a cleavable substrate for an agent 107.
Figure 2:
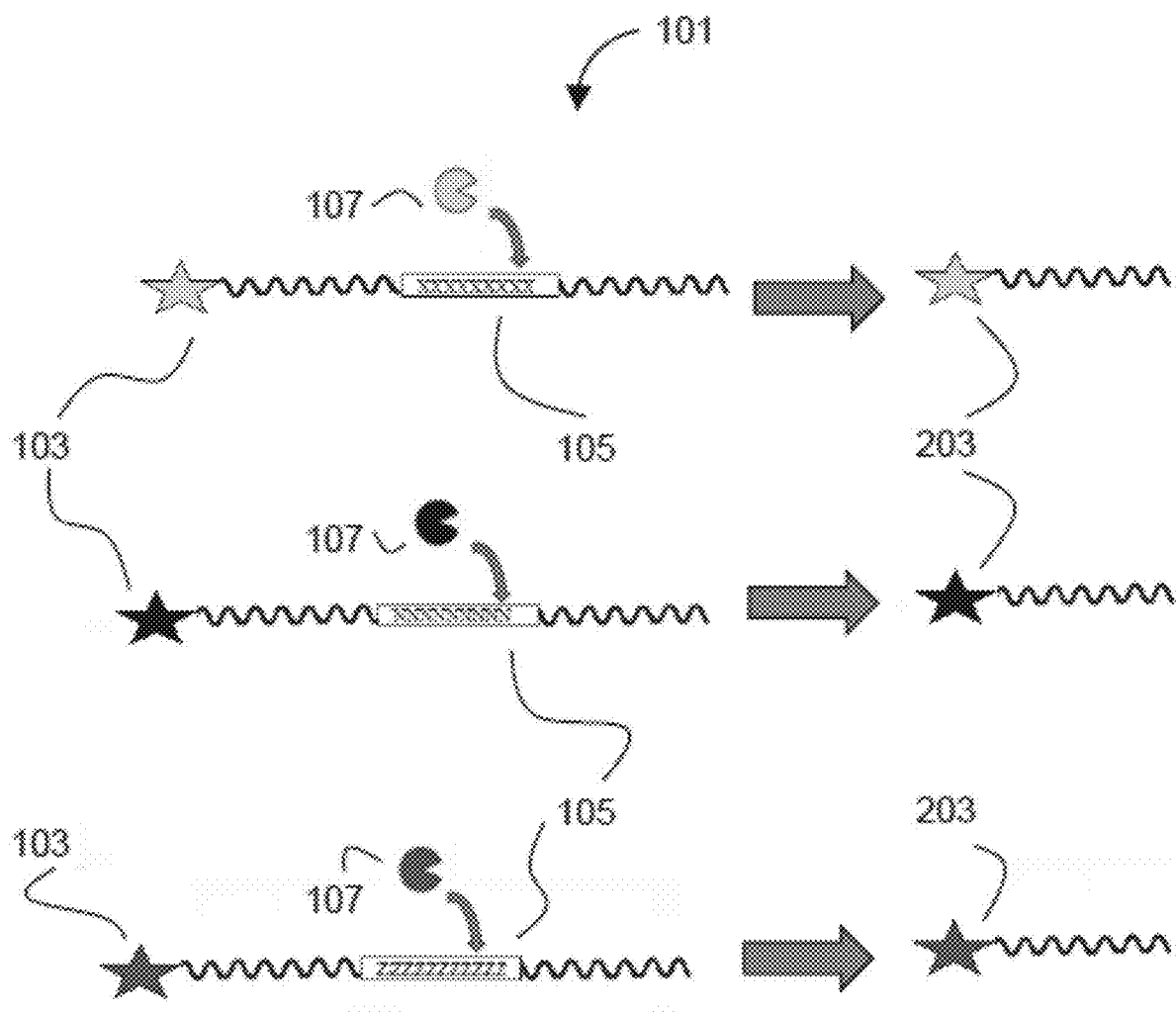
FIG. 2 shows cleavage of the reporter in a plurality of the probes. As shown, cleavage by the agent 107 of the cleavable linker 105 results in the reporters 103 being cleaved from the probe 101. Once cleaved, the cleaved reporters 203 can be detected and/or distinguished from un-cleaved reporters 103. The presence and detection of cleaved reporters 203 indicates that the agents 107 are present and active in a sample. In addition, the absence of an agent activity may be used for detection associated with a decrease in activity. The activity of the agents can be quantified based on, for example, the rate at which the cleavage reaction takes place or the amount of cleaved reporters in a sample or by other means such as a ratio of rates against an appropriate control or a ratio of cleaved reporters against an appropriate control.
Figure 3:
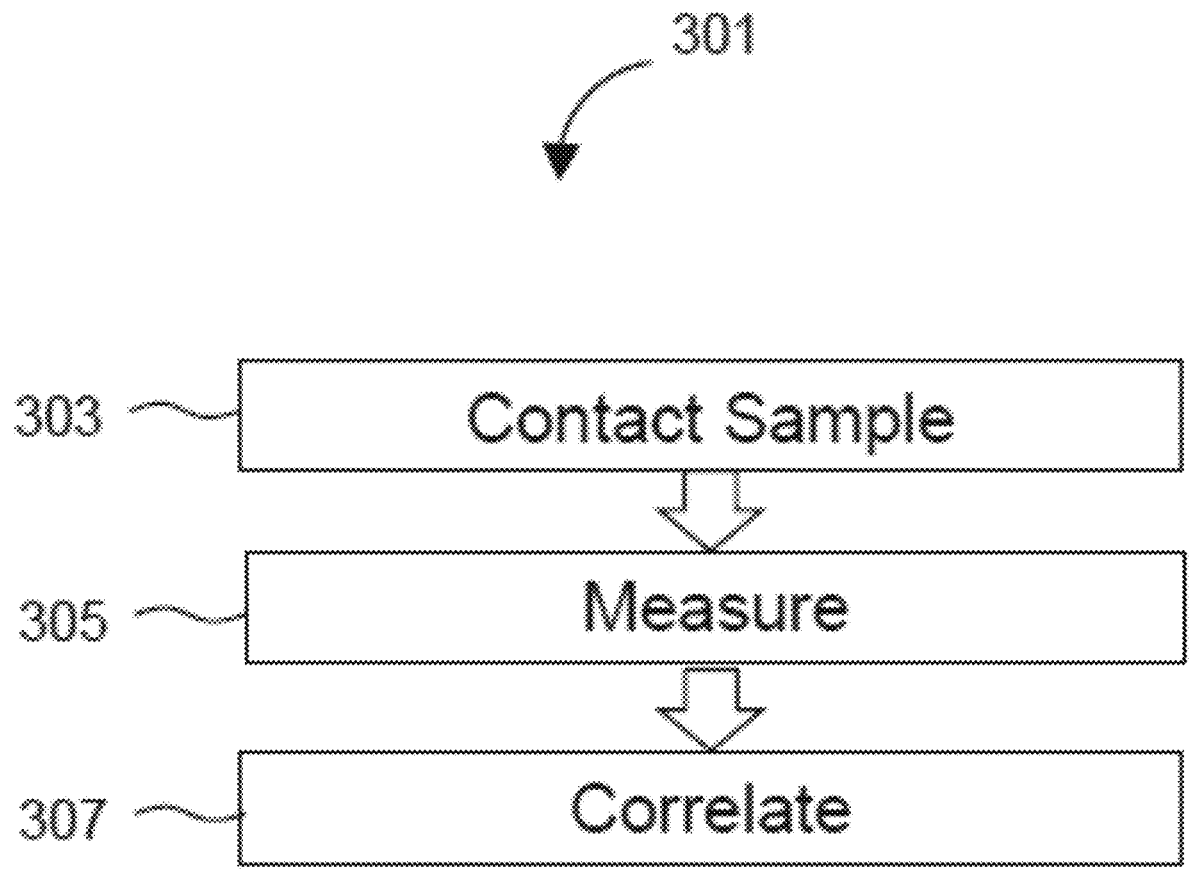
FIG. 3 illustrates a method 301 of evaluating a biological condition in a subject using the probes 101.
Figure 4:
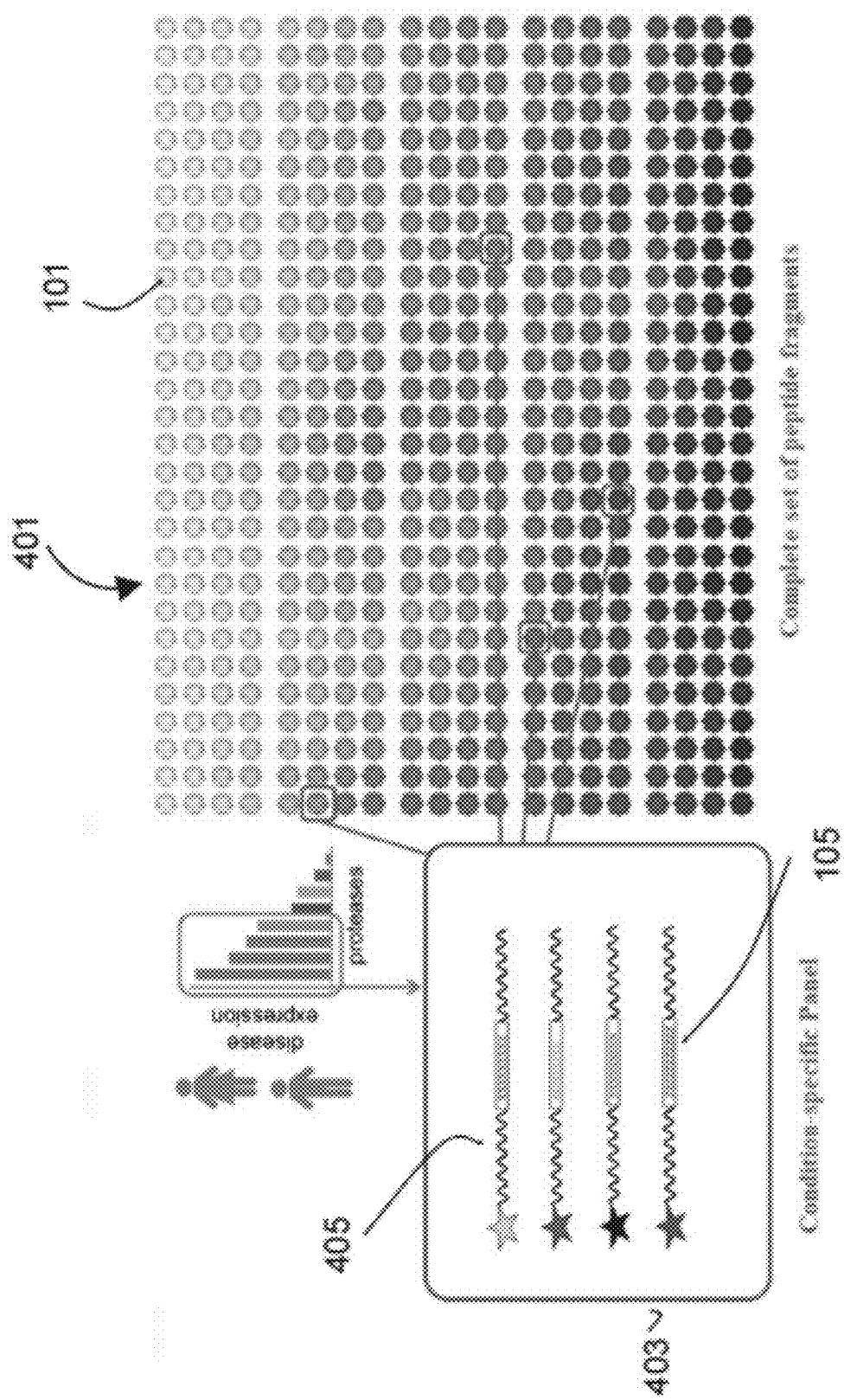
FIG. 4 shows the selection of probes to use in a composition to analyze the activities of agents to analyze one or more particular, biological conditions or disease states. The activity of one or more agents may be associated with a biological condition or disease state. This may include the progression of a particular condition or state over time. Thus, to evaluate a biological condition or disease state in a subject, probes that can be cleaved by agents of interest are selected from the library for inclusion in a condition-specific panel 403. The selected probes 405 of the condition-specific panel are differentially labeled so that the activity of the predetermined proteases can be measured 305. The different probes 101, including those included in library 401, may include features that confer properties to the fragments that ensure accurate, multiplex detection of agent activity. Such properties include, for example improved cleavage, detection, solubility, stability, reproducibility, robustness and/or expanded compatibility with different types of reporter.
Figure 5:
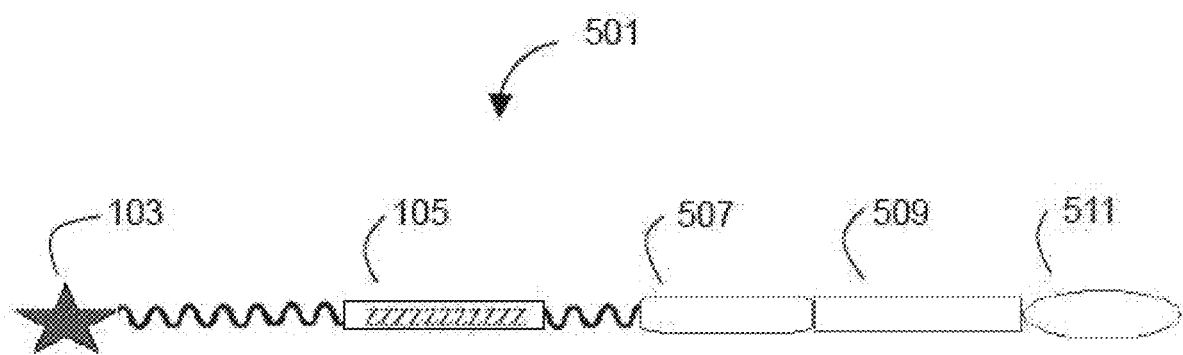
FIG. 5 shows a schematic of a probe 501 that includes a spacer 507, a solubility tag 509, a quencher and a covalent or non-covalent attachment site 511. The respective positions of these components can, in principle, be interconverted.
Figure 6A:
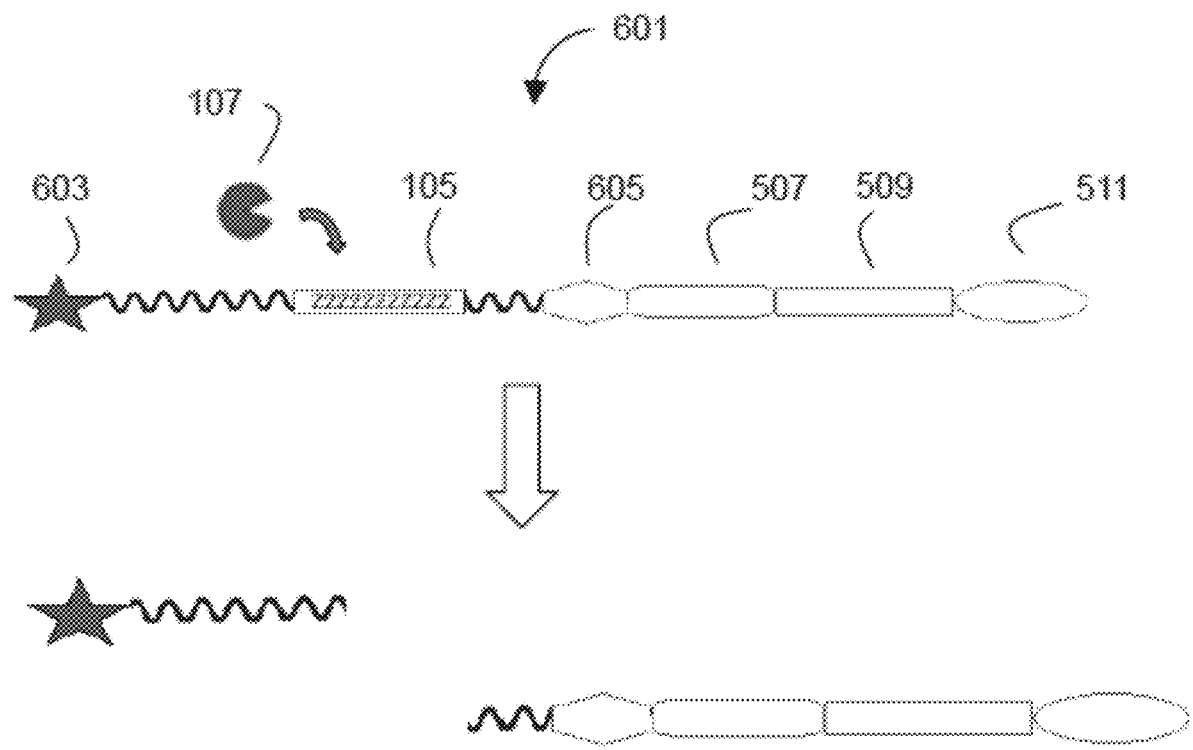
FIG. 6A-C shows cleavage of the probe.
Figure 6B:
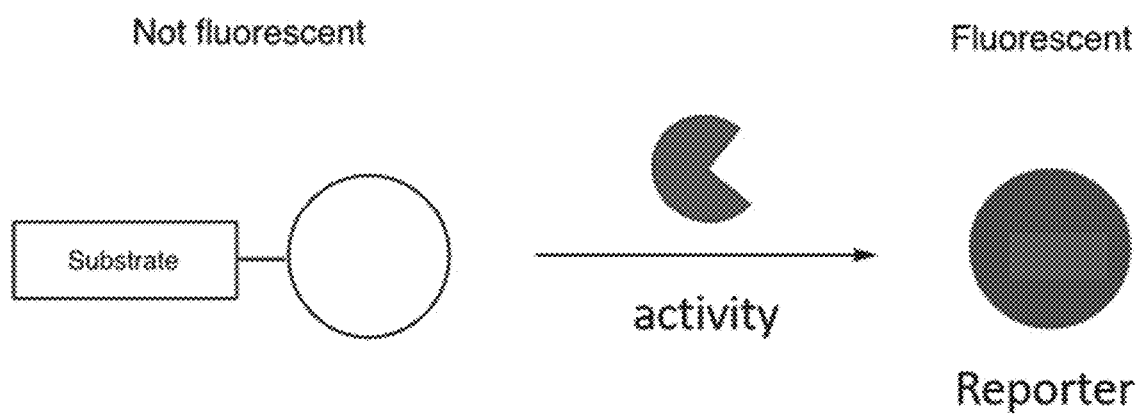
Figure 6C:
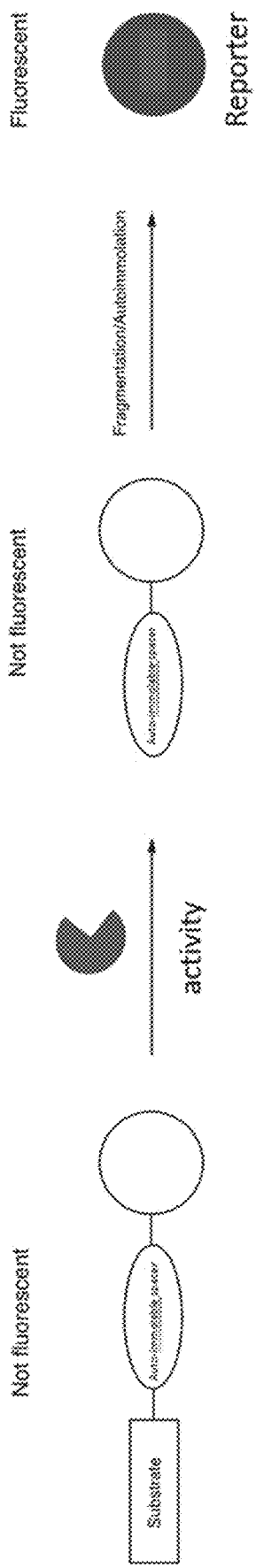
Figure 7A:
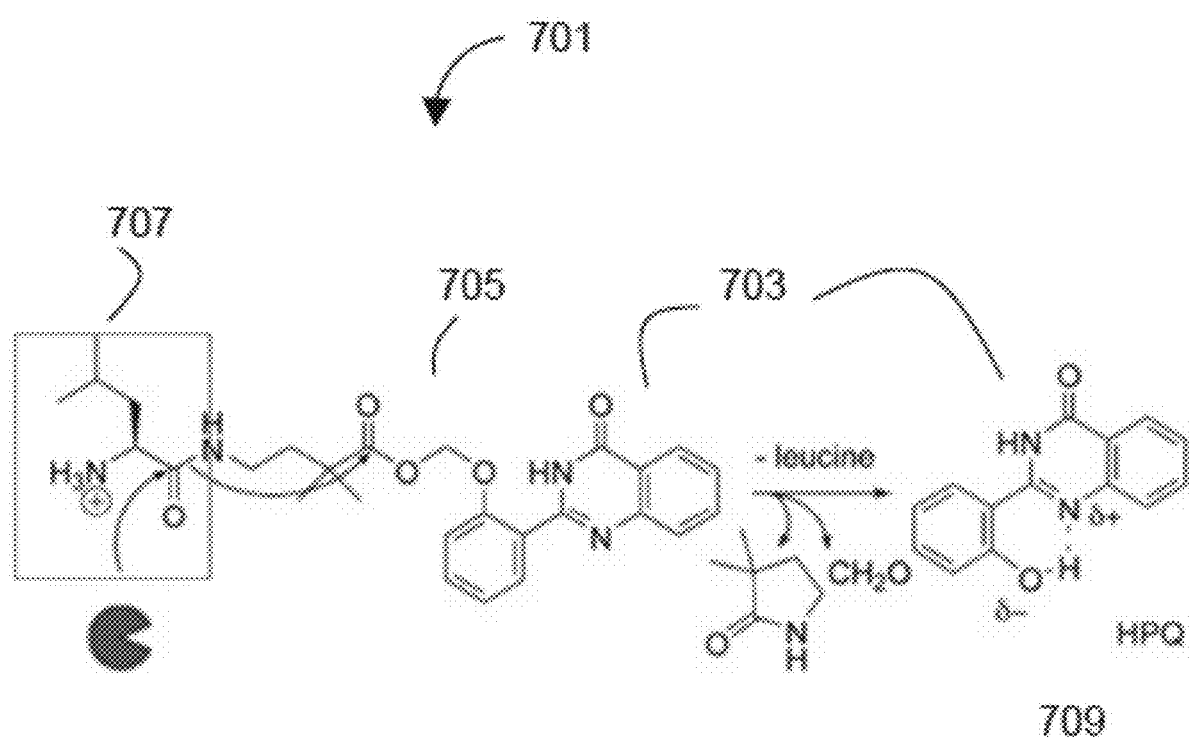
FIG. 7A-C shows reaction processes for HPQ fluorophore.
Figure 7B:
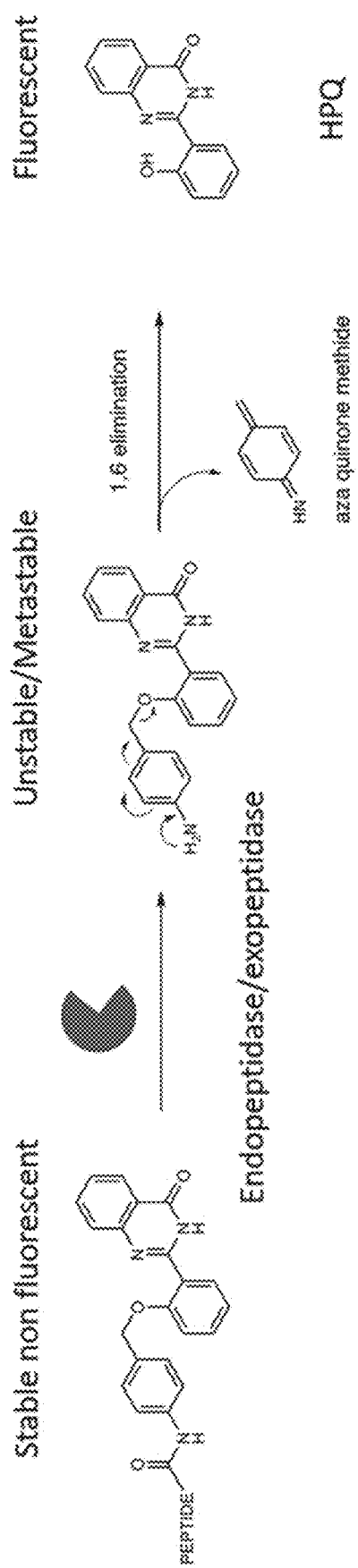
Figure 7C:
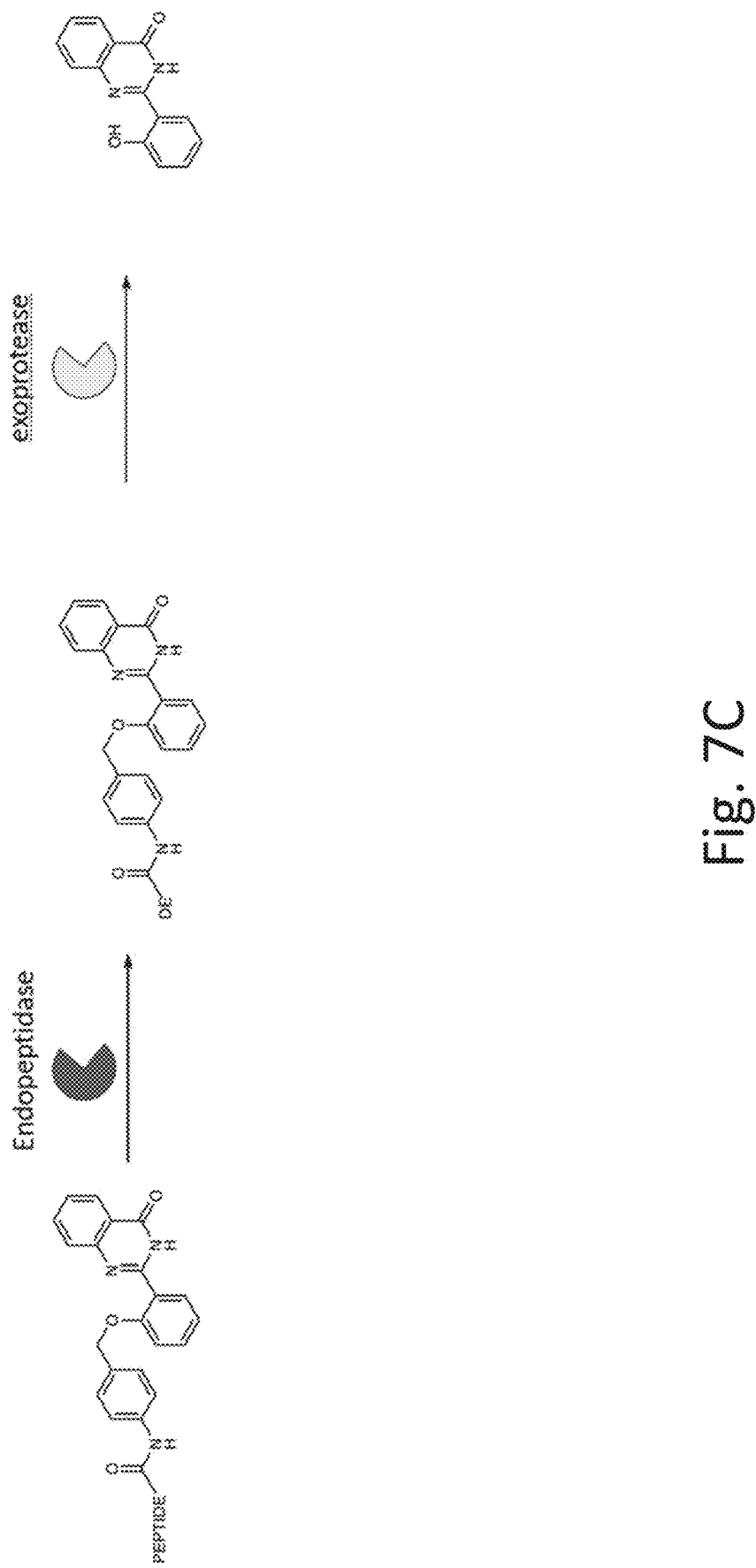
Figure 14:
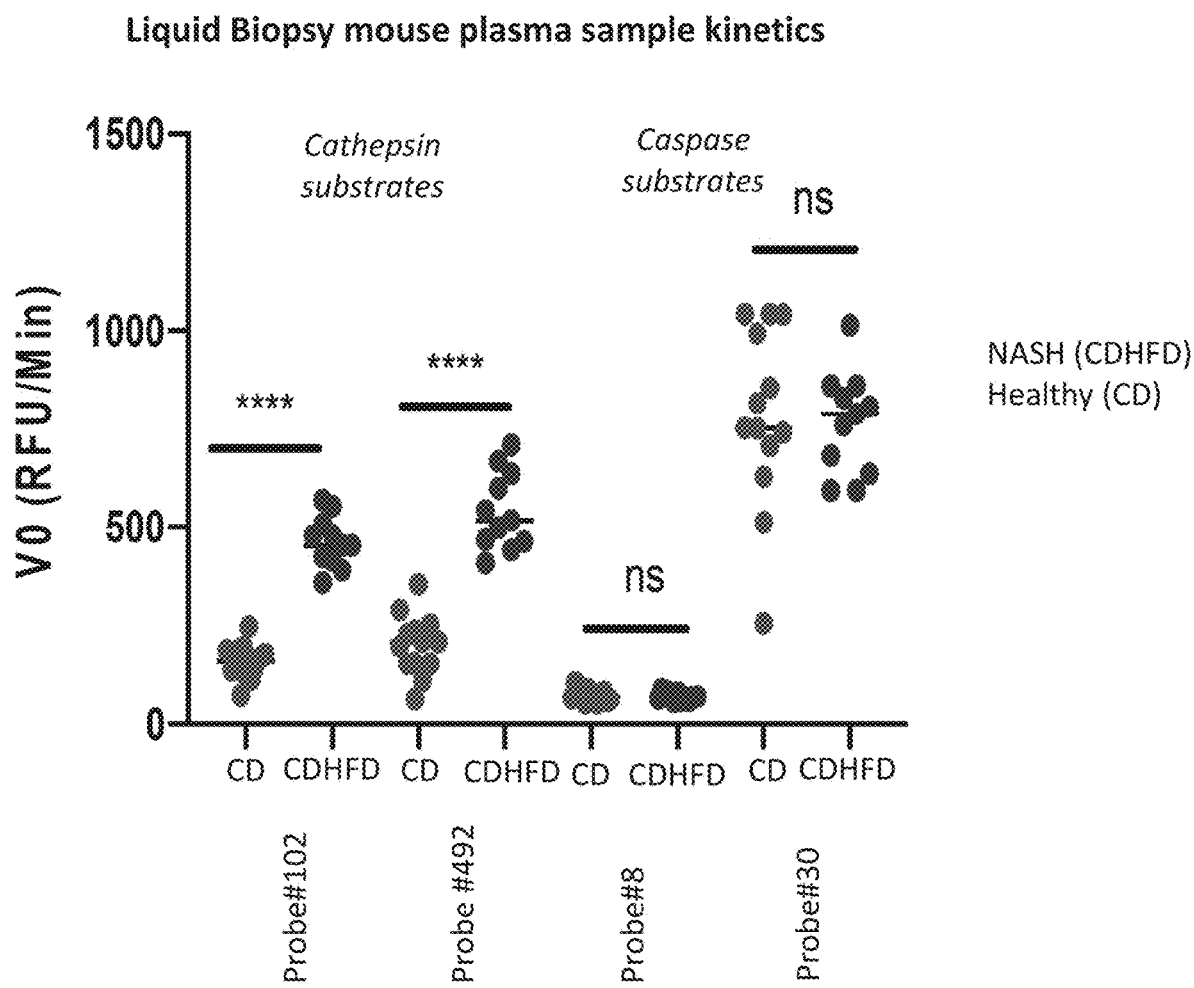
FIG. 14 shows that the probes can accurately detect and differentiate between samples from patients diagnosed with NASH via liver biopsy and healthy patient samples when encountering NASH-related proteases in mice $K_2$EDTA plasma.
Figures 15A, 15B:
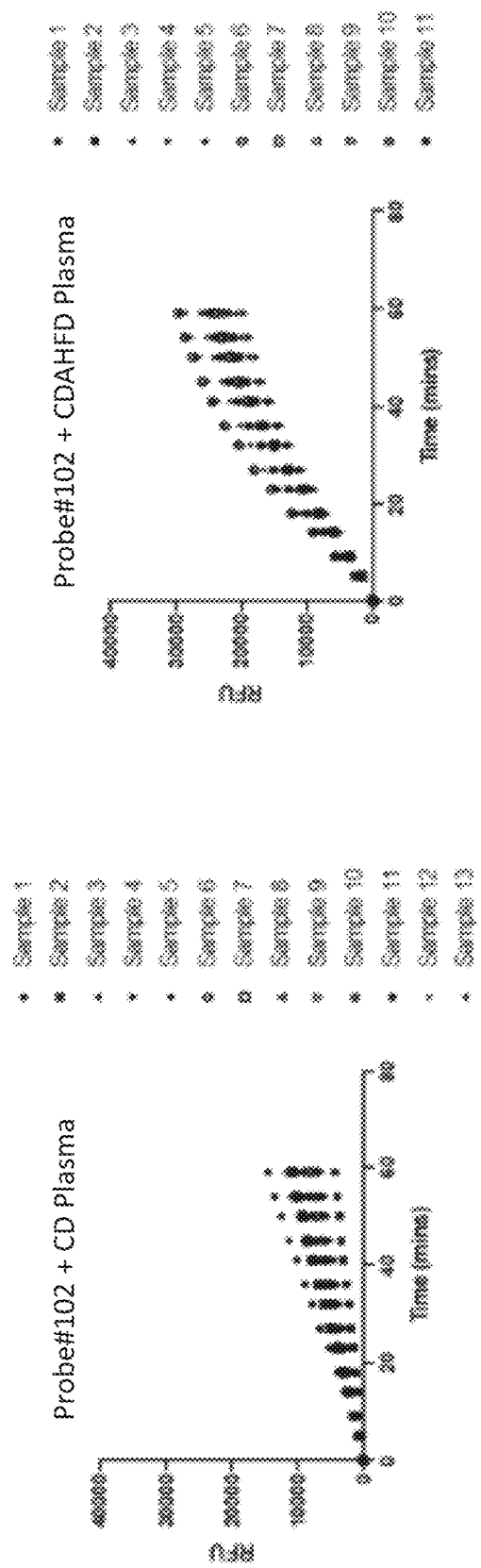
FIG. 15A-B provide experimental results showing that a specific peptide linker of the present application can differentiate between NASH-related protease activity in healthy mice and NASH+ samples from K2EDTA mice plasma.

As shown in FIG. 14, the probes of the present application were able to measure the activity of NASH-related proteases as expressed in Relative Fluorescent Unit (RFU) per minute in the two mouse populations. Probes measuring cathepsin activity were 3-fold higher in protease cleavage kinetics in mice with NASH compared to healthy mice. In contrast, probes sensing caspase activity showed no change in detectable activity between healthy and NASH mice. FIG. 15A and FIG. 15B show the subset of results for one probe, Probe #102, in detecting NASH-related protease activity; here, the use of the fluorescent reporter and quencher, like those discussed in FIG. 5, were shown to accurately measure the activity levels of NASH-related proteases in the plasma of healthy mice (FIG. 15A) and NASH mice (FIG. 15B).

Thus, probes of the present application can accurately detect the activity levels of proteases associated with a biological condition or disease-state in a subject, ex vivo, using a body fluid sample.

Example 2: Detection of NASH Protease Activity in Plasma in Mice

As shown in FIG. 14, the probes of the present application are able to accurately detect protease activity of NASH related proteases in the plasma samples taken from two mice populations, as explained in Example 1 and FIG. 13, in a multiplex format. A single plasma sample was contacted with the probes for each predetermined protease to provide a multiplex assessment of protease activity in the sample.

Figure 16:
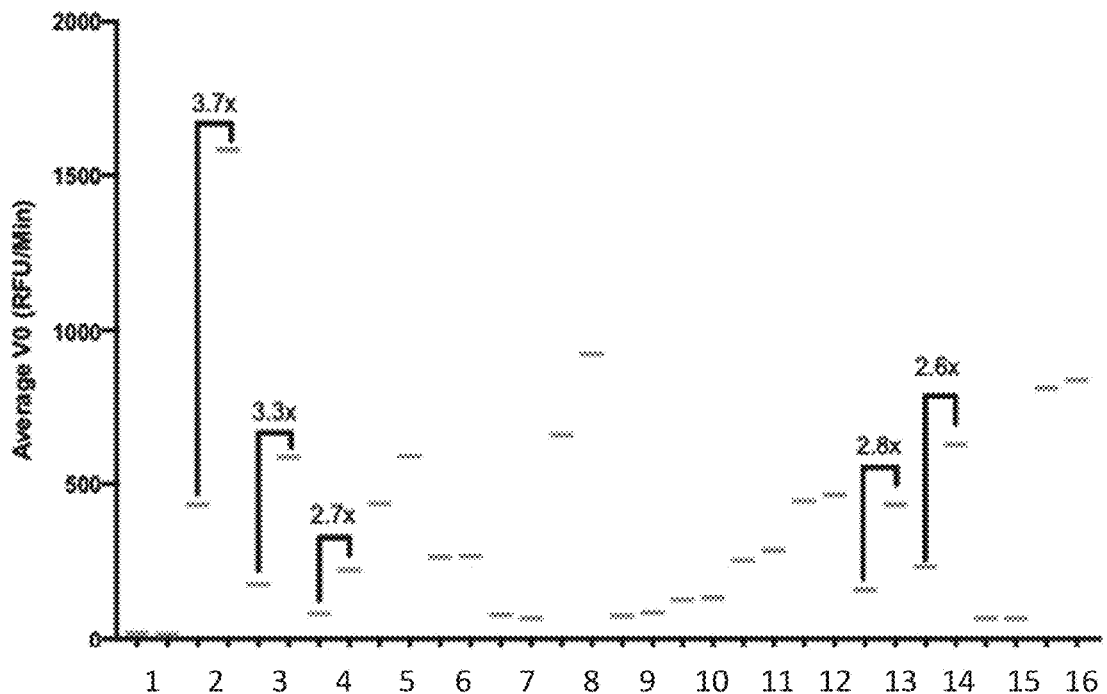
FIG. 16 provides experimental results comparing the ex vivo probes and their ability to distinguish between NASH (CDHFD) samples (the right data point) and healthy (CD) samples (the left data point).

In FIG. 16, for each set of probes, the protease activity in healthy mice is shown on the left, while the protease activity in NASH mice is shown on the right. As shown, the probes of the present application were able to measure increases in NASH-related protease activity.

Figure 17:
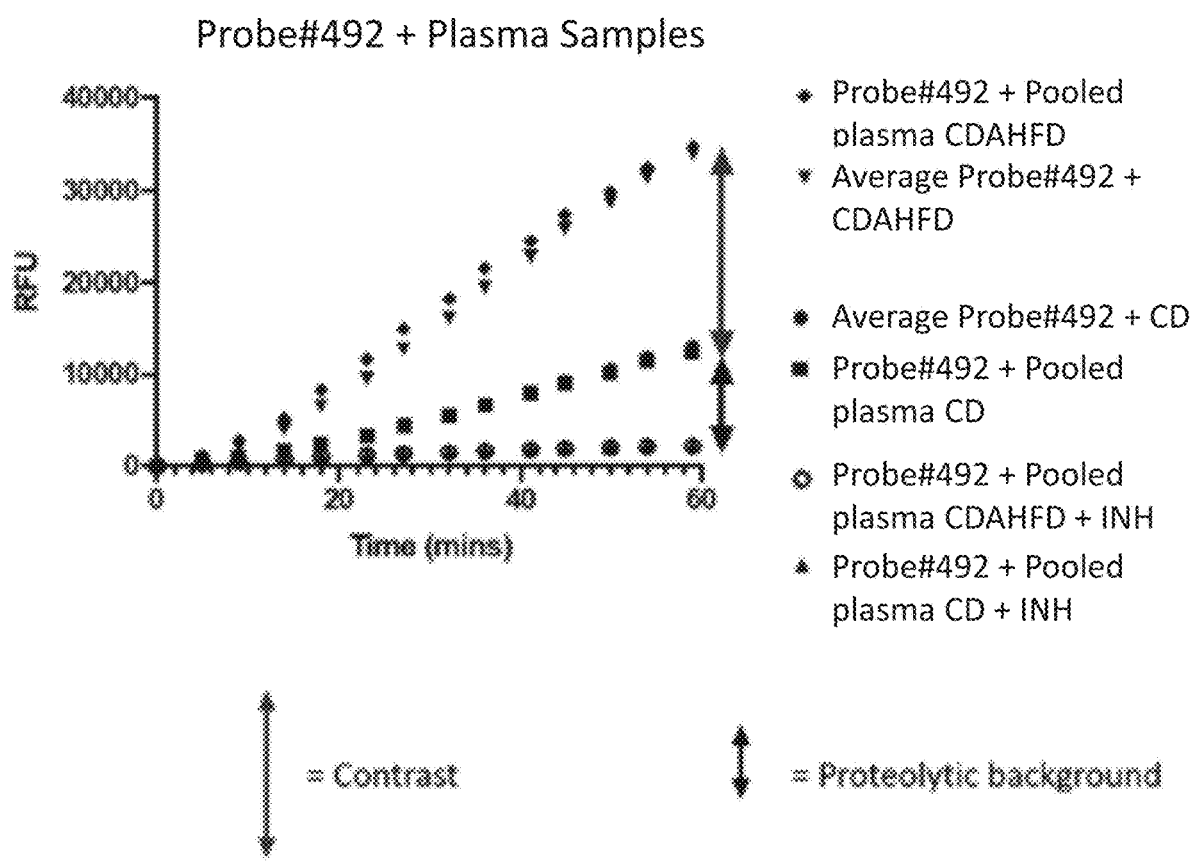
FIG. 17 provides raw experimental results showing that the measured rate of fluorescence increase for Probe #492 can be ascribed to protease activity and to NASH disease in K2EDTA mice plasma The average rate of fluorescence increase over n=10 samples matches pooled plasma (n=10) increase of fluorescence in both disease and healthy conditions.
Figure 18:
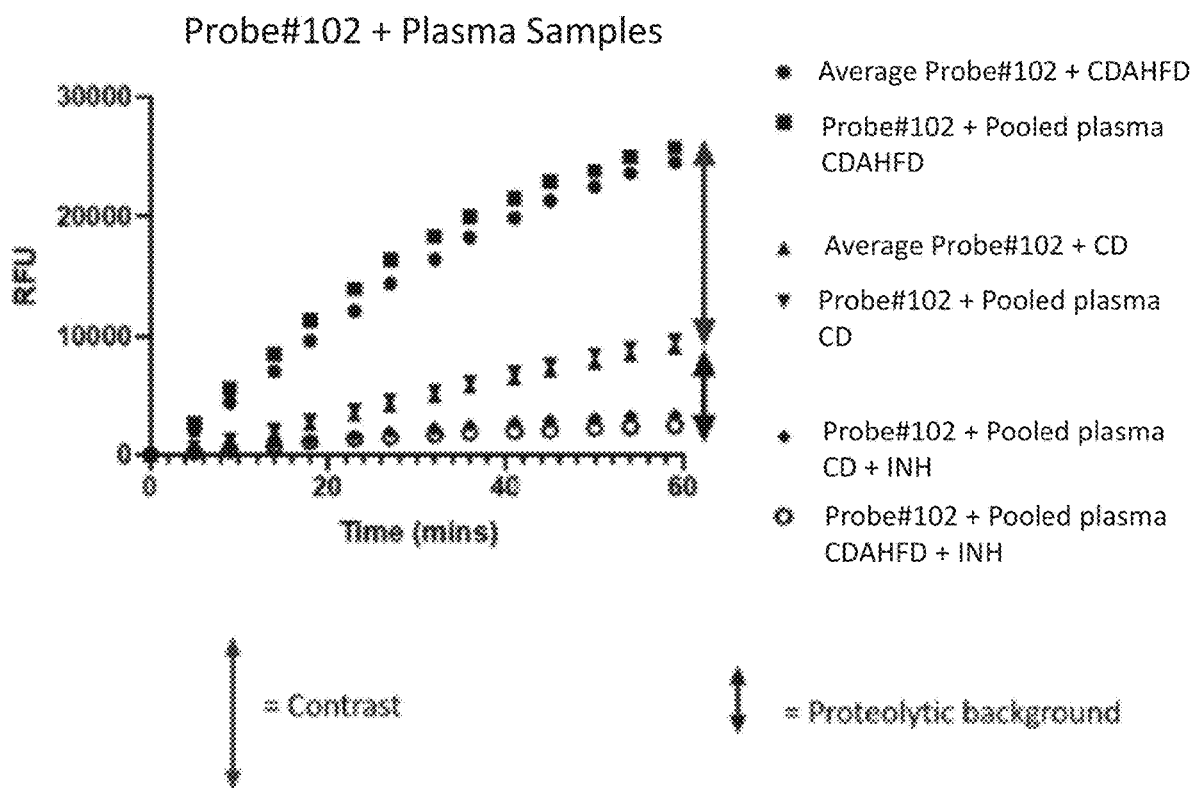
FIG. 18 provides experimental results showing that the measure rate of fluorescence increase for Probe #102 can be ascribed to protease activity and to NASH disease in K2EDTA mice plasma. The average rate of fluorescence increase over n=10 samples matches pooled plasma (n=10) increase of fluorescence in both disease and healthy conditions.

As shown in FIG. 17 and FIG. 18, protease activity measured as RFU/min was similar in pooled plasma samples within the same group of animals than the average of protease activity from each animal from that group. Furthermore, adding a broad protease inhibitor cocktail (INH) completely abrogated protease activity in both healthy and NASH animal groups, providing evidence that the fluorescent signal measured over time depends on proteolytic activities.

Figure 19B:
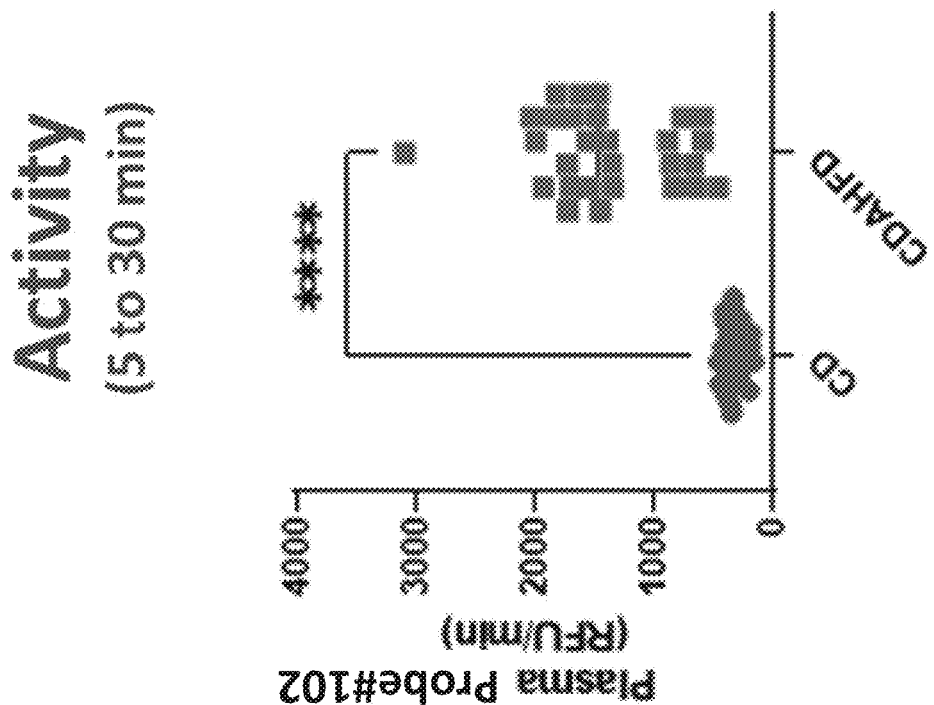
FIG. 19A-B provides experimental results showing that activity, not abundance, is responsible for determination of disease-based protease activity differences in K2EDTA mouse plasma samples.
Figure 19A:
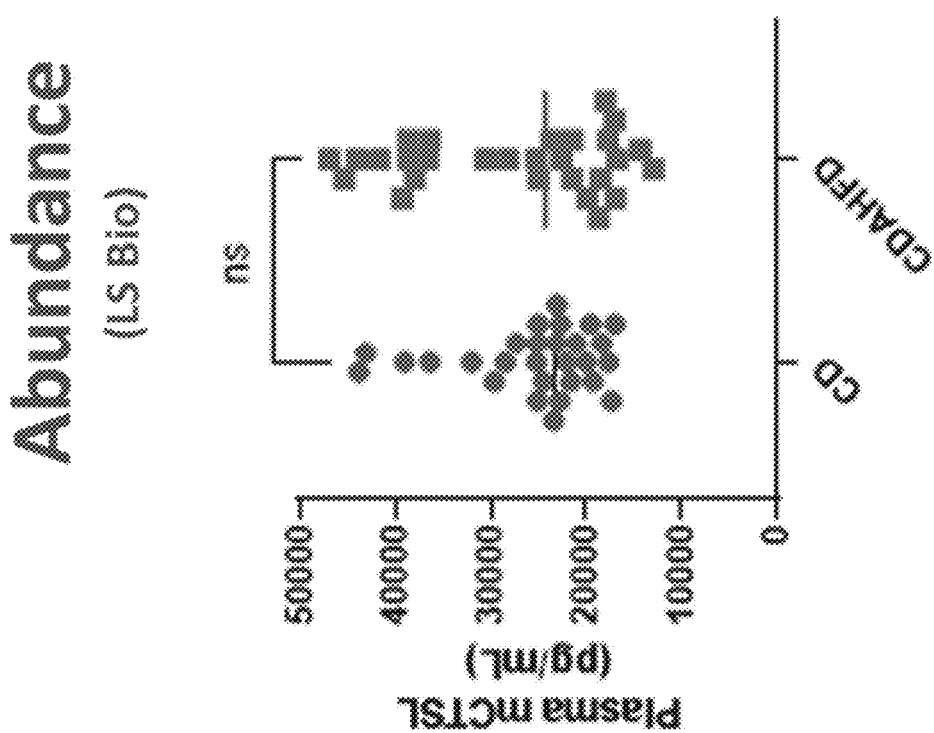

FIG. 19A and FIG. 19B show that, when studying samples of mouse plasma, activity, not abundance, is more important in differentiating between healthy samples and NASH samples. Although abundance of NASH-related proteases (here cathepsin L, or CTSL) may be comparable between healthy CD mice and NASH CDAHFD mice (FIG. 19A), the activity levels of these proteases are not (FIG. 19B). In this experiment, protease abundance was measured using an ELISA kit from LS Bio while activity was measured using the Probe #102 (a CTSL sensing probe) fluorescence assay described in Example 1.

Thus, probes of the present application can accurately detect the activity levels of proteases associated with a biological condition or disease-state in a subject, ex vivo, using a body fluid sample such as plasma in a multiplex format.

Example 3: Liquid Biopsy Determines Progression Versus Regression of NASH

In this experiment, the probes of the present application were able to differentiate among healthy mice, NASH mice, and NASH mice that were undergoing disease regression.

Figure 20:
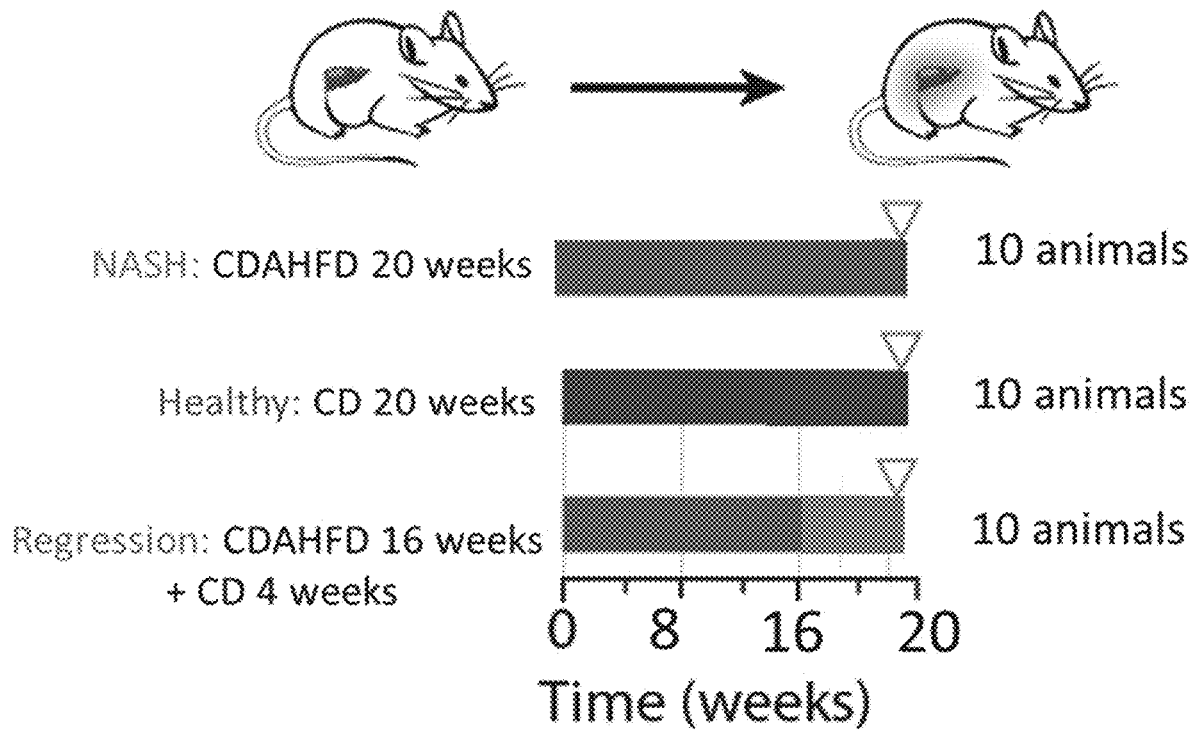
FIG. 20 outlines an experimental design of the present application.
Figures 21A, 21B, 21C:
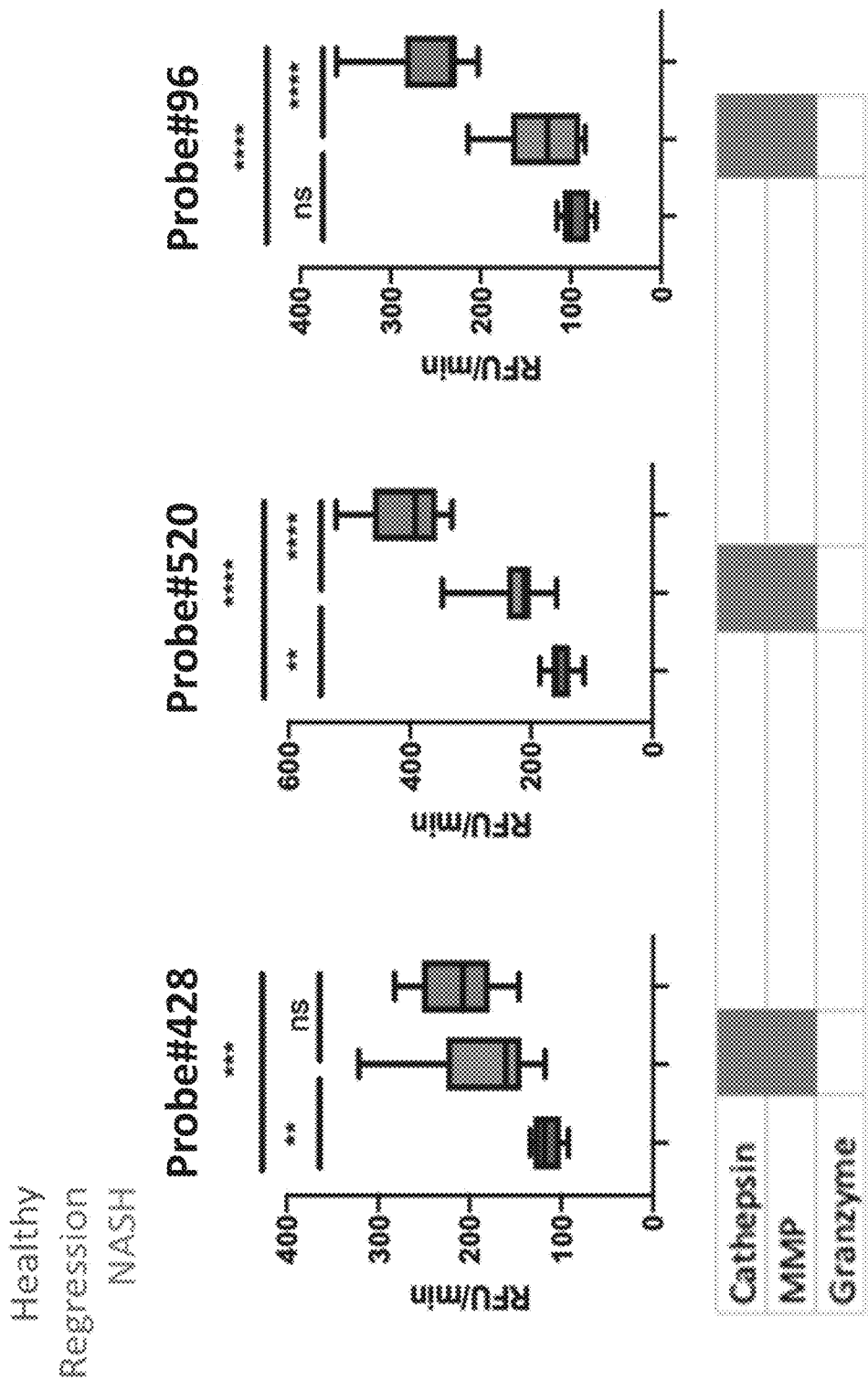

FIG. 20 shows the experimental design including three groups of mice: CDAHFD NASH mice for 20 weeks (NASH progression), healthy CD mice for 20 weeks, and mice fed a CDAHFD for 16 weeks before being switched to a chow diet for 4 weeks (NASH regression). Plasma samples were collected from all animals at 20 weeks.

As seen in FIGS. 21A-F, several probes were used to contact the thawed plasma, as described in Example 1, and this resulted in clear differentiation between the healthy, regression, and NASH samples. The probes showing the most differentiation in NASH were linked to cathepsin and/or MMP protease activities.

This experiment showed that not only can we differentiate between healthy and diseased samples, but it can also differentiate among healthy, disease-progressing, and disease-regressing samples.

Example 4: Liquid Biopsy Applications Towards Fulminant Hepatitis in Mice

In this experiment, another mouse liver-disease model—that for fulminant hepatitis—was studied to determine the wider uses of the present application. This experiment served to develop the ex vivo assay technology for applications in hepatitis models using plasma and existing sensors in the FRET substrate library.

Figure 22:
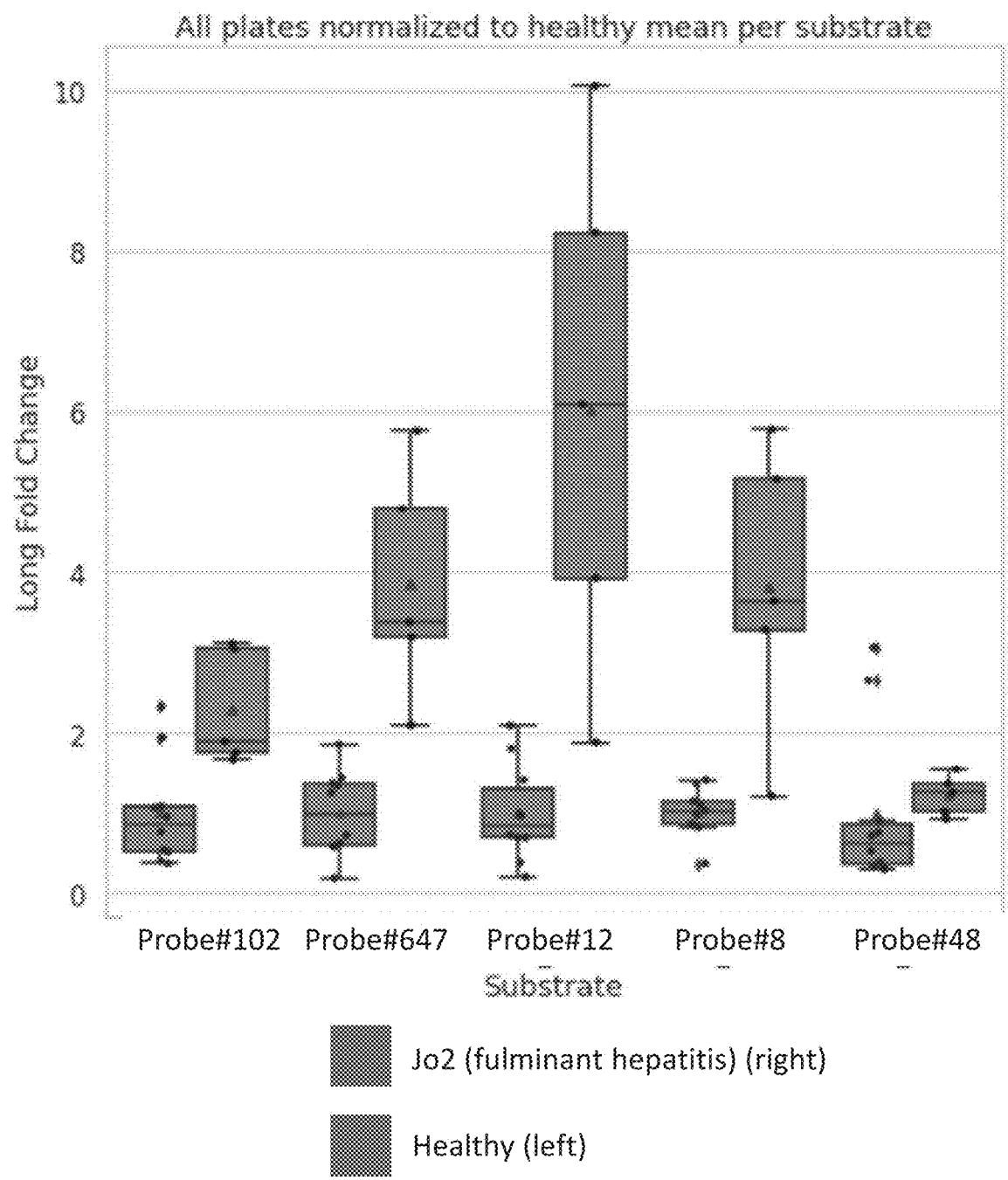
FIG. 22 provides experimental results showing the probes can distinguish between healthy and the J02 mouse model of fulminant hepatitis samples ex vivo. The Jo2 antibody shows cytolytic activity against cell lines expressing mouse Fas by inducing apoptosis.
Figure 23:
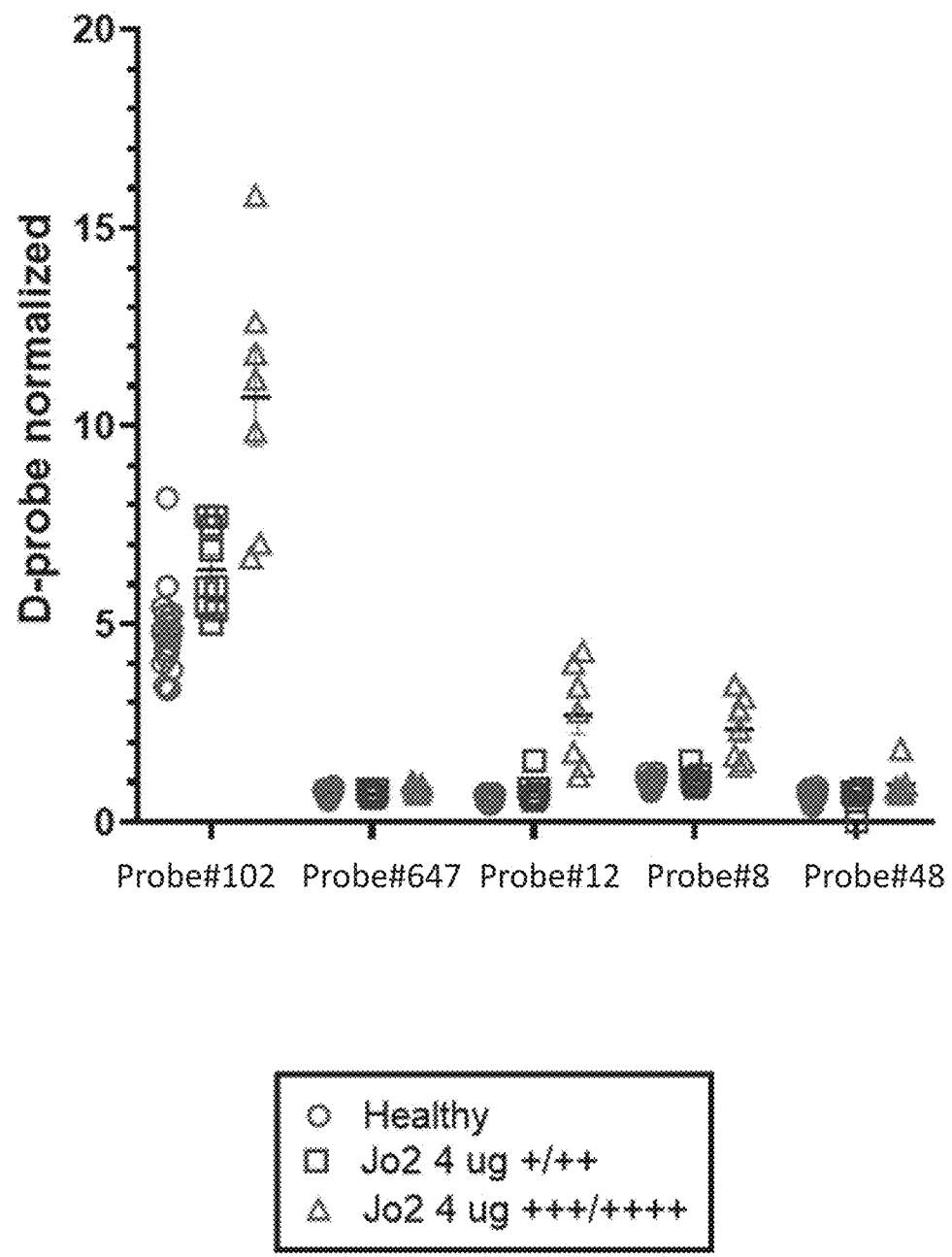
FIG. 23 provides experimental results showing the probes can distinguish between healthy and fulminant hepatitis samples in vivo in a mice model. +/++ group denotes mild hepatitis symptoms and +++/++++ group denotes fulminant hepatitis based on physio-pathological examination of mice. The Jo2 antibody shows cytolytic activity against cell lines expressing mouse Fas by inducing apoptosis.

Fulminant hepatitis is induced after injection intraperitoneal of monoclonal antibody anti-CD95 (Jo2, BD biosciences, 4 ug/animal), and mouse plasma samples were collected 3 hours after Jo2 injection. As shown in FIG. 22, when the probes contacted the mouse plasma samples using the method described previously in Example 1, the probes were able to differentiate between healthy and Jo2 samples ex vivo. FIG. 23 shows the same results in vivo, with the same mice receiving the injectable probe formulation for direct comparison with the ex vivo approach.

The Jo2 hepatitis model demonstrates differential probe cleavage compared to NASH liver model data in mice. Predominantly Caspase centric probes (Probe #647, Probe #8, Probe #12) show contrast that is specific and sensitive to the Jo2 model. The comparison with mass spectrometry data also aligns and confirms high concordance with the ex vivo approach, which is reassuring to confirm the existence of a biologically relevant signal.

Figure 24:
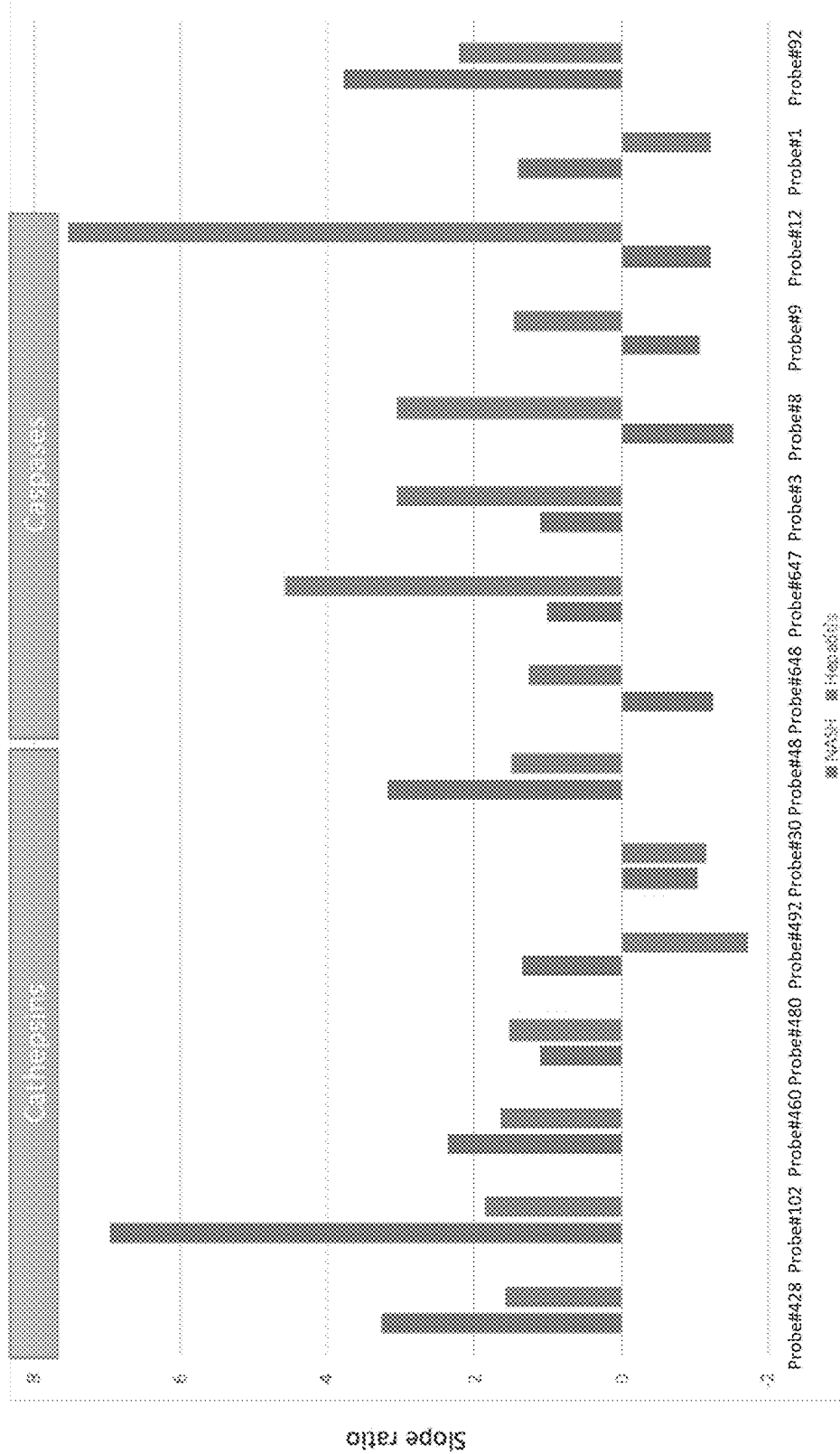
FIG. 24 shows that peptide fragments can distinguish between two different preclinical models of liver disease due to their distinct biological mechanisms.

FIG. 24 demonstrates that for two preclinical models of liver disease, the application can distinctly identify each disease due to the distinct biological mechanisms underlying protease activity of each disease (i.e., cathepsin activity in NASH and caspase activity in hepatitis).

Example 5: Detecting NASH in Human Plasma

This experiment relates to the detection of NASH in humans.

Figure 25:
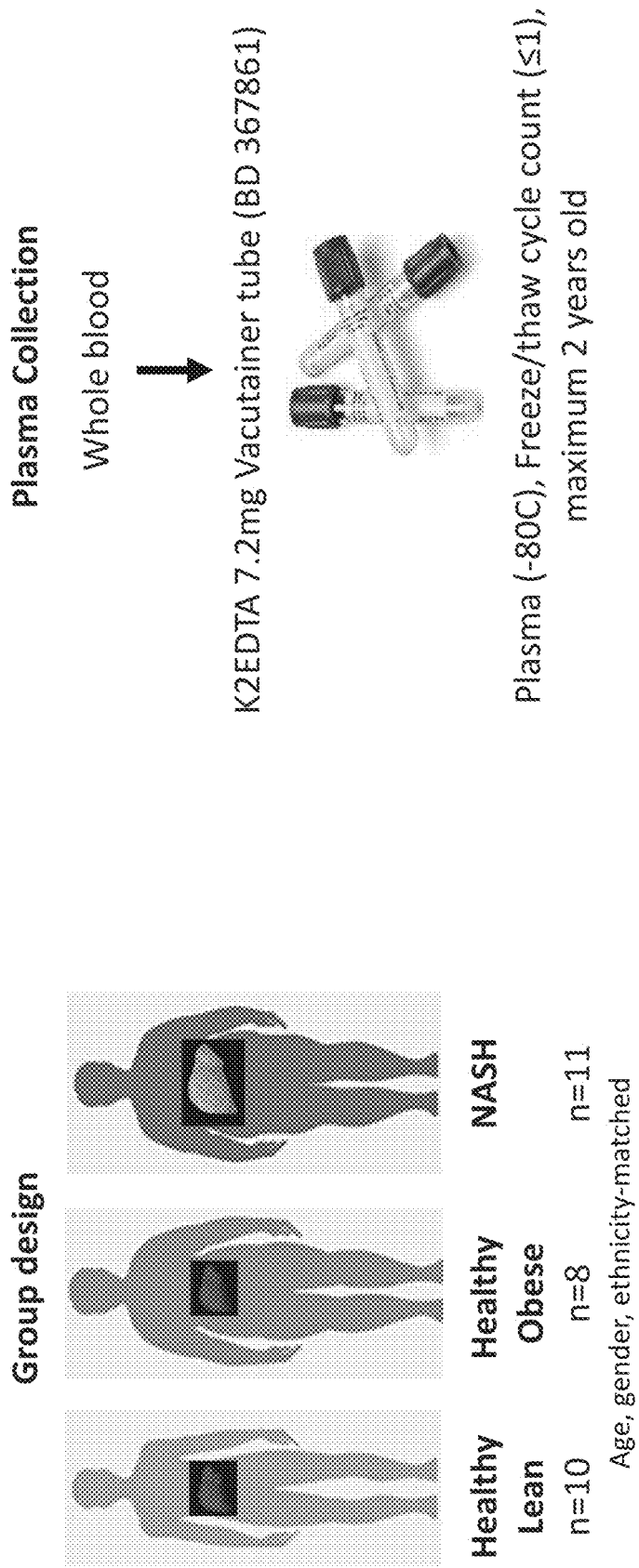
FIG. 25 outlines an experimental design of the present application.

As shown in FIG. 25, blood samples were collected from human subjects that were diagnosed as healthy/lean, healthy/obese, or NASH. Plasma was obtained from these blood samples in the same method as used in Example 1. The plasma was stored at −80C for no more than 2 years and with a freeze/thaw cycle count of ≤1 for each sample.

Figure 26:
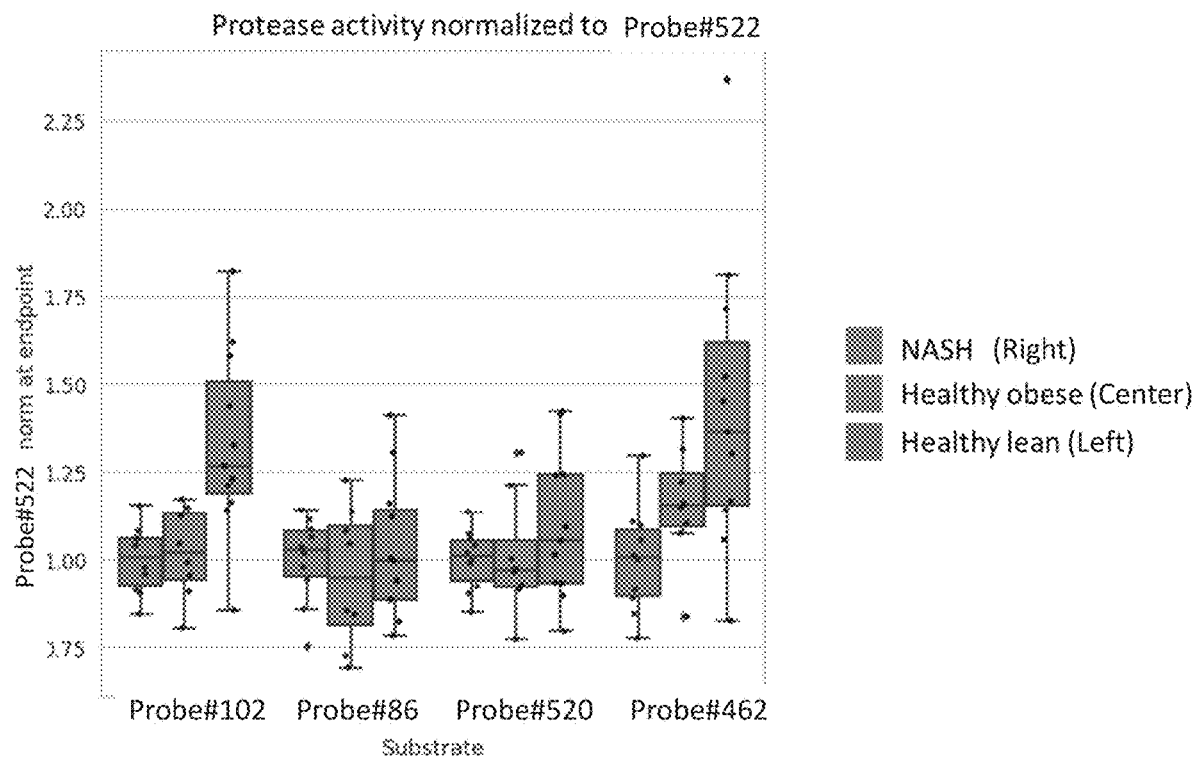
FIG. 26 provides experimental results showing the probes can distinguish between healthy, Obese and NASH human samples.

As shown in FIG. 26, when the probes contacted the human plasma samples using the method described in Example 1, increased fluorescence levels over time were observed in NASH samples when compared to healthy, allowing differentiation between the protease activity levels of healthy and NASH samples.

Figure 27:
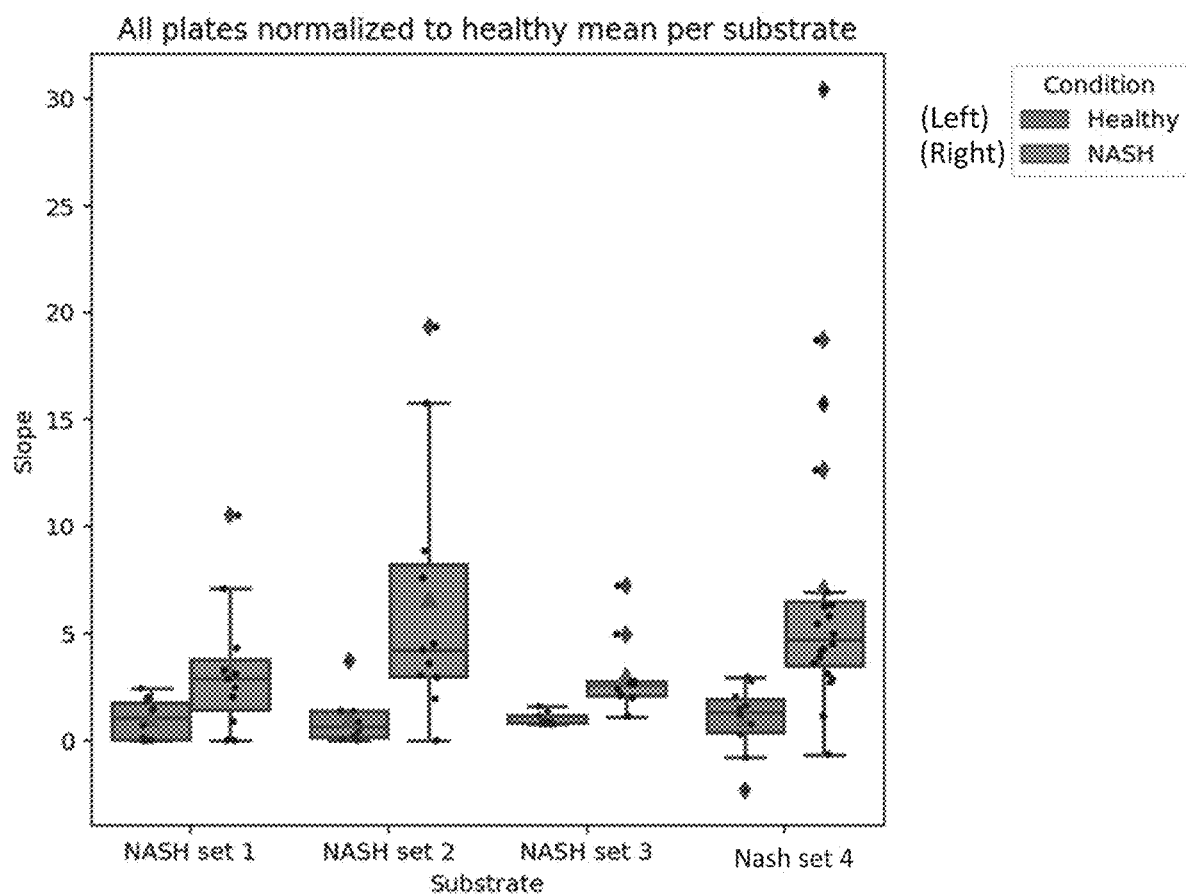
FIG. 27 provides experimental results that show reproducibility among independent sample cohorts with various collection dates, collection protocols, shipment etc.

FIG. 27 shows high levels of reproducibility in the application's ability to differentiate between healthy and NASH samples when independent sample cohorts were tested.

Figure 28:
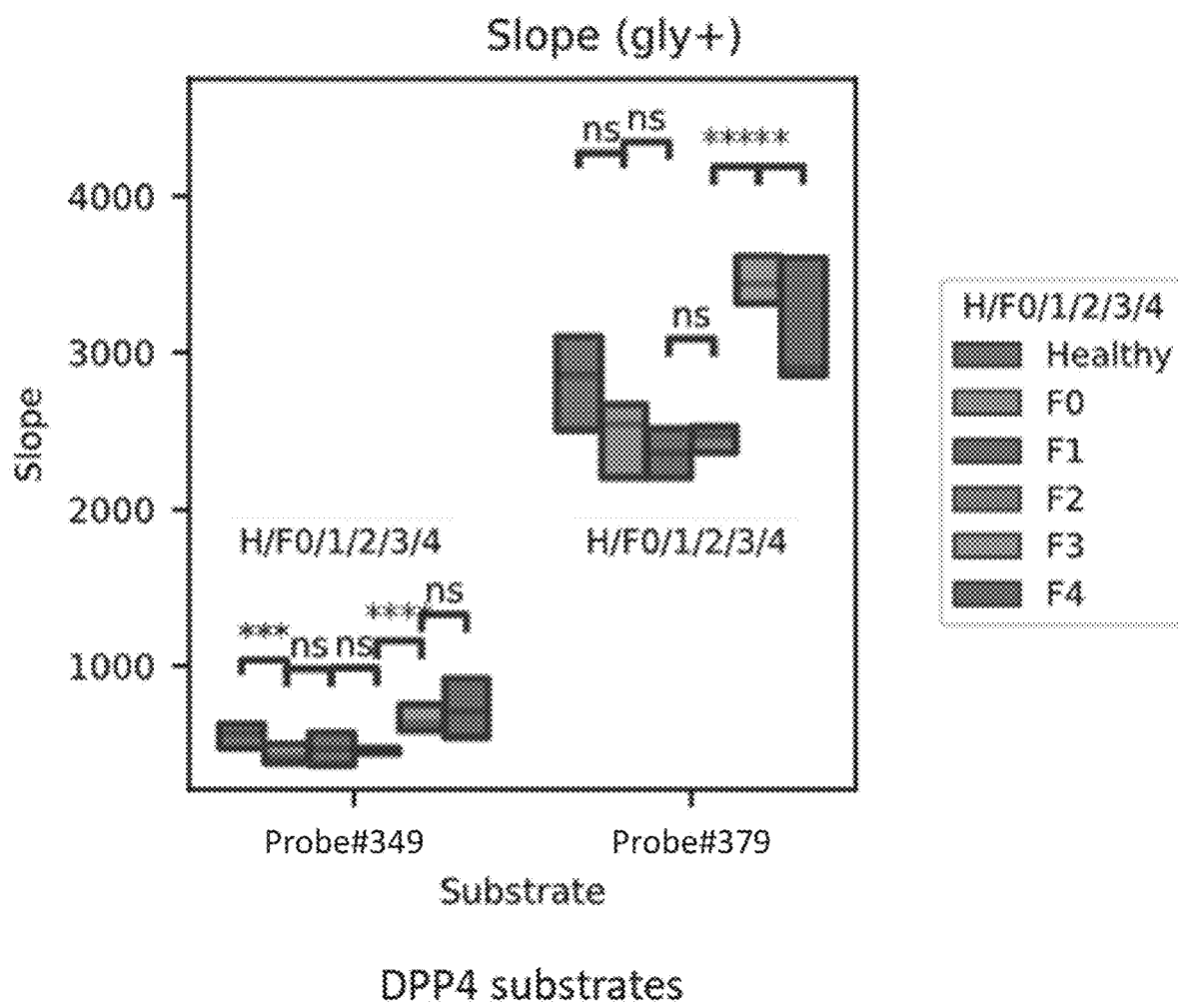
FIG. 28 provides experimental results showing the peptide fragments can distinguish between different stages of NASH disease progression in specific assay conditions.

FIG. 28 further demonstrates that the application is not only able to differentiate between healthy and NASH human samples, but it is, surprisingly, also able to differentiate between early-stage (F0-F2) and late-stage (F3+) NASH. The entire F0-F4 data set contains 100 NASH samples, and the experiment was conducted using the method from Example 1.

Figure 29:
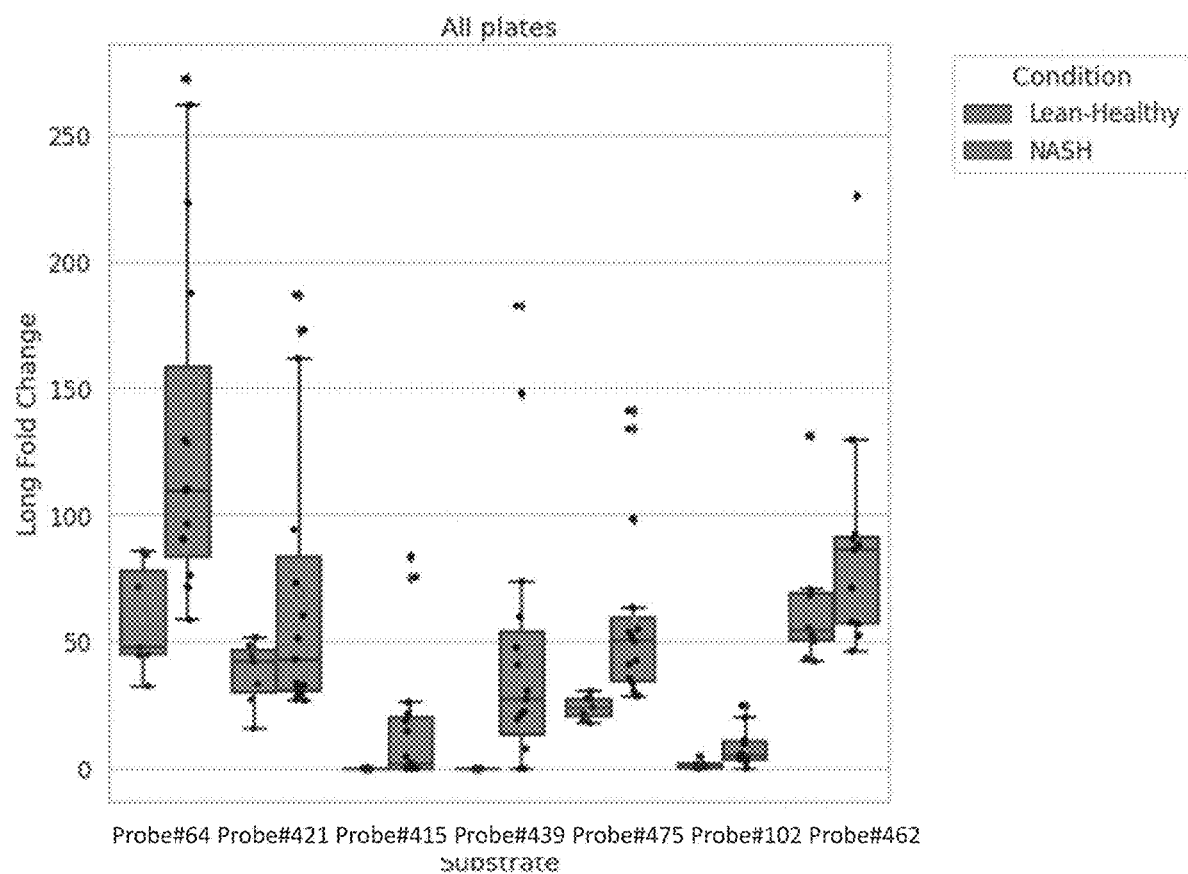
FIG. 29 provides experimental results showing the multiplicity of the peptide fragments able to distinguish between NASH and Healthy human K2EDTA plasma.

As shown in FIG. 29, multiple probes of the present application are able to differentiate between healthy and NASH samples in humans—this multiplicity furnishes a lower false-positive rate when testing samples This experiment demonstrates the application is highly adept at differentiating between healthy and NASH (and different fibrosis stages of NASH) in a non-invasive manner in human subjects.

Example 6: Mechanism of Function of Liquid Biopsy

In this experiment, the specific protease cleaved by a specific probe is determined in order to show the specificity of the application regarding the disease differences it detects. This experiment also shows that protease activity, not abundance, is the driving factor in the application's determination of disease-markers in a sample.

For this experiment, all plasma samples were prepared individually and diluted 1/10e in PBS with inhibitor added directly to the samples. Inhibitor was prepared at 15× concentration to final. Substrates were diluted in DI water at 18 uM, such that the final concentration on the plate would be 6 uM. All samples were prepared such that their last dilution on the plate would not affect the desired final concentration. 10 ul of each individual sample was pipetted into their corresponding wells, and the plate was then spun down in the centrifuge at 1500 RPM for 30 seconds to coat the bottom of each well with the sample. 5 ul of the 18 uM substrate solution was pipetted into each well being used on a 384 well plate, and then the plate was spun down in the centrifuge at 1500 rpm for 30 seconds. The plate was placed immediately in the plate reader at 37° C. for a 30-minute-long fluorescence kinetic read at 485/535 extended gain.

To assess the proteolytic cleavage pattern of Probe #102, samples were tested using a pool of broad inhibitors for serine, cysteine, threonine, MMP and aspartic protease family members (broad inhibitor) to assess general protease activity, AEBSF for serine proteases, E64 for cysteine proteases, CTSi for broad cathepsin inhibition of cathepsins L, S, K and B, or specific inhibitors for cathepsin K (L00625), for cathepsin L (SID) or cathepsin B (CA074).

All E64 (broad cysteine), SID (CTSL) and the CTSi (CTSL, S, K, B) inhibitors decreased NASH signal significantly with less decrease in signal for healthy, indicating that the nature of the decrease in signal was disease-specific. When using the broad inhibitor or E64, we observed a greater than 6-fold decrease in the RFU signal contrast between NASH and healthy samples, indicating that a cysteine protease was responsible for the disease contrast. Broad cathepsin inhibitor CTSi decreased NASH by 47% while only decreasing healthy by 18%, demonstrating that a cathepsin was responsible for the disease contrast. A specific cathepsin inhibitor for CTSL (SID) decreased NASH by 60% while only decreasing healthy by 33%. Both NASH and healthy decreased with the addition of the serine inhibitor, AEBSF. NASH was inhibited 65%, while healthy was inhibited at 60%. The similar decrease in RFU for both NASH and healthy indicates that the AEBSF signal being sensed by Probe #102 is not a significant contributor to the disease specific signal and of a background nature.

Specific inhibitors for cathepsin K and B, L006235 and CA074, respectively, did not significantly decrease signal for NASH or healthy samples.

Figures 30C, 30D:
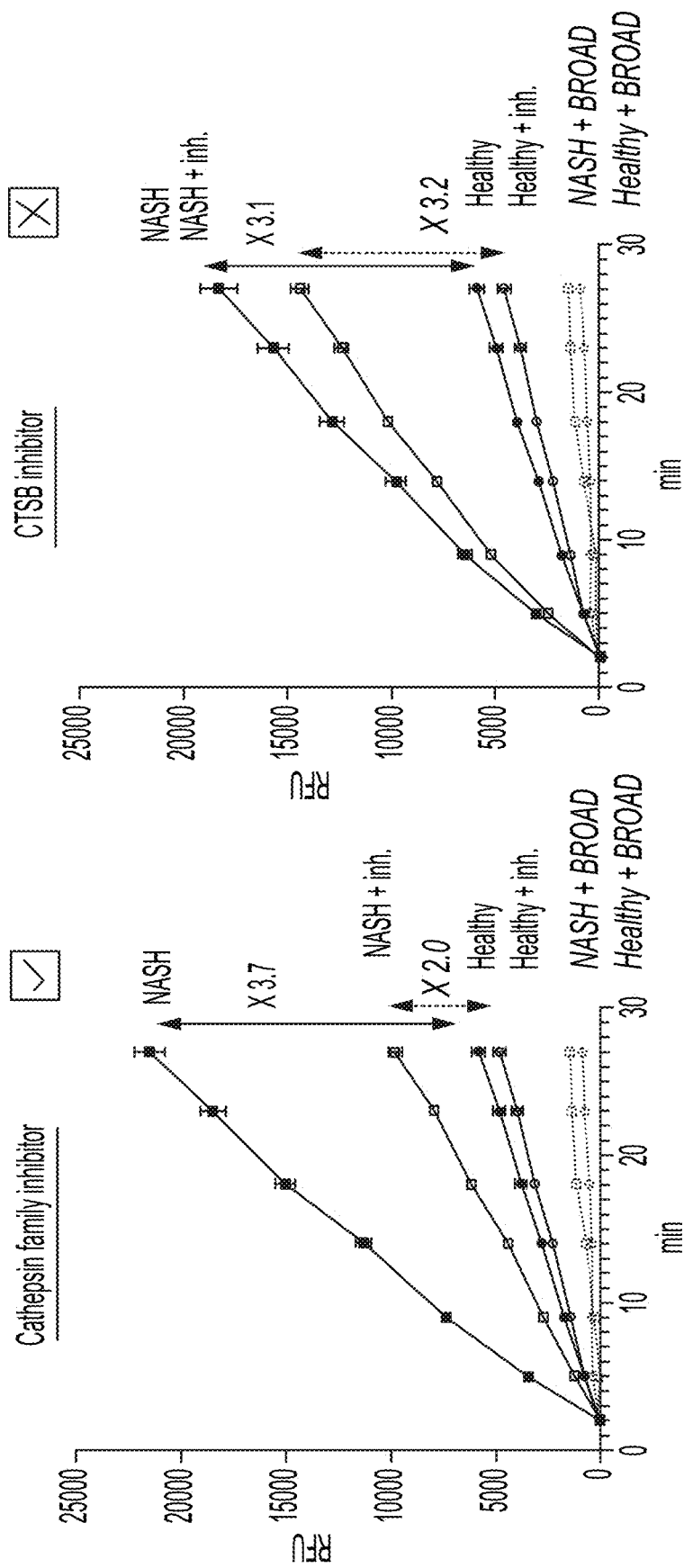
Figure 30F:
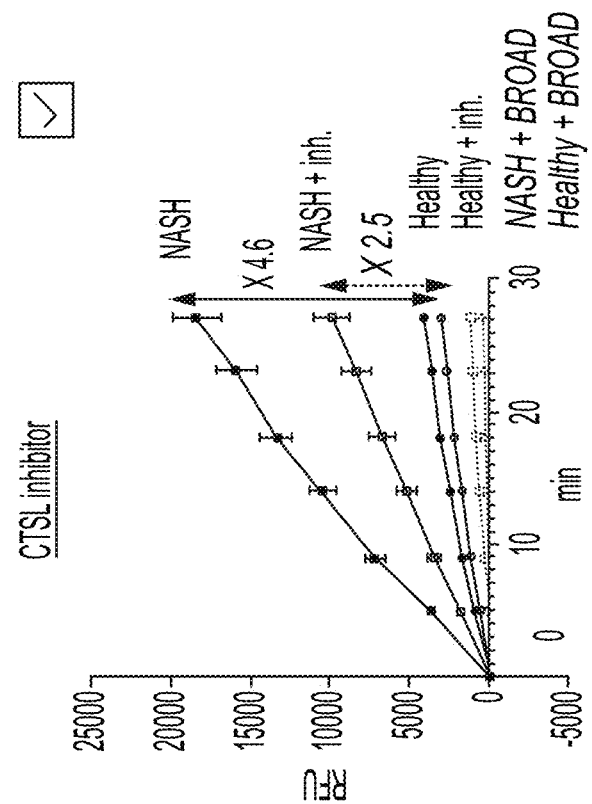
Figure 30E:
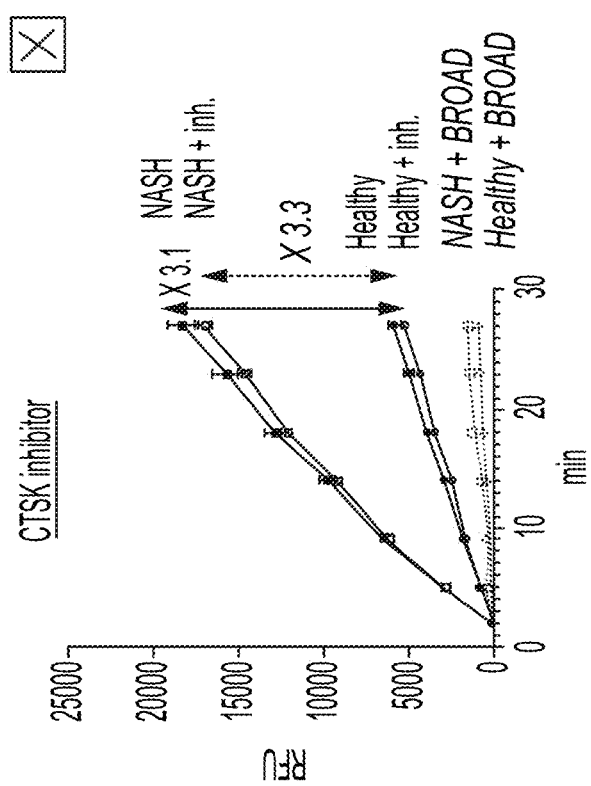

FIG. 30A demonstrates Probe #102 in combination with broad protease inhibitors to show that Probe #102 specifically contacts a protease in order to determine the difference between healthy and NASH samples. FIG. 30B shows that Probe #102 contacts a cysteine protease, and FIG. 30C further limits this to a cathepsin family protease. FIG. 30D-F test individual cathepsins to show that Probe #102 specifically responds to the activity of cathepsin L (CTSL), a NASH-related protease. Thus, cathepsin L activity is responsible for the disease vs. healthy differences in protease activity in samples as recognized by the application.

Figure 31A:
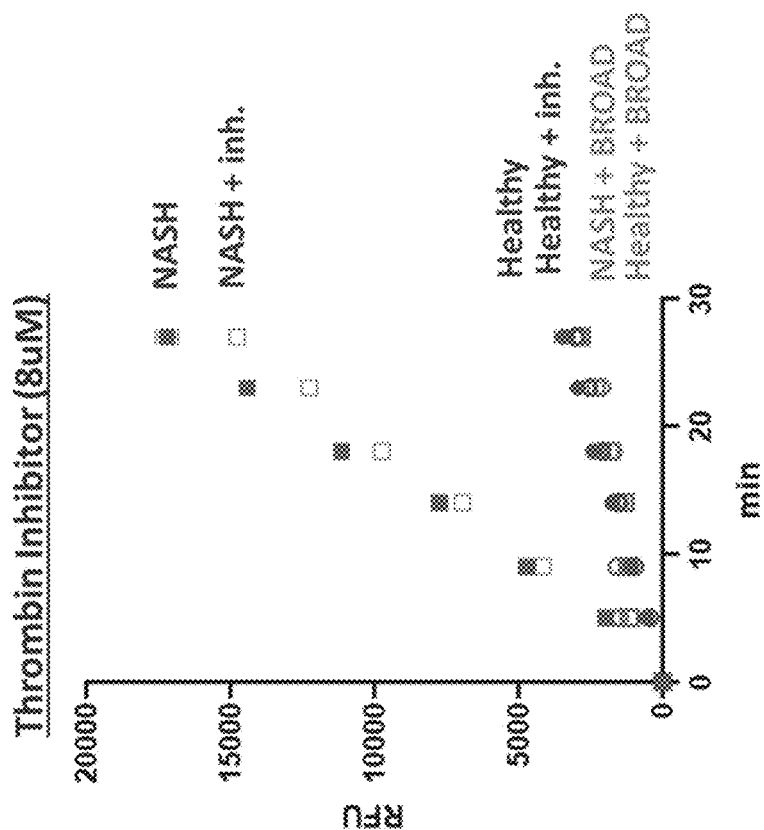
FIG. 31A-B provides experimental results showing that two common promiscuous proteases abundant in plasma are not responsible for determination of disease-based protease activity differences in NASH samples in K2EDTA mice plasma.
Figure 31B:
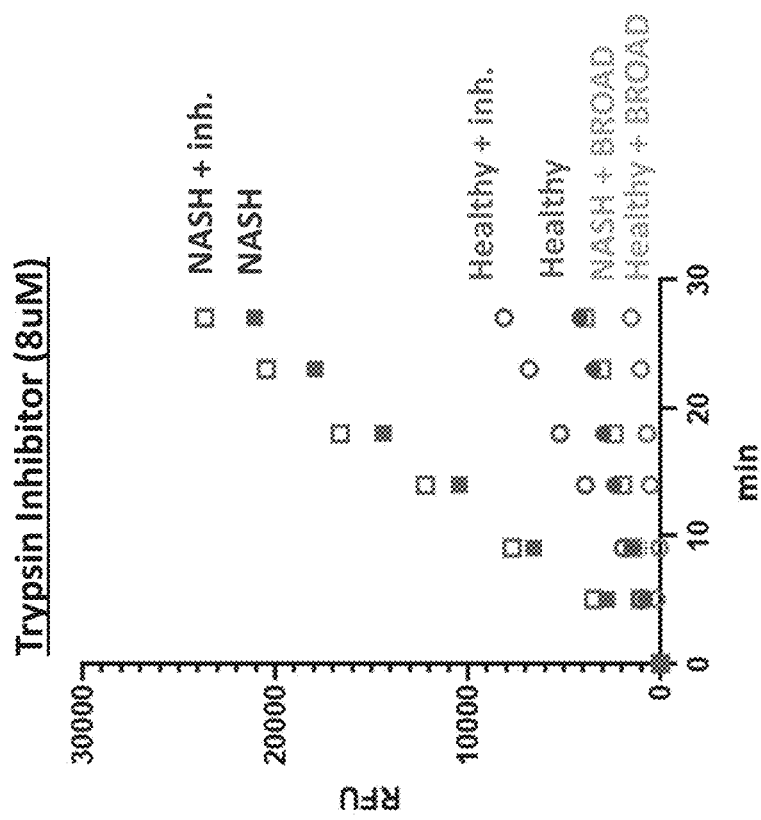

As shown in FIG. 31A-B, the application's discrimination between healthy and NASH tissue is not caused by either trypsin or thrombin, both promiscuous proteases that are constantly present in blood.

Figure 32B:
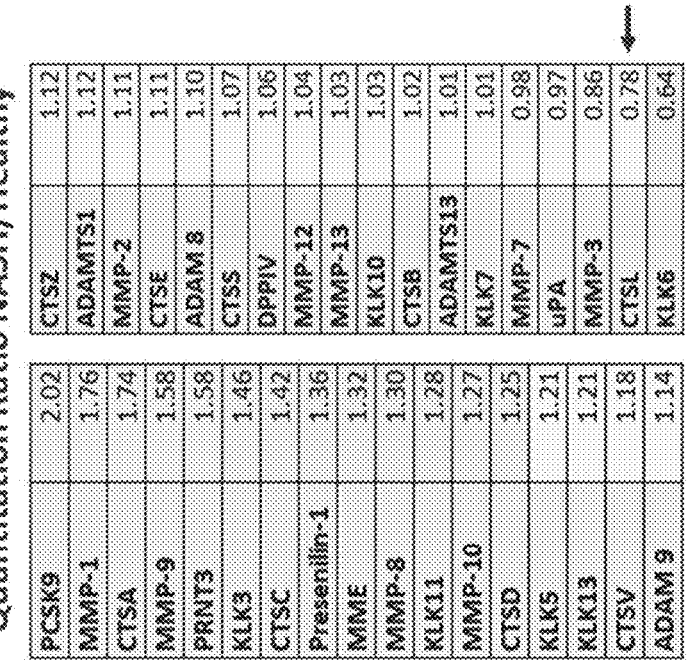
FIG. 32A-B provides experimental results showing that activity, not abundance, is responsible for determination of disease-based protease activity differences in human samples.
Figure 32A:
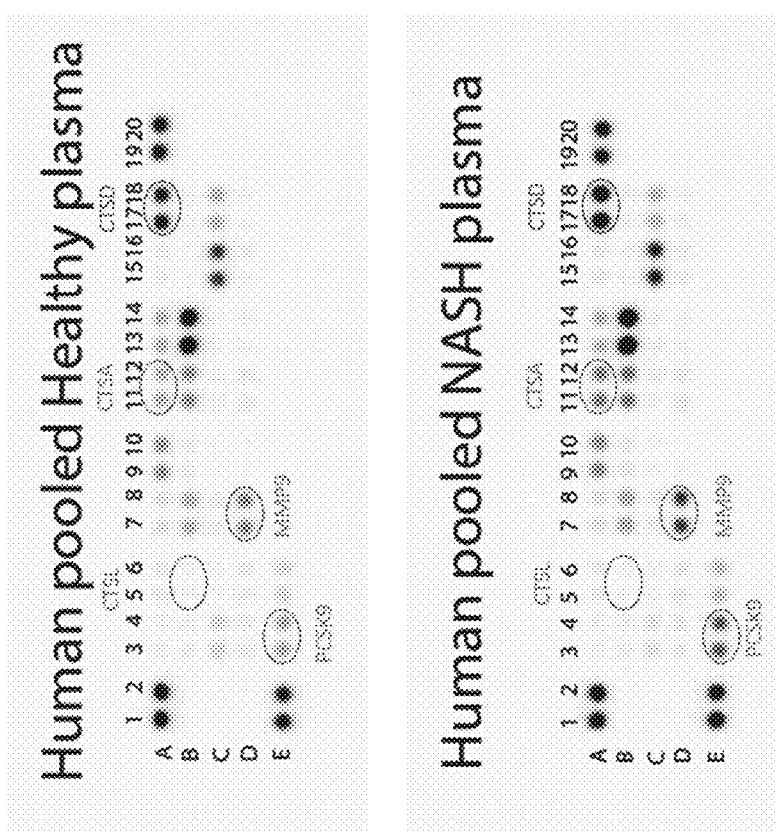

As shown in FIG. 32A-B, protease activity is the true measure of disease, rather than protease quantity. This corroborates the previous determination in mice that activity is more important than abundance as previously seen in Example 2 and as previously shown in FIG. 19.

Figure 33B:
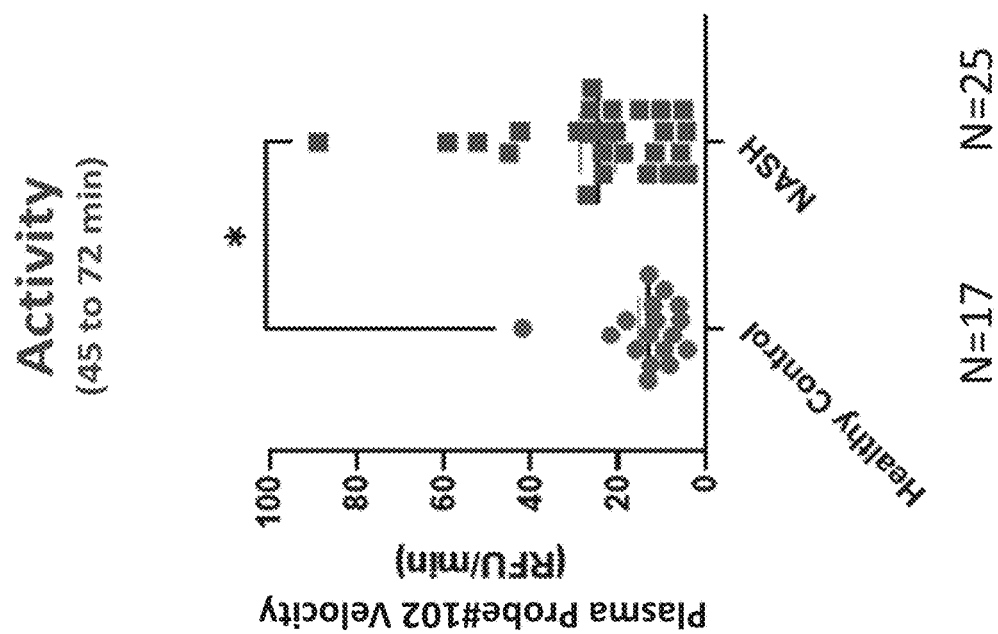
FIG. 33A-B shows that although Cathepsin-L is equally abundant in both healthy and NASH human samples, the differences in its activity levels allow for the differentiation between healthy and NASH samples.
Figure 33A:
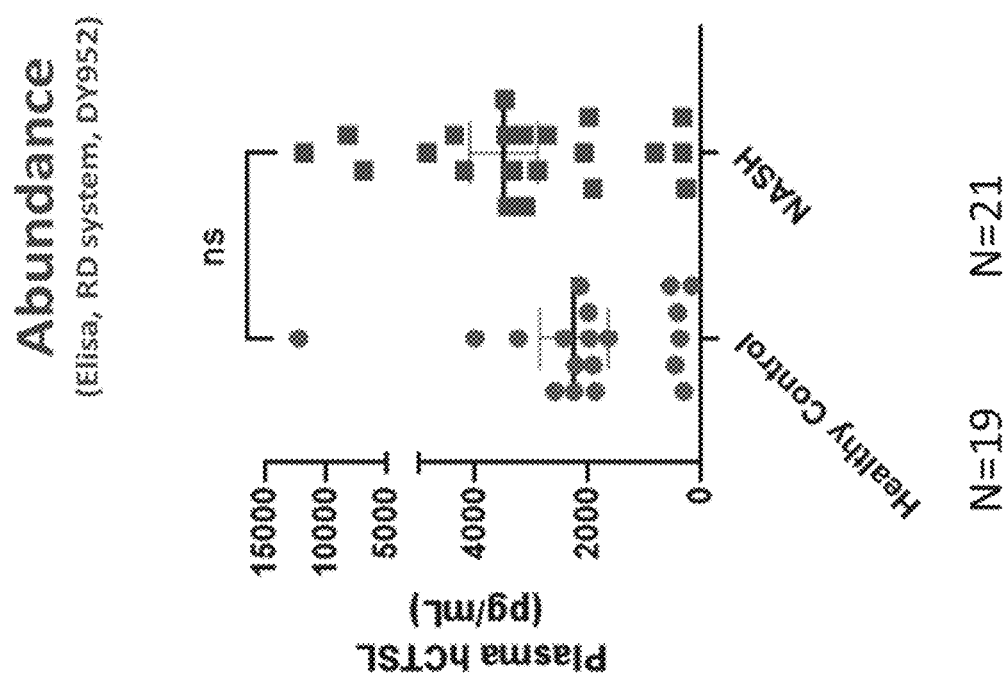

More specifically, FIG. 33 demonstrates that although CTSL is equally abundant in both healthy and NASH human samples, CTSL activity is different between these two sample populations.

The application is shown to function by measuring the activity levels, rather than the abundance of specific disease-related proteases, to give an accurate determination of a specific disease in a sample.

Example 7: Liquid Biopsy Applications Toward COVID Diagnosis

In this example, the application is directed toward diagnosing COVID.

Initial experiments with COVID used K2EDTA and Lithium Heparin collected plasma. Samples were thawed on ice from storage in −80° C. and were then diluted to 10% in PBS. After the samples were prepared, the volume was split in half and broad protease inhibitors were added to one tube—100× dilution final, 67× in the tube. 10 uL of each sample were placed into a well in a 96-well plate, and the plates were stored on ice. Substrates were prepared at 18 uM in ddH2O using 1 mM stock prepared in DMF. 5 uL of substrate were added to each well. The 96-well plates were spun down at 1000 RPM for <30 seconds. The plates were read on Biotek Synergy H1 plate reader, Ex/Em=485/535 with a cycling time of 4 mins 30 seconds using a kinetic read, extended dynamic range for 1 hour.

Figures 34A, 34B:
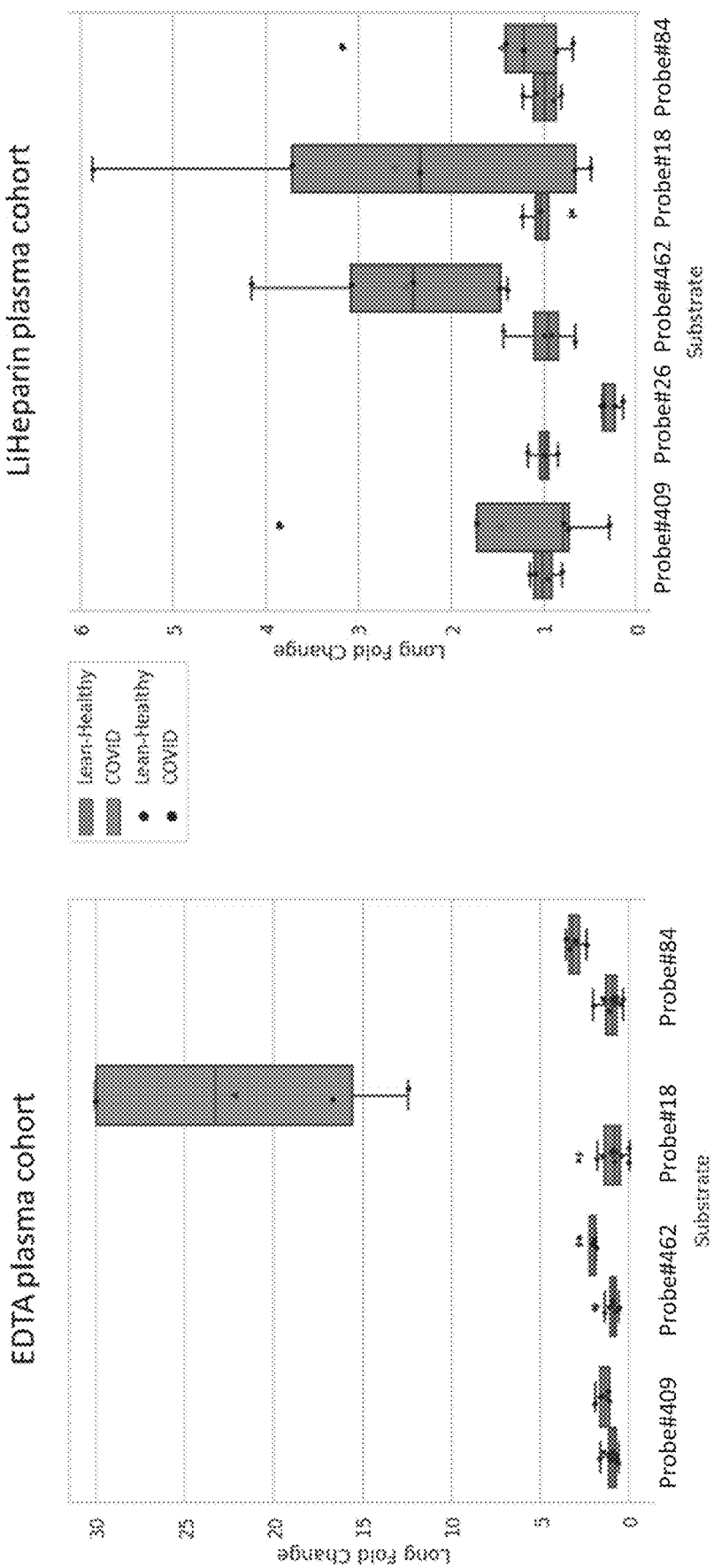
FIG. 34A-B provides experimental evidence that the probes can detect both host response and presence of the COVID virus in plasma under two different conditions of plasma collection.

As shown in FIG. 34A-B, multiple sensors demonstrated differential cleavage between COVID and healthy samples. Probe #462, Probe #18 and Probe #84 demonstrated contrast in both sets and Probe #409, the SARS CoV2 coronavirus substrate, showed modest contrast in the K2 EDTA samples.

Figure 35:
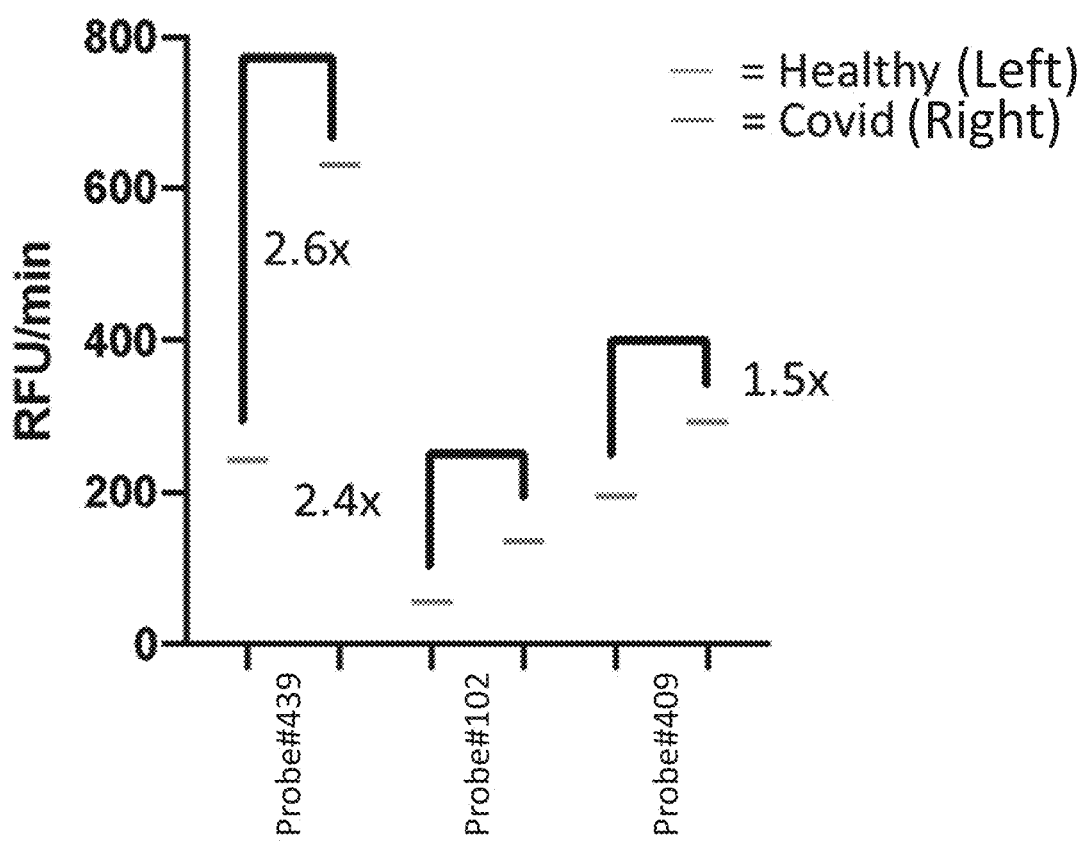
FIG. 35 provides experimental data that the probes can differentiate between healthy swab samples and COVID swab samples.

As shown in FIG. 35, COVID positive and COVID negative swabs (as determined by PCR at the clinical site) were combined with LBx sensors to determine if protease activity can be sensed ex vivo using swabs.

Figure 36B:
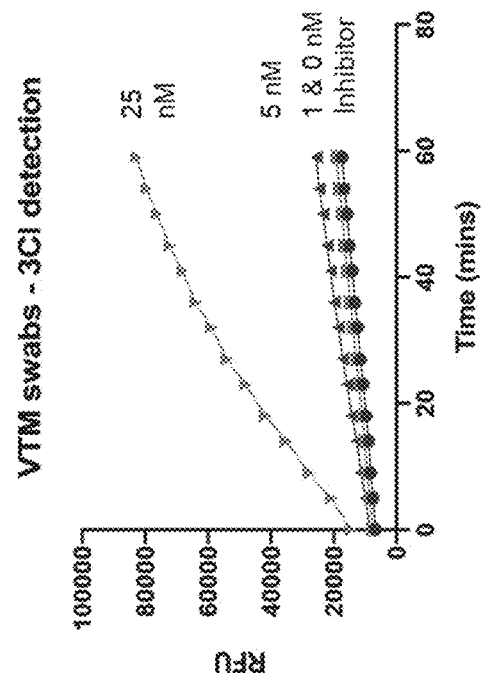
FIG. 36A-B provides experimental data showing that 3C1 protease from SARS-COV2 can be detected when spiked in saliva or swab samples.
Figure 36A:
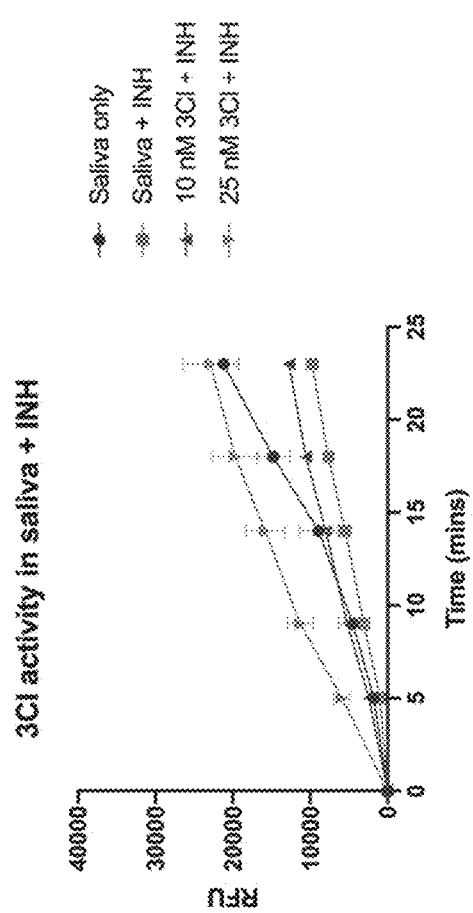
Figure 37:
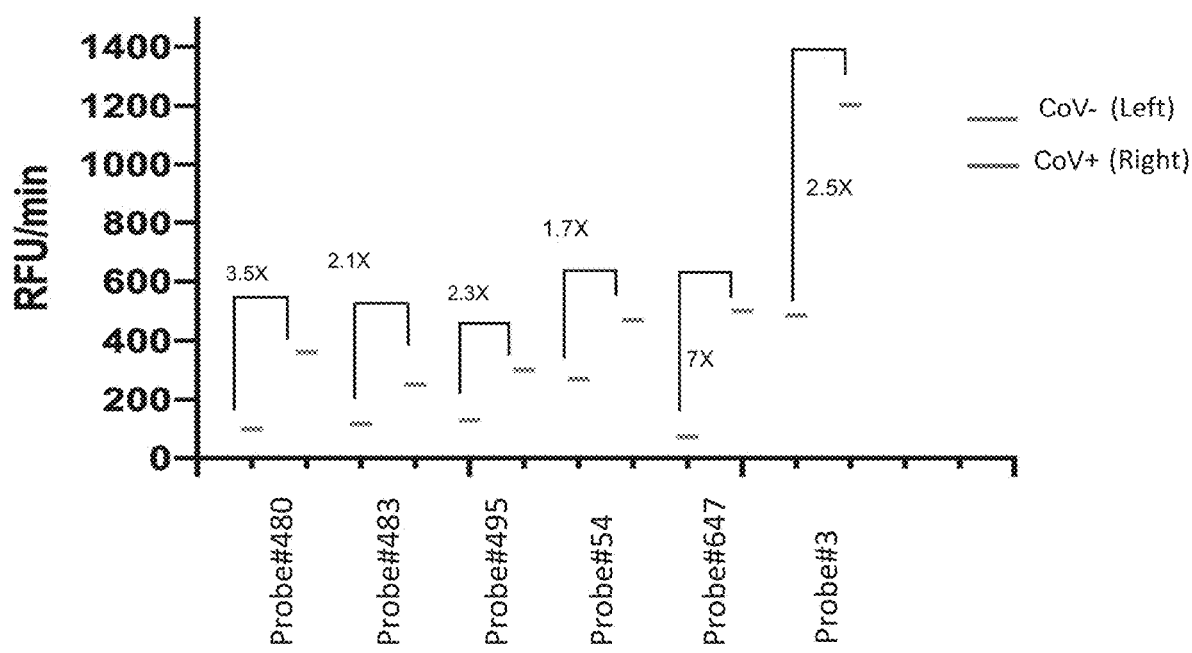
FIG. 37 shows several probes that are capable of differentiating between healthy and COVID samples.

Samples were thawed on ice and then diluted to 10% in DPBS (neutral pH 7.4, Gibco). Where required, samples were pooled according to condition with equal volumes of each sample per condition and then subsequently diluted in DPBS. After the samples are prepared, the volume was split in half and broad protease inhibitors were added to 1 tube—100× dilution final, 67× in the tube. 10 uL of each sample was added into the corresponding wells of a 96-well plate, and the plates were stored on ice. Substrates were prepared at 18 uM in ddH2O using 1 mM stock prepared in DMF. 5 uL of substrate was added to each sample in the 96-well plate, and the plates were spun down at 1000× rpm for <30 seconds. Plates were read on a Biotek Synergy H1 plate reader, Ex/Em=485/535 with a cycling time of 4 mins 30 seconds using a kinetic read, extended dynamic range for 2 hours. FIGS. 36A-B shows both swabs and saliva samples treated with viral transport media (VTM), which contains some proteases in the serum after contact with the probes of the application. However, when swabs were tested using the method from experiment 1 using a saline media instead of VTM, as shown in FIG. 37, clear differences could be seen between COVID- and COVID+ samples (as determined by clinical PCR testing). The saline media swabs give superior protease activity signal compared to the VTM swabs as they were collected in saline media with no additives. This shows the application has broad applicability across biofluids.

Figure 38A:
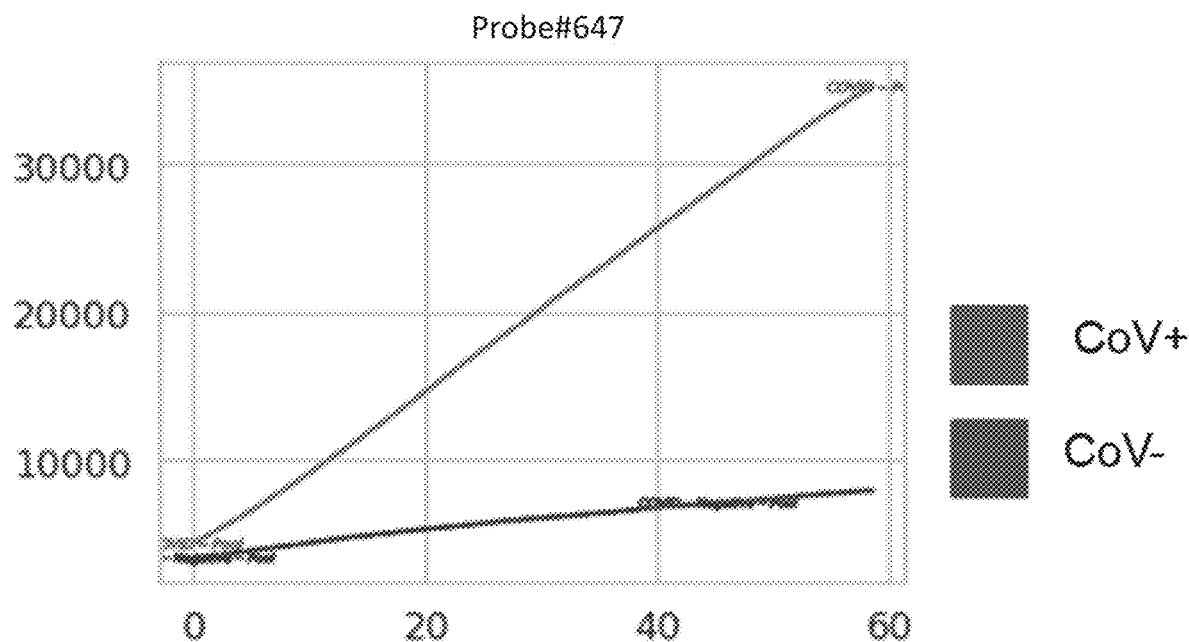
FIG. 38A provides experimental evidence that the Probe #647 can detect the activity of COVID-related proteases to differentiate between healthy and COVID pooled swab samples conditioned in saline.
Figure 38B:
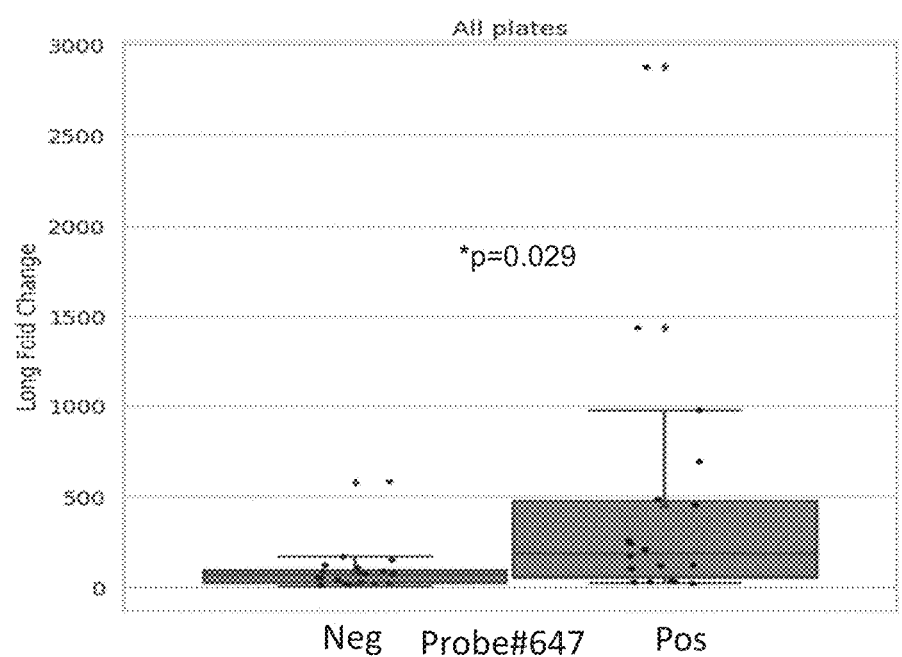
FIG. 38B shows that there are significant differences (p=0.029) between COVID+(n=18) and COVID-(n–19) samples.
Figure 38C:
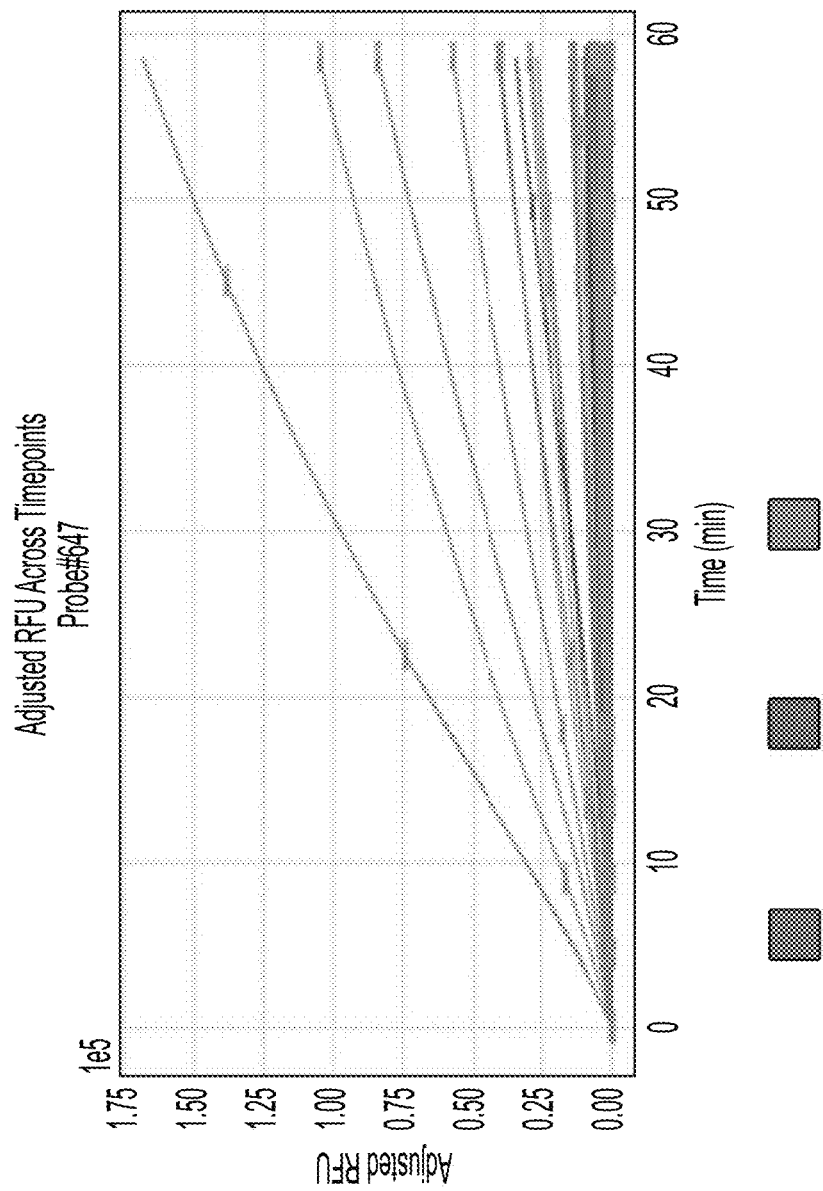
FIG. 38C shows the adjusted RFU across timepoints for COVID+(7 samples were active) and COVID-(1 sample was active) samples.

The specific probe, Probe #647, was shown to be a key differentiator between COVID+ and COVID-samples, as shown in FIG. 38A-C.

Figures 39A, 39B:
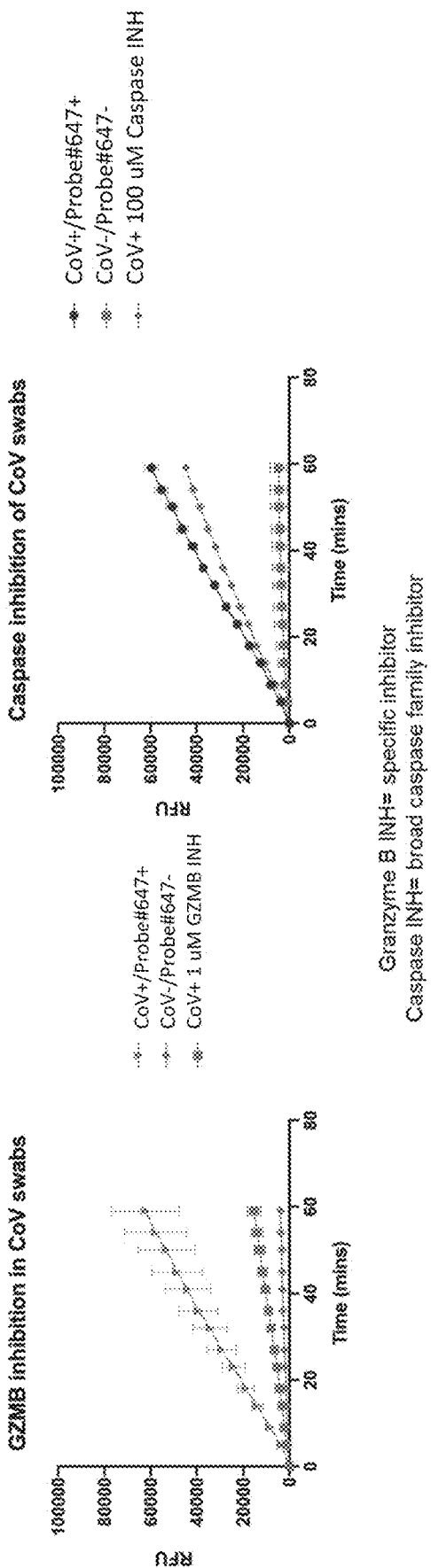
FIG. 39A-B provides experimental evidence that Granzyme B, a protease linked to other autoimmune diseases, is the protease that allows Probe #647 to differentiate between healthy and COVID samples.

As shown in FIGS. 39A-B, Probe #647 signal measures the activity of protease Granzyme B to differentiate between healthy and COVID samples. Granzyme B is a protease that is linked to other autoimmune diseases and viral infections, showing the application can be applied to a wide range of disease biology.

Biotin and Probe #647 were conjugated by dissolving stock Probe #647 powder at 2 mM in 50/50 DMF/PBS. Biotin-Maleimide was reconstituted from powder at 100 mM and diluted to the following concentrations—2 mM, 3 mM and 6 mM in PBS. Three reaction mixtures were created with the following molar equivalents: 1) 1:1-10 uL to 10 uL 2 mM Biotin+2 mM Probe #647, 2) 1:1.5-10 to 10 uL 3 mM Biotin+2 mM Probe #647, and 3) 1:3-10 to 10 uL 6 mM Biotin+2 mM Probe #647. Once mixed, these were inverted on a Hula sample mixer for 2 hours at room temperature. Once the conjugation reactions were completed, recombinant proteases and samples were tested using 100 nM recombinant Granzyme B with 6 uM Probe #647-Biotin conjugate from above 3 reactions. These were then incubated for multiple time points—0 mins, 5 minutes, 30 minutes, 1 hour and optional O/N. They were then diluted up 1:20 and paper strips were dipped into the mixture and the paper strip was read visually. Once the activity was confirmed using recombinant proteases, results were confirmed in strong COVID+ saline swab samples and COVID-saline swab samples (as determined by clinical PCR testing). 10 uL of dilute saline swab sample was combined with 5 uL Probe #647-Biotin conjugate and incubated for multiple time points—0 hours and 2 hours. Post-reaction, the sample was diluted 1:20 and read visually with the paper strip.

The use of a paper strip test to monitor Granzyme B activity using the probes of the application is shown in FIG. 40. This point of care test for the detection of protease cleavage of a biotin-tagged 5FAM sensor has implications for disease monitoring and response in real-time.

Example 8: Liquid Biopsy Applications Towards Pancreatic Ductal Adenocarcinoma

In this example, the application is directed toward diagnosing pancreatic ductal adenocarcinoma (PDAC).

As shown in FIG. 41A-B, when human plasma is contacted with the probes of the application using the method from Experiment 1, one can distinguish between the protease activity of healthy and PDAC human plasma samples.

Furthermore, as shown in FIG. 42, the probes are able to differentiate among healthy, PDAC, and pancreatitis samples.

This experiment continues to show that there is broad applicability for the application regarding different types of diseases that have different protease biology.

Figure 8:
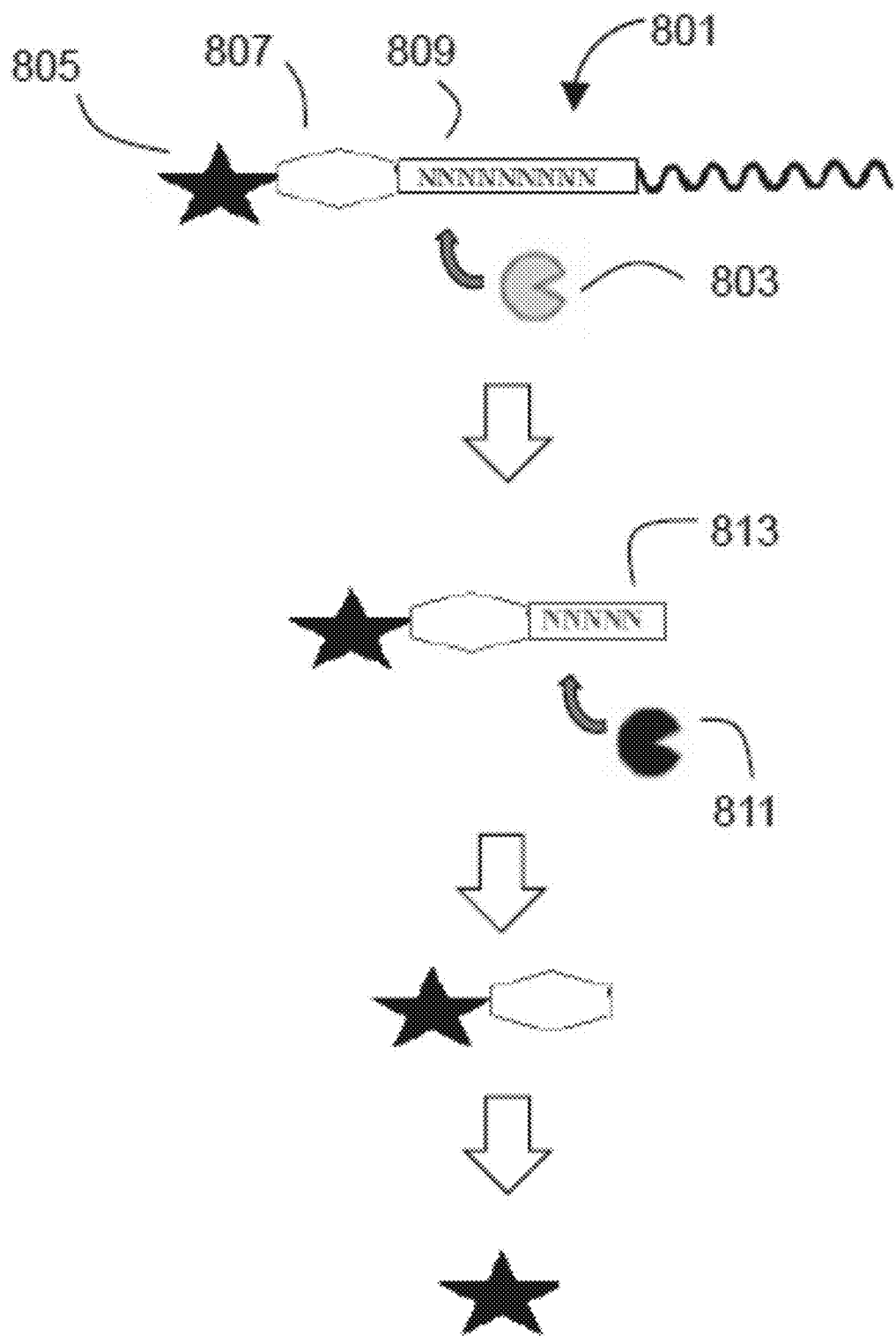
FIG. 8 shows a method using a probe 801 with an auto-immolative spacer 807, precipitating or non precipitating fluorescent reporter 805, and an enzyme/protease substrate 809 cleaved by a predetermined enzyme/endoprotease 803. The probe includes an enzyme/protease substrate 809 that is cleaved by two predetermined enzymes/proteases. The first of these enzymes/proteases, is the enzyme/endoprotease 803 of interest in the sample. The enzyme/endoprotease 803 in the fluid sample cleaves the enzyme/protease substrate 809. However, because 803, cannot cleave completely/the terminal or penultimate amino acids in the protease substrate from the spacer 807. Thus, a predetermined exopeptidase/enzyme 811 is introduced to the sample. The exopeptidase/enzyme can be spiked into the fluid sample, before, after, or during incubation with the endoprotease/enzyme 803. The enzyme/protease substrate 805 is engineered such that cleavage by the enzyme/endoprotease 803 results in a second enzyme/protease substrate 813 that can be cleaved by the predetermined enzyme/exopeptidase 811. Cleavage by 811 causes the spacer 807 to dissociate from the precipitating/non-precipitating fluorophore reporter 805, such the reporter 805 provides an intense fluorescent signal.
Figure 9:
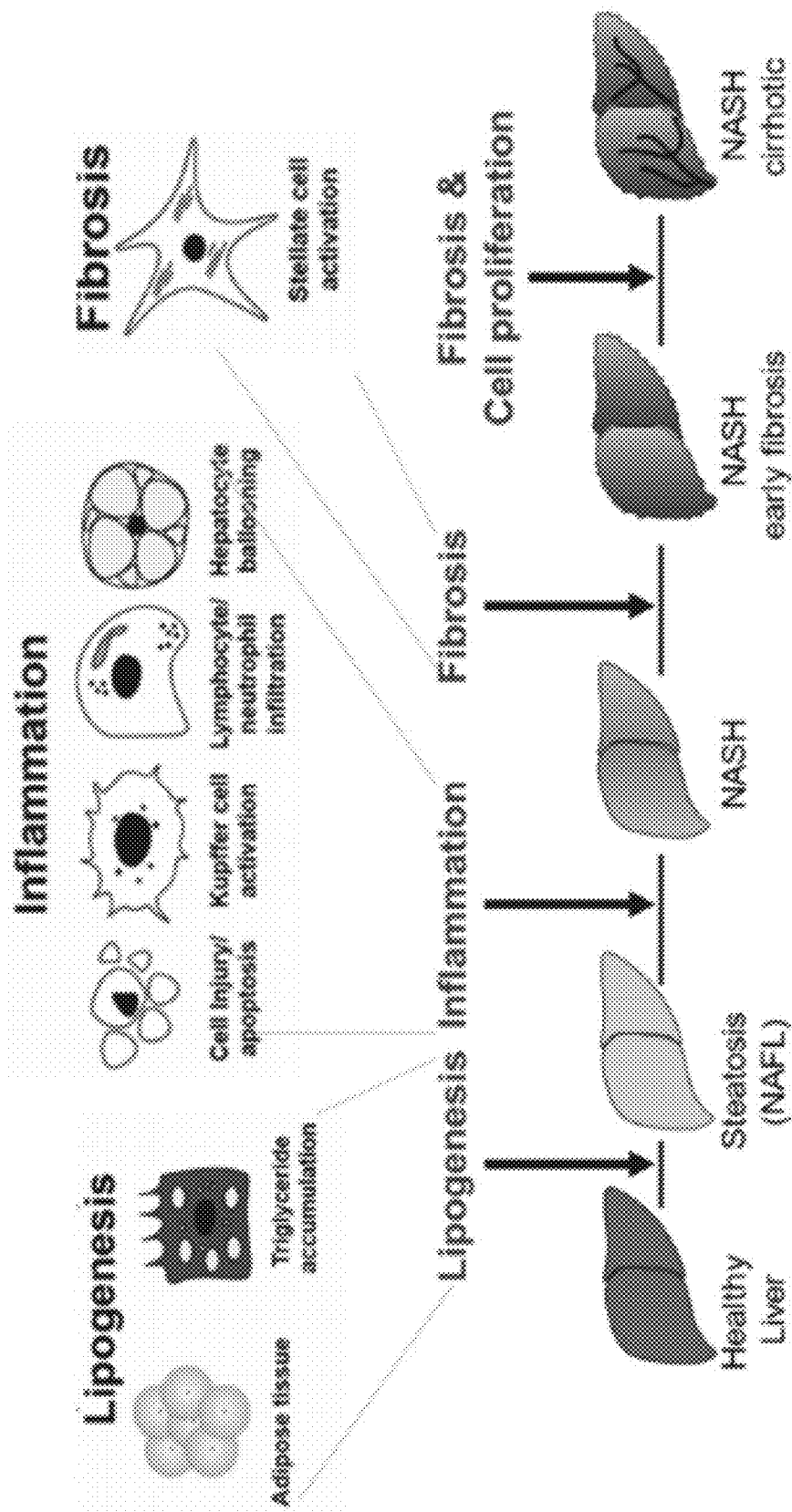
FIG. 9 shows the progression of NASH.

Example 9: Probes with a Fluorescent Reporter Will Accurately Measure NASH-Related Protease Activity Levels in Mice In this prophetic experiment, probes of the present disclosure that include a precipitating fluorescent reporter and a protease substrate cleavable by an endoprotease, like the probes discussed in FIG. 8, will be able to accurately measure the activity levels of NASH-related proteases in healthy mice and NASH mice.

The probes will be engineered such that the protease substrate could be cleaved by a protease such as endoprotease caspase 8, thereby resulting in a second protease substrate linked to a precipitating fluorescent reporter by an auto-immolative spacer. Alternatively, the second protease substrate could be cleaved by the endoprotease CTSD.

Spiking the plasma samples with an excess of CTSD would not result in a measured increase in caspase 8 activity. Thus, in the absence of caspase 8 to cleave the protease substrate, the second substrate will be unavailable for cleavage by CTSD, which will ultimately prevent precipitation of the fluorescent reporter.

However, upon addition of small concentrations of caspase 8 to the fluid sample, a strong signal will be detected by the precipitating fluorophores. Thus, caspase 8 will be able to cleave the protease substrate, thereby resulting in the second protease substrate, which will be cleaved by CTSD. This ultimately will lead to dissociation of the spacer from the precipitating fluorescent reporter, thereby resulting in a fluorescent signal.

Plasma samples with probes having distinguishable precipitating fluorescent reporters will be pooled after incubation with caspase 8 and CTSD. Individually, the plasma samples will be taken from either healthy mice or those with NASH to determine the differences between healthy and NASH samples through detection of caspase 8.

Example 10: Detecting Alternative Enzymes

In this experiment, measurement of alternative enzymes' activities for disease detection is explored. Different enzyme classes include peroxidases, lipases, esterases, phospholipases, amylase etc.

FIG. 43 shows a schematic diagram for detection of Chlorination and peroxidation activity of MPO using the EnzChek© Myeloperoxidase Activity Assay Kit. AH represents the nonfluorescent Amplex© UltraRed substrate, and A represents its fluorescent oxidation product. Hydrogen peroxide converts MPO to MPO-I and MPO is inactive without the presence of hydrogen peroxide. Amplex® UltraRed is then oxidized by MPO-I and creates the fluorescent oxidation product A which can be read at Ex/Em=530/590.

FIG. 44A-C shows the results for detecting peroxidases. FIG. 44A shows that MPO activities are different between healthy mice and mice with NASH. FIG. 44B shows that MPO activities are different between mice fed on a standard ChowDiet (CD), and mice fed on a choline-deficient, L-amino acid-defined, high-fat diet (CDAHFD). FIG. 44C shows that MPO activities are different between healthy subjects and subjects with rheumatoid arthritis. This result shows that we are capable of detecting differential activity in NASH in plasma and rheumatoid arthritis in human pools in synovial fluid.

FIG. 45A-B shows the pooled results of spiked recombinant protease in human plasma using resorufin oleate as substrate. FIG. 46A shows result of 3 recombinant enzymes—carboxylesterase 1, phospholipase A2 and lipoprotein lipase. FIG. 46B shows the result of various concentrations of lipoprotein lipase. This result demonstrates that Resorufin oleate and butyrate were promising for detection of broad range of enzymes.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

SEQUENCE LISTING

```
Sequence total quantity: 1364
SEQ ID NO: 1            moltype = AA  length = 5
FEATURE                 Location/Qualifiers
source                  1..5
                        mol_type = protein
                        organism = synthetic construct
                        note = Description of Artificial Sequence: Synthetic peptide
SEQUENCE: 1
SGRSG                                                                           5

SEQ ID NO: 2            moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 2
PGPREG                                                                          6

SEQ ID NO: 3            moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 3
```

```
IEPDSGSQ                                                                8

SEQ ID NO: 4            moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 4
VVADSSMES                                                               9

SEQ ID NO: 5            moltype = AA  length = 4
FEATURE                 Location/Qualifiers
source                  1..4
                        mol_type = protein
                        organism = synthetic construct
                        note = Description of Artificial Sequence: Synthetic peptide
SEQUENCE: 5
PTSY                                                                    4

SEQ ID NO: 6            moltype = AA  length = 4
FEATURE                 Location/Qualifiers
source                  1..4
                        mol_type = protein
                        organism = synthetic construct
                        note = Description of Artificial Sequence: Synthetic peptide
SEQUENCE: 6
YRFK                                                                    4

SEQ ID NO: 7            moltype = AA  length = 4
FEATURE                 Location/Qualifiers
source                  1..4
                        mol_type = protein
                        organism = synthetic construct
                        note = Description of Artificial Sequence: Synthetic peptide
SEQUENCE: 7
KVPL                                                                    4

SEQ ID NO: 8            moltype = AA  length = 5
FEATURE                 Location/Qualifiers
source                  1..5
                        mol_type = protein
                        organism = synthetic construct
                        note = Description of Artificial Sequence: Synthetic peptide
SEQUENCE: 8
VDVAD                                                                   5

SEQ ID NO: 9            moltype = AA  length = 4
FEATURE                 Location/Qualifiers
source                  1..4
                        mol_type = protein
                        organism = synthetic construct
                        note = Description of Artificial Sequence: Synthetic peptide
SEQUENCE: 9
LETD                                                                    4

SEQ ID NO: 10           moltype = AA  length = 4
FEATURE                 Location/Qualifiers
source                  1..4
                        mol_type = protein
                        organism = synthetic construct
                        note = Description of Artificial Sequence: Synthetic peptide
SEQUENCE: 10
LEHD                                                                    4

SEQ ID NO: 11           moltype = AA  length = 4
FEATURE                 Location/Qualifiers
source                  1..4
                        mol_type = protein
                        organism = synthetic construct
                        note = Description of Artificial Sequence: Synthetic peptide
SEQUENCE: 11
REQD                                                                    4

SEQ ID NO: 12           moltype = AA  length = 4
FEATURE                 Location/Qualifiers
source                  1..4
                        mol_type = protein
                        organism = synthetic construct
```

-continued

```
SEQUENCE: 12                                    note = Description of Artificial Sequence: Synthetic peptide
DEVD                                                                                    4

SEQ ID NO: 13           moltype = AA  length = 4
FEATURE                 Location/Qualifiers
source                  1..4
                        mol_type = protein
                        organism = synthetic construct
                        note = Description of Artificial Sequence: Synthetic peptide
SEQUENCE: 13
VEID                                                                                    4

SEQ ID NO: 14           moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 14
VQVDGW                                                                                  6

SEQ ID NO: 15           moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 15
YEVDGW                                                                                  6

SEQ ID NO: 16           moltype = AA  length = 4
FEATURE                 Location/Qualifiers
source                  1..4
                        mol_type = protein
                        organism = synthetic construct
                        note = Description of Artificial Sequence: Synthetic peptide
SEQUENCE: 16
LEVD                                                                                    4

SEQ ID NO: 17           moltype = AA  length = 4
FEATURE                 Location/Qualifiers
source                  1..4
                        mol_type = protein
                        organism = synthetic construct
                        note = Description of Artificial Sequence: Synthetic peptide
SEQUENCE: 17
IEVE                                                                                    4

SEQ ID NO: 18           moltype = AA  length = 4
FEATURE                 Location/Qualifiers
source                  1..4
                        mol_type = protein
                        organism = synthetic construct
                        note = Description of Artificial Sequence: Synthetic peptide
SEQUENCE: 18
AAPV                                                                                    4

SEQ ID NO: 19           moltype = AA  length = 4
FEATURE                 Location/Qualifiers
source                  1..4
                        mol_type = protein
                        organism = synthetic construct
                        note = Description of Artificial Sequence: Synthetic peptide
SEQUENCE: 19
FFKF                                                                                    4

SEQ ID NO: 20           moltype = AA  length = 7
FEATURE                 Location/Qualifiers
source                  1..7
                        mol_type = protein
                        organism = synthetic construct
                        note = Description of Artificial Sequence: Synthetic peptide
SEQUENCE: 20
GRRGKGG                                                                                 7

SEQ ID NO: 21           moltype = AA  length = 4
FEATURE                 Location/Qualifiers
source                  1..4
```

```
SEQ ID NO: 21                               moltype = AA  length = 4
FEATURE                                     Location/Qualifiers
source                                      1..4
                                            mol_type = protein
                                            organism = synthetic construct
                                            note = Description of Artificial Sequence: Synthetic peptide
SEQUENCE: 21
VKKR                                                                                4

SEQ ID NO: 22                               moltype = AA  length = 7
FEATURE                                     Location/Qualifiers
source                                      1..7
                                            mol_type = protein
                                            organism = synthetic construct
                                            note = Description of Artificial Sequence: Synthetic peptide
SITE                                        4
                                            note = p-Nitro phenylalanine
SEQUENCE: 22
FAAFFVL                                                                             7

SEQ ID NO: 23                               moltype =   length =
SEQUENCE: 23
000

SEQ ID NO: 24                               moltype = AA  length = 5
FEATURE                                     Location/Qualifiers
source                                      1..5
                                            mol_type = protein
                                            organism = synthetic construct
                                            note = Description of Artificial Sequence: Synthetic peptide
SEQUENCE: 24
KQKLR                                                                               5

SEQ ID NO: 25                               moltype = AA  length = 8
FEATURE                                     Location/Qualifiers
source                                      1..8
                                            mol_type = protein
                                            organism = synthetic construct
                                            note = Description of Artificial Sequence: Synthetic peptide
SEQUENCE: 25
RPPGFSAF                                                                            8

SEQ ID NO: 26                               moltype =   length =
SEQUENCE: 26
000

SEQ ID NO: 27                               moltype =   length =
SEQUENCE: 27
000

SEQ ID NO: 28                               moltype = AA  length = 5
FEATURE                                     Location/Qualifiers
source                                      1..5
                                            mol_type = protein
                                            organism = synthetic construct
                                            note = Description of Artificial Sequence: Synthetic peptide
SEQUENCE: 28
LPLGL                                                                               5

SEQ ID NO: 29                               moltype = AA  length = 5
FEATURE                                     Location/Qualifiers
source                                      1..5
                                            mol_type = protein
                                            organism = synthetic construct
                                            note = Description of Artificial Sequence: Synthetic peptide
SEQUENCE: 29
KPLGL                                                                               5

SEQ ID NO: 30                               moltype = AA  length = 6
FEATURE                                     Location/Qualifiers
source                                      1..6
                                            mol_type = protein
                                            organism = synthetic construct
                                            note = Description of Artificial Sequence: Synthetic peptide
SITE                                        1
                                            note = gamma aminobutyric acid
SEQUENCE: 30
XPQGLE                                                                              6

SEQ ID NO: 31                               moltype = AA  length = 6
FEATURE                                     Location/Qualifiers
source                                      1..6
```

```
SEQUENCE: 31
PKPLAL                                                              6

SEQ ID NO: 32         moltype = AA   length = 7
FEATURE               Location/Qualifiers
source                1..7
                      mol_type = protein
                      organism = synthetic construct
                      note = Description of Artificial Sequence: Synthetic peptide
SEQUENCE: 32
GPSGIHV                                                             7

SEQ ID NO: 33         moltype = AA   length = 12
FEATURE               Location/Qualifiers
source                1..12
                      mol_type = protein
                      organism = synthetic construct
                      note = Description of Artificial Sequence: Synthetic peptide
SEQUENCE: 33
WAHRTTFYRR GA                                                       12

SEQ ID NO: 34         moltype = AA   length = 8
FEATURE               Location/Qualifiers
source                1..8
                      mol_type = protein
                      organism = synthetic construct
                      note = Description of Artificial Sequence: Synthetic peptide
SEQUENCE: 34
WKLRSSKQ                                                            8

SEQ ID NO: 35         moltype =    length =
SEQUENCE: 35
000

SEQ ID NO: 36         moltype = AA   length = 5
FEATURE               Location/Qualifiers
source                1..5
                      mol_type = protein
                      organism = synthetic construct
                      note = Description of Artificial Sequence: Synthetic peptide
SEQUENCE: 36
SYRIF                                                               5

SEQ ID NO: 37         moltype =    length =
SEQUENCE: 37
000

SEQ ID NO: 38         moltype = AA   length = 8
FEATURE               Location/Qualifiers
source                1..8
                      mol_type = protein
                      organism = synthetic construct
                      note = Description of Artificial Sequence: Synthetic peptide
SEQUENCE: 38
TAFRSAYG                                                            8

SEQ ID NO: 39         moltype = AA   length = 9
FEATURE               Location/Qualifiers
source                1..9
                      mol_type = protein
                      organism = synthetic construct
                      note = Description of Artificial Sequence: Synthetic peptide
SEQUENCE: 39
WAAFRFSQA                                                           9

SEQ ID NO: 40         moltype =    length =
SEQUENCE: 40
000

SEQ ID NO: 41         moltype =    length =
SEQUENCE: 41
000

SEQ ID NO: 42         moltype = AA   length = 7
FEATURE               Location/Qualifiers
source                1..7
```

```
                            mol_type = protein
                            organism = synthetic construct
                            note = Description of Artificial Sequence: Synthetic peptide
SEQUENCE: 42
KLRSSKQ                                                                                   7

SEQ ID NO: 43               moltype = AA   length = 4
FEATURE                     Location/Qualifiers
source                      1..4
                            mol_type = protein
                            organism = synthetic construct
                            note = Description of Artificial Sequence: Synthetic peptide
SEQUENCE: 43
YASR                                                                                      4

SEQ ID NO: 44               moltype = AA   length = 10
FEATURE                     Location/Qualifiers
source                      1..10
                            mol_type = protein
                            organism = synthetic construct
                            note = Description of Artificial Sequence: Synthetic peptide
SEQUENCE: 44
RFAQAQQQLP                                                                               10

SEQ ID NO: 45               moltype = AA   length = 8
FEATURE                     Location/Qualifiers
source                      1..8
                            mol_type = protein
                            organism = synthetic construct
                            note = Description of Artificial Sequence: Synthetic peptide
SEQUENCE: 45
KPAKFFRL                                                                                  8

SEQ ID NO: 46               moltype = AA   length = 9
FEATURE                     Location/Qualifiers
source                      1..9
                            mol_type = protein
                            organism = synthetic construct
                            note = Description of Artificial Sequence: Synthetic peptide
SITE                        6
                            note = L-Homophenylalanine
SEQUENCE: 46
PRAAAXTSP                                                                                 9

SEQ ID NO: 47               moltype = AA   length = 10
FEATURE                     Location/Qualifiers
source                      1..10
                            mol_type = protein
                            organism = synthetic construct
                            note = Description of Artificial Sequence: Synthetic peptide
SEQUENCE: 47
VGPQRFSGAP                                                                               10

SEQ ID NO: 48               moltype = AA   length = 9
FEATURE                     Location/Qualifiers
source                      1..9
                            mol_type = protein
                            organism = synthetic construct
                            note = Description of Artificial Sequence: Synthetic peptide
SITE                        7
                            note = L-Homophenylalanine
SEQUENCE: 48
FFLAQAXRS                                                                                 9

SEQ ID NO: 49               moltype = AA   length = 6
FEATURE                     Location/Qualifiers
source                      1..6
                            mol_type = protein
                            organism = synthetic construct
                            note = Description of Artificial Sequence: Synthetic peptide
SEQUENCE: 49
PLAQAV                                                                                    6

SEQ ID NO: 50               moltype = AA   length = 8
FEATURE                     Location/Qualifiers
source                      1..8
                            mol_type = protein
                            organism = synthetic construct
                            note = Description of Artificial Sequence: Synthetic peptide
```

```
SEQUENCE: 50
RTAAVFRP                                                                           8

SEQ ID NO: 51          moltype = AA  length = 13
FEATURE                Location/Qualifiers
source                 1..13
                       mol_type = protein
                       organism = synthetic construct
                       note = Description of Artificial Sequence: Synthetic peptide
SEQUENCE: 51
DVQEFRGVTA VIR                                                                    13

SEQ ID NO: 52          moltype = AA  length = 10
FEATURE                Location/Qualifiers
source                 1..10
                       mol_type = protein
                       organism = synthetic construct
                       note = Description of Artificial Sequence: Synthetic peptide
SEQUENCE: 52
TEGEARGSVI                                                                        10

SEQ ID NO: 53          moltype =     length =
SEQUENCE: 53
000

SEQ ID NO: 54          moltype = AA  length = 7
FEATURE                Location/Qualifiers
source                 1..7
                       mol_type = protein
                       organism = synthetic construct
                       note = Description of Artificial Sequence: Synthetic peptide
SEQUENCE: 54
PLFAERK                                                                            7

SEQ ID NO: 55          moltype = AA  length = 4
FEATURE                Location/Qualifiers
source                 1..4
                       mol_type = protein
                       organism = synthetic construct
                       note = Description of Artificial Sequence: Synthetic peptide
SEQUENCE: 55
LLVY                                                                               4

SEQ ID NO: 56          moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 56
QQKRKIVL                                                                           8

SEQ ID NO: 57          moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 57
ASHLGLAR                                                                           8

SEQ ID NO: 58          moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 58
LPSRSSKI                                                                           8

SEQ ID NO: 59          moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 59
STGRNGFK                                                                           8
```

```
SEQ ID NO: 60            moltype = AA  length = 8
FEATURE                  Location/Qualifiers
source                   1..8
                         mol_type = protein
                         organism = synthetic construct
                         note = Description of Artificial Sequence: Synthetic peptide
SEQUENCE: 60
SLLRSEET                                                                          8

SEQ ID NO: 61            moltype = AA  length = 8
FEATURE                  Location/Qualifiers
source                   1..8
                         mol_type = protein
                         organism = synthetic construct
                         note = Description of Artificial Sequence: Synthetic peptide
SEQUENCE: 61
HRGRTLEI                                                                          8

SEQ ID NO: 62            moltype = AA  length = 8
FEATURE                  Location/Qualifiers
source                   1..8
                         mol_type = protein
                         organism = synthetic construct
                         note = Description of Artificial Sequence: Synthetic peptide
SEQUENCE: 62
YLGRSYKV                                                                          8

SEQ ID NO: 63            moltype = AA  length = 8
FEATURE                  Location/Qualifiers
source                   1..8
                         mol_type = protein
                         organism = synthetic construct
                         note = Description of Artificial Sequence: Synthetic peptide
SEQUENCE: 63
EKQRIIGG                                                                          8

SEQ ID NO: 64            moltype = AA  length = 8
FEATURE                  Location/Qualifiers
source                   1..8
                         mol_type = protein
                         organism = synthetic construct
                         note = Description of Artificial Sequence: Synthetic peptide
SEQUENCE: 64
QRQRIIGG                                                                          8

SEQ ID NO: 65            moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 65
LQRIYK                                                                            6

SEQ ID NO: 66            moltype = AA  length = 8
FEATURE                  Location/Qualifiers
source                   1..8
                         mol_type = protein
                         organism = synthetic construct
                         note = Description of Artificial Sequence: Synthetic peptide
SEQUENCE: 66
SLGRKIQI                                                                          8

SEQ ID NO: 67            moltype = AA  length = 13
FEATURE                  Location/Qualifiers
source                   1..13
                         mol_type = protein
                         organism = synthetic construct
                         note = Description of Artificial Sequence: Synthetic peptide
SEQUENCE: 67
HAAPRSADIQ IDI                                                                   13

SEQ ID NO: 68            moltype =     length =
SEQUENCE: 68
000

SEQ ID NO: 69            moltype = AA  length = 4
FEATURE                  Location/Qualifiers
source                   1..4
```

```
SEQUENCE: 69
SLGR                                                                4

SEQ ID NO: 70           moltype = AA  length = 4
FEATURE                 Location/Qualifiers
source                  1..4
                        mol_type = protein
                        organism = synthetic construct
                        note = Description of Artificial Sequence: Synthetic peptide
SEQUENCE: 70
GLQR                                                                4

SEQ ID NO: 71           moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 71
SVARTLLV                                                            8

SEQ ID NO: 72           moltype = AA  length = 5
FEATURE                 Location/Qualifiers
source                  1..5
                        mol_type = protein
                        organism = synthetic construct
                        note = Description of Artificial Sequence: Synthetic peptide
SEQUENCE: 72
GRIFG                                                               5

SEQ ID NO: 73           moltype =     length =
SEQUENCE: 73
000

SEQ ID NO: 74           moltype = AA  length = 5
FEATURE                 Location/Qualifiers
source                  1..5
                        mol_type = protein
                        organism = synthetic construct
                        note = Description of Artificial Sequence: Synthetic peptide
SEQUENCE: 74
GFSPY                                                               5

SEQ ID NO: 75           moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 75
WELRHAGH                                                            8

SEQ ID NO: 76           moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 76
RQSRIVGGE                                                           9

SEQ ID NO: 77           moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 77
EQAVYQTI                                                            8

SEQ ID NO: 78           moltype = AA  length = 11
FEATURE                 Location/Qualifiers
source                  1..11
                        mol_type = protein
                        organism = synthetic construct
                        note = Description of Artificial Sequence: Synthetic peptide
```

-continued

```
SEQUENCE: 78
VAYSGENTFG F                                                                    11

SEQ ID NO: 79          moltype =   length =
SEQUENCE: 79
000

SEQ ID NO: 80          moltype = AA  length = 4
FEATURE                Location/Qualifiers
source                 1..4
                       mol_type = protein
                       organism = synthetic construct
                       note = Description of Artificial Sequence: Synthetic peptide
SEQUENCE: 80
ATAD                                                                             4

SEQ ID NO: 81          moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 81
RPLESNAV                                                                         8

SEQ ID NO: 82          moltype = AA  length = 7
FEATURE                Location/Qualifiers
source                 1..7
                       mol_type = protein
                       organism = synthetic construct
                       note = Description of Artificial Sequence: Synthetic peptide
SEQUENCE: 82
RPLGLAR                                                                          7

SEQ ID NO: 83          moltype = AA  length = 4
FEATURE                Location/Qualifiers
source                 1..4
                       mol_type = protein
                       organism = synthetic construct
                       note = Description of Artificial Sequence: Synthetic peptide
SEQUENCE: 83
AAFF                                                                             4

SEQ ID NO: 84          moltype = AA  length = 7
FEATURE                Location/Qualifiers
source                 1..7
                       mol_type = protein
                       organism = synthetic construct
                       note = Description of Artificial Sequence: Synthetic peptide
SEQUENCE: 84
RVKRGLA                                                                          7

SEQ ID NO: 85          moltype =   length =
SEQUENCE: 85
000

SEQ ID NO: 86          moltype = AA  length = 18
FEATURE                Location/Qualifiers
source                 1..18
                       mol_type = protein
                       organism = synthetic construct
                       note = Description of Artificial Sequence: Synthetic peptide
SITE                   4
                       note = D-Methionine
SITE                   5
                       note = D-Glutamic Acid
SITE                   8
                       note = D-Asparagine
SITE                   9
                       note = D-Aspartic Acid
SITE                   10
                       note = D-Asparagine
SITE                   11
                       note = D-Glutamic Acid
SITE                   12
                       note = D-Glutamic Acid
SITE                   16
                       note = D-Serine
SITE                   18
```

```
                         note = D-Arginine
SEQUENCE: 86
CGGMEGVNDN EEGFFSAR                                                            18

SEQ ID NO: 87            moltype = AA  length = 8
FEATURE                  Location/Qualifiers
source                   1..8
                         mol_type = protein
                         organism = synthetic construct
                         note = Description of Artificial Sequence: Synthetic peptide
SEQUENCE: 87
GPQGIWGQ                                                                        8

SEQ ID NO: 88            moltype = AA  length = 7
FEATURE                  Location/Qualifiers
source                   1..7
                         mol_type = protein
                         organism = synthetic construct
                         note = Description of Artificial Sequence: Synthetic peptide
SEQUENCE: 88
GLVPRGS                                                                         7

SEQ ID NO: 89            moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 89
GPVGLI                                                                          6

SEQ ID NO: 90            moltype = AA  length = 8
FEATURE                  Location/Qualifiers
source                   1..8
                         mol_type = protein
                         organism = synthetic construct
                         note = Description of Artificial Sequence: Synthetic peptide
SEQUENCE: 90
GPWGIWGQ                                                                        8

SEQ ID NO: 91            moltype = AA  length = 9
FEATURE                  Location/Qualifiers
source                   1..9
                         mol_type = protein
                         organism = synthetic construct
                         note = Description of Artificial Sequence: Synthetic peptide
SEQUENCE: 91
GPVPLSLVM                                                                       9

SEQ ID NO: 92            moltype = AA  length = 7
FEATURE                  Location/Qualifiers
source                   1..7
                         mol_type = protein
                         organism = synthetic construct
                         note = Description of Artificial Sequence: Synthetic peptide
SITE                     2
                         note = D-Phenylalanine
SITE                     3
                         note = piperidine carboxylic acid
SEQUENCE: 92
GFXRSGG                                                                         7

SEQ ID NO: 93            moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 93
PLGMRG                                                                          6

SEQ ID NO: 94            moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 94
PLGMRG                                                                          6
```

-continued

```
SEQ ID NO: 95            moltype = AA   length = 6
FEATURE                  Location/Qualifiers
source                   1..6
                         mol_type = protein
                         organism = synthetic construct
                         note = Description of Artificial Sequence: Synthetic peptide
SITE                     2
                         note = L-cyclohexylalanine
SITE                     4
                         note = L- Methyl cysteine
SEQUENCE: 95
PAGCHA                                                                              6

SEQ ID NO: 96            moltype = AA   length = 9
FEATURE                  Location/Qualifiers
source                   1..9
                         mol_type = protein
                         organism = synthetic construct
                         note = Description of Artificial Sequence: Synthetic peptide
SEQUENCE: 96
RPLALWESQ                                                                           9

SEQ ID NO: 97            moltype = AA   length = 10
FEATURE                  Location/Qualifiers
source                   1..10
                         mol_type = protein
                         organism = synthetic construct
                         note = Description of Artificial Sequence: Synthetic peptide
SEQUENCE: 97
SGKGPRQITA                                                                         10

SEQ ID NO: 98            moltype = AA   length = 10
FEATURE                  Location/Qualifiers
source                   1..10
                         mol_type = protein
                         organism = synthetic construct
                         note = Description of Artificial Sequence: Synthetic peptide
SEQUENCE: 98
SGPLFYSVTA                                                                         10

SEQ ID NO: 99            moltype = AA   length = 9
FEATURE                  Location/Qualifiers
source                   1..9
                         mol_type = protein
                         organism = synthetic construct
                         note = Description of Artificial Sequence: Synthetic peptide
SEQUENCE: 99
SGRIFLRTA                                                                           9

SEQ ID NO: 100           moltype = AA   length = 10
FEATURE                  Location/Qualifiers
source                   1..10
                         mol_type = protein
                         organism = synthetic construct
                         note = Description of Artificial Sequence: Synthetic peptide
SEQUENCE: 100
SGRSENIRTA                                                                         10

SEQ ID NO: 101           moltype = AA   length = 5
FEATURE                  Location/Qualifiers
source                   1..5
                         mol_type = protein
                         organism = synthetic construct
                         note = Description of Artificial Sequence: Synthetic peptide
SEQUENCE: 101
GSGGS                                                                               5

SEQ ID NO: 102           moltype = AA   length = 10
FEATURE                  Location/Qualifiers
source                   1..10
                         mol_type = protein
                         organism = synthetic construct
                         note = Description of Artificial Sequence: Synthetic peptide
SEQUENCE: 102
KPILFFRLKG                                                                         10

SEQ ID NO: 103           moltype = AA   length = 6
FEATURE                  Location/Qualifiers
```

```
                            -continued source                  1..6
                        mol_type = protein
                        organism = synthetic construct
                        note = Description of Artificial Sequence: Synthetic peptide
SITE                    6
                        note = Norleucine
SEQUENCE: 103
AWESRX                                                                          6

SEQ ID NO: 104          moltype = AA  length = 6
FEATURE                 Location/Qualifiers
source                  1..6
                        mol_type = protein
                        organism = synthetic construct
                        note = Description of Artificial Sequence: Synthetic peptide
SITE                    6
                        note = Norleucine
SEQUENCE: 104
NEKSGX                                                                          6

SEQ ID NO: 105          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 105
NATIVY                                                                          6

SEQ ID NO: 106          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 106
DPFVVS                                                                          6

SEQ ID NO: 107          moltype = AA  length = 6
FEATURE                 Location/Qualifiers
source                  1..6
                        mol_type = protein
                        organism = synthetic construct
                        note = Description of Artificial Sequence: Synthetic peptide
SITE                    3
                        note = Norleucine
SEQUENCE: 107
FHXFTK                                                                          6

SEQ ID NO: 108          moltype = AA  length = 6
FEATURE                 Location/Qualifiers
source                  1..6
                        mol_type = protein
                        organism = synthetic construct
                        note = Description of Artificial Sequence: Synthetic peptide
SITE                    1
                        note = Norleucine
SEQUENCE: 108
XNWHKH                                                                          6

SEQ ID NO: 109          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 109
FARRWG                                                                          6

SEQ ID NO: 110          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 110
PGKWSK                                                                          6

SEQ ID NO: 111          moltype = AA  length = 6
```

| FEATURE | Location/Qualifiers |
|---|---|
| source | 1..6<br>mol_type = protein<br>organism = synthetic construct<br>note = Description of Artificial Sequence: Synthetic peptide |

SEQUENCE: 111
YEEAQP 6

| SEQ ID NO: 112 | moltype = AA  length = 6 |
|---|---|
| FEATURE | Location/Qualifiers |
| source | 1..6<br>mol_type = protein<br>organism = synthetic construct<br>note = Description of Artificial Sequence: Synthetic peptide |

SEQUENCE: 112
YGAIKK 6

| SEQ ID NO: 113 | moltype = AA  length = 6 |
|---|---|
| FEATURE | Location/Qualifiers |
| source | 1..6<br>mol_type = protein<br>organism = synthetic construct<br>note = Description of Artificial Sequence: Synthetic peptide |
| SITE | 3<br>note = Norleucine |

SEQUENCE: 113
TSXEGY 6

| SEQ ID NO: 114 | moltype = AA  length = 6 |
|---|---|
| FEATURE | Location/Qualifiers |
| source | 1..6<br>mol_type = protein<br>organism = synthetic construct<br>note = Description of Artificial Sequence: Synthetic peptide |

SEQUENCE: 114
PNNFGS 6

| SEQ ID NO: 115 | moltype = AA  length = 6 |
|---|---|
| FEATURE | Location/Qualifiers |
| source | 1..6<br>mol_type = protein<br>organism = synthetic construct<br>note = Description of Artificial Sequence: Synthetic peptide |

SEQUENCE: 115
EDTRNT 6

| SEQ ID NO: 116 | moltype = AA  length = 6 |
|---|---|
| FEATURE | Location/Qualifiers |
| source | 1..6<br>mol_type = protein<br>organism = synthetic construct<br>note = Description of Artificial Sequence: Synthetic peptide |

SEQUENCE: 116
KDLEQS 6

| SEQ ID NO: 117 | moltype = AA  length = 6 |
|---|---|
| FEATURE | Location/Qualifiers |
| source | 1..6<br>mol_type = protein<br>organism = synthetic construct<br>note = Description of Artificial Sequence: Synthetic peptide |

SEQUENCE: 117
AALHND 6

| SEQ ID NO: 118 | moltype = AA  length = 6 |
|---|---|
| FEATURE | Location/Qualifiers |
| source | 1..6<br>mol_type = protein<br>organism = synthetic construct<br>note = Description of Artificial Sequence: Synthetic peptide |

SEQUENCE: 118
ADSFFK 6

| SEQ ID NO: 119 | moltype = AA  length = 6 |
|---|---|
| FEATURE | Location/Qualifiers |
| source | 1..6<br>mol_type = protein<br>organism = synthetic construct<br>note = Description of Artificial Sequence: Synthetic peptide |

```
SEQUENCE: 119
ITFWRA                                                                           6

SEQ ID NO: 120            moltype = AA  length = 6
FEATURE                   Location/Qualifiers
source                    1..6
                          mol_type = protein
                          organism = synthetic construct
                          note = Description of Artificial Sequence: Synthetic peptide
SITE                      4
                          note = Norleucine
SEQUENCE: 120
LSDXRL                                                                           6

SEQ ID NO: 121            moltype = AA  length = 6
FEATURE                   Location/Qualifiers
source                    1..6
                          mol_type = protein
                          organism = synthetic construct
                          note = Description of Artificial Sequence: Synthetic peptide
SEQUENCE: 121
EVGWTY                                                                           6

SEQ ID NO: 122            moltype = AA  length = 6
FEATURE                   Location/Qualifiers
source                    1..6
                          mol_type = protein
                          organism = synthetic construct
                          note = Description of Artificial Sequence: Synthetic peptide
SITE                      6
                          note = Norleucine
SEQUENCE: 122
IAFRQX                                                                           6

SEQ ID NO: 123            moltype = AA  length = 6
FEATURE                   Location/Qualifiers
source                    1..6
                          mol_type = protein
                          organism = synthetic construct
                          note = Description of Artificial Sequence: Synthetic peptide
SITE                      6
                          note = Norleucine
SEQUENCE: 123
YNIHTX                                                                           6

SEQ ID NO: 124            moltype = AA  length = 6
FEATURE                   Location/Qualifiers
source                    1..6
                          mol_type = protein
                          organism = synthetic construct
                          note = Description of Artificial Sequence: Synthetic peptide
SITE                      1
                          note = Norleucine
SEQUENCE: 124
XLWANH                                                                           6

SEQ ID NO: 125            moltype = AA  length = 6
FEATURE                   Location/Qualifiers
source                    1..6
                          mol_type = protein
                          organism = synthetic construct
                          note = Description of Artificial Sequence: Synthetic peptide
SEQUENCE: 125
LYSVQV                                                                           6

SEQ ID NO: 126            moltype = AA  length = 6
FEATURE                   Location/Qualifiers
source                    1..6
                          mol_type = protein
                          organism = synthetic construct
                          note = Description of Artificial Sequence: Synthetic peptide
SITE                      4
                          note = Norleucine
SEQUENCE: 126
SHIXSN                                                                           6

SEQ ID NO: 127            moltype = AA  length = 6
FEATURE                   Location/Qualifiers
source                    1..6
```

```
                              mol_type = protein
                              organism = synthetic construct
                              note = Description of Artificial Sequence: Synthetic peptide
SEQUENCE: 127
KLLIDV                                                                                6

SEQ ID NO: 128                moltype = AA   length = 6
FEATURE                       Location/Qualifiers
source                        1..6
                              mol_type = protein
                              organism = synthetic construct
                              note = Description of Artificial Sequence: Synthetic peptide
SITE                          2
                              note = Norleucine
SEQUENCE: 128
EXGVFD                                                                                6

SEQ ID NO: 129                moltype = AA   length = 6
FEATURE                       Location/Qualifiers
source                        1..6
                              mol_type = protein
                              organism = synthetic construct
                              note = Description of Artificial Sequence: Synthetic peptide
SEQUENCE: 129
HQAYTL                                                                                6

SEQ ID NO: 130                moltype = AA   length = 6
FEATURE                       Location/Qualifiers
source                        1..6
                              mol_type = protein
                              organism = synthetic construct
                              note = Description of Artificial Sequence: Synthetic peptide
SEQUENCE: 130
YVRKIQ                                                                                6

SEQ ID NO: 131                moltype = AA   length = 6
FEATURE                       Location/Qualifiers
source                        1..6
                              mol_type = protein
                              organism = synthetic construct
                              note = Description of Artificial Sequence: Synthetic peptide
SEQUENCE: 131
DRENSP                                                                                6

SEQ ID NO: 132                moltype = AA   length = 6
FEATURE                       Location/Qualifiers
source                        1..6
                              mol_type = protein
                              organism = synthetic construct
                              note = Description of Artificial Sequence: Synthetic peptide
SEQUENCE: 132
KYDKPR                                                                                6

SEQ ID NO: 133                moltype = AA   length = 6
FEATURE                       Location/Qualifiers
source                        1..6
                              mol_type = protein
                              organism = synthetic construct
                              note = Description of Artificial Sequence: Synthetic peptide
SEQUENCE: 133
RPWKQL                                                                                6

SEQ ID NO: 134                moltype = AA   length = 6
FEATURE                       Location/Qualifiers
source                        1..6
                              mol_type = protein
                              organism = synthetic construct
                              note = Description of Artificial Sequence: Synthetic peptide
SEQUENCE: 134
APLQRY                                                                                6

SEQ ID NO: 135                moltype = AA   length = 6
FEATURE                       Location/Qualifiers
source                        1..6
                              mol_type = protein
                              organism = synthetic construct
                              note = Description of Artificial Sequence: Synthetic peptide
SITE                          6
                              note = Norleucine
```

```
SEQUENCE: 135
YQGQKX                                                                      6

SEQ ID NO: 136          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 136
GRISSI                                                                      6

SEQ ID NO: 137          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 137
HSLTNV                                                                      6

SEQ ID NO: 138          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 138
EWDFPE                                                                      6

SEQ ID NO: 139          moltype = AA  length = 6
FEATURE                 Location/Qualifiers
source                  1..6
                        mol_type = protein
                        organism = synthetic construct
                        note = Description of Artificial Sequence: Synthetic peptide
SITE                    4
                        note = Norleucine
SEQUENCE: 139
YLAXDG                                                                      6

SEQ ID NO: 140          moltype = AA  length = 6
FEATURE                 Location/Qualifiers
source                  1..6
                        mol_type = protein
                        organism = synthetic construct
                        note = Description of Artificial Sequence: Synthetic peptide
SITE                    4
                        note = Norleucine
SEQUENCE: 140
FIYXPT                                                                      6

SEQ ID NO: 141          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 141
GHETWV                                                                      6

SEQ ID NO: 142          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 142
DYIGDE                                                                      6

SEQ ID NO: 143          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 143
AGTAHP                                                                      6
```

```
SEQ ID NO: 144            moltype = AA   length = 6
FEATURE                   Location/Qualifiers
source                    1..6
                          mol_type = protein
                          organism = synthetic construct
                          note = Description of Artificial Sequence: Synthetic peptide
SITE                      2
                          note = Norleucine
SEQUENCE: 144
VXTEIW                                                                          6

SEQ ID NO: 145            moltype = AA   length = 6
FEATURE                   Location/Qualifiers
source                    1..6
                          mol_type = protein
                          organism = synthetic construct
                          note = Description of Artificial Sequence: Synthetic peptide
SEQUENCE: 145
PDDWQN                                                                          6

SEQ ID NO: 146            moltype = AA   length = 6
FEATURE                   Location/Qualifiers
source                    1..6
                          mol_type = protein
                          organism = synthetic construct
                          note = Description of Artificial Sequence: Synthetic peptide
SEQUENCE: 146
GLNQEY                                                                          6

SEQ ID NO: 147            moltype = AA   length = 6
FEATURE                   Location/Qualifiers
source                    1..6
                          mol_type = protein
                          organism = synthetic construct
                          note = Description of Artificial Sequence: Synthetic peptide
SEQUENCE: 147
YRDAVA                                                                          6

SEQ ID NO: 148            moltype = AA   length = 6
FEATURE                   Location/Qualifiers
source                    1..6
                          mol_type = protein
                          organism = synthetic construct
                          note = Description of Artificial Sequence: Synthetic peptide
SEQUENCE: 148
TGPKGN                                                                          6

SEQ ID NO: 149            moltype = AA   length = 6
FEATURE                   Location/Qualifiers
source                    1..6
                          mol_type = protein
                          organism = synthetic construct
                          note = Description of Artificial Sequence: Synthetic peptide
SEQUENCE: 149
DHVPQI                                                                          6

SEQ ID NO: 150            moltype = AA   length = 6
FEATURE                   Location/Qualifiers
source                    1..6
                          mol_type = protein
                          organism = synthetic construct
                          note = Description of Artificial Sequence: Synthetic peptide
SEQUENCE: 150
NKEPIL                                                                          6

SEQ ID NO: 151            moltype = AA   length = 6
FEATURE                   Location/Qualifiers
source                    1..6
                          mol_type = protein
                          organism = synthetic construct
                          note = Description of Artificial Sequence: Synthetic peptide
SITE                      4
                          note = Norleucine
SEQUENCE: 151
VWNXVH                                                                          6

SEQ ID NO: 152            moltype = AA   length = 6
FEATURE                   Location/Qualifiers
source                    1..6
```

```
                        mol_type = protein
                        organism = synthetic construct
                        note = Description of Artificial Sequence: Synthetic peptide
SEQUENCE: 152
PVIIEH                                                                           6

SEQ ID NO: 153          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 153
FQTDNL                                                                           6

SEQ ID NO: 154          moltype = AA  length = 6
FEATURE                 Location/Qualifiers
source                  1..6
                        mol_type = protein
                        organism = synthetic construct
                        note = Description of Artificial Sequence: Synthetic peptide
SITE                    3
                        note = Norleucine
SEQUENCE: 154
RFXHGI                                                                           6

SEQ ID NO: 155          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 155
YAERTT                                                                           6

SEQ ID NO: 156          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 156
NRGELP                                                                           6

SEQ ID NO: 157          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 157
HHYFNY                                                                           6

SEQ ID NO: 158          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 158
STPYYH                                                                           6

SEQ ID NO: 159          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 159
WFYPSA                                                                           6

SEQ ID NO: 160          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 160
SEFLFS                                                                           6
```

```
SEQ ID NO: 161            moltype = AA   length = 6
FEATURE                   Location/Qualifiers
source                    1..6
                          mol_type = protein
                          organism = synthetic construct
                          note = Description of Artificial Sequence: Synthetic peptide
SEQUENCE: 161
WYKTQY                                                                         6

SEQ ID NO: 162            moltype = AA   length = 6
FEATURE                   Location/Qualifiers
source                    1..6
                          mol_type = protein
                          organism = synthetic construct
                          note = Description of Artificial Sequence: Synthetic peptide
SEQUENCE: 162
VTHLKV                                                                         6

SEQ ID NO: 163            moltype = AA   length = 6
FEATURE                   Location/Qualifiers
source                    1..6
                          mol_type = protein
                          organism = synthetic construct
                          note = Description of Artificial Sequence: Synthetic peptide
SEQUENCE: 163
INGGFS                                                                         6

SEQ ID NO: 164            moltype = AA   length = 6
FEATURE                   Location/Qualifiers
source                    1..6
                          mol_type = protein
                          organism = synthetic construct
                          note = Description of Artificial Sequence: Synthetic peptide
SEQUENCE: 164
TVLGLD                                                                         6

SEQ ID NO: 165            moltype = AA   length = 6
FEATURE                   Location/Qualifiers
source                    1..6
                          mol_type = protein
                          organism = synthetic construct
                          note = Description of Artificial Sequence: Synthetic peptide
SITE                      5
                          note = Norleucine
SEQUENCE: 165
SYWPXQ                                                                         6

SEQ ID NO: 166            moltype = AA   length = 6
FEATURE                   Location/Qualifiers
source                    1..6
                          mol_type = protein
                          organism = synthetic construct
                          note = Description of Artificial Sequence: Synthetic peptide
SEQUENCE: 166
ASQQHR                                                                         6

SEQ ID NO: 167            moltype = AA   length = 6
FEATURE                   Location/Qualifiers
source                    1..6
                          mol_type = protein
                          organism = synthetic construct
                          note = Description of Artificial Sequence: Synthetic peptide
SEQUENCE: 167
KNPAKA                                                                         6

SEQ ID NO: 168            moltype = AA   length = 6
FEATURE                   Location/Qualifiers
source                    1..6
                          mol_type = protein
                          organism = synthetic construct
                          note = Description of Artificial Sequence: Synthetic peptide
SITE                      1
                          note = Norleucine
SEQUENCE: 168
XYWLVE                                                                         6

SEQ ID NO: 169            moltype = AA   length = 6
FEATURE                   Location/Qualifiers
```

```
source                  1..6
                        mol_type = protein
                        organism = synthetic construct
                        note = Description of Artificial Sequence: Synthetic peptide
SEQUENCE: 169
SWWIFE                                                                          6

SEQ ID NO: 170          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 170
VNYEQD                                                                          6

SEQ ID NO: 171          moltype = AA  length = 6
FEATURE                 Location/Qualifiers
source                  1..6
                        mol_type = protein
                        organism = synthetic construct
                        note = Description of Artificial Sequence: Synthetic peptide
SITE                    4
                        note = Norleucine
SEQUENCE: 171
HFFXAE                                                                          6

SEQ ID NO: 172          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 172
DIPPHW                                                                          6

SEQ ID NO: 173          moltype = AA  length = 6
FEATURE                 Location/Qualifiers
source                  1..6
                        mol_type = protein
                        organism = synthetic construct
                        note = Description of Artificial Sequence: Synthetic peptide
SITE                    5
                        note = Norleucine
SEQUENCE: 173
VDQWXW                                                                          6

SEQ ID NO: 174          moltype = AA  length = 6
FEATURE                 Location/Qualifiers
source                  1..6
                        mol_type = protein
                        organism = synthetic construct
                        note = Description of Artificial Sequence: Synthetic peptide
SITE                    5
                        note = Norleucine
SEQUENCE: 174
LRSLXK                                                                          6

SEQ ID NO: 175          moltype = AA  length = 6
FEATURE                 Location/Qualifiers
source                  1..6
                        mol_type = protein
                        organism = synthetic construct
                        note = Description of Artificial Sequence: Synthetic peptide
SITE                    1
                        note = Norleucine
SITE                    2
                        note = Norleucine
SEQUENCE: 175
XXIRHA                                                                          6

SEQ ID NO: 176          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 176
HDVKFI                                                                          6
```

```
SEQ ID NO: 177           moltype = AA   length = 6
FEATURE                  Location/Qualifiers
source                   1..6
                         mol_type = protein
                         organism = synthetic construct
                         note = Description of Artificial Sequence: Synthetic peptide
SEQUENCE: 177
KRVQFL                                                                   6

SEQ ID NO: 178           moltype = AA   length = 6
FEATURE                  Location/Qualifiers
source                   1..6
                         mol_type = protein
                         organism = synthetic construct
                         note = Description of Artificial Sequence: Synthetic peptide
SITE                     3
                         note = Norleucine
SEQUENCE: 178
RDXYAE                                                                   6

SEQ ID NO: 179           moltype = AA   length = 6
FEATURE                  Location/Qualifiers
source                   1..6
                         mol_type = protein
                         organism = synthetic construct
                         note = Description of Artificial Sequence: Synthetic peptide
SITE                     2
                         note = Norleucine
SEQUENCE: 179
LXIYFE                                                                   6

SEQ ID NO: 180           moltype = AA   length = 6
FEATURE                  Location/Qualifiers
source                   1..6
                         mol_type = protein
                         organism = synthetic construct
                         note = Description of Artificial Sequence: Synthetic peptide
SEQUENCE: 180
LRTKQS                                                                   6

SEQ ID NO: 181           moltype = AA   length = 6
FEATURE                  Location/Qualifiers
source                   1..6
                         mol_type = protein
                         organism = synthetic construct
                         note = Description of Artificial Sequence: Synthetic peptide
SEQUENCE: 181
WHGQQY                                                                   6

SEQ ID NO: 182           moltype = AA   length = 6
FEATURE                  Location/Qualifiers
source                   1..6
                         mol_type = protein
                         organism = synthetic construct
                         note = Description of Artificial Sequence: Synthetic peptide
SEQUENCE: 182
GPEGTI                                                                   6

SEQ ID NO: 183           moltype = AA   length = 6
FEATURE                  Location/Qualifiers
source                   1..6
                         mol_type = protein
                         organism = synthetic construct
                         note = Description of Artificial Sequence: Synthetic peptide
SEQUENCE: 183
ELDPIP                                                                   6

SEQ ID NO: 184           moltype = AA   length = 6
FEATURE                  Location/Qualifiers
source                   1..6
                         mol_type = protein
                         organism = synthetic construct
                         note = Description of Artificial Sequence: Synthetic peptide
SEQUENCE: 184
GRAADF                                                                   6

SEQ ID NO: 185           moltype = AA   length = 6
FEATURE                  Location/Qualifiers
```

```
source                  1..6
                        mol_type = protein
                        organism = synthetic construct
                        note = Description of Artificial Sequence: Synthetic peptide
SEQUENCE: 185
HFIDYI                                                                            6

SEQ ID NO: 186          moltype = AA  length = 6
FEATURE                 Location/Qualifiers
source                  1..6
                        mol_type = protein
                        organism = synthetic construct
                        note = Description of Artificial Sequence: Synthetic peptide
SITE                    2
                        note = Norleucine
SITE                    3
                        note = Norleucine
SEQUENCE: 186
SXXRVH                                                                            6

SEQ ID NO: 187          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 187
SFRKII                                                                            6

SEQ ID NO: 188          moltype = AA  length = 6
FEATURE                 Location/Qualifiers
source                  1..6
                        mol_type = protein
                        organism = synthetic construct
                        note = Description of Artificial Sequence: Synthetic peptide
SITE                    4
                        note = Norleucine
SEQUENCE: 188
TYEXFS                                                                            6

SEQ ID NO: 189          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 189
HLLGFY                                                                            6

SEQ ID NO: 190          moltype = AA  length = 6
FEATURE                 Location/Qualifiers
source                  1..6
                        mol_type = protein
                        organism = synthetic construct
                        note = Description of Artificial Sequence: Synthetic peptide
SITE                    1
                        note = Norleucine
SEQUENCE: 190
XWTALT                                                                            6

SEQ ID NO: 191          moltype = AA  length = 6
FEATURE                 Location/Qualifiers
source                  1..6
                        mol_type = protein
                        organism = synthetic construct
                        note = Description of Artificial Sequence: Synthetic peptide
SITE                    4
                        note = Norleucine
SEQUENCE: 191
IWNXVY                                                                            6

SEQ ID NO: 192          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 192
RRNPLW                                                                            6
```

```
SEQ ID NO: 193          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 193
RWYGGI                                                                              6

SEQ ID NO: 194          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 194
KTGDAR                                                                              6

SEQ ID NO: 195          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 195
NYWEAN                                                                              6

SEQ ID NO: 196          moltype = AA   length = 6
FEATURE                 Location/Qualifiers
source                  1..6
                        mol_type = protein
                        organism = synthetic construct
                        note = Description of Artificial Sequence: Synthetic peptide
SITE                    1
                        note = Norleucine
SEQUENCE: 196
XQFDTS                                                                              6

SEQ ID NO: 197          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 197
KRGAVE                                                                              6

SEQ ID NO: 198          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 198
SLKPTE                                                                              6

SEQ ID NO: 199          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 199
ENDRLP                                                                              6

SEQ ID NO: 200          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 200
NSYQVQ                                                                              6

SEQ ID NO: 201          moltype = AA   length = 6
FEATURE                 Location/Qualifiers
source                  1..6
                        mol_type = protein
```

```
SEQUENCE: 201
YPKEYL                                                                6

SEQ ID NO: 202         moltype = AA   length = 6
FEATURE                Location/Qualifiers
source                 1..6
                       mol_type = protein
                       organism = synthetic construct
                       note = Description of Artificial Sequence: Synthetic peptide
SEQUENCE: 202
INNKWQ                                                                6

SEQ ID NO: 203         moltype = AA   length = 6
FEATURE                Location/Qualifiers
source                 1..6
                       mol_type = protein
                       organism = synthetic construct
                       note = Description of Artificial Sequence: Synthetic peptide
SITE                   1
                       note = Norleucine
SEQUENCE: 203
XEFQGW                                                                6

SEQ ID NO: 204         moltype = AA   length = 6
FEATURE                Location/Qualifiers
source                 1..6
                       mol_type = protein
                       organism = synthetic construct
                       note = Description of Artificial Sequence: Synthetic peptide
SEQUENCE: 204
PVRSTN                                                                6

SEQ ID NO: 205         moltype = AA   length = 6
FEATURE                Location/Qualifiers
source                 1..6
                       mol_type = protein
                       organism = synthetic construct
                       note = Description of Artificial Sequence: Synthetic peptide
SEQUENCE: 205
SQAIKV                                                                6

SEQ ID NO: 206         moltype = AA   length = 6
FEATURE                Location/Qualifiers
source                 1..6
                       mol_type = protein
                       organism = synthetic construct
                       note = Description of Artificial Sequence: Synthetic peptide
SITE                   3
                       note = Norleucine
SEQUENCE: 206
WAXLYH                                                                6

SEQ ID NO: 207         moltype = AA   length = 6
FEATURE                Location/Qualifiers
source                 1..6
                       mol_type = protein
                       organism = synthetic construct
                       note = Description of Artificial Sequence: Synthetic peptide
SEQUENCE: 207
ISWIHA                                                                6

SEQ ID NO: 208         moltype = AA   length = 5
FEATURE                Location/Qualifiers
source                 1..5
                       mol_type = protein
                       organism = synthetic construct
                       note = Description of Artificial Sequence: Synthetic peptide
SEQUENCE: 208
AHDIV                                                                 5

SEQ ID NO: 209         moltype = AA   length = 6
FEATURE                Location/Qualifiers
source                 1..6
                       mol_type = protein
                       organism = synthetic construct
                       note = Description of Artificial Sequence: Synthetic peptide
SEQUENCE: 209
```

RHNVAS                                                                                       6

SEQ ID NO: 210           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 210
SVFVIE                                                                                       6

SEQ ID NO: 211           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 211
FAKYYK                                                                                       6

SEQ ID NO: 212           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 212
PYNTLQ                                                                                       6

SEQ ID NO: 213           moltype = AA  length = 6
FEATURE                  Location/Qualifiers
source                   1..6
                         mol_type = protein
                         organism = synthetic construct
                         note = Description of Artificial Sequence: Synthetic peptide
SITE                     1
                         note = Norleucine
SITE                     6
                         note = Norleucine
SEQUENCE: 213
XDWGHX                                                                                       6

SEQ ID NO: 214           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 214
SNREWF                                                                                       6

SEQ ID NO: 215           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 215
GKSEHT                                                                                       6

SEQ ID NO: 216           moltype = AA  length = 6
FEATURE                  Location/Qualifiers
source                   1..6
                         mol_type = protein
                         organism = synthetic construct
                         note = Description of Artificial Sequence: Synthetic peptide
SITE                     3
                         note = Norleucine
SEQUENCE: 216
FPXTDQ                                                                                       6

SEQ ID NO: 217           moltype = AA  length = 6
FEATURE                  Location/Qualifiers
source                   1..6
                         mol_type = protein
                         organism = synthetic construct
                         note = Description of Artificial Sequence: Synthetic peptide
SITE                     6
                         note = Norleucine

```
SEQUENCE: 217
WSKFWX                                                                      6

SEQ ID NO: 218         moltype = AA  length = 6
FEATURE                Location/Qualifiers
source                 1..6
                       mol_type = protein
                       organism = synthetic construct
                       note = Description of Artificial Sequence: Synthetic peptide
SEQUENCE: 218
RFTRPH                                                                      6

SEQ ID NO: 219         moltype = AA  length = 6
FEATURE                Location/Qualifiers
source                 1..6
                       mol_type = protein
                       organism = synthetic construct
                       note = Description of Artificial Sequence: Synthetic peptide
SITE                   4
                       note = Norleucine
SEQUENCE: 219
QETXKD                                                                      6

SEQ ID NO: 220         moltype = AA  length = 6
FEATURE                Location/Qualifiers
source                 1..6
                       mol_type = protein
                       organism = synthetic construct
                       note = Description of Artificial Sequence: Synthetic peptide
SEQUENCE: 220
HWWDVL                                                                      6

SEQ ID NO: 221         moltype = AA  length = 6
FEATURE                Location/Qualifiers
source                 1..6
                       mol_type = protein
                       organism = synthetic construct
                       note = Description of Artificial Sequence: Synthetic peptide
SITE                   5
                       note = Norleucine
SEQUENCE: 221
FNLVXS                                                                      6

SEQ ID NO: 222         moltype = AA  length = 6
FEATURE                Location/Qualifiers
source                 1..6
                       mol_type = protein
                       organism = synthetic construct
                       note = Description of Artificial Sequence: Synthetic peptide
SEQUENCE: 222
SAWRQR                                                                      6

SEQ ID NO: 223         moltype = AA  length = 6
FEATURE                Location/Qualifiers
source                 1..6
                       mol_type = protein
                       organism = synthetic construct
                       note = Description of Artificial Sequence: Synthetic peptide
SEQUENCE: 223
TFHIFL                                                                      6

SEQ ID NO: 224         moltype = AA  length = 6
FEATURE                Location/Qualifiers
source                 1..6
                       mol_type = protein
                       organism = synthetic construct
                       note = Description of Artificial Sequence: Synthetic peptide
SEQUENCE: 224
WPQHVK                                                                      6

SEQ ID NO: 225         moltype = AA  length = 6
FEATURE                Location/Qualifiers
source                 1..6
                       mol_type = protein
                       organism = synthetic construct
                       note = Description of Artificial Sequence: Synthetic peptide
SITE                   3
                       note = Norleucine
SEQUENCE: 225
```

LIXHKN                                                                           6

SEQ ID NO: 226          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 226
QDLEQP                                                                           6

SEQ ID NO: 227          moltype = AA   length = 6
FEATURE                 Location/Qualifiers
source                  1..6
                        mol_type = protein
                        organism = synthetic construct
                        note = Description of Artificial Sequence: Synthetic peptide
SITE                    5
                        note = Norleucine
SEQUENCE: 227
HQKKXP                                                                           6

SEQ ID NO: 228          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 228
GVTWLN                                                                           6

SEQ ID NO: 229          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 229
AGEPFK                                                                           6

SEQ ID NO: 230          moltype = AA   length = 6
FEATURE                 Location/Qualifiers
source                  1..6
                        mol_type = protein
                        organism = synthetic construct
                        note = Description of Artificial Sequence: Synthetic peptide
SITE                    3
                        note = Norleucine
SEQUENCE: 230
SRXATT                                                                           6

SEQ ID NO: 231          moltype = AA   length = 6
FEATURE                 Location/Qualifiers
source                  1..6
                        mol_type = protein
                        organism = synthetic construct
                        note = Description of Artificial Sequence: Synthetic peptide
SITE                    4
                        note = Norleucine
SEQUENCE: 231
LAFXNH                                                                           6

SEQ ID NO: 232          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 232
PPSGLS                                                                           6

SEQ ID NO: 233          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 233
YTHSSP                                                                           6

```
SEQ ID NO: 234         moltype = AA  length = 6
FEATURE                Location/Qualifiers
source                 1..6
                       mol_type = protein
                       organism = synthetic construct
                       note = Description of Artificial Sequence: Synthetic peptide
SEQUENCE: 234
DGSHYR                                                                          6

SEQ ID NO: 235         moltype = AA  length = 6
FEATURE                Location/Qualifiers
source                 1..6
                       mol_type = protein
                       organism = synthetic construct
                       note = Description of Artificial Sequence: Synthetic peptide
SITE                   2
                       note = Norleucine
SEQUENCE: 235
YXGNGY                                                                          6

SEQ ID NO: 236         moltype = AA  length = 6
FEATURE                Location/Qualifiers
source                 1..6
                       mol_type = protein
                       organism = synthetic construct
                       note = Description of Artificial Sequence: Synthetic peptide
SEQUENCE: 236
DSITVS                                                                          6

SEQ ID NO: 237         moltype = AA  length = 6
FEATURE                Location/Qualifiers
source                 1..6
                       mol_type = protein
                       organism = synthetic construct
                       note = Description of Artificial Sequence: Synthetic peptide
SEQUENCE: 237
QTPNIQ                                                                          6

SEQ ID NO: 238         moltype = AA  length = 6
FEATURE                Location/Qualifiers
source                 1..6
                       mol_type = protein
                       organism = synthetic construct
                       note = Description of Artificial Sequence: Synthetic peptide
SEQUENCE: 238
KLFFGY                                                                          6

SEQ ID NO: 239         moltype = AA  length = 6
FEATURE                Location/Qualifiers
source                 1..6
                       mol_type = protein
                       organism = synthetic construct
                       note = Description of Artificial Sequence: Synthetic peptide
SEQUENCE: 239
TQNFNW                                                                          6

SEQ ID NO: 240         moltype = AA  length = 6
FEATURE                Location/Qualifiers
source                 1..6
                       mol_type = protein
                       organism = synthetic construct
                       note = Description of Artificial Sequence: Synthetic peptide
SEQUENCE: 240
YSDHEV                                                                          6

SEQ ID NO: 241         moltype = AA  length = 6
FEATURE                Location/Qualifiers
source                 1..6
                       mol_type = protein
                       organism = synthetic construct
                       note = Description of Artificial Sequence: Synthetic peptide
SEQUENCE: 241
RYVVPA                                                                          6

SEQ ID NO: 242         moltype = AA  length = 6
FEATURE                Location/Qualifiers
source                 1..6
                       mol_type = protein
```

```
SEQUENCE: 242
ILHRIR                                                                  6

SEQ ID NO: 243          moltype = AA  length = 6
FEATURE                 Location/Qualifiers
source                  1..6
                        mol_type = protein
                        organism = synthetic construct
                        note = Description of Artificial Sequence: Synthetic peptide
SITE                    6
                        note = Norleucine
SEQUENCE: 243
ESDNQX                                                                  6

SEQ ID NO: 244          moltype = AA  length = 6
FEATURE                 Location/Qualifiers
source                  1..6
                        mol_type = protein
                        organism = synthetic construct
                        note = Description of Artificial Sequence: Synthetic peptide
SITE                    6
                        note = Norleucine
SEQUENCE: 244
YDDKGX                                                                  6

SEQ ID NO: 245          moltype = AA  length = 6
FEATURE                 Location/Qualifiers
source                  1..6
                        mol_type = protein
                        organism = synthetic construct
                        note = Description of Artificial Sequence: Synthetic peptide
SITE                    4
                        note = Norleucine
SEQUENCE: 245
QLSXVW                                                                  6

SEQ ID NO: 246          moltype = AA  length = 6
FEATURE                 Location/Qualifiers
source                  1..6
                        mol_type = protein
                        organism = synthetic construct
                        note = Description of Artificial Sequence: Synthetic peptide
SITE                    6
                        note = Norleucine
SEQUENCE: 246
PGGERX                                                                  6

SEQ ID NO: 247          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 247
WKHHPD                                                                  6

SEQ ID NO: 248          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 248
QWVDED                                                                  6

SEQ ID NO: 249          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 249
NAYNEI                                                                  6

SEQ ID NO: 250          moltype = AA  length = 6
FEATURE                 Location/Qualifiers
source                  1..6
```

```
                         mol_type = protein
                         organism = synthetic construct
                         note = Description of Artificial Sequence: Synthetic peptide
SEQUENCE: 250
EEKAPR                                                                          6

SEQ ID NO: 251           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 251
PWQIGK                                                                          6

SEQ ID NO: 252           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 252
IAQVGN                                                                          6

SEQ ID NO: 253           moltype = AA  length = 6
FEATURE                  Location/Qualifiers
source                   1..6
                         mol_type = protein
                         organism = synthetic construct
                         note = Description of Artificial Sequence: Synthetic peptide
SITE                     2
                         note = Norleucine
SEQUENCE: 253
VXRQSE                                                                          6

SEQ ID NO: 254           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 254
TERVDA                                                                          6

SEQ ID NO: 255           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 255
WLRWRL                                                                          6

SEQ ID NO: 256           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 256
WKTKGQ                                                                          6

SEQ ID NO: 257           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 257
QSNGDV                                                                          6

SEQ ID NO: 258           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 258
TLFYAL                                                                          6
```

```
SEQ ID NO: 259           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 259
TVTLNP                                                                          6

SEQ ID NO: 260           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 260
YAFGRK                                                                          6

SEQ ID NO: 261           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 261
DYNYWD                                                                          6

SEQ ID NO: 262           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 262
EWHEII                                                                          6

SEQ ID NO: 263           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 263
QKAAWD                                                                          6

SEQ ID NO: 264           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 264
DNTSAD                                                                          6

SEQ ID NO: 265           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 265
HEGEYV                                                                          6

SEQ ID NO: 266           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 266
WSPSFK                                                                          6

SEQ ID NO: 267           moltype = AA  length = 6
FEATURE                  Location/Qualifiers
source                   1..6
                         mol_type = protein
                         organism = synthetic construct
                         note = Description of Artificial Sequence: Synthetic peptide
```

```
SEQUENCE: 267
HDEHWT                                                                               6

SEQ ID NO: 268           moltype = AA  length = 6
FEATURE                  Location/Qualifiers
source                   1..6
                         mol_type = protein
                         organism = synthetic construct
                         note = Description of Artificial Sequence: Synthetic peptide
SITE                     4
                         note = Norleucine
SEQUENCE: 268
YVWXRD                                                                               6

SEQ ID NO: 269           moltype = AA  length = 6
FEATURE                  Location/Qualifiers
source                   1..6
                         mol_type = protein
                         organism = synthetic construct
                         note = Description of Artificial Sequence: Synthetic peptide
SITE                     1
                         note = Norleucine
SITE                     4
                         note = Norleucine
SEQUENCE: 269
XDPXKF                                                                               6

SEQ ID NO: 270           moltype = AA  length = 6
FEATURE                  Location/Qualifiers
source                   1..6
                         mol_type = protein
                         organism = synthetic construct
                         note = Description of Artificial Sequence: Synthetic peptide
SITE                     1
                         note = Norleucine
SITE                     3
                         note = Norleucine
SEQUENCE: 270
XRXFWD                                                                               6

SEQ ID NO: 271           moltype = AA  length = 6
FEATURE                  Location/Qualifiers
source                   1..6
                         mol_type = protein
                         organism = synthetic construct
                         note = Description of Artificial Sequence: Synthetic peptide
SITE                     6
                         note = Norleucine
SEQUENCE: 271
DIAITX                                                                               6

SEQ ID NO: 272           moltype = AA  length = 6
FEATURE                  Location/Qualifiers
source                   1..6
                         mol_type = protein
                         organism = synthetic construct
                         note = Description of Artificial Sequence: Synthetic peptide
SITE                     3
                         note = Norleucine
SEQUENCE: 272
PIXRFH                                                                               6

SEQ ID NO: 273           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 273
VWQGYI                                                                               6

SEQ ID NO: 274           moltype = AA  length = 6
FEATURE                  Location/Qualifiers
source                   1..6
                         mol_type = protein
                         organism = synthetic construct
                         note = Description of Artificial Sequence: Synthetic peptide
SITE                     3
                         note = Norleucine
```

```
SEQUENCE: 274
KKXSNP                                                                          6

SEQ ID NO: 275          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 275
GHPLSP                                                                          6

SEQ ID NO: 276          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 276
VRQHKP                                                                          6

SEQ ID NO: 277          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 277
AQNFYR                                                                          6

SEQ ID NO: 278          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 278
VAGKSI                                                                          6

SEQ ID NO: 279          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 279
LVGQVN                                                                          6

SEQ ID NO: 280          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 280
QVKHFT                                                                          6

SEQ ID NO: 281          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 281
QKSVVS                                                                          6

SEQ ID NO: 282          moltype = AA  length = 6
FEATURE                 Location/Qualifiers
source                  1..6
                        mol_type = protein
                        organism = synthetic construct
                        note = Description of Artificial Sequence: Synthetic peptide
SITE                    2
                        note = Norleucine
SEQUENCE: 282
YXQEWL                                                                          6

SEQ ID NO: 283          moltype = AA  length = 6
FEATURE                 Location/Qualifiers
```

```
                                -continued source                  1..6
                        mol_type = protein
                        organism = synthetic construct
                        note = Description of Artificial Sequence: Synthetic peptide
SITE                    2
                        note = Norleucine
SEQUENCE: 283
GXYIDE                                                                          6

SEQ ID NO: 284          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 284
NAGSKF                                                                          6

SEQ ID NO: 285          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 285
EFVHNP                                                                          6

SEQ ID NO: 286          moltype = AA   length = 6
FEATURE                 Location/Qualifiers
source                  1..6
                        mol_type = protein
                        organism = synthetic construct
                        note = Description of Artificial Sequence: Synthetic peptide
SITE                    3
                        note = Norleucine
SEQUENCE: 286
WEXVKI                                                                          6

SEQ ID NO: 287          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 287
WVGASH                                                                          6

SEQ ID NO: 288          moltype = AA   length = 6
FEATURE                 Location/Qualifiers
source                  1..6
                        mol_type = protein
                        organism = synthetic construct
                        note = Description of Artificial Sequence: Synthetic peptide
SITE                    6
                        note = Norleucine
SEQUENCE: 288
ITTLYX                                                                          6

SEQ ID NO: 289          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 289
GHIDEY                                                                          6

SEQ ID NO: 290          moltype = AA   length = 6
FEATURE                 Location/Qualifiers
source                  1..6
                        mol_type = protein
                        organism = synthetic construct
                        note = Description of Artificial Sequence: Synthetic peptide
SITE                    3
                        note = Norleucine
SEQUENCE: 290
KVXDYG                                                                          6

SEQ ID NO: 291          moltype = AA   length = 6
```

|                         |                                                                                                                                                                                                                                   |   |
|-------------------------|-----------------------------------------------------------------------------------------------------------------------------------------------------------------------------------------------------------------------------------|---|
| FEATURE                 | Location/Qualifiers                                                                                                                                                                                                               |   |
| source                  | 1..6<br>mol_type = protein<br>organism = synthetic construct<br>note = Description of Artificial Sequence: Synthetic peptide                                                                                                      |   |
| SITE                    | 6<br>note = Norleucine                                                                                                                                                                                                            |   |
| SEQUENCE: 291<br>QEKQTX |                                                                                                                                                                                                                                   | 6 |
| SEQ ID NO: 292<br>FEATURE | moltype = AA  length = 6<br>Location/Qualifiers                                                                                                                                                                                 |   |
| source                  | 1..6<br>mol_type = protein<br>organism = synthetic construct<br>note = Description of Artificial Sequence: Synthetic peptide                                                                                                      |   |
| SEQUENCE: 292<br>EVGHEA |                                                                                                                                                                                                                                   | 6 |
| SEQ ID NO: 293<br>FEATURE | moltype = AA  length = 6<br>Location/Qualifiers                                                                                                                                                                                 |   |
| source                  | 1..6<br>mol_type = protein<br>organism = synthetic construct<br>note = Description of Artificial Sequence: Synthetic peptide                                                                                                      |   |
| SEQUENCE: 293<br>AWEGQY |                                                                                                                                                                                                                                   | 6 |
| SEQ ID NO: 294<br>FEATURE | moltype = AA  length = 6<br>Location/Qualifiers                                                                                                                                                                                 |   |
| source                  | 1..6<br>mol_type = protein<br>organism = synthetic construct<br>note = Description of Artificial Sequence: Synthetic peptide                                                                                                      |   |
| SEQUENCE: 294<br>FLVQWT |                                                                                                                                                                                                                                   | 6 |
| SEQ ID NO: 295<br>FEATURE | moltype = AA  length = 6<br>Location/Qualifiers                                                                                                                                                                                 |   |
| source                  | 1..6<br>mol_type = protein<br>organism = synthetic construct<br>note = Description of Artificial Sequence: Synthetic peptide                                                                                                      |   |
| SEQUENCE: 295<br>SKWGYW |                                                                                                                                                                                                                                   | 6 |
| SEQ ID NO: 296<br>FEATURE | moltype = AA  length = 6<br>Location/Qualifiers                                                                                                                                                                                 |   |
| source                  | 1..6<br>mol_type = protein<br>organism = synthetic construct<br>note = Description of Artificial Sequence: Synthetic peptide                                                                                                      |   |
| SITE                    | 5<br>note = Norleucine                                                                                                                                                                                                            |   |
| SEQUENCE: 296<br>TWISXQ |                                                                                                                                                                                                                                   | 6 |
| SEQ ID NO: 297<br>FEATURE | moltype = AA  length = 6<br>Location/Qualifiers                                                                                                                                                                                 |   |
| source                  | 1..6<br>mol_type = protein<br>organism = synthetic construct<br>note = Description of Artificial Sequence: Synthetic peptide                                                                                                      |   |
| SEQUENCE: 297<br>VIDKDF |                                                                                                                                                                                                                                   | 6 |
| SEQ ID NO: 298<br>FEATURE | moltype = AA  length = 6<br>Location/Qualifiers                                                                                                                                                                                 |   |
| source                  | 1..6<br>mol_type = protein<br>organism = synthetic construct<br>note = Description of Artificial Sequence: Synthetic peptide                                                                                                      |   |
| SEQUENCE: 298<br>VKFAIY |                                                                                                                                                                                                                                   | 6 |
| SEQ ID NO: 299<br>FEATURE | moltype = AA  length = 6<br>Location/Qualifiers                                                                                                                                                                                 |   |
| source                  | 1..6<br>mol_type = protein                                                                                                                                                                                                        |   |

```
                        organism = synthetic construct
                        note = Description of Artificial Sequence: Synthetic peptide
SITE                    4
                        note = Norleucine
SEQUENCE: 299
HNQXKS                                                                          6

SEQ ID NO: 300          moltype = AA  length = 6
FEATURE                 Location/Qualifiers
source                  1..6
                        mol_type = protein
                        organism = synthetic construct
                        note = Description of Artificial Sequence: Synthetic peptide
SITE                    6
                        note = Norleucine
SEQUENCE: 300
QYVFFX                                                                          6

SEQ ID NO: 301          moltype = AA  length = 6
FEATURE                 Location/Qualifiers
source                  1..6
                        mol_type = protein
                        organism = synthetic construct
                        note = Description of Artificial Sequence: Synthetic peptide
SITE                    6
                        note = Norleucine
SEQUENCE: 301
YNPREX                                                                          6

SEQ ID NO: 302          moltype = AA  length = 6
FEATURE                 Location/Qualifiers
source                  1..6
                        mol_type = protein
                        organism = synthetic construct
                        note = Description of Artificial Sequence: Synthetic peptide
SITE                    4
                        note = Norleucine
SEQUENCE: 302
KHGXPE                                                                          6

SEQ ID NO: 303          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 303
WSREYW                                                                          6

SEQ ID NO: 304          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 304
IDRVDK                                                                          6

SEQ ID NO: 305          moltype = AA  length = 9
FEATURE                 Location/Qualifiers
source                  1..9
                        mol_type = protein
                        organism = synthetic construct
                        note = Description of Artificial Sequence: Synthetic peptide
SITE                    8
                        note = Lysine modified with a CPQ2 quencher
SITE                    9
                        note = Hydroxy leucine
SEQUENCE: 305
GDRENSPKL                                                                       9

SEQ ID NO: 306          moltype = AA  length = 9
FEATURE                 Location/Qualifiers
source                  1..9
                        mol_type = protein
                        organism = synthetic construct
                        note = Description of Artificial Sequence: Synthetic peptide
SITE                    9
                        note = Hydroxy lysine modified with a CPQ2 quencher
```

```
SEQUENCE: 306
GDRENSPLK                                                                        9

SEQ ID NO: 307           moltype = AA  length = 8
FEATURE                  Location/Qualifiers
source                   1..8
                         mol_type = protein
                         organism = synthetic construct
                         note = Description of Artificial Sequence: Synthetic peptide
SITE                     7
                         note = Lysine modified with a CPQ2 quencher
SITE                     8
                         note = Hydroxy Glutamine
SEQUENCE: 307
NAGSKFKQ                                                                         8

SEQ ID NO: 308           moltype = AA  length = 8
FEATURE                  Location/Qualifiers
source                   1..8
                         mol_type = protein
                         organism = synthetic construct
                         note = Description of Artificial Sequence: Synthetic peptide
SITE                     8
                         note = Hydroxy lysine modified with a CPQ2 quencher
SEQUENCE: 308
NAGSKFQK                                                                         8

SEQ ID NO: 309           moltype = AA  length = 9
FEATURE                  Location/Qualifiers
source                   1..9
                         mol_type = protein
                         organism = synthetic construct
                         note = Description of Artificial Sequence: Synthetic peptide
SITE                     8
                         note = Lysine modified with a CPQ2 quencher
SITE                     9
                         note = Hydroxy Valine
SEQUENCE: 309
GHLLGFYKV                                                                        9

SEQ ID NO: 310           moltype = AA  length = 9
FEATURE                  Location/Qualifiers
source                   1..9
                         mol_type = protein
                         organism = synthetic construct
                         note = Description of Artificial Sequence: Synthetic peptide
SITE                     9
                         note = Hydroxy lysine modified with a CPQ2 quencher
SEQUENCE: 310
GHLLGFYVK                                                                        9

SEQ ID NO: 311           moltype = AA  length = 9
FEATURE                  Location/Qualifiers
source                   1..9
                         mol_type = protein
                         organism = synthetic construct
                         note = Description of Artificial Sequence: Synthetic peptide
SITE                     7
                         note = Norleucine
SITE                     8
                         note = Lysine modified with a CPQ2 quencher
SITE                     9
                         note = Hydroxy Norleucine
SEQUENCE: 311
GQEKQTXKX                                                                        9

SEQ ID NO: 312           moltype = AA  length = 9
FEATURE                  Location/Qualifiers
source                   1..9
                         mol_type = protein
                         organism = synthetic construct
                         note = Description of Artificial Sequence: Synthetic peptide
SITE                     7
                         note = Norleucine
SITE                     8
                         note = Norleucine
SITE                     9
                         note = Hydroxy lysine modified with a CPQ2 quencher
SEQUENCE: 312
```

```
GQEKQTXXK                                                     9

SEQ ID NO: 313          moltype = AA  length = 10
FEATURE                 Location/Qualifiers
source                  1..10
                        mol_type = protein
                        organism = synthetic construct
                        note = Description of Artificial Sequence: Synthetic peptide
SITE                    1
                        note = D-Lysine
SITE                    9
                        note = Lysine modified with a CPQ2 quencher
SITE                    10
                        note = Hydroxy Tryptophan
SEQUENCE: 313
KGDPFVVSKW                                                    10

SEQ ID NO: 314          moltype = AA  length = 10
FEATURE                 Location/Qualifiers
source                  1..10
                        mol_type = protein
                        organism = synthetic construct
                        note = Description of Artificial Sequence: Synthetic peptide
SITE                    1
                        note = D-Lysine
SITE                    10
                        note = Hydroxy lysine modified with a CPQ2 quencher
SEQUENCE: 314
KGDPFVVSWK                                                    10

SEQ ID NO: 315          moltype = AA  length = 8
FEATURE                 Location/Qualifiers
source                  1..8
                        mol_type = protein
                        organism = synthetic construct
                        note = Description of Artificial Sequence: Synthetic peptide
SITE                    7
                        note = Lysine modified with a CPQ2 quencher
SITE                    8
                        note = Hydroxy Arginine
SEQUENCE: 315
NAYNEIKR                                                      8

SEQ ID NO: 316          moltype = AA  length = 8
FEATURE                 Location/Qualifiers
source                  1..8
                        mol_type = protein
                        organism = synthetic construct
                        note = Description of Artificial Sequence: Synthetic peptide
SITE                    8
                        note = Hydroxy lysine modified with a CPQ2 quencher
SEQUENCE: 316
NAYNEIRK                                                      8

SEQ ID NO: 317          moltype = AA  length = 8
FEATURE                 Location/Qualifiers
source                  1..8
                        mol_type = protein
                        organism = synthetic construct
                        note = Description of Artificial Sequence: Synthetic peptide
SITE                    2
                        note = Norleucine
SITE                    7
                        note = Lysine modified with a CPQ2 quencher
SITE                    8
                        note = Hydroxy Asparagine
SEQUENCE: 317
VXRQSEKN                                                      8

SEQ ID NO: 318          moltype = AA  length = 8
FEATURE                 Location/Qualifiers
source                  1..8
                        mol_type = protein
                        organism = synthetic construct
                        note = Description of Artificial Sequence: Synthetic peptide
SITE                    2
                        note = Norleucine
SITE                    8
                        note = Hydroxy lysine modified with a CPQ2 quencher
```

-continued

```
SEQUENCE: 318
VXRQSENK                                                                    8

SEQ ID NO: 319          moltype = AA  length = 8
FEATURE                 Location/Qualifiers
source                  1..8
                        mol_type = protein
                        organism = synthetic construct
                        note = Description of Artificial Sequence: Synthetic peptide
SITE                    6
                        note = Norleucine
SITE                    7
                        note = Lysine modified with a CPQ2 quencher
SITE                    8
                        note = Hydroxy Isoleucine
SEQUENCE: 319
YNPREXKI                                                                    8

SEQ ID NO: 320          moltype = AA  length = 8
FEATURE                 Location/Qualifiers
source                  1..8
                        mol_type = protein
                        organism = synthetic construct
                        note = Description of Artificial Sequence: Synthetic peptide
SITE                    6
                        note = Norleucine
SITE                    8
                        note = Hydroxy lysine modified with a CPQ2 quencher
SEQUENCE: 320
YNPREXIK                                                                    8

SEQ ID NO: 321          moltype = AA  length = 8
FEATURE                 Location/Qualifiers
source                  1..8
                        mol_type = protein
                        organism = synthetic construct
                        note = Description of Artificial Sequence: Synthetic peptide
SITE                    7
                        note = Lysine modified with a CPQ2 quencher
SITE                    8
                        note = Hydroxy Lysine
SEQUENCE: 321
EFVHNPKK                                                                    8

SEQ ID NO: 322          moltype = AA  length = 8
FEATURE                 Location/Qualifiers
source                  1..8
                        mol_type = protein
                        organism = synthetic construct
                        note = Description of Artificial Sequence: Synthetic peptide
SITE                    8
                        note = Hydroxy lysine modified with a CPQ2 quencher
SEQUENCE: 322
EFVHNPKK                                                                    8

SEQ ID NO: 323          moltype = AA  length = 8
FEATURE                 Location/Qualifiers
source                  1..8
                        mol_type = protein
                        organism = synthetic construct
                        note = Description of Artificial Sequence: Synthetic peptide
SITE                    7
                        note = Lysine modified with a CPQ2 quencher
SITE                    8
                        note = Hydroxy Histidine
SEQUENCE: 323
KRVQFLKH                                                                    8

SEQ ID NO: 324          moltype = AA  length = 8
FEATURE                 Location/Qualifiers
source                  1..8
                        mol_type = protein
                        organism = synthetic construct
                        note = Description of Artificial Sequence: Synthetic peptide
SITE                    8
                        note = Hydroxy lysine modified with a CPQ2 quencher
SEQUENCE: 324
KRVQFLHK                                                                    8
```

```
SEQ ID NO: 325          moltype = AA  length = 8
FEATURE                 Location/Qualifiers
source                  1..8
                        mol_type = protein
                        organism = synthetic construct
                        note = Description of Artificial Sequence: Synthetic peptide
SITE                    3
                        note = Norleucine
SITE                    7
                        note = Lysine modified with a CPQ2 quencher
SITE                    8
                        note = Hydroxy Glycine
SEQUENCE: 325
LIXHKNKG                                                                 8

SEQ ID NO: 326          moltype = AA  length = 8
FEATURE                 Location/Qualifiers
source                  1..8
                        mol_type = protein
                        organism = synthetic construct
                        note = Description of Artificial Sequence: Synthetic peptide
SITE                    3
                        note = Norleucine
SITE                    8
                        note = Hydroxy lysine modified with a CPQ2 quencher
SEQUENCE: 326
LIXHKNGK                                                                 8

SEQ ID NO: 327          moltype = AA  length = 8
FEATURE                 Location/Qualifiers
source                  1..8
                        mol_type = protein
                        organism = synthetic construct
                        note = Description of Artificial Sequence: Synthetic peptide
SITE                    3
                        note = Norleucine
SITE                    7
                        note = Lysine modified with a CPQ2 quencher
SITE                    8
                        note = Hydroxy Serine
SEQUENCE: 327
WAXLYHKS                                                                 8

SEQ ID NO: 328          moltype = AA  length = 8
FEATURE                 Location/Qualifiers
source                  1..8
                        mol_type = protein
                        organism = synthetic construct
                        note = Description of Artificial Sequence: Synthetic peptide
SITE                    3
                        note = Norleucine
SITE                    8
                        note = Hydroxy lysine modified with a CPQ2 quencher
SEQUENCE: 328
WAXLYHSK                                                                 8

SEQ ID NO: 329          moltype = AA  length = 8
FEATURE                 Location/Qualifiers
source                  1..8
                        mol_type = protein
                        organism = synthetic construct
                        note = Description of Artificial Sequence: Synthetic peptide
SITE                    7
                        note = Lysine modified with a CPQ2 quencher
SITE                    8
                        note = Hydroxy Tyrosine
SEQUENCE: 329
AHDIVNKY                                                                 8

SEQ ID NO: 330          moltype = AA  length = 8
FEATURE                 Location/Qualifiers
source                  1..8
                        mol_type = protein
                        organism = synthetic construct
                        note = Description of Artificial Sequence: Synthetic peptide
SITE                    8
                        note = Hydroxy lysine modified with a CPQ2 quencher
SEQUENCE: 330
AHDIVNYK                                                                 8
```

```
SEQ ID NO: 331            moltype = AA   length = 8
FEATURE                   Location/Qualifiers
source                    1..8
                          mol_type = protein
                          organism = synthetic construct
                          note = Description of Artificial Sequence: Synthetic peptide
SITE                      7
                          note = Lysine modified with a CPQ2 quencher
SITE                      8
                          note = Hydroxy Proline
SEQUENCE: 331
SVFVIEKP                                                                              8

SEQ ID NO: 332            moltype = AA   length = 8
FEATURE                   Location/Qualifiers
source                    1..8
                          mol_type = protein
                          organism = synthetic construct
                          note = Description of Artificial Sequence: Synthetic peptide
SITE                      8
                          note = Hydroxy lysine modified with a CPQ2 quencher
SEQUENCE: 332
SVFVIEPK                                                                              8

SEQ ID NO: 333            moltype = AA   length = 8
FEATURE                   Location/Qualifiers
source                    1..8
                          mol_type = protein
                          organism = synthetic construct
                          note = Description of Artificial Sequence: Synthetic peptide
SITE                      7
                          note = Lysine modified with a CPQ2 quencher
SITE                      8
                          note = Hydroxy Glutamic Acid
SEQUENCE: 333
PPSGLSKE                                                                              8

SEQ ID NO: 334            moltype = AA   length = 8
FEATURE                   Location/Qualifiers
source                    1..8
                          mol_type = protein
                          organism = synthetic construct
                          note = Description of Artificial Sequence: Synthetic peptide
SITE                      8
                          note = Hydroxy lysine modified with a CPQ2 quencher
SEQUENCE: 334
PPSGLSEK                                                                              8

SEQ ID NO: 335            moltype = AA   length = 8
FEATURE                   Location/Qualifiers
source                    1..8
                          mol_type = protein
                          organism = synthetic construct
                          note = Description of Artificial Sequence: Synthetic peptide
SITE                      7
                          note = Lysine modified with a CPQ2 quencher
SITE                      8
                          note = Hydroxy Phenylalanine
SEQUENCE: 335
RWYGGIKF                                                                              8

SEQ ID NO: 336            moltype = AA   length = 8
FEATURE                   Location/Qualifiers
source                    1..8
                          mol_type = protein
                          organism = synthetic construct
                          note = Description of Artificial Sequence: Synthetic peptide
SITE                      8
                          note = Hydroxy lysine modified with a CPQ2 quencher
SEQUENCE: 336
RWYGGIFK                                                                              8

SEQ ID NO: 337            moltype = AA   length = 8
FEATURE                   Location/Qualifiers
source                    1..8
                          mol_type = protein
                          organism = synthetic construct
                          note = Description of Artificial Sequence: Synthetic peptide
```

```
SITE                      6
                          note = Norleucine
SITE                      7
                          note = Lysine modified with a CPQ2 quencher
SITE                      8
                          note = Hydroxy Aspartic Acid
SEQUENCE: 337
QYVFFXKD                                                                        8

SEQ ID NO: 338            moltype = AA  length = 8
FEATURE                   Location/Qualifiers
source                    1..8
                          mol_type = protein
                          organism = synthetic construct
                          note = Description of Artificial Sequence: Synthetic peptide
SITE                      6
                          note = Norleucine
SITE                      8
                          note = Hydroxy lysine modified with a CPQ2 quencher
SEQUENCE: 338
QYVFFXDK                                                                        8

SEQ ID NO: 339            moltype = AA  length = 8
FEATURE                   Location/Qualifiers
source                    1..8
                          mol_type = protein
                          organism = synthetic construct
                          note = Description of Artificial Sequence: Synthetic peptide
SITE                      7
                          note = Lysine modified with a CPQ2 quencher
SITE                      8
                          note = Hydroxy Threonine
SEQUENCE: 339
FAKYYKKT                                                                        8

SEQ ID NO: 340            moltype = AA  length = 8
FEATURE                   Location/Qualifiers
source                    1..8
                          mol_type = protein
                          organism = synthetic construct
                          note = Description of Artificial Sequence: Synthetic peptide
SITE                      8
                          note = Hydroxy lysine modified with a CPQ2 quencher
SEQUENCE: 340
FAKYYKTK                                                                        8

SEQ ID NO: 341            moltype = AA  length = 8
FEATURE                   Location/Qualifiers
source                    1..8
                          mol_type = protein
                          organism = synthetic construct
                          note = Description of Artificial Sequence: Synthetic peptide
SITE                      7
                          note = Lysine modified with a CPQ2 quencher
SITE                      8
                          note = Hydroxy Alanine
SEQUENCE: 341
QVKHFTKA                                                                        8

SEQ ID NO: 342            moltype = AA  length = 8
FEATURE                   Location/Qualifiers
source                    1..8
                          mol_type = protein
                          organism = synthetic construct
                          note = Description of Artificial Sequence: Synthetic peptide
SITE                      8
                          note = Hydroxy lysine modified with a CPQ2 quencher
SEQUENCE: 342
QVKHFTAK                                                                        8

SEQ ID NO: 343            moltype =    length =
SEQUENCE: 343
000

SEQ ID NO: 344            moltype = AA  length = 8
FEATURE                   Location/Qualifiers
source                    1..8
                          mol_type = protein
                          organism = synthetic construct
```

```
                        note = Description of Artificial Sequence: Synthetic peptide
SITE                    2
                        note = carboxy-fluorescein-L-lysine
SEQUENCE: 344
HKDRENSP                                                                            8

SEQ ID NO: 345          moltype = AA   length = 8
FEATURE                 Location/Qualifiers
source                  1..8
                        mol_type = protein
                        organism = synthetic construct
                        note = Description of Artificial Sequence: Synthetic peptide
SITE                    1
                        note = carboxy-fluorescein-L-lysine
SEQUENCE: 345
KHDRENSP                                                                            8

SEQ ID NO: 346          moltype = AA   length = 8
FEATURE                 Location/Qualifiers
source                  1..8
                        mol_type = protein
                        organism = synthetic construct
                        note = Description of Artificial Sequence: Synthetic peptide
SITE                    2
                        note = carboxy-fluorescein-L-lysine
SEQUENCE: 346
WKNAGSKF                                                                            8

SEQ ID NO: 347          moltype = AA   length = 8
FEATURE                 Location/Qualifiers
source                  1..8
                        mol_type = protein
                        organism = synthetic construct
                        note = Description of Artificial Sequence: Synthetic peptide
SITE                    1
                        note = carboxy-fluorescein-L-lysine
SEQUENCE: 347
KWNAGSKF                                                                            8

SEQ ID NO: 348          moltype = AA   length = 8
FEATURE                 Location/Qualifiers
source                  1..8
                        mol_type = protein
                        organism = synthetic construct
                        note = Description of Artificial Sequence: Synthetic peptide
SITE                    2
                        note = carboxy-fluorescein-L-lysine
SEQUENCE: 348
SKHLLGFY                                                                            8

SEQ ID NO: 349          moltype = AA   length = 8
FEATURE                 Location/Qualifiers
source                  1..8
                        mol_type = protein
                        organism = synthetic construct
                        note = Description of Artificial Sequence: Synthetic peptide
SITE                    1
                        note = carboxy-fluorescein-L-lysine
SEQUENCE: 349
KSHLLGFY                                                                            8

SEQ ID NO: 350          moltype = AA   length = 8
FEATURE                 Location/Qualifiers
source                  1..8
                        mol_type = protein
                        organism = synthetic construct
                        note = Description of Artificial Sequence: Synthetic peptide
SITE                    2
                        note = carboxy-fluorescein-L-lysine
SITE                    8
                        note = Norleucine
SEQUENCE: 350
KKQEKQTX                                                                            8

SEQ ID NO: 351          moltype = AA   length = 8
FEATURE                 Location/Qualifiers
source                  1..8
                        mol_type = protein
                        organism = synthetic construct
```

```
                        note = Description of Artificial Sequence: Synthetic peptide
SITE                    1
                        note = carboxy-fluorescein-L-lysine
SITE                    8
                        note = Norleucine
SEQUENCE: 351
KKQEKQTX                                                                    8

SEQ ID NO: 352          moltype = AA   length = 8
FEATURE                 Location/Qualifiers
source                  1..8
                        mol_type = protein
                        organism = synthetic construct
                        note = Description of Artificial Sequence: Synthetic peptide
SITE                    2
                        note = carboxy-fluorescein-L-lysine
SEQUENCE: 352
GKDPFVVS                                                                    8

SEQ ID NO: 353          moltype = AA   length = 8
FEATURE                 Location/Qualifiers
source                  1..8
                        mol_type = protein
                        organism = synthetic construct
                        note = Description of Artificial Sequence: Synthetic peptide
SITE                    1
                        note = carboxy-fluorescein-L-lysine
SEQUENCE: 353
KGDPFVVS                                                                    8

SEQ ID NO: 354          moltype = AA   length = 8
FEATURE                 Location/Qualifiers
source                  1..8
                        mol_type = protein
                        organism = synthetic construct
                        note = Description of Artificial Sequence: Synthetic peptide
SITE                    2
                        note = carboxy-fluorescein-L-lysine
SEQUENCE: 354
PKNAYNEI                                                                    8

SEQ ID NO: 355          moltype = AA   length = 8
FEATURE                 Location/Qualifiers
source                  1..8
                        mol_type = protein
                        organism = synthetic construct
                        note = Description of Artificial Sequence: Synthetic peptide
SITE                    1
                        note = carboxy-fluorescein-L-lysine
SEQUENCE: 355
KPNAYNEI                                                                    8

SEQ ID NO: 356          moltype = AA   length = 8
FEATURE                 Location/Qualifiers
source                  1..8
                        mol_type = protein
                        organism = synthetic construct
                        note = Description of Artificial Sequence: Synthetic peptide
SITE                    2
                        note = carboxy-fluorescein-L-lysine
SITE                    4
                        note = Norleucine
SEQUENCE: 356
DKVXRQSE                                                                    8

SEQ ID NO: 357          moltype = AA   length = 8
FEATURE                 Location/Qualifiers
source                  1..8
                        mol_type = protein
                        organism = synthetic construct
                        note = Description of Artificial Sequence: Synthetic peptide
SITE                    1
                        note = carboxy-fluorescein-L-lysine
SITE                    4
                        note = Norleucine
SEQUENCE: 357
KDVXRQSE                                                                    8

SEQ ID NO: 358          moltype = AA   length = 8
```

```
FEATURE                 Location/Qualifiers
source                  1..8
                        mol_type = protein
                        organism = synthetic construct
                        note = Description of Artificial Sequence: Synthetic peptide
SITE                    2
                        note = carboxy-fluorescein-L-lysine
SITE                    8
                        note = Norleucine
SEQUENCE: 358
EKYNPREX                                                                        8

SEQ ID NO: 359          moltype = AA  length = 8
FEATURE                 Location/Qualifiers
source                  1..8
                        mol_type = protein
                        organism = synthetic construct
                        note = Description of Artificial Sequence: Synthetic peptide
SITE                    1
                        note = carboxy-fluorescein-L-lysine
SITE                    8
                        note = Norleucine
SEQUENCE: 359
KEYNPREX                                                                        8

SEQ ID NO: 360          moltype = AA  length = 8
FEATURE                 Location/Qualifiers
source                  1..8
                        mol_type = protein
                        organism = synthetic construct
                        note = Description of Artificial Sequence: Synthetic peptide
SITE                    2
                        note = carboxy-fluorescein-L-lysine
SEQUENCE: 360
TKEFVHNP                                                                        8

SEQ ID NO: 361          moltype = AA  length = 8
FEATURE                 Location/Qualifiers
source                  1..8
                        mol_type = protein
                        organism = synthetic construct
                        note = Description of Artificial Sequence: Synthetic peptide
SITE                    1
                        note = carboxy-fluorescein-L-lysine
SEQUENCE: 361
KTEFVHNP                                                                        8

SEQ ID NO: 362          moltype = AA  length = 8
FEATURE                 Location/Qualifiers
source                  1..8
                        mol_type = protein
                        organism = synthetic construct
                        note = Description of Artificial Sequence: Synthetic peptide
SITE                    2
                        note = carboxy-fluorescein-L-lysine
SEQUENCE: 362
QKKRVQFL                                                                        8

SEQ ID NO: 363          moltype = AA  length = 8
FEATURE                 Location/Qualifiers
source                  1..8
                        mol_type = protein
                        organism = synthetic construct
                        note = Description of Artificial Sequence: Synthetic peptide
SITE                    1
                        note = carboxy-fluorescein-L-lysine
SEQUENCE: 363
KQKRVQFL                                                                        8

SEQ ID NO: 364          moltype = AA  length = 8
FEATURE                 Location/Qualifiers
source                  1..8
                        mol_type = protein
                        organism = synthetic construct
                        note = Description of Artificial Sequence: Synthetic peptide
SITE                    2
                        note = carboxy-fluorescein-L-lysine
SITE                    5
                        note = Norleucine
```

```
SEQUENCE: 364
YKLIXHKN                                                                    8

SEQ ID NO: 365           moltype = AA   length = 8
FEATURE                  Location/Qualifiers
source                   1..8
                         mol_type = protein
                         organism = synthetic construct
                         note = Description of Artificial Sequence: Synthetic peptide
SITE                     1
                         note = carboxy-fluorescein-L-lysine
SITE                     5
                         note = Norleucine
SEQUENCE: 365
KYLIXHKN                                                                    8

SEQ ID NO: 366           moltype = AA   length = 8
FEATURE                  Location/Qualifiers
source                   1..8
                         mol_type = protein
                         organism = synthetic construct
                         note = Description of Artificial Sequence: Synthetic peptide
SITE                     2
                         note = carboxy-fluorescein-L-lysine
SITE                     5
                         note = Norleucine
SEQUENCE: 366
FKWAXLYH                                                                    8

SEQ ID NO: 367           moltype = AA   length = 8
FEATURE                  Location/Qualifiers
source                   1..8
                         mol_type = protein
                         organism = synthetic construct
                         note = Description of Artificial Sequence: Synthetic peptide
SITE                     1
                         note = carboxy-fluorescein-L-lysine
SITE                     5
                         note = Norleucine
SEQUENCE: 367
KFWAXLYH                                                                    8

SEQ ID NO: 368           moltype = AA   length = 8
FEATURE                  Location/Qualifiers
source                   1..8
                         mol_type = protein
                         organism = synthetic construct
                         note = Description of Artificial Sequence: Synthetic peptide
SITE                     2
                         note = carboxy-fluorescein-L-lysine
SEQUENCE: 368
IKAHDIVN                                                                    8

SEQ ID NO: 369           moltype = AA   length = 8
FEATURE                  Location/Qualifiers
source                   1..8
                         mol_type = protein
                         organism = synthetic construct
                         note = Description of Artificial Sequence: Synthetic peptide
SITE                     1
                         note = carboxy-fluorescein-L-lysine
SEQUENCE: 369
KIAHDIVN                                                                    8

SEQ ID NO: 370           moltype = AA   length = 8
FEATURE                  Location/Qualifiers
source                   1..8
                         mol_type = protein
                         organism = synthetic construct
                         note = Description of Artificial Sequence: Synthetic peptide
SITE                     2
                         note = carboxy-fluorescein-L-lysine
SEQUENCE: 370
VKSVFVIE                                                                    8

SEQ ID NO: 371           moltype = AA   length = 8
FEATURE                  Location/Qualifiers
source                   1..8
                         mol_type = protein
```

```
                              organism = synthetic construct
                              note = Description of Artificial Sequence: Synthetic peptide
SITE                          1
                              note = carboxy-fluorescein-L-lysine
SEQUENCE: 371
KVSVFVIE                                                                                8

SEQ ID NO: 372                moltype = AA  length = 8
FEATURE                       Location/Qualifiers
source                        1..8
                              mol_type = protein
                              organism = synthetic construct
                              note = Description of Artificial Sequence: Synthetic peptide
SITE                          1
                              note = Norleucine
SITE                          2
                              note = carboxy-fluorescein-L-lysine
SEQUENCE: 372
XKPPSGLS                                                                                8

SEQ ID NO: 373                moltype = AA  length = 8
FEATURE                       Location/Qualifiers
source                        1..8
                              mol_type = protein
                              organism = synthetic construct
                              note = Description of Artificial Sequence: Synthetic peptide
SITE                          1
                              note = carboxy-fluorescein-L-lysine
SITE                          2
                              note = Norleucine
SEQUENCE: 373
KXPPSGLS                                                                                8

SEQ ID NO: 374                moltype = AA  length = 8
FEATURE                       Location/Qualifiers
source                        1..8
                              mol_type = protein
                              organism = synthetic construct
                              note = Description of Artificial Sequence: Synthetic peptide
SITE                          2
                              note = carboxy-fluorescein-L-lysine
SEQUENCE: 374
LKRWYGGI                                                                                8

SEQ ID NO: 375                moltype = AA  length = 8
FEATURE                       Location/Qualifiers
source                        1..8
                              mol_type = protein
                              organism = synthetic construct
                              note = Description of Artificial Sequence: Synthetic peptide
SITE                          1
                              note = carboxy-fluorescein-L-lysine
SEQUENCE: 375
KLRWYGGI                                                                                8

SEQ ID NO: 376                moltype = AA  length = 8
FEATURE                       Location/Qualifiers
source                        1..8
                              mol_type = protein
                              organism = synthetic construct
                              note = Description of Artificial Sequence: Synthetic peptide
SITE                          2
                              note = carboxy-fluorescein-L-lysine
SITE                          8
                              note = Norleucine
SEQUENCE: 376
NKQYVFFX                                                                                8

SEQ ID NO: 377                moltype = AA  length = 8
FEATURE                       Location/Qualifiers
source                        1..8
                              mol_type = protein
                              organism = synthetic construct
                              note = Description of Artificial Sequence: Synthetic peptide
SITE                          1
                              note = carboxy-fluorescein-L-lysine
SITE                          8
                              note = Norleucine
SEQUENCE: 377
```

```
KNQYVFFX                                                                              8

SEQ ID NO: 378          moltype = AA  length = 8
FEATURE                 Location/Qualifiers
source                  1..8
                        mol_type = protein
                        organism = synthetic construct
                        note = Description of Artificial Sequence: Synthetic peptide
SITE                    2
                        note = carboxy-fluorescein-L-lysine
SEQUENCE: 378
AKFAKYYK                                                                              8

SEQ ID NO: 379          moltype = AA  length = 8
FEATURE                 Location/Qualifiers
source                  1..8
                        mol_type = protein
                        organism = synthetic construct
                        note = Description of Artificial Sequence: Synthetic peptide
SITE                    1
                        note = carboxy-fluorescein-L-lysine
SEQUENCE: 379
KAFAKYYK                                                                              8

SEQ ID NO: 380          moltype = AA  length = 8
FEATURE                 Location/Qualifiers
source                  1..8
                        mol_type = protein
                        organism = synthetic construct
                        note = Description of Artificial Sequence: Synthetic peptide
SITE                    2
                        note = carboxy-fluorescein-L-lysine
SEQUENCE: 380
RKQVKHFT                                                                              8

SEQ ID NO: 381          moltype = AA  length = 8
FEATURE                 Location/Qualifiers
source                  1..8
                        mol_type = protein
                        organism = synthetic construct
                        note = Description of Artificial Sequence: Synthetic peptide
SITE                    1
                        note = carboxy-fluorescein-L-lysine
SEQUENCE: 381
KRQVKHFT                                                                              8

SEQ ID NO: 382          moltype =     length =
SEQUENCE: 382
000

SEQ ID NO: 383          moltype = AA  length = 9
FEATURE                 Location/Qualifiers
source                  1..9
                        mol_type = protein
                        organism = synthetic construct
                        note = Description of Artificial Sequence: Synthetic peptide
SITE                    1
                        note = D-Lysine
SITE                    2
                        note = D-Proline
SITE                    3
                        note = D-Isoleucine
SITE                    4
                        note = D-Leucine
SITE                    5
                        note = D-Phenylalanine
SITE                    6
                        note = D-Phenylalanine
SITE                    7
                        note = D-Arginine
SITE                    8
                        note = D-Leucine
SITE                    9
                        note = D-Lysine
SEQUENCE: 383
KPILFFRLK                                                                             9

SEQ ID NO: 384          moltype =     length =
SEQUENCE: 384
```

-continued

000

SEQ ID NO: 385    moltype =    length =
SEQUENCE: 385
000

SEQ ID NO: 386    moltype =    length =
SEQUENCE: 386
000

SEQ ID NO: 387    moltype =    length =
SEQUENCE: 387
000

SEQ ID NO: 388    moltype =    length =
SEQUENCE: 388
000

SEQ ID NO: 389    moltype =    length =
SEQUENCE: 389
000

SEQ ID NO: 390    moltype =    length =
SEQUENCE: 390
000

SEQ ID NO: 391    moltype =    length =
SEQUENCE: 391
000

SEQ ID NO: 392    moltype =    length =
SEQUENCE: 392
000

SEQ ID NO: 393    moltype =    length =
SEQUENCE: 393
000

SEQ ID NO: 394    moltype =    length =
SEQUENCE: 394
000

SEQ ID NO: 395    moltype =    length =
SEQUENCE: 395
000

SEQ ID NO: 396    moltype =    length =
SEQUENCE: 396
000

SEQ ID NO: 397    moltype =    length =
SEQUENCE: 397
000

SEQ ID NO: 398    moltype =    length =
SEQUENCE: 398
000

SEQ ID NO: 399    moltype =    length =
SEQUENCE: 399
000

SEQ ID NO: 400    moltype =    length =
SEQUENCE: 400
000

SEQ ID NO: 401    moltype =    length =
SEQUENCE: 401
000

SEQ ID NO: 402    moltype =    length =
SEQUENCE: 402
000

SEQ ID NO: 403    moltype =    length =
SEQUENCE: 403
000

SEQ ID NO: 404    moltype =    length =

```
SEQUENCE: 404
000

SEQ ID NO: 405          moltype =    length =
SEQUENCE: 405
000

SEQ ID NO: 406          moltype = AA   length = 4
FEATURE                 Location/Qualifiers
source                  1..4
                        mol_type = protein
                        organism = synthetic construct
                        note = Description of Artificial Sequence: Synthetic peptide
SEQUENCE: 406
LRGG                                                                          4

SEQ ID NO: 407          moltype = AA   length = 5
FEATURE                 Location/Qualifiers
source                  1..5
                        mol_type = protein
                        organism = synthetic construct
                        note = Description of Artificial Sequence: Synthetic peptide
SEQUENCE: 407
RLRGG                                                                         5

SEQ ID NO: 408          moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 408
RELNGGAPI                                                                     9

SEQ ID NO: 409          moltype = AA   length = 11
FEATURE                 Location/Qualifiers
source                  1..11
                        mol_type = protein
                        organism = synthetic construct
                        note = Description of Artificial Sequence: Synthetic peptide
SEQUENCE: 409
TSAVLQSGFR K                                                                 11

SEQ ID NO: 410          moltype = AA   length = 11
FEATURE                 Location/Qualifiers
source                  1..11
                        mol_type = protein
                        organism = synthetic construct
                        note = Description of Artificial Sequence: Synthetic peptide
SEQUENCE: 410
SGVTFQGKFK K                                                                 11

SEQ ID NO: 411          moltype = AA   length = 4
FEATURE                 Location/Qualifiers
source                  1..4
                        mol_type = protein
                        organism = synthetic construct
                        note = Description of Artificial Sequence: Synthetic peptide
SEQUENCE: 411
AAFA                                                                          4

SEQ ID NO: 412          moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 412
HGDQMAQKS                                                                     9

SEQ ID NO: 413          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 413
GPLGMR                                                                        6
```

| | | |
|---|---|---|
| SEQ ID NO: 414<br>FEATURE<br>source<br><br><br><br>SITE<br><br>SEQUENCE: 414<br>FFLAQAFRSK | moltype = AA   length = 10<br>Location/Qualifiers<br>1..10<br>mol_type = protein<br>organism = synthetic construct<br>note = Description of Artificial Sequence: Synthetic peptide<br>7<br>note = L-homophenylalanine<br> | <br><br><br><br><br><br><br><br><br>10 |
| SEQ ID NO: 415<br>FEATURE<br>source<br><br><br><br>SEQUENCE: 415<br>AHAVSRIRIY LLPAK | moltype = AA   length = 15<br>Location/Qualifiers<br>1..15<br>mol_type = protein<br>organism = synthetic construct<br>note = Description of Artificial Sequence: Synthetic peptide<br> | <br><br><br><br><br><br><br>15 |
| SEQ ID NO: 416<br>FEATURE<br>source<br><br><br><br>SEQUENCE: 416<br>PLALWAR | moltype = AA   length = 7<br>Location/Qualifiers<br>1..7<br>mol_type = protein<br>organism = synthetic construct<br>note = Description of Artificial Sequence: Synthetic peptide<br> | <br><br><br><br><br><br><br>7 |
| SEQ ID NO: 417<br>FEATURE<br>source<br><br><br><br>SITE<br><br>SEQUENCE: 417<br>PLACWAR | moltype = AA   length = 7<br>Location/Qualifiers<br>1..7<br>mol_type = protein<br>organism = synthetic construct<br>note = Description of Artificial Sequence: Synthetic peptide<br>4<br>note = S-para-methoxybenzyl cysteine<br> | <br><br><br><br><br><br><br><br><br>7 |
| SEQ ID NO: 418<br>FEATURE<br>source<br><br><br><br>SEQUENCE: 418<br>APRWIQD | moltype = AA   length = 7<br>Location/Qualifiers<br>1..7<br>mol_type = protein<br>organism = synthetic construct<br>note = Description of Artificial Sequence: Synthetic peptide<br> | <br><br><br><br><br><br><br>7 |
| SEQ ID NO: 419<br>FEATURE<br>source<br><br><br><br>SEQUENCE: 419<br>LREQQRLKS | moltype = AA   length = 9<br>Location/Qualifiers<br>1..9<br>mol_type = protein<br>organism = synthetic construct<br>note = Description of Artificial Sequence: Synthetic peptide<br> | <br><br><br><br><br><br><br>9 |
| SEQ ID NO: 420<br>FEATURE<br>source<br><br><br><br>SEQUENCE: 420<br>EFPIYVFLPA KK | moltype = AA   length = 12<br>Location/Qualifiers<br>1..12<br>mol_type = protein<br>organism = synthetic construct<br>note = Description of Artificial Sequence: Synthetic peptide<br> | <br><br><br><br><br><br><br>12 |
| SEQ ID NO: 421<br>FEATURE<br>source<br><br><br><br>SEQUENCE: 421<br>GAANLVRGG | moltype = AA   length = 9<br>Location/Qualifiers<br>1..9<br>mol_type = protein<br>organism = synthetic construct<br>note = Description of Artificial Sequence: Synthetic peptide<br> | <br><br><br><br><br><br><br>9 |
| SEQ ID NO: 422<br>FEATURE<br>source | moltype = AA   length = 8<br>Location/Qualifiers<br>1..8 | |

| | |
|---|---|
| | mol_type = protein<br>organism = synthetic construct<br>note = Description of Artificial Sequence: Synthetic peptide |
| SEQUENCE: 422<br>GYAELRMG | 8 |
| SEQ ID NO: 423<br>FEATURE<br>source | moltype = AA length = 9<br>Location/Qualifiers<br>1..9<br>mol_type = protein<br>organism = synthetic construct<br>note = Description of Artificial Sequence: Synthetic peptide |
| SEQUENCE: 423<br>AAGAMFLEA | 9 |
| SEQ ID NO: 424<br>FEATURE<br>source | moltype = AA length = 13<br>Location/Qualifiers<br>1..13<br>mol_type = protein<br>organism = synthetic construct<br>note = Description of Artificial Sequence: Synthetic peptide |
| SEQUENCE: 424<br>LGGSGQRGRK ALE | 13 |
| SEQ ID NO: 425<br>FEATURE<br>source | moltype = AA length = 13<br>Location/Qualifiers<br>1..13<br>mol_type = protein<br>organism = synthetic construct<br>note = Description of Artificial Sequence: Synthetic peptide |
| SEQUENCE: 425<br>LGGSGHYGRS GLE | 13 |
| SEQ ID NO: 426<br>FEATURE<br>source | moltype = AA length = 4<br>Location/Qualifiers<br>1..4<br>mol_type = protein<br>organism = synthetic construct<br>note = Description of Artificial Sequence: Synthetic peptide |
| SEQUENCE: 426<br>YGRS | 4 |
| SEQ ID NO: 427<br>FEATURE<br>source | moltype = AA length = 5<br>Location/Qualifiers<br>1..5<br>mol_type = protein<br>organism = synthetic construct<br>note = Description of Artificial Sequence: Synthetic peptide |
| SEQUENCE: 427<br>FRGRK | 5 |
| SEQ ID NO: 428<br>FEATURE<br>source | moltype = AA length = 8<br>Location/Qualifiers<br>1..8<br>mol_type = protein<br>organism = synthetic construct<br>note = Description of Artificial Sequence: Synthetic peptide |
| SEQUENCE: 428<br>DRRKKLTQ | 8 |
| SEQ ID NO: 429<br>FEATURE<br>source | moltype = AA length = 6<br>Location/Qualifiers<br>1..6<br>mol_type = protein<br>organism = synthetic construct<br>note = Description of Artificial Sequence: Synthetic peptide |
| SEQUENCE: 429<br>HPGGPQ | 6 |
| SEQ ID NO: 430<br>FEATURE<br>source | moltype = AA length = 7<br>Location/Qualifiers<br>1..7<br>mol_type = protein<br>organism = synthetic construct<br>note = Description of Artificial Sequence: Synthetic peptide |
| SEQUENCE: 430<br>KLRFSKQ | 7 |
| SEQ ID NO: 431 | moltype = AA length = 8 |

```
FEATURE                 Location/Qualifiers
source                  1..8
                        mol_type = protein
                        organism = synthetic construct
                        note = Description of Artificial Sequence: Synthetic peptide
SEQUENCE: 431
AIKFFSAQ                                                                          8

SEQ ID NO: 432          moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 432
AIKFFVRQ                                                                          8

SEQ ID NO: 433          moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 433
RPPGFSAFK                                                                         9

SEQ ID NO: 434          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 434
FAPQLS                                                                            6

SEQ ID NO: 435          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 435
FAAQMA                                                                            6

SEQ ID NO: 436          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 436
GMPANQ                                                                            6

SEQ ID NO: 437          moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 437
LSGRSDNH                                                                          8

SEQ ID NO: 438          moltype = AA  length = 10
FEATURE                 Location/Qualifiers
source                  1..10
                        mol_type = protein
                        organism = synthetic construct
                        note = Description of Artificial Sequence: Synthetic peptide
SEQUENCE: 438
MAALITRPDF                                                                       10

SEQ ID NO: 439          moltype = AA  length = 10
FEATURE                 Location/Qualifiers
source                  1..10
                        mol_type = protein
                        organism = synthetic construct
                        note = Description of Artificial Sequence: Synthetic peptide
SEQUENCE: 439
MAAAITRPRF                                                                       10
```

```
SEQ ID NO: 440          moltype = AA  length = 10
FEATURE                 Location/Qualifiers
source                  1..10
                        mol_type = protein
                        organism = synthetic construct
                        note = Description of Artificial Sequence: Synthetic peptide
SEQUENCE: 440
MAALIVRPDL                                                              10

SEQ ID NO: 441          moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 441
TSGPNQEQE                                                                9

SEQ ID NO: 442          moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 442
TAGPNQEQE                                                                9

SEQ ID NO: 443          moltype = AA  length = 7
FEATURE                 Location/Qualifiers
source                  1..7
                        mol_type = protein
                        organism = synthetic construct
                        note = Description of Artificial Sequence: Synthetic peptide
SEQUENCE: 443
GPGPNQA                                                                  7

SEQ ID NO: 444          moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 444
ASGPAGPA                                                                 8

SEQ ID NO: 445          moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 445
ERGETGPSG                                                                9

SEQ ID NO: 446          moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 446
VSQELGQR                                                                 8

SEQ ID NO: 447          moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 447
TGPPGYPTG                                                                9

SEQ ID NO: 448          moltype = AA  length = 7
FEATURE                 Location/Qualifiers
source                  1..7
                        mol_type = protein
                        organism = synthetic construct
                        note = Description of Artificial Sequence: Synthetic peptide
```

```
SEQUENCE: 448
TRLPVYQ                                                                                  7

SEQ ID NO: 449             moltype = AA  length = 8
FEATURE                    Location/Qualifiers
source                     1..8
                           mol_type = protein
                           organism = synthetic construct
                           note = Description of Artificial Sequence: Synthetic peptide
SEQUENCE: 449
RQARVVGG                                                                                 8

SEQ ID NO: 450             moltype = AA  length = 8
FEATURE                    Location/Qualifiers
source                     1..8
                           mol_type = protein
                           organism = synthetic construct
                           note = Description of Artificial Sequence: Synthetic peptide
SEQUENCE: 450
RQRRVVGG                                                                                 8

SEQ ID NO: 451             moltype = AA  length = 8
FEATURE                    Location/Qualifiers
source                     1..8
                           mol_type = protein
                           organism = synthetic construct
                           note = Description of Artificial Sequence: Synthetic peptide
SEQUENCE: 451
RQARAVGG                                                                                 8

SEQ ID NO: 452             moltype = AA  length = 8
FEATURE                    Location/Qualifiers
source                     1..8
                           mol_type = protein
                           organism = synthetic construct
                           note = Description of Artificial Sequence: Synthetic peptide
SEQUENCE: 452
RKRRGSRG                                                                                 8

SEQ ID NO: 453             moltype = AA  length = 8
FEATURE                    Location/Qualifiers
source                     1..8
                           mol_type = protein
                           organism = synthetic construct
                           note = Description of Artificial Sequence: Synthetic peptide
SEQUENCE: 453
KQSRKFVP                                                                                 8

SEQ ID NO: 454             moltype = AA  length = 5
FEATURE                    Location/Qualifiers
source                     1..5
                           mol_type = protein
                           organism = synthetic construct
                           note = Description of Artificial Sequence: Synthetic peptide
SEQUENCE: 454
VTGRS                                                                                    5

SEQ ID NO: 455             moltype = AA  length = 6
FEATURE                    Location/Qualifiers
source                     1..6
                           mol_type = protein
                           organism = synthetic construct
                           note = Description of Artificial Sequence: Synthetic peptide
SEQUENCE: 455
LKSRVK                                                                                   6

SEQ ID NO: 456             moltype = AA  length = 10
FEATURE                    Location/Qualifiers
source                     1..10
                           mol_type = protein
                           organism = synthetic construct
                           note = Description of Artificial Sequence: Synthetic peptide
SEQUENCE: 456
GIGAVLKVLT                                                                              10

SEQ ID NO: 457             moltype = AA  length = 10
FEATURE                    Location/Qualifiers
source                     1..10
                           mol_type = protein
```

```
                        organism = synthetic construct
                        note = Description of Artificial Sequence: Synthetic peptide
SEQUENCE: 457
GLPALISWIK                                                              10

SEQ ID NO: 458          moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 458
SEVNLDAEF                                                               9

SEQ ID NO: 459          moltype = AA   length = 13
FEATURE                 Location/Qualifiers
source                  1..13
                        mol_type = protein
                        organism = synthetic construct
                        note = Description of Artificial Sequence: Synthetic peptide
SEQUENCE: 459
EEKPICFFRL GKE                                                          13

SEQ ID NO: 460          moltype = AA   length = 13
FEATURE                 Location/Qualifiers
source                  1..13
                        mol_type = protein
                        organism = synthetic construct
                        note = Description of Artificial Sequence: Synthetic peptide
SEQUENCE: 460
EEKPILFFRL GKE                                                          13

SEQ ID NO: 461          moltype = AA   length = 8
FEATURE                 Location/Qualifiers
source                  1..8
                        mol_type = protein
                        organism = synthetic construct
                        note = Description of Artificial Sequence: Synthetic peptide
SEQUENCE: 461
APSSVIAA                                                                8

SEQ ID NO: 462          moltype = AA   length = 8
FEATURE                 Location/Qualifiers
source                  1..8
                        mol_type = protein
                        organism = synthetic construct
                        note = Description of Artificial Sequence: Synthetic peptide
SEQUENCE: 462
KKAKRNAL                                                                8

SEQ ID NO: 463          moltype = AA   length = 10
FEATURE                 Location/Qualifiers
source                  1..10
                        mol_type = protein
                        organism = synthetic construct
                        note = Description of Artificial Sequence: Synthetic peptide
SEQUENCE: 463
WTNTSANYNL                                                              10

SEQ ID NO: 464          moltype = AA   length = 4
FEATURE                 Location/Qualifiers
source                  1..4
                        mol_type = protein
                        organism = synthetic construct
                        note = Description of Artificial Sequence: Synthetic peptide
SEQUENCE: 464
RVRR                                                                    4

SEQ ID NO: 465          moltype = AA   length = 5
FEATURE                 Location/Qualifiers
source                  1..5
                        mol_type = protein
                        organism = synthetic construct
                        note = Description of Artificial Sequence: Synthetic peptide
SEQUENCE: 465
ERTKR                                                                   5

SEQ ID NO: 466          moltype = AA   length = 12
FEATURE                 Location/Qualifiers
```

|  |  |  |
|---|---|---|
| source | 1..12<br>mol_type = protein<br>organism = synthetic construct<br>note = Description of Artificial Sequence: Synthetic peptide | |
| SEQUENCE: 466<br>RYQIKPLKST DE | | 12 |
| SEQ ID NO: 467<br>FEATURE<br>source | moltype = AA  length = 11<br>Location/Qualifiers<br>1..11<br>mol_type = protein<br>organism = synthetic construct<br>note = Description of Artificial Sequence: Synthetic peptide | |
| SITE | 8<br>note = L-homophenylalanine | |
| SEQUENCE: 467<br>WELRHQAFRS K | | 11 |
| SEQ ID NO: 468<br>FEATURE<br>source | moltype = AA  length = 12<br>Location/Qualifiers<br>1..12<br>mol_type = protein<br>organism = synthetic construct<br>note = Description of Artificial Sequence: Synthetic peptide | |
| SITE | 6<br>note = L- Methyl cysteine | |
| SEQUENCE: 468<br>SGAFKCLKDG AG | | 12 |
| SEQ ID NO: 469<br>FEATURE<br>source | moltype = AA  length = 6<br>Location/Qualifiers<br>1..6<br>mol_type = protein<br>organism = synthetic construct<br>note = Description of Artificial Sequence: Synthetic peptide | |
| SEQUENCE: 469<br>YVADGW | | 6 |
| SEQ ID NO: 470<br>FEATURE<br>source | moltype = AA  length = 6<br>Location/Qualifiers<br>1..6<br>mol_type = protein<br>organism = synthetic construct<br>note = Description of Artificial Sequence: Synthetic peptide | |
| SEQUENCE: 470<br>WEHDGW | | 6 |
| SEQ ID NO: 471<br>FEATURE<br>source | moltype = AA  length = 7<br>Location/Qualifiers<br>1..7<br>mol_type = protein<br>organism = synthetic construct<br>note = Description of Artificial Sequence: Synthetic peptide | |
| SEQUENCE: 471<br>YVADAPV | | 7 |
| SEQ ID NO: 472<br>FEATURE<br>source | moltype = AA  length = 7<br>Location/Qualifiers<br>1..7<br>mol_type = protein<br>organism = synthetic construct<br>note = Description of Artificial Sequence: Synthetic peptide | |
| SEQUENCE: 472<br>RPPGFSA | | 7 |
| SEQ ID NO: 473<br>FEATURE<br>source | moltype = AA  length = 7<br>Location/Qualifiers<br>1..7<br>mol_type = protein<br>organism = synthetic construct<br>note = Description of Artificial Sequence: Synthetic peptide | |
| SEQUENCE: 473<br>GSPAFLA | | 7 |
| SEQ ID NO: 474<br>FEATURE<br>source | moltype = AA  length = 7<br>Location/Qualifiers<br>1..7<br>mol_type = protein<br>organism = synthetic construct | |

-continued

```
                       note = Description of Artificial Sequence: Synthetic peptide
SEQUENCE: 474
AGFSLPA                                                                       7

SEQ ID NO: 475         moltype = AA  length = 10
FEATURE                Location/Qualifiers
source                 1..10
                       mol_type = protein
                       organism = synthetic construct
                       note = Description of Artificial Sequence: Synthetic peptide
SEQUENCE: 475
RWHTVGLRWE                                                                   10

SEQ ID NO: 476         moltype =   length =
SEQUENCE: 476
000

SEQ ID NO: 477         moltype = AA  length = 10
FEATURE                Location/Qualifiers
source                 1..10
                       mol_type = protein
                       organism = synthetic construct
                       note = Description of Artificial Sequence: Synthetic peptide
SEQUENCE: 477
RWPPMGLPWE                                                                   10

SEQ ID NO: 478         moltype = AA  length = 6
FEATURE                Location/Qualifiers
source                 1..6
                       mol_type = protein
                       organism = synthetic construct
                       note = Description of Artificial Sequence: Synthetic peptide
SEQUENCE: 478
RPKPVE                                                                        6

SEQ ID NO: 479         moltype = AA  length = 4
FEATURE                Location/Qualifiers
source                 1..4
                       mol_type = protein
                       organism = synthetic construct
                       note = Description of Artificial Sequence: Synthetic peptide
SEQUENCE: 479
IETD                                                                          4

SEQ ID NO: 480         moltype = AA  length = 7
FEATURE                Location/Qualifiers
source                 1..7
                       mol_type = protein
                       organism = synthetic construct
                       note = Description of Artificial Sequence: Synthetic peptide
SEQUENCE: 480
VGPDFGR                                                                       7

SEQ ID NO: 481         moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 481
GIEFDSGGC                                                                     9

SEQ ID NO: 482         moltype = AA  length = 7
FEATURE                Location/Qualifiers
source                 1..7
                       mol_type = protein
                       organism = synthetic construct
                       note = Description of Artificial Sequence: Synthetic peptide
SEQUENCE: 482
GDFLRRV                                                                       7

SEQ ID NO: 483         moltype =   length =
SEQUENCE: 483
000

SEQ ID NO: 484         moltype = AA  length = 10
FEATURE                Location/Qualifiers
source                 1..10
                       mol_type = protein
```

```
                         organism = synthetic construct
                         note = Description of Artificial Sequence: Synthetic peptide
SEQUENCE: 484
YATWSMIAAH                                                                10

SEQ ID NO: 485           moltype = AA   length = 10
FEATURE                  Location/Qualifiers
source                   1..10
                         mol_type = protein
                         organism = synthetic construct
                         note = Description of Artificial Sequence: Synthetic peptide
SEQUENCE: 485
VIMWRLTVGT                                                                10

SEQ ID NO: 486           moltype = AA   length = 10
FEATURE                  Location/Qualifiers
source                   1..10
                         mol_type = protein
                         organism = synthetic construct
                         note = Description of Artificial Sequence: Synthetic peptide
SEQUENCE: 486
RRVLALQQEL                                                                10

SEQ ID NO: 487           moltype = AA   length = 10
FEATURE                  Location/Qualifiers
source                   1..10
                         mol_type = protein
                         organism = synthetic construct
                         note = Description of Artificial Sequence: Synthetic peptide
SEQUENCE: 487
LATWPLSGLW                                                                10

SEQ ID NO: 488           moltype = AA   length = 10
FEATURE                  Location/Qualifiers
source                   1..10
                         mol_type = protein
                         organism = synthetic construct
                         note = Description of Artificial Sequence: Synthetic peptide
SEQUENCE: 488
NTPNWLVNAV                                                                10

SEQ ID NO: 489           moltype = AA   length = 13
FEATURE                  Location/Qualifiers
source                   1..13
                         mol_type = protein
                         organism = synthetic construct
                         note = Description of Artificial Sequence: Synthetic peptide
SEQUENCE: 489
SPLAQAVRSS SRK                                                            13

SEQ ID NO: 490           moltype = AA   length = 10
FEATURE                  Location/Qualifiers
source                   1..10
                         mol_type = protein
                         organism = synthetic construct
                         note = Description of Artificial Sequence: Synthetic peptide
SEQUENCE: 490
QMPGRLSMAF                                                                10

SEQ ID NO: 491           moltype = AA   length = 5
FEATURE                  Location/Qualifiers
source                   1..5
                         mol_type = protein
                         organism = synthetic construct
                         note = Description of Artificial Sequence: Synthetic peptide
SEQUENCE: 491
PLGLR                                                                     5

SEQ ID NO: 492           moltype = AA   length = 10
FEATURE                  Location/Qualifiers
source                   1..10
                         mol_type = protein
                         organism = synthetic construct
                         note = Description of Artificial Sequence: Synthetic peptide
SEQUENCE: 492
QRANSIRVTW                                                                10

SEQ ID NO: 493           moltype = AA   length = 5
FEATURE                  Location/Qualifiers
```

```
source              1..5
                    mol_type = protein
                    organism = synthetic construct
                    note = Description of Artificial Sequence: Synthetic peptide
SEQUENCE: 493
PLAVR                                                                         5

SEQ ID NO: 494      moltype = AA  length = 10
FEATURE             Location/Qualifiers
source              1..10
                    mol_type = protein
                    organism = synthetic construct
                    note = Description of Artificial Sequence: Synthetic peptide
SEQUENCE: 494
LLAVPAANTV                                                                   10

SEQ ID NO: 495      moltype = AA  length = 8
FEATURE             Location/Qualifiers
source              1..8
                    mol_type = protein
                    organism = synthetic construct
                    note = Description of Artificial Sequence: Synthetic peptide
SEQUENCE: 495
GPQGLRGQ                                                                      8

SEQ ID NO: 496      moltype = AA  length = 10
FEATURE             Location/Qualifiers
source              1..10
                    mol_type = protein
                    organism = synthetic construct
                    note = Description of Artificial Sequence: Synthetic peptide
SEQUENCE: 496
RTGLYLYNST                                                                   10

SEQ ID NO: 497      moltype = AA  length = 14
FEATURE             Location/Qualifiers
source              1..14
                    mol_type = protein
                    organism = synthetic construct
                    note = Description of Artificial Sequence: Synthetic peptide
SEQUENCE: 497
RKKLTQSKFV GGAE                                                              14

SEQ ID NO: 498      moltype = AA  length = 4
FEATURE             Location/Qualifiers
source              1..4
                    mol_type = protein
                    organism = synthetic construct
                    note = Description of Artificial Sequence: Synthetic peptide
SEQUENCE: 498
KHYR                                                                          4

SEQ ID NO: 499      moltype =     length =
SEQUENCE: 499
000

SEQ ID NO: 500      moltype = AA  length = 7
FEATURE             Location/Qualifiers
source              1..7
                    mol_type = protein
                    organism = synthetic construct
                    note = Description of Artificial Sequence: Synthetic peptide
SEQUENCE: 500
PRPFNYL                                                                       7

SEQ ID NO: 501      moltype = AA  length = 7
FEATURE             Location/Qualifiers
source              1..7
                    mol_type = protein
                    organism = synthetic construct
                    note = Description of Artificial Sequence: Synthetic peptide
SEQUENCE: 501
APFEMSA                                                                       7

SEQ ID NO: 502      moltype = AA  length = 7
FEATURE             Location/Qualifiers
source              1..7
                    mol_type = protein
                    organism = synthetic construct
```

```
SEQUENCE: 502
APFEFSA                                                               7

SEQ ID NO: 503          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 503
PLGFRV                                                                6

SEQ ID NO: 504          moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 504
RPLALWRS                                                              8

SEQ ID NO: 505          moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 505
RPLALEESQ                                                             9

SEQ ID NO: 506          moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 506
RPLALWRSQ                                                             9

SEQ ID NO: 507          moltype = AA  length = 11
FEATURE                 Location/Qualifiers
source                  1..11
                        mol_type = protein
                        organism = synthetic construct
                        note = Description of Artificial Sequence: Synthetic peptide
SEQUENCE: 507
RNALAVERTA S                                                         11

SEQ ID NO: 508          moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 508
RPKPQQFW                                                              8

SEQ ID NO: 509          moltype = AA  length = 10
FEATURE                 Location/Qualifiers
source                  1..10
                        mol_type = protein
                        organism = synthetic construct
                        note = Description of Artificial Sequence: Synthetic peptide
SEQUENCE: 509
SGSNPYKYTA                                                           10

SEQ ID NO: 510          moltype = AA  length = 10
FEATURE                 Location/Qualifiers
source                  1..10
                        mol_type = protein
                        organism = synthetic construct
                        note = Description of Artificial Sequence: Synthetic peptide
SEQUENCE: 510
SGSNPYGYTA                                                           10

SEQ ID NO: 511          moltype = AA  length = 10
FEATURE                 Location/Qualifiers
source                  1..10
```

```
                         mol_type = protein
                         organism = synthetic construct
                         note = Description of Artificial Sequence: Synthetic peptide
SEQUENCE: 511
SGTLSELHTA                                                              10

SEQ ID NO: 512           moltype = AA  length = 10
FEATURE                  Location/Qualifiers
source                   1..10
                         mol_type = protein
                         organism = synthetic construct
                         note = Description of Artificial Sequence: Synthetic peptide
SEQUENCE: 512
SGTISHLHTA                                                              10

SEQ ID NO: 513           moltype = AA  length = 13
FEATURE                  Location/Qualifiers
source                   1..13
                         mol_type = protein
                         organism = synthetic construct
                         note = Description of Artificial Sequence: Synthetic peptide
SITE                     3
                         note = L-Ornithine
SITE                     8
                         note = L-homophenylalanine
SEQUENCE: 513
SGXRSHPFTL YTA                                                          13

SEQ ID NO: 514           moltype = AA  length = 13
FEATURE                  Location/Qualifiers
source                   1..13
                         mol_type = protein
                         organism = synthetic construct
                         note = Description of Artificial Sequence: Synthetic peptide
SITE                     3
                         note = L-Ornithine
SITE                     8
                         note = L-homophenylalanine
SEQUENCE: 514
SGXRSHGFFL YTA                                                          13

SEQ ID NO: 515           moltype = AA  length = 10
FEATURE                  Location/Qualifiers
source                   1..10
                         mol_type = protein
                         organism = synthetic construct
                         note = Description of Artificial Sequence: Synthetic peptide
SEQUENCE: 515
SGESLAYYTA                                                              10

SEQ ID NO: 516           moltype = AA  length = 10
FEATURE                  Location/Qualifiers
source                   1..10
                         mol_type = protein
                         organism = synthetic construct
                         note = Description of Artificial Sequence: Synthetic peptide
SEQUENCE: 516
SGHMHAALTA                                                              10

SEQ ID NO: 517           moltype = AA  length = 8
FEATURE                  Location/Qualifiers
source                   1..8
                         mol_type = protein
                         organism = synthetic construct
                         note = Description of Artificial Sequence: Synthetic peptide
SITE                     5
                         note = D-isoleucine
SEQUENCE: 517
ILSRIVGG                                                                8

SEQ ID NO: 518           moltype = AA  length = 8
FEATURE                  Location/Qualifiers
source                   1..8
                         mol_type = protein
                         organism = synthetic construct
                         note = Description of Artificial Sequence: Synthetic peptide
SITE                     4
                         note = D-arginine
SITE                     5
```

```
                    note = D-isoleucine
SITE                6
                    note = D-valine
SEQUENCE: 518
ILSRIVGG                                                                    8

SEQ ID NO: 519      moltype = AA  length = 8
FEATURE             Location/Qualifiers
source              1..8
                    mol_type = protein
                    organism = synthetic construct
                    note = Description of Artificial Sequence: Synthetic peptide
SEQUENCE: 519
RQRRALEK                                                                    8

SEQ ID NO: 520      moltype = AA  length = 8
FEATURE             Location/Qualifiers
source              1..8
                    mol_type = protein
                    organism = synthetic construct
                    note = Description of Artificial Sequence: Synthetic peptide
SEQUENCE: 520
KPISLISS                                                                    8

SEQ ID NO: 521      moltype = AA  length = 8
FEATURE             Location/Qualifiers
source              1..8
                    mol_type = protein
                    organism = synthetic construct
                    note = Description of Artificial Sequence: Synthetic peptide
SEQUENCE: 521
QKGRYKQE                                                                    8

SEQ ID NO: 522      moltype = AA  length = 8
FEATURE             Location/Qualifiers
source              1..8
                    mol_type = protein
                    organism = synthetic construct
                    note = Description of Artificial Sequence: Synthetic peptide
SEQUENCE: 522
GPLGLRSW                                                                    8

SEQ ID NO: 523      moltype = AA  length = 8
FEATURE             Location/Qualifiers
source              1..8
                    mol_type = protein
                    organism = synthetic construct
                    note = Description of Artificial Sequence: Synthetic peptide
SEQUENCE: 523
GPLGVRGK                                                                    8

SEQ ID NO: 524      moltype = AA  length = 7
FEATURE             Location/Qualifiers
source              1..7
                    mol_type = protein
                    organism = synthetic construct
                    note = Description of Artificial Sequence: Synthetic peptide
SITE                2
                    note = D-Phenylalanine
SEQUENCE: 524
GFPRSGG                                                                     7

SEQ ID NO: 525      moltype =     length =
SEQUENCE: 525
000

SEQ ID NO: 526      moltype =     length =
SEQUENCE: 526
000

SEQ ID NO: 527      moltype =     length =
SEQUENCE: 527
000

SEQ ID NO: 528      moltype =     length =
SEQUENCE: 528
000

SEQ ID NO: 529      moltype =     length =
```

-continued

| | | |
|---|---|---|
| SEQUENCE: 529 000 | | |
| SEQ ID NO: 530 SEQUENCE: 530 000 | moltype = | length = |
| SEQ ID NO: 531 SEQUENCE: 531 000 | moltype = | length = |
| SEQ ID NO: 532 SEQUENCE: 532 000 | moltype = | length = |
| SEQ ID NO: 533 SEQUENCE: 533 000 | moltype = | length = |
| SEQ ID NO: 534 SEQUENCE: 534 000 | moltype = | length = |
| SEQ ID NO: 535 SEQUENCE: 535 000 | moltype = | length = |
| SEQ ID NO: 536 SEQUENCE: 536 000 | moltype = | length = |
| SEQ ID NO: 537 SEQUENCE: 537 000 | moltype = | length = |
| SEQ ID NO: 538 SEQUENCE: 538 000 | moltype = | length = |
| SEQ ID NO: 539 SEQUENCE: 539 000 | moltype = | length = |
| SEQ ID NO: 540 SEQUENCE: 540 000 | moltype = | length = |
| SEQ ID NO: 541 SEQUENCE: 541 000 | moltype = | length = |
| SEQ ID NO: 542 SEQUENCE: 542 000 | moltype = | length = |
| SEQ ID NO: 543 SEQUENCE: 543 000 | moltype = | length = |
| SEQ ID NO: 544 SEQUENCE: 544 000 | moltype = | length = |
| SEQ ID NO: 545 SEQUENCE: 545 000 | moltype = | length = |
| SEQ ID NO: 546 SEQUENCE: 546 000 | moltype = | length = |
| SEQ ID NO: 547 SEQUENCE: 547 000 | moltype = | length = |
| SEQ ID NO: 548 SEQUENCE: 548 000 | moltype = | length = |

```
SEQ ID NO: 549          moltype =    length =
SEQUENCE: 549
000

SEQ ID NO: 550          moltype =    length =
SEQUENCE: 550
000

SEQ ID NO: 551          moltype = AA   length = 4
FEATURE                 Location/Qualifiers
source                  1..4
                        mol_type = protein
                        organism = synthetic construct
                        note = Description of Artificial Sequence: Synthetic peptide
SEQUENCE: 551
WEHD                                                                     4

SEQ ID NO: 552          moltype =    length =
SEQUENCE: 552
000

SEQ ID NO: 553          moltype =    length =
SEQUENCE: 553
000

SEQ ID NO: 554          moltype =    length =
SEQUENCE: 554
000

SEQ ID NO: 555          moltype = AA   length = 4
FEATURE                 Location/Qualifiers
source                  1..4
                        mol_type = protein
                        organism = synthetic construct
                        note = Description of Artificial Sequence: Synthetic peptide
SEQUENCE: 555
AAPM                                                                     4

SEQ ID NO: 556          moltype = AA   length = 4
FEATURE                 Location/Qualifiers
source                  1..4
                        mol_type = protein
                        organism = synthetic construct
                        note = Description of Artificial Sequence: Synthetic peptide
SEQUENCE: 556
AEPF                                                                     4

SEQ ID NO: 557          moltype =    length =
SEQUENCE: 557
000

SEQ ID NO: 558          moltype =    length =
SEQUENCE: 558
000

SEQ ID NO: 559          moltype =    length =
SEQUENCE: 559
000

SEQ ID NO: 560          moltype =    length =
SEQUENCE: 560
000

SEQ ID NO: 561          moltype =    length =
SEQUENCE: 561
000

SEQ ID NO: 562          moltype =    length =
SEQUENCE: 562
000

SEQ ID NO: 563          moltype =    length =
SEQUENCE: 563
000

SEQ ID NO: 564          moltype =    length =
SEQUENCE: 564
000
```

```
SEQ ID NO: 565              moltype =    length =
SEQUENCE: 565
000

SEQ ID NO: 566              moltype =    length =
SEQUENCE: 566
000

SEQ ID NO: 567              moltype = AA   length = 4
FEATURE                     Location/Qualifiers
source                      1..4
                            mol_type = protein
                            organism = synthetic construct
                            note = Description of Artificial Sequence: Synthetic peptide
SEQUENCE: 567
AAPV                                                                        4

SEQ ID NO: 568              moltype =    length =
SEQUENCE: 568
000

SEQ ID NO: 569              moltype =    length =
SEQUENCE: 569
000

SEQ ID NO: 570              moltype = AA   length = 5
FEATURE                     Location/Qualifiers
source                      1..5
                            mol_type = protein
                            organism = synthetic construct
                            note = Description of Artificial Sequence: Synthetic peptide
SEQUENCE: 570
GPLGP                                                                       5

SEQ ID NO: 571              moltype = AA   length = 5
FEATURE                     Location/Qualifiers
source                      1..5
                            mol_type = protein
                            organism = synthetic construct
                            note = Description of Artificial Sequence: Synthetic peptide
SEQUENCE: 571
KQKER                                                                       5

SEQ ID NO: 572              moltype = AA   length = 4
FEATURE                     Location/Qualifiers
source                      1..4
                            mol_type = protein
                            organism = synthetic construct
                            note = Description of Artificial Sequence: Synthetic peptide
SEQUENCE: 572
RVRR                                                                        4

SEQ ID NO: 573              moltype = AA   length = 4
FEATURE                     Location/Qualifiers
source                      1..4
                            mol_type = protein
                            organism = synthetic construct
                            note = Description of Artificial Sequence: Synthetic peptide
SEQUENCE: 573
IEGR                                                                        4

SEQ ID NO: 574              moltype =    length =
SEQUENCE: 574
000

SEQ ID NO: 575              moltype = AA   length = 4
FEATURE                     Location/Qualifiers
source                      1..4
                            mol_type = protein
                            organism = synthetic construct
                            note = Description of Artificial Sequence: Synthetic peptide
SEQUENCE: 575
AAPV                                                                        4

SEQ ID NO: 576              moltype = AA   length = 8
FEATURE                     Location/Qualifiers
source                      1..8
                            mol_type = protein
                            organism = synthetic construct
```

```
SEQUENCE: 576
RPFHLLVY                                                                     8

SEQ ID NO: 577         moltype = AA  length = 7
FEATURE                Location/Qualifiers
source                 1..7
                       mol_type = protein
                       organism = synthetic construct
                       note = Description of Artificial Sequence: Synthetic peptide
SITE                   1
                       note = amino-n-butyric acid
SITE                   4
                       note = guamidine-L-phenylalanine
SEQUENCE: 577
XWSFTVF                                                                      7

SEQ ID NO: 578         moltype = AA  length = 6
FEATURE                Location/Qualifiers
source                 1..6
                       mol_type = protein
                       organism = synthetic construct
                       note = Description of Artificial Sequence: Synthetic peptide
SEQUENCE: 578
HSSKLQ                                                                       6

SEQ ID NO: 579         moltype =    length =
SEQUENCE: 579
000

SEQ ID NO: 580         moltype = AA  length = 8
FEATURE                Location/Qualifiers
source                 1..8
                       mol_type = protein
                       organism = synthetic construct
                       note = Description of Artificial Sequence: Synthetic peptide
SITE                   7
                       note = dinitrobenzylation of lysine
SITE                   8
                       note = Hydroxy leucine
SEQUENCE: 580
DRENSPKL                                                                     8

SEQ ID NO: 581         moltype = AA  length = 10
FEATURE                Location/Qualifiers
source                 1..10
                       mol_type = protein
                       organism = synthetic construct
                       note = Description of Artificial Sequence: Synthetic peptide
SITE                   1
                       note = D-Lysine
SITE                   2
                       note = D-Lysine
SITE                   10
                       note = dinitrobenzylation of hydroxy lysine
SEQUENCE: 581
KKDRENSPLK                                                                  10

SEQ ID NO: 582         moltype = AA  length = 8
FEATURE                Location/Qualifiers
source                 1..8
                       mol_type = protein
                       organism = synthetic construct
                       note = Description of Artificial Sequence: Synthetic peptide
SITE                   7
                       note = dinitrobenzylation of lysine
SITE                   8
                       note = Hydroxy Glutamine
SEQUENCE: 582
NAGSKFKQ                                                                     8

SEQ ID NO: 583         moltype = AA  length = 8
FEATURE                Location/Qualifiers
source                 1..8
                       mol_type = protein
                       organism = synthetic construct
                       note = Description of Artificial Sequence: Synthetic peptide
SITE                   8
                       note = dinitrobenzylation of hydroxy lysine
```

```
SEQUENCE: 583
NAGSKFQK                                                                         8

SEQ ID NO: 584           moltype = AA  length = 8
FEATURE                  Location/Qualifiers
source                   1..8
                         mol_type = protein
                         organism = synthetic construct
                         note = Description of Artificial Sequence: Synthetic peptide
SITE                     7
                         note = dinitrobenzylation of lysine
SITE                     8
                         note = Hydroxy Valine
SEQUENCE: 584
HLLGFYKV                                                                         8

SEQ ID NO: 585           moltype = AA  length = 8
FEATURE                  Location/Qualifiers
source                   1..8
                         mol_type = protein
                         organism = synthetic construct
                         note = Description of Artificial Sequence: Synthetic peptide
SITE                     8
                         note = dinitrobenzylation of hydroxy lysine
SEQUENCE: 585
HLLGFYVK                                                                         8

SEQ ID NO: 586           moltype = AA  length = 8
FEATURE                  Location/Qualifiers
source                   1..8
                         mol_type = protein
                         organism = synthetic construct
                         note = Description of Artificial Sequence: Synthetic peptide
SITE                     6
                         note = Norleucine
SITE                     7
                         note = dinitrobenzylation of lysine
SITE                     8
                         note = Hydroxy Norleucine
SEQUENCE: 586
QEKQTXKX                                                                         8

SEQ ID NO: 587           moltype = AA  length = 8
FEATURE                  Location/Qualifiers
source                   1..8
                         mol_type = protein
                         organism = synthetic construct
                         note = Description of Artificial Sequence: Synthetic peptide
SITE                     6
                         note = Norleucine
SITE                     7
                         note = Norleucine
SITE                     8
                         note = dinitrobenzylation of hydroxy lysine
SEQUENCE: 587
QEKQTXXK                                                                         8

SEQ ID NO: 588           moltype = AA  length = 8
FEATURE                  Location/Qualifiers
source                   1..8
                         mol_type = protein
                         organism = synthetic construct
                         note = Description of Artificial Sequence: Synthetic peptide
SITE                     7
                         note = dinitrobenzylation of lysine
SITE                     8
                         note = Hydroxy Tryptophan
SEQUENCE: 588
DPFVVSKW                                                                         8

SEQ ID NO: 589           moltype = AA  length = 8
FEATURE                  Location/Qualifiers
source                   1..8
                         mol_type = protein
                         organism = synthetic construct
                         note = Description of Artificial Sequence: Synthetic peptide
SITE                     8
                         note = dinitrobenzylation of hydroxy lysine
SEQUENCE: 589
```

```
DPFVVSWK                                                             8

SEQ ID NO: 590          moltype = AA  length = 8
FEATURE                 Location/Qualifiers
source                  1..8
                        mol_type = protein
                        organism = synthetic construct
                        note = Description of Artificial Sequence: Synthetic peptide
SITE                    7
                        note = dinitrobenzylation of lysine
SITE                    8
                        note = Hydroxy Arginine
SEQUENCE: 590
NAYNEIKR                                                             8

SEQ ID NO: 591          moltype = AA  length = 8
FEATURE                 Location/Qualifiers
source                  1..8
                        mol_type = protein
                        organism = synthetic construct
                        note = Description of Artificial Sequence: Synthetic peptide
SITE                    8
                        note = dinitrobenzylation of hydroxy lysine
SEQUENCE: 591
NAYNEIRK                                                             8

SEQ ID NO: 592          moltype = AA  length = 8
FEATURE                 Location/Qualifiers
source                  1..8
                        mol_type = protein
                        organism = synthetic construct
                        note = Description of Artificial Sequence: Synthetic peptide
SITE                    2
                        note = Norleucine
SITE                    7
                        note = dinitrobenzylation of lysine
SITE                    8
                        note = Hydroxy Asparagine
SEQUENCE: 592
VXRQSEKN                                                             8

SEQ ID NO: 593          moltype = AA  length = 8
FEATURE                 Location/Qualifiers
source                  1..8
                        mol_type = protein
                        organism = synthetic construct
                        note = Description of Artificial Sequence: Synthetic peptide
SITE                    2
                        note = Norleucine
SITE                    8
                        note = dinitrobenzylation of hydroxy lysine
SEQUENCE: 593
VXRQSENK                                                             8

SEQ ID NO: 594          moltype = AA  length = 8
FEATURE                 Location/Qualifiers
source                  1..8
                        mol_type = protein
                        organism = synthetic construct
                        note = Description of Artificial Sequence: Synthetic peptide
SITE                    6
                        note = Norleucine
SITE                    7
                        note = dinitrobenzylation of lysine
SITE                    8
                        note = Hydroxy Isoleucine
SEQUENCE: 594
YNPREXKI                                                             8

SEQ ID NO: 595          moltype = AA  length = 8
FEATURE                 Location/Qualifiers
source                  1..8
                        mol_type = protein
                        organism = synthetic construct
                        note = Description of Artificial Sequence: Synthetic peptide
SITE                    6
                        note = Norleucine
SITE                    8
                        note = dinitrobenzylation of hydroxy lysine
```

```
SEQUENCE: 595
YNPREXIK                                                                    8

SEQ ID NO: 596          moltype = AA  length = 8
FEATURE                 Location/Qualifiers
source                  1..8
                        mol_type = protein
                        organism = synthetic construct
                        note = Description of Artificial Sequence: Synthetic peptide
SITE                    7
                        note = dinitrobenzylation of lysine
SITE                    8
                        note = Hydroxy Lysine
SEQUENCE: 596
EFVHNPKK                                                                    8

SEQ ID NO: 597          moltype = AA  length = 8
FEATURE                 Location/Qualifiers
source                  1..8
                        mol_type = protein
                        organism = synthetic construct
                        note = Description of Artificial Sequence: Synthetic peptide
SITE                    8
                        note = dinitrobenzylation of hydroxy lysine
SEQUENCE: 597
EFVHNPKK                                                                    8

SEQ ID NO: 598          moltype = AA  length = 8
FEATURE                 Location/Qualifiers
source                  1..8
                        mol_type = protein
                        organism = synthetic construct
                        note = Description of Artificial Sequence: Synthetic peptide
SITE                    7
                        note = dinitrobenzylation of lysine
SITE                    8
                        note = Hydroxy Histidine
SEQUENCE: 598
KRVQFLKH                                                                    8

SEQ ID NO: 599          moltype = AA  length = 8
FEATURE                 Location/Qualifiers
source                  1..8
                        mol_type = protein
                        organism = synthetic construct
                        note = Description of Artificial Sequence: Synthetic peptide
SITE                    8
                        note = dinitrobenzylation of hydroxy lysine
SEQUENCE: 599
KRVQFLHK                                                                    8

SEQ ID NO: 600          moltype = AA  length = 8
FEATURE                 Location/Qualifiers
source                  1..8
                        mol_type = protein
                        organism = synthetic construct
                        note = Description of Artificial Sequence: Synthetic peptide
SITE                    3
                        note = Norleucine
SITE                    7
                        note = dinitrobenzylation of lysine
SITE                    8
                        note = Hydroxy Glycine
SEQUENCE: 600
LIXHKNKG                                                                    8

SEQ ID NO: 601          moltype = AA  length = 8
FEATURE                 Location/Qualifiers
source                  1..8
                        mol_type = protein
                        organism = synthetic construct
                        note = Description of Artificial Sequence: Synthetic peptide
SITE                    3
                        note = Norleucine
SITE                    8
                        note = dinitrobenzylation of hydroxy lysine
SEQUENCE: 601
LIXHKNGK                                                                    8
```

```
SEQ ID NO: 602          moltype = AA  length = 8
FEATURE                 Location/Qualifiers
source                  1..8
                        mol_type = protein
                        organism = synthetic construct
                        note = Description of Artificial Sequence: Synthetic peptide
SITE                    3
                        note = Norleucine
SITE                    7
                        note = dinitrobenzylation of lysine
SITE                    8
                        note = Hydroxy Serine
SEQUENCE: 602
WAXLYHKS                                                                         8

SEQ ID NO: 603          moltype = AA  length = 8
FEATURE                 Location/Qualifiers
source                  1..8
                        mol_type = protein
                        organism = synthetic construct
                        note = Description of Artificial Sequence: Synthetic peptide
SITE                    3
                        note = Norleucine
SITE                    8
                        note = dinitrobenzylation of hydroxy lysine
SEQUENCE: 603
WAXLYHSK                                                                         8

SEQ ID NO: 604          moltype = AA  length = 8
FEATURE                 Location/Qualifiers
source                  1..8
                        mol_type = protein
                        organism = synthetic construct
                        note = Description of Artificial Sequence: Synthetic peptide
SITE                    7
                        note = dinitrobenzylation of lysine
SITE                    8
                        note = Hydroxy Tyrosine
SEQUENCE: 604
AHDIVNKY                                                                         8

SEQ ID NO: 605          moltype = AA  length = 8
FEATURE                 Location/Qualifiers
source                  1..8
                        mol_type = protein
                        organism = synthetic construct
                        note = Description of Artificial Sequence: Synthetic peptide
SITE                    8
                        note = dinitrobenzylation of hydroxy lysine
SEQUENCE: 605
AHDIVNYK                                                                         8

SEQ ID NO: 606          moltype = AA  length = 8
FEATURE                 Location/Qualifiers
source                  1..8
                        mol_type = protein
                        organism = synthetic construct
                        note = Description of Artificial Sequence: Synthetic peptide
SITE                    7
                        note = dinitrobenzylation of lysine
SITE                    8
                        note = Hydroxy Proline
SEQUENCE: 606
SVFVIEKP                                                                         8

SEQ ID NO: 607          moltype = AA  length = 8
FEATURE                 Location/Qualifiers
source                  1..8
                        mol_type = protein
                        organism = synthetic construct
                        note = Description of Artificial Sequence: Synthetic peptide
SITE                    8
                        note = dinitrobenzylation of hydroxy lysine
SEQUENCE: 607
SVFVIEPK                                                                         8

SEQ ID NO: 608          moltype = AA  length = 8
FEATURE                 Location/Qualifiers
source                  1..8
```

```
                        mol_type = protein
                        organism = synthetic construct
                        note = Description of Artificial Sequence: Synthetic peptide
SITE                    7
                        note = dinitrobenzylation of lysine
SITE                    8
                        note = Hydroxy Glutamic Acid
SEQUENCE: 608
PPSGLSKE                                                                        8

SEQ ID NO: 609          moltype = AA   length = 8
FEATURE                 Location/Qualifiers
source                  1..8
                        mol_type = protein
                        organism = synthetic construct
                        note = Description of Artificial Sequence: Synthetic peptide
SITE                    8
                        note = dinitrobenzylation of hydroxy lysine
SEQUENCE: 609
PPSGLSEK                                                                        8

SEQ ID NO: 610          moltype = AA   length = 8
FEATURE                 Location/Qualifiers
source                  1..8
                        mol_type = protein
                        organism = synthetic construct
                        note = Description of Artificial Sequence: Synthetic peptide
SITE                    7
                        note = dinitrobenzylation of lysine
SITE                    8
                        note = Hydroxy Phenylalanine
SEQUENCE: 610
RWYGGIKF                                                                        8

SEQ ID NO: 611          moltype = AA   length = 8
FEATURE                 Location/Qualifiers
source                  1..8
                        mol_type = protein
                        organism = synthetic construct
                        note = Description of Artificial Sequence: Synthetic peptide
SITE                    8
                        note = dinitrobenzylation of hydroxy lysine
SEQUENCE: 611
RWYGGIFK                                                                        8

SEQ ID NO: 612          moltype = AA   length = 8
FEATURE                 Location/Qualifiers
source                  1..8
                        mol_type = protein
                        organism = synthetic construct
                        note = Description of Artificial Sequence: Synthetic peptide
SITE                    6
                        note = Norleucine
SITE                    7
                        note = dinitrobenzylation of lysine
SITE                    8
                        note = Hydroxy Aspartic Acid
SEQUENCE: 612
QYVFFXKD                                                                        8

SEQ ID NO: 613          moltype = AA   length = 8
FEATURE                 Location/Qualifiers
source                  1..8
                        mol_type = protein
                        organism = synthetic construct
                        note = Description of Artificial Sequence: Synthetic peptide
SITE                    6
                        note = Norleucine
SITE                    8
                        note = dinitrobenzylation of hydroxy lysine
SEQUENCE: 613
QYVFFXDK                                                                        8

SEQ ID NO: 614          moltype = AA   length = 8
FEATURE                 Location/Qualifiers
source                  1..8
                        mol_type = protein
                        organism = synthetic construct
                        note = Description of Artificial Sequence: Synthetic peptide
```

```
SITE                      7
                          note = dinitrobenzylation of lysine
SITE                      8
                          note = Hydroxy Threonine
SEQUENCE: 614
FAKYYKKT                                                                      8

SEQ ID NO: 615            moltype = AA   length = 8
FEATURE                   Location/Qualifiers
source                    1..8
                          mol_type = protein
                          organism = synthetic construct
                          note = Description of Artificial Sequence: Synthetic peptide
SITE                      8
                          note = dinitrobenzylation of hydroxy lysine
SEQUENCE: 615
FAKYYKTK                                                                      8

SEQ ID NO: 616            moltype = AA   length = 8
FEATURE                   Location/Qualifiers
source                    1..8
                          mol_type = protein
                          organism = synthetic construct
                          note = Description of Artificial Sequence: Synthetic peptide
SITE                      7
                          note = dinitrobenzylation of lysine
SITE                      8
                          note = Hydroxy Alanine
SEQUENCE: 616
QVKHFTKA                                                                      8

SEQ ID NO: 617            moltype = AA   length = 8
FEATURE                   Location/Qualifiers
source                    1..8
                          mol_type = protein
                          organism = synthetic construct
                          note = Description of Artificial Sequence: Synthetic peptide
SITE                      8
                          note = dinitrobenzylation of hydroxy lysine
SEQUENCE: 617
QVKHFTAK                                                                      8

SEQ ID NO: 618            moltype = AA   length = 7
FEATURE                   Location/Qualifiers
source                    1..7
                          mol_type = protein
                          organism = synthetic construct
                          note = Description of Artificial Sequence: Synthetic peptide
SITE                      7
                          note = dinitrobenzylation of hydroxy lysine
SEQUENCE: 618
YVADAPK                                                                       7

SEQ ID NO: 619            moltype = AA   length = 7
FEATURE                   Location/Qualifiers
source                    1..7
                          mol_type = protein
                          organism = synthetic construct
                          note = Description of Artificial Sequence: Synthetic peptide
SEQUENCE: 619
KGISSQY                                                                       7

SEQ ID NO: 620            moltype = AA   length = 7
FEATURE                   Location/Qualifiers
source                    1..7
                          mol_type = protein
                          organism = synthetic construct
                          note = Description of Artificial Sequence: Synthetic peptide
SEQUENCE: 620
ALPALQN                                                                       7

SEQ ID NO: 621            moltype = AA   length = 5
FEATURE                   Location/Qualifiers
source                    1..5
                          mol_type = protein
                          organism = synthetic construct
                          note = Description of Artificial Sequence: Synthetic peptide
SEQUENCE: 621
HRFRG                                                                         5
```

```
SEQ ID NO: 622            moltype = AA   length = 9
FEATURE                   Location/Qualifiers
source                    1..9
                          mol_type = protein
                          organism = synthetic construct
                          note = Description of Artificial Sequence: Synthetic peptide
SEQUENCE: 622
APEEIMDQQ                                                              9

SEQ ID NO: 623            moltype = AA   length = 7
FEATURE                   Location/Qualifiers
source                    1..7
                          mol_type = protein
                          organism = synthetic construct
                          note = Description of Artificial Sequence: Synthetic peptide
SEQUENCE: 623
SRKSQQY                                                                7

SEQ ID NO: 624            moltype = AA   length = 7
FEATURE                   Location/Qualifiers
source                    1..7
                          mol_type = protein
                          organism = synthetic construct
                          note = Description of Artificial Sequence: Synthetic peptide
SEQUENCE: 624
SKGRSLI                                                                7

SEQ ID NO: 625            moltype = AA   length = 7
FEATURE                   Location/Qualifiers
source                    1..7
                          mol_type = protein
                          organism = synthetic construct
                          note = Description of Artificial Sequence: Synthetic peptide
SEQUENCE: 625
FAQSIPK                                                                7

SEQ ID NO: 626            moltype = AA   length = 7
FEATURE                   Location/Qualifiers
source                    1..7
                          mol_type = protein
                          organism = synthetic construct
                          note = Description of Artificial Sequence: Synthetic peptide
SEQUENCE: 626
RQRRVVG                                                                7

SEQ ID NO: 627            moltype = AA   length = 8
FEATURE                   Location/Qualifiers
source                    1..8
                          mol_type = protein
                          organism = synthetic construct
                          note = Description of Artificial Sequence: Synthetic peptide
SEQUENCE: 627
ERGETGPS                                                               8

SEQ ID NO: 628            moltype = AA   length = 6
FEATURE                   Location/Qualifiers
source                    1..6
                          mol_type = protein
                          organism = synthetic construct
                          note = Description of Artificial Sequence: Synthetic peptide
SEQUENCE: 628
ASGPSS                                                                 6

SEQ ID NO: 629            moltype = AA   length = 4
FEATURE                   Location/Qualifiers
source                    1..4
                          mol_type = protein
                          organism = synthetic construct
                          note = Description of Artificial Sequence: Synthetic peptide
SEQUENCE: 629
YRFR                                                                   4

SEQ ID NO: 630            moltype = AA   length = 7
FEATURE                   Location/Qualifiers
source                    1..7
                          mol_type = protein
                          organism = synthetic construct
                          note = Description of Artificial Sequence: Synthetic peptide
```

```
SEQUENCE: 630
KLFSSKQ                                                                    7

SEQ ID NO: 631          moltype = AA  length = 5
FEATURE                 Location/Qualifiers
source                  1..5
                        mol_type = protein
                        organism = synthetic construct
                        note = Description of Artificial Sequence: Synthetic peptide
SEQUENCE: 631
IVPRG                                                                      5

SEQ ID NO: 632          moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 632
IRRSSYFK                                                                   8

SEQ ID NO: 633          moltype = AA  length = 6
FEATURE                 Location/Qualifiers
source                  1..6
                        mol_type = protein
                        organism = synthetic construct
                        note = Description of Artificial Sequence: Synthetic peptide
SITE                    1
                        note = benzyl-L-histidine
SITE                    2
                        note = L-tert-leucine
SITE                    6
                        note = L-methionine-sulfoxide
SEQUENCE: 633
HXPSDM                                                                     6

SEQ ID NO: 634          moltype = AA  length = 8
FEATURE                 Location/Qualifiers
source                  1..8
                        mol_type = protein
                        organism = synthetic construct
                        note = Description of Artificial Sequence: Synthetic peptide
SITE                    1
                        note = norvaline
SITE                    4
                        note = L-octahydroindole-2-carboxylic acid
SEQUENCE: 634
XIEXDFGR                                                                   8

SEQ ID NO: 635          moltype =     length =
SEQUENCE: 635
000

SEQ ID NO: 636          moltype =     length =
SEQUENCE: 636
000

SEQ ID NO: 637          moltype =     length =
SEQUENCE: 637
000

SEQ ID NO: 638          moltype = AA  length = 6
FEATURE                 Location/Qualifiers
source                  1..6
                        mol_type = protein
                        organism = synthetic construct
                        note = Description of Artificial Sequence: Synthetic peptide
SITE                    1
                        note = benzyl-L-histidine
SITE                    2
                        note = L-tert-leucine
SITE                    6
                        note = L-methionine-sulfoxide
SEQUENCE: 638
HXPSDM                                                                     6

SEQ ID NO: 639          moltype =     length =
SEQUENCE: 639
000
```

```
SEQ ID NO: 640         moltype =    length =
SEQUENCE: 640
000

SEQ ID NO: 641         moltype =    length =
SEQUENCE: 641
000

SEQ ID NO: 642         moltype =    length =
SEQUENCE: 642
000

SEQ ID NO: 643         moltype =    length =
SEQUENCE: 643
000

SEQ ID NO: 644         moltype = AA   length = 6
FEATURE                Location/Qualifiers
source                 1..6
                       mol_type = protein
                       organism = synthetic construct
                       note = Description of Artificial Sequence: Synthetic peptide
SITE                   4
                       note = guamidine-L-phenylalanine
SEQUENCE: 644
FVTFSW                                                                  6

SEQ ID NO: 645         moltype =    length =
SEQUENCE: 645
000

SEQ ID NO: 646         moltype =    length =
SEQUENCE: 646
000

SEQ ID NO: 647         moltype = AA   length = 7
FEATURE                Location/Qualifiers
source                 1..7
                       mol_type = protein
                       organism = synthetic construct
                       note = Description of Artificial Sequence: Synthetic peptide
SEQUENCE: 647
AIEPDSG                                                                 7

SEQ ID NO: 648         moltype = AA   length = 7
FEATURE                Location/Qualifiers
source                 1..7
                       mol_type = protein
                       organism = synthetic construct
                       note = Description of Artificial Sequence: Synthetic peptide
SEQUENCE: 648
AIEFDSG                                                                 7

SEQ ID NO: 649         moltype = AA   length = 7
FEATURE                Location/Qualifiers
source                 1..7
                       mol_type = protein
                       organism = synthetic construct
                       note = Description of Artificial Sequence: Synthetic peptide
SEQUENCE: 649
AAEAISD                                                                 7

SEQ ID NO: 650         moltype = AA   length = 8
FEATURE                Location/Qualifiers
source                 1..8
                       mol_type = protein
                       organism = synthetic construct
                       note = Description of Artificial Sequence: Synthetic peptide
SEQUENCE: 650
AGGAQMGA                                                                8

SEQ ID NO: 651         moltype = AA   length = 8
FEATURE                Location/Qualifiers
source                 1..8
                       mol_type = protein
                       organism = synthetic construct
                       note = Description of Artificial Sequence: Synthetic peptide
SEQUENCE: 651
```

| | |
|---|---|
| AQPDALNV | 8 |
| SEQ ID NO: 652<br>FEATURE<br>source | moltype = AA length = 8<br>Location/Qualifiers<br>1..8<br>mol_type = protein<br>organism = synthetic construct<br>note = Description of Artificial Sequence: Synthetic peptide |
| SEQUENCE: 652<br>ATDVTTTP | 8 |
| SEQ ID NO: 653<br>FEATURE<br>source | moltype = AA length = 8<br>Location/Qualifiers<br>1..8<br>mol_type = protein<br>organism = synthetic construct<br>note = Description of Artificial Sequence: Synthetic peptide |
| SEQUENCE: 653<br>DIVTVANA | 8 |
| SEQ ID NO: 654<br>FEATURE<br>source | moltype = AA length = 8<br>Location/Qualifiers<br>1..8<br>mol_type = protein<br>organism = synthetic construct<br>note = Description of Artificial Sequence: Synthetic peptide |
| SEQUENCE: 654<br>DLGLKSVP | 8 |
| SEQ ID NO: 655<br>FEATURE<br>source | moltype = AA length = 8<br>Location/Qualifiers<br>1..8<br>mol_type = protein<br>organism = synthetic construct<br>note = Description of Artificial Sequence: Synthetic peptide |
| SEQUENCE: 655<br>DVMASNKR | 8 |
| SEQ ID NO: 656<br>FEATURE<br>source | moltype = AA length = 8<br>Location/Qualifiers<br>1..8<br>mol_type = protein<br>organism = synthetic construct<br>note = Description of Artificial Sequence: Synthetic peptide |
| SEQUENCE: 656<br>ESDELNTI | 8 |
| SEQ ID NO: 657<br>FEATURE<br>source | moltype = AA length = 8<br>Location/Qualifiers<br>1..8<br>mol_type = protein<br>organism = synthetic construct<br>note = Description of Artificial Sequence: Synthetic peptide |
| SEQUENCE: 657<br>FHPLHSKI | 8 |
| SEQ ID NO: 658<br>FEATURE<br>source | moltype = AA length = 7<br>Location/Qualifiers<br>1..7<br>mol_type = protein<br>organism = synthetic construct<br>note = Description of Artificial Sequence: Synthetic peptide |
| SEQUENCE: 658<br>HARLVHV | 7 |
| SEQ ID NO: 659<br>FEATURE<br>source | moltype = AA length = 8<br>Location/Qualifiers<br>1..8<br>mol_type = protein<br>organism = synthetic construct<br>note = Description of Artificial Sequence: Synthetic peptide |
| SEQUENCE: 659<br>HIANVERV | 8 |
| SEQ ID NO: 660<br>FEATURE<br>source | moltype = AA length = 8<br>Location/Qualifiers<br>1..8<br>mol_type = protein<br>organism = synthetic construct |

```
                        note = Description of Artificial Sequence: Synthetic peptide
SEQUENCE: 660
KAAATQKK                                                                         8

SEQ ID NO: 661          moltype = AA   length = 8
FEATURE                 Location/Qualifiers
source                  1..8
                        mol_type = protein
                        organism = synthetic construct
                        note = Description of Artificial Sequence: Synthetic peptide
SEQUENCE: 661
LATASTMD                                                                         8

SEQ ID NO: 662          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 662
LGPKGQT                                                                          7

SEQ ID NO: 663          moltype = AA   length = 8
FEATURE                 Location/Qualifiers
source                  1..8
                        mol_type = protein
                        organism = synthetic construct
                        note = Description of Artificial Sequence: Synthetic peptide
SEQUENCE: 663
LSLPETGE                                                                         8

SEQ ID NO: 664          moltype = AA   length = 8
FEATURE                 Location/Qualifiers
source                  1..8
                        mol_type = protein
                        organism = synthetic construct
                        note = Description of Artificial Sequence: Synthetic peptide
SEQUENCE: 664
NLAGILKE                                                                         8

SEQ ID NO: 665          moltype = AA   length = 8
FEATURE                 Location/Qualifiers
source                  1..8
                        mol_type = protein
                        organism = synthetic construct
                        note = Description of Artificial Sequence: Synthetic peptide
SEQUENCE: 665
NPGMSEPV                                                                         8

SEQ ID NO: 666          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 666
PFGCHAK                                                                          7

SEQ ID NO: 667          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 667
PLGLRWW                                                                          7

SEQ ID NO: 668          moltype = AA   length = 8
FEATURE                 Location/Qualifiers
source                  1..8
                        mol_type = protein
                        organism = synthetic construct
                        note = Description of Artificial Sequence: Synthetic peptide
SEQUENCE: 668
QMGVMQGV                                                                         8

SEQ ID NO: 669          moltype = AA   length = 8
FEATURE                 Location/Qualifiers
source                  1..8
```

```
                            mol_type = protein
                            organism = synthetic construct
                            note = Description of Artificial Sequence: Synthetic peptide
SEQUENCE: 669
QTCKCSCK                                                              8

SEQ ID NO: 670              moltype = AA  length = 8
FEATURE                     Location/Qualifiers
source                      1..8
                            mol_type = protein
                            organism = synthetic construct
                            note = Description of Artificial Sequence: Synthetic peptide
SEQUENCE: 670
QWAGLVEK                                                              8

SEQ ID NO: 671              moltype = AA  length = 8
FEATURE                     Location/Qualifiers
source                      1..8
                            mol_type = protein
                            organism = synthetic construct
                            note = Description of Artificial Sequence: Synthetic peptide
SEQUENCE: 671
RPAVMTSP                                                              8

SEQ ID NO: 672              moltype = AA  length = 8
FEATURE                     Location/Qualifiers
source                      1..8
                            mol_type = protein
                            organism = synthetic construct
                            note = Description of Artificial Sequence: Synthetic peptide
SEQUENCE: 672
TLRELHLD                                                              8

SEQ ID NO: 673              moltype = AA  length = 8
FEATURE                     Location/Qualifiers
source                      1..8
                            mol_type = protein
                            organism = synthetic construct
                            note = Description of Artificial Sequence: Synthetic peptide
SEQUENCE: 673
TPPPSQGK                                                              8

SEQ ID NO: 674              moltype = AA  length = 8
FEATURE                     Location/Qualifiers
source                      1..8
                            mol_type = protein
                            organism = synthetic construct
                            note = Description of Artificial Sequence: Synthetic peptide
SEQUENCE: 674
TSEDLVVQ                                                              8

SEQ ID NO: 675              moltype = AA  length = 8
FEATURE                     Location/Qualifiers
source                      1..8
                            mol_type = protein
                            organism = synthetic construct
                            note = Description of Artificial Sequence: Synthetic peptide
SEQUENCE: 675
VWAAEAIS                                                              8

SEQ ID NO: 676              moltype =     length =
SEQUENCE: 676
000

SEQ ID NO: 677              moltype =     length =
SEQUENCE: 677
000

SEQ ID NO: 678              moltype = AA  length = 8
FEATURE                     Location/Qualifiers
source                      1..8
                            mol_type = protein
                            organism = synthetic construct
                            note = Description of Artificial Sequence: Synthetic probe
SITE                        8
                            note = Lysine modified with a CPQ2 quencher
SEQUENCE: 678
GSGRSGGK                                                              8
```

```
SEQ ID NO: 679          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 679
GPGPREGGK                                                                        9

SEQ ID NO: 680          moltype = AA   length = 11
FEATURE                 Location/Qualifiers
source                  1..11
                        mol_type = protein
                        organism = synthetic construct
                        note = Description of Artificial Sequence: Synthetic probe
SITE                    11
                        note = Lysine modified with a CPQ2 quencher
SEQUENCE: 680
GIEPDSGSQG K                                                                    11

SEQ ID NO: 681          moltype = AA   length = 12
FEATURE                 Location/Qualifiers
source                  1..12
                        mol_type = protein
                        organism = synthetic construct
                        note = Description of Artificial Sequence: Synthetic probe
SITE                    12
                        note = Lysine modified with a CPQ2 quencher
SEQUENCE: 681
GVVADSSMES GK                                                                   12

SEQ ID NO: 682          moltype = AA   length = 7
FEATURE                 Location/Qualifiers
source                  1..7
                        mol_type = protein
                        organism = synthetic construct
                        note = Description of Artificial Sequence: Synthetic probe
SITE                    7
                        note = Lysine modified with a CPQ2 quencher
SEQUENCE: 682
GPTSYGK                                                                          7

SEQ ID NO: 683          moltype = AA   length = 7
FEATURE                 Location/Qualifiers
source                  1..7
                        mol_type = protein
                        organism = synthetic construct
                        note = Description of Artificial Sequence: Synthetic probe
SITE                    7
                        note = Lysine modified with a CPQ2 quencher
SEQUENCE: 683
GYRFKGK                                                                          7

SEQ ID NO: 684          moltype = AA   length = 7
FEATURE                 Location/Qualifiers
source                  1..7
                        mol_type = protein
                        organism = synthetic construct
                        note = Description of Artificial Sequence: Synthetic probe
SITE                    7
                        note = Lysine modified with a CPQ2 quencher
SEQUENCE: 684
GKVPLGK                                                                          7

SEQ ID NO: 685          moltype = AA   length = 8
FEATURE                 Location/Qualifiers
source                  1..8
                        mol_type = protein
                        organism = synthetic construct
                        note = Description of Artificial Sequence: Synthetic probe
SITE                    8
                        note = Lysine modified with a CPQ2 quencher
SEQUENCE: 685
GVDVADGK                                                                         8

SEQ ID NO: 686          moltype = AA   length = 7
FEATURE                 Location/Qualifiers
```

```
source                  1..7
                        mol_type = protein
                        organism = synthetic construct
                        note = Description of Artificial Sequence: Synthetic probe
SITE                    7
                        note = Lysine modified with a CPQ2 quencher
SEQUENCE: 686
GLETDGK                                                                          7

SEQ ID NO: 687          moltype = AA   length = 7
FEATURE                 Location/Qualifiers
source                  1..7
                        mol_type = protein
                        organism = synthetic construct
                        note = Description of Artificial Sequence: Synthetic probe
SITE                    7
                        note = Lysine modified with a CPQ2 quencher
SEQUENCE: 687
GLEHDGK                                                                          7

SEQ ID NO: 688          moltype = AA   length = 7
FEATURE                 Location/Qualifiers
source                  1..7
                        mol_type = protein
                        organism = synthetic construct
                        note = Description of Artificial Sequence: Synthetic probe
SITE                    7
                        note = Lysine modified with a CPQ2 quencher
SEQUENCE: 688
GREQDGK                                                                          7

SEQ ID NO: 689          moltype = AA   length = 7
FEATURE                 Location/Qualifiers
source                  1..7
                        mol_type = protein
                        organism = synthetic construct
                        note = Description of Artificial Sequence: Synthetic probe
SITE                    7
                        note = Lysine modified with a CPQ2 quencher
SEQUENCE: 689
GDEVDGK                                                                          7

SEQ ID NO: 690          moltype = AA   length = 7
FEATURE                 Location/Qualifiers
source                  1..7
                        mol_type = protein
                        organism = synthetic construct
                        note = Description of Artificial Sequence: Synthetic probe
SITE                    7
                        note = Lysine modified with a CPQ2 quencher
SEQUENCE: 690
GVEIDGK                                                                          7

SEQ ID NO: 691          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 691
GVQVDGWGK                                                                        9

SEQ ID NO: 692          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 692
GYEVDGWGK                                                                        9

SEQ ID NO: 693          moltype = AA   length = 7
FEATURE                 Location/Qualifiers
source                  1..7
                        mol_type = protein
```

```
SITE              7
                  note = Lysine modified with a CPQ2 quencher
SEQUENCE: 693
GLEVDGK                                                                    7

SEQ ID NO: 694    moltype = AA  length = 7
FEATURE           Location/Qualifiers
source            1..7
                  mol_type = protein
                  organism = synthetic construct
                  note = Description of Artificial Sequence: Synthetic probe
SITE              7
                  note = Lysine modified with a CPQ2 quencher
SEQUENCE: 694
GIEVEGK                                                                    7

SEQ ID NO: 695    moltype = AA  length = 7
FEATURE           Location/Qualifiers
source            1..7
                  mol_type = protein
                  organism = synthetic construct
                  note = Description of Artificial Sequence: Synthetic probe
SITE              7
                  note = Lysine modified with a CPQ2 quencher
SEQUENCE: 695
GAAPVGK                                                                    7

SEQ ID NO: 696    moltype = AA  length = 7
FEATURE           Location/Qualifiers
source            1..7
                  mol_type = protein
                  organism = synthetic construct
                  note = Description of Artificial Sequence: Synthetic probe
SITE              7
                  note = Lysine modified with a CPQ2 quencher
SEQUENCE: 696
GFFKFGK                                                                    7

SEQ ID NO: 697    moltype = AA  length = 10
FEATURE           Location/Qualifiers
source            1..10
                  mol_type = protein
                  organism = synthetic construct
                  note = Description of Artificial Sequence: Synthetic probe
SITE              10
                  note = Lysine modified with a CPQ2 quencher
SEQUENCE: 697
GGRRGKGGGK                                                                10

SEQ ID NO: 698    moltype = AA  length = 7
FEATURE           Location/Qualifiers
source            1..7
                  mol_type = protein
                  organism = synthetic construct
                  note = Description of Artificial Sequence: Synthetic probe
SITE              7
                  note = Lysine modified with a CPQ2 quencher
SEQUENCE: 698
GVKKRGK                                                                    7

SEQ ID NO: 699    moltype = AA  length = 10
FEATURE           Location/Qualifiers
source            1..10
                  mol_type = protein
                  organism = synthetic construct
                  note = Description of Artificial Sequence: Synthetic probe
SITE              5
                  note = p-Nitro phenylalanine
SITE              10
                  note = Lysine modified with a CPQ2 quencher
SEQUENCE: 699
GFAAFFVLGK                                                                10

SEQ ID NO: 700    moltype = AA  length = 6
FEATURE           Location/Qualifiers
source            1..6
                  mol_type = protein
```

| | | |
|---|---|---|
| | organism = synthetic construct | |
| | note = Description of Artificial Sequence: Synthetic probe | |
| SITE | 6 | |
| | note = Lysine modified with a CPQ2 quencher | |
| SEQUENCE: 700 | | |
| GVVRGK | | 6 |
| | | |
| SEQ ID NO: 701 | moltype = AA   length = 8 | |
| FEATURE | Location/Qualifiers | |
| source | 1..8 | |
| | mol_type = protein | |
| | organism = synthetic construct | |
| | note = Description of Artificial Sequence: Synthetic probe | |
| SITE | 8 | |
| | note = Lysine modified with a CPQ2 quencher | |
| SEQUENCE: 701 | | |
| GKQKLRGK | | 8 |
| | | |
| SEQ ID NO: 702 | moltype = AA   length = 11 | |
| FEATURE | Location/Qualifiers | |
| source | 1..11 | |
| | mol_type = protein | |
| | organism = synthetic construct | |
| | note = Description of Artificial Sequence: Synthetic probe | |
| SITE | 11 | |
| | note = Lysine modified with a CPQ2 quencher | |
| SEQUENCE: 702 | | |
| GRPPGFSAFG K | | 11 |
| | | |
| SEQ ID NO: 703 | moltype = AA   length = 6 | |
| FEATURE | Location/Qualifiers | |
| source | 1..6 | |
| | mol_type = protein | |
| | organism = synthetic construct | |
| | note = Description of Artificial Sequence: Synthetic probe | |
| SITE | 6 | |
| | note = Lysine modified with a CPQ2 quencher | |
| SEQUENCE: 703 | | |
| GGPRGK | | 6 |
| | | |
| SEQ ID NO: 704 | moltype = AA   length = 5 | |
| FEATURE | Location/Qualifiers | |
| source | 1..5 | |
| | mol_type = protein | |
| | organism = synthetic construct | |
| | note = Description of Artificial Sequence: Synthetic probe | |
| SITE | 5 | |
| | note = Lysine modified with a CPQ2 quencher | |
| SEQUENCE: 704 | | |
| GFRGK | | 5 |
| | | |
| SEQ ID NO: 705 | moltype = AA   length = 8 | |
| FEATURE | Location/Qualifiers | |
| source | 1..8 | |
| | mol_type = protein | |
| | organism = synthetic construct | |
| | note = Description of Artificial Sequence: Synthetic probe | |
| SITE | 8 | |
| | note = Lysine modified with a CPQ2 quencher | |
| SEQUENCE: 705 | | |
| GLPLGLGK | | 8 |
| | | |
| SEQ ID NO: 706 | moltype = AA   length = 8 | |
| FEATURE | Location/Qualifiers | |
| source | 1..8 | |
| | mol_type = protein | |
| | organism = synthetic construct | |
| | note = Description of Artificial Sequence: Synthetic probe | |
| SITE | 8 | |
| | note = Lysine modified with a CPQ2 quencher | |
| SEQUENCE: 706 | | |
| GKPLGLGK | | 8 |
| | | |
| SEQ ID NO: 707 | moltype = AA   length = 9 | |
| FEATURE | Location/Qualifiers | |
| source | 1..9 | |
| | mol_type = protein | |
| | organism = synthetic construct | |
| | note = Description of Artificial Sequence: Synthetic probe | |

```
SITE                      2
                          note = gamma aminobutyric acid
SITE                      9
                          note = Lysine modified with a CPQ2 quencher
SEQUENCE: 707
GXPQGLEGK                                                                        9

SEQ ID NO: 708            moltype = AA  length = 9
FEATURE                   Location/Qualifiers
source                    1..9
                          mol_type = protein
                          organism = synthetic construct
                          note = Description of Artificial Sequence: Synthetic probe
SITE                      9
                          note = Lysine modified with a CPQ2 quencher
SEQUENCE: 708
GPKPLALGK                                                                        9

SEQ ID NO: 709            moltype = AA  length = 10
FEATURE                   Location/Qualifiers
source                    1..10
                          mol_type = protein
                          organism = synthetic construct
                          note = Description of Artificial Sequence: Synthetic probe
SITE                      10
                          note = Lysine modified with a CPQ2 quencher
SEQUENCE: 709
GGPSGIHVGK                                                                      10

SEQ ID NO: 710            moltype = AA  length = 15
FEATURE                   Location/Qualifiers
source                    1..15
                          mol_type = protein
                          organism = synthetic construct
                          note = Description of Artificial Sequence: Synthetic probe
SITE                      15
                          note = Lysine modified with a CPQ2 quencher
SEQUENCE: 710
GWAHRTTFYR RGAGK                                                                15

SEQ ID NO: 711            moltype = AA  length = 11
FEATURE                   Location/Qualifiers
source                    1..11
                          mol_type = protein
                          organism = synthetic construct
                          note = Description of Artificial Sequence: Synthetic probe
SITE                      11
                          note = Lysine modified with a CPQ2 quencher
SEQUENCE: 711
GWKLRSSKQG K                                                                    11

SEQ ID NO: 712            moltype = AA  length = 6
FEATURE                   Location/Qualifiers
source                    1..6
                          mol_type = protein
                          organism = synthetic construct
                          note = Description of Artificial Sequence: Synthetic probe
SITE                      6
                          note = Lysine modified with a CPQ2 quencher
SEQUENCE: 712
GPFRGK                                                                           6

SEQ ID NO: 713            moltype = AA  length = 8
FEATURE                   Location/Qualifiers
source                    1..8
                          mol_type = protein
                          organism = synthetic construct
                          note = Description of Artificial Sequence: Synthetic probe
SITE                      8
                          note = Lysine modified with a CPQ2 quencher
SEQUENCE: 713
GSYRIFGK                                                                         8

SEQ ID NO: 714            moltype = AA  length = 6
FEATURE                   Location/Qualifiers
source                    1..6
                          mol_type = protein
                          organism = synthetic construct
                          note = Description of Artificial Sequence: Synthetic probe
```

```
SITE                    6
                        note = Lysine modified with a CPQ2 quencher
SEQUENCE: 714
GRPYGK                                                                  6

SEQ ID NO: 715          moltype = AA  length = 11
FEATURE                 Location/Qualifiers
source                  1..11
                        mol_type = protein
                        organism = synthetic construct
                        note = Description of Artificial Sequence: Synthetic probe
SITE                    11
                        note = Lysine modified with a CPQ2 quencher
SEQUENCE: 715
GTAFRSAYGG K                                                            11

SEQ ID NO: 716          moltype = AA  length = 12
FEATURE                 Location/Qualifiers
source                  1..12
                        mol_type = protein
                        organism = synthetic construct
                        note = Description of Artificial Sequence: Synthetic probe
SITE                    12
                        note = Lysine modified with a CPQ2 quencher
SEQUENCE: 716
GWAAFRFSQA GK                                                           12

SEQ ID NO: 717          moltype = AA  length = 6
FEATURE                 Location/Qualifiers
source                  1..6
                        mol_type = protein
                        organism = synthetic construct
                        note = Description of Artificial Sequence: Synthetic probe
SITE                    6
                        note = Lysine modified with a CPQ2 quencher
SEQUENCE: 717
GVPRGK                                                                  6

SEQ ID NO: 718          moltype =     length =
SEQUENCE: 718
000

SEQ ID NO: 719          moltype = AA  length = 10
FEATURE                 Location/Qualifiers
source                  1..10
                        mol_type = protein
                        organism = synthetic construct
                        note = Description of Artificial Sequence: Synthetic probe
SITE                    10
                        note = Lysine modified with a CPQ2 quencher
SEQUENCE: 719
GKLRSSKQGK                                                              10

SEQ ID NO: 720          moltype = AA  length = 7
FEATURE                 Location/Qualifiers
source                  1..7
                        mol_type = protein
                        organism = synthetic construct
                        note = Description of Artificial Sequence: Synthetic probe
SITE                    7
                        note = Lysine modified with a CPQ2 quencher
SEQUENCE: 720
GYASRGK                                                                 7

SEQ ID NO: 721          moltype = AA  length = 13
FEATURE                 Location/Qualifiers
source                  1..13
                        mol_type = protein
                        organism = synthetic construct
                        note = Description of Artificial Sequence: Synthetic probe
SITE                    13
                        note = Lysine modified with a CPQ2 quencher
SEQUENCE: 721
GRFAQAQQQL PGK                                                          13

SEQ ID NO: 722          moltype = AA  length = 11
FEATURE                 Location/Qualifiers
source                  1..11
                        mol_type = protein
```

-continued

```
                          organism = synthetic construct
                          note = Description of Artificial Sequence: Synthetic probe
SITE                      11
                          note = Lysine modified with a CPQ2 quencher
SEQUENCE: 722
GKPAKFFRLG K                                                                    11

SEQ ID NO: 723            moltype = AA  length = 12
FEATURE                   Location/Qualifiers
source                    1..12
                          mol_type = protein
                          organism = synthetic construct
                          note = Description of Artificial Sequence: Synthetic probe
SITE                      7
                          note = L-Homophenylalanine
SITE                      12
                          note = Lysine modified with a CPQ2 quencher
SEQUENCE: 723
GPRAAAXTSP GK                                                                   12

SEQ ID NO: 724            moltype = AA  length = 13
FEATURE                   Location/Qualifiers
source                    1..13
                          mol_type = protein
                          organism = synthetic construct
                          note = Description of Artificial Sequence: Synthetic probe
SITE                      13
                          note = Lysine modified with a CPQ2 quencher
SEQUENCE: 724
GVGPQRFSGA PGK                                                                  13

SEQ ID NO: 725            moltype = AA  length = 12
FEATURE                   Location/Qualifiers
source                    1..12
                          mol_type = protein
                          organism = synthetic construct
                          note = Description of Artificial Sequence: Synthetic probe
SITE                      8
                          note = L-Homophenylalanine
SITE                      12
                          note = Lysine modified with a CPQ2 quencher
SEQUENCE: 725
GFFLAQAXRS GK                                                                   12

SEQ ID NO: 726            moltype = AA  length = 9
FEATURE                   Location/Qualifiers
source                    1..9
                          mol_type = protein
                          organism = synthetic construct
                          note = Description of Artificial Sequence: Synthetic probe
SITE                      9
                          note = Lysine modified with a CPQ2 quencher
SEQUENCE: 726
GPLAQAVGK                                                                        9

SEQ ID NO: 727            moltype = AA  length = 11
FEATURE                   Location/Qualifiers
source                    1..11
                          mol_type = protein
                          organism = synthetic construct
                          note = Description of Artificial Sequence: Synthetic probe
SITE                      11
                          note = Lysine modified with a CPQ2 quencher
SEQUENCE: 727
GRTAAVFRPG K                                                                    11

SEQ ID NO: 728            moltype = AA  length = 16
FEATURE                   Location/Qualifiers
source                    1..16
                          mol_type = protein
                          organism = synthetic construct
                          note = Description of Artificial Sequence: Synthetic probe
SITE                      16
                          note = Lysine modified with a CPQ2 quencher
SEQUENCE: 728
GDVQEFRGVT AVIRGK                                                               16

SEQ ID NO: 729            moltype = AA  length = 13
FEATURE                   Location/Qualifiers
```

```
                                  -continued source              1..13
                    mol_type = protein
                    organism = synthetic construct
                    note = Description of Artificial Sequence: Synthetic probe
SITE                13
                    note = Lysine modified with a CPQ2 quencher
SEQUENCE: 729
GTEGEARGSV IGK                                                              13

SEQ ID NO: 730      moltype = AA  length = 6
FEATURE             Location/Qualifiers
source              1..6
                    mol_type = protein
                    organism = synthetic construct
                    note = Description of Artificial Sequence: Synthetic probe
SITE                2
                    note = D-Leucine
SITE                6
                    note = Lysine modified with a CPQ2 quencher
SEQUENCE: 730
GLTRGK                                                                       6

SEQ ID NO: 731      moltype = AA  length = 10
FEATURE             Location/Qualifiers
source              1..10
                    mol_type = protein
                    organism = synthetic construct
                    note = Description of Artificial Sequence: Synthetic probe
SITE                10
                    note = Lysine modified with a CPQ2 quencher
SEQUENCE: 731
GPLFAERKGK                                                                  10

SEQ ID NO: 732      moltype = AA  length = 7
FEATURE             Location/Qualifiers
source              1..7
                    mol_type = protein
                    organism = synthetic construct
                    note = Description of Artificial Sequence: Synthetic probe
SITE                7
                    note = Lysine modified with a CPQ2 quencher
SEQUENCE: 732
GLLVYGK                                                                      7

SEQ ID NO: 733      moltype = AA  length = 11
FEATURE             Location/Qualifiers
source              1..11
                    mol_type = protein
                    organism = synthetic construct
                    note = Description of Artificial Sequence: Synthetic probe
SITE                11
                    note = Lysine modified with a CPQ2 quencher
SEQUENCE: 733
GQQKRKIVLG K                                                                11

SEQ ID NO: 734      moltype = AA  length = 11
FEATURE             Location/Qualifiers
source              1..11
                    mol_type = protein
                    organism = synthetic construct
                    note = Description of Artificial Sequence: Synthetic probe
SITE                11
                    note = Lysine modified with a CPQ2 quencher
SEQUENCE: 734
GASHLGLARG K                                                                11

SEQ ID NO: 735      moltype = AA  length = 11
FEATURE             Location/Qualifiers
source              1..11
                    mol_type = protein
                    organism = synthetic construct
                    note = Description of Artificial Sequence: Synthetic probe
SITE                11
                    note = Lysine modified with a CPQ2 quencher
SEQUENCE: 735
GLPSRSSKIG K                                                                11

SEQ ID NO: 736      moltype = AA  length = 11
FEATURE             Location/Qualifiers
```

| | |
|---|---|
| source | 1..11<br>mol_type = protein<br>organism = synthetic construct<br>note = Description of Artificial Sequence: Synthetic probe |
| SITE | 11<br>note = Lysine modified with a CPQ2 quencher |
| SEQUENCE: 736 | |
| GSTGRNGFKG K | 11 |
| SEQ ID NO: 737<br>FEATURE<br>source | moltype = AA   length = 11<br>Location/Qualifiers<br>1..11<br>mol_type = protein<br>organism = synthetic construct<br>note = Description of Artificial Sequence: Synthetic probe |
| SITE | 11<br>note = Lysine modified with a CPQ2 quencher |
| SEQUENCE: 737 | |
| GSLLRSEETG K | 11 |
| SEQ ID NO: 738<br>FEATURE<br>source | moltype = AA   length = 11<br>Location/Qualifiers<br>1..11<br>mol_type = protein<br>organism = synthetic construct<br>note = Description of Artificial Sequence: Synthetic probe |
| SITE | 11<br>note = Lysine modified with a CPQ2 quencher |
| SEQUENCE: 738 | |
| GHRGRTLEIG K | 11 |
| SEQ ID NO: 739<br>FEATURE<br>source | moltype = AA   length = 11<br>Location/Qualifiers<br>1..11<br>mol_type = protein<br>organism = synthetic construct<br>note = Description of Artificial Sequence: Synthetic probe |
| SITE | 11<br>note = Lysine modified with a CPQ2 quencher |
| SEQUENCE: 739 | |
| GYLGRSYKVG K | 11 |
| SEQ ID NO: 740<br>FEATURE<br>source | moltype = AA   length = 11<br>Location/Qualifiers<br>1..11<br>mol_type = protein<br>organism = synthetic construct<br>note = Description of Artificial Sequence: Synthetic probe |
| SITE | 11<br>note = Lysine modified with a CPQ2 quencher |
| SEQUENCE: 740 | |
| GEKQRIIGGG K | 11 |
| SEQ ID NO: 741<br>FEATURE<br>source | moltype = AA   length = 11<br>Location/Qualifiers<br>1..11<br>mol_type = protein<br>organism = synthetic construct<br>note = Description of Artificial Sequence: Synthetic probe |
| SITE | 11<br>note = Lysine modified with a CPQ2 quencher |
| SEQUENCE: 741 | |
| GQRQRIIGGG K | 11 |
| SEQ ID NO: 742<br>FEATURE<br>source | moltype = AA   length = 9<br>Location/Qualifiers<br>1..9<br>mol_type = protein<br>organism = synthetic construct<br>note = Description of Artificial Sequence: Synthetic probe |
| SITE | 9<br>note = Lysine modified with a CPQ2 quencher |
| SEQUENCE: 742 | |
| GLQRIYKGK | 9 |
| SEQ ID NO: 743<br>FEATURE<br>source | moltype = AA   length = 11<br>Location/Qualifiers<br>1..11<br>mol_type = protein |

| | |
|---|---|
| | organism = synthetic construct<br>note = Description of Artificial Sequence: Synthetic probe |
| SITE | 11<br>note = Lysine modified with a CPQ2 quencher |
| SEQUENCE: 743 | |
| GSLGRKIQIG K | 11 |
| SEQ ID NO: 744<br>FEATURE<br>source | moltype = AA  length = 16<br>Location/Qualifiers<br>1..16<br>mol_type = protein<br>organism = synthetic construct<br>note = Description of Artificial Sequence: Synthetic probe |
| SITE | 16<br>note = Lysine modified with a CPQ2 quencher |
| SEQUENCE: 744 | |
| GHAAPRSADI QIDIGK | 16 |
| SEQ ID NO: 745<br>FEATURE<br>source | moltype = AA  length = 6<br>Location/Qualifiers<br>1..6<br>mol_type = protein<br>organism = synthetic construct<br>note = Description of Artificial Sequence: Synthetic probe |
| SITE | 6<br>note = Lysine modified with a CPQ2 quencher |
| SEQUENCE: 745 | |
| GFGRGK | 6 |
| SEQ ID NO: 746<br>FEATURE<br>source | moltype = AA  length = 7<br>Location/Qualifiers<br>1..7<br>mol_type = protein<br>organism = synthetic construct<br>note = Description of Artificial Sequence: Synthetic probe |
| SITE | 7<br>note = Lysine modified with a CPQ2 quencher |
| SEQUENCE: 746 | |
| GSLGRGK | 7 |
| SEQ ID NO: 747<br>FEATURE<br>source | moltype = AA  length = 7<br>Location/Qualifiers<br>1..7<br>mol_type = protein<br>organism = synthetic construct<br>note = Description of Artificial Sequence: Synthetic probe |
| SITE | 7<br>note = Lysine modified with a CPQ2 quencher |
| SEQUENCE: 747 | |
| GGLQRGK | 7 |
| SEQ ID NO: 748<br>FEATURE<br>source | moltype = AA  length = 11<br>Location/Qualifiers<br>1..11<br>mol_type = protein<br>organism = synthetic construct<br>note = Description of Artificial Sequence: Synthetic probe |
| SITE | 11<br>note = Lysine modified with a CPQ2 quencher |
| SEQUENCE: 748 | |
| GSVARTLLVG K | 11 |
| SEQ ID NO: 749<br>FEATURE<br>source | moltype = AA  length = 8<br>Location/Qualifiers<br>1..8<br>mol_type = protein<br>organism = synthetic construct<br>note = Description of Artificial Sequence: Synthetic probe |
| SITE | 8<br>note = Lysine modified with a CPQ2 quencher |
| SEQUENCE: 749 | |
| GGRIFGGK | 8 |
| SEQ ID NO: 750<br>FEATURE<br>source | moltype = AA  length = 6<br>Location/Qualifiers<br>1..6<br>mol_type = protein<br>organism = synthetic construct<br>note = Description of Artificial Sequence: Synthetic probe |

| | | |
|---|---|---|
| SITE | 6 | |
| | note = Lysine modified with a CPQ2 quencher | |
| SEQUENCE: 750 | | |
| GAPKGK | | 6 |

| | | |
|---|---|---|
| SEQ ID NO: 751 | moltype = AA   length = 8 | |
| FEATURE | Location/Qualifiers | |
| source | 1..8 | |
| | mol_type = protein | |
| | organism = synthetic construct | |
| | note = Description of Artificial Sequence: Synthetic probe | |
| SITE | 8 | |
| | note = Lysine modified with a CPQ2 quencher | |
| SEQUENCE: 751 | | |
| GGFSPYGK | | 8 |

| | | |
|---|---|---|
| SEQ ID NO: 752 | moltype = AA   length = 11 | |
| FEATURE | Location/Qualifiers | |
| source | 1..11 | |
| | mol_type = protein | |
| | organism = synthetic construct | |
| | note = Description of Artificial Sequence: Synthetic probe | |
| SITE | 11 | |
| | note = Lysine modified with a CPQ2 quencher | |
| SEQUENCE: 752 | | |
| GWELRHAGHG K | | 11 |

| | | |
|---|---|---|
| SEQ ID NO: 753 | moltype = AA   length = 12 | |
| FEATURE | Location/Qualifiers | |
| source | 1..12 | |
| | mol_type = protein | |
| | organism = synthetic construct | |
| | note = Description of Artificial Sequence: Synthetic probe | |
| SITE | 12 | |
| | note = Lysine modified with a CPQ2 quencher | |
| SEQUENCE: 753 | | |
| GRQSRIVGGE GK | | 12 |

| | | |
|---|---|---|
| SEQ ID NO: 754 | moltype = AA   length = 11 | |
| FEATURE | Location/Qualifiers | |
| source | 1..11 | |
| | mol_type = protein | |
| | organism = synthetic construct | |
| | note = Description of Artificial Sequence: Synthetic probe | |
| SITE | 11 | |
| | note = Lysine modified with a CPQ2 quencher | |
| SEQUENCE: 754 | | |
| GEQAVYQTIG K | | 11 |

| | | |
|---|---|---|
| SEQ ID NO: 755 | moltype = AA   length = 14 | |
| FEATURE | Location/Qualifiers | |
| source | 1..14 | |
| | mol_type = protein | |
| | organism = synthetic construct | |
| | note = Description of Artificial Sequence: Synthetic probe | |
| SITE | 14 | |
| | note = Lysine modified with a CPQ2 quencher | |
| SEQUENCE: 755 | | |
| GVAYSGENTF GFGK | | 14 |

| | | |
|---|---|---|
| SEQ ID NO: 756 | moltype = AA   length = 6 | |
| FEATURE | Location/Qualifiers | |
| source | 1..6 | |
| | mol_type = protein | |
| | organism = synthetic construct | |
| | note = Description of Artificial Sequence: Synthetic probe | |
| SITE | 6 | |
| | note = Lysine modified with a CPQ2 quencher | |
| SEQUENCE: 756 | | |
| GGGRGK | | 6 |

| | | |
|---|---|---|
| SEQ ID NO: 757 | moltype = AA   length = 7 | |
| FEATURE | Location/Qualifiers | |
| source | 1..7 | |
| | mol_type = protein | |
| | organism = synthetic construct | |
| | note = Description of Artificial Sequence: Synthetic probe | |
| SITE | 7 | |
| | note = Lysine modified with a CPQ2 quencher | |

```
SEQUENCE: 757
GATADGK                                                                    7

SEQ ID NO: 758         moltype = AA  length = 11
FEATURE                Location/Qualifiers
source                 1..11
                       mol_type = protein
                       organism = synthetic construct
                       note = Description of Artificial Sequence: Synthetic probe
SITE                   11
                       note = Lysine modified with a CPQ2 quencher
SEQUENCE: 758
GRPLESNAVG K                                                              11

SEQ ID NO: 759         moltype = AA  length = 10
FEATURE                Location/Qualifiers
source                 1..10
                       mol_type = protein
                       organism = synthetic construct
                       note = Description of Artificial Sequence: Synthetic probe
SITE                   10
                       note = Lysine modified with a CPQ2 quencher
SEQUENCE: 759
GRPLGLARGK                                                                10

SEQ ID NO: 760         moltype = AA  length = 7
FEATURE                Location/Qualifiers
source                 1..7
                       mol_type = protein
                       organism = synthetic construct
                       note = Description of Artificial Sequence: Synthetic probe
SITE                   7
                       note = Lysine modified with a CPQ2 quencher
SEQUENCE: 760
GAAFFGK                                                                    7

SEQ ID NO: 761         moltype = AA  length = 10
FEATURE                Location/Qualifiers
source                 1..10
                       mol_type = protein
                       organism = synthetic construct
                       note = Description of Artificial Sequence: Synthetic probe
SITE                   10
                       note = Lysine modified with a CPQ2 quencher
SEQUENCE: 761
GRVKRGLAGK                                                                10

SEQ ID NO: 762         moltype = AA  length = 6
FEATURE                Location/Qualifiers
source                 1..6
                       mol_type = protein
                       organism = synthetic construct
                       note = Description of Artificial Sequence: Synthetic probe
SITE                   6
                       note = Lysine modified with a CPQ2 quencher
SEQUENCE: 762
GAALGK                                                                     6

SEQ ID NO: 763         moltype = AA  length = 20
FEATURE                Location/Qualifiers
source                 1..20
                       mol_type = protein
                       organism = synthetic construct
                       note = Description of Artificial Sequence: Synthetic probe
SITE                   4
                       note = D-Methionine
SITE                   5
                       note = D-Glutamic Acid
SITE                   8
                       note = D-Asparagine
SITE                   9
                       note = D-Aspartic Acid
SITE                   10
                       note = D-Asparagine
SITE                   11
                       note = D-Glutamic Acid
SITE                   12
                       note = D-Glutamic Acid
SITE                   16
```

|  |  |
|---|---|
|  | note = D-Serine |
| SITE | 18 |
|  | note = D-Arginine |
| SITE | 20 |
|  | note = Lysine modified with a CPQ2 quencher |
| SEQUENCE: 763 | |
| CGGMEGVNDN EEGFFSARGK | 20 |
| SEQ ID NO: 764 | moltype = AA   length = 10 |
| FEATURE | Location/Qualifiers |
| source | 1..10 |
|  | mol_type = protein |
|  | organism = synthetic construct |
|  | note = Description of Artificial Sequence: Synthetic probe |
| SITE | 10 |
|  | note = Lysine modified with a CPQ2 quencher |
| SEQUENCE: 764 | |
| GGPQGIWGQK | 10 |
| SEQ ID NO: 765 | moltype = AA   length = 10 |
| FEATURE | Location/Qualifiers |
| source | 1..10 |
|  | mol_type = protein |
|  | organism = synthetic construct |
|  | note = Description of Artificial Sequence: Synthetic probe |
| SITE | 10 |
|  | note = Lysine modified with a CPQ2 quencher |
| SEQUENCE: 765 | |
| GGLVPRGSGK | 10 |
| SEQ ID NO: 766 | moltype = AA   length = 9 |
| FEATURE | Location/Qualifiers |
| source | 1..9 |
|  | mol_type = protein |
|  | organism = synthetic construct |
|  | note = Description of Artificial Sequence: Synthetic probe |
| SITE | 9 |
|  | note = Lysine modified with a CPQ2 quencher |
| SEQUENCE: 766 | |
| GGPVGLIGK | 9 |
| SEQ ID NO: 767 | moltype = AA   length = 11 |
| FEATURE | Location/Qualifiers |
| source | 1..11 |
|  | mol_type = protein |
|  | organism = synthetic construct |
|  | note = Description of Artificial Sequence: Synthetic probe |
| SITE | 11 |
|  | note = Lysine modified with a CPQ2 quencher |
| SEQUENCE: 767 | |
| GGPWGIWGQG K | 11 |
| SEQ ID NO: 768 | moltype = AA   length = 11 |
| FEATURE | Location/Qualifiers |
| source | 1..11 |
|  | mol_type = protein |
|  | organism = synthetic construct |
|  | note = Description of Artificial Sequence: Synthetic probe |
| SITE | 11 |
|  | note = Lysine modified with a CPQ2 quencher |
| SEQUENCE: 768 | |
| GGPVPLSLVM K | 11 |
| SEQ ID NO: 769 | moltype = AA   length = 10 |
| FEATURE | Location/Qualifiers |
| source | 1..10 |
|  | mol_type = protein |
|  | organism = synthetic construct |
|  | note = Description of Artificial Sequence: Synthetic probe |
| SITE | 3 |
|  | note = D-Phenylalanine |
| SITE | 4 |
|  | note = piperidine carboxylic acid |
| SITE | 10 |
|  | note = Lysine modified with a CPQ2 quencher |
| SEQUENCE: 769 | |
| GGFXRSGGGK | 10 |
| SEQ ID NO: 770 | moltype = AA   length = 10 |

```
FEATURE              Location/Qualifiers
source               1..10
                     mol_type = protein
                     organism = synthetic construct
                     note = Description of Artificial Sequence: Synthetic probe
SITE                 3
                     note = D-Phenylalanine
SITE                 4
                     note = piperidine carboxylic acid
SITE                 10
                     note = Lysine modified with a CPQ2 quencher
SEQUENCE: 770
GGFXKSGGGK                                                                     10

SEQ ID NO: 771       moltype = AA   length = 9
FEATURE              Location/Qualifiers
source               1..9
                     mol_type = protein
                     organism = synthetic construct
                     note = Description of Artificial Sequence: Synthetic probe
SITE                 9
                     note = Lysine modified with a CPQ2 quencher
SEQUENCE: 771
GPLGMRGGK                                                                       9

SEQ ID NO: 772       moltype = AA   length = 9
FEATURE              Location/Qualifiers
source               1..9
                     mol_type = protein
                     organism = synthetic construct
                     note = Description of Artificial Sequence: Synthetic probe
SITE                 3
                     note = L-cyclohexylalanine
SITE                 5
                     note = L- Methyl cysteine
SITE                 9
                     note = Lysine modified with a CPQ2 quencher
SEQUENCE: 772
GPAGCHAGK                                                                       9

SEQ ID NO: 773       moltype = AA   length = 12
FEATURE              Location/Qualifiers
source               1..12
                     mol_type = protein
                     organism = synthetic construct
                     note = Description of Artificial Sequence: Synthetic probe
SITE                 12
                     note = Lysine modified with a CPQ2 quencher
SEQUENCE: 773
GRPLALWESQ GK                                                                  12

SEQ ID NO: 774       moltype = AA   length = 11
FEATURE              Location/Qualifiers
source               1..11
                     mol_type = protein
                     organism = synthetic construct
                     note = Description of Artificial Sequence: Synthetic probe
SITE                 11
                     note = Lysine modified with a CPQ2 quencher
SEQUENCE: 774
SGKGPRQITA K                                                                   11

SEQ ID NO: 775       moltype = AA   length = 11
FEATURE              Location/Qualifiers
source               1..11
                     mol_type = protein
                     organism = synthetic construct
                     note = Description of Artificial Sequence: Synthetic probe
SITE                 11
                     note = Lysine modified with a CPQ2 quencher
SEQUENCE: 775
SGPLFYSVTA K                                                                   11

SEQ ID NO: 776       moltype = AA   length = 10
FEATURE              Location/Qualifiers
source               1..10
                     mol_type = protein
                     organism = synthetic construct
                     note = Description of Artificial Sequence: Synthetic probe
```

```
SITE                    10
                        note = Lysine modified with a CPQ2 quencher
SEQUENCE: 776
SGRIFLRTAK                                                                    10

SEQ ID NO: 777          moltype = AA  length = 11
FEATURE                 Location/Qualifiers
source                  1..11
                        mol_type = protein
                        organism = synthetic construct
                        note = Description of Artificial Sequence: Synthetic probe
SITE                    11
                        note = Lysine modified with a CPQ2 quencher
SEQUENCE: 777
SGRSENIRTA K                                                                  11

SEQ ID NO: 778          moltype = AA  length = 7
FEATURE                 Location/Qualifiers
source                  1..7
                        mol_type = protein
                        organism = synthetic construct
                        note = Description of Artificial Sequence: Synthetic probe
SITE                    7
                        note = Lysine modified with a CPQ2 quencher
SEQUENCE: 778
GGSGGSK                                                                        7

SEQ ID NO: 779          moltype = AA  length = 12
FEATURE                 Location/Qualifiers
source                  1..12
                        mol_type = protein
                        organism = synthetic construct
                        note = Description of Artificial Sequence: Synthetic probe
SITE                    12
                        note = Lysine modified with a CPQ2 quencher
SEQUENCE: 779
GKPILFFRLK GK                                                                 12

SEQ ID NO: 780          moltype = AA  length = 9
FEATURE                 Location/Qualifiers
source                  1..9
                        mol_type = protein
                        organism = synthetic construct
                        note = Description of Artificial Sequence: Synthetic probe
SITE                    7
                        note = Norleucine
SITE                    9
                        note = lysine amide modified with a CPQ2 quencher
SEQUENCE: 780
GAWESRXGK                                                                      9

SEQ ID NO: 781          moltype = AA  length = 9
FEATURE                 Location/Qualifiers
source                  1..9
                        mol_type = protein
                        organism = synthetic construct
                        note = Description of Artificial Sequence: Synthetic probe
SITE                    7
                        note = Norleucine
SITE                    9
                        note = lysine amide modified with a CPQ2 quencher
SEQUENCE: 781
GNEKSGXGK                                                                      9

SEQ ID NO: 782          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 782
GNATIVYGK                                                                      9

SEQ ID NO: 783          moltype = AA  length = 9
FEATURE                 Location/Qualifiers
source                  1..9
                        mol_type = protein
```

```
                            -continued organism = synthetic construct
                        note = Description of Artificial Sequence: Synthetic probe
SITE                    9
                        note = Lysine modified with a CPQ2 quencher
SEQUENCE: 783
GDPFVVSGK                                                                        9

SEQ ID NO: 784          moltype = AA  length = 9
FEATURE                 Location/Qualifiers
source                  1..9
                        mol_type = protein
                        organism = synthetic construct
                        note = Description of Artificial Sequence: Synthetic probe
SITE                    4
                        note = Norleucine
SITE                    9
                        note = Lysine modified with a CPQ2 quencher
SEQUENCE: 784
GFHXFTKGK                                                                        9

SEQ ID NO: 785          moltype = AA  length = 9
FEATURE                 Location/Qualifiers
source                  1..9
                        mol_type = protein
                        organism = synthetic construct
                        note = Description of Artificial Sequence: Synthetic probe
SITE                    2
                        note = Norleucine
SITE                    9
                        note = lysine amide modified with a CPQ2 quencher
SEQUENCE: 785
GXNWHKHGK                                                                        9

SEQ ID NO: 786          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 786
GFARRWGGK                                                                        9

SEQ ID NO: 787          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 787
GPGKWSKGK                                                                        9

SEQ ID NO: 788          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 788
GYEEAQPGK                                                                        9

SEQ ID NO: 789          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 789
GYGAIKKGK                                                                        9

SEQ ID NO: 790          moltype = AA  length = 9
FEATURE                 Location/Qualifiers
```

```
source                  1..9
                        mol_type = protein
                        organism = synthetic construct
                        note = Description of Artificial Sequence: Synthetic probe
SITE                    4
                        note = Norleucine
SITE                    9
                        note = Lysine modified with a CPQ2 quencher
SEQUENCE: 790
GTSXEGYGK                                                                      9

SEQ ID NO: 791          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 791
GPNNFGSGK                                                                      9

SEQ ID NO: 792          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 792
GEDTRNTGK                                                                      9

SEQ ID NO: 793          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 793
GKDLEQSGK                                                                      9

SEQ ID NO: 794          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 794
GAALHNDGK                                                                      9

SEQ ID NO: 795          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 795
GADSFFKGK                                                                      9

SEQ ID NO: 796          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 796
GITFWRAGK                                                                      9

SEQ ID NO: 797          moltype = AA  length = 9
FEATURE                 Location/Qualifiers
```

-continued

```
source                   1..9
                         mol_type = protein
                         organism = synthetic construct
                         note = Description of Artificial Sequence: Synthetic probe
SITE                     5
                         note = Norleucine
SITE                     9
                         note = lysine amide modified with a CPQ2 quencher
SEQUENCE: 797
GLSDXRLGK                                                                         9

SEQ ID NO: 798           moltype = AA   length = 9
FEATURE                  Location/Qualifiers
source                   1..9
                         mol_type = protein
                         organism = synthetic construct
                         note = Description of Artificial Sequence: Synthetic probe
SITE                     9
                         note = Lysine modified with a CPQ2 quencher
SEQUENCE: 798
GEVGWTYGK                                                                         9

SEQ ID NO: 799           moltype = AA   length = 9
FEATURE                  Location/Qualifiers
source                   1..9
                         mol_type = protein
                         organism = synthetic construct
                         note = Description of Artificial Sequence: Synthetic probe
SITE                     7
                         note = Norleucine
SITE                     9
                         note = lysine amide modified with a CPQ2 quencher
SEQUENCE: 799
GIAFRQXGK                                                                         9

SEQ ID NO: 800           moltype = AA   length = 9
FEATURE                  Location/Qualifiers
source                   1..9
                         mol_type = protein
                         organism = synthetic construct
                         note = Description of Artificial Sequence: Synthetic probe
SITE                     7
                         note = Norleucine
SITE                     9
                         note = Lysine modified with a CPQ2 quencher
SEQUENCE: 800
GYNIHTXGK                                                                         9

SEQ ID NO: 801           moltype = AA   length = 9
FEATURE                  Location/Qualifiers
source                   1..9
                         mol_type = protein
                         organism = synthetic construct
                         note = Description of Artificial Sequence: Synthetic probe
SITE                     2
                         note = Norleucine
SITE                     9
                         note = Lysine modified with a CPQ2 quencher
SEQUENCE: 801
GXLWANHGK                                                                         9

SEQ ID NO: 802           moltype = AA   length = 9
FEATURE                  Location/Qualifiers
source                   1..9
                         mol_type = protein
                         organism = synthetic construct
                         note = Description of Artificial Sequence: Synthetic probe
SITE                     9
                         note = Lysine modified with a CPQ2 quencher
SEQUENCE: 802
GLYSVQVGK                                                                         9

SEQ ID NO: 803           moltype = AA   length = 9
FEATURE                  Location/Qualifiers
source                   1..9
                         mol_type = protein
                         organism = synthetic construct
                         note = Description of Artificial Sequence: Synthetic probe
SITE                     5
```

```
                        note = Norleucine
SITE                    9
                        note = Lysine modified with a CPQ2 quencher
SEQUENCE: 803
GSHIXSNGK                                                                9

SEQ ID NO: 804          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 804
GKLLIDVGK                                                                9

SEQ ID NO: 805          moltype = AA   length = 9
FEATURE                 Location/Qualifiers
source                  1..9
                        mol_type = protein
                        organism = synthetic construct
                        note = Description of Artificial Sequence: Synthetic probe
SITE                    3
                        note = Norleucine
SITE                    9
                        note = Lysine modified with a CPQ2 quencher
SEQUENCE: 805
GEXGVFDGK                                                                9

SEQ ID NO: 806          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 806
GHQAYTLGK                                                                9

SEQ ID NO: 807          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 807
GYVRKIQGK                                                                9

SEQ ID NO: 808          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 808
GDRENSPGK                                                                9

SEQ ID NO: 809          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 809
GKYDKPRGK                                                                9

SEQ ID NO: 810          moltype = AA   length = 9
FEATURE                 Location/Qualifiers
source                  1..9
                        mol_type = protein
                        organism = synthetic construct
```

```
                        note = Description of Artificial Sequence: Synthetic probe
SITE                    9
                        note = Lysine modified with a CPQ2 quencher
SEQUENCE: 810
GRPWKQLGK                                                                        9

SEQ ID NO: 811          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 811
GAPLQRYGK                                                                        9

SEQ ID NO: 812          moltype = AA   length = 9
FEATURE                 Location/Qualifiers
source                  1..9
                        mol_type = protein
                        organism = synthetic construct
                        note = Description of Artificial Sequence: Synthetic probe
SITE                    7
                        note = Norleucine
SITE                    9
                        note = lysine amide modified with a CPQ2 quencher
SEQUENCE: 812
GYQGQKXGK                                                                        9

SEQ ID NO: 813          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 813
GGRISSIGK                                                                        9

SEQ ID NO: 814          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 814
GHSLTNVGK                                                                        9

SEQ ID NO: 815          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 815
GEWDFPEGK                                                                        9

SEQ ID NO: 816          moltype = AA   length = 9
FEATURE                 Location/Qualifiers
source                  1..9
                        mol_type = protein
                        organism = synthetic construct
                        note = Description of Artificial Sequence: Synthetic probe
SITE                    5
                        note = Norleucine
SITE                    9
                        note = Lysine modified with a CPQ2 quencher
SEQUENCE: 816
GYLAXDGGK                                                                        9

SEQ ID NO: 817          moltype = AA   length = 9
FEATURE                 Location/Qualifiers
source                  1..9
```

```
                          mol_type = protein
                          organism = synthetic construct
                          note = Description of Artificial Sequence: Synthetic probe
SITE                      5
                          note = Norleucine
SITE                      9
                          note = Lysine modified with a CPQ2 quencher
SEQUENCE: 817
GFIYXPTGK                                                                          9

SEQ ID NO: 818            moltype = AA  length = 9
FEATURE                   Location/Qualifiers
source                    1..9
                          mol_type = protein
                          organism = synthetic construct
                          note = Description of Artificial Sequence: Synthetic probe
SITE                      9
                          note = Lysine modified with a CPQ2 quencher
SEQUENCE: 818
GGHETWVGK                                                                          9

SEQ ID NO: 819            moltype = AA  length = 9
FEATURE                   Location/Qualifiers
source                    1..9
                          mol_type = protein
                          organism = synthetic construct
                          note = Description of Artificial Sequence: Synthetic probe
SITE                      9
                          note = Lysine modified with a CPQ2 quencher
SEQUENCE: 819
GDYIGDEGK                                                                          9

SEQ ID NO: 820            moltype = AA  length = 9
FEATURE                   Location/Qualifiers
source                    1..9
                          mol_type = protein
                          organism = synthetic construct
                          note = Description of Artificial Sequence: Synthetic probe
SITE                      9
                          note = Lysine modified with a CPQ2 quencher
SEQUENCE: 820
GAGTAHPGK                                                                          9

SEQ ID NO: 821            moltype = AA  length = 9
FEATURE                   Location/Qualifiers
source                    1..9
                          mol_type = protein
                          organism = synthetic construct
                          note = Description of Artificial Sequence: Synthetic probe
SITE                      3
                          note = Norleucine
SITE                      9
                          note = Lysine modified with a CPQ2 quencher
SEQUENCE: 821
GVXTEIWGK                                                                          9

SEQ ID NO: 822            moltype = AA  length = 9
FEATURE                   Location/Qualifiers
source                    1..9
                          mol_type = protein
                          organism = synthetic construct
                          note = Description of Artificial Sequence: Synthetic probe
SITE                      9
                          note = Lysine modified with a CPQ2 quencher
SEQUENCE: 822
GPDDWQNGK                                                                          9

SEQ ID NO: 823            moltype = AA  length = 9
FEATURE                   Location/Qualifiers
source                    1..9
                          mol_type = protein
                          organism = synthetic construct
                          note = Description of Artificial Sequence: Synthetic probe
SITE                      9
                          note = Lysine modified with a CPQ2 quencher
SEQUENCE: 823
GGLNQEYGK                                                                          9

SEQ ID NO: 824            moltype = AA  length = 9
```

```
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 824
GYRDAVAGK                                                                         9

SEQ ID NO: 825          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 825
GTGPKGNGK                                                                         9

SEQ ID NO: 826          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 826
GDHVPQIGK                                                                         9

SEQ ID NO: 827          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 827
GNKEPILGK                                                                         9

SEQ ID NO: 828          moltype = AA   length = 9
FEATURE                 Location/Qualifiers
source                  1..9
                        mol_type = protein
                        organism = synthetic construct
                        note = Description of Artificial Sequence: Synthetic probe
SITE                    5
                        note = Norleucine
SITE                    9
                        note = Lysine modified with a CPQ2 quencher
SEQUENCE: 828
GVWNXVHGK                                                                         9

SEQ ID NO: 829          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 829
GPVIIEHGK                                                                         9

SEQ ID NO: 830          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 830
GFQTDNLGK                                                                         9

SEQ ID NO: 831          moltype = AA   length = 9
```

```
FEATURE              Location/Qualifiers
source               1..9
                     mol_type = protein
                     organism = synthetic construct
                     note = Description of Artificial Sequence: Synthetic probe
SITE                 4
                     note = Norleucine
SITE                 9
                     note = Lysine modified with a CPQ2 quencher
SEQUENCE: 831
GRFXHGIGK                                                                     9

SEQ ID NO: 832       moltype = AA  length = 9
FEATURE              Location/Qualifiers
source               1..9
                     mol_type = protein
                     organism = synthetic construct
                     note = Description of Artificial Sequence: Synthetic probe
SITE                 9
                     note = lysine amide modified with a CPQ2 quencher
SEQUENCE: 832
GYAERTTGK                                                                     9

SEQ ID NO: 833       moltype = AA  length = 9
FEATURE              Location/Qualifiers
source               1..9
                     mol_type = protein
                     organism = synthetic construct
                     note = Description of Artificial Sequence: Synthetic probe
SITE                 9
                     note = lysine amide modified with a CPQ2 quencher
SEQUENCE: 833
GNRGELPGK                                                                     9

SEQ ID NO: 834       moltype = AA  length = 9
FEATURE              Location/Qualifiers
source               1..9
                     mol_type = protein
                     organism = synthetic construct
                     note = Description of Artificial Sequence: Synthetic probe
SITE                 9
                     note = Lysine modified with a CPQ2 quencher
SEQUENCE: 834
GHHYFNYGK                                                                     9

SEQ ID NO: 835       moltype = AA  length = 9
FEATURE              Location/Qualifiers
source               1..9
                     mol_type = protein
                     organism = synthetic construct
                     note = Description of Artificial Sequence: Synthetic probe
SITE                 9
                     note = Lysine modified with a CPQ2 quencher
SEQUENCE: 835
GSTPYYHGK                                                                     9

SEQ ID NO: 836       moltype = AA  length = 9
FEATURE              Location/Qualifiers
source               1..9
                     mol_type = protein
                     organism = synthetic construct
                     note = Description of Artificial Sequence: Synthetic probe
SITE                 9
                     note = Lysine modified with a CPQ2 quencher
SEQUENCE: 836
GWFYPSAGK                                                                     9

SEQ ID NO: 837       moltype = AA  length = 9
FEATURE              Location/Qualifiers
source               1..9
                     mol_type = protein
                     organism = synthetic construct
                     note = Description of Artificial Sequence: Synthetic probe
SITE                 9
                     note = Lysine modified with a CPQ2 quencher
SEQUENCE: 837
GSEFLFSGK                                                                     9

SEQ ID NO: 838       moltype = AA  length = 9
```

```
FEATURE                   Location/Qualifiers
source                    1..9
                          mol_type = protein
                          organism = synthetic construct
                          note = Description of Artificial Sequence: Synthetic probe
SITE                      9
                          note = lysine amide modified with a CPQ2 quencher
SEQUENCE: 838
GWYKTQYGK                                                                            9

SEQ ID NO: 839            moltype = AA  length = 9
FEATURE                   Location/Qualifiers
source                    1..9
                          mol_type = protein
                          organism = synthetic construct
                          note = Description of Artificial Sequence: Synthetic probe
SITE                      9
                          note = Lysine modified with a CPQ2 quencher
SEQUENCE: 839
GVTHLKVGK                                                                            9

SEQ ID NO: 840            moltype = AA  length = 9
FEATURE                   Location/Qualifiers
source                    1..9
                          mol_type = protein
                          organism = synthetic construct
                          note = Description of Artificial Sequence: Synthetic probe
SITE                      9
                          note = Lysine modified with a CPQ2 quencher
SEQUENCE: 840
GINGGFSGK                                                                            9

SEQ ID NO: 841            moltype = AA  length = 9
FEATURE                   Location/Qualifiers
source                    1..9
                          mol_type = protein
                          organism = synthetic construct
                          note = Description of Artificial Sequence: Synthetic probe
SITE                      9
                          note = Lysine modified with a CPQ2 quencher
SEQUENCE: 841
GTVLGLDGK                                                                            9

SEQ ID NO: 842            moltype = AA  length = 9
FEATURE                   Location/Qualifiers
source                    1..9
                          mol_type = protein
                          organism = synthetic construct
                          note = Description of Artificial Sequence: Synthetic probe
SITE                      6
                          note = Norleucine
SITE                      9
                          note = Lysine modified with a CPQ2 quencher
SEQUENCE: 842
GSYWPXQGK                                                                            9

SEQ ID NO: 843            moltype = AA  length = 9
FEATURE                   Location/Qualifiers
source                    1..9
                          mol_type = protein
                          organism = synthetic construct
                          note = Description of Artificial Sequence: Synthetic probe
SITE                      9
                          note = Lysine modified with a CPQ2 quencher
SEQUENCE: 843
GASQQHRGK                                                                            9

SEQ ID NO: 844            moltype = AA  length = 9
FEATURE                   Location/Qualifiers
source                    1..9
                          mol_type = protein
                          organism = synthetic construct
                          note = Description of Artificial Sequence: Synthetic probe
SITE                      9
                          note = Lysine modified with a CPQ2 quencher
SEQUENCE: 844
GKNPAKAGK                                                                            9

SEQ ID NO: 845            moltype = AA  length = 9
```

```
FEATURE                 Location/Qualifiers
source                  1..9
                        mol_type = protein
                        organism = synthetic construct
                        note = Description of Artificial Sequence: Synthetic probe
SITE                    2
                        note = Norleucine
SITE                    9
                        note = Lysine modified with a CPQ2 quencher
SEQUENCE: 845
GXYWLVEGK                                                                        9

SEQ ID NO: 846          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 846
GSWWIFEGK                                                                        9

SEQ ID NO: 847          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 847
GVNYEQDGK                                                                        9

SEQ ID NO: 848          moltype = AA  length = 9
FEATURE                 Location/Qualifiers
source                  1..9
                        mol_type = protein
                        organism = synthetic construct
                        note = Description of Artificial Sequence: Synthetic probe
SITE                    5
                        note = Norleucine
SITE                    9
                        note = Lysine modified with a CPQ2 quencher
SEQUENCE: 848
GHFFXAEGK                                                                        9

SEQ ID NO: 849          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 849
GDIPPHWGK                                                                        9

SEQ ID NO: 850          moltype = AA  length = 9
FEATURE                 Location/Qualifiers
source                  1..9
                        mol_type = protein
                        organism = synthetic construct
                        note = Description of Artificial Sequence: Synthetic probe
SITE                    6
                        note = Norleucine
SITE                    9
                        note = Lysine modified with a CPQ2 quencher
SEQUENCE: 850
GVDQWXWGK                                                                        9

SEQ ID NO: 851          moltype = AA  length = 9
FEATURE                 Location/Qualifiers
source                  1..9
                        mol_type = protein
                        organism = synthetic construct
                        note = Description of Artificial Sequence: Synthetic probe
SITE                    6
                        note = Norleucine
```

```
SITE                    9
                        note = Lysine modified with a CPQ2 quencher
SEQUENCE: 851
GLRSLXKGK                                                                   9

SEQ ID NO: 852          moltype = AA   length = 9
FEATURE                 Location/Qualifiers
source                  1..9
                        mol_type = protein
                        organism = synthetic construct
                        note = Description of Artificial Sequence: Synthetic probe
SITE                    2
                        note = Norleucine
SITE                    3
                        note = Norleucine
SITE                    9
                        note = Lysine modified with a CPQ2 quencher
SEQUENCE: 852
GXXIRHAGK                                                                   9

SEQ ID NO: 853          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 853
GHDVKFIGK                                                                   9

SEQ ID NO: 854          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 854
GKRVQFLGK                                                                   9

SEQ ID NO: 855          moltype = AA   length = 9
FEATURE                 Location/Qualifiers
source                  1..9
                        mol_type = protein
                        organism = synthetic construct
                        note = Description of Artificial Sequence: Synthetic probe
SITE                    4
                        note = Norleucine
SITE                    9
                        note = lysine amide modified with a CPQ2 quencher
SEQUENCE: 855
GRDXYAEGK                                                                   9

SEQ ID NO: 856          moltype = AA   length = 9
FEATURE                 Location/Qualifiers
source                  1..9
                        mol_type = protein
                        organism = synthetic construct
                        note = Description of Artificial Sequence: Synthetic probe
SITE                    3
                        note = Norleucine
SITE                    9
                        note = Lysine modified with a CPQ2 quencher
SEQUENCE: 856
GLXIYFEGK                                                                   9

SEQ ID NO: 857          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 857
GLRTKQSGK                                                                   9
```

| | | |
|---|---|---|
| SEQ ID NO: 858<br>FEATURE<br>source<br><br>SITE<br><br>SEQUENCE: 858<br>GWHGQQYGK | moltype = AA length = 9<br>Location/Qualifiers<br>1..9<br>mol_type = protein<br>organism = synthetic construct<br>note = Description of Artificial Sequence: Synthetic probe<br>9<br>note = Lysine modified with a CPQ2 quencher | 9 |
| SEQ ID NO: 859<br>FEATURE<br>source<br><br>SITE<br><br>SEQUENCE: 859<br>GGPEGTIGK | moltype = AA length = 9<br>Location/Qualifiers<br>1..9<br>mol_type = protein<br>organism = synthetic construct<br>note = Description of Artificial Sequence: Synthetic probe<br>9<br>note = Lysine modified with a CPQ2 quencher | 9 |
| SEQ ID NO: 860<br>FEATURE<br>source<br><br>SITE<br><br>SEQUENCE: 860<br>GELDPIPGK | moltype = AA length = 9<br>Location/Qualifiers<br>1..9<br>mol_type = protein<br>organism = synthetic construct<br>note = Description of Artificial Sequence: Synthetic probe<br>9<br>note = Lysine modified with a CPQ2 quencher | 9 |
| SEQ ID NO: 861<br>FEATURE<br>source<br><br>SITE<br><br>SEQUENCE: 861<br>GGRAADFGK | moltype = AA length = 9<br>Location/Qualifiers<br>1..9<br>mol_type = protein<br>organism = synthetic construct<br>note = Description of Artificial Sequence: Synthetic probe<br>9<br>note = lysine amide modified with a CPQ2 quencher | 9 |
| SEQ ID NO: 862<br>FEATURE<br>source<br><br>SITE<br><br>SEQUENCE: 862<br>GHFIDYIGK | moltype = AA length = 9<br>Location/Qualifiers<br>1..9<br>mol_type = protein<br>organism = synthetic construct<br>note = Description of Artificial Sequence: Synthetic probe<br>9<br>note = Lysine modified with a CPQ2 quencher | 9 |
| SEQ ID NO: 863<br>FEATURE<br>source<br><br>SITE<br><br>SITE<br><br>SITE<br><br>SEQUENCE: 863<br>GSXXRVHGK | moltype = AA length = 9<br>Location/Qualifiers<br>1..9<br>mol_type = protein<br>organism = synthetic construct<br>note = Description of Artificial Sequence: Synthetic probe<br>3<br>note = Norleucine<br>4<br>note = Norleucine<br>9<br>note = Lysine modified with a CPQ2 quencher | 9 |
| SEQ ID NO: 864<br>FEATURE<br>source<br><br>SITE<br><br>SEQUENCE: 864 | moltype = AA length = 9<br>Location/Qualifiers<br>1..9<br>mol_type = protein<br>organism = synthetic construct<br>note = Description of Artificial Sequence: Synthetic probe<br>9<br>note = Lysine modified with a CPQ2 quencher | |

```
GSFRKIIGK                                                                       9

SEQ ID NO: 865          moltype = AA  length = 9
FEATURE                 Location/Qualifiers
source                  1..9
                        mol_type = protein
                        organism = synthetic construct
                        note = Description of Artificial Sequence: Synthetic probe
SITE                    5
                        note = Norleucine
SITE                    9
                        note = Lysine modified with a CPQ2 quencher
SEQUENCE: 865
GTYEXFSGK                                                                       9

SEQ ID NO: 866          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 866
GHLLGFYGK                                                                       9

SEQ ID NO: 867          moltype = AA  length = 9
FEATURE                 Location/Qualifiers
source                  1..9
                        mol_type = protein
                        organism = synthetic construct
                        note = Description of Artificial Sequence: Synthetic probe
SITE                    2
                        note = Norleucine
SITE                    9
                        note = Lysine modified with a CPQ2 quencher
SEQUENCE: 867
GXWTALTGK                                                                       9

SEQ ID NO: 868          moltype = AA  length = 9
FEATURE                 Location/Qualifiers
source                  1..9
                        mol_type = protein
                        organism = synthetic construct
                        note = Description of Artificial Sequence: Synthetic probe
SITE                    5
                        note = Norleucine
SITE                    9
                        note = Lysine modified with a CPQ2 quencher
SEQUENCE: 868
GIWNXVYGK                                                                       9

SEQ ID NO: 869          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 869
GRRNPLWGK                                                                       9

SEQ ID NO: 870          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 870
GRWYGGIGK                                                                       9

SEQ ID NO: 871          moltype = AA  length = 9
FEATURE                 Location/Qualifiers
source                  1..9
                        mol_type = protein
                        organism = synthetic construct
```

```
                       note = Description of Artificial Sequence: Synthetic probe
SITE                   9
                       note = Lysine modified with a CPQ2 quencher
SEQUENCE: 871
GKTGDARGK                                                                      9

SEQ ID NO: 872         moltype = AA   length = 9
FEATURE                Location/Qualifiers
source                 1..9
                       mol_type = protein
                       organism = synthetic construct
                       note = Description of Artificial Sequence: Synthetic probe
SITE                   9
                       note = Lysine modified with a CPQ2 quencher
SEQUENCE: 872
GNYWEANGK                                                                      9

SEQ ID NO: 873         moltype = AA   length = 9
FEATURE                Location/Qualifiers
source                 1..9
                       mol_type = protein
                       organism = synthetic construct
                       note = Description of Artificial Sequence: Synthetic probe
SITE                   2
                       note = Norleucine
SITE                   9
                       note = Lysine modified with a CPQ2 quencher
SEQUENCE: 873
GXQFDTSGK                                                                      9

SEQ ID NO: 874         moltype = AA   length = 9
FEATURE                Location/Qualifiers
source                 1..9
                       mol_type = protein
                       organism = synthetic construct
                       note = Description of Artificial Sequence: Synthetic probe
SITE                   9
                       note = Lysine modified with a CPQ2 quencher
SEQUENCE: 874
GKRGAVEGK                                                                      9

SEQ ID NO: 875         moltype = AA   length = 9
FEATURE                Location/Qualifiers
source                 1..9
                       mol_type = protein
                       organism = synthetic construct
                       note = Description of Artificial Sequence: Synthetic probe
SITE                   9
                       note = lysine amide modified with a CPQ2 quencher
SEQUENCE: 875
GSLKPTEGK                                                                      9

SEQ ID NO: 876         moltype = AA   length = 9
FEATURE                Location/Qualifiers
source                 1..9
                       mol_type = protein
                       organism = synthetic construct
                       note = Description of Artificial Sequence: Synthetic probe
SITE                   9
                       note = lysine amide modified with a CPQ2 quencher
SEQUENCE: 876
GENDRLPGK                                                                      9

SEQ ID NO: 877         moltype = AA   length = 9
FEATURE                Location/Qualifiers
source                 1..9
                       mol_type = protein
                       organism = synthetic construct
                       note = Description of Artificial Sequence: Synthetic probe
SITE                   9
                       note = Lysine modified with a CPQ2 quencher
SEQUENCE: 877
GNSYQVQGK                                                                      9

SEQ ID NO: 878         moltype = AA   length = 9
FEATURE                Location/Qualifiers
source                 1..9
                       mol_type = protein
                       organism = synthetic construct
```

```
SITE                        9
                            note = Description of Artificial Sequence: Synthetic probe
                            note = lysine amide modified with a CPQ2 quencher
SEQUENCE: 878
GYPKEYLGK                                                                           9

SEQ ID NO: 879              moltype = AA  length = 9
FEATURE                     Location/Qualifiers
source                      1..9
                            mol_type = protein
                            organism = synthetic construct
                            note = Description of Artificial Sequence: Synthetic probe
SITE                        9
                            note = lysine amide modified with a CPQ2 quencher
SEQUENCE: 879
GINNKWQGK                                                                           9

SEQ ID NO: 880              moltype = AA  length = 9
FEATURE                     Location/Qualifiers
source                      1..9
                            mol_type = protein
                            organism = synthetic construct
                            note = Description of Artificial Sequence: Synthetic probe
SITE                        2
                            note = Norleucine
SITE                        9
                            note = Lysine modified with a CPQ2 quencher
SEQUENCE: 880
GXEFQGWGK                                                                           9

SEQ ID NO: 881              moltype = AA  length = 9
FEATURE                     Location/Qualifiers
source                      1..9
                            mol_type = protein
                            organism = synthetic construct
                            note = Description of Artificial Sequence: Synthetic probe
SITE                        9
                            note = lysine amide modified with a CPQ2 quencher
SEQUENCE: 881
GPVRSTNGK                                                                           9

SEQ ID NO: 882              moltype = AA  length = 9
FEATURE                     Location/Qualifiers
source                      1..9
                            mol_type = protein
                            organism = synthetic construct
                            note = Description of Artificial Sequence: Synthetic probe
SITE                        9
                            note = lysine amide modified with a CPQ2 quencher
SEQUENCE: 882
GSQAIKVGK                                                                           9

SEQ ID NO: 883              moltype = AA  length = 9
FEATURE                     Location/Qualifiers
source                      1..9
                            mol_type = protein
                            organism = synthetic construct
                            note = Description of Artificial Sequence: Synthetic probe
SITE                        4
                            note = Norleucine
SITE                        9
                            note = Lysine modified with a CPQ2 quencher
SEQUENCE: 883
GWAXLYHGK                                                                           9

SEQ ID NO: 884              moltype = AA  length = 9
FEATURE                     Location/Qualifiers
source                      1..9
                            mol_type = protein
                            organism = synthetic construct
                            note = Description of Artificial Sequence: Synthetic probe
SITE                        9
                            note = Lysine modified with a CPQ2 quencher
SEQUENCE: 884
GISWIHAGK                                                                           9

SEQ ID NO: 885              moltype = AA  length = 9
FEATURE                     Location/Qualifiers
source                      1..9
```

```
                        mol_type = protein
                        organism = synthetic construct
                        note = Description of Artificial Sequence: Synthetic probe
SITE                    9
                        note = Lysine modified with a CPQ2 quencher
SEQUENCE: 885
GAHDIVNGK                                                                        9

SEQ ID NO: 886          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 886
GRHNVASGK                                                                        9

SEQ ID NO: 887          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 887
GSVFVIEGK                                                                        9

SEQ ID NO: 888          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 888
GFAKYYKGK                                                                        9

SEQ ID NO: 889          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 889
GPYNTLQGK                                                                        9

SEQ ID NO: 890          moltype = AA  length = 9
FEATURE                 Location/Qualifiers
source                  1..9
                        mol_type = protein
                        organism = synthetic construct
                        note = Description of Artificial Sequence: Synthetic probe
SITE                    2
                        note = Norleucine
SITE                    7
                        note = Norleucine
SITE                    9
                        note = Lysine modified with a CPQ2 quencher
SEQUENCE: 890
GXDWGHXGK                                                                        9

SEQ ID NO: 891          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 891
GSNREWFGK                                                                        9

SEQ ID NO: 892          moltype = AA  length = 9
```

```
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 892
GGKSEHTGK                                                                        9

SEQ ID NO: 893          moltype = AA  length = 9
FEATURE                 Location/Qualifiers
source                  1..9
                        mol_type = protein
                        organism = synthetic construct
                        note = Description of Artificial Sequence: Synthetic probe
SITE                    4
                        note = Norleucine
SITE                    9
                        note = Lysine modified with a CPQ2 quencher
SEQUENCE: 893
GFPXTDQGK                                                                        9

SEQ ID NO: 894          moltype = AA  length = 9
FEATURE                 Location/Qualifiers
source                  1..9
                        mol_type = protein
                        organism = synthetic construct
                        note = Description of Artificial Sequence: Synthetic probe
SITE                    7
                        note = Norleucine
SITE                    9
                        note = Lysine modified with a CPQ2 quencher
SEQUENCE: 894
GWSKFWXGK                                                                        9

SEQ ID NO: 895          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 895
GRFTRPHGK                                                                        9

SEQ ID NO: 896          moltype = AA  length = 9
FEATURE                 Location/Qualifiers
source                  1..9
                        mol_type = protein
                        organism = synthetic construct
                        note = Description of Artificial Sequence: Synthetic probe
SITE                    5
                        note = Norleucine
SITE                    9
                        note = lysine amide modified with a CPQ2 quencher
SEQUENCE: 896
GQETXKDGK                                                                        9

SEQ ID NO: 897          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 897
GHWWDVLGK                                                                        9

SEQ ID NO: 898          moltype = AA  length = 9
FEATURE                 Location/Qualifiers
source                  1..9
                        mol_type = protein
                        organism = synthetic construct
                        note = Description of Artificial Sequence: Synthetic probe
SITE                    6
                        note = Norleucine
```

```
                                       -continued
SITE                    9
                        note = Lysine modified with a CPQ2 quencher
SEQUENCE: 898
GFNLVXSGK                                                                     9

SEQ ID NO: 899          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 899
GSAWRQRGK                                                                     9

SEQ ID NO: 900          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 900
GTFHIFLGK                                                                     9

SEQ ID NO: 901          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 901
GWPQHVKGK                                                                     9

SEQ ID NO: 902          moltype = AA  length = 9
FEATURE                 Location/Qualifiers
source                  1..9
                        mol_type = protein
                        organism = synthetic construct
                        note = Description of Artificial Sequence: Synthetic probe
SITE                    4
                        note = Norleucine
SITE                    9
                        note = Lysine modified with a CPQ2 quencher
SEQUENCE: 902
GLIXHKNGK                                                                     9

SEQ ID NO: 903          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 903
GQDLEQPGK                                                                     9

SEQ ID NO: 904          moltype = AA  length = 9
FEATURE                 Location/Qualifiers
source                  1..9
                        mol_type = protein
                        organism = synthetic construct
                        note = Description of Artificial Sequence: Synthetic probe
SITE                    6
                        note = Norleucine
SITE                    9
                        note = lysine amide modified with a CPQ2 quencher
SEQUENCE: 904
GHQKKXPGK                                                                     9

SEQ ID NO: 905          moltype = AA  length = 9
FEATURE                 Location/Qualifiers
source                  1..9
                        mol_type = protein
```

```
                         organism = synthetic construct
                         note = Description of Artificial Sequence: Synthetic probe
SITE                     9
                         note = Lysine modified with a CPQ2 quencher
SEQUENCE: 905
GGVTWLNGK                                                                          9

SEQ ID NO: 906           moltype = AA   length = 9
FEATURE                  Location/Qualifiers
source                   1..9
                         mol_type = protein
                         organism = synthetic construct
                         note = Description of Artificial Sequence: Synthetic probe
SITE                     9
                         note = lysine amide modified with a CPQ2 quencher
SEQUENCE: 906
GAGEPFKGK                                                                          9

SEQ ID NO: 907           moltype = AA   length = 9
FEATURE                  Location/Qualifiers
source                   1..9
                         mol_type = protein
                         organism = synthetic construct
                         note = Description of Artificial Sequence: Synthetic probe
SITE                     4
                         note = Norleucine
SITE                     9
                         note = lysine amide modified with a CPQ2 quencher
SEQUENCE: 907
GSRXATTGK                                                                          9

SEQ ID NO: 908           moltype = AA   length = 9
FEATURE                  Location/Qualifiers
source                   1..9
                         mol_type = protein
                         organism = synthetic construct
                         note = Description of Artificial Sequence: Synthetic probe
SITE                     5
                         note = Norleucine
SITE                     9
                         note = Lysine modified with a CPQ2 quencher
SEQUENCE: 908
GLAFXNHGK                                                                          9

SEQ ID NO: 909           moltype = AA   length = 9
FEATURE                  Location/Qualifiers
source                   1..9
                         mol_type = protein
                         organism = synthetic construct
                         note = Description of Artificial Sequence: Synthetic probe
SITE                     9
                         note = Lysine modified with a CPQ2 quencher
SEQUENCE: 909
GPPSGLSGK                                                                          9

SEQ ID NO: 910           moltype = AA   length = 9
FEATURE                  Location/Qualifiers
source                   1..9
                         mol_type = protein
                         organism = synthetic construct
                         note = Description of Artificial Sequence: Synthetic probe
SITE                     9
                         note = Lysine modified with a CPQ2 quencher
SEQUENCE: 910
GYTHSSPGK                                                                          9

SEQ ID NO: 911           moltype = AA   length = 9
FEATURE                  Location/Qualifiers
source                   1..9
                         mol_type = protein
                         organism = synthetic construct
                         note = Description of Artificial Sequence: Synthetic probe
SITE                     9
                         note = Lysine modified with a CPQ2 quencher
SEQUENCE: 911
GDGSHYRGK                                                                          9

SEQ ID NO: 912           moltype = AA   length = 9
FEATURE                  Location/Qualifiers
```

```
source                      1..9
                            mol_type = protein
                            organism = synthetic construct
                            note = Description of Artificial Sequence: Synthetic probe
SITE                        3
                            note = Norleucine
SITE                        9
                            note = Lysine modified with a CPQ2 quencher
SEQUENCE: 912
GYXGNGYGK                                                                            9

SEQ ID NO: 913              moltype = AA   length = 9
FEATURE                     Location/Qualifiers
source                      1..9
                            mol_type = protein
                            organism = synthetic construct
                            note = Description of Artificial Sequence: Synthetic probe
SITE                        9
                            note = Lysine modified with a CPQ2 quencher
SEQUENCE: 913
GDSITVSGK                                                                            9

SEQ ID NO: 914              moltype = AA   length = 9
FEATURE                     Location/Qualifiers
source                      1..9
                            mol_type = protein
                            organism = synthetic construct
                            note = Description of Artificial Sequence: Synthetic probe
SITE                        9
                            note = Lysine modified with a CPQ2 quencher
SEQUENCE: 914
GQTPNIQGK                                                                            9

SEQ ID NO: 915              moltype = AA   length = 9
FEATURE                     Location/Qualifiers
source                      1..9
                            mol_type = protein
                            organism = synthetic construct
                            note = Description of Artificial Sequence: Synthetic probe
SITE                        9
                            note = lysine amide modified with a CPQ2 quencher
SEQUENCE: 915
GKLFFGYGK                                                                            9

SEQ ID NO: 916              moltype = AA   length = 9
FEATURE                     Location/Qualifiers
source                      1..9
                            mol_type = protein
                            organism = synthetic construct
                            note = Description of Artificial Sequence: Synthetic probe
SITE                        9
                            note = Lysine modified with a CPQ2 quencher
SEQUENCE: 916
GTQNFNWGK                                                                            9

SEQ ID NO: 917              moltype = AA   length = 9
FEATURE                     Location/Qualifiers
source                      1..9
                            mol_type = protein
                            organism = synthetic construct
                            note = Description of Artificial Sequence: Synthetic probe
SITE                        9
                            note = Lysine modified with a CPQ2 quencher
SEQUENCE: 917
GYSDHEVGK                                                                            9

SEQ ID NO: 918              moltype = AA   length = 9
FEATURE                     Location/Qualifiers
source                      1..9
                            mol_type = protein
                            organism = synthetic construct
                            note = Description of Artificial Sequence: Synthetic probe
SITE                        9
                            note = lysine amide modified with a CPQ2 quencher
SEQUENCE: 918
GRYVVPAGK                                                                            9

SEQ ID NO: 919              moltype = AA   length = 9
FEATURE                     Location/Qualifiers
```

```
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 919
GILHRIRGK                                                                        9

SEQ ID NO: 920          moltype = AA  length = 9
FEATURE                 Location/Qualifiers
source                  1..9
                        mol_type = protein
                        organism = synthetic construct
                        note = Description of Artificial Sequence: Synthetic probe
SITE                    7
                        note = Norleucine
SITE                    9
                        note = Lysine modified with a CPQ2 quencher
SEQUENCE: 920
GESDNQXGK                                                                        9

SEQ ID NO: 921          moltype = AA  length = 9
FEATURE                 Location/Qualifiers
source                  1..9
                        mol_type = protein
                        organism = synthetic construct
                        note = Description of Artificial Sequence: Synthetic probe
SITE                    7
                        note = Norleucine
SITE                    9
                        note = lysine amide modified with a CPQ2 quencher
SEQUENCE: 921
GYDDKGXGK                                                                        9

SEQ ID NO: 922          moltype = AA  length = 9
FEATURE                 Location/Qualifiers
source                  1..9
                        mol_type = protein
                        organism = synthetic construct
                        note = Description of Artificial Sequence: Synthetic probe
SITE                    5
                        note = Norleucine
SITE                    9
                        note = Lysine modified with a CPQ2 quencher
SEQUENCE: 922
GQLSXVWGK                                                                        9

SEQ ID NO: 923          moltype = AA  length = 9
FEATURE                 Location/Qualifiers
source                  1..9
                        mol_type = protein
                        organism = synthetic construct
                        note = Description of Artificial Sequence: Synthetic probe
SITE                    7
                        note = Norleucine
SITE                    9
                        note = lysine amide modified with a CPQ2 quencher
SEQUENCE: 923
GPGGERXGK                                                                        9

SEQ ID NO: 924          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 924
GWKHHPDGK                                                                        9

SEQ ID NO: 925          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
```

```
                        note = Lysine modified with a CPQ2 quencher
SEQUENCE: 925
GQWVDEDGK                                                                    9

SEQ ID NO: 926          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 926
GNAYNEIGK                                                                    9

SEQ ID NO: 927          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 927
GEEKAPRGK                                                                    9

SEQ ID NO: 928          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 928
GPWQIGKGK                                                                    9

SEQ ID NO: 929          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 929
GIAQVGNGK                                                                    9

SEQ ID NO: 930          moltype = AA   length = 9
FEATURE                 Location/Qualifiers
source                  1..9
                        mol_type = protein
                        organism = synthetic construct
                        note = Description of Artificial Sequence: Synthetic probe
SITE                    3
                        note = Norleucine
SITE                    9
                        note = lysine amide modified with a CPQ2 quencher
SEQUENCE: 930
GVXRQSEGK                                                                    9

SEQ ID NO: 931          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 931
GTERVDAGK                                                                    9

SEQ ID NO: 932          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
```

```
                        note = Lysine modified with a CPQ2 quencher
SEQUENCE: 932
GWLRWRLGK                                                                 9

SEQ ID NO: 933          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 933
GWKTKGQGK                                                                 9

SEQ ID NO: 934          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 934
GQSNGDVGK                                                                 9

SEQ ID NO: 935          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 935
GTLFYALGK                                                                 9

SEQ ID NO: 936          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 936
GTVTLNPGK                                                                 9

SEQ ID NO: 937          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 937
GYAFGRKGK                                                                 9

SEQ ID NO: 938          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 938
GDYNYWDGK                                                                 9

SEQ ID NO: 939          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 939
```

```
GEWHEIIGK                                                                     9

SEQ ID NO: 940          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 940
GQKAAWDGK                                                                     9

SEQ ID NO: 941          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 941
GDNTSADGK                                                                     9

SEQ ID NO: 942          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 942
GHEGEYVGK                                                                     9

SEQ ID NO: 943          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 943
GWSPSFKGK                                                                     9

SEQ ID NO: 944          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 944
GHDEHWTGK                                                                     9

SEQ ID NO: 945          moltype = AA  length = 9
FEATURE                 Location/Qualifiers
source                  1..9
                        mol_type = protein
                        organism = synthetic construct
                        note = Description of Artificial Sequence: Synthetic probe
SITE                    5
                        note = Norleucine
SITE                    9
                        note = lysine amide modified with a CPQ2 quencher
SEQUENCE: 945
GYVWXRDGK                                                                     9

SEQ ID NO: 946          moltype = AA  length = 9
FEATURE                 Location/Qualifiers
source                  1..9
                        mol_type = protein
                        organism = synthetic construct
                        note = Description of Artificial Sequence: Synthetic probe
SITE                    2
                        note = Norleucine
SITE                    5
```

```
                              note = Norleucine
SITE                          9
                              note = lysine amide modified with a CPQ2 quencher
SEQUENCE: 946
GXDPXKFGK                                                                      9

SEQ ID NO: 947                moltype = AA  length = 9
FEATURE                       Location/Qualifiers
source                        1..9
                              mol_type = protein
                              organism = synthetic construct
                              note = Description of Artificial Sequence: Synthetic probe
SITE                          2
                              note = Norleucine
SITE                          4
                              note = Norleucine
SITE                          9
                              note = lysine amide modified with a CPQ2 quencher
SEQUENCE: 947
GXRXFWDGK                                                                      9

SEQ ID NO: 948                moltype = AA  length = 9
FEATURE                       Location/Qualifiers
source                        1..9
                              mol_type = protein
                              organism = synthetic construct
                              note = Description of Artificial Sequence: Synthetic probe
SITE                          7
                              note = Norleucine
SITE                          9
                              note = Lysine modified with a CPQ2 quencher
SEQUENCE: 948
GDIAITXGK                                                                      9

SEQ ID NO: 949                moltype = AA  length = 9
FEATURE                       Location/Qualifiers
source                        1..9
                              mol_type = protein
                              organism = synthetic construct
                              note = Description of Artificial Sequence: Synthetic probe
SITE                          4
                              note = Norleucine
SITE                          9
                              note = Lysine modified with a CPQ2 quencher
SEQUENCE: 949
GPIXRFHGK                                                                      9

SEQ ID NO: 950                moltype = AA  length = 9
FEATURE                       Location/Qualifiers
source                        1..9
                              mol_type = protein
                              organism = synthetic construct
                              note = Description of Artificial Sequence: Synthetic probe
SITE                          9
                              note = Lysine modified with a CPQ2 quencher
SEQUENCE: 950
GVWQGYIGK                                                                      9

SEQ ID NO: 951                moltype = AA  length = 9
FEATURE                       Location/Qualifiers
source                        1..9
                              mol_type = protein
                              organism = synthetic construct
                              note = Description of Artificial Sequence: Synthetic probe
SITE                          4
                              note = Norleucine
SITE                          9
                              note = Lysine modified with a CPQ2 quencher
SEQUENCE: 951
GKKXSNPGK                                                                      9

SEQ ID NO: 952                moltype = AA  length = 9
FEATURE                       Location/Qualifiers
source                        1..9
                              mol_type = protein
                              organism = synthetic construct
                              note = Description of Artificial Sequence: Synthetic probe
SITE                          9
                              note = Lysine modified with a CPQ2 quencher
```

```
SEQUENCE: 952
GGHPLSPGK                                                                9

SEQ ID NO: 953          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 953
GVRQHKPGK                                                                9

SEQ ID NO: 954          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 954
GAQNFYRGK                                                                9

SEQ ID NO: 955          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 955
GVAGKSIGK                                                                9

SEQ ID NO: 956          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 956
GLVGQVNGK                                                                9

SEQ ID NO: 957          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 957
GQVKHFTGK                                                                9

SEQ ID NO: 958          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 958
GQKSVVSGK                                                                9

SEQ ID NO: 959          moltype = AA  length = 9
FEATURE                 Location/Qualifiers
source                  1..9
                        mol_type = protein
                        organism = synthetic construct
                        note = Description of Artificial Sequence: Synthetic probe
SITE                    3
                        note = Norleucine
SITE                    9
                        note = Lysine modified with a CPQ2 quencher
```

```
SEQUENCE: 959
GYXQEWLGK                                                                          9

SEQ ID NO: 960          moltype = AA  length = 9
FEATURE                 Location/Qualifiers
source                  1..9
                        mol_type = protein
                        organism = synthetic construct
                        note = Description of Artificial Sequence: Synthetic probe
SITE                    3
                        note = Norleucine
SITE                    9
                        note = Lysine modified with a CPQ2 quencher
SEQUENCE: 960
GGXYIDEGK                                                                          9

SEQ ID NO: 961          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 961
GNAGSKFGK                                                                          9

SEQ ID NO: 962          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 962
GEFVHNPGK                                                                          9

SEQ ID NO: 963          moltype = AA  length = 9
FEATURE                 Location/Qualifiers
source                  1..9
                        mol_type = protein
                        organism = synthetic construct
                        note = Description of Artificial Sequence: Synthetic probe
SITE                    4
                        note = Norleucine
SITE                    9
                        note = lysine amide modified with a CPQ2 quencher
SEQUENCE: 963
GWEXVKIGK                                                                          9

SEQ ID NO: 964          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 964
GWVGASHGK                                                                          9

SEQ ID NO: 965          moltype = AA  length = 9
FEATURE                 Location/Qualifiers
source                  1..9
                        mol_type = protein
                        organism = synthetic construct
                        note = Description of Artificial Sequence: Synthetic probe
SITE                    7
                        note = Norleucine
SITE                    9
                        note = Lysine modified with a CPQ2 quencher
SEQUENCE: 965
GITTLYXGK                                                                          9

SEQ ID NO: 966          moltype = AA  length = 9
FEATURE                 Location/Qualifiers
source                  1..9
                        mol_type = protein
```

```
                        -continued
                        organism = synthetic construct
                        note = Description of Artificial Sequence: Synthetic probe
SITE                    9
                        note = Lysine modified with a CPQ2 quencher
SEQUENCE: 966
GGHIDEYGK                                                                        9

SEQ ID NO: 967          moltype = AA   length = 9
FEATURE                 Location/Qualifiers
source                  1..9
                        mol_type = protein
                        organism = synthetic construct
                        note = Description of Artificial Sequence: Synthetic probe
SITE                    4
                        note = Norleucine
SITE                    9
                        note = lysine amide modified with a CPQ2 quencher
SEQUENCE: 967
GKVXDYGGK                                                                        9

SEQ ID NO: 968          moltype = AA   length = 9
FEATURE                 Location/Qualifiers
source                  1..9
                        mol_type = protein
                        organism = synthetic construct
                        note = Description of Artificial Sequence: Synthetic probe
SITE                    7
                        note = Norleucine
SITE                    9
                        note = lysine amide modified with a CPQ2 quencher
SEQUENCE: 968
GQEKQTXGK                                                                        9

SEQ ID NO: 969          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 969
GEVGHEAGK                                                                        9

SEQ ID NO: 970          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 970
GAWEGQYGK                                                                        9

SEQ ID NO: 971          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 971
GFLVQWTGK                                                                        9

SEQ ID NO: 972          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 972
GSKWGYWGK                                                                        9

SEQ ID NO: 973          moltype = AA   length = 9
FEATURE                 Location/Qualifiers
```

```
                        -continued source                  1..9
                        mol_type = protein
                        organism = synthetic construct
                        note = Description of Artificial Sequence: Synthetic probe
SITE                    6
                        note = Norleucine
SITE                    9
                        note = Lysine modified with a CPQ2 quencher
SEQUENCE: 973
GTWISXQGK                                                                        9

SEQ ID NO: 974          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 974
GVIDKDFGK                                                                        9

SEQ ID NO: 975          moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 975
GVKFAIYGK                                                                        9

SEQ ID NO: 976          moltype = AA  length = 9
FEATURE                 Location/Qualifiers
source                  1..9
                        mol_type = protein
                        organism = synthetic construct
                        note = Description of Artificial Sequence: Synthetic probe
SITE                    5
                        note = Norleucine
SITE                    9
                        note = Lysine modified with a CPQ2 quencher
SEQUENCE: 976
GHNQXKSGK                                                                        9

SEQ ID NO: 977          moltype = AA  length = 9
FEATURE                 Location/Qualifiers
source                  1..9
                        mol_type = protein
                        organism = synthetic construct
                        note = Description of Artificial Sequence: Synthetic probe
SITE                    7
                        note = Norleucine
SITE                    9
                        note = Lysine modified with a CPQ2 quencher
SEQUENCE: 977
GQYVFFXGK                                                                        9

SEQ ID NO: 978          moltype = AA  length = 9
FEATURE                 Location/Qualifiers
source                  1..9
                        mol_type = protein
                        organism = synthetic construct
                        note = Description of Artificial Sequence: Synthetic probe
SITE                    7
                        note = Norleucine
SITE                    9
                        note = lysine amide modified with a CPQ2 quencher
SEQUENCE: 978
GYNPREXGK                                                                        9

SEQ ID NO: 979          moltype = AA  length = 9
FEATURE                 Location/Qualifiers
source                  1..9
                        mol_type = protein
                        organism = synthetic construct
                        note = Description of Artificial Sequence: Synthetic probe
SITE                    5
```

```
                        note = Norleucine
SITE                    9
                        note = Lysine modified with a CPQ2 quencher
SEQUENCE: 979
GKHGXPEGK                                                                      9

SEQ ID NO: 980          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = lysine amide modified with a CPQ2 quencher
SEQUENCE: 980
GWSREYWGK                                                                      9

SEQ ID NO: 981          moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 981
GIDRVDKGK                                                                      9

SEQ ID NO: 982          moltype = AA   length = 11
FEATURE                 Location/Qualifiers
source                  1..11
                        mol_type = protein
                        organism = synthetic construct
                        note = Description of Artificial Sequence: Synthetic probe
SITE                    1
                        note = D-Lysine
SITE                    2
                        note = D-Lysine
SITE                    10
                        note = Lysine modified with a CPQ2 quencher
SITE                    11
                        note = Hydroxy leucine
SEQUENCE: 982
KKGDRENSPK L                                                                  11

SEQ ID NO: 983          moltype = AA   length = 11
FEATURE                 Location/Qualifiers
source                  1..11
                        mol_type = protein
                        organism = synthetic construct
                        note = Description of Artificial Sequence: Synthetic probe
SITE                    1
                        note = D-Lysine
SITE                    2
                        note = D-Lysine
SITE                    11
                        note = Hydroxy lysine modified with a CPQ2 quencher
SEQUENCE: 983
KKGDRENSPL K                                                                  11

SEQ ID NO: 984          moltype = AA   length = 9
FEATURE                 Location/Qualifiers
source                  1..9
                        mol_type = protein
                        organism = synthetic construct
                        note = Description of Artificial Sequence: Synthetic probe
SITE                    8
                        note = Lysine modified with a CPQ2 quencher
SITE                    9
                        note = Hydroxy Glutamine
SEQUENCE: 984
GNAGSKFKQ                                                                      9

SEQ ID NO: 985          moltype = AA   length = 9
FEATURE                 Location/Qualifiers
source                  1..9
                        mol_type = protein
                        organism = synthetic construct
                        note = Description of Artificial Sequence: Synthetic probe
```

```
SITE                        9
                            note = Hydroxy lysine modified with a CPQ2 quencher
SEQUENCE: 985
GNAGSKFQK                                                                    9

SEQ ID NO: 986              moltype = AA  length = 11
FEATURE                     Location/Qualifiers
source                      1..11
                            mol_type = protein
                            organism = synthetic construct
                            note = Description of Artificial Sequence: Synthetic probe
SITE                        1
                            note = D-Lysine
SITE                        2
                            note = D-Lysine
SITE                        10
                            note = Lysine modified with a CPQ2 quencher
SITE                        11
                            note = Hydroxy Valine
SEQUENCE: 986
KKGHLLGFYK V                                                                11

SEQ ID NO: 987              moltype = AA  length = 11
FEATURE                     Location/Qualifiers
source                      1..11
                            mol_type = protein
                            organism = synthetic construct
                            note = Description of Artificial Sequence: Synthetic probe
SITE                        1
                            note = D-Lysine
SITE                        2
                            note = D-Lysine
SITE                        11
                            note = Hydroxy lysine modified with a CPQ2 quencher
SEQUENCE: 987
KKGHLLGFYV K                                                                11

SEQ ID NO: 988              moltype = AA  length = 11
FEATURE                     Location/Qualifiers
source                      1..11
                            mol_type = protein
                            organism = synthetic construct
                            note = Description of Artificial Sequence: Synthetic probe
SITE                        1
                            note = D-Lysine
SITE                        2
                            note = D-Lysine
SITE                        9
                            note = Norleucine
SITE                        10
                            note = Lysine modified with a CPQ2 quencher
SITE                        11
                            note = Hydroxy Norleucine
SEQUENCE: 988
KKGQEKQTXK X                                                                11

SEQ ID NO: 989              moltype = AA  length = 11
FEATURE                     Location/Qualifiers
source                      1..11
                            mol_type = protein
                            organism = synthetic construct
                            note = Description of Artificial Sequence: Synthetic probe
SITE                        1
                            note = D-Lysine
SITE                        2
                            note = D-Lysine
SITE                        9
                            note = Norleucine
SITE                        10
                            note = Norleucine
SITE                        11
                            note = Hydroxy lysine modified with a CPQ2 quencher
SEQUENCE: 989
KKGQEKQTXX K                                                                11

SEQ ID NO: 990              moltype = AA  length = 10
FEATURE                     Location/Qualifiers
source                      1..10
                            mol_type = protein
```

| | | |
|---|---|---|
| | | organism = synthetic construct<br>note = Description of Artificial Sequence: Synthetic probe |
| SITE | 1 | |
| | | note = D-Lysine |
| SITE | 9 | |
| | | note = Lysine modified with a CPQ2 quencher |
| SITE | 10 | |
| | | note = Hydroxy Tryptophan |
| SEQUENCE: 990 | | |
| KGDPFVVSKW | | 10 |
| | | |
| SEQ ID NO: 991 | moltype = AA length = 10 | |
| FEATURE | Location/Qualifiers | |
| source | 1..10 | |
| | mol_type = protein | |
| | organism = synthetic construct | |
| | note = Description of Artificial Sequence: Synthetic probe | |
| SITE | 1 | |
| | note = D-Lysine | |
| SITE | 10 | |
| | note = Hydroxy lysine modified with a CPQ2 quencher | |
| SEQUENCE: 991 | | |
| KGDPFVVSWK | | 10 |
| | | |
| SEQ ID NO: 992 | moltype = AA length = 9 | |
| FEATURE | Location/Qualifiers | |
| source | 1..9 | |
| | mol_type = protein | |
| | organism = synthetic construct | |
| | note = Description of Artificial Sequence: Synthetic probe | |
| SITE | 8 | |
| | note = Lysine modified with a CPQ2 quencher | |
| SITE | 9 | |
| | note = Hydroxy Arginine | |
| SEQUENCE: 992 | | |
| GNAYNEIKR | | 9 |
| | | |
| SEQ ID NO: 993 | moltype = AA length = 9 | |
| FEATURE | Location/Qualifiers | |
| source | 1..9 | |
| | mol_type = protein | |
| | organism = synthetic construct | |
| | note = Description of Artificial Sequence: Synthetic probe | |
| SITE | 9 | |
| | note = Hydroxy lysine modified with a CPQ2 quencher | |
| SEQUENCE: 993 | | |
| GNAYNEIRK | | 9 |
| | | |
| SEQ ID NO: 994 | moltype = AA length = 9 | |
| FEATURE | Location/Qualifiers | |
| source | 1..9 | |
| | mol_type = protein | |
| | organism = synthetic construct | |
| | note = Description of Artificial Sequence: Synthetic probe | |
| SITE | 3 | |
| | note = Norleucine | |
| SITE | 8 | |
| | note = Lysine modified with a CPQ2 quencher | |
| SITE | 9 | |
| | note = Hydroxy Asparagine | |
| SEQUENCE: 994 | | |
| GVXRQSEKN | | 9 |
| | | |
| SEQ ID NO: 995 | moltype = AA length = 9 | |
| FEATURE | Location/Qualifiers | |
| source | 1..9 | |
| | mol_type = protein | |
| | organism = synthetic construct | |
| | note = Description of Artificial Sequence: Synthetic probe | |
| SITE | 3 | |
| | note = Norleucine | |
| SITE | 9 | |
| | note = Lysine modified with a CPQ2 quencher | |
| SEQUENCE: 995 | | |
| GVXRQSENK | | 9 |
| | | |
| SEQ ID NO: 996 | moltype = AA length = 9 | |
| FEATURE | Location/Qualifiers | |
| source | 1..9 | |

```
                        mol_type = protein
                        organism = synthetic construct
                        note = Description of Artificial Sequence: Synthetic probe
SITE                    7
                        note = Norleucine
SITE                    8
                        note = Lysine modified with a CPQ2 quencher
SITE                    9
                        note = Hydroxy Isoleucine
SEQUENCE: 996
GYNPREXKI                                                                        9

SEQ ID NO: 997          moltype = AA   length = 9
FEATURE                 Location/Qualifiers
source                  1..9
                        mol_type = protein
                        organism = synthetic construct
                        note = Description of Artificial Sequence: Synthetic probe
SITE                    7
                        note = Norleucine
SITE                    9
                        note = Hydroxy lysine modified with a CPQ2 quencher
SEQUENCE: 997
GYNPREXIK                                                                        9

SEQ ID NO: 998          moltype = AA   length = 10
FEATURE                 Location/Qualifiers
source                  1..10
                        mol_type = protein
                        organism = synthetic construct
                        note = Description of Artificial Sequence: Synthetic probe
SITE                    1
                        note = D-Lysine
SITE                    9
                        note = Lysine modified with a CPQ2 quencher
SITE                    10
                        note = Hydroxy Lysine
SEQUENCE: 998
KGEFVHNPKK                                                                      10

SEQ ID NO: 999          moltype = AA   length = 10
FEATURE                 Location/Qualifiers
source                  1..10
                        mol_type = protein
                        organism = synthetic construct
                        note = Description of Artificial Sequence: Synthetic probe
SITE                    1
                        note = D-Lysine
SITE                    10
                        note = Hydroxy lysine modified with a CPQ2 quencher
SEQUENCE: 999
KGEFVHNPKK                                                                      10

SEQ ID NO: 1000         moltype = AA   length = 9
FEATURE                 Location/Qualifiers
source                  1..9
                        mol_type = protein
                        organism = synthetic construct
                        note = Description of Artificial Sequence: Synthetic probe
SITE                    8
                        note = Lysine modified with a CPQ2 quencher
SITE                    9
                        note = Hydroxy Histidine
SEQUENCE: 1000
GKRVQFLKH                                                                        9

SEQ ID NO: 1001         moltype = AA   length = 9
FEATURE                 Location/Qualifiers
source                  1..9
                        mol_type = protein
                        organism = synthetic construct
                        note = Description of Artificial Sequence: Synthetic probe
SITE                    9
                        note = Hydroxy lysine modified with a CPQ2 quencher
SEQUENCE: 1001
GKRVQFLHK                                                                        9

SEQ ID NO: 1002         moltype = AA   length = 10
FEATURE                 Location/Qualifiers
```

```
                        -continued source                  1..10
                        mol_type = protein
                        organism = synthetic construct
                        note = Description of Artificial Sequence: Synthetic probe
SITE                    1
                        note = D-Lysine
SITE                    5
                        note = Norleucine
SITE                    9
                        note = Lysine modified with a CPQ2 quencher
SITE                    10
                        note = Hydroxy Glycine
SEQUENCE: 1002
KGLIXHKNKG                                                                    10

SEQ ID NO: 1003         moltype = AA  length = 10
FEATURE                 Location/Qualifiers
source                  1..10
                        mol_type = protein
                        organism = synthetic construct
                        note = Description of Artificial Sequence: Synthetic probe
SITE                    1
                        note = D-Lysine
SITE                    5
                        note = Norleucine
SITE                    10
                        note = Hydroxy lysine modified with a CPQ2 quencher
SEQUENCE: 1003
KGLIXHKNGK                                                                    10

SEQ ID NO: 1004         moltype = AA  length = 11
FEATURE                 Location/Qualifiers
source                  1..11
                        mol_type = protein
                        organism = synthetic construct
                        note = Description of Artificial Sequence: Synthetic probe
SITE                    1
                        note = D-Lysine
SITE                    2
                        note = D-Lysine
SITE                    6
                        note = Norleucine
SITE                    10
                        note = Lysine modified with a CPQ2 quencher
SITE                    11
                        note = Hydroxy Serine
SEQUENCE: 1004
KKGWAXLYHK S                                                                  11

SEQ ID NO: 1005         moltype = AA  length = 11
FEATURE                 Location/Qualifiers
source                  1..11
                        mol_type = protein
                        organism = synthetic construct
                        note = Description of Artificial Sequence: Synthetic probe
SITE                    1
                        note = D-Lysine
SITE                    2
                        note = D-Lysine
SITE                    6
                        note = Norleucine
SITE                    11
                        note = Hydroxy lysine modified with a CPQ2 quencher
SEQUENCE: 1005
KKGWAXLYHS K                                                                  11

SEQ ID NO: 1006         moltype = AA  length = 11
FEATURE                 Location/Qualifiers
source                  1..11
                        mol_type = protein
                        organism = synthetic construct
                        note = Description of Artificial Sequence: Synthetic probe
SITE                    1
                        note = D-Lysine
SITE                    2
                        note = D-Lysine
SITE                    10
                        note = Lysine modified with a CPQ2 quencher
SITE                    11
```

```
                           note = Hydroxy Tyrosine
SEQUENCE: 1006
KKGAHDIVNK Y                                                            11

SEQ ID NO: 1007        moltype = AA  length = 11
FEATURE                Location/Qualifiers
source                 1..11
                       mol_type = protein
                       organism = synthetic construct
                       note = Description of Artificial Sequence: Synthetic probe
SITE                   1
                       note = D-Lysine
SITE                   2
                       note = D-Lysine
SITE                   11
                       note = Hydroxy lysine modified with a CPQ2 quencher
SEQUENCE: 1007
KKGAHDIVNY K                                                            11

SEQ ID NO: 1008        moltype = AA  length = 10
FEATURE                Location/Qualifiers
source                 1..10
                       mol_type = protein
                       organism = synthetic construct
                       note = Description of Artificial Sequence: Synthetic probe
SITE                   1
                       note = D-Lysine
SITE                   9
                       note = Lysine modified with a CPQ2 quencher
SITE                   10
                       note = Hydroxy Proline
SEQUENCE: 1008
KGSVFVIEKP                                                              10

SEQ ID NO: 1009        moltype = AA  length = 10
FEATURE                Location/Qualifiers
source                 1..10
                       mol_type = protein
                       organism = synthetic construct
                       note = Description of Artificial Sequence: Synthetic probe
SITE                   1
                       note = D-Lysine
SITE                   10
                       note = Hydroxy lysine modified with a CPQ2 quencher
SEQUENCE: 1009
KGSVFVIEPK                                                              10

SEQ ID NO: 1010        moltype = AA  length = 10
FEATURE                Location/Qualifiers
source                 1..10
                       mol_type = protein
                       organism = synthetic construct
                       note = Description of Artificial Sequence: Synthetic probe
SITE                   1
                       note = D-Lysine
SITE                   9
                       note = Lysine modified with a CPQ2 quencher
SITE                   10
                       note = Hydroxy Glutamic Acid
SEQUENCE: 1010
KGPPSGLSKE                                                              10

SEQ ID NO: 1011        moltype = AA  length = 10
FEATURE                Location/Qualifiers
source                 1..10
                       mol_type = protein
                       organism = synthetic construct
                       note = Description of Artificial Sequence: Synthetic probe
SITE                   1
                       note = D-Lysine
SITE                   10
                       note = Hydroxy lysine modified with a CPQ2 quencher
SEQUENCE: 1011
KGPPSGLSEK                                                              10

SEQ ID NO: 1012        moltype = AA  length = 11
FEATURE                Location/Qualifiers
source                 1..11
                       mol_type = protein
```

```
                        organism = synthetic construct
                        note = Description of Artificial Sequence: Synthetic probe
SITE                    1
                        note = D-Lysine
SITE                    2
                        note = D-Lysine
SITE                    10
                        note = Lysine modified with a CPQ2 quencher
SITE                    11
                        note = Hydroxy Phenylalanine
SEQUENCE: 1012
KKGRWYGGIK F                                                                    11

SEQ ID NO: 1013         moltype = AA  length = 11
FEATURE                 Location/Qualifiers
source                  1..11
                        mol_type = protein
                        organism = synthetic construct
                        note = Description of Artificial Sequence: Synthetic probe
SITE                    1
                        note = D-Lysine
SITE                    2
                        note = D-Lysine
SITE                    11
                        note = Hydroxy lysine modified with a CPQ2 quencher
SEQUENCE: 1013
KKGRWYGGIF K                                                                    11

SEQ ID NO: 1014         moltype = AA  length = 10
FEATURE                 Location/Qualifiers
source                  1..10
                        mol_type = protein
                        organism = synthetic construct
                        note = Description of Artificial Sequence: Synthetic probe
SITE                    1
                        note = D-Lysine
SITE                    8
                        note = Norleucine
SITE                    9
                        note = Lysine modified with a CPQ2 quencher
SITE                    10
                        note = Hydroxy Aspartic Acid
SEQUENCE: 1014
KGQYVFFXKD                                                                      10

SEQ ID NO: 1015         moltype = AA  length = 10
FEATURE                 Location/Qualifiers
source                  1..10
                        mol_type = protein
                        organism = synthetic construct
                        note = Description of Artificial Sequence: Synthetic probe
SITE                    1
                        note = D-Lysine
SITE                    8
                        note = Norleucine
SITE                    10
                        note = Hydroxy lysine modified with a CPQ2 quencher
SEQUENCE: 1015
KGQYVFFXDK                                                                      10

SEQ ID NO: 1016         moltype = AA  length = 10
FEATURE                 Location/Qualifiers
source                  1..10
                        mol_type = protein
                        organism = synthetic construct
                        note = Description of Artificial Sequence: Synthetic probe
SITE                    1
                        note = D-Lysine
SITE                    9
                        note = Lysine modified with a CPQ2 quencher
SITE                    10
                        note = Hydroxy Threonine
SEQUENCE: 1016
KGFAKYYKKT                                                                      10

SEQ ID NO: 1017         moltype = AA  length = 10
FEATURE                 Location/Qualifiers
source                  1..10
                        mol_type = protein
```

```
                            organism = synthetic construct
                            note = Description of Artificial Sequence: Synthetic probe
SITE                        1
                            note = D-Lysine
SITE                        10
                            note = Hydroxy lysine modified with a CPQ2 quencher
SEQUENCE: 1017
KGFAKYYKTK                                                                   10

SEQ ID NO: 1018             moltype = AA  length = 10
FEATURE                     Location/Qualifiers
source                      1..10
                            mol_type = protein
                            organism = synthetic construct
                            note = Description of Artificial Sequence: Synthetic probe
SITE                        1
                            note = D-Lysine
SITE                        9
                            note = Lysine modified with a CPQ2 quencher
SITE                        10
                            note = Hydroxy Alanine
SEQUENCE: 1018
KGQVKHFTKA                                                                   10

SEQ ID NO: 1019             moltype = AA  length = 10
FEATURE                     Location/Qualifiers
source                      1..10
                            mol_type = protein
                            organism = synthetic construct
                            note = Description of Artificial Sequence: Synthetic probe
SITE                        1
                            note = D-Lysine
SITE                        10
                            note = Hydroxy lysine modified with a CPQ2 quencher
SEQUENCE: 1019
KGQVKHFTAK                                                                   10

SEQ ID NO: 1020             moltype =    length =
SEQUENCE: 1020
000

SEQ ID NO: 1021             moltype = AA  length = 10
FEATURE                     Location/Qualifiers
source                      1..10
                            mol_type = protein
                            organism = synthetic construct
                            note = Description of Artificial Sequence: Synthetic probe
SITE                        2
                            note = carboxy-fluorescein-L-lysine
SITE                        10
                            note = lysine amide modified with a CPQ2 quencher
SEQUENCE: 1021
HKDRENSPGK                                                                   10

SEQ ID NO: 1022             moltype = AA  length = 10
FEATURE                     Location/Qualifiers
source                      1..10
                            mol_type = protein
                            organism = synthetic construct
                            note = Description of Artificial Sequence: Synthetic probe
SITE                        1
                            note = carboxy-fluorescein-L-lysine
SITE                        10
                            note = lysine amide modified with a CPQ2 quencher
SEQUENCE: 1022
KHDRENSPGK                                                                   10

SEQ ID NO: 1023             moltype = AA  length = 11
FEATURE                     Location/Qualifiers
source                      1..11
                            mol_type = protein
                            organism = synthetic construct
                            note = Description of Artificial Sequence: Synthetic probe
SITE                        2
                            note = carboxy-fluorescein-L-lysine
SITE                        10
                            note = D-Lysine
SITE                        11
                            note = lysine amide modified with a CPQ2 quencher
```

-continued

```
SEQUENCE: 1023
WKNAGSKFGK K                                                                        11

SEQ ID NO: 1024         moltype = AA  length = 11
FEATURE                 Location/Qualifiers
source                  1..11
                        mol_type = protein
                        organism = synthetic construct
                        note = Description of Artificial Sequence: Synthetic probe
SITE                    1
                        note = carboxy-fluorescein-L-lysine
SITE                    10
                        note = D-Lysine
SITE                    11
                        note = lysine amide modified with a CPQ2 quencher
SEQUENCE: 1024
KWNAGSKFGK K                                                                        11

SEQ ID NO: 1025         moltype = AA  length = 11
FEATURE                 Location/Qualifiers
source                  1..11
                        mol_type = protein
                        organism = synthetic construct
                        note = Description of Artificial Sequence: Synthetic probe
SITE                    2
                        note = carboxy-fluorescein-L-lysine
SITE                    10
                        note = D-Lysine
SITE                    11
                        note = lysine amide modified with a CPQ2 quencher
SEQUENCE: 1025
SKHLLGFYGK K                                                                        11

SEQ ID NO: 1026         moltype = AA  length = 11
FEATURE                 Location/Qualifiers
source                  1..11
                        mol_type = protein
                        organism = synthetic construct
                        note = Description of Artificial Sequence: Synthetic probe
SITE                    1
                        note = carboxy-fluorescein-L-lysine
SITE                    10
                        note = D-Lysine
SITE                    11
                        note = lysine amide modified with a CPQ2 quencher
SEQUENCE: 1026
KSHLLGFYGK K                                                                        11

SEQ ID NO: 1027         moltype = AA  length = 10
FEATURE                 Location/Qualifiers
source                  1..10
                        mol_type = protein
                        organism = synthetic construct
                        note = Description of Artificial Sequence: Synthetic probe
SITE                    2
                        note = carboxy-fluorescein-L-lysine
SITE                    8
                        note = Norleucine
SITE                    10
                        note = lysine amide modified with a CPQ2 quencher
SEQUENCE: 1027
KKQEKQTXGK                                                                          10

SEQ ID NO: 1028         moltype = AA  length = 10
FEATURE                 Location/Qualifiers
source                  1..10
                        mol_type = protein
                        organism = synthetic construct
                        note = Description of Artificial Sequence: Synthetic probe
SITE                    1
                        note = carboxy-fluorescein-L-lysine
SITE                    8
                        note = Norleucine
SITE                    10
                        note = lysine amide modified with a CPQ2 quencher
SEQUENCE: 1028
KKQEKQTXGK                                                                          10

SEQ ID NO: 1029         moltype = AA  length = 10
```

```
FEATURE              Location/Qualifiers
source               1..10
                     mol_type = protein
                     organism = synthetic construct
                     note = Description of Artificial Sequence: Synthetic probe
SITE                 2
                     note = carboxy-fluorescein-L-lysine
SITE                 10
                     note = lysine amide modified with a CPQ2 quencher
SEQUENCE: 1029
GKDPFVVSGK                                                                    10

SEQ ID NO: 1030      moltype = AA  length = 10
FEATURE              Location/Qualifiers
source               1..10
                     mol_type = protein
                     organism = synthetic construct
                     note = Description of Artificial Sequence: Synthetic probe
SITE                 1
                     note = carboxy-fluorescein-L-lysine
SITE                 10
                     note = lysine amide modified with a CPQ2 quencher
SEQUENCE: 1030
KGDPFVVSGK                                                                    10

SEQ ID NO: 1031      moltype = AA  length = 10
FEATURE              Location/Qualifiers
source               1..10
                     mol_type = protein
                     organism = synthetic construct
                     note = Description of Artificial Sequence: Synthetic probe
SITE                 2
                     note = carboxy-fluorescein-L-lysine
SITE                 10
                     note = lysine amide modified with a CPQ2 quencher
SEQUENCE: 1031
PKNAYNEIGK                                                                    10

SEQ ID NO: 1032      moltype = AA  length = 10
FEATURE              Location/Qualifiers
source               1..10
                     mol_type = protein
                     organism = synthetic construct
                     note = Description of Artificial Sequence: Synthetic probe
SITE                 1
                     note = carboxy-fluorescein-L-lysine
SITE                 10
                     note = lysine amide modified with a CPQ2 quencher
SEQUENCE: 1032
KPNAYNEIGK                                                                    10

SEQ ID NO: 1033      moltype = AA  length = 11
FEATURE              Location/Qualifiers
source               1..11
                     mol_type = protein
                     organism = synthetic construct
                     note = Description of Artificial Sequence: Synthetic probe
SITE                 2
                     note = carboxy-fluorescein-L-lysine
SITE                 4
                     note = Norleucine
SITE                 10
                     note = D-Lysine
SITE                 11
                     note = lysine amide modified with a CPQ2 quencher
SEQUENCE: 1033
DKVXRQSEGK K                                                                  11

SEQ ID NO: 1034      moltype = AA  length = 11
FEATURE              Location/Qualifiers
source               1..11
                     mol_type = protein
                     organism = synthetic construct
                     note = Description of Artificial Sequence: Synthetic probe
SITE                 1
                     note = carboxy-fluorescein-L-lysine
SITE                 4
                     note = Norleucine
SITE                 10
```

```
                           -continued
                            note = D-Lysine
SITE                        11
                            note = lysine amide modified with a CPQ2 quencher
SEQUENCE: 1034
KDVXRQSEGK K                                                         11

SEQ ID NO: 1035             moltype = AA   length = 11
FEATURE                     Location/Qualifiers
source                      1..11
                            mol_type = protein
                            organism = synthetic construct
                            note = Description of Artificial Sequence: Synthetic probe
SITE                        2
                            note = carboxy-fluorescein-L-lysine
SITE                        8
                            note = Norleucine
SITE                        10
                            note = D-Lysine
SITE                        11
                            note = lysine amide modified with a CPQ2 quencher
SEQUENCE: 1035
EKYNPREXGK K                                                         11

SEQ ID NO: 1036             moltype = AA   length = 11
FEATURE                     Location/Qualifiers
source                      1..11
                            mol_type = protein
                            organism = synthetic construct
                            note = Description of Artificial Sequence: Synthetic probe
SITE                        1
                            note = carboxy-fluorescein-L-lysine
SITE                        8
                            note = Norleucine
SITE                        10
                            note = D-Lysine
SITE                        11
                            note = lysine amide modified with a CPQ2 quencher
SEQUENCE: 1036
KEYNPREXGK K                                                         11

SEQ ID NO: 1037             moltype = AA   length = 11
FEATURE                     Location/Qualifiers
source                      1..11
                            mol_type = protein
                            organism = synthetic construct
                            note = Description of Artificial Sequence: Synthetic probe
SITE                        2
                            note = carboxy-fluorescein-L-lysine
SITE                        10
                            note = D-Lysine
SITE                        11
                            note = lysine amide modified with a CPQ2 quencher
SEQUENCE: 1037
TKEFVHNPGK K                                                         11

SEQ ID NO: 1038             moltype = AA   length = 11
FEATURE                     Location/Qualifiers
source                      1..11
                            mol_type = protein
                            organism = synthetic construct
                            note = Description of Artificial Sequence: Synthetic probe
SITE                        1
                            note = carboxy-fluorescein-L-lysine
SITE                        10
                            note = D-Lysine
SITE                        11
                            note = lysine amide modified with a CPQ2 quencher
SEQUENCE: 1038
KTEFVHNPGK K                                                         11

SEQ ID NO: 1039             moltype = AA   length = 10
FEATURE                     Location/Qualifiers
source                      1..10
                            mol_type = protein
                            organism = synthetic construct
                            note = Description of Artificial Sequence: Synthetic probe
SITE                        2
                            note = carboxy-fluorescein-L-lysine
SITE                        10
```

```
                        note = lysine amide modified with a CPQ2 quencher
SEQUENCE: 1039
QKKRVQFLGK                                                              10

SEQ ID NO: 1040         moltype = AA   length = 10
FEATURE                 Location/Qualifiers
source                  1..10
                        mol_type = protein
                        organism = synthetic construct
                        note = Description of Artificial Sequence: Synthetic probe
SITE                    1
                        note = carboxy-fluorescein-L-lysine
SITE                    10
                        note = lysine amide modified with a CPQ2 quencher
SEQUENCE: 1040
KQKRVQFLGK                                                              10

SEQ ID NO: 1041         moltype = AA   length = 10
FEATURE                 Location/Qualifiers
source                  1..10
                        mol_type = protein
                        organism = synthetic construct
                        note = Description of Artificial Sequence: Synthetic probe
SITE                    2
                        note = carboxy-fluorescein-L-lysine
SITE                    5
                        note = Norleucine
SITE                    10
                        note = lysine amide modified with a CPQ2 quencher
SEQUENCE: 1041
YKLIXHKNGK                                                              10

SEQ ID NO: 1042         moltype = AA   length = 10
FEATURE                 Location/Qualifiers
source                  1..10
                        mol_type = protein
                        organism = synthetic construct
                        note = Description of Artificial Sequence: Synthetic probe
SITE                    1
                        note = carboxy-fluorescein-L-lysine
SITE                    5
                        note = Norleucine
SITE                    10
                        note = lysine amide modified with a CPQ2 quencher
SEQUENCE: 1042
KYLIXHKNGK                                                              10

SEQ ID NO: 1043         moltype = AA   length = 11
FEATURE                 Location/Qualifiers
source                  1..11
                        mol_type = protein
                        organism = synthetic construct
                        note = Description of Artificial Sequence: Synthetic probe
SITE                    2
                        note = carboxy-fluorescein-L-lysine
SITE                    5
                        note = Norleucine
SITE                    10
                        note = D-Lysine
SITE                    11
                        note = lysine amide modified with a CPQ2 quencher
SEQUENCE: 1043
FKWAXLYHGK K                                                            11

SEQ ID NO: 1044         moltype = AA   length = 11
FEATURE                 Location/Qualifiers
source                  1..11
                        mol_type = protein
                        organism = synthetic construct
                        note = Description of Artificial Sequence: Synthetic probe
SITE                    1
                        note = carboxy-fluorescein-L-lysine
SITE                    5
                        note = Norleucine
SITE                    10
                        note = D-Lysine
SITE                    11
                        note = lysine amide modified with a CPQ2 quencher
SEQUENCE: 1044
```

```
KFWAXLYHGK K                                                                         11

SEQ ID NO: 1045         moltype = AA  length = 11
FEATURE                 Location/Qualifiers
source                  1..11
                        mol_type = protein
                        organism = synthetic construct
                        note = Description of Artificial Sequence: Synthetic probe
SITE                    2
                        note = carboxy-fluorescein-L-lysine
SITE                    10
                        note = D-Lysine
SITE                    11
                        note = lysine amide modified with a CPQ2 quencher
SEQUENCE: 1045
IKAHDIVNGK K                                                                         11

SEQ ID NO: 1046         moltype = AA  length = 11
FEATURE                 Location/Qualifiers
source                  1..11
                        mol_type = protein
                        organism = synthetic construct
                        note = Description of Artificial Sequence: Synthetic probe
SITE                    1
                        note = carboxy-fluorescein-L-lysine
SITE                    10
                        note = D-Lysine
SITE                    11
                        note = lysine amide modified with a CPQ2 quencher
SEQUENCE: 1046
KIAHDIVNGK K                                                                         11

SEQ ID NO: 1047         moltype = AA  length = 10
FEATURE                 Location/Qualifiers
source                  1..10
                        mol_type = protein
                        organism = synthetic construct
                        note = Description of Artificial Sequence: Synthetic probe
SITE                    2
                        note = carboxy-fluorescein-L-lysine
SITE                    10
                        note = lysine amide modified with a CPQ2 quencher
SEQUENCE: 1047
VKSVFVIEGK                                                                           10

SEQ ID NO: 1048         moltype = AA  length = 10
FEATURE                 Location/Qualifiers
source                  1..10
                        mol_type = protein
                        organism = synthetic construct
                        note = Description of Artificial Sequence: Synthetic probe
SITE                    1
                        note = carboxy-fluorescein-L-lysine
SITE                    10
                        note = lysine amide modified with a CPQ2 quencher
SEQUENCE: 1048
KVSVFVIEGK                                                                           10

SEQ ID NO: 1049         moltype = AA  length = 10
FEATURE                 Location/Qualifiers
source                  1..10
                        mol_type = protein
                        organism = synthetic construct
                        note = Description of Artificial Sequence: Synthetic probe
SITE                    1
                        note = Norleucine
SITE                    2
                        note = carboxy-fluorescein-L-lysine
SITE                    10
                        note = lysine amide modified with a CPQ2 quencher
SEQUENCE: 1049
XKPPSGLSGK                                                                           10

SEQ ID NO: 1050         moltype = AA  length = 10
FEATURE                 Location/Qualifiers
source                  1..10
                        mol_type = protein
                        organism = synthetic construct
                        note = Description of Artificial Sequence: Synthetic probe
```

-continued

| | |
|---|---|
| SITE | 1 |
| | note = carboxy-fluorescein-L-lysine |
| SITE | 2 |
| | note = Norleucine |
| SITE | 10 |
| | note = lysine amide modified with a CPQ2 quencher |
| SEQUENCE: 1050 | |
| KXPPSGLSGK | 10 |
| | |
| SEQ ID NO: 1051 | moltype = AA  length = 11 |
| FEATURE | Location/Qualifiers |
| source | 1..11 |
| | mol_type = protein |
| | organism = synthetic construct |
| | note = Description of Artificial Sequence: Synthetic probe |
| SITE | 2 |
| | note = carboxy-fluorescein-L-lysine |
| SITE | 10 |
| | note = D-Lysine |
| SITE | 11 |
| | note = lysine amide modified with a CPQ2 quencher |
| SEQUENCE: 1051 | |
| LKRWYGGIGK K | 11 |
| | |
| SEQ ID NO: 1052 | moltype = AA  length = 11 |
| FEATURE | Location/Qualifiers |
| source | 1..11 |
| | mol_type = protein |
| | organism = synthetic construct |
| | note = Description of Artificial Sequence: Synthetic probe |
| SITE | 1 |
| | note = carboxy-fluorescein-L-lysine |
| SITE | 10 |
| | note = D-Lysine |
| SITE | 11 |
| | note = lysine amide modified with a CPQ2 quencher |
| SEQUENCE: 1052 | |
| KLRWYGGIGK K | 11 |
| | |
| SEQ ID NO: 1053 | moltype = AA  length = 10 |
| FEATURE | Location/Qualifiers |
| source | 1..10 |
| | mol_type = protein |
| | organism = synthetic construct |
| | note = Description of Artificial Sequence: Synthetic probe |
| SITE | 2 |
| | note = carboxy-fluorescein-L-lysine |
| SITE | 8 |
| | note = Norleucine |
| SITE | 10 |
| | note = lysine amide modified with a CPQ2 quencher |
| SEQUENCE: 1053 | |
| NKQYVFFXGK | 10 |
| | |
| SEQ ID NO: 1054 | moltype = AA  length = 10 |
| FEATURE | Location/Qualifiers |
| source | 1..10 |
| | mol_type = protein |
| | organism = synthetic construct |
| | note = Description of Artificial Sequence: Synthetic probe |
| SITE | 1 |
| | note = carboxy-fluorescein-L-lysine |
| SITE | 8 |
| | note = Norleucine |
| SITE | 10 |
| | note = lysine amide modified with a CPQ2 quencher |
| SEQUENCE: 1054 | |
| KNQYVFFXGK | 10 |
| | |
| SEQ ID NO: 1055 | moltype = AA  length = 10 |
| FEATURE | Location/Qualifiers |
| source | 1..10 |
| | mol_type = protein |
| | organism = synthetic construct |
| | note = Description of Artificial Sequence: Synthetic probe |
| SITE | 2 |
| | note = carboxy-fluorescein-L-lysine |
| SITE | 10 |
| | note = lysine amide modified with a CPQ2 quencher |

```
SEQUENCE: 1055
AKFAKYYKGK                                                                      10

SEQ ID NO: 1058              moltype = AA  length = 10
FEATURE                      Location/Qualifiers
source                       1..10
                             mol_type = protein
                             organism = synthetic construct
                             note = Description of Artificial Sequence: Synthetic probe
SITE                         1
                             note = carboxy-fluorescein-L-lysine
SITE                         10
                             note = lysine amide modified with a CPQ2 quencher
SEQUENCE: 1056
KAFAKYYKGK                                                                      10

SEQ ID NO: 1057              moltype = AA  length = 10
FEATURE                      Location/Qualifiers
source                       1..10
                             mol_type = protein
                             organism = synthetic construct
                             note = Description of Artificial Sequence: Synthetic probe
SITE                         2
                             note = carboxy-fluorescein-L-lysine
SITE                         10
                             note = lysine amide modified with a CPQ2 quencher
SEQUENCE: 1057
RKQVKHFTGK                                                                      10

SEQ ID NO: 1058              moltype = AA  length = 10
FEATURE                      Location/Qualifiers
source                       1..10
                             mol_type = protein
                             organism = synthetic construct
                             note = Description of Artificial Sequence: Synthetic probe
SITE                         1
                             note = carboxy-fluorescein-L-lysine
SITE                         10
                             note = lysine amide modified with a CPQ2 quencher
SEQUENCE: 1058
KRQVKHFTGK                                                                      10

SEQ ID NO: 1059              moltype = AA  length = 4
FEATURE                      Location/Qualifiers
source                       1..4
                             mol_type = protein
                             organism = synthetic construct
                             note = Description of Artificial Sequence: Synthetic probe
SITE                         1
                             note = carboxy-fluorescein-L-lysine
SITE                         4
                             note = lysine amide modified with a CPQ2 quencher
SEQUENCE: 1059
KPPK                                                                             4

SEQ ID NO: 1060              moltype = AA  length = 12
FEATURE                      Location/Qualifiers
source                       1..12
                             mol_type = protein
                             organism = synthetic construct
                             note = Description of Artificial Sequence: Synthetic probe
SITE                         2
                             note = D-Lysine
SITE                         3
                             note = D-Proline
SITE                         4
                             note = D-Isoleucine
SITE                         5
                             note = D-Leucine
SITE                         6
                             note = D-Phenylalanine
SITE                         7
                             note = D-Phenylalanine
SITE                         8
                             note = D-Arginine
SITE                         9
                             note = D-Leucine
SITE                         10
                             note = D-Lysine
```

| | | |
|---|---|---|
| SITE | 12<br>note = Lysine modified with a CPQ2 quencher | |
| SEQUENCE: 1060<br>GKPILFFRLK GK | | 12 |
| SEQ ID NO: 1061<br>SEQUENCE: 1061<br>000 | moltype =     length = | |
| SEQ ID NO: 1062<br>SEQUENCE: 1062<br>000 | moltype =     length = | |
| SEQ ID NO: 1063<br>SEQUENCE: 1063<br>000 | moltype =     length = | |
| SEQ ID NO: 1064<br>SEQUENCE: 1064<br>000 | moltype =     length = | |
| SEQ ID NO: 1065<br>SEQUENCE: 1065<br>000 | moltype =     length = | |
| SEQ ID NO: 1066<br>SEQUENCE: 1066<br>000 | moltype =     length = | |
| SEQ ID NO: 1067<br>SEQUENCE: 1067<br>000 | moltype =     length = | |
| SEQ ID NO: 1068<br>FEATURE<br>source | moltype = AA   length = 4<br>Location/Qualifiers<br>1..4<br>mol_type = protein<br>organism = synthetic construct | |
| SEQUENCE: 1068<br>ZGGR | | 4 |
| SEQ ID NO: 1069<br>SEQUENCE: 1069<br>000 | moltype =     length = | |
| SEQ ID NO: 1070<br>SEQUENCE: 1070<br>000 | moltype =     length = | |
| SEQ ID NO: 1071<br>SEQUENCE: 1071<br>000 | moltype =     length = | |
| SEQ ID NO: 1072<br>SEQUENCE: 1072<br>000 | moltype =     length = | |
| SEQ ID NO: 1073<br>SEQUENCE: 1073<br>000 | moltype =     length = | |
| SEQ ID NO: 1074<br>SEQUENCE: 1074<br>000 | moltype =     length = | |
| SEQ ID NO: 1075<br>FEATURE<br>source | moltype = AA   length = 4<br>Location/Qualifiers<br>1..4<br>mol_type = protein<br>organism = synthetic construct | |
| SEQUENCE: 1075<br>ZGPR | | 4 |
| SEQ ID NO: 1076<br>SEQUENCE: 1076<br>000 | moltype =     length = | |
| SEQ ID NO: 1077<br>SEQUENCE: 1077 | moltype =     length = | |

```
SEQ ID NO: 1078           moltype = AA  length = 4
FEATURE                   Location/Qualifiers
source                    1..4
                          mol_type = protein
                          organism = synthetic construct
SEQUENCE: 1078
ZLLR                                                                    4

SEQ ID NO: 1079           moltype =     length =
SEQUENCE: 1079
000

SEQ ID NO: 1080           moltype =     length =
SEQUENCE: 1080
000

SEQ ID NO: 1081           moltype =     length =
SEQUENCE: 1081
000

SEQ ID NO: 1082           moltype = AA  length = 5
FEATURE                   Location/Qualifiers
source                    1..5
                          mol_type = protein
                          organism = synthetic construct
                          note = Description of Artificial Sequence: Synthetic probe
SEQUENCE: 1082
ZLRGG                                                                   5

SEQ ID NO: 1083           moltype = AA  length = 8
FEATURE                   Location/Qualifiers
source                    1..8
                          mol_type = protein
                          organism = synthetic construct
                          note = Description of Artificial Sequence: Synthetic probe
SITE                      8
                          note = Lysine modified with a CPQ2 quencher
SEQUENCE: 1083
GRLRGGGK                                                                8

SEQ ID NO: 1084           moltype = AA  length = 12
FEATURE                   Location/Qualifiers
source                    1..12
                          mol_type = protein
                          organism = synthetic construct
                          note = Description of Artificial Sequence: Synthetic probe
SITE                      12
                          note = Lysine modified with a CPQ2 quencher
SEQUENCE: 1084
GRELNGGAPI GK                                                          12

SEQ ID NO: 1085           moltype = AA  length = 14
FEATURE                   Location/Qualifiers
source                    1..14
                          mol_type = protein
                          organism = synthetic construct
                          note = Description of Artificial Sequence: Synthetic probe
SITE                      14
                          note = Lysine modified with a CPQ2 quencher
SEQUENCE: 1085
GTSAVLQSGF RKGK                                                        14

SEQ ID NO: 1086           moltype = AA  length = 14
FEATURE                   Location/Qualifiers
source                    1..14
                          mol_type = protein
                          organism = synthetic construct
                          note = Description of Artificial Sequence: Synthetic probe
SITE                      14
                          note = Lysine modified with a CPQ2 quencher
SEQUENCE: 1086
GSGVTFQGKF KKGK                                                        14

SEQ ID NO: 1087           moltype = AA  length = 7
FEATURE                   Location/Qualifiers
source                    1..7
                          mol_type = protein
```

```
                    organism = synthetic construct
                    note = Description of Artificial Sequence: Synthetic probe
SITE                7
                    note = Lysine modified with a CPQ2 quencher
SEQUENCE: 1087
GAAFAGK                                                                         7

SEQ ID NO: 1088     moltype = AA  length = 11
FEATURE             Location/Qualifiers
source              1..11
                    mol_type = protein
                    organism = synthetic construct
                    note = Description of Artificial Sequence: Synthetic probe
SITE                11
                    note = Lysine modified with a CPQ2 quencher
SEQUENCE: 1088
GHGDQMAQKS K                                                                    11

SEQ ID NO: 1089     moltype = AA  length = 9
FEATURE             Location/Qualifiers
source              1..9
                    mol_type = protein
                    organism = synthetic construct
                    note = Description of Artificial Sequence: Synthetic probe
SITE                9
                    note = Lysine modified with a CPQ2 quencher
SEQUENCE: 1089
GGPLGMRGK                                                                       9

SEQ ID NO: 1090     moltype = AA  length = 12
FEATURE             Location/Qualifiers
source              1..12
                    mol_type = protein
                    organism = synthetic construct
                    note = Description of Artificial Sequence: Synthetic probe
SITE                8
                    note = L-homophenylalanine
SITE                12
                    note = Lysine modified with a CPQ2 quencher
SEQUENCE: 1090
GFFLAQAFRS KK                                                                   12

SEQ ID NO: 1091     moltype = AA  length = 17
FEATURE             Location/Qualifiers
source              1..17
                    mol_type = protein
                    organism = synthetic construct
                    note = Description of Artificial Sequence: Synthetic probe
SITE                17
                    note = Lysine modified with a CPQ2 quencher
SEQUENCE: 1091
GAHAVSRIRI YLLPAKK                                                              17

SEQ ID NO: 1092     moltype = AA  length = 9
FEATURE             Location/Qualifiers
source              1..9
                    mol_type = protein
                    organism = synthetic construct
                    note = Description of Artificial Sequence: Synthetic probe
SITE                9
                    note = Lysine modified with a CPQ2 quencher
SEQUENCE: 1092
GPLALWARK                                                                       9

SEQ ID NO: 1093     moltype = AA  length = 9
FEATURE             Location/Qualifiers
source              1..9
                    mol_type = protein
                    organism = synthetic construct
                    note = Description of Artificial Sequence: Synthetic probe
SITE                5
                    note = S-para-methoxybenzyl cysteine
SITE                9
                    note = Lysine modified with a CPQ2 quencher
SEQUENCE: 1093
GPLACWARK                                                                       9

SEQ ID NO: 1094     moltype = AA  length = 9
FEATURE             Location/Qualifiers
```

```
                        -continued source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 1094
GAPRWIQDK                                                                        9

SEQ ID NO: 1095         moltype = AA   length = 11
FEATURE                 Location/Qualifiers
source                  1..11
                        mol_type = protein
                        organism = synthetic construct
                        note = Description of Artificial Sequence: Synthetic probe
SITE                    11
                        note = Lysine modified with a CPQ2 quencher
SEQUENCE: 1095
GLREQQRLKS K                                                                    11

SEQ ID NO: 1096         moltype = AA   length = 14
FEATURE                 Location/Qualifiers
source                  1..14
                        mol_type = protein
                        organism = synthetic construct
                        note = Description of Artificial Sequence: Synthetic probe
SITE                    14
                        note = Lysine modified with a CPQ2 quencher
SEQUENCE: 1096
GEFPIYVFLP AKKK                                                                 14

SEQ ID NO: 1097         moltype = AA   length = 11
FEATURE                 Location/Qualifiers
source                  1..11
                        mol_type = protein
                        organism = synthetic construct
                        note = Description of Artificial Sequence: Synthetic probe
SITE                    11
                        note = Lysine modified with a CPQ2 quencher
SEQUENCE: 1097
GGAANLVRGG K                                                                    11

SEQ ID NO: 1098         moltype = AA   length = 11
FEATURE                 Location/Qualifiers
source                  1..11
                        mol_type = protein
                        organism = synthetic construct
                        note = Description of Artificial Sequence: Synthetic probe
SITE                    11
                        note = Lysine modified with a CPQ2 quencher
SEQUENCE: 1098
GGYAELRMGG K                                                                    11

SEQ ID NO: 1099         moltype = AA   length = 11
FEATURE                 Location/Qualifiers
source                  1..11
                        mol_type = protein
                        organism = synthetic construct
                        note = Description of Artificial Sequence: Synthetic probe
SITE                    11
                        note = Lysine modified with a CPQ2 quencher
SEQUENCE: 1099
GAAGAMFLEA K                                                                    11

SEQ ID NO: 1100         moltype = AA   length = 16
FEATURE                 Location/Qualifiers
source                  1..16
                        mol_type = protein
                        organism = synthetic construct
                        note = Description of Artificial Sequence: Synthetic probe
SITE                    16
                        note = Lysine modified with a CPQ2 quencher
SEQUENCE: 1100
GLGGSGQRGR KALEGK                                                               16

SEQ ID NO: 1101         moltype = AA   length = 16
FEATURE                 Location/Qualifiers
source                  1..16
                        mol_type = protein
```

```
                            organism = synthetic construct
                            note = Description of Artificial Sequence: Synthetic probe
SITE                        16
                            note = Lysine modified with a CPQ2 quencher
SEQUENCE: 1101
GLGGSGHYGR SGLEGK                                                           16

SEQ ID NO: 1102             moltype = AA   length = 7
FEATURE                     Location/Qualifiers
source                      1..7
                            mol_type = protein
                            organism = synthetic construct
                            note = Description of Artificial Sequence: Synthetic probe
SITE                        7
                            note = Lysine modified with a CPQ2 quencher
SEQUENCE: 1102
GYGRSGK                                                                      7

SEQ ID NO: 1103             moltype = AA   length = 8
FEATURE                     Location/Qualifiers
source                      1..8
                            mol_type = protein
                            organism = synthetic construct
                            note = Description of Artificial Sequence: Synthetic probe
SITE                        8
                            note = Lysine modified with a CPQ2 quencher
SEQUENCE: 1103
GFRGRKGK                                                                     8

SEQ ID NO: 1104             moltype = AA   length = 11
FEATURE                     Location/Qualifiers
source                      1..11
                            mol_type = protein
                            organism = synthetic construct
                            note = Description of Artificial Sequence: Synthetic probe
SITE                        11
                            note = Lysine modified with a CPQ2 quencher
SEQUENCE: 1104
GDRRKKLTQG K                                                                11

SEQ ID NO: 1105             moltype = AA   length = 9
FEATURE                     Location/Qualifiers
source                      1..9
                            mol_type = protein
                            organism = synthetic construct
                            note = Description of Artificial Sequence: Synthetic probe
SITE                        9
                            note = Lysine modified with a CPQ2 quencher
SEQUENCE: 1105
GHPGGPQGK                                                                    9

SEQ ID NO: 1106             moltype = AA   length = 10
FEATURE                     Location/Qualifiers
source                      1..10
                            mol_type = protein
                            organism = synthetic construct
                            note = Description of Artificial Sequence: Synthetic probe
SITE                        10
                            note = Lysine modified with a CPQ2 quencher
SEQUENCE: 1106
GKLRFSKQGK                                                                  10

SEQ ID NO: 1107             moltype = AA   length = 11
FEATURE                     Location/Qualifiers
source                      1..11
                            mol_type = protein
                            organism = synthetic construct
                            note = Description of Artificial Sequence: Synthetic probe
SITE                        11
                            note = Lysine modified with a CPQ2 quencher
SEQUENCE: 1107
GAIKFFSAQG K                                                                11

SEQ ID NO: 1108             moltype = AA   length = 11
FEATURE                     Location/Qualifiers
source                      1..11
                            mol_type = protein
                            organism = synthetic construct
                            note = Description of Artificial Sequence: Synthetic probe
```

| | | |
|---|---|---|
| SITE | 11<br>note = Lysine modified with a CPQ2 quencher | |
| SEQUENCE: 1108<br>GAIKFFVRQG K | | 11 |
| SEQ ID NO: 1109<br>FEATURE<br>source | moltype = AA   length = 12<br>Location/Qualifiers<br>1..12<br>mol_type = protein<br>organism = synthetic construct<br>note = Description of Artificial Sequence: Synthetic probe | |
| SITE | 12<br>note = Lysine modified with a CPQ2 quencher | |
| SEQUENCE: 1109<br>GRPPGFSAFK GK | | 12 |
| SEQ ID NO: 1110<br>FEATURE<br>source | moltype = AA   length = 9<br>Location/Qualifiers<br>1..9<br>mol_type = protein<br>organism = synthetic construct<br>note = Description of Artificial Sequence: Synthetic probe | |
| SITE | 9<br>note = Lysine modified with a CPQ2 quencher | |
| SEQUENCE: 1110<br>GFAPQLSGK | | 9 |
| SEQ ID NO: 1111<br>FEATURE<br>source | moltype = AA   length = 9<br>Location/Qualifiers<br>1..9<br>mol_type = protein<br>organism = synthetic construct<br>note = Description of Artificial Sequence: Synthetic probe | |
| SITE | 9<br>note = Lysine modified with a CPQ2 quencher | |
| SEQUENCE: 1111<br>GFAAQMAGK | | 9 |
| SEQ ID NO: 1112<br>FEATURE<br>source | moltype = AA   length = 9<br>Location/Qualifiers<br>1..9<br>mol_type = protein<br>organism = synthetic construct<br>note = Description of Artificial Sequence: Synthetic probe | |
| SITE | 9<br>note = Lysine modified with a CPQ2 quencher | |
| SEQUENCE: 1112<br>GGMPANQGK | | 9 |
| SEQ ID NO: 1113<br>FEATURE<br>source | moltype = AA   length = 11<br>Location/Qualifiers<br>1..11<br>mol_type = protein<br>organism = synthetic construct<br>note = Description of Artificial Sequence: Synthetic probe | |
| SITE | 11<br>note = Lysine modified with a CPQ2 quencher | |
| SEQUENCE: 1113<br>GLSGRSDNHG K | | 11 |
| SEQ ID NO: 1114<br>FEATURE<br>source | moltype = AA   length = 13<br>Location/Qualifiers<br>1..13<br>mol_type = protein<br>organism = synthetic construct<br>note = Description of Artificial Sequence: Synthetic probe | |
| SITE | 13<br>note = Lysine modified with a CPQ2 quencher | |
| SEQUENCE: 1114<br>GMAALITRPD FGK | | 13 |
| SEQ ID NO: 1115<br>FEATURE<br>source | moltype = AA   length = 13<br>Location/Qualifiers<br>1..13<br>mol_type = protein<br>organism = synthetic construct<br>note = Description of Artificial Sequence: Synthetic probe | |
| SITE | 13<br>note = Lysine modified with a CPQ2 quencher | |

```
SEQUENCE: 1115
GMAAAITRPR FGK                                                            13

SEQ ID NO: 1116          moltype = AA  length = 13
FEATURE                  Location/Qualifiers
source                   1..13
                         mol_type = protein
                         organism = synthetic construct
                         note = Description of Artificial Sequence: Synthetic probe
SITE                     13
                         note = Lysine modified with a CPQ2 quencher
SEQUENCE: 1116
GMAALIVRPD LGK                                                            13

SEQ ID NO: 1117          moltype = AA  length = 12
FEATURE                  Location/Qualifiers
source                   1..12
                         mol_type = protein
                         organism = synthetic construct
                         note = Description of Artificial Sequence: Synthetic probe
SITE                     12
                         note = Lysine modified with a CPQ2 quencher
SEQUENCE: 1117
GTSGPNQEQE GK                                                             12

SEQ ID NO: 1118          moltype = AA  length = 12
FEATURE                  Location/Qualifiers
source                   1..12
                         mol_type = protein
                         organism = synthetic construct
                         note = Description of Artificial Sequence: Synthetic probe
SITE                     12
                         note = Lysine modified with a CPQ2 quencher
SEQUENCE: 1118
GTAGPNQEQE GK                                                             12

SEQ ID NO: 1119          moltype = AA  length = 10
FEATURE                  Location/Qualifiers
source                   1..10
                         mol_type = protein
                         organism = synthetic construct
                         note = Description of Artificial Sequence: Synthetic probe
SITE                     10
                         note = Lysine modified with a CPQ2 quencher
SEQUENCE: 1119
GGPGPNQAGK                                                                10

SEQ ID NO: 1120          moltype = AA  length = 11
FEATURE                  Location/Qualifiers
source                   1..11
                         mol_type = protein
                         organism = synthetic construct
                         note = Description of Artificial Sequence: Synthetic probe
SITE                     11
                         note = Lysine modified with a CPQ2 quencher
SEQUENCE: 1120
GASGPAGPAG K                                                              11

SEQ ID NO: 1121          moltype = AA  length = 12
FEATURE                  Location/Qualifiers
source                   1..12
                         mol_type = protein
                         organism = synthetic construct
                         note = Description of Artificial Sequence: Synthetic probe
SITE                     12
                         note = Lysine modified with a CPQ2 quencher
SEQUENCE: 1121
GERGETGPSG GK                                                             12

SEQ ID NO: 1122          moltype = AA  length = 11
FEATURE                  Location/Qualifiers
source                   1..11
                         mol_type = protein
                         organism = synthetic construct
                         note = Description of Artificial Sequence: Synthetic probe
SITE                     11
                         note = Lysine modified with a CPQ2 quencher
SEQUENCE: 1122
GVSQELGQRG K                                                              11
```

```
SEQ ID NO: 1123        moltype = AA   length = 12
FEATURE                Location/Qualifiers
source                 1..12
                       mol_type = protein
                       organism = synthetic construct
                       note = Description of Artificial Sequence: Synthetic probe
SITE                   12
                       note = Lysine modified with a CPQ2 quencher
SEQUENCE: 1123
GTGPPGYPTG GK                                                                 12

SEQ ID NO: 1124        moltype = AA   length = 10
FEATURE                Location/Qualifiers
source                 1..10
                       mol_type = protein
                       organism = synthetic construct
                       note = Description of Artificial Sequence: Synthetic probe
SITE                   10
                       note = Lysine modified with a CPQ2 quencher
SEQUENCE: 1124
GTRLPVYQGK                                                                    10

SEQ ID NO: 1125        moltype = AA   length = 11
FEATURE                Location/Qualifiers
source                 1..11
                       mol_type = protein
                       organism = synthetic construct
                       note = Description of Artificial Sequence: Synthetic probe
SITE                   11
                       note = Lysine modified with a CPQ2 quencher
SEQUENCE: 1125
GRQARVVGGG K                                                                  11

SEQ ID NO: 1126        moltype = AA   length = 11
FEATURE                Location/Qualifiers
source                 1..11
                       mol_type = protein
                       organism = synthetic construct
                       note = Description of Artificial Sequence: Synthetic probe
SITE                   11
                       note = Lysine modified with a CPQ2 quencher
SEQUENCE: 1126
GRQRRVVGGG K                                                                  11

SEQ ID NO: 1127        moltype = AA   length = 11
FEATURE                Location/Qualifiers
source                 1..11
                       mol_type = protein
                       organism = synthetic construct
                       note = Description of Artificial Sequence: Synthetic probe
SITE                   11
                       note = Lysine modified with a CPQ2 quencher
SEQUENCE: 1127
GRQARAVGGG K                                                                  11

SEQ ID NO: 1128        moltype = AA   length = 11
FEATURE                Location/Qualifiers
source                 1..11
                       mol_type = protein
                       organism = synthetic construct
                       note = Description of Artificial Sequence: Synthetic probe
SITE                   11
                       note = Lysine modified with a CPQ2 quencher
SEQUENCE: 1128
GRKRRGSRGG K                                                                  11

SEQ ID NO: 1129        moltype = AA   length = 11
FEATURE                Location/Qualifiers
source                 1..11
                       mol_type = protein
                       organism = synthetic construct
                       note = Description of Artificial Sequence: Synthetic probe
SITE                   11
                       note = Lysine modified with a CPQ2 quencher
SEQUENCE: 1129
GKQSRKFVPG K                                                                  11

SEQ ID NO: 1130        moltype = AA   length = 8
```

```
FEATURE               Location/Qualifiers
source                1..8
                      mol_type = protein
                      organism = synthetic construct
                      note = Description of Artificial Sequence: Synthetic probe
SITE                  8
                      note = Lysine modified with a CPQ2 quencher
SEQUENCE: 1130
GVTGRSGK                                                                        8

SEQ ID NO: 1131       moltype = AA  length = 9
FEATURE               Location/Qualifiers
source                1..9
                      mol_type = protein
                      organism = synthetic construct
                      note = Description of Artificial Sequence: Synthetic probe
SITE                  9
                      note = Lysine modified with a CPQ2 quencher
SEQUENCE: 1131
GLKSRVKGK                                                                       9

SEQ ID NO: 1132       moltype = AA  length = 13
FEATURE               Location/Qualifiers
source                1..13
                      mol_type = protein
                      organism = synthetic construct
                      note = Description of Artificial Sequence: Synthetic probe
SITE                  13
                      note = Lysine modified with a CPQ2 quencher
SEQUENCE: 1132
GGIGAVLKVL TGK                                                                 13

SEQ ID NO: 1133       moltype = AA  length = 13
FEATURE               Location/Qualifiers
source                1..13
                      mol_type = protein
                      organism = synthetic construct
                      note = Description of Artificial Sequence: Synthetic probe
SITE                  13
                      note = Lysine modified with a CPQ2 quencher
SEQUENCE: 1133
GGLPALISWI KGK                                                                 13

SEQ ID NO: 1134       moltype = AA  length = 12
FEATURE               Location/Qualifiers
source                1..12
                      mol_type = protein
                      organism = synthetic construct
                      note = Description of Artificial Sequence: Synthetic probe
SITE                  12
                      note = Lysine modified with a CPQ2 quencher
SEQUENCE: 1134
GSEVNLDAEF GK                                                                  12

SEQ ID NO: 1135       moltype = AA  length = 16
FEATURE               Location/Qualifiers
source                1..16
                      mol_type = protein
                      organism = synthetic construct
                      note = Description of Artificial Sequence: Synthetic probe
SITE                  16
                      note = Lysine modified with a CPQ2 quencher
SEQUENCE: 1135
GEEKPICFFR LGKEGK                                                              16

SEQ ID NO: 1136       moltype = AA  length = 16
FEATURE               Location/Qualifiers
source                1..16
                      mol_type = protein
                      organism = synthetic construct
                      note = Description of Artificial Sequence: Synthetic probe
SITE                  16
                      note = Lysine modified with a CPQ2 quencher
SEQUENCE: 1136
GEEKPILFFR LGKEGK                                                              16

SEQ ID NO: 1137       moltype = AA  length = 11
FEATURE               Location/Qualifiers
source                1..11
```

```
                            mol_type = protein
                            organism = synthetic construct
                            note = Description of Artificial Sequence: Synthetic probe
SITE                        11
                            note = Lysine modified with a CPQ2 quencher
SEQUENCE: 1137
GAPSSVIAAG K                                                                          11

SEQ ID NO: 1138             moltype = AA  length = 11
FEATURE                     Location/Qualifiers
source                      1..11
                            mol_type = protein
                            organism = synthetic construct
                            note = Description of Artificial Sequence: Synthetic probe
SITE                        11
                            note = Lysine modified with a CPQ2 quencher
SEQUENCE: 1138
GKKAKRNALG K                                                                          11

SEQ ID NO: 1139             moltype = AA  length = 13
FEATURE                     Location/Qualifiers
source                      1..13
                            mol_type = protein
                            organism = synthetic construct
                            note = Description of Artificial Sequence: Synthetic probe
SITE                        13
                            note = Lysine modified with a CPQ2 quencher
SEQUENCE: 1139
GWTNTSANYN LGK                                                                        13

SEQ ID NO: 1140             moltype = AA  length = 7
FEATURE                     Location/Qualifiers
source                      1..7
                            mol_type = protein
                            organism = synthetic construct
                            note = Description of Artificial Sequence: Synthetic probe
SITE                        7
                            note = Lysine modified with a CPQ2 quencher
SEQUENCE: 1140
GRVRRGK                                                                                7

SEQ ID NO: 1141             moltype = AA  length = 8
FEATURE                     Location/Qualifiers
source                      1..8
                            mol_type = protein
                            organism = synthetic construct
                            note = Description of Artificial Sequence: Synthetic probe
SITE                        8
                            note = Lysine modified with a CPQ2 quencher
SEQUENCE: 1141
GERTKRGK                                                                               8

SEQ ID NO: 1142             moltype = AA  length = 15
FEATURE                     Location/Qualifiers
source                      1..15
                            mol_type = protein
                            organism = synthetic construct
                            note = Description of Artificial Sequence: Synthetic probe
SITE                        15
                            note = Lysine modified with a CPQ2 quencher
SEQUENCE: 1142
GRYQIKPLKS TDEGK                                                                      15

SEQ ID NO: 1143             moltype = AA  length = 14
FEATURE                     Location/Qualifiers
source                      1..14
                            mol_type = protein
                            organism = synthetic construct
                            note = Description of Artificial Sequence: Synthetic probe
SITE                        9
                            note = L-homophenylalanine
SITE                        14
                            note = Lysine modified with a CPQ2 quencher
SEQUENCE: 1143
GWELRHQAFR SKGK                                                                       14

SEQ ID NO: 1144             moltype = AA  length = 15
FEATURE                     Location/Qualifiers
source                      1..15
```

```
                            mol_type = protein
                            organism = synthetic construct
                            note = Description of Artificial Sequence: Synthetic probe
SITE                        7
                            note = L- Methyl cysteine
SITE                        15
                            note = Lysine modified with a CPQ2 quencher
SEQUENCE: 1144
GSGAFKCLKD GAGGK                                                              15

SEQ ID NO: 1145             moltype = AA   length = 9
FEATURE                     Location/Qualifiers
source                      1..9
                            mol_type = protein
                            organism = synthetic construct
                            note = Description of Artificial Sequence: Synthetic probe
SITE                        9
                            note = Lysine modified with a CPQ2 quencher
SEQUENCE: 1145
GYVADGWGK                                                                      9

SEQ ID NO: 1146             moltype = AA   length = 9
FEATURE                     Location/Qualifiers
source                      1..9
                            mol_type = protein
                            organism = synthetic construct
                            note = Description of Artificial Sequence: Synthetic probe
SITE                        9
                            note = Lysine modified with a CPQ2 quencher
SEQUENCE: 1146
GWEHDGWGK                                                                      9

SEQ ID NO: 1147             moltype = AA   length = 10
FEATURE                     Location/Qualifiers
source                      1..10
                            mol_type = protein
                            organism = synthetic construct
                            note = Description of Artificial Sequence: Synthetic probe
SITE                        10
                            note = Lysine modified with a CPQ2 quencher
SEQUENCE: 1147
GYVADAPVGK                                                                    10

SEQ ID NO: 1148             moltype = AA   length = 10
FEATURE                     Location/Qualifiers
source                      1..10
                            mol_type = protein
                            organism = synthetic construct
                            note = Description of Artificial Sequence: Synthetic probe
SITE                        10
                            note = Lysine modified with a CPQ2 quencher
SEQUENCE: 1148
GRPPGFSAGK                                                                    10

SEQ ID NO: 1149             moltype = AA   length = 10
FEATURE                     Location/Qualifiers
source                      1..10
                            mol_type = protein
                            organism = synthetic construct
                            note = Description of Artificial Sequence: Synthetic probe
SITE                        10
                            note = Lysine modified with a CPQ2 quencher
SEQUENCE: 1149
GGSPAFLAGK                                                                    10

SEQ ID NO: 1150             moltype = AA   length = 10
FEATURE                     Location/Qualifiers
source                      1..10
                            mol_type = protein
                            organism = synthetic construct
                            note = Description of Artificial Sequence: Synthetic probe
SITE                        10
                            note = Lysine modified with a CPQ2 quencher
SEQUENCE: 1150
GAGFSLPAGK                                                                    10

SEQ ID NO: 1151             moltype = AA   length = 13
FEATURE                     Location/Qualifiers
source                      1..13
```

```
                        mol_type = protein
                        organism = synthetic construct
                        note = Description of Artificial Sequence: Synthetic probe
SITE                    13
                        note = Lysine modified with a CPQ2 quencher
SEQUENCE: 1151
GRWHTVGLRW EGK                                                                    13

SEQ ID NO: 1152         moltype = AA  length = 6
FEATURE                 Location/Qualifiers
source                  1..6
                        mol_type = protein
                        organism = synthetic construct
                        note = Description of Artificial Sequence: Synthetic probe
SITE                    6
                        note = Lysine modified with a CPQ2 quencher
SEQUENCE: 1152
GLEQGK                                                                             6

SEQ ID NO: 1153         moltype = AA  length = 13
FEATURE                 Location/Qualifiers
source                  1..13
                        mol_type = protein
                        organism = synthetic construct
                        note = Description of Artificial Sequence: Synthetic probe
SITE                    13
                        note = Lysine modified with a CPQ2 quencher
SEQUENCE: 1153
GRWPPMGLPW EGK                                                                    13

SEQ ID NO: 1154         moltype = AA  length = 9
FEATURE                 Location/Qualifiers
source                  1..9
                        mol_type = protein
                        organism = synthetic construct
                        note = Description of Artificial Sequence: Synthetic probe
SITE                    9
                        note = Lysine modified with a CPQ2 quencher
SEQUENCE: 1154
GRPKPVEGK                                                                          9

SEQ ID NO: 1155         moltype = AA  length = 7
FEATURE                 Location/Qualifiers
source                  1..7
                        mol_type = protein
                        organism = synthetic construct
                        note = Description of Artificial Sequence: Synthetic probe
SITE                    7
                        note = Lysine modified with a CPQ2 quencher
SEQUENCE: 1155
GIETDGK                                                                            7

SEQ ID NO: 1156         moltype = AA  length = 10
FEATURE                 Location/Qualifiers
source                  1..10
                        mol_type = protein
                        organism = synthetic construct
                        note = Description of Artificial Sequence: Synthetic probe
SITE                    10
                        note = Lysine modified with a CPQ2 quencher
SEQUENCE: 1156
GVGPDFGRGK                                                                        10

SEQ ID NO: 1157         moltype = AA  length = 12
FEATURE                 Location/Qualifiers
source                  1..12
                        mol_type = protein
                        organism = synthetic construct
                        note = Description of Artificial Sequence: Synthetic probe
SITE                    12
                        note = Lysine modified with a CPQ2 quencher
SEQUENCE: 1157
GGIEFDSGGC GK                                                                     12

SEQ ID NO: 1158         moltype = AA  length = 10
FEATURE                 Location/Qualifiers
source                  1..10
                        mol_type = protein
                        organism = synthetic construct
```

```
                    note = Description of Artificial Sequence: Synthetic probe
SITE                10
                    note = Lysine modified with a CPQ2 quencher
SEQUENCE: 1158
GGDFLRRVGK                                                                    10

SEQ ID NO: 1159     moltype = AA   length = 6
FEATURE             Location/Qualifiers
source              1..6
                    mol_type = protein
                    organism = synthetic construct
                    note = Description of Artificial Sequence: Synthetic probe
SITE                6
                    note = Lysine modified with a CPQ2 quencher
SEQUENCE: 1159
GAALGK                                                                         6

SEQ ID NO: 1160     moltype = AA   length = 13
FEATURE             Location/Qualifiers
source              1..13
                    mol_type = protein
                    organism = synthetic construct
                    note = Description of Artificial Sequence: Synthetic probe
SITE                13
                    note = Lysine modified with a CPQ2 quencher
SEQUENCE: 1160
GYATWSMIAA HGK                                                                13

SEQ ID NO: 1161     moltype = AA   length = 13
FEATURE             Location/Qualifiers
source              1..13
                    mol_type = protein
                    organism = synthetic construct
                    note = Description of Artificial Sequence: Synthetic probe
SITE                13
                    note = Lysine modified with a CPQ2 quencher
SEQUENCE: 1161
GVIMWRLTVG TGK                                                                13

SEQ ID NO: 1162     moltype = AA   length = 13
FEATURE             Location/Qualifiers
source              1..13
                    mol_type = protein
                    organism = synthetic construct
                    note = Description of Artificial Sequence: Synthetic probe
SITE                13
                    note = Lysine modified with a CPQ2 quencher
SEQUENCE: 1162
GRRVLALQQE LGK                                                                13

SEQ ID NO: 1163     moltype = AA   length = 13
FEATURE             Location/Qualifiers
source              1..13
                    mol_type = protein
                    organism = synthetic construct
                    note = Description of Artificial Sequence: Synthetic probe
SITE                13
                    note = Lysine modified with a CPQ2 quencher
SEQUENCE: 1163
GLATWPLSGL WGK                                                                13

SEQ ID NO: 1164     moltype = AA   length = 13
FEATURE             Location/Qualifiers
source              1..13
                    mol_type = protein
                    organism = synthetic construct
                    note = Description of Artificial Sequence: Synthetic probe
SITE                13
                    note = Lysine modified with a CPQ2 quencher
SEQUENCE: 1164
GNTPNWLVNA VGK                                                                13

SEQ ID NO: 1165     moltype = AA   length = 16
FEATURE             Location/Qualifiers
source              1..16
                    mol_type = protein
                    organism = synthetic construct
                    note = Description of Artificial Sequence: Synthetic probe
SITE                16
```

-continued

```
                          note = Lysine modified with a CPQ2 quencher
SEQUENCE: 1165
GSPLAQAVRS SSRKGK                                                       16

SEQ ID NO: 1166           moltype = AA   length = 13
FEATURE                   Location/Qualifiers
source                    1..13
                          mol_type = protein
                          organism = synthetic construct
                          note = Description of Artificial Sequence: Synthetic probe
SITE                      13
                          note = Lysine modified with a CPQ2 quencher
SEQUENCE: 1166
GQMPGRLSMA FGK                                                          13

SEQ ID NO: 1167           moltype = AA   length = 8
FEATURE                   Location/Qualifiers
source                    1..8
                          mol_type = protein
                          organism = synthetic construct
                          note = Description of Artificial Sequence: Synthetic probe
SITE                      8
                          note = Lysine modified with a CPQ2 quencher
SEQUENCE: 1167
GPLGLRGK                                                                8

SEQ ID NO: 1168           moltype = AA   length = 13
FEATURE                   Location/Qualifiers
source                    1..13
                          mol_type = protein
                          organism = synthetic construct
                          note = Description of Artificial Sequence: Synthetic probe
SITE                      13
                          note = Lysine modified with a CPQ2 quencher
SEQUENCE: 1168
GQRANSIRVT WGK                                                          13

SEQ ID NO: 1169           moltype = AA   length = 8
FEATURE                   Location/Qualifiers
source                    1..8
                          mol_type = protein
                          organism = synthetic construct
                          note = Description of Artificial Sequence: Synthetic probe
SITE                      8
                          note = Lysine modified with a CPQ2 quencher
SEQUENCE: 1169
GPLAVRGK                                                                8

SEQ ID NO: 1170           moltype = AA   length = 13
FEATURE                   Location/Qualifiers
source                    1..13
                          mol_type = protein
                          organism = synthetic construct
                          note = Description of Artificial Sequence: Synthetic probe
SITE                      13
                          note = Lysine modified with a CPQ2 quencher
SEQUENCE: 1170
GLLAVPAANT VGK                                                          13

SEQ ID NO: 1171           moltype = AA   length = 11
FEATURE                   Location/Qualifiers
source                    1..11
                          mol_type = protein
                          organism = synthetic construct
                          note = Description of Artificial Sequence: Synthetic probe
SITE                      11
                          note = Lysine modified with a CPQ2 quencher
SEQUENCE: 1171
GGPQGLRGQG K                                                            11

SEQ ID NO: 1172           moltype = AA   length = 13
FEATURE                   Location/Qualifiers
source                    1..13
                          mol_type = protein
                          organism = synthetic construct
                          note = Description of Artificial Sequence: Synthetic probe
SITE                      13
                          note = Lysine modified with a CPQ2 quencher
SEQUENCE: 1172
```

```
GRTGLYLYNS TGK                                                        13

SEQ ID NO: 1173          moltype = AA  length = 17
FEATURE                  Location/Qualifiers
source                   1..17
                         mol_type = protein
                         organism = synthetic construct
                         note = Description of Artificial Sequence: Synthetic probe
SITE                     17
                         note = Lysine modified with a CPQ2 quencher
SEQUENCE: 1173
GRKKLTQSKF VGGAEGK                                                    17

SEQ ID NO: 1174          moltype = AA  length = 7
FEATURE                  Location/Qualifiers
source                   1..7
                         mol_type = protein
                         organism = synthetic construct
                         note = Description of Artificial Sequence: Synthetic probe
SITE                     7
                         note = Lysine modified with a CPQ2 quencher
SEQUENCE: 1174
GKHYRGK                                                                7

SEQ ID NO: 1175          moltype = AA  length = 6
FEATURE                  Location/Qualifiers
source                   1..6
                         mol_type = protein
                         organism = synthetic construct
                         note = Description of Artificial Sequence: Synthetic probe
SITE                     6
                         note = Lysine modified with a CPQ2 quencher
SEQUENCE: 1175
GQARGK                                                                 6

SEQ ID NO: 1176          moltype = AA  length = 10
FEATURE                  Location/Qualifiers
source                   1..10
                         mol_type = protein
                         organism = synthetic construct
                         note = Description of Artificial Sequence: Synthetic probe
SITE                     10
                         note = Lysine modified with a CPQ2 quencher
SEQUENCE: 1176
GPRPFNYLGK                                                            10

SEQ ID NO: 1177          moltype = AA  length = 10
FEATURE                  Location/Qualifiers
source                   1..10
                         mol_type = protein
                         organism = synthetic construct
                         note = Description of Artificial Sequence: Synthetic probe
SITE                     10
                         note = Lysine modified with a CPQ2 quencher
SEQUENCE: 1177
GAPFEMSAGK                                                            10

SEQ ID NO: 1178          moltype = AA  length = 10
FEATURE                  Location/Qualifiers
source                   1..10
                         mol_type = protein
                         organism = synthetic construct
                         note = Description of Artificial Sequence: Synthetic probe
SITE                     10
                         note = Lysine modified with a CPQ2 quencher
SEQUENCE: 1178
GAPFEFSAGK                                                            10

SEQ ID NO: 1179          moltype = AA  length = 9
FEATURE                  Location/Qualifiers
source                   1..9
                         mol_type = protein
                         organism = synthetic construct
                         note = Description of Artificial Sequence: Synthetic probe
SITE                     9
                         note = Lysine modified with a CPQ2 quencher
SEQUENCE: 1179
GPLGFRVGK                                                              9
```

```
SEQ ID NO: 1180          moltype = AA  length = 11
FEATURE                  Location/Qualifiers
source                   1..11
                         mol_type = protein
                         organism = synthetic construct
                         note = Description of Artificial Sequence: Synthetic probe
SITE                     11
                         note = Lysine modified with a CPQ2 quencher
SEQUENCE: 1180
GRPLALWRSG K                                                                   11

SEQ ID NO: 1181          moltype = AA  length = 12
FEATURE                  Location/Qualifiers
source                   1..12
                         mol_type = protein
                         organism = synthetic construct
                         note = Description of Artificial Sequence: Synthetic probe
SITE                     12
                         note = Lysine modified with a CPQ2 quencher
SEQUENCE: 1181
GRPLALEESQ GK                                                                  12

SEQ ID NO: 1182          moltype = AA  length = 12
FEATURE                  Location/Qualifiers
source                   1..12
                         mol_type = protein
                         organism = synthetic construct
                         note = Description of Artificial Sequence: Synthetic probe
SITE                     12
                         note = Lysine modified with a CPQ2 quencher
SEQUENCE: 1182
GRPLALWRSQ GK                                                                  12

SEQ ID NO: 1183          moltype = AA  length = 14
FEATURE                  Location/Qualifiers
source                   1..14
                         mol_type = protein
                         organism = synthetic construct
                         note = Description of Artificial Sequence: Synthetic probe
SITE                     14
                         note = Lysine modified with a CPQ2 quencher
SEQUENCE: 1183
GRNALAVERT ASGK                                                                14

SEQ ID NO: 1184          moltype = AA  length = 11
FEATURE                  Location/Qualifiers
source                   1..11
                         mol_type = protein
                         organism = synthetic construct
                         note = Description of Artificial Sequence: Synthetic probe
SITE                     11
                         note = Lysine modified with a CPQ2 quencher
SEQUENCE: 1184
GRPKPQQFWG K                                                                   11

SEQ ID NO: 1185          moltype = AA  length = 11
FEATURE                  Location/Qualifiers
source                   1..11
                         mol_type = protein
                         organism = synthetic construct
                         note = Description of Artificial Sequence: Synthetic probe
SITE                     11
                         note = Lysine modified with a CPQ2 quencher
SEQUENCE: 1185
SGSNPYKYTA K                                                                   11

SEQ ID NO: 1186          moltype = AA  length = 11
FEATURE                  Location/Qualifiers
source                   1..11
                         mol_type = protein
                         organism = synthetic construct
                         note = Description of Artificial Sequence: Synthetic probe
SITE                     11
                         note = Lysine modified with a CPQ2 quencher
SEQUENCE: 1186
SGSNPYGYTA K                                                                   11

SEQ ID NO: 1187          moltype = AA  length = 11
FEATURE                  Location/Qualifiers
```

```
source                 1..11
                       mol_type = protein
                       organism = synthetic construct
                       note = Description of Artificial Sequence: Synthetic probe
SITE                   11
                       note = Lysine modified with a CPQ2 quencher
SEQUENCE: 1187
SGTLSELHTA K                                                                    11

SEQ ID NO: 1188        moltype = AA   length = 11
FEATURE                Location/Qualifiers
source                 1..11
                       mol_type = protein
                       organism = synthetic construct
                       note = Description of Artificial Sequence: Synthetic probe
SITE                   11
                       note = Lysine modified with a CPQ2 quencher
SEQUENCE: 1188
SGTISHLHTA K                                                                    11

SEQ ID NO: 1189        moltype = AA   length = 14
FEATURE                Location/Qualifiers
source                 1..14
                       mol_type = protein
                       organism = synthetic construct
                       note = Description of Artificial Sequence: Synthetic probe
SITE                   3
                       note = L-Ornithine
SITE                   8
                       note = L-homophenylalanine
SITE                   14
                       note = Lysine modified with a CPQ2 quencher
SEQUENCE: 1189
SGXRSHPFTL YTAK                                                                 14

SEQ ID NO: 1190        moltype = AA   length = 14
FEATURE                Location/Qualifiers
source                 1..14
                       mol_type = protein
                       organism = synthetic construct
                       note = Description of Artificial Sequence: Synthetic probe
SITE                   3
                       note = L-Ornithine
SITE                   8
                       note = L-homophenylalanine
SITE                   14
                       note = Lysine modified with a CPQ2 quencher
SEQUENCE: 1190
SGXRSHGFFL YTAK                                                                 14

SEQ ID NO: 1191        moltype = AA   length = 11
FEATURE                Location/Qualifiers
source                 1..11
                       mol_type = protein
                       organism = synthetic construct
                       note = Description of Artificial Sequence: Synthetic probe
SITE                   11
                       note = Lysine modified with a CPQ2 quencher
SEQUENCE: 1191
SGESLAYYTA K                                                                    11

SEQ ID NO: 1192        moltype = AA   length = 11
FEATURE                Location/Qualifiers
source                 1..11
                       mol_type = protein
                       organism = synthetic construct
                       note = Description of Artificial Sequence: Synthetic probe
SITE                   11
                       note = Lysine modified with a CPQ2 quencher
SEQUENCE: 1192
SGHMHAALTA K                                                                    11

SEQ ID NO: 1193        moltype = AA   length = 11
FEATURE                Location/Qualifiers
source                 1..11
                       mol_type = protein
                       organism = synthetic construct
                       note = Description of Artificial Sequence: Synthetic probe
SITE                   6
```

```
                    note = D-isoleucine
SITE                11
                    note = Lysine modified with a CPQ2 quencher
SEQUENCE: 1193
GILSRIVGGG K                                                              11

SEQ ID NO: 1194     moltype = AA  length = 11
FEATURE             Location/Qualifiers
source              1..11
                    mol_type = protein
                    organism = synthetic construct
                    note = Description of Artificial Sequence: Synthetic probe
SITE                5
                    note = D-arginine
SITE                6
                    note = D-isoleucine
SITE                7
                    note = D-valine
SITE                11
                    note = Lysine modified with a CPQ2 quencher
SEQUENCE: 1194
GILSRIVGGG K                                                              11

SEQ ID NO: 1195     moltype = AA  length = 11
FEATURE             Location/Qualifiers
source              1..11
                    mol_type = protein
                    organism = synthetic construct
                    note = Description of Artificial Sequence: Synthetic probe
SITE                11
                    note = Lysine modified with a CPQ2 quencher
SEQUENCE: 1195
GRQRRALEKG K                                                              11

SEQ ID NO: 1196     moltype = AA  length = 11
FEATURE             Location/Qualifiers
source              1..11
                    mol_type = protein
                    organism = synthetic construct
                    note = Description of Artificial Sequence: Synthetic probe
SITE                11
                    note = Lysine modified with a CPQ2 quencher
SEQUENCE: 1196
GKPISLISSG K                                                              11

SEQ ID NO: 1197     moltype = AA  length = 11
FEATURE             Location/Qualifiers
source              1..11
                    mol_type = protein
                    organism = synthetic construct
                    note = Description of Artificial Sequence: Synthetic probe
SITE                11
                    note = Lysine modified with a CPQ2 quencher
SEQUENCE: 1197
GQKGRYKQEG K                                                              11

SEQ ID NO: 1198     moltype = AA  length = 10
FEATURE             Location/Qualifiers
source              1..10
                    mol_type = protein
                    organism = synthetic construct
                    note = Description of Artificial Sequence: Synthetic probe
SITE                10
                    note = Lysine modified with a CPQ2 quencher
SEQUENCE: 1198
GGPLGLRSWK                                                                10

SEQ ID NO: 1199     moltype = AA  length = 10
FEATURE             Location/Qualifiers
source              1..10
                    mol_type = protein
                    organism = synthetic construct
                    note = Description of Artificial Sequence: Synthetic probe
SITE                10
                    note = Lysine modified with a CPQ2 quencher
SEQUENCE: 1199
GGPLGVRGKK                                                                10

SEQ ID NO: 1200     moltype = AA  length = 10
```

| | |
|---|---|
| FEATURE | Location/Qualifiers |
| source | 1..10<br>mol_type = protein<br>organism = synthetic construct<br>note = Description of Artificial Sequence: Synthetic probe |
| SITE | 3<br>note = D-Phenylalanine |
| SITE | 10<br>note = Lysine modified with a CPQ2 quencher |
| SEQUENCE: 1200 | |
| GGFPRSGGGK | 10 |
| | |
| SEQ ID NO: 1201<br>SEQUENCE: 1201<br>000 | moltype =   length = |
| SEQ ID NO: 1202<br>SEQUENCE: 1202<br>000 | moltype =   length = |
| SEQ ID NO: 1203<br>SEQUENCE: 1203<br>000 | moltype =   length = |
| SEQ ID NO: 1204<br>SEQUENCE: 1204<br>000 | moltype =   length = |
| SEQ ID NO: 1205<br>SEQUENCE: 1205<br>000 | moltype =   length = |
| SEQ ID NO: 1206<br>SEQUENCE: 1206<br>000 | moltype =   length = |
| SEQ ID NO: 1207<br>SEQUENCE: 1207<br>000 | moltype =   length = |
| SEQ ID NO: 1208<br>SEQUENCE: 1208<br>000 | moltype =   length = |
| SEQ ID NO: 1209<br>SEQUENCE: 1209<br>000 | moltype =   length = |
| SEQ ID NO: 1210<br>SEQUENCE: 1210<br>000 | moltype =   length = |
| SEQ ID NO: 1211<br>SEQUENCE: 1211<br>000 | moltype =   length = |
| SEQ ID NO: 1212<br>SEQUENCE: 1212<br>000 | moltype =   length = |
| SEQ ID NO: 1213<br>SEQUENCE: 1213<br>000 | moltype =   length = |
| SEQ ID NO: 1214<br>SEQUENCE: 1214<br>000 | moltype =   length = |
| SEQ ID NO: 1215<br>FEATURE<br>source | moltype = AA   length = 4<br>Location/Qualifiers<br>1..4<br>mol_type = protein<br>organism = synthetic construct |
| SEQUENCE: 1215 | |
| ZVAN | 4 |
| SEQ ID NO: 1216<br>SEQUENCE: 1216<br>000 | moltype =   length = |

```
SEQ ID NO: 1217        moltype =    length =
SEQUENCE: 1217
000

SEQ ID NO: 1218        moltype =    length =
SEQUENCE: 1218
000

SEQ ID NO: 1219        moltype =    length =
SEQUENCE: 1219
000

SEQ ID NO: 1220        moltype = AA   length = 4
FEATURE                Location/Qualifiers
source                 1..4
                       mol_type = protein
                       organism = synthetic construct
SEQUENCE: 1220
ZVVR                                                                          4

SEQ ID NO: 1221        moltype =    length =
SEQUENCE: 1221
000

SEQ ID NO: 1222        moltype =    length =
SEQUENCE: 1222
000

SEQ ID NO: 1223        moltype =    length =
SEQUENCE: 1223
000

SEQ ID NO: 1224        moltype =    length =
SEQUENCE: 1224
000

SEQ ID NO: 1225        moltype =    length =
SEQUENCE: 1225
000

SEQ ID NO: 1226        moltype =    length =
SEQUENCE: 1226
000

SEQ ID NO: 1227        moltype = AA   length = 4
FEATURE                Location/Qualifiers
source                 1..4
                       mol_type = protein
                       organism = synthetic construct
                       note = Description of Artificial Sequence: Synthetic probe
SITE                   1
                       note = acetyl tryptophan
SEQUENCE: 1227
WEHD                                                                          4

SEQ ID NO: 1228        moltype =    length =
SEQUENCE: 1228
000

SEQ ID NO: 1229        moltype =    length =
SEQUENCE: 1229
000

SEQ ID NO: 1230        moltype =    length =
SEQUENCE: 1230
000

SEQ ID NO: 1231        moltype = AA   length = 4
FEATURE                Location/Qualifiers
source                 1..4
                       mol_type = protein
                       organism = synthetic construct
                       note = Description of Artificial Sequence: Synthetic probe
SEQUENCE: 1231
AAPM                                                                          4

SEQ ID NO: 1232        moltype = AA   length = 4
FEATURE                Location/Qualifiers
```

```
source                  1..4
                        mol_type = protein
                        organism = synthetic construct
                        note = Description of Artificial Sequence: Synthetic probe
SEQUENCE: 1232
AEPF                                                                              4

SEQ ID NO: 1233         moltype =   length =
SEQUENCE: 1233
000

SEQ ID NO: 1234         moltype =   length =
SEQUENCE: 1234
000

SEQ ID NO: 1235         moltype =   length =
SEQUENCE: 1235
000

SEQ ID NO: 1236         moltype =   length =
SEQUENCE: 1236
000

SEQ ID NO: 1237         moltype =   length =
SEQUENCE: 1237
000

SEQ ID NO: 1238         moltype =   length =
SEQUENCE: 1238
000

SEQ ID NO: 1239         moltype =   length =
SEQUENCE: 1239
000

SEQ ID NO: 1240         moltype =   length =
SEQUENCE: 1240
000

SEQ ID NO: 1241         moltype =   length =
SEQUENCE: 1241
000

SEQ ID NO: 1242         moltype =   length =
SEQUENCE: 1242
000

SEQ ID NO: 1243         moltype = AA   length = 4
FEATURE                 Location/Qualifiers
source                  1..4
                        mol_type = protein
                        organism = synthetic construct
                        note = Description of Artificial Sequence: Synthetic probe
SEQUENCE: 1243
AAPV                                                                              4

SEQ ID NO: 1244         moltype =   length =
SEQUENCE: 1244
000

SEQ ID NO: 1245         moltype = AA   length = 4
FEATURE                 Location/Qualifiers
source                  1..4
                        mol_type = protein
                        organism = synthetic construct
SEQUENCE: 1245
ZVKM                                                                              4

SEQ ID NO: 1246         moltype = AA   length = 5
FEATURE                 Location/Qualifiers
source                  1..5
                        mol_type = protein
                        organism = synthetic construct
                        note = Description of Artificial Sequence: Synthetic probe
SEQUENCE: 1246
GPLGP                                                                             5

SEQ ID NO: 1247         moltype = AA   length = 5
FEATURE                 Location/Qualifiers
```

|  |  |
|---|---|
| source | 1..5<br>mol_type = protein<br>organism = synthetic construct<br>note = Description of Artificial Sequence: Synthetic probe |
| SITE | 1<br>note = acetyl lysine |
| SEQUENCE: 1247 |  |
| KQKLR | 5 |
|  |  |
| SEQ ID NO: 1248<br>FEATURE<br>source | moltype = AA   length = 4<br>Location/Qualifiers<br>1..4<br>mol_type = protein<br>organism = synthetic construct<br>note = Description of Artificial Sequence: Synthetic probe |
| SITE | 1<br>note = Butyloxycarbonyl arginine |
| SEQUENCE: 1248 |  |
| RVRR | 4 |
|  |  |
| SEQ ID NO: 1249<br>FEATURE<br>source | moltype = AA   length = 4<br>Location/Qualifiers<br>1..4<br>mol_type = protein<br>organism = synthetic construct<br>note = Description of Artificial Sequence: Synthetic probe |
| SITE | 1<br>note = Butyloxycarbonyl isoleucine |
| SEQUENCE: 1249 |  |
| IEGR | 4 |
|  |  |
| SEQ ID NO: 1250<br>SEQUENCE: 1250<br>000 | moltype =    length = |
|  |  |
| SEQ ID NO: 1251<br>FEATURE<br>source | moltype = AA   length = 4<br>Location/Qualifiers<br>1..4<br>mol_type = protein<br>organism = synthetic construct<br>note = Description of Artificial Sequence: Synthetic probe |
| SEQUENCE: 1251 |  |
| AAPV | 4 |
|  |  |
| SEQ ID NO: 1252<br>FEATURE<br>source | moltype = AA   length = 8<br>Location/Qualifiers<br>1..8<br>mol_type = protein<br>organism = synthetic construct<br>note = Description of Artificial Sequence: Synthetic probe |
| SEQUENCE: 1252 |  |
| RPFHLLVY | 8 |
|  |  |
| SEQ ID NO: 1253<br>FEATURE<br>source | moltype = AA   length = 7<br>Location/Qualifiers<br>1..7<br>mol_type = protein<br>organism = synthetic construct<br>note = Description of Artificial Sequence: Synthetic probe |
| SITE | 1<br>note = amino-n-butyric acid |
| SITE | 4<br>note = guamidine-L-phenylalanine |
| SEQUENCE: 1253 |  |
| XWSFTVF | 7 |
|  |  |
| SEQ ID NO: 1254<br>FEATURE<br>source | moltype = AA   length = 6<br>Location/Qualifiers<br>1..6<br>mol_type = protein<br>organism = synthetic construct<br>note = Description of Artificial Sequence: Synthetic probe |
| SEQUENCE: 1254 |  |
| HSSKLQ | 6 |
|  |  |
| SEQ ID NO: 1255<br>SEQUENCE: 1255<br>000 | moltype =    length = |

```
SEQ ID NO: 1256         moltype = AA   length = 10
FEATURE                 Location/Qualifiers
source                  1..10
                        mol_type = protein
                        organism = synthetic construct
                        note = Description of Artificial Sequence: Synthetic probe
SITE                    1
                        note = D-Lysine
SITE                    2
                        note = D-Lysine
SITE                    9
                        note = dinitrobenzylation of lysine
SEQUENCE: 1256
KKDRENSPKL                                                                        10

SEQ ID NO: 1257         moltype = AA   length = 10
FEATURE                 Location/Qualifiers
source                  1..10
                        mol_type = protein
                        organism = synthetic construct
                        note = Description of Artificial Sequence: Synthetic probe
SITE                    1
                        note = D-Lysine
SITE                    2
                        note = D-Lysine
SITE                    10
                        note = dinitrobenzylation of lysine
SEQUENCE: 1257
KKDRENSPLK                                                                        10

SEQ ID NO: 1258         moltype = AA   length = 8
FEATURE                 Location/Qualifiers
source                  1..8
                        mol_type = protein
                        organism = synthetic construct
                        note = Description of Artificial Sequence: Synthetic probe
SITE                    7
                        note = dinitrobenzylation of lysine
SEQUENCE: 1258
NAGSKFKQ                                                                          8

SEQ ID NO: 1259         moltype = AA   length = 8
FEATURE                 Location/Qualifiers
source                  1..8
                        mol_type = protein
                        organism = synthetic construct
                        note = Description of Artificial Sequence: Synthetic probe
SITE                    8
                        note = dinitrobenzylation of lysine
SEQUENCE: 1259
NAGSKFQK                                                                          8

SEQ ID NO: 1260         moltype = AA   length = 10
FEATURE                 Location/Qualifiers
source                  1..10
                        mol_type = protein
                        organism = synthetic construct
                        note = Description of Artificial Sequence: Synthetic probe
SITE                    1
                        note = D-Lysine
SITE                    2
                        note = D-Lysine
SITE                    9
                        note = dinitrobenzylation of lysine
SEQUENCE: 1260
KKHLLGFYKV                                                                        10

SEQ ID NO: 1261         moltype = AA   length = 10
FEATURE                 Location/Qualifiers
source                  1..10
                        mol_type = protein
                        organism = synthetic construct
                        note = Description of Artificial Sequence: Synthetic probe
SITE                    1
                        note = D-Lysine
SITE                    2
                        note = D-Lysine
SITE                    10
                        note = dinitrobenzylation of lysine
```

```
SEQUENCE: 1261
KKHLLGFYVK                                                                  10

SEQ ID NO: 1262          moltype = AA   length = 10
FEATURE                  Location/Qualifiers
source                   1..10
                         mol_type = protein
                         organism = synthetic construct
                         note = Description of Artificial Sequence: Synthetic probe
SITE                     1
                         note = D-Lysine
SITE                     2
                         note = D-Lysine
SITE                     8
                         note = Norleucine
SITE                     9
                         note = dinitrobenzylation of lysine
SITE                     10
                         note = Norleucine
SEQUENCE: 1262
KKQEKQTXKX                                                                  10

SEQ ID NO: 1263          moltype = AA   length = 10
FEATURE                  Location/Qualifiers
source                   1..10
                         mol_type = protein
                         organism = synthetic construct
                         note = Description of Artificial Sequence: Synthetic probe
SITE                     1
                         note = D-Lysine
SITE                     2
                         note = D-Lysine
SITE                     8
                         note = Norleucine
SITE                     9
                         note = Norleucine
SITE                     10
                         note = dinitrobenzylation of lysine
SEQUENCE: 1263
KKQEKQTXXK                                                                  10

SEQ ID NO: 1264          moltype = AA   length = 9
FEATURE                  Location/Qualifiers
source                   1..9
                         mol_type = protein
                         organism = synthetic construct
                         note = Description of Artificial Sequence: Synthetic probe
SITE                     1
                         note = D-Lysine
SITE                     8
                         note = dinitrobenzylation of lysine
SEQUENCE: 1264
KDPFVVSKW                                                                   9

SEQ ID NO: 1265          moltype = AA   length = 9
FEATURE                  Location/Qualifiers
source                   1..9
                         mol_type = protein
                         organism = synthetic construct
                         note = Description of Artificial Sequence: Synthetic probe
SITE                     1
                         note = D-Lysine
SITE                     9
                         note = dinitrobenzylation of lysine
SEQUENCE: 1265
KDPFVVSWK                                                                   9

SEQ ID NO: 1266          moltype = AA   length = 8
FEATURE                  Location/Qualifiers
source                   1..8
                         mol_type = protein
                         organism = synthetic construct
                         note = Description of Artificial Sequence: Synthetic probe
SITE                     7
                         note = dinitrobenzylation of lysine
SEQUENCE: 1266
NAYNEIKR                                                                    8

SEQ ID NO: 1267          moltype = AA   length = 8
```

```
FEATURE                 Location/Qualifiers
source                  1..8
                        mol_type = protein
                        organism = synthetic construct
                        note = Description of Artificial Sequence: Synthetic probe
SITE                    8
                        note = dinitrobenzylation of lysine
SEQUENCE: 1267
NAYNEIRK                                                                         8

SEQ ID NO: 1268         moltype = AA   length = 8
FEATURE                 Location/Qualifiers
source                  1..8
                        mol_type = protein
                        organism = synthetic construct
                        note = Description of Artificial Sequence: Synthetic probe
SITE                    2
                        note = Norleucine
SITE                    7
                        note = dinitrobenzylation of lysine
SEQUENCE: 1268
VXRQSEKN                                                                         8

SEQ ID NO: 1269         moltype = AA   length = 8
FEATURE                 Location/Qualifiers
source                  1..8
                        mol_type = protein
                        organism = synthetic construct
                        note = Description of Artificial Sequence: Synthetic probe
SITE                    2
                        note = Norleucine
SITE                    8
                        note = dinitrobenzylation of lysine
SEQUENCE: 1269
VXRQSENK                                                                         8

SEQ ID NO: 1270         moltype = AA   length = 8
FEATURE                 Location/Qualifiers
source                  1..8
                        mol_type = protein
                        organism = synthetic construct
                        note = Description of Artificial Sequence: Synthetic probe
SITE                    6
                        note = Norleucine
SITE                    7
                        note = dinitrobenzylation of lysine
SEQUENCE: 1270
YNPREXKI                                                                         8

SEQ ID NO: 1271         moltype = AA   length = 8
FEATURE                 Location/Qualifiers
source                  1..8
                        mol_type = protein
                        organism = synthetic construct
                        note = Description of Artificial Sequence: Synthetic probe
SITE                    6
                        note = Norleucine
SITE                    8
                        note = dinitrobenzylation of lysine
SEQUENCE: 1271
YNPREXIK                                                                         8

SEQ ID NO: 1272         moltype = AA   length = 9
FEATURE                 Location/Qualifiers
source                  1..9
                        mol_type = protein
                        organism = synthetic construct
                        note = Description of Artificial Sequence: Synthetic probe
SITE                    1
                        note = D-Lysine
SITE                    8
                        note = dinitrobenzylation of lysine
SEQUENCE: 1272
KEFVHNPKK                                                                        9

SEQ ID NO: 1273         moltype = AA   length = 9
FEATURE                 Location/Qualifiers
source                  1..9
                        mol_type = protein
```

```
                        organism = synthetic construct
                        note = Description of Artificial Sequence: Synthetic probe
SITE                    1
                        note = D-Lysine
SITE                    9
                        note = dinitrobenzylation of lysine
SEQUENCE: 1273
KEFVHNPKK                                                                        9

SEQ ID NO: 1274         moltype = AA   length = 8
FEATURE                 Location/Qualifiers
source                  1..8
                        mol_type = protein
                        organism = synthetic construct
                        note = Description of Artificial Sequence: Synthetic probe
SITE                    7
                        note = dinitrobenzylation of lysine
SEQUENCE: 1274
KRVQFLKH                                                                         8

SEQ ID NO: 1275         moltype = AA   length = 8
FEATURE                 Location/Qualifiers
source                  1..8
                        mol_type = protein
                        organism = synthetic construct
                        note = Description of Artificial Sequence: Synthetic probe
SITE                    8
                        note = dinitrobenzylation of lysine
SEQUENCE: 1275
KRVQFLHK                                                                         8

SEQ ID NO: 1276         moltype = AA   length = 9
FEATURE                 Location/Qualifiers
source                  1..9
                        mol_type = protein
                        organism = synthetic construct
                        note = Description of Artificial Sequence: Synthetic probe
SITE                    1
                        note = D-Lysine
SITE                    4
                        note = Norleucine
SITE                    8
                        note = dinitrobenzylation of lysine
SEQUENCE: 1276
KLIXHKNKG                                                                        9

SEQ ID NO: 1277         moltype = AA   length = 9
FEATURE                 Location/Qualifiers
source                  1..9
                        mol_type = protein
                        organism = synthetic construct
                        note = Description of Artificial Sequence: Synthetic probe
SITE                    1
                        note = D-Lysine
SITE                    4
                        note = Norleucine
SITE                    9
                        note = dinitrobenzylation of lysine
SEQUENCE: 1277
KLIXHKNGK                                                                        9

SEQ ID NO: 1278         moltype = AA   length = 10
FEATURE                 Location/Qualifiers
source                  1..10
                        mol_type = protein
                        organism = synthetic construct
                        note = Description of Artificial Sequence: Synthetic probe
SITE                    1
                        note = D-Lysine
SITE                    2
                        note = D-Lysine
SITE                    5
                        note = Norleucine
SITE                    9
                        note = dinitrobenzylation of lysine
SEQUENCE: 1278
KKWAXLYHKS                                                                      10

SEQ ID NO: 1279         moltype = AA   length = 10
```

```
FEATURE              Location/Qualifiers
source               1..10
                     mol_type = protein
                     organism = synthetic construct
                     note = Description of Artificial Sequence: Synthetic probe
SITE                 1
                     note = D-Lysine
SITE                 2
                     note = D-Lysine
SITE                 5
                     note = Norleucine
SITE                 10
                     note = dinitrobenzylation of lysine
SEQUENCE: 1279
KKWAXLYHSK                                                                   10

SEQ ID NO: 1280      moltype = AA   length = 10
FEATURE              Location/Qualifiers
source               1..10
                     mol_type = protein
                     organism = synthetic construct
                     note = Description of Artificial Sequence: Synthetic probe
SITE                 1
                     note = D-Lysine
SITE                 2
                     note = D-Lysine
SITE                 9
                     note = dinitrobenzylation of lysine
SEQUENCE: 1280
KKAHDIVNKY                                                                   10

SEQ ID NO: 1281      moltype = AA   length = 10
FEATURE              Location/Qualifiers
source               1..10
                     mol_type = protein
                     organism = synthetic construct
                     note = Description of Artificial Sequence: Synthetic probe
SITE                 1
                     note = D-Lysine
SITE                 2
                     note = D-Lysine
SITE                 10
                     note = dinitrobenzylation of lysine
SEQUENCE: 1281
KKAHDIVNYK                                                                   10

SEQ ID NO: 1282      moltype = AA   length = 9
FEATURE              Location/Qualifiers
source               1..9
                     mol_type = protein
                     organism = synthetic construct
                     note = Description of Artificial Sequence: Synthetic probe
SITE                 1
                     note = D-Lysine
SITE                 8
                     note = dinitrobenzylation of lysine
SEQUENCE: 1282
KSVFVIEKP                                                                     9

SEQ ID NO: 1283      moltype = AA   length = 9
FEATURE              Location/Qualifiers
source               1..9
                     mol_type = protein
                     organism = synthetic construct
                     note = Description of Artificial Sequence: Synthetic probe
SITE                 1
                     note = D-Lysine
SITE                 9
                     note = dinitrobenzylation of lysine
SEQUENCE: 1283
KSVFVIEPK                                                                     9

SEQ ID NO: 1284      moltype = AA   length = 9
FEATURE              Location/Qualifiers
source               1..9
                     mol_type = protein
                     organism = synthetic construct
                     note = Description of Artificial Sequence: Synthetic probe
SITE                 1
```

|   |   |   |
|---|---|---|
| | note = D-Lysine | |
| SITE | 8 | |
| | note = dinitrobenzylation of lysine | |
| SEQUENCE: 1284 | | |
| KPPSGLSKE | | 9 |
| | | |
| SEQ ID NO: 1285 | moltype = AA  length = 9 | |
| FEATURE | Location/Qualifiers | |
| source | 1..9 | |
| | mol_type = protein | |
| | organism = synthetic construct | |
| | note = Description of Artificial Sequence: Synthetic probe | |
| SITE | 1 | |
| | note = D-Lysine | |
| SITE | 9 | |
| | note = dinitrobenzylation of lysine | |
| SEQUENCE: 1285 | | |
| KPPSGLSEK | | 9 |
| | | |
| SEQ ID NO: 1286 | moltype = AA  length = 10 | |
| FEATURE | Location/Qualifiers | |
| source | 1..10 | |
| | mol_type = protein | |
| | organism = synthetic construct | |
| | note = Description of Artificial Sequence: Synthetic probe | |
| SITE | 1 | |
| | note = D-Lysine | |
| SITE | 2 | |
| | note = D-Lysine | |
| SITE | 9 | |
| | note = dinitrobenzylation of lysine | |
| SEQUENCE: 1286 | | |
| KKRWYGGIKF | | 10 |
| | | |
| SEQ ID NO: 1287 | moltype = AA  length = 10 | |
| FEATURE | Location/Qualifiers | |
| source | 1..10 | |
| | mol_type = protein | |
| | organism = synthetic construct | |
| | note = Description of Artificial Sequence: Synthetic probe | |
| SITE | 1 | |
| | note = D-Lysine | |
| SITE | 2 | |
| | note = D-Lysine | |
| SITE | 10 | |
| | note = dinitrobenzylation of lysine | |
| SEQUENCE: 1287 | | |
| KKRWYGGIFK | | 10 |
| | | |
| SEQ ID NO: 1288 | moltype = AA  length = 9 | |
| FEATURE | Location/Qualifiers | |
| source | 1..9 | |
| | mol_type = protein | |
| | organism = synthetic construct | |
| | note = Description of Artificial Sequence: Synthetic probe | |
| SITE | 1 | |
| | note = D-Lysine | |
| SITE | 7 | |
| | note = Norleucine | |
| SITE | 8 | |
| | note = dinitrobenzylation of lysine | |
| SEQUENCE: 1288 | | |
| KQYVFFXKD | | 9 |
| | | |
| SEQ ID NO: 1289 | moltype = AA  length = 9 | |
| FEATURE | Location/Qualifiers | |
| source | 1..9 | |
| | mol_type = protein | |
| | organism = synthetic construct | |
| | note = Description of Artificial Sequence: Synthetic probe | |
| SITE | 1 | |
| | note = D-Lysine | |
| SITE | 7 | |
| | note = Norleucine | |
| SITE | 9 | |
| | note = dinitrobenzylation of lysine | |
| SEQUENCE: 1289 | | |
| KQYVFFXDK | | 9 |

-continued

| | |
|---|---|
| SEQ ID NO: 1290 | moltype = AA  length = 9 |
| FEATURE | Location/Qualifiers |
| source | 1..9 |
| | mol_type = protein |
| | organism = synthetic construct |
| | note = Description of Artificial Sequence: Synthetic probe |
| SITE | 1 |
| | note = D-Lysine |
| SITE | 8 |
| | note = dinitrobenzylation of lysine |
| SEQUENCE: 1290 | |
| KFAKYYKKT | 9 |

| | |
|---|---|
| SEQ ID NO: 1291 | moltype = AA  length = 9 |
| FEATURE | Location/Qualifiers |
| source | 1..9 |
| | mol_type = protein |
| | organism = synthetic construct |
| | note = Description of Artificial Sequence: Synthetic probe |
| SITE | 1 |
| | note = D-Lysine |
| SITE | 9 |
| | note = dinitrobenzylation of lysine |
| SEQUENCE: 1291 | |
| KFAKYYKTK | 9 |

| | |
|---|---|
| SEQ ID NO: 1292 | moltype = AA  length = 9 |
| FEATURE | Location/Qualifiers |
| source | 1..9 |
| | mol_type = protein |
| | organism = synthetic construct |
| | note = Description of Artificial Sequence: Synthetic probe |
| SITE | 1 |
| | note = D-Lysine |
| SITE | 8 |
| | note = dinitrobenzylation of lysine |
| SEQUENCE: 1292 | |
| KQVKHFTKA | 9 |

| | |
|---|---|
| SEQ ID NO: 1293 | moltype = AA  length = 9 |
| FEATURE | Location/Qualifiers |
| source | 1..9 |
| | mol_type = protein |
| | organism = synthetic construct |
| | note = Description of Artificial Sequence: Synthetic probe |
| SITE | 1 |
| | note = D-Lysine |
| SITE | 9 |
| | note = dinitrobenzylation of lysine |
| SEQUENCE: 1293 | |
| KQVKHFTAK | 9 |

| | |
|---|---|
| SEQ ID NO: 1294 | moltype = AA  length = 8 |
| FEATURE | Location/Qualifiers |
| source | 1..8 |
| | mol_type = protein |
| | organism = synthetic construct |
| | note = Description of Artificial Sequence: Synthetic probe |
| SITE | 1 |
| | note = D-Lysine |
| SITE | 8 |
| | note = dinitrobenzylation of lysine |
| SEQUENCE: 1294 | |
| KYVADAPK | 8 |

| | |
|---|---|
| SEQ ID NO: 1295 | moltype = AA  length = 9 |
| FEATURE | Location/Qualifiers |
| source | 1..9 |
| | mol_type = protein |
| | organism = synthetic construct |
| | note = Description of Artificial Sequence: Synthetic probe |
| SITE | 9 |
| | note = dinitrobenzylation of lysine amide |
| SEQUENCE: 1295 | |
| GKGISSQYK | 9 |

| | |
|---|---|
| SEQ ID NO: 1296 | moltype = AA  length = 9 |
| FEATURE | Location/Qualifiers |
| source | 1..9 |

|   |   |
|---|---|
| | mol_type = protein<br>organism = synthetic construct<br>note = Description of Artificial Sequence: Synthetic probe |
| SITE | 9<br>note = dinitrobenzylation of lysine |
| SEQUENCE: 1296<br>GALPALQNK | 9 |
| SEQ ID NO: 1297<br>FEATURE<br>source | moltype = AA  length = 7<br>Location/Qualifiers<br>1..7<br>mol_type = protein<br>organism = synthetic construct<br>note = Description of Artificial Sequence: Synthetic probe |
| SITE | 7<br>note = dinitrobenzylation of lysine amide |
| SEQUENCE: 1297<br>GHRFRGK | 7 |
| SEQ ID NO: 1298<br>FEATURE<br>source | moltype = AA  length = 11<br>Location/Qualifiers<br>1..11<br>mol_type = protein<br>organism = synthetic construct<br>note = Description of Artificial Sequence: Synthetic probe |
| SITE | 11<br>note = dinitrobenzylation of lysine |
| SEQUENCE: 1298<br>GAPEEIMDQQ K | 11 |
| SEQ ID NO: 1299<br>FEATURE<br>source | moltype = AA  length = 9<br>Location/Qualifiers<br>1..9<br>mol_type = protein<br>organism = synthetic construct<br>note = Description of Artificial Sequence: Synthetic probe |
| SITE | 9<br>note = dinitrobenzylation of lysine amide |
| SEQUENCE: 1299<br>GSRKSQQYK | 9 |
| SEQ ID NO: 1300<br>FEATURE<br>source | moltype = AA  length = 10<br>Location/Qualifiers<br>1..10<br>mol_type = protein<br>organism = synthetic construct<br>note = Description of Artificial Sequence: Synthetic probe |
| SITE | 10<br>note = dinitrobenzylation of lysine amide |
| SEQUENCE: 1300<br>GSKGRSLIGK | 10 |
| SEQ ID NO: 1301<br>FEATURE<br>source | moltype = AA  length = 9<br>Location/Qualifiers<br>1..9<br>mol_type = protein<br>organism = synthetic construct<br>note = Description of Artificial Sequence: Synthetic probe |
| SITE | 9<br>note = dinitrobenzylation of lysine |
| SEQUENCE: 1301<br>GFAQSIPKK | 9 |
| SEQ ID NO: 1302<br>FEATURE<br>source | moltype = AA  length = 10<br>Location/Qualifiers<br>1..10<br>mol_type = protein<br>organism = synthetic construct<br>note = Description of Artificial Sequence: Synthetic probe |
| SITE | 10<br>note = dinitrobenzylation of lysine amide |
| SEQUENCE: 1302<br>GRQRRVVGGK | 10 |
| SEQ ID NO: 1303<br>FEATURE<br>source | moltype = AA  length = 11<br>Location/Qualifiers<br>1..11<br>mol_type = protein<br>organism = synthetic construct |

```
                    note = Description of Artificial Sequence: Synthetic probe
SITE                11
                    note = dinitrobenzylation of lysine amide
SEQUENCE: 1303
GERGETGTGPSG K                                                              11

SEQ ID NO: 1304     moltype = AA   length = 9
FEATURE             Location/Qualifiers
source              1..9
                    mol_type = protein
                    organism = synthetic construct
                    note = Description of Artificial Sequence: Synthetic probe
SITE                9
                    note = dinitrobenzylation of lysine
SEQUENCE: 1304
GASGPSSGK                                                                    9

SEQ ID NO: 1305     moltype = AA   length = 7
FEATURE             Location/Qualifiers
source              1..7
                    mol_type = protein
                    organism = synthetic construct
                    note = Description of Artificial Sequence: Synthetic probe
SITE                7
                    note = dinitrobenzylation of lysine amide
SEQUENCE: 1305
GYRFRGK                                                                      7

SEQ ID NO: 1306     moltype = AA   length = 9
FEATURE             Location/Qualifiers
source              1..9
                    mol_type = protein
                    organism = synthetic construct
                    note = Description of Artificial Sequence: Synthetic probe
SITE                9
                    note = dinitrobenzylation of lysine amide
SEQUENCE: 1306
GKLFSSKQK                                                                    9

SEQ ID NO: 1307     moltype = AA   length = 7
FEATURE             Location/Qualifiers
source              1..7
                    mol_type = protein
                    organism = synthetic construct
                    note = Description of Artificial Sequence: Synthetic probe
SITE                7
                    note = dinitrobenzylation of lysine amide
SEQUENCE: 1307
GIVPRGK                                                                      7

SEQ ID NO: 1308     moltype = AA   length = 10
FEATURE             Location/Qualifiers
source              1..10
                    mol_type = protein
                    organism = synthetic construct
                    note = Description of Artificial Sequence: Synthetic probe
SITE                10
                    note = dinitrobenzylation of lysine amide
SEQUENCE: 1308
GIRRSSYFKK                                                                  10

SEQ ID NO: 1309     moltype = AA   length = 10
FEATURE             Location/Qualifiers
source              1..10
                    mol_type = protein
                    organism = synthetic construct
                    note = Description of Artificial Sequence: Synthetic probe
SITE                2
                    note = benzyl-L-histidine
SITE                3
                    note = L-tert-leucine
SITE                7
                    note = L-methionine-sulfoxide
SITE                9
                    note = dinitrobenzylation of lysine
SEQUENCE: 1309
GHXPSDMGKG                                                                  10

SEQ ID NO: 1310     moltype = AA   length = 9
```

```
FEATURE              Location/Qualifiers
source               1..9
                     mol_type = protein
                     organism = synthetic construct
                     note = Description of Artificial Sequence: Synthetic probe
SITE                 1
                     note = norvaline
SITE                 4
                     note = L-octahydroindole-2-carboxylic acid
SITE                 9
                     note = dinitrobenzylation of lysine amide
SEQUENCE: 1310
XIEXDFGRK                                                                      9

SEQ ID NO: 1311      moltype = AA  length = 4
FEATURE              Location/Qualifiers
source               1..4
                     mol_type = protein
                     organism = synthetic construct
                     note = Description of Artificial Sequence: Synthetic probe
SITE                 1
                     note = acetyl histidine
SITE                 2
                     note = D-threonine
SITE                 3
                     note = 2,3,4,5,6-pentafluoro-L-penylalanine
SEQUENCE: 1311
HTFR                                                                           4

SEQ ID NO: 1312      moltype =    length =
SEQUENCE: 1312
000

SEQ ID NO: 1313      moltype =    length =
SEQUENCE: 1313
000

SEQ ID NO: 1314      moltype =    length =
SEQUENCE: 1314
000

SEQ ID NO: 1315      moltype =    length =
SEQUENCE: 1315
000

SEQ ID NO: 1316      moltype =    length =
SEQUENCE: 1316
000

SEQ ID NO: 1317      moltype = AA  length = 7
FEATURE              Location/Qualifiers
source               1..7
                     mol_type = protein
                     organism = synthetic construct
                     note = Description of Artificial Sequence: Synthetic probe
SITE                 2
                     note = 2,3-diaminopropionic acid
SITE                 3
                     note = L-Ornithine
SITE                 4
                     note = 3-chloro-L-phenylalanine
SITE                 5
                     note = S-para-methoxybenzyl cysteine
SITE                 7
                     note = dinitrobenzylation of lysine amide
SEQUENCE: 1317
GXXFCGK                                                                        7

SEQ ID NO: 1318      moltype = AA  length = 7
FEATURE              Location/Qualifiers
source               1..7
                     mol_type = protein
                     organism = synthetic construct
                     note = Description of Artificial Sequence: Synthetic probe
SITE                 2
                     note = L-cyclohexylalanine
SITE                 4
                     note = homoserine
SITE                 7
```

```
                        note = dinitrobenzylation of lysine amide
SEQUENCE: 1318
GXLXRGK                                                                 7

SEQ ID NO: 1319         moltype = AA   length = 7
FEATURE                 Location/Qualifiers
source                  1..7
                        mol_type = protein
                        organism = synthetic construct
                        note = Description of Artificial Sequence: Synthetic probe
SITE                    4
                        note = guamidine-L-phenylalanine
SITE                    7
                        note = dinitrobenzylation of lysine amide
SEQUENCE: 1319
FVTFSWK                                                                 7

SEQ ID NO: 1320         moltype = AA   length = 7
FEATURE                 Location/Qualifiers
source                  1..7
                        mol_type = protein
                        organism = synthetic construct
                        note = Description of Artificial Sequence: Synthetic probe
SITE                    2
                        note = homocyclohexylalnine
SITE                    3
                        note = phenylalanine derivative with a guanidine group in
                         the para position
SITE                    4
                        note = L-octahydroindole-2-carboxylic acid
SITE                    7
                        note = dinitrobenzylation of lysine amide
SEQUENCE: 1320
GXFXRGK                                                                 7

SEQ ID NO: 1321         moltype = AA   length = 7
FEATURE                 Location/Qualifiers
source                  1..7
                        mol_type = protein
                        organism = synthetic construct
                        note = Description of Artificial Sequence: Synthetic probe
SITE                    2
                        note = benzyloxy-L-norleucine
SITE                    3
                        note = methylsulfonylbutanoic acid
SITE                    4
                        note = L-octahydroindole-2-carboxylic acid
SITE                    5
                        note = L-alpha-aminobutyric acid
SITE                    7
                        note = dinitrobenzylation of lysine amide
SEQUENCE: 1321
GXMXXGK                                                                 7

SEQ ID NO: 1322         moltype = AA   length = 10
FEATURE                 Location/Qualifiers
source                  1..10
                        mol_type = protein
                        organism = synthetic construct
                        note = Description of Artificial Sequence: Synthetic probe
SITE                    10
                        note = Lysine modified with a CPQ2 quencher
SEQUENCE: 1322
GAIEPDSGGK                                                             10

SEQ ID NO: 1323         moltype = AA   length = 14
FEATURE                 Location/Qualifiers
source                  1..14
                        mol_type = protein
                        organism = synthetic construct
                        note = Description of Artificial Sequence: Synthetic probe
SITE                    10
                        note = Lysine modified with a CPQ2 quencher
SITE                    11
                        note = D-Lysine
SITE                    12
                        note = D-Lysine
SITE                    14
                        note = cysteine amide
```

```
SEQUENCE: 1323
GAIEFDSGGK KKGC                                                                          14

SEQ ID NO: 1324         moltype = AA  length = 13
FEATURE                 Location/Qualifiers
source                  1..13
                        mol_type = protein
                        organism = synthetic construct
                        note = Description of Artificial Sequence: Synthetic probe
SITE                    11
                        note = Lysine modified with a CPQ2 quencher
SITE                    12
                        note = D-Lysine
SITE                    13
                        note = D-Lysine
SEQUENCE: 1324
GGAAEAISDA KKK                                                                           13

SEQ ID NO: 1325         moltype = AA  length = 13
FEATURE                 Location/Qualifiers
source                  1..13
                        mol_type = protein
                        organism = synthetic construct
                        note = Description of Artificial Sequence: Synthetic probe
SITE                    11
                        note = Lysine modified with a CPQ2 quencher
SITE                    12
                        note = D-Lysine
SITE                    13
                        note = D-Lysine
SEQUENCE: 1325
GGAGGAQMGA KKK                                                                           13

SEQ ID NO: 1326         moltype = AA  length = 13
FEATURE                 Location/Qualifiers
source                  1..13
                        mol_type = protein
                        organism = synthetic construct
                        note = Description of Artificial Sequence: Synthetic probe
SITE                    11
                        note = Lysine modified with a CPQ2 quencher
SITE                    12
                        note = D-Lysine
SITE                    13
                        note = D-Lysine
SEQUENCE: 1326
GGAQPDALNV KKK                                                                           13

SEQ ID NO: 1327         moltype = AA  length = 13
FEATURE                 Location/Qualifiers
source                  1..13
                        mol_type = protein
                        organism = synthetic construct
                        note = Description of Artificial Sequence: Synthetic probe
SITE                    11
                        note = Lysine modified with a CPQ2 quencher
SITE                    12
                        note = D-Lysine
SITE                    13
                        note = D-Lysine
SEQUENCE: 1327
GGATDVTTTP KKK                                                                           13

SEQ ID NO: 1328         moltype = AA  length = 13
FEATURE                 Location/Qualifiers
source                  1..13
                        mol_type = protein
                        organism = synthetic construct
                        note = Description of Artificial Sequence: Synthetic probe
SITE                    11
                        note = Lysine modified with a CPQ2 quencher
SITE                    12
                        note = D-Lysine
SITE                    13
                        note = D-Lysine
SEQUENCE: 1328
GGDIVTVANA KKK                                                                           13

SEQ ID NO: 1329         moltype = AA  length = 13
```

```
FEATURE                     Location/Qualifiers
source                      1..13
                            mol_type = protein
                            organism = synthetic construct
                            note = Description of Artificial Sequence: Synthetic probe
SITE                        11
                            note = Lysine modified with a CPQ2 quencher
SITE                        12
                            note = D-Lysine
SITE                        13
                            note = D-Lysine
SEQUENCE: 1329
GGDLGLKSVP KKK                                                                    13

SEQ ID NO: 1330             moltype = AA   length = 13
FEATURE                     Location/Qualifiers
source                      1..13
                            mol_type = protein
                            organism = synthetic construct
                            note = Description of Artificial Sequence: Synthetic probe
SITE                        11
                            note = Lysine modified with a CPQ2 quencher
SITE                        12
                            note = D-Lysine
SITE                        13
                            note = D-Lysine
SEQUENCE: 1330
GGDVMASNKR KKK                                                                    13

SEQ ID NO: 1331             moltype = AA   length = 13
FEATURE                     Location/Qualifiers
source                      1..13
                            mol_type = protein
                            organism = synthetic construct
                            note = Description of Artificial Sequence: Synthetic probe
SITE                        11
                            note = Lysine modified with a CPQ2 quencher
SITE                        12
                            note = D-Lysine
SITE                        13
                            note = D-Lysine
SEQUENCE: 1331
GGESDELNTI KKK                                                                    13

SEQ ID NO: 1332             moltype = AA   length = 13
FEATURE                     Location/Qualifiers
source                      1..13
                            mol_type = protein
                            organism = synthetic construct
                            note = Description of Artificial Sequence: Synthetic probe
SITE                        11
                            note = Lysine modified with a CPQ2 quencher
SITE                        12
                            note = D-Lysine
SITE                        13
                            note = D-Lysine
SEQUENCE: 1332
GGFHPLHSKI KKK                                                                    13

SEQ ID NO: 1333             moltype = AA   length = 13
FEATURE                     Location/Qualifiers
source                      1..13
                            mol_type = protein
                            organism = synthetic construct
                            note = Description of Artificial Sequence: Synthetic probe
SITE                        11
                            note = Lysine modified with a CPQ2 quencher
SITE                        12
                            note = D-Lysine
SITE                        13
                            note = D-Lysine
SEQUENCE: 1333
GGGHARLVHV KKK                                                                    13

SEQ ID NO: 1334             moltype = AA   length = 13
FEATURE                     Location/Qualifiers
source                      1..13
                            mol_type = protein
                            organism = synthetic construct
```

-continued

```
                        note = Description of Artificial Sequence: Synthetic probe
SITE                    11
                        note = Lysine modified with a CPQ2 quencher
SITE                    12
                        note = D-Lysine
SITE                    13
                        note = D-Lysine
SEQUENCE: 1334
GGHIANVERV KKK                                                          13

SEQ ID NO: 1335         moltype = AA   length = 13
FEATURE                 Location/Qualifiers
source                  1..13
                        mol_type = protein
                        organism = synthetic construct
                        note = Description of Artificial Sequence: Synthetic probe
SITE                    11
                        note = Lysine modified with a CPQ2 quencher
SITE                    12
                        note = D-Lysine
SITE                    13
                        note = D-Lysine
SEQUENCE: 1335
GGKAAATQKK KKK                                                          13

SEQ ID NO: 1336         moltype = AA   length = 13
FEATURE                 Location/Qualifiers
source                  1..13
                        mol_type = protein
                        organism = synthetic construct
                        note = Description of Artificial Sequence: Synthetic probe
SITE                    11
                        note = Lysine modified with a CPQ2 quencher
SITE                    12
                        note = D-Lysine
SITE                    13
                        note = D-Lysine
SEQUENCE: 1336
GGLATASTMD KKK                                                          13

SEQ ID NO: 1337         moltype = AA   length = 13
FEATURE                 Location/Qualifiers
source                  1..13
                        mol_type = protein
                        organism = synthetic construct
                        note = Description of Artificial Sequence: Synthetic probe
SITE                    11
                        note = Lysine modified with a CPQ2 quencher
SITE                    12
                        note = D-Lysine
SITE                    13
                        note = D-Lysine
SEQUENCE: 1337
GGLGPKGQTG KKK                                                          13

SEQ ID NO: 1338         moltype = AA   length = 13
FEATURE                 Location/Qualifiers
source                  1..13
                        mol_type = protein
                        organism = synthetic construct
                        note = Description of Artificial Sequence: Synthetic probe
SITE                    11
                        note = Lysine modified with a CPQ2 quencher
SITE                    12
                        note = D-Lysine
SITE                    13
                        note = D-Lysine
SEQUENCE: 1338
GGLSLPETGE KKK                                                          13

SEQ ID NO: 1339         moltype = AA   length = 13
FEATURE                 Location/Qualifiers
source                  1..13
                        mol_type = protein
                        organism = synthetic construct
                        note = Description of Artificial Sequence: Synthetic probe
SITE                    11
                        note = Lysine modified with a CPQ2 quencher
SITE                    12
```

```
                        note = D-Lysine
SITE                    13
                        note = D-Lysine
SEQUENCE: 1339
GGNLAGILKE KKK                                                                  13

SEQ ID NO: 1340         moltype = AA  length = 13
FEATURE                 Location/Qualifiers
source                  1..13
                        mol_type = protein
                        organism = synthetic construct
                        note = Description of Artificial Sequence: Synthetic probe
SITE                    11
                        note = Lysine modified with a CPQ2 quencher
SITE                    12
                        note = D-Lysine
SITE                    13
                        note = D-Lysine
SEQUENCE: 1340
GGNPGMSEPV KKK                                                                  13

SEQ ID NO: 1341         moltype = AA  length = 12
FEATURE                 Location/Qualifiers
source                  1..12
                        mol_type = protein
                        organism = synthetic construct
                        note = Description of Artificial Sequence: Synthetic probe
SITE                    10
                        note = Lysine modified with a CPQ2 quencher
SITE                    11
                        note = D-Lysine
SITE                    12
                        note = D-Lysine
SEQUENCE: 1341
GGPFGCHAKK KK                                                                   12

SEQ ID NO: 1342         moltype = AA  length = 12
FEATURE                 Location/Qualifiers
source                  1..12
                        mol_type = protein
                        organism = synthetic construct
                        note = Description of Artificial Sequence: Synthetic probe
SITE                    10
                        note = Lysine modified with a CPQ2 quencher
SITE                    11
                        note = D-Lysine
SITE                    12
                        note = D-Lysine
SEQUENCE: 1342
GGPLGLRWWK KK                                                                   12

SEQ ID NO: 1343         moltype = AA  length = 13
FEATURE                 Location/Qualifiers
source                  1..13
                        mol_type = protein
                        organism = synthetic construct
                        note = Description of Artificial Sequence: Synthetic probe
SITE                    11
                        note = Lysine modified with a CPQ2 quencher
SITE                    12
                        note = D-Lysine
SITE                    13
                        note = D-Lysine
SEQUENCE: 1343
GGQMGVMQGV KKK                                                                  13

SEQ ID NO: 1344         moltype = AA  length = 13
FEATURE                 Location/Qualifiers
source                  1..13
                        mol_type = protein
                        organism = synthetic construct
                        note = Description of Artificial Sequence: Synthetic probe
SITE                    11
                        note = Lysine modified with a CPQ2 quencher
SITE                    12
                        note = D-Lysine
SITE                    13
                        note = D-Lysine
SEQUENCE: 1344
```

| | | |
|---|---|---|
| GGQTCKCSCK KKK | | 13 |
| SEQ ID NO: 1345 | moltype = AA   length = 13 | |
| FEATURE | Location/Qualifiers | |
| source | 1..13 | |
| | mol_type = protein | |
| | organism = synthetic construct | |
| | note = Description of Artificial Sequence: Synthetic probe | |
| SITE | 11 | |
| | note = Lysine modified with a CPQ2 quencher | |
| SITE | 12 | |
| | note = D-Lysine | |
| SITE | 13 | |
| | note = D-Lysine | |
| SEQUENCE: 1345 | | |
| GGQWAGLVEK KKK | | 13 |
| SEQ ID NO: 1346 | moltype = AA   length = 13 | |
| FEATURE | Location/Qualifiers | |
| source | 1..13 | |
| | mol_type = protein | |
| | organism = synthetic construct | |
| | note = Description of Artificial Sequence: Synthetic probe | |
| SITE | 11 | |
| | note = Lysine modified with a CPQ2 quencher | |
| SITE | 12 | |
| | note = D-Lysine | |
| SITE | 13 | |
| | note = D-Lysine | |
| SEQUENCE: 1346 | | |
| GGRPAVMTSP KKK | | 13 |
| SEQ ID NO: 1347 | moltype = AA   length = 13 | |
| FEATURE | Location/Qualifiers | |
| source | 1..13 | |
| | mol_type = protein | |
| | organism = synthetic construct | |
| | note = Description of Artificial Sequence: Synthetic probe | |
| SITE | 11 | |
| | note = Lysine modified with a CPQ2 quencher | |
| SITE | 12 | |
| | note = D-Lysine | |
| SITE | 13 | |
| | note = D-Lysine | |
| SEQUENCE: 1347 | | |
| GGTLRELHLD KKK | | 13 |
| SEQ ID NO: 1348 | moltype = AA   length = 13 | |
| FEATURE | Location/Qualifiers | |
| source | 1..13 | |
| | mol_type = protein | |
| | organism = synthetic construct | |
| | note = Description of Artificial Sequence: Synthetic probe | |
| SITE | 11 | |
| | note = Lysine modified with a CPQ2 quencher | |
| SITE | 12 | |
| | note = D-Lysine | |
| SITE | 13 | |
| | note = D-Lysine | |
| SEQUENCE: 1348 | | |
| GGTPPPSQGK KKK | | 13 |
| SEQ ID NO: 1349 | moltype = AA   length = 13 | |
| FEATURE | Location/Qualifiers | |
| source | 1..13 | |
| | mol_type = protein | |
| | organism = synthetic construct | |
| | note = Description of Artificial Sequence: Synthetic probe | |
| SITE | 11 | |
| | note = Lysine modified with a CPQ2 quencher | |
| SITE | 12 | |
| | note = D-Lysine | |
| SITE | 13 | |
| | note = D-Lysine | |
| SEQUENCE: 1349 | | |
| GGTSEDLVVQ KKK | | 13 |
| SEQ ID NO: 1350 | moltype = AA   length = 13 | |
| FEATURE | Location/Qualifiers | |

```
source                  1..13
                        mol_type = protein
                        organism = synthetic construct
                        note = Description of Artificial Sequence: Synthetic probe
SITE                    11
                        note = Lysine modified with a CPQ2 quencher
SITE                    12
                        note = D-Lysine
SITE                    13
                        note = D-Lysine
SEQUENCE: 1350
GGVWAAEAIS KKK                                                                    13

SEQ ID NO: 1351         moltype =    length =
SEQUENCE: 1351
000

SEQ ID NO: 1352         moltype =    length =
SEQUENCE: 1352
000

SEQ ID NO: 1353         moltype = AA   length = 9
FEATURE                 Location/Qualifiers
source                  1..9
                        mol_type = protein
                        organism = synthetic construct
                        note = Description of Artificial Sequence: Synthetic probe
VARIANT                 4
                        note = R or K
SITE                    9
                        note = lysine amide modified with a CPQ2 quencher
SEQUENCE: 1353
GWYKTQYGK                                                                          9

SEQ ID NO: 1354         moltype = AA   length = 9
FEATURE                 Location/Qualifiers
source                  1..9
                        mol_type = protein
                        organism = synthetic construct
                        note = Description of Artificial Sequence: Synthetic probe
VARIANT                 4
                        note = R or K
SITE                    9
                        note = Lysine modified with a CPQ2 quencher
SEQUENCE: 1354
GFARRWGGK                                                                          9

SEQ ID NO: 1355         moltype = AA   length = 9
FEATURE                 Location/Qualifiers
source                  1..9
                        mol_type = protein
                        organism = synthetic construct
                        note = Description of Artificial Sequence: Synthetic probe
VARIANT                 4
                        note = F, Y, L or W
SITE                    6
                        note = Norleucine
SITE                    9
                        note = Lysine modified with a CPQ2 quencher
SEQUENCE: 1355
GSYWPXQGK                                                                          9

SEQ ID NO: 1356         moltype = AA   length = 9
FEATURE                 Location/Qualifiers
source                  1..9
                        mol_type = protein
                        organism = synthetic construct
                        note = Description of Artificial Sequence: Synthetic probe
VARIANT                 4
                        note = F or Y
SITE                    5
                        note = Norleucine
SITE                    9
                        note = Lysine modified with a CPQ2 quencher
SEQUENCE: 1356
GFIYXPTGK                                                                          9

SEQ ID NO: 1357         moltype = AA   length = 9
FEATURE                 Location/Qualifiers
```

| | | |
|---|---|---|
| source | 1..9<br>mol_type = protein<br>organism = synthetic construct<br>note = Description of Artificial Sequence: Synthetic probe | |
| VARIANT | 3<br>note = T, I or V | |
| SITE | 9<br>note = lysine amide modified with a CPQ2 quencher | |
| SEQUENCE: 1357<br>GVIDKDFGK | | 9 |
| SEQ ID NO: 1358<br>FEATURE<br>source | moltype = AA  length = 9<br>Location/Qualifiers<br>1..9<br>mol_type = protein<br>organism = synthetic construct<br>note = Description of Artificial Sequence: Synthetic probe | |
| VARIANT | 5<br>note = K or R | |
| SITE | 9<br>note = Lysine modified with a CPQ2 quencher | |
| SEQUENCE: 1358<br>GFARRWGGK | | 9 |
| SEQ ID NO: 1359<br>FEATURE<br>source | moltype = AA  length = 10<br>Location/Qualifiers<br>1..10<br>mol_type = protein<br>organism = synthetic construct<br>note = Description of Artificial Sequence: Synthetic probe | |
| SITE | 1<br>note = D-Lysine | |
| SITE | 9<br>note = Lysine modified with a CPQ2 quencher | |
| VARIANT | 10<br>note = Hydroxy Lysine or hydroxy arginine | |
| SEQUENCE: 1359<br>KGEFVHNPKK | | 10 |
| SEQ ID NO: 1360<br>FEATURE<br>source | moltype = AA  length = 9<br>Location/Qualifiers<br>1..9<br>mol_type = protein<br>organism = synthetic construct<br>note = Description of Artificial Sequence: Synthetic probe | |
| SITE | 8<br>note = Lysine modified with a CPQ2 quencher | |
| VARIANT | 9<br>note = Hydroxy Arginine, Hydroxy Lysine or Hydroxy Histidine | |
| SEQUENCE: 1360<br>GNAYNEIKR | | 9 |
| SEQ ID NO: 1361<br>FEATURE<br>source | moltype = AA  length = 11<br>Location/Qualifiers<br>1..11<br>mol_type = protein<br>organism = synthetic construct<br>note = Description of Artificial Sequence: Synthetic probe | |
| VARIANT | 1<br>note = W, G or F | |
| SITE | 2<br>note = carboxy-fluorescein-L-lysine | |
| SITE | 10<br>note = D-Lysine | |
| SITE | 11<br>note = lysine amide modified with a CPQ2 quencher | |
| SEQUENCE: 1361<br>WKNAGSKFGK K | | 11 |
| SEQ ID NO: 1362<br>FEATURE<br>source | moltype = AA  length = 10<br>Location/Qualifiers<br>1..10<br>mol_type = protein<br>organism = synthetic construct<br>note = Description of Artificial Sequence: Synthetic probe | |
| VARIANT | 1<br>note = Q or K | |
| SITE | 2<br>note = carboxy-fluorescein-L-lysine | |

```
SITE                    10
                        note = lysine amide modified with a CPQ2 quencher
SEQUENCE: 1362
QKKRVQFLGK                                                                         10

SEQ ID NO: 1363         moltype = AA  length = 4
FEATURE                 Location/Qualifiers
source                  1..4
                        mol_type = protein
                        organism = synthetic construct
SITE                    1
                        note = D-Lysine
SITE                    2
                        note = D-Lysine
SEQUENCE: 1363
KKGC                                                                               4

SEQ ID NO: 1364         moltype = AA  length = 4
FEATURE                 Location/Qualifiers
source                  1..4
                        mol_type = protein
                        organism = synthetic construct
SITE                    1
                        note = D-Lysine
SITE                    2
                        note = D-Lysine
SITE                    4
                        note = cysteine amide
SEQUENCE: 1364
KKGC                                                                               4
```

What is claimed is:

1. A method, comprising:
   a. collecting a body fluid sample from a subject;
   b. contacting the body fluid sample from the subject with one or more synthetic molecules ex vivo,
      i. wherein said one or more synthetic molecules comprise a plurality of reporters and a plurality of cleavable peptide linkers, wherein a first cleavable peptide linker of said plurality of cleavable peptide linkers is coupled to a first reporter of said plurality of reporters, wherein a second cleavable peptide linker of said plurality of cleavable peptide linkers is coupled to a second reporter of said plurality of reporters, and wherein the reporter of said plurality of reporters is directly connected to the cleavable peptide linker of said plurality of cleavable peptide linkers through a covalent bond,
      ii. wherein said one or more synthetic molecules react with a plurality of extracellular or circulating enzymes from said body fluid sample, wherein a first enzyme of said plurality of extracellular or circulating enzymes cleaves said first cleavable peptide linker and releases said first reporter from said one or more synthetic molecules, wherein said release of said first reporter forms a first detectable signal, and wherein a second enzyme of said plurality of extracellular or circulating enzymes cleaves said second cleavable peptide linker and releases said second reporter from said one or more synthetic molecules, wherein said release of said second reporter forms a second detectable signal; and
   c. detecting said first detectable signal or said second detectable signal.

2. The method of claim 1, wherein said body fluid sample is selected from the group consisting of blood, plasma, bone marrow fluid, lymphatic fluid, saliva, spinal fluid, synovial fluid, semen, and vaginal fluid.

3. The method of claim 1, wherein said plurality of extracellular or circulating enzymes comprises disease-related proteases.

4. The method of claim 3, wherein said disease-related proteases are selected from the group consisting of an A20 (TNFa-induced protein 3), an abhydrolase domain containing 4, an abhydrolase domain containing 12, an abhydrolase domain containing 12B, an abhydrolase domain containing 13, an acrosin, an acylaminoacyl-peptidase, a disintegrin and metalloproteinase (ADAM), an ADAM1a, an ADAM2 (Fertilin-b), an ADAM3B, an ADAM4, an ADAM4B, an ADAM5, an ADAM6, an ADAM7, an ADAM8, an ADAM9, an ADAM10, an ADAM11, an ADAM12 metalloprotease, an ADAM15, an ADAM17, an ADAM18, an ADAM19, an ADAM20, an ADAM21, an ADAM22, an ADAM23, an ADAM28, an ADAM29, an ADAM30, an ADAM32, an ADAM33, a disintegrin and metalloproteinase with thrombospondin motifs (ADAMTS), an ADAMTS1, an ADAMTS2, an ADAMTS3, an ADAMTS4, an ADAMTS5/11, an ADAMTS6, an ADAMTS7, an ADAMTS8, an ADAMTS9, an ADAMTS10, an ADAMTS12, an ADAMTS13, an ADAMTS14, an ADAMTS15, an ADAMTS16, an ADAMTS17, an ADAMTS18, an ADAMTS19, an ADAMTS20, an adipocyte-enh. binding protein 1, an Afg3-like protein 1, an Afg3-like protein 2, an airway-trypsin-like protease, an aminoacylase, an aminopeptidase A, an aminopeptidase B, an aminopeptidase B-like 1, an aminopeptidase MAMS/L-RAP, an aminopeptidase N, an aminopeptidase O, an aminopeptidase P homologue, an aminopeptidase P1, an aminopeptidase PILS, an aminopeptidase Q, an aminopeptidase-like 1, an AMSH/STAMBP, an AMSH-LP/STAMBPL1, an angiotensin-converting enzyme 1 (ACE1), an angiotensin-converting enzyme 2 (ACE2), an angiotensin-converting enzyme 3 (ACE3), an anionic trypsin (II), an apolipoprotein (a), an archaemetzincin-1, an archaemetzincin-2, an aspartoacylase, an aspartoacylase-3, an aspartyl aminopeptidase, an ataxin-3, an ataxin-3 like, an ATP/GTP binding protein 1, an ATP/GTP binding protein-like 2, an ATP/GTP binding protein-like 3, an ATP/GTP binding protein-like 4, an ATP/GTP binding protein-like 5, an ATP23 peptidase, an autophagin-1, an autophagin-2, an autophagin-3, an autophagin-4, an azurocidin, a beta lactamase, a beta-secretase 1, a beta-secretase 2, a bleomycin hydrolase, a brain serine proteinase 2, a BRCC36 (BRCA2-containing complex, sub 3), a calpain, a calpain 1, a calpain 2, a calpain 3, a calpain 4, a calpain 5, a calpain 6, a calpain 7, a calpain 7-like, a calpain 8, a calpain 9, a calpain 10, a calpain 11, a calpain 12, a calpain 13, a calpain 14, a calpain 15 (Solh protein), a cysteine protease, a carboxypeptidase A1, a carboxypeptidase A2, a carboxypeptidase A3, a carboxypeptidase A4, a carboxypeptidase A5, a carboxypeptidase A6, a carboxypeptidase B, a carboxypeptidase D, a carboxypeptidase E, a carboxypeptidase M, a carboxypeptidase N, a carboxypeptidase O, a carboxypeptidase U, a carboxypeptidase X1, a carboxypeptidase X2, a carboxypeptidase Z, a carnosine dipeptidase 1, a carnosine dipeptidase 2, a caspase recruitment domain family, member 8, a caspase, a caspase-1, a caspase-2, a caspase-3, a caspase-4/11, a caspase-5, a caspase-6, a caspase-7, a caspase-8, a caspase-9, a caspase-10, a caspase-12, a caspase-14, a caspase-14-like, a casper/FLIP, a cathepsin, a cathepsin A (CTSA), a cathepsin B (CTSB), a cathepsin C (CTSC), a cathepsin D (CTSD), a cathepsin E (CTSE), a cathepsin F, a cathepsin G, a cathepsin H (CTSH), a cathepsin K (CTSK), a cathepsin L (CTSL), a cathepsin L2, a cathepsin O, a cathepsin S (CTSS), a cathepsin V (CTSV), a cathepsin W, a cathepsin Z (CTSZ), a cationic trypsin, a cezanne/OTU domain containing 7B, a cezanne-2, a CGI-58, a chymase, a chymopasin, a chymosin, a chymotrypsin B, a chymotrypsin C, a coagulation factor IXa, a coagulation factor VIIa, a coagulation factor Xa, a coagulation factor XIa, a coagulation factor XIIa, a collagenase 1, a collagenase 2, a collagenase 3, a complement protease C1r serine protease, a complement protease C1s serine protease, a complement C1r-homolog, a complement component 2, a complement component C1ra, a complement component C1sa, a complement factor B, a complement factor D, a complement factor D-like, a complement factor I, a COPS6, a corin, a CSN5 (JAB1), a cylindromatosis protein, a cytosol alanyl aminopep.-like 1, a cytosol alanyl aminopeptidase, a DDI-related protease, a DECYSIN, a Derl-like domain family, member 1, a Derl-like domain family, member 2, a Derl-like domain family, member 3, a DESC1 protease, a desert hedgehog protein, a desumoylating isopeptidase 1, a desumoylating isopeptidase 2, a dihydroorotase, a dihydropyrimidinase, a dihydropyrimidinase-related protein 1, a dihydropyrimidinase-related protein 2, a dihydropyrimidinase-related protein 3, a dihydropyrimidinase-related protein 4, a dihydropyrimidinase-related protein 5, a DINE peptidase, a dipeptidyl peptidase (DPP), a dipeptidyl peptidase (DPP1), a dipeptidyl-peptidase 4 (DPP4), a dipeptidyl-peptidase 6 (DPP6), a dipeptidyl-peptidase 8 (DPP8), a dipeptidyl-peptidase 9 (DPP9), a dipeptidyl-peptidase II, a dipeptidyl-peptidase III, a dipeptidyl-peptidase 10 (DPP10), a DJ-1, a DNA-damage inducible protein, a DNA-damage inducible protein 2, a DUB-1, a DUB-2, a DUB2a, a DUB2a-like, a DUB2a-like2, a DUB6, or a combination thereof.

5. The method of claim 1, wherein said plurality of extracellular or circulating enzymes comprises an endoprotease or an exoprotease.

6. The method of claim 5, wherein said endoprotease comprises a design of XmAYn or AXnB, wherein A is a single amino acid and A and B are amino acid pairs recognized by a particular endoprotease, X and Y are any amino acid labeled or not with a reporter, and m, and n are zero or any integer.

7. The method of claim 5, wherein said exoprotease comprises a design of XmAYn or AXnB, wherein A is a single amino acid and A and B are amino acid pairs recognized by a particular exoprotease, X and Y are any amino acid labeled or not with a reporter, and m, and n are zero or any integer.

8. The method of claim 1, wherein said plurality of cleavable peptide linkers comprises at least one amino acid sequence of SEQ ID Nos: 1-677.

9. The method of claim 1, wherein said plurality of reporters comprises a fluorescent label comprising a 5-carboxyfluorescein (5-FAM), a 7-amino-4-carbamoylmethylcoumarin (ACC), a 7-Amino-4-methylcoumarin (AMC), a 2-Aminobenzoyl (Abz), a Cy7, a Cy5, a Cy3 or a (5-((2-Aminoethyl)amino)naphthalene-1-sulfonic acid) (EDANS).

10. The method of claim 9, wherein said one or more synthetic molecules further comprise a fluorescent quencher comprising a BHQ0, BHQ1, BHQ2, BHQ3, BBQ650, ATTO 540Q, ATTO 580Q, ATTO 612Q, CPQ2, QSY-21, QSY-35, QSY-7, QSY-9, DABCYL (4-([4'-dimethylamino)phenyl]azo)benzoyl), Dnp (2,4-dinitrophenyl) or Eclipse.

11. The method of claim 1, wherein said one or more synthetic molecules further comprise a carrier.

12. The method of claim 11, wherein said carrier comprises a native, labeled or synthetic protein, a synthetic chemical polymer of precisely known chemical composition or with a distribution around a mean molecular weight, an oligonucleotide, a phosphorodiamidate morpholino oligomer (PMO), a foldamer, a lipid, a lipid micelle, a nanoparticle, a solid support made of polystyrene, polypropylene or any other type of plastic, or any combination thereof.

13. The method of claim 12, wherein said nanoparticle ranges in size from 10 nm to 100 nm.

14. The method of claim 1, further comprising determining a disease or condition of said subject based on said detecting of said first detectable signal or said second detectable signal.

15. The method of claim 14, wherein said disease or condition comprises a cancer.

16. The method of claim 15, wherein said cancer comprises adenoid cystic carcinoma, adrenal gland tumors, amyloidosis, anal cancer, appendix cancer, astrocytoma, ataxia-telangiectasia, Beckwith-Wiedemann syndrome, bile duct cancer (cholangiocarcinoma), Birt-Hogg-Dubé Syndrome, bladder cancer, bone cancer (sarcoma of the bone), brain stem glioma, brain tumors, breast cancer, Carney complex, central nervous system tumors, cervical cancer, colorectal cancer, Cowden Syndrome, craniopharyngioma, Desmoid tumors, desmoplastic infantile ganglioglioma, ependymoma, esophageal cancer, Ewing sarcoma, eye cancer, eyelid cancer, familial adenomatous polyposis, familial GIST, familial malignant melanoma, familial pancreatic cancer, gallbladder cancer, gastrointestinal stromal tumors (GIST), germ cell tumors, gestational trophoblastic disease, head and neck cancer, breast and ovarian cancer, diffuse gastric cancer, leiomyosarcoma and renal cell cancer, mixed polyposis syndrome, papillary renal carcinoma, juvenile polyposis syndrome, kidney cancer, lacrimal gland tumors, laryngeal and hypopharyngeal cancer, leukemia, myeloid leukemia, lymphoblastic leukemia, eosinophilic leukemia, Li-Fraumeni syndrome, liver cancer, lung cancer, Hodgkin lung cancer, non-Hodgkin lung cancer, Lynch syndrome, mastocytosis, medulloblastoma, melanoma, meningioma, mesothelioma, multiple endocrine neoplasia, multiple myeloma, myelodysplastic syndrome, nasal cavity and paranasal sinus cancer, nasopharyngeal cancer, neuroblastoma, neuroendocrine tumors, neurofibromatosis, nevoid basal cell carcinoma syndrome, oral and oropharyngeal cancer, osteosarcoma, ovarian cancer, fallopian tube cancer, peritoneal cancer, pancreatic cancer, parathyroid cancer, penile cancer, Peutz-Jeghers syndrome, phenochromocytoma, paraganglioma, pituitary gland tumors, pleuropulmonary blastoma, prostate cancer, retinoblastoma, rhabdomyosarcoma, salivary gland cancer, Kaposi sarcoma, soft tissue sarcoma, sarcoma, non-melanoma skin cancer, small bowel cancer, stomach cancer, testicular cancer, thymoma and thymic carcinoma, thyroid cancer, tuberous sclerosis complex, uterine cancer, vaginal cancer, von Hippel-Lindau syndrome, vulvar cancer, Waldenstrom macroglobulinemia, Werner syndrome, Wilms tumors, or xeroderma pigmentosum, or any combination thereof.

17. The method of claim 15, wherein said cancer is not pancreatic ductal adenocarcinoma or non-small cell lung cancer.

18. The method of claim 14, further comprising determining a stage of said disease or condition.

19. The method of claim 14, wherein said disease or condition is a certain fibrosis stage or a certain nonalcoholic fatty liver disease activity score (NAS) of Non-alcoholic steatohepatitis (NASH).

20. The method of claim 1, wherein said subject is a human subject.

21. The method of claim 1, wherein in (c), detecting said first detectable signal or said second detectable signal comprises detecting a rate of formation or an amount of said first detectable signal or said second detectable signal.

22. The method of claim 1, wherein in (c), said detecting comprises detecting said first detectable signal and said second detectable signal.

23. The method of claim 1, wherein a synthetic molecule of said one or more synthetic molecules comprises said first cleavable peptide linker, said first reporter, said second cleavable peptide linker, and said second reporter.

24. The method of claim 1, wherein a first synthetic molecule of said one or more synthetic molecules comprises said first cleavable peptide linker and said first reporter, and wherein a second synthetic molecule of said one or more synthetic molecules comprises said second cleavable peptide linker and said second reporter.

25. The method of claim 1, wherein said first reporter and said second reporter are different.

26. The method of claim 1, wherein said first reporter and said second reporter are the same.

* * * * *